US009023617B2

(12) United States Patent
Bloom et al.

(10) Patent No.: US 9,023,617 B2

(45) Date of Patent: May 5, 2015

(54) INSULATED HERPESVIRUS-DERIVED GENE EXPRESSION CASSETTES FOR SUSTAINED AND REGULATABLE GENE EXPRESSION

(75) Inventors: David C. Bloom, Gainesville, FL (US); Antonio L. Amelio, Vera Beach, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 1888 days.

(21) Appl. No.: 10/590,136

(22) PCT Filed: Feb. 17, 2005

(86) PCT No.: PCT/US2005/005461

§ 371 (c)(1), (2), (4) Date: Nov. 22, 2006

(87) PCT Pub. No.: WO2005/080581

PCT Pub. Date: Sep. 1, 2005

(65) Prior Publication Data

US 2007/0154456 A1 Jul. 5, 2007

Related U.S. Application Data

(60) Provisional application No. 60/545,375, filed on Feb. 17, 2004.

(51) Int. Cl.

*C12N 15/86* (2006.01)
*C12N 15/85* (2006.01)
*A61K 48/00* (2006.01)

(52) U.S. Cl.

CPC ................ *C12N 15/85* (2013.01); *A61K 48/00* (2013.01); *C12N 15/86* (2013.01); *C12N 2710/16611* (2013.01); *C12N 2710/16642* (2013.01); *C12N 2710/16643* (2013.01); *C12N 2830/007* (2013.01); *C12N 2830/40* (2013.01); *C12N 2830/60* (2013.01)

(58) Field of Classification Search

CPC ........ A61K 48/00; C12N 15/85; C12N 15/86; C12N 2710/16611; C12N 2710/16642

USPC .................. 424/93.2; 435/325, 456; 977/802

See application file for complete search history.

(56) References Cited

U.S. PATENT DOCUMENTS

2003/0082142 A1 5/2003 Coffin

FOREIGN PATENT DOCUMENTS

WO 98/30707 7/1998

OTHER PUBLICATIONS

GenBank HSV complete genome downloaded Jul. 31, 2010.*

GenBank LAP promoter regions downloaded Jul. 31, 2010.*

Bloom, D.C., "ChiPping away at LAT function." Invited symposium talk, 29th International Herpesvirus Workshop, pp. 1-36. Jul. 25-30, 2004, Reno, NV, USA.

Amelio, A.L., McAnany, P.J., and D.C. Bloom. "Identification of a Chromatin Insulator-like element within the HSV-1 LAT Region that Binds CCCTC-Binding Factor and Displays Enhancer-Blocking Activity." J. Virol. 80:2358-2368, Mar. 2006.

Amelio AL, and Bloom DC., "Identification of a Chromatin Insulator with Enhancer-Blocking Activity Located within the HSV-1 LAT region." p. 1. Poster presentation, 30th International Herpesvirus Workshop, Jul. 2005, Turku, Finland (Abstract attached).

Amelio, A.L., "Factors involved in epigenetic regulation of the HSV-1 reactivation critical region (rcr) during latency and reactivation." pp. 1-204. Doctoral Dissertation, University of Florida. Dec. 2005.

Palmer J A et al., Development and Optimization of Herpes Simplex Virus Vectors for Multiple Long-Term Delivery to the Peripheral Nervous System. Journal of Virology, The American Society for Microbiology, US, vol. 74, No. 12, Jun. 2000, pp. 5604-5618.

Lachmann R H et al., Utilization of the Herpes Simplex Virus Type 1 Latency-Associated Regulatory Region to Drive Stable Reporter Gene Expression in the Nervous System. Journal of Virology, The American Society for Microbiology, US, vol. 71, No. 4, Apr. 1997, pp. 3197-3207.

Perng Guey-Chuen et al., The Spontaneous Reactivation Function of the Herpes Simplex Virus Type 1 Lat Gene Resides Completely Within the First 1.5 Kilobases of the 8.3—Kilobase Primary Transcript. Journal of Virology, vol. 70, No. 2, 1996, pp. 976-984.

West A G et al., Insulators: Many Functions, Many Mechanisms Genes and Development, Cold Spring Harbor Laboratory Press, New York, US, vol. 16, No. 3, Feb. 1, 2002, pp. 271-288.

Berthomme Herve et al., Evidence for a Bidirectional Element Located Downstream From the Herpes Simple Virus Type 1 Latency-Associated Promoter That Increases Its Activity During Latency. Journal of Virology, vol. 74, No. 8, Apr. 2000, pp. 3613-3622.

Kubat, N. J . et al., The Herpes Simplex Virus Type 1 Latency-Associated Transcript (Lat) Enhancer/Rcr Is Hyperacetylated During Latency Independently of LAT Transcription. Journal of Virology, vol. 78, No. 22, Nov. 2004, pp. 12508-12518.

Glorioso J C et al., Development and Application of Herpes Simplex Virus Vectors for Human Gene Therapy. Annual Review of Microbiology, Annual Reviews Inc., Palo Alto, CA, US, vol. 49, 1995, pp. 675-710.

(Continued)

*Primary Examiner* — Catherine Hibbert

(74) *Attorney, Agent, or Firm* — Haynes and Boone, LLP

(57) ABSTRACT

Disclosed are genetic expression cassettes, and vector comprising them useful for the delivery of nucleic acid segments encoding selected therapeutic constructs (including for example, peptides, polypeptides, ribozymes, and catalytic RN molecules), to selected cells and tissues of vertebrate animals. The disclosed genetic constructs are useful in the development of gene therapy vectors, including for example, viral vectors such as HSV, retroviral, lentiviral, AV, and rAAV vectors. The expression cassettes disclosed herein provide new tools in the field of gene therapy, and for the treatment of mammalian, and in particular, human diseases, disorders, and dysfunctions. The disclosed compositions may be utilized in a variety of investigative, diagnostic and therapeutic regimens, including the prevention and treatment of a variety of human diseases.

24 Claims, 11 Drawing Sheets

(56) References Cited

OTHER PUBLICATIONS

Figure 1:
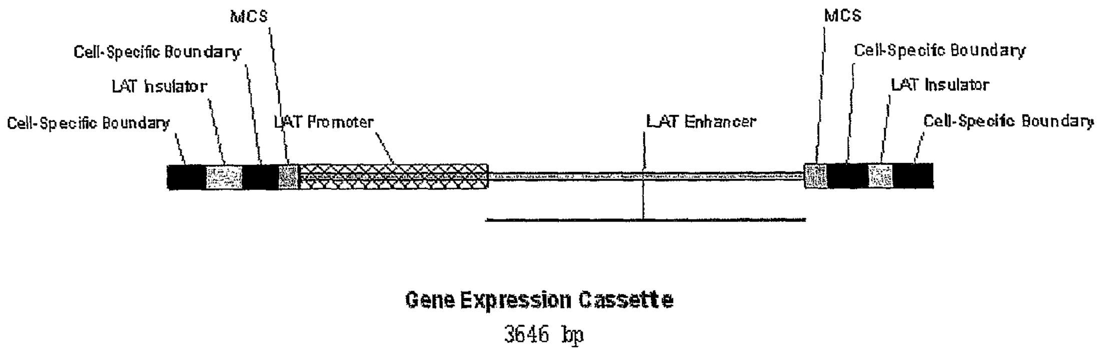

Chen, Qi et al., "CTCF-Dependent Chromatin Boundary Element between the Latency-Associated Transcript and ICP0 Promoters in the Herpes Simplex Virus Type 1 Genome," Journal of Virology, 81:5192-5201, May 2007.

Amelio, Antonio L., "A Chromatin Insulator-Like Element in the Herpes Simplex Virus Type 1 Latency-Associated Transcript Region Binds CCCTC-Binding Factor and Displays Enhancer-Blocking and Silencing Activities," Journal of Virology 80:2358-2368, Mar. 2006.

* cited by examiner

SEQUENCE LISTING

```
<160> NUMBER OF SEQ ID NOS: 111

<210> SEQ ID NO 1
<211> LENGTH: 21
<212> TYPE: DNA
<213> ORGANISM: Herpes simplex virus

<400> SEQUENCE: 1

tgaaccccag ccccagaaac c                                    21


<210> SEQ ID NO 2
<211> LENGTH: 22
<212> TYPE: DNA
<213> ORGANISM: Herpes simplex virus

<400> SEQUENCE: 2

cgagtaaacc atgttaagga cc                                   22


<210> SEQ ID NO 3
<211> LENGTH: 24
<212> TYPE: DNA
<213> ORGANISM: Herpes simplex virus

<400> SEQUENCE: 3

ctgatcacgc ggctgctgta cacc                                 24
```

-continued

<210> SEQ ID NO 4
<211> LENGTH: 24
<212> TYPE: DNA
<213> ORGANISM: Herpes simplex virus

<400> SEQUENCE: 4
ggtgatgaag gagctgctgt tgcg 24

<210> SEQ ID NO 5
<211> LENGTH: 19
<212> TYPE: DNA
<213> ORGANISM: Herpes simplex virus

<400> SEQUENCE: 5
catcaccgac ccggagagc 19

<210> SEQ ID NO 6
<211> LENGTH: 22
<212> TYPE: DNA
<213> ORGANISM: Herpes simplex virus

<400> SEQUENCE: 6
gggccaggcg cttgttggtg ta 22

<210> SEQ ID NO 7
<211> LENGTH: 20
<212> TYPE: DNA
<213> ORGANISM: Oryctolagus cuniculus

<400> SEQUENCE: 7
aagatctggc accacacctt 20

<210> SEQ ID NO 8
<211> LENGTH: 20
<212> TYPE: DNA
<213> ORGANISM: Oryctolagus cuniculus

<400> SEQUENCE: 8
cgaacatgat ctgggtcatc 20

<210> SEQ ID NO 9
<211> LENGTH: 20
<212> TYPE: DNA
<213> ORGANISM: Mus musculus

<400> SEQUENCE: 9
ggagcctaaa cctgtctgtc 20

<210> SEQ ID NO 10
<211> LENGTH: 20
<212> TYPE: DNA
<213> ORGANISM: Mus musculus

<400> SEQUENCE: 10
gtgtgtcata gctcaagagg 20

<210> SEQ ID NO 11
<211> LENGTH: 26
<212> TYPE: DNA
<213> ORGANISM: Mus musculus

<400> SEQUENCE: 11
actcagtcca aacatataca agatgc 26

-continued

<210> SEQ ID NO 12
<211> LENGTH: 25
<212> TYPE: DNA
<213> ORGANISM: Mus musculus

<400> SEQUENCE: 12
ctatctacaa caaacttctc ctggg 25

<210> SEQ ID NO 13
<211> LENGTH: 16
<212> TYPE: DNA
<213> ORGANISM: Herpes simplex virus

<400> SEQUENCE: 13
gcatgcgtcg cccaac 16

<210> SEQ ID NO 14
<211> LENGTH: 20
<212> TYPE: DNA
<213> ORGANISM: Herpes simplex virus

<400> SEQUENCE: 14
cagttagatt gcatgtgatc 20

<210> SEQ ID NO 15
<211> LENGTH: 20
<212> TYPE: DNA
<213> ORGANISM: Herpes simplex virus

<400> SEQUENCE: 15
ctctgtggtt aacaccagag 20

<210> SEQ ID NO 16
<211> LENGTH: 20
<212> TYPE: DNA
<213> ORGANISM: Herpes simplex virus

<400> SEQUENCE: 16
gtctgtcttg gatgtatcgc 20

<210> SEQ ID NO 17
<211> LENGTH: 17
<212> TYPE: DNA
<213> ORGANISM: Herpes simplex virus

<400> SEQUENCE: 17
caacgctact gcaaaac 17

<210> SEQ ID NO 18
<211> LENGTH: 16
<212> TYPE: DNA
<213> ORGANISM: Herpes simplex virus

<400> SEQUENCE: 18
gacggggtgc tgtaac 16

<210> SEQ ID NO 19
<211> LENGTH: 17
<212> TYPE: DNA
<213> ORGANISM: Herpes simplex virus

<400> SEQUENCE: 19
cacgaacgac gggagcg 17

<210> SEQ ID NO 20
<211> LENGTH: 17
<212> TYPE: DNA
<213> ORGANISM: Herpes simplex virus

<400> SEQUENCE: 20
cacccaaggt gcttacc 17

<210> SEQ ID NO 21
<211> LENGTH: 17
<212> TYPE: DNA
<213> ORGANISM: Herpes simplex virus

<400> SEQUENCE: 21
cgtgatcgcc tgtctcc 17

<210> SEQ ID NO 22
<211> LENGTH: 17
<212> TYPE: DNA
<213> ORGANISM: Herpes simplex virus

<400> SEQUENCE: 22
cattgccaat cgaaccc 17

<210> SEQ ID NO 23
<211> LENGTH: 20
<212> TYPE: DNA
<213> ORGANISM: Herpes simplex virus

<400> SEQUENCE: 23
ccttgccgtg gtcctgtgga 20

<210> SEQ ID NO 24
<211> LENGTH: 20
<212> TYPE: DNA
<213> ORGANISM: Herpes simplex virus

<400> SEQUENCE: 24
gttggggttt ggggtcgatg 20

<210> SEQ ID NO 25
<211> LENGTH: 11
<212> TYPE: DNA
<213> ORGANISM: Artificial
<220> FEATURE:
<223> OTHER INFORMATION: Synthetic oligonucleotide

<400> SEQUENCE: 25
acgcaccccc a 11

<210> SEQ ID NO 26
<211> LENGTH: 208
<212> TYPE: DNA
<213> ORGANISM: Artificial
<220> FEATURE:
<223> OTHER INFORMATION: Synthetic oligonucleotide

<400> SEQUENCE: 26
taactggctc ccctctcccc cctctcccct ctcccccctc tcccctctcc ccccctctcc 60
cctctccccc cctctcccct ctcccccccct ctcccctctc ccccccctctc ccctctcccc 120 ccctctcccc tctccccccc tctcccctct cccccccctct cccctctccc cccctctccc 180
ctctcccccc ctctcccctc tgctcttt 208

<210> SEQ ID NO 27
<211> LENGTH: 205
<212> TYPE: DNA
<213> ORGANISM: Artificial
<220> FEATURE:
<223> OTHER INFORMATION: Synthetic oligonucleotide

<400> SEQUENCE: 27
ctctgtggtt aacaccagag cctgcccaac ataggccccc cactcccacg cacccccact 60
cccacgcacc cccactccca cgcaccccca ctcccacgca cccccactcc cacgcacccc 120
cactcccacg cacccccact cccacgcacc cccactccca cgcaccccca ctcccacgca 180
tccccgcgat acatccaaca cagac 205

<210> SEQ ID NO 28
<211> LENGTH: 239
<212> TYPE: DNA
<213> ORGANISM: Artificial
<220> FEATURE:
<223> OTHER INFORMATION: Synthetic oligonucleotide

<400> SEQUENCE: 28
cggcgtctgg ccgctcctcc ccccgctcct ccccccgctc ctccccccgc tcctcccccc 60
gctcctcccc ccgctcctcc ccccgctcct ccccccgctc ctccccccgc tcctcccccg 120
ctcctccccc cgctcctccc cccgctcctc cccccgctcc tccccccgct cctcccccg 180 ctcctccccc cgctcctccc cccgctcctc cccccgctcc tccccccgct cccgcggcc 239

<210> SEQ ID NO 29
<211> LENGTH: 581
<212> TYPE: DNA
<213> ORGANISM: Artificial
<220> FEATURE:
<223> OTHER INFORMATION: Synthetic oligonucleotide

<400> SEQUENCE: 29
caccaccgcc ccctccccag ccccagccct ccccagcccc agccctcccc ggccccagcc 60
ctccccggcc ccagccctcc ccggccccag ccctccccgg ccccagccct ccccggcccc 120
agccctcccc ggccccagcc ctccccggcg cgtcccgcgc tccctcgggg gggttcgggc 180
atctctacct cagtgccgcc aatctcaggt cagagatcca aaccctccgg gggcgcccgc 240
gcaccaccac cgcccctcgc cccctcccgc ccctcgcccc ctcccgcccc tcgcccctc 300 ccgcccctcg ccccctcccg cccctcgccc cctcccgccc ctcgcccccct cccgcccctc 360 gcccccctccc gcccctcgcc ccctcccgcc cctcgccccc tcccgcccct cgcccccctcc 420 cgcccctcgc cccctcccgc ccctcgcccc ctcccgcccc tcgcccccctc ccgcccctcg 480 ccccctcccg cccctcgccc cctcccgccc ctcgcccccct cccgcccctc gcccccctccc 540 gcccctcgcc ccctcccgcc cctcgccccc tcccgcccct c 581

<210> SEQ ID NO 30
<211> LENGTH: 115
<212> TYPE: DNA
<213> ORGANISM: Artificial
<220> FEATURE:
<223> OTHER INFORMATION: Synthetic oligonucleotide

<400> SEQUENCE: 30 ctcccccccct gcgcccccgc ctcctccccc ctgcgccccc gcctcctccc ccctgcgccc 60
ccgcctcctc cccctgcgcc cccgcctcct cccccctgcg cccccgcctc ctccc 115

<210> SEQ ID NO 31
<211> LENGTH: 140
<212> TYPE: DNA
<213> ORGANISM: Artificial
<220> FEATURE:
<223> OTHER INFORMATION: Synthetic oligonucleotide

<400> SEQUENCE: 31
ccctcaccca cccacccctc acccacccac ccctcaccca cccacccctc acccacccac 60
ccctcaccca cccacccctc acccacccac ccctcaccca cccacccctc acccacccac 120
ccctcaccca cccacccctc 140

<210> SEQ ID NO 32
<211> LENGTH: 12
<212> TYPE: DNA
<213> ORGANISM: Herpes simplex virus

<400> SEQUENCE: 32
ggagcggggg ga 12

<210> SEQ ID NO 33
<211> LENGTH: 9
<212> TYPE: DNA
<213> ORGANISM: Herpes simplex virus

<400> SEQUENCE: 33 cccccgcga 9

<210> SEQ ID NO 34
<211> LENGTH: 16
<212> TYPE: DNA
<213> ORGANISM: Herpes simplex virus

<400> SEQUENCE: 34
gggggtgcgt gggagt 16

<210> SEQ ID NO 35
<211> LENGTH: 17
<212> TYPE: DNA
<213> ORGANISM: Herpes simplex virus

<400> SEQUENCE: 35
ggggagaggg gagaggg 17

<210> SEQ ID NO 36
<211> LENGTH: 6
<212> TYPE: DNA
<213> ORGANISM: Herpes simplex virus

<400> SEQUENCE: 36 tggggc 6

<210> SEQ ID NO 37
<211> LENGTH: 17
<212> TYPE: DNA
<213> ORGANISM: Herpes simplex virus

<400> SEQUENCE: 37
ctcccctctc cccccct 17

<210> SEQ ID NO 38
<211> LENGTH: 16
<212> TYPE: DNA
<213> ORGANISM: Herpes simplex virus

<400> SEQUENCE: 38
gcacccccac tcccac 16

<210> SEQ ID NO 39
<211> LENGTH: 9
<212> TYPE: DNA
<213> ORGANISM: Herpes simplex virus

<400> SEQUENCE: 39 cgcgggggt 9

<210> SEQ ID NO 40
<211> LENGTH: 12
<212> TYPE: DNA
<213> ORGANISM: Herpes simplex virus

<400> SEQUENCE: 40
ccgctcctcc cc 12

<210> SEQ ID NO 41
<211> LENGTH: 16
<212> TYPE: DNA
<213> ORGANISM: Herpes simplex virus

<400> SEQUENCE: 41
ccctccccgg ccccag 16

<210> SEQ ID NO 42
<211> LENGTH: 17
<212> TYPE: DNA
<213> ORGANISM: Herpes simplex virus

<400> SEQUENCE: 42
ccgcccctcg ccccctc 17

<210> SEQ ID NO 43
<211> LENGTH: 22
<212> TYPE: DNA
<213> ORGANISM: Herpes simplex virus

<400> SEQUENCE: 43
gggcggagga ggggggacgc gg 22

<210> SEQ ID NO 44
<211> LENGTH: 15
<212> TYPE: DNA
<213> ORGANISM: Herpes simplex virus

<400> SEQUENCE: 44
tgggtgggtg gggag 15

<210> SEQ ID NO 45
<211> LENGTH: 22
<212> TYPE: DNA
<213> ORGANISM: Herpes simplex virus

<400> SEQUENCE: 45
ccccctcctc cgcccccgcg tc 22

<210> SEQ ID NO 46
<211> LENGTH: 17
<212> TYPE: DNA
<213> ORGANISM: Herpes simplex virus

<400> SEQUENCE: 46
cgaggggcgg gaggggg 17

<210> SEQ ID NO 47
<211> LENGTH: 16
<212> TYPE: DNA
<213> ORGANISM: Herpes simplex virus

<400> SEQUENCE: 47
gccggggagg gctggg 16

<210> SEQ ID NO 48
<211> LENGTH: 12
<212> TYPE: DNA
<213> ORGANISM: Herpes simplex virus

<400> SEQUENCE: 48
ggagcggggg ga 12

<210> SEQ ID NO 49
<211> LENGTH: 15
<212> TYPE: DNA
<213> ORGANISM: Herpes simplex virus

<400> SEQUENCE: 49
cccgccgccg gggtc 15

<210> SEQ ID NO 50
<211> LENGTH: 19
<212> TYPE: DNA
<213> ORGANISM: Herpes simplex virus

<400> SEQUENCE: 50
cccctccgac cccctgacg 19

<210> SEQ ID NO 51
<211> LENGTH: 15
<212> TYPE: DNA
<213> ORGANISM: Herpes simplex virus

<400> SEQUENCE: 51
ccgcctcctc ctcct 15

<210> SEQ ID NO 52
<211> LENGTH: 21
<212> TYPE: DNA
<213> ORGANISM: Herpes simplex virus

<400> SEQUENCE: 52
cgcgcggcgg ccgggcgggg g 21

<210> SEQ ID NO 53
<211> LENGTH: 15
<212> TYPE: DNA
<213> ORGANISM: Herpes simplex virus

<400> SEQUENCE: 53
ggcaggggcg gctgg 15

<210> SEQ ID NO 54
<211> LENGTH: 9
<212> TYPE: DNA
<213> ORGANISM: Herpes simplex virus

<400> SEQUENCE: 54 cctcccgcc 9

<210> SEQ ID NO 55
<211> LENGTH: 21
<212> TYPE: DNA
<213> ORGANISM: Herpes simplex virus

<400> SEQUENCE: 55
gcgcgccccc gcccggccgc c 21

<210> SEQ ID NO 56
<211> LENGTH: 11
<212> TYPE: DNA
<213> ORGANISM: Herpes simplex virus

<400> SEQUENCE: 56
gcccgacccc c 11

<210> SEQ ID NO 57
<211> LENGTH: 19
<212> TYPE: DNA
<213> ORGANISM: Herpes simplex virus

<400> SEQUENCE: 57
gggggtcgga ggggcgtca 19

<210> SEQ ID NO 58
<211> LENGTH: 15
<212> TYPE: DNA
<213> ORGANISM: Herpes simplex virus

<400> SEQUENCE: 58
ccggcggcgg ggacc 15

<210> SEQ ID NO 59
<211> LENGTH: 15
<212> TYPE: DNA
<213> ORGANISM: Herpes simplex virus

<400> SEQUENCE: 59
cccgcggccg cctcc 15

<210> SEQ ID NO 60
<211> LENGTH: 15
<212> TYPE: DNA
<213> ORGANISM: Herpes simplex virus

<400> SEQUENCE: 60
ccgcccgccc gaccc 15

<210> SEQ ID NO 61
<211> LENGTH: 13
<212> TYPE: DNA
<213> ORGANISM: Herpes simplex virus

<400> SEQUENCE: 61
ccggggggac ggg 13

<210> SEQ ID NO 62
<211> LENGTH: 11
<212> TYPE: DNA
<213> ORGANISM: Herpes simplex virus

<400> SEQUENCE: 62
cccccccgtc g 11

<210> SEQ ID NO 63
<211> LENGTH: 8
<212> TYPE: DNA
<213> ORGANISM: Herpes simplex virus

<400> SEQUENCE: 63 ccccgtcc 8

<210> SEQ ID NO 64
<211> LENGTH: 15
<212> TYPE: DNA
<213> ORGANISM: Herpes simplex virus

<400> SEQUENCE: 64
cgggggtcgg gcggg 15

<210> SEQ ID NO 65
<211> LENGTH: 15
<212> TYPE: DNA
<213> ORGANISM: Herpes simplex virus

<400> SEQUENCE: 65
cgcgggggag gcggc 15

<210> SEQ ID NO 66
<211> LENGTH: 12
<212> TYPE: DNA
<213> ORGANISM: Herpes simplex virus

<400> SEQUENCE: 66
ccgggagccc gc 12

<210> SEQ ID NO 67
<211> LENGTH: 11
<212> TYPE: DNA
<213> ORGANISM: Herpes simplex virus

<400> SEQUENCE: 67
gcgggcggtc c 11

<210> SEQ ID NO 68
<211> LENGTH: 12
<212> TYPE: DNA
<213> ORGANISM: Herpes simplex virus

<400> SEQUENCE: 68
gcccaggccc gc 12

<210> SEQ ID NO 69
<211> LENGTH: 18
<212> TYPE: DNA
<213> ORGANISM: Herpes simplex virus

<400> SEQUENCE: 69
gcccggcgcc caagtccc 18

<210> SEQ ID NO 70
<211> LENGTH: 27
<212> TYPE: DNA
<213> ORGANISM: Herpes simplex virus

<400> SEQUENCE: 70
ccagaagcag agaggggcgg gggctcc 27

<210> SEQ ID NO 71
<211> LENGTH: 60
<212> TYPE: DNA
<213> ORGANISM: Herpes simplex virus

<400> SEQUENCE: 71
ggagaagcac aagacccaca cacgcgcggc aggggcacgg aggcgggggg aggcccggga 60

<210> SEQ ID NO 72
<211> LENGTH: 15
<212> TYPE: DNA
<213> ORGANISM: Herpes simplex virus

<400> SEQUENCE: 72
aggggggcga gggga 15

<210> SEQ ID NO 73
<211> LENGTH: 17
<212> TYPE: DNA
<213> ORGANISM: Herpes simplex virus

<400> SEQUENCE: 73
gggggtgcgg gggcggt 17

<210> SEQ ID NO 74
<211> LENGTH: 9
<212> TYPE: DNA
<213> ORGANISM: Herpes simplex virus

<400> SEQUENCE: 74 gggcagcag 9

<210> SEQ ID NO 75
<211> LENGTH: 20
<212> TYPE: DNA
<213> ORGANISM: Herpes simplex virus

<400> SEQUENCE: 75
cctcccctcc cccgcgcccc 20

<210> SEQ ID NO 76
<211> LENGTH: 15
<212> TYPE: DNA
<213> ORGANISM: Herpes simplex virus

<400> SEQUENCE: 76
ccttcccctc gcccg 15

<210> SEQ ID NO 77
<211> LENGTH: 60
<212> TYPE: DNA
<213> ORGANISM: Herpes simplex virus

<400> SEQUENCE: 77
ctcccgggcc tccccccgcc tccgtgcccc tgccgcgcgt gtgtgggtct cgggcttctc 60

<210> SEQ ID NO 78
<211> LENGTH: 27
<212> TYPE: DNA
<213> ORGANISM: Herpes simplex virus

<400> SEQUENCE: 78
gggagccccc gcccctctct gcttctg 27

<210> SEQ ID NO 79
<211> LENGTH: 11
<212> TYPE: DNA
<213> ORGANISM: Herpes simplex virus

<400> SEQUENCE: 79
gcggaccgcc c 11

<210> SEQ ID NO 80
<211> LENGTH: 12
<212> TYPE: DNA
<213> ORGANISM: Herpes simplex virus

<400> SEQUENCE: 80
gggcgggctc cc 12

<210> SEQ ID NO 81
<211> LENGTH: 11
<212> TYPE: DNA
<213> ORGANISM: Herpes simplex virus

<400> SEQUENCE: 81
ctcccgtccc c 11

<210> SEQ ID NO 82
<211> LENGTH: 26
<212> TYPE: DNA
<213> ORGANISM: Herpes simplex virus

<400> SEQUENCE: 82
ccccgcgcac ccctcgccct cccctc 26

<210> SEQ ID NO 83
<211> LENGTH: 18
<212> TYPE: DNA
<213> ORGANISM: Herpes simplex virus

<400> SEQUENCE: 83
ccacccccgc ccccacca 18

<210> SEQ ID NO 84
<211> LENGTH: 26
<212> TYPE: DNA
<213> ORGANISM: Herpes simplex virus

<400> SEQUENCE: 84
gggcgagggg tgcgcggggg agggga 26

<210> SEQ ID NO 85
<211> LENGTH: 11
<212> TYPE: DNA

<213> ORGANISM: Herpes simplex virus

<400> SEQUENCE: 85
gggaggggga c 11

<210> SEQ ID NO 86
<211> LENGTH: 12
<212> TYPE: DNA
<213> ORGANISM: Herpes simplex virus

<400> SEQUENCE: 86
ccgggagccc gc 12

<210> SEQ ID NO 87
<211> LENGTH: 26
<212> TYPE: DNA
<213> ORGANISM: Pseudo rabies virus

<400> SEQUENCE: 87
cctttccccc aaccccctcg ttcccc 26

<210> SEQ ID NO 88
<211> LENGTH: 21
<212> TYPE: DNA
<213> ORGANISM: Pseudo rabies virus

<400> SEQUENCE: 88
ggggagatgg ggagaggaga t 21

<210> SEQ ID NO 89
<211> LENGTH: 15
<212> TYPE: DNA
<213> ORGANISM: Pseudo rabies virus

<400> SEQUENCE: 89
gggacggagg ggaga 15

<210> SEQ ID NO 90
<211> LENGTH: 10
<212> TYPE: DNA
<213> ORGANISM: Pseudo rabies virus

<400> SEQUENCE: 90
ccccaagtcc 10

<210> SEQ ID NO 91
<211> LENGTH: 11
<212> TYPE: DNA
<213> ORGANISM: Pseudo rabies virus

<400> SEQUENCE: 91
gggacggcgg g 11

<210> SEQ ID NO 92
<211> LENGTH: 15
<212> TYPE: DNA
<213> ORGANISM: Pseudo rabies virus

<400> SEQUENCE: 92
cgccctctct cccac 15

<210> SEQ ID NO 93
<211> LENGTH: 11

<212> TYPE: DNA
<213> ORGANISM: Pseudo rabies virus

<400> SEQUENCE: 93
aaggggtctc t 11

<210> SEQ ID NO 94
<211> LENGTH: 12
<212> TYPE: DNA
<213> ORGANISM: Pseudo rabies virus

<400> SEQUENCE: 94
tgggggagag ga 12

<210> SEQ ID NO 95
<211> LENGTH: 11
<212> TYPE: DNA
<213> ORGANISM: Pseudo rabies virus

<400> SEQUENCE: 95
ggggggagtc t 11

<210> SEQ ID NO 96
<211> LENGTH: 22
<212> TYPE: DNA
<213> ORGANISM: Pseudo rabies virus

<400> SEQUENCE: 96
gcataacccc tccccctaat ct 22

<210> SEQ ID NO 97
<211> LENGTH: 19
<212> TYPE: DNA
<213> ORGANISM: Pseudo rabies virus

<400> SEQUENCE: 97
tgtggtggtc tctgtgttg 19

<210> SEQ ID NO 98
<211> LENGTH: 35
<212> TYPE: DNA
<213> ORGANISM: Pseudo rabies virus

<400> SEQUENCE: 98
ggggtggaga cggtggaggg agaggggagt gggat 35

<210> SEQ ID NO 99
<211> LENGTH: 10
<212> TYPE: DNA
<213> ORGANISM: Pseudo rabies virus

<400> SEQUENCE: 99
gggggagtcc 10

<210> SEQ ID NO 100
<211> LENGTH: 10
<212> TYPE: DNA
<213> ORGANISM: Pseudo rabies virus

<400> SEQUENCE: 100
ggactccccc 10

<210> SEQ ID NO 101

-continued

<211> LENGTH: 35
<212> TYPE: DNA
<213> ORGANISM: Pseudo rabies virus

<400> SEQUENCE: 101
ctctccctcc accgtctcca ccccatccca ctccc 35

<210> SEQ ID NO 102
<211> LENGTH: 19
<212> TYPE: DNA
<213> ORGANISM: Pseudo rabies virus

<400> SEQUENCE: 102
accaccacac aacacagag 19

<210> SEQ ID NO 103
<211> LENGTH: 22
<212> TYPE: DNA
<213> ORGANISM: Pseudo rabies virus

<400> SEQUENCE: 103
gggggagggg ttatgcagat ta 22

<210> SEQ ID NO 104
<211> LENGTH: 15
<212> TYPE: DNA
<213> ORGANISM: Varicella virus

<400> SEQUENCE: 104
gagggagagg cggag 15

<210> SEQ ID NO 105
<211> LENGTH: 42
<212> TYPE: DNA
<213> ORGANISM: Varicella virus

<400> SEQUENCE: 105
gcgggatcgg gctttcggga agcggccgag gtgggcgcga cg 42

<210> SEQ ID NO 106
<211> LENGTH: 9
<212> TYPE: DNA
<213> ORGANISM: Varicella virus

<400> SEQUENCE: 106 gcccgcgca 9

<210> SEQ ID NO 107
<211> LENGTH: 27
<212> TYPE: DNA
<213> ORGANISM: Varicella virus

<400> SEQUENCE: 107
ccccgccgat ggggaggggg cgcggta 27

<210> SEQ ID NO 108
<211> LENGTH: 27
<212> TYPE: DNA
<213> ORGANISM: Varicella virus

<400> SEQUENCE: 108
catcggcggg gtaccgcgcc ccctccc 27

<210> SEQ ID NO 109
<211> LENGTH: 152261
<212> TYPE: DNA
<213> ORGANISM: Human herpes virus strain 1

<400> SEQUENCE: 109
agcccgggcc ccccgcgggc gcgcgcgcgc gcaaaaaagg cgggcggcgg tccgggcggc 60
gtgcgcgcgc gcggcgggcg tggggggcgg ggccgcggga gcgggggggag gagcgggggg 120 aggagcgggg ggaggagcgg ggggaggagc ggggggagga gcggggggag gagcgggggg 180
aggagcgggg ggaggagcgg ggggaggagc ggggggagga gcggggggag gagcgggggg 240
aggagcgggg ggaggagcgg ggggaggagc ggggggagga gcggggggag gagcgggggg 300
aggagcgggg ggaggagcgg ccagacgccg aaaacgggcc ccccccaaaa cacacccccc 360
gggggtcgcg cgcggccctt taaagcggtg gcggcgggca gcccgggccc cccgcggccg 420
agactagcga gttagacagg caagcactac tcgcctctgc acgcacatgc ttgcctgtca 480
aactctacca ccccggcacg ctctctgtct ccatggcccg ccgccgccgc catcgcggcc 540
cccgccgccc ccggccgccc gggcccacgg gcgccgtccc aaccgcacag tcccaggtaa 600
cctccacgcc caactcggaa cccgcggtca ggagcgcgcc cgcggccgcc ccgccgccgc 660
cccccgccgg tgggccccg ccttcttgtt cgctgctgct gcgccagtgg ctccacgttc 720
ccgagtccgc gtccgacgac gacgatgacg acgactggcc ggacagcccc ccgcccgagc 780
cggcgccaga ggcccggccc accgccgccg ccccccggcc ccggccccca ccgcccggcg 840
tgggcccggg gggcggggct gacccctccc accccccctc gcgccccttc cgccttccgc 900
cgcgcctcgc cctccgcctg cgcgtcaccg cggagcacct ggcgcgcctg cgcctgcgac 960
gcgcgggcgg ggaggggggcg ccggagcccc ccgcgacccc cgcgaccccc gcgacccccg 1020
cgacccccgc gacccccgcg cgggtgcgct tctcgcccca cgtccgggtg cgccacctgg 1080
tggtctgggc ctcggccgcc cgcctggcgc gccgcggctc gtgggcccgc gagcgggccg 1140
accgggctcg gttccggcgc cgggtggcgg aggccgaggc ggtcatcggg ccgtgcctgg 1200
ggcccgaggc ccgtgcccgg gccctggccc gcggagccgg cccggcgaac tcggtctaac 1260
gttacacccg aggcggcctg ggtcttccgc ggagctcccg ggagctccgc accaagccgc 1320
tctccggaga gacgatggca ggagccgcgc atatatacgc ttggagccag cccgccctca 1380
cagggcgggc cgcctcgggg gcgggactgg ccaatcggcg gccgccagcg cggcggggcc 1440
cggccaacca gcgtccgccg agtcttcggg gcccggccca ttgggcggga gttaccgccc 1500
aatgggccgg gccgcccact tcccggtatg gtaattaaaa acttgcaaga ggccttgttc 1560
cgcttcccgg tatggtaatt agaaactcat taatgggcgg ccccggccgc ccttcccgct 1620
tccggcaatt cccgcggccc ttaatgggca accccggtat tccccgcctc ccgcgccgcg 1680
cgtaaccact cccctggggt tccgggttat gctaattgct tttttggcgg aacacacggc 1740
ccctcgcgca ttggcccgcg ggtcgctcaa tgaacccgca ttggtcccct ggggttccgg 1800
gtatggtaat gagtttcttc gggaaggcgg gaagccccgg ggcaccgacg caggccaagc 1860
ccctgttgcg tcggcgggag gggcatgcta atggggttct ttgggggaca ccgggttggg 1920
cccccaaatc gggggccggg ccgtgcatgc taatgatatt ctttgggggc gccgggttgg 1980
tccccgggga cggggccgcc ccgcggtggg cctgcctccc ctgggacgcg cggccattgg 2040
gggaatcgtc actgccgccc ctttggggag gggaaaggcg tggggtataa gttagccctg 2100
gcccgacagt ctggtcgcat ttgcacctcg gcactcggag cgagacgcag cagccaggca 2160

-continued

```
gactcgggcc gccccctctc cgcatcacca cagaagcccc gcctacgttg cgacccccag   2220
ggaccctccg tccgcgaccc tccagccgca tacgaccccc atggagcccc gccccggagc   2280
gagtacccgc cggcctgagg gccgccccca gcgcgaggtg aggggccggg cgccatgtct   2340
ggggcgccat attggggggc gccatattgg ggggcgccat gttgggggac ccccgaccct   2400
tacactggaa ccggccgcca tgttggggga cccccactca tacacgggag ccgggcgcca   2460
tgttggggcg ccatgttagg gggcgtggaa ccccgtgaca ctatatatac agggaccggg   2520
ggcgccatgt tagggggtgc ggaaccccct gaccctatat atacagggac cggggtcgcc   2580
ctgttggggg tcgccatgtg accccctgac tttatatata cagaccccca acacatacac   2640
atggcccctt tgactcagac gcagggcccg gggtcgccgt gggacccccct gactcataca   2700
cagagacacg cccccacaac aaacacacaa ggaccggggt cgccgtgttg ggggcgtggt   2760
ccccactgac tcatacgcag gccccccctta ctcacacgca tctagggggg tggggaggag   2820
ccgcccgcca tatttggggg acgccgtggg acccccgact ccggtgcgtc tggagggcgg   2880
gagaagaggg aagaagaggg gtcgggatcc aaaggacgga cccagaccac ctttggttgc   2940
agacccctttt ctccccctc ttccgaggcc agcagggggg caggactttg tgaggcgggg   3000
gggggagagg gggaactcgt gggtgctgat tgacgcggga aatcccccccc cattcttacc   3060
cgcccccctt ttttcccctt agcccgcccc ggatgtctgg gtgtttccct gcgaccgaga   3120
cctgccggac agcagcgact ctgaggcgga gaccgaagtg ggggggcggg gggacgccga   3180
ccaccatgac gacgactccg cctccgaggc ggacagcacg gacacggaac tgttcgagac   3240
ggggctgctg gggccgcagg gcgtggatgg gggggcggtc tcgggggggga gccccccccg   3300
cgaggaagac cccggcagtt gcgggggcgc ccccccctcga gaggacgggg ggagcgacga   3360
gggcgacgtg tgcgccgtgt gcacggatga gatcgcgccc cacctgcgct gcgacacctt   3420
cccgtgcatg caccgcttct gcatcccgtg catgaaaacc tggatgcaat tgcgcaacac   3480
ctgcccgctg tgcaacgcca agctggtgta cctgatagtg ggcgtgacgc ccagcgggtc   3540
gttcagcacc atcccgatcg tgaacgaccc ccagacccgc atggaggccg aggaggccgt   3600
cagggcgggc acggccgtgg actttatctg gacgggcaat cagcggttcg ccccgcggta   3660
cctgaccctg ggggggcaca cggtgagggc cctgtcgccc acccacccgg agcccaccac   3720
ggacgaggat gacgacgacc tggacgacgg tgaggcgggg ggcggcaagg accctggggg   3780
aggaggagga ggagggggggg ggagggagga ataggcgggc gggcgaggaa agggcgggcc   3840
ggggaggggg cgtaacctga tcgcgccccc cgttgtctct tgcagcagac tacgtaccgc   3900
ccgccccccg ccggacgccc cgcgcccccc cacgcagagg cgccgccgcg ccccccgtga   3960
cgggcggggc gtctcacgca gccccccagc cggccgcggc tcggacagcg ccccccctcgg   4020
cgcccatcgg gccacacggc agcagtaaca ccaacaccac caccaacagc agcggcggcg   4080
gcggctcccg ccagtcgcga gccgcggcgc cgcgggggggc gtctggcccc tccgggggggg   4140
ttggggttgg ggttggggtt gttgaagcgg aggcggggcg gccgaggggc cggacgggcc   4200
cccttgtcaa cagacccgcc cccccttgcaa acaacagaga ccccatagtg atcagcgact   4260
cccccccggc ctctccccac aggcccccccg cggcgcccat gccaggctcc gcccccccgcc   4320
ccgggccccc cgcgtccgcg gccgcgtcgg gacccgcgcg cccccgcgcg gccgtggccc   4380
cgtgcgtgcg agcgccgcct ccggggcccg gcccccgcgc cccggccccc ggggcggagc   4440
cggccgcccg ccccgcggac gcgcgccgtg tgccccagtc gcactcgtcc ctggctcagg   4500
ccgcgaacca agaacagagt ctgtgccggg cgcgtgcgac ggtggcgcgc ggctcggggg   4560
```

-continued

```
ggccgggcgt ggagggtggg cacgggccct cccgcggcgc cgccccctcc ggcgccgccc   4620
cgctcccctc cgccgcctct gtcgagcagg aggcggcggt gcgtccgagg aagaggcgcg   4680
ggtcgggcca ggaaaacccc tccccccagt ccacgcgtcc ccccctcgcg ccggcagggg   4740
ccaagagggc ggcgacgcac cccccctccg actcagggcc gggggggcgc ggccagggtg   4800
ggcccgggac ccccctgacg tcctcggcgg cctccgcctc ttcctcctct gcctcttcct   4860
cctcggcccc gacccccgcg ggggccgcct cttccgccgc cggggccgcg tcctcctccg   4920
cttccgcctc ctcgggcggg gccgtcggtg ccctgggagg gagacaagag gaaacctccc   4980
tcggcccccg cgctgcttct gggccgcggg ggccgaggaa gtgtgcccgg aagacgcgcc   5040
acgcggagac ttccggggcc gtccccgcgg gcggcctcac gcgctacctg cccatctcgg   5100
gggtctctag cgtggtcgcc ctgtcgcctt acgtgaacaa gactatcacg ggggactgcc   5160
tgcccatcct ggacatggag acggggaaca tcggggcgta cgtggtcctg gtggaccaga   5220
cgggaaacat ggcgacccgg ctgcgggccg cggtccccgg ctggagccgc cgcaccctgc   5280
tccccgagac cgcgggtaac cacgtgatgc cccccgagta cccgacggcc cccgcgtcgg   5340
agtggaacag cctctggatg acccccgtgg ggaacatgct gttcgaccag ggcaccctag   5400
tgggcgccct ggacttccgc agcctgcggt ctcggcaccc gtggtccggg gagcaggggg   5460
cgtcgacccg ggacgaggga aaacaataag ggacgccccc cgtgtttgtg gggagggggg   5520
ggtcgggcgc tgggtggtct ctggccgcgc ccactacacc agccaatccg tgtcggggag   5580
gggaaaagtg aaagacacgg gcaccacaca ccagcgggtc ttttgtgttg gccctaataa   5640
aaaaaaactc aggggatttt tgctgtctgt tgggaaataa aggtttactt ttgtatcttt   5700
tccctgtctg tgttggatgt atcgcgggga tgcgtgggag tgggggtgcg tgggagtggg   5760
ggtgcgtggg agtgggggtg cgtgggagtg ggggtgcgtg ggagtggggg tgcgtgggag   5820
tgggggtgcg tgggagtggg ggtgcgtggg agtgggggtg cgtgggagtg ggggtgccat   5880
gttgggcagg ctctggtgtt aaccacagag ccgcggcccg ggctgcctga ccaccgatcc   5940
ccgaaagcat cctgccactg gcatggagcc agaaccacag tgggttgggt gtgggtgtta   6000
agtttccgcg agcgcctgcc cgcccggact gacctggcct ctggccgcca caaagggcgg   6060
ggggggttaa ctacactata gggcaacaaa ggatgggagg ggtggcgggg cgggacgggg   6120
cgcccaaaag gggtcggcc acaccacaga cgtgggtgtt ggggggtggg gcggaggggt   6180
gggggggggg gagacagaaa caggaacata gttagaaaac aagaatgcgg tgcagccaga   6240
gaatcacagg agacgagggg atgggcgtgt tggttaccaa cccacaccca ggcatgctcg   6300
gtggtatgaa ggaggggggg cggtgcttct tagagaccgc cgggggacgt ggggttggtg   6360
tgcaaaggca cgcgcacccg cgcggccagg tgggccggta ctccatcccc ccctcccccg   6420
acccttccca cccccgcgtg ccagagatca ccccggtccc ccggcacccg ccactcctcc   6480
gtatcctcgc tttaggaaca actttagggg gggtacacac gcgccgtgca tttccttcca   6540
caccccccct cccccgcact cccccccccc aggcagtaag acccaagcat agagagccag   6600
gcacaaaaac acaggcgggg tgggacacat gccttcttgg agtacgtggg tcattggcgt   6660
ggggggttac agcgacaccg gccgaccccc tggcggtctt ccagccggcc cttagataag   6720
ggggcagttg gtggtcggac gggtaagtaa cagagtctga ctaagggtgg gaggggggga   6780
aaagaacggg ctggtgtgct gtaacacgag cccacccgcg agtggcgtgg ccgaccttag   6840
cctctggggc gccccctgtc gtttgggtcc ccccctcta ttggggagaa gcaggtgtct   6900
```

-continued

```
aacctacctg gaaacgcggc gtctttgttg aacgacaccg gggcgccctc gacgagtggg   6960
ataacggggg aggaagggag ggaggagggt actgggggtg aagaaggggg gggggagaag   7020
cgagaacagg aaaggcgatg gagcccggca gaacaccgag gaaaaaaaaa ccacagcgca   7080
tgcgccgggc cgttgtgggg ccccgggccg gggcccettg ggtccgccgg ggccccgggc   7140
cgggccgcca cgggggccgg ccgttggcgg taaccccgag tgttcatctc aggccccggg   7200
ccgggaaccc ggaaaagcct ccggggggcc tttttcgcgt cgcgtgccgg cgagcgggtc   7260
cggacggggc ccggaccgcc gcggtcgggg gcccctcgtc ccgggccgta cgcggccttc   7320
gccccgtgag gggacagacg aacgaaacat tccggcgacg gaacgaaaaa caccccagac   7380
gggttaaaga aacagaaacc gcaaccccca ccacccccga aacggggaaa acgaaaaaac   7440
agaccagcgg ccggccggcg cttaggggga ggatgtcgcc gacgcccctt ggccgccccg   7500
gctgcagggg ggcccggaga gccgcggcac ccggacgcgc ccggaaagtc tttcgcacca   7560
cccgcgatcg gcacggccgc gcccccgctt ttataaaggc tgagatgacg cagcaaaaac   7620
aggccacagc accacgtggg taggtgatgt aattttattt tcctcgtctg cggcctaatg   7680
gatttccggg cgcggtgccc ctgtctgcag agcacttaac ggattgatat ctcgcgggca   7740
cgcgcgccct taatggaccg gcgcggggcg gggggccgga tacccacacg ggcggggggg   7800
gggtgtcgcg ggccgtctgc tggcccgcgg ccacataaac aatgactctg ggcctttctg   7860
cctctgccgc ttgtgagtgc gcgcgccggc tctgcggtgt cggcggcggc tgcggcggct   7920
gcggcggccg ccgtgttcgg tctcggtagc cggccggcgg gtggactcgc ggggggccgg   7980
agggtggaag gcaggggggt gtaggatggg tatcaggact tccacttccc gtccttccat   8040
cccccgttcc cctcggttgt tcctcgcctc ccccaacacc ccgccgcttt ccgttggggt   8100
tgttattgtt gtcgggatcg tgcgggccgg gggtcgccgg ggcaggggcg ggggcgtggg   8160
cgggggtgct cgtcgatcga ccgggctcag tgggggcgtg gggtgggtgg gagaaggcga   8220
ggagactggg gtgggggtgt cggtgggtgg ttgtttttttg tggttgtttt tgtgtctgtt   8280
cccgtccccc gtcaccccct ccctccgtcc cctccgtccc cccgtcgcgg gtgtttgtgt   8340
ttgtttattc cgacattggt ttatttaaat aaacacagcc gttctgcgtg tctgttcttg   8400
cgtgtggctg ggggcttata tgtggggtcc cgggggcggg atggggttta gcggcggggg   8460
gcggcgcgcc ggacggggcg ctggagataa cggcccccgg ggaacggggg accggggctg   8520
ggtatcccga ggtgggtggg tgggcggcgg tggccgggcc gggccgggcc gggccgggcc   8580
gggtgggcgg ggtttggaaa aacgaggagg aggaggagaa ggcggggggg ggggagacgg   8640
ggggaaagca aggacacggc ccggggggtg ggagcgcggg ccgggccgct cgtaagagcc   8700
gcgacccggc cgccggggag cgttgtcgcc gtcggtctgc cggccccccgt ccctcccttt   8760
tttgaccaac cagcgccccc ccccccccctc accaccattc ctactaccac caccaccacc   8820
accaccgaca cctcccgcgc acccccgccc acatcccccc ccaacccgca ccaccagcac   8880
gggttggggg tagcagggga tcaaaggggg gcaaagcggc ggggcggttc gggggggggg   8940
gggggggcg ggaaaccaag taggcccgcc catccgcggc ccctcccggc agccacgccc   9000
ccagcgtcgg gtgtcacggg gaaagagcag aggggagagg ggagaggggg ggagagggga   9060
gaggggggga gaggggagag ggggggagag gggagagggg gggagagggg agaggggggg   9120
agaggggaga gggggggaga ggggagaggg gggagagggg gagagggggg gagaggggag   9180
agggggggag aggggagagg gggggagagg gggtatataa accaacgaaa agcgcgggaa   9240
cggggatacg gggcttgtgt ggcacgacgt cgtggttgtg ttactgggca aacacttggg   9300
```

-continued

```
gactgtaggt ttctgtgggt gccgacccta ggcgctatgg ggattttggg ttgggtcggg   9360
cttattgccg ttggggtttt gtgtgtgcgg gggggcttgc cttcaaccga atatgttatt   9420
cggagtcggg tggctcgaga ggtgggggat atattaaagg tgccttgtgt gccgctcccg   9480
tctgacgatc ttgattggcg ttacgagacc ccctcggcta taaactatgc tttgatagac   9540
ggtatatttt tgcgttatca ctgtcccgga ttggacacgg tcttgtggga taggcatgcc   9600
cagaaggcat attgggttaa ccccttttta tttgtggcgg gtttttttgga ggacttgagt   9660
taccccgcgt ttcctgccaa cacccaggaa acagaaacgc gcttggccct ttataaagag   9720
atacgccagg cgctggacag tcgcaagcag gccgccagcc acacacctgt gaaggctggg   9780
tgtgtgaact ttgactattc gcgcacccgc cgctgtgtag ggcgacagga tttgggacct   9840
accaacggaa cgtctggacg gaccccggtt ctgccgccgg acgatgaagc gggcctgcag   9900
ccgaagcccc tcaccacgcc gccgcccatc atcgccacgt cggaccccac cccgcgacgg   9960
gacgccgcca caaaaagcag acgccgacga ccccactccc ggcgcctcta acgatgcctc  10020
gacggaaacc cgtccgggtt cggggggcga accggccgcc tgtcgctcgt cagggccggc  10080
ggcgctcctc gccgccctag aggctggtcc cgctggtgtg acgttttcct cgtccgcgcc  10140
ccccgaccct cccatggatt taacaaacgg gggggtgtcg cctgcggcga cctcggcgcc  10200
tctggactgg accacgtttc ggcgtgtgtt tctgatcgac gacgcgtggc ggcccctgat  10260
ggagcctgag ctggcgaacc ccttaaccgc ccacctcctg gccgaatata atcgtcggtg  10320
ccagaccgaa gaggtgctgc cgccgcggga ggatgtgttt tcgtggactc gttattgcac  10380
ccccgacgag gtgcgcgtgg ttatcatcgg ccaggaccca tatcaccacc ccggccaggc  10440
gcacggactt gcgtttagcg tgcgcgcgaa cgtgccgcct cccccgagtc ttcggaatgt  10500
cttggcggcc gtcaagaact gttatcccga ggcacggatg agcggccacg gttgcctgga  10560
aaagtgggcg cgggacggcg tcctgttact aaacacgacc ctgaccgtca agcgcggggc  10620
ggcggcgtcc cactctagaa tcggttggga ccgtttcgtg ggcggagtta tccgccggtt  10680
ggccgcgcgc cgccccggcc tggtgtttat gctctggggc acacacgccc agaatgccat  10740
caggccggac cctcgggtcc attgcgtcct caagttttcg cacccgtcgc ccctctccaa  10800
ggttccgttc ggaacctgcc agcatttcct cgtggcgaac cgatacctcg agacccggtc  10860
gatttcaccc atcgactggt cggtttgaaa ggcatcgacg tccggggttt ttgtcggtgg  10920
gggcttttgg gtatttccga tgaataaaga cggttaatgg ttaaacctct ggtctcatac  10980
gggtcggtga tgtcgggcgt cgggggagag ggagttccct ctgcgcttgc gattctagcc  11040
tcgtggggct ggacgttcga cacgccaaac cacgagtcgg ggatatcgcc agatacgact  11100
cccgcagatt ccattcgggg tgccgctgtg gcctcacctg accaaccttt acacgggggc  11160
ccggaacggg aggccacagc gccgtctttc tccccaacgc gcgcggatga cggcccgccc  11220
tgtaccgacg ggccctacgt gacgtttgat accctgttta tggtgtcgtc gatcgacgaa  11280
ttagggcgtc gccagctcac ggacaccatc cgcaaggacc tgcggttgtc gctggccaag  11340
tttagcattg cgtgcaccaa gacctcctcg ttttcgggaa acgccccgcg ccaccacaga  11400
cgcggggcgt tccagcgcgg cacgcgggcg ccgcgcagca acaaaagcct ccagatgttt  11460
gtgttgtgca aacgcgccca cgccgctcga gtgcgagagc agcttcgggt cgttattcag  11520
tcccgcaagc cgcgcaagta ttacacgcga tcttcggacg ggcggctctg ccccgccgtc  11580
cccgtgttcg tccacgagtt cgtctcgtcc gagccaatgc gcctccaccg agataacgtc  11640
```

-continued

```
atgctggcct cgggggccga gtaaccgccc cccccccatg ccaccctcac tgcccgtcgc  11700
gcgtgtttga tgttaataaa taacacataa atttggctgg ttgtttgttg tctttaatgg  11760
accgcccgca aggggggggg ggcatttcag tgtcgggtga cgagcgcgat ccggccggga  11820
tcctaggacc ccaaaagttt gtctgcgtat tccagggcgg ggctcagttg aatctcccgc  11880
agcacctcta ccagcaggtc cgcggtgggc tggagaaact cggccgtccc ggggcaggcg  11940
gttgtcgggg gtggaggcgc ggcgcccacc ccgtgtgccg cgcctggcgt ctcctctggg  12000
ggcgacccgt aaatggttgc agtgatgtaa atggtgtccg cggtccagac cacggtcaaa  12060
atgccggccg tggcgctccg ggcgctttcg ccgcgcgagg agctgaccca ggagtcgaac  12120
ggatacgcgt acatatgggc gtcccacccg cgttcgagct tctggttgct gtcccggcct  12180
ataaagcggt aggcacaaaa ttcggcgcga cagtcgataa tcaccaacag cccaatgggg  12240
gtgtgctgga taacaacgcc tccgcgcggc aggcggtcct ggcgctcccg gccccgtacc  12300
atgatcgcgc gggtgccgta ctcaaaaaca tgcaccacct gcgcggcgtc gggcagtgcg  12360
ctggtcagcg aggccctggc gtggcatagg ctatacgcga tggtcgtctg tggattggac  12420
atctcgcggt gggtagtgag tcccccgggc cgggttcggt ggaactgtaa ggggacggcg  12480
ggttaataga caatgaccac gttcggatcg cgcagagccg atagtatgtg ctcactaatg  12540
acgtcatcgc gctcgtggcg ctcccggagc ggatttaagt tcatgcgaag gaattcggag  12600
gaggtggtgc gggacatggc cacgtacgcg ctgttgaggc gcaggttgcc gggcgtaaag  12660
cagatggcga ccttgtccag gctaaggccc tgggagcgcg tgatggtcat ggcaagcttg  12720
gagctgatgc cgtagtcggc gtttatggcc atggccagct ccgtagagtc aatggactcg  12780
acaaactcgc tgatgttggt gttgacgacg gacatgaagc cgtgttggtc ccgcaagacc  12840
acgtaaggca ggggggcctc ttccagtaac tcggccacgt tggccgtcgc gtgccgcctc  12900
cgcagctcgt ccgcaaaggc aaacacccgt gcgtacgtgt atcccatgag cgtataattg  12960
tccgtctgca gggcgacgga catcagcccc ccgcgcggcg agccggtcag catctcgcag  13020
ccccggaaga taacgttgtc cacgtacgtg ctaaaggggg cgacttcaaa tgcctccccg  13080
aagagctctt ggaggattcg gaatctcccg aggaaggccc gcttcagcag cgcaaactgg  13140
gtgtgaacgg cggcggtggt ctccggttcc ccgggggtgt agtggcagta aaacacgtcg  13200
agctgttgtt cgtccagccc cgcgaaaata acgtcgaggt cgtcgtcggg aaaatcgtcc  13260
gggcccccgt cccgcggccc cagttgctta aaatcaaacg cacgctcgcc gggggcgcct  13320
gcgtcggcca ttaccgacgc ctgcgtcggc acccccgaag atttggggcg cagagacaga  13380
atctccgccg ttagttctcc catgcgggcg taggcgaggg tcctctgggt cgcatccagg  13440
cccgggcgct gcagaaagtt gtaaaaggag ataagcccgc taaatatgag ccgcgacagg  13500
aacctgtagg caaactccac cgaagtctcc ccctgagtct ttacaaagct gtcgtcacgc  13560
aacactgcct cgaaggcccg gaacgtccca ctaaacccaa aaaccagttt tcgcaggcgc  13620
gcggtcaccg cgatctggct gttgaggacg taagtgacgt cgttgcgggc cacgaccagc  13680
tgctgtttgc tgtgcacctc gcagcgcatg tgccccgcgt cctggtcctg gctctgcgag  13740
tagttggtga tgcggctggc gttggccgtg agccactttt caatcgtcag gccgggctgg  13800
tgtgtcagcc gtcggtattc gtcaaactcc ttgaccgaca cgaacgtaag cacggggagg  13860
gtgaacacga cgaactcccc ctcacgggtc accttcaggt aggcgtggag cttggccatg  13920
tacgcgctca cctctttgtg ggaggagaac agccgcgtcc agccggggag gttggcgggg  13980
ttggtgatgt agttttccgg gacgacgaag cgatccacga actgcatgtg ctcctcggtg  14040
```

atgggcaggc cgtactccag caccttcatg aggttaccga actcgtgctc gacgcaccgt 14100
ttgttgttaa taaaaatggc ccagctatac gagaggcggg cgtactcgcg cagcgtgcgg 14160
ttgcagatga ggtacgtgag cacgttctcg ctctggcgga cggaacaccg cagtttctgg 14220
tgctcgaagg tcgactccag ggacgccgtc tgcgtcggcg agcccacaca caccaacacg 14280
ggccgcaggc gggccgcgta ctgggggggtg tggtacaggg cgttaatcat ccaccagcaa 14340
tacaccacgg ccgtgaggag gtgacgccca aggagcccgg cctcgtcgat gacgatcacg 14400
ttgctgcggg taaaggccgg cagcgccccg tgggtggccg gggccaaccg cgtcagggcg 14460
ccctcggcca accccagggt ccgttccagg gcggccaggg cgcgaaactc gttccgcaac 14520
tcctcgcccc cggaggcggc cagggcgcgc ttcgtgaggt ccaaaatcac ctcccagtag 14580
tacgtcagat ctcgtcgctg caggtcctcc agcgaggcgg ggttgctggt cagggtgtac 14640
gggtactgtc ccagttgggc ctggacgtga ttcccgcgaa acccaaattc atgaaagatg 14700
gtgttgatgg gtcggctgag aaaggcgccc gagagtttgg cgtacatgtt ttgggccgca 14760
atgcgcgtgg cgcccgtcac cacacagtcc aagacctcgt tgattgtctg cacgcacgtg 14820
ctctttccgg agccagcgtt gccggtgata agatacaccg cgaacggaaa ctccctgagg 14880
ggcaggcctg cgggggactc taaggccgcc acgtcccgga accactgcag atggggcact 14940
tgcgctccgt cgagctgttg ttgcgagagc tctcggatgc gcttaaggat tggctgcacc 15000
ccgtgcatag acgtaaaatt taaaaaggcc tcggccctcc ctggaacggc tggtcggtcc 15060
ccgggttgct gaaggtgcgg cgggccgggt ttctgtccgt ctagctggcg ctccccgccg 15120
gccgccgcca tgaccgcacc acgctcgcgg gcccccacta cgcgtgcgcg gggggacacg 15180
gaagcgctgt gctcccccga ggacggctgg gtaaaggttc accccagccc cggtacgatg 15240
ctgttccgcg agattctcca cgggcagctg gggtataccg agggccaggg ggtgtacaac 15300
gtcgtccggt ccagcgaggc gaccacccgg cagctgcagg cggcgatctt tcacgcgctc 15360
ctcaacgcca ccacttaccg ggacctcgag gcggactggc tcggccacgt ggcggcccgc 15420
ggtctgcagc cccaacggct ggttcgccgg tacaggaacg cccgggaggc ggatatcgcc 15480
ggggtggccg agcgggtgtt cgacacgtgg cggaacacgc ttaggacgac gctgctggac 15540
tttgcccacg ggttggtcgc ctgctttgcg ccgggcggcc cgagcggccc gtcaagcttc 15600
cccaaatata tcgactggct gacgtgcctg gggctggtcc ccatattacg caagcgacaa 15660
gaagggggtg tgacgcaggg tctgagggcg tttctcaagc agcacccgct gacccgccag 15720
ctggccacgg tcgcggaggc cgcggagcgc gccggccccg ggtttttttga gctggcgctg 15780
gccttcgact ccacgcgcgt ggcggactac gaccgcgtgt atatctacta caaccaccgc 15840
cggggcgact ggctcgtgcg agaccccatc agcgggcagc gcggagaatg tctggtgctg 15900
tggcccccct tgtggaccgg ggaccgtctg gtcttcgatt cgcccgtcca gcggctgttt 15960
cccgagatcg tcgcgtgtca ctccctccgg gaacacgcgc acgtctgccg gctgcgcaat 16020
accgcgtccg tcaaggtgct gctggggcgc aagagcgaca gcgagcgcgg ggtggccggt 16080
gccgcgcggg tcgttaacaa ggtgttgggg gaggacgacg agaccaaggc cgggtcggcc 16140
gcctcgcgcc tcgtgcggct tatcatcaac atgaagggca tgcgccacgt aggcgacatt 16200
aacgacaccg tgcgttccta cctcgacgag gccgggggggc acctgataga cgccccggcc 16260
gtcgacggta ccctccctgg attcggcaag ggcggaaaca gccgcgggtc tgcgggccag 16320
gaccaggggg ggcgggcgcc gcagcttcgc caggccttcc gcacggccgt ggttaacaac 16380

-continued

```
atcaacggcg tgttggaggg ctatataaat aacctgtttg gaaccatcga gcgcctgcgc  16440
gagaccaacg cgggcctggc gacccaattg caggagcgcg accgcgagct ccggcgcgca  16500
acagcggggg ccctggagcg ccagcagcgc gcggccgacc tggcggccga gtccgtgacc  16560
ggtggatgcg gcagccgccc tgcgggggcg gacctgctcc gggccgacta tgacattatc  16620
gacgtcagca agtccatgga cgacgacacg tacgtcgcca acagctttca gcacccgtac  16680
atcccttcgt acgcccagga cctggagcgc ctgtcgcgcc tctgggagca cgagctggtg  16740
cgctgtttta aaattctgtg tcaccgcaac aaccagggcc aagagacgtc gatctcgtac  16800
tccagcgggg cgatcgccgc attcgtcgcc ccctactttg agtcagtgct tcgggccccc  16860
cgggtaggcg cgcccatcac gggctccgat gtcatcctgg gggaggagga gttatgggat  16920
gcggtgttta agaaaacccg cctgcaaacg tacctgacag acatcgcggc cctgttcgtc  16980
gcggacgtcc agcacgcagc gctgccccccg cccccctccc cggtcggcgc cgatttccgg  17040
cccggcgcgt ccccgcgggg ccggtccaga tcgcggtcgc ccggaagaac tgcgcgaggc  17100
gcgccggacc agggcggggg catcgggcac cgggatggcc gccgcgacgg ccgacgatga  17160
ggggtcggcc gccaccatcc tcaagcaggc catcgccggg gaccgcagcc tggtcgaggc  17220
ggccgaggcg attagccagc agacgctgct ccgcctggcc tgcgaggtgc gccaggtcgg  17280
cgaccgccag ccgcggttta ccgccaccag catcgcgcgc gtcgacgtcg cgcctgggtg  17340
ccggttgcgg ttcgttctgg acgggagtcc cgaggacgcc tatgtgacgt cggaggatta  17400
ctttaagcgc tgctgcggcc agtccagtta tcgcggcttc gcggtggcgg tcctgacggc  17460
caacgaggac cacgtgcaca gcctggccgt gcccccccctc gttctgctgc accggttctc  17520
cctgttcaac cccagggacc tcctggactt tgagcttgcc tgtctgctga tgtacctgga  17580
gaactgcccc cgaagccacg ccaccccgtc gacctttgcc aaggttctgg cgtggctcgg  17640
ggtcgcgggt cgccgcacgt ccccattcga acgcgttcgc tgccttttcc tccgcagttg  17700
ccactgggtc ctaaacacac tcatgttcat ggtgtacgta aaaccgttcg acgacgagtt  17760
cgtcctgccc cactggtaca tggcccggta cctgctggcc aacaacccgc cccccgttct  17820
ctcggccctg ttctgtgcca ccccgacgag ctcctcattc cggctgccgg ggccgccccc  17880
ccgctccgac tgcgtggcct ataaccccgc cgggatcatg gggagctgct gggcgtcgga  17940
ggaggtgcgc gcgcctctgg tctattggtg gctttcggag accccaaaac gacagacgtc  18000
gtcgctgttt tatcagtttt gttgaatttt aggaaataaa cccggttttg tttctgtggc  18060
ctcccgacgg atgcgcgtgt ccttactccg tcttggtggg tgggtggctg tgtatggcgt  18120
cccatctgtg cggggagggg ggcaagtcgg cacgtattcg gacagactca agcacacacg  18180
ggggagcgct cttgtctcag ggcaatgttt ttattggtca aactcaggca aacagaaacg  18240
acatcttgtc gtcaaaggga tacacaaact tccccccctc gccccatact cccgccagca  18300
ccccggtaaa caccaactca atctcgcgca ggatttcgcg caggtgatga gcgcagtcca  18360
cggggggggag cacaaggggc cgcgggtata gatcgacggg gacgccgacc gactccccgc  18420
ctccgggaca gacacgcacg acgcgccgcc agtagtgctc tgcgtccagc aaggcgccgc  18480
cgcggaaggc agtggggggc aaggggtcgc tggcctcaaa gggggacacc cgaacgctcc  18540
agtactccgc gtccaaccgt ttattaaacg cgtccaagat aaggcggtcg caggcgtcct  18600
ccataaggcc ccgggccgtg agtgcgtcct cctccggcac gcatgccgtt gtcaggccca  18660
ggacccgtcg cagcgtgtcg cgtacgaccc ctgccgccgt ggtgtacgcg ggcccgcgga  18720
gaggaaatcc cccaagatgg tcagtgttgt cgcgggagtt ccagaaccac actcccgcct  18780
```

ggctccaggc gactgcgtgg gtgtagacgc cctcgagggc caggcacagt gggtgccgca 18840
gccggacggc gttggcccta agcacggctc ccacggccgt ctcgatggcc cgccgggcgt 18900
cctcgatcac cccggaagcc gcatccgcgt cttgggggtc cacgttaaag acaccccaga 18960
acgcaccccc atcgcccccg cagaccgcga acttcaccga gctggccgtc tcctcgatct 19020
gcaggcagac ggcggccatt accccaccca ggagctgccg cagcgcaggg caggcgttgc 19080
acgtgtccgg gaccaggcgc tccaagacgg ccccggccca gggctctgag ggagcggcca 19140
ccaccagcgc gtccagtctt gctaggcccg tccggccgtg gggtccgcc agcccgctcc 19200 ccccgaggtc ggccagggcc gccaggagct gggcgcgaag tccggggaag caaaaccgcg 19260
ccgtccagac gggcccgacg gccgcgggcg ggtctaacag ttggatgatt ttagtggcgg 19320
gatgccaccg cgccaccgcc tcccgcaccg cgggcaggag gcatccggct gccgccgagg 19380
ccacgccggg ccaggctcgc ggggggagga cgaccctggc ccccaccgcg ggccaggccc 19440
ccaggagcgc ggcgtaagcg gccgcggccc cgcgcaccag gtcccgtgcc gactcggccg 19500
tggccggcac ggtgaacgtg ggccaacccg gaaaccccag gacggcaaag tacgggacgg 19560
gtcccccccg gacctcaaac tcgggcccca gaaaggcaaa gacgggggcc agggccccgg 19620
gggcggcgtg gaccgtggta tgccactgcc ggaaaagggc gacgagcgcc ggcgcggaga 19680
acttctcgcc ggcgcttaca aagtagtcgt aatcgcgggg cagcagcacc cgtgccgtga 19740
ctcgttgcgg gtgcccgcgt ggccgcaggc ccacctcgca cacctcgacc aggtccccga 19800
acgcgccctc cttcttgatc ggcggaaacg caagagtctg gtattcgcgc gcaaatagcg 19860
cggttccggt ggtgatgtta acggtcagcg aagcggcgga cgcgcactgg ggggtgtcgc 19920
gaatggccgc caggcgcgcc cacgccagcc gcgcgtcggg atgctcggca acgcgcgccg 19980
ccagggccat agggtcgatg tcaatgttgg cctccgcgac caggagagcg gcgcgagggg 20040
cggcgggcgg gccccacgac gctctctcaa ctttcaccac cagtcccgtg cgtgggtccg 20100
agccgatacg cagcggggcg aacagggcca ccggcccggt ctggcgctcc agggccgcca 20160
ggacgcacgc gtacagcgcc cgccacagag tcgggttctc caggggctcc agcggggagg 20220
cggccggcgt cgtcgcggcg cgggcggccg ccacgacggc ctggacggag acgtccgcgg 20280
agccgtagaa atcccgcagc tccgtcgcgg tgacggagac ctccgcaaag cgcgcgcgac 20340
cctcccctgc ggcgttgcga catacaaaat acaccagggc gtggaagtac tcgcgagcgc 20400
gggggggcag ccataccgcg taaagggtaa tggcgctgac gctctcctcc acccacacga 20460
tatctgcggt gtccatcgca cggcccctaa ggatcacggg cggtctgtgg gtcccatgct 20520
gccgtgcctg gccgggcccg gtgggtcgcg gaaaccggtg acgggggggg ggcggttttt 20580
ggggttgggg tgggggtggg aaacggcccg ggtccggggg ccaacttggc ccctcggtgc 20640
gttccggcaa cagcgccgcc ggtccgcgga cgaccacgta ccgaacgagt gcggtcccga 20700
gacttatagg gtgctaaagt tcaccgcccc ctgcatcatg ggccaggcct cggtggggag 20760
ctccgacagc gccgcctcca ggatgatgtc agcgttgggg ttggcgctgg atgagtgcgt 20820
gcgcaaacag cgcccccacg cgggcacgcg tagcttgaag cgcgcgcccg caaactcccg 20880
cttgtgggcc ataagcaggg cgtacagctg cctgtgggtc cggcaggcgc tgtggtcgat 20940
gtggtgggcg tccaacaacc ccacgattgt ctgtttggtg aggtttttaa cgcgccccgc 21000
cccgggaaac gtctgcgtgc ttttggccat ctgcacgcca aacagttcgc cccagattat 21060
cttgaacagc gccaccgcgt ggtccgtctc gctaacggac ccgcgcgggg gacagccgct 21120

-continued

```
tagggcgtcg gcgacgcgct tgacggcttc ctccgagagc agaagtccgt cggttacgtt  21180
acagtggccc agttcgaaca ccagctgcat gtagcggtcg tagtgggggg tcagtaggtc  21240
cagcacgtca tcggggccga aggtcctccc agatccccg gccgccgagt cccaatgcag  21300
gcgcgcggcc atggtgctgc acaggcacaa cagctcccag acgggggtta cgttcagggt  21360
gggggcagg gccacgagct ccagctctcc ggtgacgttg atcgtgggga tgacgcccgt  21420
ggcgtagtgg tcatagatcc gccgaaatat ggcgctgctg cgggtggcca tgggaacgcg  21480
gagacaggcc tccagcaacg ccaggtaaat aaaccgcgtg cgtcccatca ggctgttgag  21540
gttgcgcatg agcgcgacaa tttccgccgg cgcgacatcg gaccggaggt atttttcgac  21600
gaaaagaccc acctcctccg tctcggcggc ctgggccggc agcgacgcct cgggatcccg  21660
gcaccgcagc tcccgtagat cgcgctgggc cctgagggcg tcgaaatgta cgccccgcaa  21720
aaacagacag aagtcctttg gggtcagggt atcgtcgtgt ccccagaagc gcacgcgtat  21780
gcagtttagg gtcagcagca tgtgaaggat gttaaggctg tccgagagac acgccagcgt  21840
gcatctctca aagtagtgtt tgtaacggaa tttgttgtag atgcgcgacc cccgccccag  21900
cgacgtgtcg catgccgacg cgtcacagcg ccccttgaac cggcgacaca gcaggtttgt  21960
gacctgggag aactgcgcgg gccactggcc gcaggaactg accacgtgat taaggagcat  22020
gggcgtaaag acgggctccg agcgcgcccc ggagccgtcc atgtaaatca gtagctcccc  22080
cttgcggagg gtgcgcaccc gtcccaggga ctggtacacg gacaccatgt ccggtccgta  22140
gttcatgggt ttcacgtagg cgaacatgcc atcaaagtgc aggggatcga agctgaggcc  22200
cacggttacg accgtcgtgt atataaccac gcggtattgg ccccacgtgg tcacgtcccc  22260
gaggggggtg agcgagtgaa gcaacagcac gcggtccgta aactgacggc agaaccgggc  22320
cacgatctcc gcgaaggaga ccgtcgacga aaaaatgcag atgttatcgc ccccgccaag  22380
gcgcgcttcc agctccccaa agaacgtggc cccccgggcc tccggagagg cgtccggaga  22440
cgggccgctc ggcggcccgg gcgggcgcag ggcagcctgc aggagctcgg tccccagacg  22500
cgggagaaac aggcaccggc gcgccgaaaa cccgggcatg gcgtactcgc cgaccaccac  22560
atgcacgttt ttttcgcccc ggagaccgca caggaagtcc accaactgcg cgttggcggt  22620
tgcgtccatg gcgatgatcc gaggacagat gcgcagcagg cgtagcatta acgcatccac  22680
gcggcccagt tgctgcatcg ttggcgaata gagctggccc agcgtcgaca taacctcgtc  22740
cagaacgagg acgtcgtagt tgttcagaag gttggggccc acgcgatgaa ggctttccac  22800
ctggacgata agtcggtgga aggggcggtc gttcataatg taattggtgg atgagaagta  22860
ggtgacaaag tcgaccaggc ctgactcagc gaaccgcgtc gctagggtct gggtaaaact  22920
ccgacgacag gagacgacga gcacactcgt gtccggagag tggatcgctt cccgcagcca  22980
gcggatcagc gcggtagttt ttcccgaccc cattggcgcg cggaccacag tcacgcacct  23040
ggccgtcggg gcgctcgcgt tggggaaggt gacgggtccg tgctgctgcc gctcgatcgt  23100
tgttttcggg tgaacccggg gcacccattc ggccaaatcc cccccgtaca acatccgcgc  23160
tagcgatacg ctcgacgtgt actgttcgca ctcgtcgtcc ccaatgggac gcccggcccc  23220
cagaggatct cccgactccg cgccccccac gaaaggcatg accggggcgc ggacggcgtg  23280
gtgggtctgg tgtgtgcagg tggcgacgtt tgtggtctct gcggtctgcg tcacggggct  23340
cctcgtcctg gcctctgtgt tccgggcacg gtttccctgc ttttacgcca cggcgagctc  23400
ttatgccggg gtgaactcca cggccgaggt gcgcgggggt gtagccgtgc ccctcaggtt  23460
ggacacgcag agccttgtgg gcacttatgt aatcacggcc gtgttgttgt tggccgtggc  23520
```

-continued

```
cgtgtatgcc gtggtcggcg ccgtgacctc ccgctacgac cgcgccctgg acgcgggccg  23580
ccgtctggct gcggcccgca tggccatgcc gcacgccacg ctgatcgccg gaaacgtctg  23640
ctcttggttg ctgcagatca ccgtcctgtt gctggcccat cgcatcagcc agctggccca  23700
cctggtttac gtcctgcact ttgcgtgtct ggtgtatttt gcggcccatt tttgcaccag  23760
gggggtcctg agcgggacgt atctgcgtca ggtgcacggc ctgatggagc tggccccgac  23820
ccatcatcgc gtcgtcggcc cggctcgcgc cgtgctgaca aacgccttgc tgttgggcgt  23880
cttcctgtgc acggccgacg ccgcggtatc cctgaatacc atcgccgcgt tcaactttaa  23940
tttttcggcc ccgggcatgc tcatctgcct gaccgtgctg ttcgccattc tcgtcgtatc  24000
gctgttgttg gtggtcgagg gggtgttgtg tcactacgtg cgcgtgttgg tgggccccca  24060
cctgggggcc gtggccgcca cgggcatcgt cggcctggcc tgcgagcact attacaccaa  24120
cggctactac gttgtggaga cgcagtggcc gggggctcag acgggagtcc gcgtcgccct  24180
cgccctggtc gccgcctttg ccctcggcat ggccgtgctc cgctgcaccc gcgcctatct  24240
gtatcacagg cggcaccaca ccaaattttt tatgcgcatg cgcgacacgc gacaccgcgc  24300
acattccgcc ctcaagcgcg tacgcagttc catgcgcgga tcgcgagacg gccgccacag  24360
gcccgcaccc ggcagcccgc ccgggattcc cgaatatgcg gaagacccct acgcgatctc  24420
atacggcggc cagctcgacc ggtacggaga ttccgacggg gagccgattt acgacgaggt  24480
ggcggacgac caaaccgacg tattgtacgc caagatacaa cacccgcggc acctgcccga  24540
cgacgatccc atctatgaca ccgttggggg gtacgacccc gagcccgccg aggaccccgt  24600
gtacagcacc gtccgccgtt ggtagctgtt tggttccgtt ttaataaacc gtttgtgttt  24660
aacccgaccg tggtgtatgt ctggtgtgtg gcgtccgatc ccgttactat caccgtcccc  24720
ccccccccct caaccccggc gattgtgggt tttttaaaaa cgacacgcgt gcgaccgtat  24780
acagaacatt gttttggttt ttattcgcta tcggacatgg ggggtggaaa ctgggtggcg  24840
gggcaggcgc ctccgggggt ccgccggtga gtgtggcgcg aggggggggtc cgatgaacgc  24900
aggcgctgtc tccccggggc ccgcgtaacc ccgcgcatat ccgggggcac gtagaaatta  24960
ccttcctctt cggactcgat atccacgacg tcaaagtcgt gggcggtcag cgagacgacc  25020
tccccgtcgt cggtgatgag gacgttgttt cggcagcagc agggccgggc cccggagaac  25080
gagaggccca tagctcggcg agcgtgtcgt cgaatgccag gcggctgctt cgctggatgg  25140
ccttatagat ctccggatcg atgcggacgg gggtaatgat cagggcgatc ggaacggcct  25200
ggttcgggag aatggacgcc ttgctgggtc ctgcggcccc gagagccccg gcgccgtcct  25260
ccaggcggaa cgttacgccc tcctccgcgc tggtgcggtg cctgccgata aacgtcacca  25320
gatgcgggtg ggggggggcag tcggggaagt ggctgtcgag cacgtagccc tgcaccaaga  25380
tctgcttaaa gttcgggtga cgggggttcg cgaagacggg ctcgcggcgg accagatccc  25440
cggagctcca ggacacgggg gagatggtgt ggcgtccgag gtcgggggcg ccaaacagaa  25500
gcacctccga gacaacgccg ctatttaact ccaccaaggc ccgatccgcg gcggagcacc  25560
gcctttttc gcccgaggcg tgggcctctg accaggcctg gtcttgcgtg acgagagcct  25620
cctccgggcc ggggacgcgc ccgggcgcga agtatcgcac gctgggcttc gggatcgacc  25680
ggataaatgc ccggaacgcc tccggggacc ggtgtgccat caagtcctcg tacgcggagg  25740
ccgtggggtc gctggggtcc atggggtcga aagcgtactt ggcccggcat ttgacctcgt  25800
aaaaggccag gggggtcttg gggactgggg ccaggtagcc gtgaatgtcc cgaggacaga  25860
```

cgagaatatc cagggacgcc ccgaccatcc ccgtgtgacc gtccatgagg accccacacg 25920
tatgcacgtt ctcttcggcg aggtcgctgg gttcgtggaa gataaagcgc cgcgtgtcgg 25980
cgccggcctc gccgccgtcg tccgcgcggc ccacgcagta gcgaaacagc aggcttcggg 26040
ccgtcggctc gttcacccgc ccgaacatca ccgccgaaga ctgtacatcc ggccgcaggc 26100
tggcgttgtg cttcagccac tggggcgaga aacacggacc ctgggggccc cagcggaggg 26160
tggatgcggt cgtgaggccc cgccggagca gggcccatag ctggcagtcg gcctggtttt 26220
gcgtggccgc ctcgtaaaac cccatgaggg gccggggcgc cacggcgtcc gcggcggccg 26280
ggggcccgcg gcgcgtcagg cgccataggt gccgaccgag tccgcggtcc accatacccg 26340
cctcctcgag gaccacggcc agggaacaca gataatccag gcgggcccag aggggaccga 26400
tggccagagg ggcgcggacg ccgcgcagca acccgcgcag gtggcgctcg aacgtctcgg 26460
ctagtatatg ggagggcagc gcgttgggga tcaccgacgc cgaccacata gagtcaaggt 26520
ccggggagtc gggatcggcg tccgggtcgc gggcgtgggt gcccccagga gatagcggaa 26580
tgtctggggt cggaggccct gaggcgtcag aaagtgccgg cgacgcggcc cggggctttt 26640
cgtctgcggt gtcggtggcg tgctgatcac gtggggggtt aacgggcgaa tgggagctcg 26700
ggtccacagc tgatgtcgtc tggggtgggg ggggcagggg acggaaggtg gttgtcagcg 26760
gaagactgtt agggcggggg cgcttggggg ggctgtcggg gccacgaggg gtgtcctcgg 26820
ccagggccca gggacgctta gtcacggtgc gtcccggcgg acatgctggg cctaccgtgg 26880
actccatttc cgagacgacg tggggggagc ggtggttgag cgcgccgccg ggtgaacgct 26940
gattctcacg acagcgcgtg ccgcgcgcac gggttggtgt gacacaggcg ggacaccagc 27000
accaggagag gcttaagctc gggaggcagc gccaccgacg acagtatcgc cttgtgtgtg 27060
tgctggtaat ttatacaccg atccgtaaac gcgcgccgaa tcttgggatt gcggaggtgg 27120
cgccggatgc cctctgggac gtcatacgcc aggccgtggg tgttggtctc ggccgagttg 27180
acaaacaggg ctgggtgcag cacgcagcga taggcgagca gggccagggc gaagtccggc 27240
gacagctggt tgttaaaata ctggtaaccg ggaaaccggg tcacgggtac gcccaggctc 27300
ggggcgacgt acacgctaac caccaactcc agcagcgtct ggcccagggc gtacaggtca 27360
accgctaacc cgacgtcgtg cttcaggcgg tggttggtaa attcggcccg ttcgttgtta 27420
aggtatttca ccaacagctc cgggggctgg ttatacccgt gacccaccag ggtgtgaaag 27480
ttggctgtgg ttagggcggt gggcatgcca aacatccggg gggacttgag gtccggctcc 27540
tggaggcaaa actgccccg ggcgatcgtg gagttggagt tgagggtgac gaggctaaag 27600
tcggcgagga cggcccgccg gagcgagacg gcgtccgacc gcagcatgac gaggatgttg 27660
gcgcacttga tatccaggtg gctgatcccg caggtggtgt ttaaaaacac aacggcgcgg 27720
gccagctccg tgaagcactg gtggagggcc gtcgagaccg aggggtttgt tgtgcgcagg 27780
gacgccagtt ggccgatata cttaccgagg tccatgtcgt acgcggggaa cactatctgt 27840
cgttgttgca gcgagaaccc gaggggcgcg atgaagccgc ggatgttgtg ggtgcggccg 27900
gcgcgtagaa cgcactcccc gaccaacagg gtcgcgatga gctcaacggc aaaccactcc 27960
ttttccttta tggtcttaac ggcaagctta tgttcgcgaa tcagttggac gtcaccgtat 28020
cccccagacc ccccgaagct tcgggccccg gggatctcga gggtcgtgta gtgtagggcg 28080
gggttgatgg cgaacacggg gctgcatagc ttgcggatgc gcgtgagggt gaggatgtgc 28140
gagggggacg agggggtgc ggttaacgcc gcctgggatc tgcgcagggg cgggcggttc 28200
agtttggccg ccgtaccggg cgtctcgggg gacgcgcggc gatgagacga gcggctcatt 28260

-continued

```
cgccatcggg atagtcccgc gcgaagccgc tcgcggaggc cggatcggtg gcgggacccg  28320
tgggaggagc gggagacggc ggcgtcctgg agagaggggc cgctggggcg cccggaggcc  28380
ccgtgggggt tggagtgtac gtaggatgcg agccaatcct tgaaggaccg ttggcgtgca  28440
ccttgggggc tgaggttagc tgccacatga ccagcaggtc gctgtctgcg ggactcatcc  28500
atccttcggc caggtcgccg tctccccaca gagaagcgtt ggtcgctgct tcctcgagtt  28560
gctcctcctg gtccgcaaga cgatcgtcca cggcgtccag gcgctcacca agcgccggat  28620
cgaggtaccg tcggtgtgcg gttagaaagt cacgacgcgc cgcttgctcc tccacgcgaa  28680
ttttaacaca ggtcgcgcgc tgtcgcatca tctctaagcg cgcgcgggac tttagccgcg  28740
cctccaattc caagtgggcc gcctttgcag ccataaaggc gccaacaaac cgaggatctt  28800
gggtgctgac gccctcccgg tgcagctgca gggtctggtc cttgtaaatc tcggctcgga  28860
ggtgcgtctc ggccaggcgt cggcgcaggg ccgcgtgggc ggcatctcgg tccattccgc  28920
caccctgcgg gcgacccggg gggtgctctg atagtctcgc gtgcccaagg cccgtgatcg  28980
gggtacttcg ccgccgcgac ccgccacccg gtgtgcgcga tgtttggtca gcagctggcg  29040
tccgacgtcc agcagtacct ggagcgcctc gagaaacaga ggcaacttaa ggtgggcgcg  29100
gacgaggcgt cggcgggcct caccatgggc ggcgatgccc tacgagtgcc ctttttagat  29160
ttcgcgaccg cgacccccaa gcgccaccag accgtggtcc ctggcgtcgg gacgctccac  29220
gactgctgcg agcactcgcc gctcttctcg gccgtggcgc ggcggctgct gtttaatagc  29280
ctggtgccgg cgcaactaaa ggggcgtgat ttcgggggcg accacacggc caagctggaa  29340
ttcctggccc ccgagttggt acgggcggtg gcgcgactgc ggtttaagga gtgcgcgccg  29400
gcggacgtgg tgcctcagcg taacgcctac tatagcgttc tgaatacgtt tcaggccctc  29460
caccgctccg aagcctttcg ccagctggtg cactttgtgc gggactttgc ccagctgctc  29520
aaaacctcct tccgggcctc cagcctcacg gagaccacgg gcccccccaa aaaacgggcc  29580
aaggtggacg tggccaccca cggccggacg tacggcacgc tggagctgtt ccaaaaaatg  29640
atccttatgc acgccaccta ctttctggcc gccgtgctcc tcggggacca cgcggagcag  29700
gtcaacacgt tcctgcgtct cgtgtttgag atccccctgt ttagcgacgc ggccgtgcgc  29760
cacttccgcc agcgcgccac cgtgtttctc gtcccccggc gccacggcaa gacctggttt  29820
ctggtgcccc tcatcgcgct gtcgctggcc tcctttcggg ggatcaagat cggctacacg  29880
gcgcacatcc gcaaggcgac cgagccggtg tttgaggaga tcgacgcctg cctgcggggc  29940
tggttcggtt cggcccgagt ggaccacgtt aaaggggaaa ccatctcctt ctcgtttccg  30000
gacgggtcgc gcagtaccat cgtgtttgcc tccagccaca acacaaacgt aagtcctctt  30060
ttctttcgca tggctctccc aaggggcccc gggtcgaccc gacccacacc cacccaccca  30120
catacacaca caaccagacg cgggaggaaa gtctgccccg tgggcactga tttttattcg  30180
ggatcgcttg aggaggcccg ggcaacggcc cgggcaacgg tggggcaact cgtagcaaat  30240
aggcgactga tgtacgaaga gaagacacac aggcgccacc cggcgctggt cggggggatg  30300
ttgtccgcgc cgcaccgtcc cccgacgacc tcttgcagac ggtccgtgat gcaaggacgg  30360
cggggggcct gcagcagggt gaccgtatcc acgggatggc caaagagaag cggacacagg  30420
ctagcatccc cctggaccgc cagggtacac tgggccatct tggcccacag acacggggcg  30480
acgcagggac aggactccgt tacgacggag gagagccaca gtgcgttggc ggaatcgatg  30540
tggggcggcg gggcgcagga ctcgcagccc cccgggtggt tggtgatcct ggccaggagc  30600
```

-continued catcccagat ggcgggccct gcttcccggt ggacagagcg accccaggtc gctgtccatg 30660
gcccagcagt agatctggcc gctggggagg tgccaccagg cccccgggcc caaggcgcag 30720
cacgcgcccg gctccggggg ggtcttcgcg gggaccagat acgcgccatc cagctcgccg 30780
accactggct cctccgcgag ctgttcggtg gttgggtcgg gggtttcctc cggggggggtg 30840 gccgcccgta tgcgtgcgaa cgtgagggtg cacaggagcg gggtcagggg gtgcgtcacg 30900
ctccggaggt ggacgatcgc gcagtagcgg cgctcgcggt taaagaaaaa gagggcaaag 30960
aaggtgttcg gggcaaccg cagcgccttg gggcgcgtca gatacagaaa aatctcgcag 31020
aagagggcgc gcccggggtc tgggttagga agggccacct gacacagagg ctcggtgagg 31080
accgttagac accgaaagat cttgagccgc tcgtccgccc gaacgacgcg ccacacaaag 31140
acggagttga caatgcgcgc gatagagtcg acgtccgtcc ccaggtcgtc gactctatcg 31200
cgcgtgccgc gagctccggc ccgggaatcc ggccggggca aggtccccgg gggaccaggc 31260
ggcgccaggg gccgccgggg tcccagctgc gccatgccgg gggcgggggg agggcaaacc 31320
ccagaggcgg gggccaacgg cgcggggagg agtgggtggg cgaggtggcc gggggaaggc 31380
gcccgctagc gagaccggcc gttcccggac gacaccttgc gacaaaacct aaggacagcg 31440
gcccgcgcga cggggtccga gaggctaagg taggccgcga tgttaatggt gaacgcaaag 31500
ccgccgggaa agacaactat gccacagagg cggcgattaa accccaggca gaggtaggcg 31560
tagctttccc cgggcaggta ttgctcgcag accctgcgtg ggctgtgga ggggacggcc 31620 tccatgaagc gacatttact ctgctcgcgt ttactgacgt caccatccat cgccacggcg 31680
attggacgat tgttaagccg cagcgtgtct ccgcttgtgc tgtagtagtc aaaaacgtaa 31740
tggccgtcgg agtcggcaaa gcgggccggg aggtcgtcgc cgagcgggac gacccgccgc 31800
ccccgaccgc cccgtccccc caggtgtgcc aggacggcca gggcatacgc ggtgtgaaaa 31860
aaggcgtcgg gggcggtccc ctcgacggcg cgcatcaggt tctcgaggag aatggggaag 31920
cgcctggtca cctcccccaa ccacgcgcgt tggtcggggc caaagtcata gcgcaggcgc 31980
tgtgagattc gcgggccgcc ctgaagcgcg gcccggatgg cctggcccag ggcccggagg 32040
cacgccagat gtatgcgcgc ggtaaaggcg acctcggcgg cgatgtcaaa gggcggcagg 32100
acggggcgcg ggtggcgcag gggcacctcg agcgcgggaa agcgtagcag cagctccgcc 32160
tgcccagcgg gagacagctg gtgggggcgc acgacgcgtt ctgcggcgca ggcctcggtc 32220
agggccgtgg ccagcgccga ggacagcagc ggagggcggg cgcgtcgccc gccccacgcc 32280
acggagttct cgtaggagac gacgacgaag cgctgcttgg ttccgtagtg gtggcgcagg 32340
accacggaga tagaacgacg gctccacagc cagtccggcc ggtcgccgcc ggccagggct 32400
tcccatccgc gatccaacca ctcgaccagc gaccgcggct ttgcggtacc aggggtaagg 32460
gttagaacgt cgttcaggat gtcctcgccc ccgggcccgt ggggcgctgg ggccacaaag 32520
cggcccccgc cggggggctc cagacccgcc agcaccgcat ctgcgtcagc cgcccccatg 32580
gcgcccccgc tgacggcctg gtgaaccagg gcgccctggc gtagccccga tgcaacgcca 32640
caggccgcac gcccggtccg cgctcggacc gggtggcggc gggtgacgtc ctgcactgcc 32700
cgctgaacca acgcgaggat ctcctcgttc tcctgtgcga tggacacgtc ctgggccgcg 32760
gtcgtgtcgc cgccgggggc cgtcagctgc tcctccgggg agatgggggg gtcggacgcc 32820
ccgacgatgg gcgggtctgc gggcgccccc gcgtggggcc gggccaaggg ctgcggacgc 32880
ggggacgcgc tttcccccag acccatggac aggtgggccg cagcctcctt cgcggccggc 32940
ggggcggcgg cgccaagcag agcgacgtag cggcacaaat gccgacagac gcgcatgatg 33000

-continued cgcgtgctgt cggccgcgta gcgcgtgttg ggggggacga gctcgtcgta actaaacaga 33060
atcacgcggg cacagctcgc ccccgagccc cacgcaaggc gcagcgccgc cacggcgtac 33120
gggtcataga cgccctgcgc gtcacacacc acgggcaggg agacgaacaa ccccccggcg 33180
ctggacgcac gcggaaggag gccagggtgt gccggcacga cgggggccag aagctccccc 33240
accgcatccg cgggcacgta ggcggcaaac gccgtgcacc acggggtaca gtcgccggtg 33300
gcatgagccc gagtctggat ttcgacctgg aagtttgcgg ccgtcccgag tccggggcgg 33360
ccgcgcatca gggcggccag agggattccc gcggccgcca ggcactcgct ggatatgatg 33420
acgtgaacca aagaccgagg gccgacccgg gccgtggccg agatcgtctg gacctcgttg 33480
gccaagtgcg cgttcatggt tcgggggtgg gtgtgggtgt gtaggcgatg cgggtccccc 33540
gagtccgcgg gaagggcgtg ggtttggcgc gcgtatgcgt attcgccaac ggaggcgtgc 33600
gtgcttatgc gcggcgcgtt tcttctgtct ctagggaatc cgaggccagg actttaacct 33660
gctctttgtc gacgaggcca actttattcg cccggatgcg gtccagacga ttatgggctt 33720
tctcaaccag gccaactgca agattatctt cgtgtcgtcc accaacaccg ggaaggccag 33780
tacgagcttt ttgtacaacc tccgcggggc cgcagacgag cttctcaacg tggtgaccta 33840
tatatgcgat gatcacatgc cgagggtggt gacgcacaca aacgccacgg cctgttcttg 33900
ttatatcctc aacaagcccg ttttcatcac gatggacggg gcggttcgcc ggaccgccga 33960
tttgtttctg gccgattcct tcatgcagga gatcatcggg ggccaggcca gggagaccgg 34020
cgacgaccgg cccgttctga ccaagtctgc gggggagcgg tttctgttgt accgcccctc 34080
gaccaccacc aacagcggcc tcatggcccc cgatttgtac gtgtacgtgg atcccgcgtt 34140
cacggccaac acccgagcct ccgggaccgg cgtcgctgtc gtcgggcggt accgcgacga 34200
ttatatcatc ttcgccctgg agcacttttt tctccgcgcg ctcacgggct cggcccccgc 34260
cgacatcgcc cgctgcgtcg tccacagtct gacgcaggtc ctggccctgc atcccggggc 34320
gtttcgcggc gtccgggtgg cggtcgaggg aaatagcagc caggactcgg ccgtcgccat 34380
cgccacgcac gtgcacacag agatgcaccg cctactggcc tcggaggggg ccgacgcggg 34440
ctcgggcccc gagcttctct tctaccactg cgagcctccc gggagcgcgg tgctgtaccc 34500
ctttttcctg ctcaacaaac agaagacgcc cgcctttgaa cactttatta aaaagtttaa 34560
ctccgggggc gtcatggcct cccaggagat cgtttccgcg acggtgcgcc tgcagaccga 34620
cccggtcgag tatctgctcg agcagctaaa taacctcacc gaaaccgtct cccccaacac 34680
tgacgtccgt acgtattccg gaaaacggaa cggcgcctcg gatgacctta tggtcgccgt 34740
cattatggcc atctacctcg cggcccaggc cggacctccg cacacattcg ctcctatcac 34800
acgcgtctcg tgagcgccca ataaacacac ccaggtatgc tacgcacgac cacggtgtcg 34860
tctgttaagg gggggggggg aagggggtgt tggcgggaag cgtgggaaca cgggggattc 34920
tctcacgacc ggcaccagta ccaccccccct gtgaacacag aaaccccaac ccaaatccca 34980
taaacatacg acacacaggc atattttgga atttcttagg tttttattta tttaggtatg 35040
ctggggtttc tccctggatg cccaccccca cccccccgtg ggtctagccg ggccttaggg 35100
atagcgtata acgggggcca tgtctccgga ccgcacaacg gccgcgccgt caaaggtgca 35160
cacccgaacc acgggagcca gggccaaggt gtctcctagt tggcccgcgt gggtcagcca 35220
ggcgacgagc gcctcgtaaa gcggcagcct tcgctctcca tcctgcatca gggccggggc 35280
ttcggggtga atgagctggg cggcctcccg cgtgacactc tgcatctgca gtagagcgtt 35340

-continued

```
cacgtacccg tcctgggcac ttagcgcaaa gagccggggg attagcgtaa ggatgatggt  35400
ggttccctcc gtgatcgagt aaaccatgtt aaggaccagc gatcgcagct cggcgtttac  35460
gggaccgagt tgttggacgt ccgccagcag cgagaggcga ctcccgttgt agtacagcac  35520
gttgaggtct ggcagccctc cggggtttct ggggctgggg ttcaggtccc ggatgcccct  35580
ggccacgagc cgcgccacga tttcgcgcgc caggggcgat ggaagcggaa cgggaaaccg  35640
caacgtgagg tccagcgaat ccaggcgcac gtccgtcgct tggccctcga acacgggcgg  35700
gacgaggctg atggggtccc cgttacagag atctacgggg gaggtgttgc gaaggttaac  35760
ggtgccggcg tgggtgaggc ccacgtccag ggggcaggcg acgattcgcg tgggaagcac  35820
ccgggtgatg accgcgggga agcgccttcg gtacgccagc aacaacccca acgtgtcggg  35880
actgacgcct ccggagacga aggattcgtg cgccacgtcg gccagcgtca gttgccggcg  35940
gatggtcggc aggaatacca cccgcccttc gcagcgctgc agcgccgccg catcggggcg  36000
cgagatgccc gagggtatcg cgatgtcagt ttcaaagccg tccgccagca tggcgccgat  36060
ccacgcggca gggagtgcag tggtggttcg ggtggcggga ggagcgcggt gggggtcagc  36120
ggcgtagcag agacgggcga ccaacctcgc ataggacggg gggtgggtct tagggggttg  36180
ggaggcgaca gggaccccag agcatgcgcg gggaggtctg tcgggcccag acgcaccgag  36240
agcgaatccg tccgcggagt cccggcttgg gttttatggg gcccggccct cggaatcgcg  36300
gcttgtcggc ggggacaaag ggggcggggc taggggcttg cggaaacaga agacgcgtgg  36360
gataaaagaa tcgcactacc ccaaggaagg gcggggcggt ttattacaga gccagtccct  36420
tgagcgggga tgcgtcatag acgagatact gcgcgaagtg ggtctcccgc gcgtgggctt  36480
ccccgttgcg ggcactgcgg aggagggcgg ggtcgctggc gcaggtgagc gggtaggcct  36540
cctgaaacag gccacacggg tcctccacga gttcgcggca ccccgggggg cgcttaaact  36600
gtacgtcgct ggcggcggtg gccgtggaca ccgccgaacc cgtctccacg atcaggcgct  36660
ccaggcagcg atgtttggcg gcgatgtcgg ccgacgtaaa gaacttaaag caggggctga  36720
gcaccggcga ggccccgttg aggtggtagg ccccgttata gagcaggtcc ccgtacgaaa  36780
atcgctgcga cgcccacggg ttggccgtgg ccgcgaaggc ccgggacggg tcgctctggc  36840
cgtggtcgta catgagggcg gtgacatccc cctccttgtc cccgcgtaa acgcccccgg  36900
cggcgcgtcc ccgggggttg cagggccggc ggaagtagtt gacgtcggtc gacacggggg  36960
tggcgataaa ctcacacacg gcgtcctggc cgtggtccat ccctgcgcgc cgcggcacct  37020
gggcgcaccc gaacacgggg acgggctggg ccggccccag gcggtttccc gccacgaccg  37080
cgttccgcag gtacacggct gccgcgttgt ccaggagagg gggagccccg cggcccaggt  37140
aaaagttttg gggaaggttg cccatgtcgg tgacggggtt gcggacggtt gccgtggcca  37200
cgacggcggt gtagcccacg cccaggtcca cgttcgcgcg cggctgggtg agcgtgaagt  37260
ttaccccccc gccagtttcg tgccgggcca cctggagctg gcccaggaag tacgcctccg  37320
acgcgcgctc cgagaacagc acgttctcag tcacaaagcg gtcctgtcgg acgacggtga  37380
acccaaaccc gggatggagg cccgtcttga gctgatgatg caaggccacg ggactgatct  37440
tgaagtaccc cgccatgagc gcgtaggtca gcgcgttctc cccggccgcg ctctcgcgga  37500
cgtgctgcac gacgggctgt cggatcgacg aaaagtagtt ggcccccaga gccgggggga  37560
ccagggggac ctgccgcgac aggtcgcgca gggccggggg gaaattgggc gcgttcgcca  37620
cgtggtcggc cccggcgaac agcgcgtgga cggggagggg gtaaaaatag tcgccatttt  37680
ggatggtatg gtccagatgc tggggggcca tcagcaggat tccggcgtgc aacgccccgt  37740
```

cgaatatgcg catgttggtg gtggacgcgg tgttggcgcc cgcgtcgggc gccgccgagc 37800
agagcagcgc cgttgtgcgt tcggccatgt tgtgggccag cacctgcagc gtgagcatgg 37860
cgggcccgtc cactaccacg cgcccgttgt gaaacatggc gttgaccgtg ttggccacca 37920
gattggccgg gtgcaggggg tgcgcggggt ccgtcacggg gtcgctgggg cactcctcgc 37980
cgggggcgat ctccgggacc accatgttct gcagggtggc gtatacgcgg tcgaagcgaa 38040
cccccgcggt gcagcagcgg ccccgcgaga aggcgggcac catcacgtag tagtaaatct 38100
tgtggtgcac ggtccagtcc gccccccggt gcggccggtc atccgcggcg tccgcggctc 38160
gggcctgggt gttgtgcagc agctggccgt cgttgcggtt gaagtccgcg gtcgccacgt 38220
tacatgccgc cgcgtacacg gggtcgtggc cccccgcgct aacccggcag tcgcgatggc 38280
ggtccagggc cgcgcgccgc atcagggcgt cacagtccca cacgaggggt ggcagcagcg 38340
ccgggtctcg cattaggtga ttcagctcgg cttgcgcctg cccgcccagc tccgggccgg 38400
tcagggtaaa gtcatcaacc agctgggcca gggcctcgac gtgcgccacc aggtcccggt 38460
acacggccat gcactcctcg ggaaggtctc ccccgaggta ggtcacgacg tacgagacca 38520
gcgagtagtc gttcacgaac gccgcgcacc gcgtgttgtt ccagtagctg gtgatgcact 38580
ggaccacgag ccgggccagg gcgcagaaga cgtgctcgct gccgtgtatg gcggcctgca 38640
gcaggtaaaa caccgccggg tagttgcggt cgtcgaacgc cccgcgaacg gcggcgatgg 38700
tggcgggggc catggcgtgg cgtcccaccc ccagctccag gccccgggcg tcccggaacg 38760
ccgccggaca tagcgccagg ggcaagttgc cgttcaccac gcgccaggtg gcctggatct 38820
cccccgggcc ggccggggga acgtcccccc ccggcagctc cacgtcggcc acccccacaa 38880
agaagtcgaa cgcggggtgc agctcaagag ccaggttggc gttgtcgggc tgcataaact 38940
gctccggggt catctggcct tccgcgaccc atcggacccg cccgtgggcc aggcgctgcc 39000
cccaggcgtt caaaaacagc tgctgcatgt ctgcggcggg gccggccggg gccgccacgt 39060
acgccccgta cggattggcg gcttcgacgg ggtcgcggtt aaggcccccg accgccgcgt 39120
caacgttcat cagcgaaggg tggcacacgg tcccgatcgc gtgttccaga gacaggcgca 39180
gcacctggcg gtccttcccc caaaaaaaca gctggcgggg cgggaaggcg cggggatccg 39240
ggtggccggg ggcggggact aggtccccgg cgtgcgcggc aaaccgttcc atgaccggat 39300
tgaacaggcc caggggcagg acgaacgtca ggtccatggc gcccaccagg gggtagggaa 39360
cgttggtggc ggcgtagatg cgcttctcca gggcctccag aaagaccagc ttctcgccga 39420
tggacaccag atccgcgcgc acgcgcgtcg tctgggggc gctctcgagc tcgtccagcg 39480
tctgccggtt caggtcgagc tgctcctcct gcatctccag caggtggcgg cccacgtcgt 39540
ccagacttcg cacggccttg cccatcacga gcgccgtgac caggttggcc ccgttcagga 39600
ccatctcgcc gtacgtcacc ggcacgtcgg cttcggtgtc ctccactttc aggaaggact 39660
gcaggaggcg ctgtttgatc ggggcggtgg tgacgagcac cccgtcgacc ggccgcccgc 39720
gcgtgtcggc atgcgtcaga cggggcacgg ccacggaggg ctgcgtggcc gtggtgaggt 39780
ccacgagcca ggcctcgacg gcctcccggc ggtggcccgc cttgcccagg aaaaagctcg 39840
tctcgcagaa gcttcgcttt agctcggcga ccagggtcgc ccgggccacc ctggtggcca 39900
ggcggccgtt gtccaggtat cgttgcatcg gcaacaacaa agccaggggc ggcgcctttt 39960
ccagcagcac gtgcagcatc tggtcggccg tgccgcgctc aaacgccccg aggacggcct 40020
ggacgttgcg agcgagctgt tggatggcgc gcaactggcg atgcgcgccg atacccgtcc 40080

-continued

```
cgtccagggc ctcccccgtg agcagggcga tggcctcggt ggccaggctg aaggcggcgt  40140
tcagggcccg gcggtcgata atcttggtca tgtaattgtg tgtgggttgc tcgatggggt  40200
gcgggccgtc gcgggcaatc agcggctggt ggacctcgaa ctgtacgcgc ccctcgttca  40260
tgtaggccag ctccggaaac ttggtacaca cgcacgccac cgacaacccg agctccagaa  40320
agcgcacgag cgacagggtg ttgcaatacg accccagcag ggcgtcgaac tcgacgtcgt  40380
acaggctgtt tgcatcggag cgcacgcggg aaaaaaaatc aaacaggcgt cgatgcgacg  40440
ccacctcgat cgtgctaagg agggacccgg tcggcaccat ggccgcggca taccggtatc  40500
ccggagggtc gcggttggga gcggccatgg ggtcgcgtgg agatcggctg tctctagcga  40560
tattggcccg gggaggctaa gatccacccc aacgcccggc cacccgtgta cgtgcccgac  40620
ggcccaaggt ccaccgaaag acacgacggg cccggaccca aaaaggcggg ggatgctgtg  40680
tgagaggccg ggtgccggtc ggggggga ggcaccggga gaaggctgcg gcctcgttcc  40740
aggagaaccc agtgtcccca acagacccgg ggacgtggga tcccaggcct tatatacccc  40800
ccccccgcc ccaccccgt tagaacgcga cgggtgcatt caagatggcc ctggtccaaa  40860
agcgtgccag gaagaaattg gcagaggcgg caaagctgtc cgccgccgcc acccacatcg  40920
aggccccggc cgcgcaggct atccccaggg cccgtgtgcg caggggatcg gtgggcggca  40980
gcatttggtt ggtggcgata aagtggaaaa gcccgtccgg actgaaggtc tcgtgggcgg  41040
cggcgaacaa ggcacacagg gccgtgcctc ccaaaaacac ggacatcccc caaaacacgg  41100
gcgccgacaa cggcagacga tccctcttga tgttaacgta caggaggagc gcccgcaccg  41160
cccacgtaac gtagtagccg acgatggcgg ccaggataca ggccggcgcc accacccttc  41220
cggtcagccc gtaatacatg cccgctgcca ccatctccaa cggcttcagg accaaaaacg  41280
accaaaggaa cagaatcacg cgctttgaaa agaccggctg ggtatggggc ggaagacgcg  41340
agtatgccga actgacaaaa aaatcagagg tgccgtacga ggacaatgaa aactgttcct  41400
ccagcggcag ttctccctcc tcccccccga aggcggcctc gtcgaccaga tctcgatcca  41460
ccagaggaag gtcatcccgc atggtcatgg ggtgtgcggt ggaggtgggg agaccgaaac  41520
cgcaaagggt cgcttacgtc agcaggatcc cgagatcaaa gacacccggg ttcttgcaca  41580
aacaccaccc gggttgcatc cgcggaggcg agtgttttga taaggccgtt ccgcgccttg  41640
atataacctt tgatgttgac cacaaaaccc ggaatttacg cctacgcccc aatgcccacg  41700
caagatgagg taggtaaccc ccccgtgggt gtgacgttgc gtttagttca ttggaggcca  41760
aggggaaaaa tggggtgggg aggaaacgga aaacccagta ggccgtgtcg ggaacacgcc  41820
cggggttgtc ctcaaaaggc agggtccata ctacggaagc cgtcgttgta ttcgagacct  41880
gcctgtgcaa cgcacgtcgg ggttgcctgt gtccggttcg gcccccaccg cgtgcggcac  41940
gcacgaggac gagtccgcgt gctttattgg cgttccaagc gttgccctcc agtttctgtt  42000
gtcggtgttc ccccataccc acgcccacat ccaccgtagg gggcctctgg gccgtgttac  42060
gtcgccgccc gcgatggagc ttagctacgc caccaccatg cactaccggg acgttgtgtt  42120
ttacgtcaca acggaccgaa accgggccta ctttgtgtgc ggggggtgtg tttattccgt  42180
ggggcggccg tgtgcctcgc agcccgggga gattgccaag tttggtctgg tcgttcgagg  42240
gacaggccca gacgaccgcg tggtcgccaa ctatgtacga agcgagctcc gacaacgcgg  42300
cctgcaggac gtgcgtccca ttggggagga cgaggtgttt ctggacagcg tgtgtcttct  42360
aaacccgaac gtgagctccg agctggatgt gattaacacg aacgacgtgg aagtgctgga  42420
cgaatgtctg gccgagtact gcacctcgct gcgaaccagc ccgggtgtgc taatatccgg  42480
```

-continued

```
gctgcgcgtg cgggcgcagg acagaatcat cgagttgttt gaacacccaa cgatagtcaa  42540
cgtttcctcg cactttgtgt ataccccgtc cccatacgtg ttcgccctgg cccaggcgca  42600
cctcccccgg ctcccgagct cgctggaggc cctggtgagc ggcctgtttg acggcatccc  42660
cgccccacgc cagccacttg acgcccacaa cccgcgcacg gatgtggtta tcacgggccg  42720
ccgcgcccca cgacccatcg ccgggtcggg ggcggggtcg gggggcgcgg gcgccaagcg  42780
ggccaccgtc agcgagttcg tgcaagtcaa acacattgac cgcgtgggcc ccgctggcgt  42840
ttcgccggcg cctccgccaa acaacaccga ctcgagttcc ctggtgcccg gggcccagga  42900
ttccgccccg cccggcccca cgctaaggga gctgtggtgg gtgttttatg ccgcagaccg  42960
ggcgctggag gagccccgcg ccgactctgg cctcacccgc gaggaggtac gtgccgtacg  43020
tgggttccgg gagcaggcgt ggaaactgtt tggctccgcg ggggccccgc gggcgtttat  43080
cggggccgcg ttgggcctga gccccctcca aaagctagcc gtttactact atatcatcca  43140
ccgagagagg cgcctgtccc ccttccccgc gctagtccgg ctcgtaggcc ggtacacaca  43200
gcgccacggc ctgtacgtcc ctcggcccga cgacccagtc ttggccgatg ccatcaacgg  43260
gctgtttcgc gacgcgctgg cggccggaac cacagccgag cagctcctca tgttcgacct  43320
tctcccccca aaggacgtgc cggtgggaag cgacgtgcag gccgacagca ccgctctgct  43380
gcgctttata gaatcgcaac gtctcgccgt ccccgggggg gtgatctccc ccgagcacgt  43440
cgcgtacctt ggtgcgttcc tgagcgtgct gtacgctggc cgcgggcgca tgtccgcagc  43500
cacgcacacc gcgcggctga caggggtgac ctccctggtg ctagcggtgg gtgacgtgga  43560
ccgtctttcc gcgtttgacc gcggagcggc gggcgcggcc agccgcacgc gggccgccgg  43620
gtacctggat gtgcttctta ccgttcgtct cgctcgctcc caacacggac agtctgtgta  43680
aaagacccca ataaacgtat atcgctacta cacccttgtg tgtcaatgga cgcctctccg  43740
gggggggggg agggaaagca aagaggggct gggggagcgg caccaccggg gcctgaacaa  43800
acaaaccaca gacacggtta cagtttattc ggtcgggcgg agaaacggcc gaagccacgc  43860
ccactttatt cgcgtctcca aaaaaacggg acacttgtcc ggagaacctt taggatgcca  43920
gccagggcgg cggtaatcat aaccacgccc agcgcagagg cggccagaaa cccgggcgca  43980
attgcggcca cgggctgcgt gtcaaaggct agcaaatgaa tgacggttcc gtttggaaat  44040
agcaacaagg ccgtggacgg cacgtcgctc gaaaacacgc ttggggcgcc ctccgtcggc  44100
ccggcggcga tttgctgctg tgtgttgtcc gtatccacca gcaacacaga catgacctcc  44160
ccggccgggg tgtagcgcat aaacacggcc cccacgagcc ccaggtcgcg ctggttttgg  44220
gtgcgcacca gccgcttgga ctcgatatcc cgggtggagc cttcgcatgt cgcggtgagg  44280
taggttagga acagtgggcg tcggacgtcg acgccggtga gcttgtagcc gatcccccgg  44340
ggcagagggg agtgggtgac gacgtagctg gcgttgtggg tgatgggtac caggatccgt  44400
ggctcgacgt tggcagactg ccccccgcac cgatgtgagg cctcagggac gaaggcgcgg  44460
atcagggcgt tgtagtgtgc ccaacgcgtc agggtcgagg cgaggccgtg ggtctgctgg  44520
gccaggactt cgaccggggt ctcggatcgg gtggcttgag ccagcgcgtc caggataaac  44580
acgctctcgt ctagatcaaa gcgcagggag gccgcgcatg gcgaaaagtg gtccggaagc  44640
caaaagaggg ttttctggtg gtcggcccgg gccagcgcgg tccggaggtc ggcgttggtc  44700
gctgcggcga cgtcggacgt acacagggcc gaggctatca gaaggctccg gcgggcgcgt  44760
tcccgctgca ccgccgaggg gacgccagcc aagaacggct gccggaggac agccgaggcg  44820
```

-continued

```
taaaatagcg cccggtggac gaccggggtg gtcagcacgc ggccccctag aaactcggca  44880
tacagggcgt cgatgagatg ggctgcgctg ggcgccactg cgtcgtacgc cgaggggcta  44940
tccagcacga aggccagctg atagcccagc gcgtgtaatg ccaagctctg ttcgcgctcc  45000
agaatctcgg ccaccaggtg ctggagccga gcctctagct gcaggcgggc cgtgggatcc  45060
aagactgaca cattaaaaaa cacagaatcc gcggcacagc ccgcggcccc gcgggcggcc  45120
aacccggcaa gcgcgcgcga gtgggccaaa aagcctagca ggtcggagag gcagaccgcg  45180
ccgtttgcgt gggcggcgtt cacgaaagca aaacccgacg tcgcgagcag ccccgttagg  45240
cgccagaaga gaggggggcg cgggccctgc tcggcgcccg cgtcccccga gaaaaactcc  45300
gcgtatgccc gcgacaggaa ctgggcgtag ttcgtgccct cctccgggta gccgcccacg  45360
cggcggaggg cgtccagcgc ggagccgttg tcggcccgcg tcagggaccc taggacaaag  45420
acccgatacc gggggccgcc cgggggcccg ggaagagccc ccgggggggtt ttcgtccgcg  45480
gggtccccga cccgatctag cgtctggccc gcggggacca ccatcacttc caccggaggg  45540
ctgtcgtgca tggatatcac gagccccatg aattcccgcc cgtagcgcgc gcgcaccagc  45600
gcggcatcgc acccgagcac cagctccccc gtcgtccaga tgcccacggg ccacgtcgag  45660
gccgacgggg agaaatacac gtacctacct ggggatctca acaggccccg ggtggccaac  45720
caggtcgtgg acgcgttgtg caggtgcgtg atgtccagct ccgtcgtcgg gtgccgccgg  45780
gccccaaccg gcggtcgggg gggcggtgta tcacgcggcc cgctcgggtg gctcgccgtc  45840
gccacgttgt ctccccgcgg gaacgtcagg gcctcggggt cagggacggc cgaaaacgtt  45900
acccaggccc gggaacgcag caacacggag gcggctggat tgtgcaagag acccttaagg  45960
ggggcgaccg aggggggagg ctgggcggtc ggctcgaccg tggtgggggc gggcaggctc  46020
gcgttcgggg gccggccgag caggtaggtc ttcgggatgt aaagcagctg gccggggtcc  46080
cgcggaaact cggccgtggt gaccaataca aaacaaaagc gctcctcgta ccagcgaaga  46140
aggggcagag atgccgtagt caggtttagt tcgtccggcg gcgccagaaa tccgcgcggt  46200
ggtttttggg ggtcgggggt gtttggcagc cacagacgcc cggtgttcgt gtcgcgccag  46260
tacatgcggt ccatgcccag gccatccaaa aaccatgggt ctgtctgctc agtccagtcg  46320
tggacctgac cccacgcaac gcccaaaata ataaccccca cgaaccataa accattcccc  46380
atgggggacc ccgtccctaa cccacggggc ccgtggctat ggcagggctt gccgccccga  46440
cgttggctgc gagccctggg ccttcacccg aacttggggg ttggggtggg gaaaaggaag  46500
aaacgcgggc gtattggtcc caatggggtc tcggtggggt atcgacagag tgccagccct  46560
gggaccgaac cccgcgttta tgaacaaacg acccaacacc cgtgcgtttt attctgtctt  46620
tttattgccg tcatagcgcg ggttccttcc ggtattgtct ccttccgtgt ttcagttagc  46680
ctcccccatc tcccgggcaa acgtgcgcgc caggtcgcag atcgtcggta tggagcctgg  46740
ggtggtgacg tgggtctgga ccatcccgga ggtaagttgc agcagggcgt cccggcagcc  46800
ggcgggcgat tggtcgtaat ccaggataaa gacatgcatg ggacggaggc gtttggccaa  46860
gacgtccaaa gcccaggcaa acacgttata caggtcgccg ttgggggcca gcaactcggg  46920
ggcccgaaac agggtaaata acgtgtcccc gatatggggt cgtgggcccg cgttgctctg  46980
gggctcggca ccctggggcg gcacggccgc ccccgaaagc tgtccccaat cctcccgcca  47040
cgacccgccg ccctgcagat accgcaccgt attggcaagc agcccataaa cgcggcgaat  47100
cgcggccagc atagccaggt caagccgctc gccggggcgc tggcgtttgg ccaggcggtc  47160
gatgtgtctg tcctccggaa gggcccccaa cacgatgttt gtgccgggca aggtcggcgg  47220
```

gatgagggcc acgaacgcca gcacggcctg gggggtcatg ctgcccataa ggtatcgcgc 47280
ggccgggtag cacaggaggg cggcgatggg atggcggtcg aagatgaggg tgagggccgg 47340
gggcggggca tgtgagctcc cagcctcccc cccgatatga ggagccagaa cggcgtcggt 47400
cacggcataa ggcatgccca ttgttatctg ggcgcttgtc attaccaccg ccgcgtcccc 47460
ggccgatatc tcaccctggt cgaggcggtg ttgtgtggtg tagatgttcg cgattgtctc 47520
ggaagccccc aacacccgcc agtaagtcat cggctcgggt acgtagacga tatcgtcgcg 47580
cgaacccagg gccaccagca gttgcgtggt ggtggttttc cccatcccgt ggggaccgtc 47640
tatataaacc cgcagtagcg tgggcatttt ctgctccagg cggacttccg tggctttttg 47700
ttgccggcga gggcgcaacg ccgtacgtcg gttgttatgg ccgcgagaac gcgcagcctg 47760
gtcgaacgca gacgcgtgtt gatggcaggg gtacgaagcc atacgcgctt ctacaaggcg 47820
ctggccgaag aggtgcggga gtttcacgcc accaagatct gcggcacgct gttgacgctg 47880
ttaagcgggt cgctgcaggg tcgctcggta ttcgaggcca cacgcgtcac cttaatatgc 47940
gaagtggacc tgggaccgcg ccgccccgac tgcatctgcg tgttcgaatt cgccaatgac 48000
aagacgctgg gcggggtttg tgtcatcata gaactaaaga catgcaaata tatttcttcc 48060
ggggacaccg ccagcaaacg cgagcaacgg gccacgggga tgaagcagct gcgccactcc 48120
ctgaagctcc tgcagtccct cgcgcctccg ggtgacaaga tagtgtacct gtgccccgtc 48180
ctggtgtttg tcgcccaacg gacgctccgc gtcagccgcg tgacccggct cgtcccgcag 48240
aaggtctccg gtaatatcac cgcagtcgtg cggatgctcc agagcctgtc cacgtatacg 48300
gtccccattg agcctaggac ccagcgagcc cgtcgccgcc gcggcggcgc cgcccggggg 48360
tctgcgagca gaccgaaaag gtcacactct ggggcgcgcg acccgcccga gtcagcggcc 48420
cgccagttac cacccgccga ccaaaccccc acctccacgg agggcggggg ggtgcttaag 48480
aggatcgcgg cgctcttctg cgtgcccgtg gccaccaaga ccaaaccccg agccgcctcc 48540
gaatgagagt gtttcgttcc ttccccctcc ccccgcgtca gacaaaccct aaccaccgct 48600
taagcggccc ccgcgaggtc cgaagactca tttggatccg gcgggagcca cccgacaaca 48660
gcccccgggt tttcccacgc cagacgccgg tccgctgtgc catcgcgccc cctcatccca 48720
ccccccatct tgtccccaaa taaaacaagg tctggtagtt aggacaacga ccgcagttct 48780
cgtgtgttat tttcgctctc cgcctctcgc agatggaccc gtactgccca tttgacgctc 48840
tggacgtctg ggaacacagg cgcttcatag tcgccgattc ccgaaacttc atcacccccg 48900
agttcccccg ggacttttgg atgtcgcccg tctttaacct cccccgggag acggcggcgg 48960
agcaggtggt cgtcctacag gcccagcgca cagcggctgc cgctgccctg gagaacgccg 49020
ccatgcaggc ggccgagctc cccgtcgata tcgagcgccg gttacgcccg atcgaacgga 49080
acgtgcacga gatcgcaggc gccctggagg cgctggagac ggcggcggcc gccgccgaag 49140
aggcggatgc cgcgcgcggg gatgagccgg cgggtggggg cgacgggggg gcgcccccgg 49200
gtctggccgt cgcggagatg gaggtccaga tcgtgcgcaa cgacccgccg ctacgatacg 49260
acaccaacct ccccgtggat ctgctacaca tggtgtacgc gggccgcggg gcgaccggct 49320
cgtcgggggt ggtgttcggg acctggtacc gcactatcca ggaccgcacc atcacggact 49380
ttcccctgac cacccgcagt gccgactttc gggacggccg tatgtccaag accttcatga 49440
cggcgctggt actgtccctg caggcgtgcg gccggctgta tgtgggccag cgccactatt 49500
ccgccttcga gtgcgccgtg ttgtgtctct acctgctgta ccgaaacacg cacggggccg 49560

-continued

```
ccgacgatag cgaccgcgct ccggtcacgt tcggggatct gctgggccgg ctgccccgct  49620
acctggcgtg cctggccgcg gtgatcggga ccgagggcgg ccggccacag taccgctacc  49680
gcgacgacaa gctccccaag acgcagttcg cggccggcgg gggccgctac gaacacggag  49740
cgctggcgtc gcacatcgtg atcgccacgc tgatgcacca cggggtgctc ccggcggccc  49800
cgggggacgt cccccgggac gcgagtaccc acgttaaccc cgacggcgtg gcgcaccacg  49860
acgacataaa ccgcgccgcc gccgcgttcc tcagccgggg ccacaaccta ttcctgtggg  49920
aggaccagac tctgctgcgg gcaaccgcga acaccataac ggccctgggc gttatccagc  49980
ggctcctcgc gaacggcaac gtgtacgcgg accgcctcaa caaccgcctg cagctgggca  50040
tgctgatccc cggagccgtc ccttcggagg ccatcgcccg tggggcctcc gggtccgact  50100
cgggggccat caagagcgga gacaacaatc tggaggcgct atgtgccaat tacgtgcttc  50160
cgctgtaccg ggccgacccg gcggtcgagc tgacccagct gtttcccggc ctggccgccc  50220
tgtgtcttga cgcccaggcg gggcggccgg tcgggtcgac gcggcgggtg gtggatatgt  50280
catcgggggc ccgccaggcg gcgctggtgc gcctcaccgc cctggaactc atcaaccgca  50340
cccgcacaaa ccccacccct gtgggggagg ttatccacgc ccacgacgcc ctggcgatcc  50400
aatacgaaca ggggcttggc ctgctggcgc agcaggcacg cattggcttg ggctccaaca  50460
ccaagcgttt ctccgcgttc aacgttagca gcgactacga catgttgtac tttttatgtc  50520
tggggttcat tccacagtac ctgtcggcgg tttagtgggt ggtgggcgag gggggagggg  50580
gcattaggga gaaaaaacaa gagcctccgt tgggttttct ttgtgcctgt actcaaaagg  50640
tcataccccg taaacggcgg gctccagtcc cggcccggcg gttggcgtga acgcaacggc  50700
gggagctggg ttagcgttta gtttagcatt cgctctcgcc tttccgcccg ccccccgacc  50760
gttgcgcctt tttttttttc gtccaccaaa gtctctgtgg gtgcgcgcat ggcagccgat  50820
gccccgggag accggatgga ggagcccctg cccgacaggg ccgtgcccat ttacgtggct  50880
gggtttttgg ccctgtatga cagcggggac tcgggcgagt tggcattgga tccggatacg  50940
gtgcgggcgg ccctgcctcc ggataaccca ctcccgatta acgtggacca ccgcgctggc  51000
tgcgaggtgg ggcgggtgct ggccgtggtc gacgaccccc gcgggccgtt ttttgtgggg  51060
ctgatcgcct gcgtgcagct ggagcgcgtc ctcgagacgg ccgccagcgc tgcgattttc  51120
gagcgccgcg ggccgccgct ctcccgggag gagcgcctgt tgtacctgat caccaactac  51180
ctgccctcgg tctccctggc cacaaaacgc ctggggggcg aggcgcaccc cgatcgcacg  51240
ctgttcgcgc acgtcgcgct gtgcgcgatc gggcggcgcc tcggcactat cgtcacctac  51300
gacaccggtc tcgacgccgc catcgcgccc tttcgccacc tgtcgccggc gtctcgcgag  51360
ggggcgcggc gactggccgc cgaggccgag ctcgcgctgt ccgggcgcac ctgggcgccc  51420
ggcgtggagg cgctgaccca cacgctgctt tccaccgccg ttaacaacat gatgctgcgg  51480
gaccgctgga gcctggtggc cgagcggcgg cggcaggccg ggatcgccgg acacacctac  51540
ctccaggcga gcgaaaaatt caaaatgtgg ggggcggagc ctgtttccgc gccggcgcgc  51600
gggtataaga acggggcccc ggagtccacg gacataccgc ccggctcgat cgctgccgcg  51660
ccgcagggtg accggtgccc aatcgtccgt cagcgcgggg tcgccttgtc cccggtactg  51720
ccccccatga accccgttcc gacatcgggc accccggccc ccgcgccgcc cggcgacggg  51780
agctacctgt ggatcccggc ctcccattac aaccagctcg tcgccggcca tgccgcgccc  51840
caaccccagc cgcattccgc gtttggtttc ccggctgcgg cggggtccgt ggcctatggg  51900
cctcacggtg cgggtctttc ccagcattac cctccccacg tcgcccatca gtatcccggg  51960
```

gtgctgttct cgggacccag cccactcgag gcgcagatag ccgcgttggt gggggccata 52020
gccgcggacc gccaggcggg cggtcagccg gccgcgggag accctggggt ccgggggtcg 52080
ggaaagcgtc gccggtacga ggcggggccg tcggagtcct actgcgacca ggacgaaccg 52140
gacgcggact acccgtacta ccccggggag gctcgaggcg cgccgcgcgg ggtcgactcc 52200
cggcgcgcgg cccgccattc tcccgggacc aacgagacca tcacggcgct gatgggggcg 52260
gtgacgtctc tgcagcagga actggcgcac atgcgggctc ggaccagcgc cccctatgga 52320
atgtacacgc cggtggcgca ctatcgccct caggtggggg agccggaacc aacaacgacc 52380
cacccggccc tttgtccccc ggaggccgtg tatcgccccc caccacacag cgccccctac 52440
ggtcctcccc agggtccggc gtcccatgcc cccactcccc cgtatgcccc agctgcctgc 52500
ccgccaggcc cgccaccgcc cccatgtcct tccacccaga cgcgcgcccc tctaccgacg 52560
gagcccgcgt tccccccgc cgccaccgga tcccaaccgg aggcatccaa cgcggaggcc 52620
ggggcccttg tcaacgccag cagcgcagca cacgtggacg ttgacacggc ccgcgccgcc 52680
gatttgttcg tctctcagat gatgggggcc cgctgattcg ccccggtctt tggtaccatg 52740
ggatgtctta ctgtatatct ttttaaataa accaggtaat accaaataag acccattggt 52800
gtatgttctt tttttattgg gaggcgcggg taggcgggta gctttacaat gcaaaagcct 52860
tcgacgtgga ggaaggcgtg gggggggggg gaatcggcac tgaccaaggg ggtccgtttt 52920
gtcacgggaa aggaaagagg aaacaggccg cggacacccg ggggagtttg tgttcccttt 52980
tctttcttcc cacacacaca aaaggcgtac caaacaaaca aaccaaaaga tgcacatgcg 53040
gtttaacacc cgtggttttt atttacaaca aaccccccat cacaggtcgt cctcgtcggc 53100
gtcaccgtct ttgttgggaa cttgggtgta gttggtgttg cggcgcttgc gcatgaccat 53160
gtcggtgacc ttggcgctga gcagcgcgct cgtgcccttc ttcttggcct tgtgttccgt 53220
gcgctccatg gcagacacca gggccatgta ccgtatcatc tcccgggcct cggctagctt 53280
ggcctcgtca aagtcgccgc cctcctcgcc ctccccggac gcgtccgggt tggtggggtt 53340
cttgagctcc ttggtggtta gcgggtacag ggccttcatg ggttgctct gcagccgcat 53400
gacgtagcga aaggcgaaga aggccgccgc caggccggcc aggaccaaca gacccacggc 53460
cagcgcccca aaggggttgg acatgaagga ggacacgccc gacacggccg ataccacgcc 53520
gcccacgatg cccatcacca ccttgccgac cgcgcgcccc aggtcgccca tcccctcgaa 53580
gaacgcgccc aggcccgcaa acatggcggc gttggcgtcg gcgtggatga ccgtgtcgat 53640
gtcggcgaag cgcaggtcgt gcagctggtt gcggcgctgg acctccgtgt agtccagcag 53700
gccgctgtcc ttgatctcgt ggcgggtgta cacctccagg gggacaaact cgtgatcctc 53760
cagcatggtg atgttgaggt cgatgaaggt gctgacggtg gtgatgtcgg cgcggctcag 53820
ctggtgggag tacgcgtact cctcgaagta cacgtagccc ccaccgaagg tgaagtagcg 53880
ccggtgtccc acggtgcacg gctcgatcgc atcgcgcgtc agccgcagct cgttgttctc 53940
ccccagctgc ccctcgacca acgggccctg gtcttcgtac cgaaagctga ccagggggcg 54000
gctgtagcag gccccgggcc gcgagctgat gcgcatcgag ttttggacga tcacgttgtc 54060
cgcggcgacc ggcacgcacg tggagacggc catcacgtcg ccgagcatcc gcgcgctcac 54120
ccgccggccc acggtggccg aggcgatggc gttggggttc agcttgcggg cctcgttcca 54180
cagggtcagc tcgtgattct gcagctcgca ccacgcgatg gcaacgcggc ccaacatatc 54240
gttgacatgg cgctgtatgt ggttgtacgt aaactgcagc ctggcgaact cgatggagga 54300
ggtggtcttg atgcgctcca cggacgcgtt ggcgctggcc ccgggcggcg ggggcgtggg 54360
gtttgggggc ttgcggctct gctcgcggag gtgttcccgc acgtacagct ccgcgagcgt 54420
gttgctgaga aggggctggt acgcgatcag aaagccccca ttggccaggt agtactgcgg 54480
ctggcccacc ttgatgtgcg tcgcgttgta cctgcgggcg aagatgcggt ccatggcgtc 54540
gcgggcgtcc ttgccgatgc agtcccccag gtccacgcgc gagagcgggt actcggtcag 54600
gttggtggtg aaggtggtgg atatggcgtc ggaagagaat cggaaggagc cgccgtactc 54660
ggagcgcagc atctcgtcca cctcctgcca cttggtcatg gtgcagaccg acgggcgctt 54720
tggcacccag tcccaggcca cggtgaactt gggggtcgtg agcaggttcc gggtggtcgg 54780
cgccgtggcc cgggccttgg tggtgaggtc gcgcgcgtag aagccgtcga cctgcttgaa 54840
gcggtcggcg gcgtagctgg tgtgttcggt gtgcgacccc tcccggtagc cgtaaaacgg 54900
ggacatgtac acaaagtcgc cagtcgccaa cacaaactcg tcgtacgggt acaccgagcg 54960
cgcgtccacc tcctcgacga tgcagtttac cgtcgtcccg taccggtgga acgcctccac 55020
ccgcgagggg ttgtacttga ggtcggtggt gtgccagccc cggctcgtgc gggtcgcggc 55080
gttggccggt ttcagctcca tgtcggtctc gtggtcgtcc cggtgaaacg cggtggtctc 55140
caggttgttg cgcacgtact tggccgtgga ccgacagacc cccttggcgt tgatcttgtc 55200
gatcacctcc tcgaagggga cgggggcgcg gtcctcaaag atccccataa actgggagta 55260
gcggtggccg aaccacacct gcgaaacggt gacgtctttg tagtacatgg tggccttgaa 55320
cttgtacggg gcgatgttct ccttgaagac caccgcgatg ccctccgtgt agttctgacc 55380
ctcgggccgg gtcgggcagc ggcgcggctg ctcgaactgc accaccgtgg cgcccgtggg 55440
gggtgggcac acgtaaaagt ttgcatcggt gttctccgcc ttgatgtccc gcaggtgctc 55500
gcgcagggtg gcgtggcccg cggcgacggt cgcgttgtcg ccggcggggc gcggcggctt 55560
tgggggtttc ggtttttctgt tcttcttcgg tttcgggtcc cccgttgggg gggcgccagg 55620
ggcgggcggc gccggagtgg cagggccccc gttcgccgcc tgggtcgcgg ccgcgacccc 55680
aggcgtgccg ggggaactcg gagccgccga cgccaccagg acccccagcg tcaaccccaa 55740
gagcgcccat acgacgaacc accggcgccc ccgcgcgggg gcgccctggc gcatggcggg 55800
actacggggg cccgtcgtgc cccccgtcag gtagcctggg ggcgaggtgc tggaggaccg 55860
agtagaggat cgagaaaacg tctcggtcgt agaccacgac cgaccggggg ccgatacagc 55920
cgtcgggggc gctctcgacg atggccacca gcggacagtc ggagtcgtac gtgagatata 55980
cgccgggcgg gtaacggtaa cgaccttcgg aggtcgggcg gctgcagtcc gggcggcgca 56040
actcgagctc cccgcaccgg tagaccgagg caaagagtgt ggtggcgata atcagctcgc 56100
gaatatatcg ccaggcggcg cgctgagtgg gcgttattcc ggaaatgccg tcaaaacagt 56160
aaaacctctg aaattcgctg acggcccaat cagcacccga gccccccgcc cccatgatga 56220
accgggcgag ctcctccttc aggtgcggca ggagccccac gttctcgacg ctgtaataca 56280
gcgcggtgtt ggggggctgg gcgaagctgt gggtggagtg atcaaagagg ggcccgttga 56340
cgagctcgaa gaagcgatgg gtgatgctgg ggagcagggc cgggtccacc tggtgtcgca 56400
ggagagacgc tcgcatgaac cggtgcgcgt cgaacacgcc cggcgccgag cggttgtcga 56460
tgaccgtgcc cgcgcccgcc gtcagggcgc agaagcgcgc gcgcgccgca aagccgttgg 56520
cgaccgcggc gaacgtcgcg ggcagcacct cgccgtggac gctgacccgc agcatcttct 56580
cgagctcccc gcgctgctcg cggacgcagc gccccaggct ggccaacgac cgcttcgtca 56640
ggcggtccgc gtacagccgc cgtcgctccc gcacgtccgc ggccgcttgc gtggcgatgt 56700

-continued

```
ccccccacgt ctcgggcccc tgccccccgg gcccgcggcg acggtcttcg tcctcgcccc  56760
cgcccccggg agctcccaac ccccgtgccc cttcctctac ggcgacacgg tccccgtcgt  56820
cgtcggggcc cgcgccgccc ttgggcgcgt ccgccgcgcc ccccgccccc atgcgcgcca  56880
gcacgcgacg cagcgcctcc tcgtcgcact gttcggggct gacgaggcgc cgcaagagcg  56940
gcgtcgtcag gtggtggtcg tagcacgcgc ggatgagcgc ctcgatctga tcgtcgggtg  57000
acgtggcctg accgccgatt attagggcgt ccaccatatc cagcgccgcc aggtggctcc  57060
cgaacgcgcg atcgaaatgc tccgcccgcc gcccgaacag cgccagttcc acggccaccg  57120
cggcggtctc ctgctgcaac tcgcgccgcg ccagcgcggt caggttgctg gcaaacgcgt  57180
ccatggtggt ctggccggcg cggtcgccgg acgcgagcca gaatcgcaat tcgctgatgg  57240
cgtacaggcc gggcgtggtg gcctgaaaca cgtcgtgcgc ctccagcagg gcgtcggcct  57300
ccttgcggac cgagtcgttc tcgggcgacg ggtggggctg cccgtcgccc cccgcggtcc  57360
gggccagcgc atggtccaac acggagagcg cccgcgcgcg gtcggcgtcc gacagcccgg  57420
cggcgtgggg caggtaccgc cgcagctcgt tggcgtccag ccgcacctgc gcctgctggg  57480
tgacgtggtt acagatacgg tccgccaggc ggcgggcgat cgtcgccccc tggttcgccg  57540
tcacacacag ttcctcgaaa cagaccgcgc aggggtggga cgggtcgcta agctccgggg  57600
ggacgataag gcccgacccc accgccccca ccataaactc ccgaacgcgc tccagcgcgg  57660
cggtggcgcc gcgcgagggg gtgatgaggt ggcagtagtt tagctgcttt agaaagttct  57720
cgacgtcgtg caggaaacac agctccatat ggacggtccc gccatacgta tccagcctga  57780
cccgttggtg atacggacag ggtcgggcca ggcccatggt ctccgtgaaa aacgccgcga  57840
cgtctcccgc ggtcgcgaac gtctccaggc tgcccaggag ccgctcgccc tcgcgccacg  57900
cgtactctag cagcaactcc agggtgaccg acagcggggt gagaaaggcc ccggcctggg  57960
cctccaggcc cggcctcaga cgacgccgca gcgcccgcac ctgaagcgcg ttcagcttca  58020
gttgggggag cttcccccgt ccgatgtggg ggtcgcaccg ccggagcagc tctatctgaa  58080
acacataggt ctgcacctgc ccgagcaggg ctaacaactt ttgacgggcc acggtgggct  58140
cggacaccgg ggcggccatc tcgcggcgcc gatctgtacc gcggccggag tatgcggtgg  58200
accgaggcgg tccgtacgct acccggcgtc tggctgagcc ccggggtccc cctcttcggg  58260
gcggcctccc gcgggcccgc cgaccggcaa gccgggagtc ggcggcgcgt gcgtttctgc  58320
tctattccca gacaccgcgg agaggaatca cggcccgccc agagatatag acacggaaca  58380
caaacaagca cggatgtcgt agcaataatt tattttacac acattccccg ccccgcccta  58440
ggttccccca ccccccaacc cctcacagca tatccaacgt caggtctccc tttttgtcgg  58500
ggggcccctc cccaaacggg tcatccccgt ggaacgcccg tttgcggccg gcaaatgccg  58560
gtcccggggc ccccgggccg ccgaacggcg tcgcgttgtc gtcctcgcag ccaaaatccc  58620
caaagttaaa cacctccccg gcgttgccga gttggctgac tagggcctcg gcctcgtgcg  58680
ccacctccag ggccgcgtcc gtcgaccact cgccgttgcc gcgctccagg gcacgcgcgg  58740
tcagctccat catctcctcg cttaggtact cgtcctccag gagcgccagc cagtcctcga  58800
tctgcagctg ctgggtgcgg ggccccaggc ttttcacggt cgccacgaac acgctactgg  58860
cgacggccgc cccgccctcg gagataatgc cccggagctg ctcgcacagc gagctttcgt  58920
gcgctccgcc gccgaggctt gaggccgcgc acacaaaccc ggcccgggga caggccagga  58980
cgaacttgcg ggtgcggtca aaaataagga gcgggcacgc gtttttgccg cccatcaggc  59040
```

-continued

```
tggcccagtt cccggcctga aacacacggt cgttgccggc catgccgtag tacttgctga  59100
tgctcaaccc caacacgacc atggggcgcg ccgccatgac gggccgcagc aggttgcagc  59160
tggcgaacat ggacgtccac gcgcccggat gcgcgtccac ggcgtccatc agcgcgcggg  59220
ccccggcctc caggcccgcc ccgccctgcg cggaccacgc ggccgcagcc tgcacgctgg  59280
ggggacggcg ggaccccgcg atgatggccg taagggtgtt gatgaagtat gtcgagtgat  59340
cgcagtaccg cagaatctgg tttgccatgt agtacatcgc cagctcgctc acgttgttgg  59400
gggccaggtt aataaagttt atcgcgccgt agtccaggga aaacttttta atgaacgcga  59460
tggtctcgat gtcctcgcgc gacaggagcc gggcgggaag ctggttgcgt tggagggccg  59520
tccagaacca ctgcgggttc ggctggttgg accccggggg cttgccgttg gggaagatgg  59580
ccgcgtggaa ctgcttcagc agaaagccca gcggtccgag gaggatgtcc acgcgcttgt  59640
cgggcttctg gtaggcgctc tggaggctgg cgacccgcgc cttggcggcc tcggacgcgt  59700
tggcgctcgc gcccgcgaac aacacgcggc tcttgacgcg cagctccttg ggaaacccca  59760
gggtcacgcg ggcaacgtcg ccctcgaagc tgctctcggc gggggccgtc tggccggccg  59820
ttaggctggg ggcgcagata gccgccccct ccgagagcgc gaccgtcagc gttttggccg  59880
acagaaaccc gttgttaaac atgtccatca cgcgccgccg cagcaccggt tggaattgat  59940
tgcgaaagtt gcgcccctcg accgactgcc cggcgaacac cccgtggcac tgactcaggg  60000
ccaggtcctg gtacacggcg aggttggatc gccgcccgag aagctgaagc agggggcacg  60060
gcccgcacgc gtacgggtcc agcgtcaggg acatggcgtg gttggcctcg cccagaccgt  60120
cgcgaaactt gaagttcctc ccctccacca ggttgcgcat cagctgctcc acctcgcggt  60180
ccacgacctg cctgacgttg ttcaccaccg tatgcagggc ctcgcggttg gtgatgatgg  60240
tctccagccg ccccatggcc gtggggaccg cctggtccac gtactgcagg gtctcgagtt  60300
cggccatgac gcgctcggtc gccgcgcggt acgtctcctg catgatggtc cgggcggtct  60360
cggatccgtc cgcgcgcttc agggccgaga aggcggcgta gtttcccagc acgtcgcagt  60420
cgctgtacat gctgttcatg gtcccgaaga cgccgatggc tccgcgggcg gcgctggcga  60480
actttggatg gcgcgcccgg aggcgcatga gcgtcgtgtg tacgcaggcg tggcgcgtgt  60540
cgaaggtgca taggttacag ggcacgtcgg tctggttgga gtccgcgacg tatcgaaaca  60600
cgtccatctc ctggcgcccg acgatcacgg cgccgtcgca gcgctccagg taaaacagca  60660
tcttggccag cagcgccggg gaaaacccac acagcatggc caggtgctcg ccggcaaatt  60720
cctgggttcc gccgacgagg ggcgcggtgg gccgaccctc gaacccgggc accacgtgtc  60780
cctcgcggtc cacctgtggg ttggccgcca cgtgggtccc gggcacgagg aagaagcggt  60840
aaaaggaggg tttgctgtgg tcctttgggt ccgccgggcc ggcgtcgtcc acctcggtga  60900
gatggagggc cgagttggtg ctaaatacca tggcccccac gagtcccgcg gcgcgcgcca  60960
ggtacgcccc gacggcgttg gcgcgggccg cggccgtgtc ctggccctcg aacagcggcc  61020
acgcggagat gtcggtgggc ggctcgtcaa agacggccat cgacacgata gactcgaggg  61080
ccagggcggc gtctccggcc atgacggagg ccaggcgctg ttcgaacccg cccgccgcgc  61140
ccttgccgcc gccgtcgcgc ccgccccgcg gggtcttacc ctggctggct tcgaaggccg  61200
tgaacgtaat gtcggcgggg agggcggcgc cctcgtggtt ttcgtcaaac gccaggtggg  61260
cggccgcgcg ggccacggcg tccacgtttc ggcatcgcag tgccacggcg gcgggtccca  61320
cgaccgcctc gaacaggagg cggttgaggg ggcggttaaa aaacggaagc gggtaggtaa  61380
atttctcccc gatcgatcgg tggttggcgt tgaacggctc tgcgatgaca cggctaaaat  61440
```

```
ccggcatgaa cagctgcaac gggtacacgg gtatgcggtg cacctccgcc ccgcctatgg  61500
ttaccttgtc cgagcctccc aggtgcagaa aggtgttgtt gatgcacacg gcctccttga  61560
agccctcggt aacgaccaga tacaggaggg cgcggtccgg gtccaggccg aggcgctcac  61620
acagcgcctc ccccgtcgtc tcgtgtttga ggtcgccggg ccggggggtg tagtccgaaa  61680
agccaaaatg gcggcgtgcc cgctcgcaaa gtcgcgtcag gttcggggcc tgggtgctgg  61740
ggtccaggtg ccggccgccg tgaaagacgt acacggacga gctgtagtgc gagggcgtca  61800
gtttcaggga caccgcggta cccccgagcc ccgtcgtgcg agaacccacg accacggcca  61860
cgttggcctc aaagccgctc tccacggtca ggcccacgac caggggcgcc acggcgacgt  61920
cggaatcgcc gctgcgtgcc gacagtaacg ccagaagctc gatgccttcg gacggacacg  61980
cgcgagcgta cacgtatccc aggggcccgg gggggacctt gatggtggtt gccgtcttgg  62040
gctttgtctc catgtccttt tgtcaatcgg tccgcgaacg gaggtaatcc cggcacgacg  62100
acggacgccc gacaaggtat gtctcccgag cgtcaaaatc cggggggggg cggcgacggt  62160
caaggggagg gttggagacc ggggttgggg aatgaatccc tccccttcac cgacaacccc  62220
ccgggtaacc acggggtcgc cgatgaaccc cggcggccgg caacgcgggg tccctgcgag  62280
aggcacagat gcttacggtc aggtgctccg ggtcgggtgc gtctggtatg cggttggtat  62340
atgtacactt tacctggggg cgtgccggtc cgccccagcc cctcccacgc cccgcgcgtc  62400
atcagccggt gggcgtggcc gctattataa aaaaagtgag aacgcgaagc gttcgcactt  62460
tgtcctaata atatatatat tattaggaca aagtgcgaac gcttcgcgtt ctcacttttt  62520
ttataatagc ggccacgccc accggctacg tcactctcct gtcggccgcc ggcggtccat  62580
aagcccggcc ggccgggccg acgcgaataa accgggccgc cggccggggc gccgcgcagc  62640
agctcgccgc ccggatccgc cagacaaaca aggcccttgc acatgccggc ccgggcgagc  62700
ctgggggtcc ggtaattttg ccatcccacc caagcggctt tttgggtttt tctcttcccc  62760
cctccccaca ttcccctctt taggggttcg ggtgggaaca accgcgatgt tttccggtgg  62820
cggcggcccg ctgtcccccg gaggaaagtc ggcggccagg gcggcgtccg ggtttttttgc  62880
gcccgccggc cctcgcggag ccagccgggg acccccgcct tgtttgaggc aaaactttta  62940
caacccctac ctcgccccag tcgggacgca acagaagccg accgggccaa cccagcgcca  63000
tacgtactat agcgaatgcg atgaatttcg attcatcgcc ccgcgggtgc tggacgagga  63060
tgcccccccg gagaagcgcg ccggggtgca cgacggtcac ctcaagcgcg cccccaaggt  63120
gtactgcggg ggggacgagc gcgacgtcct ccgcgtcggg tcgggcggct tctggccgcg  63180
gcgctcgcgc ctgtggggcg gcgtggacca cgccccggcg gggttcaacc ccaccgtcac  63240
cgtctttcac gtgtacgaca tcctggagaa cgtggagcac gcgtacggca tgcgcgcggc  63300
ccagttccac gcgcggttta tggacgccat cacaccgacg gggaccgtca tcacgctcct  63360
gggcctgact ccggaaggcc accgggtggc cgttcacgtt tacggcacgc ggcagtactt  63420
ttacatgaac aaggaggagg tcgacaggca cctacaatgc cgcgccccac gagatctctg  63480
cgagcgcatg gccgcggccc tgcgcgagtc cccgggcgcg tcgttccgcg gcatctccgc  63540
ggaccacttc gaggcggagg tggtggagcg caccgacgtg tactactacg agacgcgccc  63600
cgctctgttt taccgcgtct acgtccgaag cgggcgtgtg ctgtcgtacc tgtgcgacaa  63660
cttctgcccg gccatcaaga agtacgaggg tggggtcgac gccaccaccc ggttcatcct  63720
ggacaacccc gggttcgtca ccttcggctg gtaccgtctc aaaccgggcc ggaacaacac  63780
```

-continued

```
gctagcccag ccggcggccc cgatggcctt cgggacatcc agcgacgtcg agtttaactg  63840
tacggcggac aacctggcca tcgagggggg catgagcgac ctaccggcat acaagctcat  63900
gtgcttcgat atcgaatgca aggcgggggg ggaggacgag ctggcctttc cggtggccgg  63960
gcacccggag gacctggtca tccagatatc ctgtctgctc tacgacctgt ccaccaccgc  64020
cctggagcac gtcctcctgt tttcgctcgg ttcctgcgac ctccccgaat cccacctgaa  64080
cgagctggcg gccaggggcc tgcccacgcc cgtggttctg gaattcgaca gcgaattcga  64140
gatgctgttg gccttcatga cccttgtgaa acagtacggc cccgagttcg tgaccgggta  64200
caacatcatc aacttcgact ggcccttctt gctggccaag ctgacggaca tttacaaggt  64260
ccccctggac gggtacggcc gcatgaacgg ccggggcgtg tttcgcgtgt gggacatagg  64320
ccagagccac ttccagaagc gcagcaagat aaaggtgaac ggcatggtga acatcgacat  64380
gtacgggatt ataaccgaca agatcaagct ctcgagctac aagctcaacg ccgtggccga  64440
agccgtcctg aaggacaaga agaaggacct gagctatcgc gacatccccg cctactacgc  64500
cgccgggccc gcgcaacgcg gggtgatcgg cgagtactgc atacaggatt ccctgctggt  64560
gggccagctg ttttttaagt ttttgcccca tctggagctc tcggccgtcg cgcgcttggc  64620
gggtattaac atcacccgca ccatctacga cggccagcag atccgcgtct ttacgtgcct  64680
gctgcgcctg gccgaccaga agggctttat tctgccggac acccaggggc gatttagggg  64740
cgccgggggg gaggcgccca agcgtccggc cgcagcccgg gaggacgagg agcggccaga  64800
ggaggagggg gaggacgagg acgaacgcga ggagggcggg ggcgagcggg agccggaggg  64860
cgcgcgggag accgccggca ggcacgtggg gtaccagggg gccagggtcc ttgaccccac  64920
ttccgggttt cacgtgaacc ccgtggtggt gttcgacttt gccagcctgt accccagcat  64980
catccaggcc cacaacctgt gcttcagcac gctctccctg agggccgacg cagtggcgca  65040
cctggaggcg ggcaaggact acctggagat cgaggtgggg gggcgacggc tgttcttcgt  65100
caaggctcac gtgcgagaga gcctcctcag catcctcctg cgggactggc tcgccatgcg  65160
aaagcagatc cgctcgcgga ttccccagag cagccccgag gaggccgtgc tcctggacaa  65220
gcagcaggcc gccatcaagg tcgtgtgtaa ctcggtgtac gggttcacgg gagtgcagca  65280
cggactcctg ccgtgcctgc acgttgccgc gacggtgacg accatcggcc gcgagatgct  65340
gctcgcgacc cgcgagtacg tccacgcgcg ctgggcggcc ttcgaacagc tcctggccga  65400
tttcccggag gcggccgaca tgcgcgcccc cgggccctat tccatgcgca tcatctacgg  65460
ggacacggac tccatctttg tgctgtgccg cggcctcacg gccgccgggc tgacggccgt  65520
gggcgacaag atggcgagcc acatctcgcg cgcgctgttt ctgcccccca tcaaactcga  65580
gtgcgaaaag acgttcacca agctgctgct gatcgccaag aaaaagtaca tcggcgtcat  65640
ctacgggggt aagatgctca tcaagggcgt ggatctggtg cgcaaaaaca actgcgcgtt  65700
tatcaaccgc acctccaggg ccctggtcga cctgctgttt tacgacgata ccgtctccgg  65760
agcggccgcc gcgttagccg agcgccccgc ggaggagtgg ctggcgcgac ccctgcccga  65820
gggactgcag gcgttcgggg ccgtcctcgt agacgcccat cggcgcatca ccgacccgga  65880
gagggacatc caggactttg tcctcaccgc cgaactgagc agacacccgc gcgcgtacac  65940
caacaagcgc ctggcccacc tgacggtgta ttacaagctc atggcccgcc gcgcgcaggt  66000
cccgtccatc aaggaccgga tcccgtacgt gatcgtggcc cagacccgcg aggtagagga  66060
gacggtcgcg cggctggccg ccctccgcga gctagacgcc gccgccccag gggacgagcc  66120
cgcccccccc gcggccctgc cctccccggc caagcgcccc cgggagacgc cgtcgcctgc  66180
```

-continued

```
cgaccccccg ggaggcgcgt ccaagccccg caagctgctg gtgtccgagc tggccgagga  66240
tcccgcatac gccattgccc acggcgtcgc cctgaacacg gactattact tctcccacct  66300
gttgggggcg gcgtgcgtga cattcaaggc cctgtttggg aataacgcca agatcaccga  66360
gagtctgtta aaaaggttta ttcccgaagt gtggcacccc ccggacgacg tggccgcgcg  66420
gctccggacc gcagggttcg gggcggtggg tgccggcgct acggcggagg aaactcgtcg  66480
aatgttgcat agagcctttg atactctagc atgagccccc cgtcgaagct gatgtccctc  66540
attttacaat aaatgtctgc ggccgacacg gtcggaatct ccgcgtccgt gggtttctct  66600
gcgttgcgcc ggaccacgag cacaaacgtg ctctgccaca cgtgggcgac gaaccggtac  66660
cccgggcacg cggtgagcat ccggtctatg agccggtagt gcaggtgggc ggacgtgccg  66720
ggaaagatga cgtacagcat gtggccccgg taagtggggt ccgggtaaaa caacagccgc  66780
gggtcgcacg ccccgcctcc gcgcaggatc gtgtggacga aaaaaagctc gggttggcca  66840
agaatcccgg ccaagaggtc ctggaggggg gcgttgtggc ggtcggccaa cacgaccaag  66900
gaggccagga aggcgcgatg ctcgaatatc gtgttgatct gctgcacgaa ggccaggatt  66960
agggcctcgc ggctggtggc ggcgaaccgc ccgtctcccg cgttgcacgc gggacagcaa  67020
cccccgatgc ctaggtagta gcccatcccg gagagggtca ggcagttgtc ggccacggtc  67080
tggtccagac agaagggcag cgagacggga gtggtcttca ccaggggcac cgagagcgag  67140
cgcacgatgg cgatctcctc ggagggcgtc tgggcgaggg cggcgaaaag gccccgatag  67200
cgctggcgct cgtgtaaaca cagctcctgt ttgcgggcgt gaggcggcag gctcttccgg  67260
gaggcccgac gcaccacgcc cagagtcccg ccggccgcag aggagcgcga ccgccggcgc  67320
tccttgccgt gatagggccc gggccgggag ccgcggcgat gggggtcggt gtcatacata  67380
ggtacacagg gtgtgctcca gggacaggag cgagatcgag tggcgtctaa gcagcgcgcc  67440
cgcctcacgg acaaatgtgg cgagcgcggt gggctttggt acaaatacct gatacgtctt  67500
gaaggtgtag atgagggcac gcaacgctat gcagacacgc ccctcgaact cgttcccgca  67560
ggccagcttg gccttgtgga gcagcagctc gtcgggatgg gtggcggggg gatggccgaa  67620
cagaacccag gggtcaacct ccatctccgt aatggcgcac atggggtcac agaacatgtg  67680
cttaaagatg gcctcgggcc ccgcggcccg aagcaggctc acaaaccggc ccccgtcccc  67740
gggctgcgtc tcggggtcag cctcgagctg gtcgacgacg ggtacgatac agtcgaagag  67800
gctcgtgttg ttttccgagt agcggaccac ggaggcccgg agtctgcgca gggccagcca  67860
gtaagcacgc accagtaaca ggttacacag caggcattct ccgccggtgc gcccgcgccc  67920
ccggccgtgt ttcagcacgg tggccatcag agggcccagg tcgaggtcgg gctgggcatc  67980
gggttcggta aactgcgcaa agcgcggagc cacgtcgcgc gtgcgtgccc cgcgatgcgc  68040
ttcccaggac tggcggaccg tggcgcgacg ggcctccgcg gcagcgcgca gctggggccc  68100
cgactcccag acggcggggg tgccggcgag gagcaacagg accagatccg cgtacgccca  68160
cgtatccggc gactcctccg gctcgcggtc cccggcgacc gtctcgaatt ccccgttgcg  68220
agcggcggcg cgagtacagc agctgtcccc gcccccgcgc cgaccctccg tgcagtccag  68280
gagacgggcg caatccttcc agttcatcag cgcggtggtg agcgacggct gcgtgccgga  68340
tcccgccgcc gaccccgccc cctcctcgcc cccggaggcc aaggttccga tgagggcccg  68400
ggtggcagac tgcgccagga acgagtagtt ggagtactgc accttggcgg ctcccgggga  68460
gggcgagggc ttgggttgct tctgggcatg ccgcccgggc accccgccgt cggtacggaa  68520
```

gcagcagtgg agaaaaaagt gccggtggat gtcgtttatg gtgagggcaa agcgtgcgaa 68580
ggagccgacc agggtcgcct tcttggtgcg cagaaagtgg cggtccatga cgtacacaaa 68640
ctcgaacgcg gccacgaaga tgctagcggc gcagtggggc gcccccaggc atttggcaca 68700
gagaaacgcg taatcggcca cccactgagg cgagaggcgg taggtttgct tgtacagctc 68760
gatggtgcgg cagaccagac agggccggtc cagcgcgaag gtgtcgatgg ccgccgcgga 68820
aaagggcccg gtgtccaaaa gcccctcccc acagggatcc gggggcgggt tgcggggtcc 68880
tccgcgcccg cccgaacccc ctccgtcgcc cgcccccccg cgggcccttg agggggcggt 68940
gaccacgtcg gcggcgacgt cctcgtcgag cgtaccgacg ggcggcacac ctatcacgtg 69000
actggccgtc aggagctcgg cgcagagagc ctcgttaaga gccaggaggc tgggatcgaa 69060
ggccacatac gcgcgctcga acgcccccgc cttccagctg ctgccggggg actcttcgca 69120
caccgcgacg ctcgccagga ccccgggggg cgaagttgcc atggctgggc gggaggggcg 69180
cacgcgccag cgaactttac gggacacaat ccccgactgc gcgctgcggt cccagaccct 69240
ggagagtcta gacgcgcgct acgtctcgcg agacggcgcg catgacgcgg ccgtctggtt 69300
cgaggatatg acccccgccg agctggaggt tgtcttcccg actacggacg ccaagctgaa 69360
ctacctgtcg cggacgcagc ggctggcctc cctcctgacg tacgccgggc ctataaaagc 69420
gcccgacgac gccgccgccc cgcagacccc ggacaccgcg tgtgtgcacg gcgagctgct 69480
cgccgccaag cgggaaagat tcgcggcggt cattaaccgg ttcctggacc tgcaccagat 69540
tctgcggggc tgacgcgcgt gctgttgggc gggacggttc gcgaaccctt tggtgggttt 69600
acgcgggcac gcacgctccc atcgcgggcg ccatggcggg actgggcaag ccctacaccg 69660
gccacccagg tgacgccttc gagggtctcg ttcagcgaat tcggcttatc gtcccatcta 69720
cgttgcgggg cggggacggg gaggcgggcc cctactctcc ctccagcctc ccctccaggt 69780
gcgcctttca gtttcatggc catgacgggt ccgacgagtc gtttcccatc gagtatgtac 69840
tgcggcttat gaacgactgg gccgaggtcc cgtgcaaccc ttacctgcgc atacagaaca 69900
ccggcgtgtc ggtgctgttt caggggtttt ttcatcgccc acacaacgcc cccgggggcg 69960
cgattacgcc agagcggacc aatgtgatcc tgggctccac cgagacgacg gggctgtccc 70020
tcggcgacct ggacaccatc aaggggcggc tcggcctgga tgcccggccg atgatggcca 70080
gcatgtggat cagctgcttt gtgcgcatgc cccgcgtgca gctcgcgttt cggttcatgg 70140
gccccgaaga tgccggacgg acgagacgga tcctgtgccg cgccgccgag caggctatta 70200
cccgtcgccg ccgaacccgg cggtcccggg aggcgtacgg ggccgaggcc gggctggggg 70260
tggccggaac gggtttccgg gccagggggg acggttttgg cccgctcccc ttgttaaccc 70320
aagggccctc ccgcccgtgg caccaggccc tgcggggtct taagcaccta cggattggcc 70380
cccccgcgct cgttttggcg gcgggactcg tcctgggggc cgctatttgg tgggtggttg 70440
gtgctggcgc gcgcctataa aaaaggacgc accgccgccc taatcgccag tgcgttccgg 70500
acgccttcgc cccacacagc cctcccgacc gacaccccca tatcgcttcc cgacctccgg 70560
tcccgatggc cgtcccgcaa tttcaccgcc ccagcaccgt taccaccgat agcgtccggg 70620
cgcttggcat gcgcgggctc gtcttggcca ccaataactc tcagtttatc atggataaca 70680
accacccgca cccccagggc acccaagggg ccgtgcggga gtttctcccgc ggtcaggcgg 70740 cggcgctgac ggaccttggt ctggcccacg caaacaacac gtttaccccg cagcctatgt 70800
tcgcgggcga cgccccggcc gcctggttgc ggcccgcgtt tggcctgcgg cgcacctatt 70860
caccgtttgt cgttcgagaa ccttcgacgc ccgggacccc gtgaggcccg gggagttcct 70920
tctggggtgt tttaatcaat aaaagaccac accaacgcac gagccttgcg tttaatgtcg 70980
tgtttattca agggagtggg atagggttcg acggttcgaa acttaacaca ccaaataatc 71040
gagcgcgtct agcccagtaa catgcgcacg tgatgtaggc tggtcagcac ggcgtcgctg 71100
tgatgaagca gcgcccggcg ggtccgctgt aactgctgtt gtaggcggta acaggcgcgg 71160
atcagtaccg ccagggcgct acgaccggtg cgttgcacgt agcgtcgcga cagaactgcg 71220
tttgccgata cgggcggggg gccgaattgt aagcgcgtca cctcttggga gtcatcggcg 71280
gataacgcac tgaatggttc gttggttatg gggagtgtg gttccccagg gagtgggtcg 71340
agcgcctcgg cctcggaatc cgagaggaac aacgaggtgg cgtcggagtc ttcgtcgtca 71400
gagacataca gggtctgaag cagcgacacg ggcgggggg tagcgtcgat gtgtagcgcg 71460
agggaggatg cccacgaaga caccccagac aaggagctgc ccgtgcgtgg atttgtggaa 71520
gacgcggaag ccgggacgga tgggcggttt tgcggtgccc ggaaccgaac cgccggatac 71580
tccccgggtg ctacatgccc gttttggggc tggggttggg gctggggttg gggctggggt 71640
tggggctggg gttggggctg gggttggggc tggggttggg gttggggttg gggctggggt 71700
tggggttggg gctggggctg gggctggggc tggggctggg gctggggctg gggctggggc 71760
tggggctggg gctggggctg gggctggggc tggggctggg gctggggttg gggcgcggac 71820
aggcggctga cggtcaaatg cccccggggg cgcgcagatg tggtgggcgt ggccaccggc 71880
tgccgtgtag tggggcggcg ggaaaccggg cctccgggcg caacaccgcc ctccagcgtc 71940
aagtatgtgg ggggcgggcc tgacgtcggg ggcggggcga cgggttggac cgcgggaggc 72000
gggggagagg gacctgcggg agaggatgag gtcggctcgg ccgggttgcg gcctaaaaca 72060
ggggccgtgg ggtcggcggg gtcccagggt gaagggaggg attcccgcga ttcggacagc 72120
gacgcgacag cggggcgcgt aaggcgccgc tgcggcccgc ctacgggaac cctggggggg 72180
gttggcgcgg gacccgaggt tagcgggggg cggcggtttt cgcccccggg caaaaccgtg 72240
ccggttgcga ccgggggcgg aacgggatcg atagggagag cgggagaagc ctggccggcg 72300
gcctggggcc cgagcgggag gggcacacca gacaccaaag cgtggggcgc tggctctggg 72360
ggtttgggag gggccggggg gcgcgcgaaa tcggtaaccg gggcgaccgt gtcggggagg 72420
gcaggcggcc gccaaccctg ggtggtcgcg gaagcctggg tggcgcgcgc cagggagcgt 72480
gcccggcggt gtcggcgcgc gcgcgacccg gacgaagaag cggcagaagc gcgggaggag 72540
gcgggggggc ggggggcggt ggcatcgggg ggcgccgggg aactttgggg ggacggcaag 72600
cgccggaagt cgtcgcgggg gcccacgggc gccggccgcg tgctttcggc cgggacgccc 72660
ggtcgtgctt cgcgagccgt gactgccggc ccagggggcc gcggtgcaca ctgggacgtg 72720
gggacggact gatcggcggt gggcgaaagg gggtccgggg caaggagggg cgcggggccg 72780
ccggagtcgt cagacgcgag ctcctccagg ccgtgaatcc atgcccacat gcgagggggg 72840
acgggctcgc cgggggtggc gtcggtgaat agcgtggggg ccaggcttcc gggccccaac 72900
gagccctccg ccccaacaag gtccacaggg ccgggggtcg ggtttgggac cgaggggctc 72960
tggtcgtcgg gggcgcgctg gtacaccgga tgccccggga atagctcccc cgacaggagg 73020
gaggcgtcga acggccgccc gaggatagct cgcgcgagga aggggtcctc gtcggtggcg 73080
ctggcggcga ggacgtcctc gccgcccgcc acaaacggga gctcctcggt ggcctcgctg 73140
ccaacaaacc gcacgtcggg ggggccgggg gggtccgggt tttcccacaa caccgcgacc 73200
ggggtcatgg agatgtccac gagcaccaga cacggcgggc cccgggcgag gggccgctcg 73260

-continued

```
gcgatgagcg cggacaggcg cgggagctgt gccgccagac acgcgttttc gatcgggttc  73320
aggtcggcgt gcaggaggcg gacggcccac gtctcgatgt cggacgacac ggcatcgcgc  73380
aaggcggcgt ccggcccgcg agcgcgtgag tcaaacagcg tgagacacag ctccagctcc  73440
gactcgcggg aaaaggccgt ggtgttgcgg agcgccacga cgacgggcgc gcccaggagc  73500
actgccgcca gcaccaggtc catggccgta acgcgcgccg cgggggtgcg gtgggtggcg  73560
gcggccggca cggcgacgtg ctggcccgtg ggccggtaga gggcgttggg gggagcgggg  73620
ggtgacgcct cgcgcccccc cgaggggctc agcgtctgcc cagattccag acgcgcggtc  73680
agaagggcgt cgaaactgtc atactctgtg tagtcgtccg gaaacatgca ggtccaaaga  73740
gcgaccagag cggtgcttgg gagacacatg cgcccgagga cgctcaccgc cgccagcgcc  73800
tgggcgggac tcagctttcc cagcgcggcg ccgcgctcgg ttcccagctc ggggaccgag  73860
cgccagggcg ccagggggtc ggtttcggac aacttgccgc ggcgccagtc tgccagccgc  73920
gtgccgaaca tgaggccccg ggtcggaggg cctccggccg aaaacgctgg cagcacgcgg  73980
atgcgggcgt ctggatgcgg ggtcaggcgc tgcacgaata gcatggaatc tgctgcgttc  74040
tgaaacgcac gggggagggt gagatgcatg tactcgtgtt ggcgaaccag atccaggcgc  74100
caaaaggtgt aaatgtgttc cggggagctg gccaccagcg ccaccagcac gtcgttctcg  74160
ttaaaggaaa cgcggtgcct agtggagctc tggggtccga gcggcggccc cggggccgcc  74220
gcgtcacccc cccattccag ctgggcccag cgacacccaa actcgcgcgt gagagtggtc  74280
gcgacgaggg cgacgtagag ctcggccgcc gcatccatcg aggcccccca tctcgcctgg  74340
cggtggcgca caaagcgtcc gaagagctga aagttggcgg cctgggcgtc gctgagggcc  74400
agctgaagcc ggttgatgac ggtgaggacg tacatggccg tgacggtcga ggccgactcc  74460
agggtgtccg tcggaagcgg ggggcgaatg catgccgcct cgggacacat cagcagcgcg  74520
ccgagcttgt cggtcacggc cgggaagcag agcgcgtact gcagtggcgt tccatccggg  74580
accaaaaagc tgggggcgaa cggccgatcc agcgtactgg tggcctcgcg cagcaccagg  74640
ggccccgggc ctccgctcac tcgcaggtac gcctcgcccc ggcggcgcag catctgcggg  74700
tcggcctctt ggccgggtgg ggcggacgcc cgggcgcggg cgtctagggc gcgaagatcc  74760
acgagcaggg gcgcgggcgc ggccgccgcg cccgcgcccg tctggcctgt ggccttggcg  74820
tacgcgctat ataagcccat gcggcgttgg atgagctccc gcgcgccccg gaactcctcc  74880
accgcccatg gggccaggtc cccggccacc gcgtcgaatt ccgccaacag gccccccagg  74940
gtgtcaaagt tcatctccca ggccaccctt ggcaccacct cgtcccgcag ccgggcgctc  75000
aggtcggcgt gttgggccac gcgccccccg agctcctcca cggccccggc ccgctcggcg  75060
ctcttggcgc ccaggacgcc ctggtacttg gcgggaaggc gctcgtagtc ccgctgggct  75120
cgcagccccg acacagtgtt ggtggtgtcc tgcagggcgc gaagctgctc gcatgccgcg  75180
cgaaatccct cgggcgattt ccaggccccc ccgcgaacgc ggccgaagcg accccatacc  75240
tcgtcccact ccgcctcggc ctcctcgaga gacctccgca gggcctcgac gcggcgacgg  75300
gtgtcgaaga gcgcctgcag gcgcgcgccc tgtcgcgtca ggaggcccgg gccgtcgccg  75360
ctggccgcgc ttagcgggtg cgtctcaaag gtacgctggg catgttccaa ccaggcgacc  75420
gcctgcacgt cgagctcgcg cgccttctcc gtctggtcca ccagaatttc gacctgatcc  75480
gcgatctcct ccgccgagcg cgcctggtcc agcgtcttgg ccacggtcgc cgggacggcg  75540
accaccttca gcagggtctt cagattggcc agaccctcgg cctcgagctg ggcccggcgc  75600
tcgcgcgcgg ccagcacctc ccgcagcccc gccgtgaccc gctcggtggc ttcggcgcgc  75660
```

-continued

```
tgctgtttgg cgcgcaccac ggcgtccttg gtatcggcca ggtcctgtcg ggtcacgaat  75720
gcgacgtagt gcgcgtacgc cgtgtccttc acggggctct ggtccacgcg ctccagcgcc  75780
gccacgcacg ccaccagcgc gtcctcgctc gggcagggca gggtgacccc tgcccggaca  75840
agctcggcgg ccgccgccgg gtcgttgcgc accgcggata tctcctccgc ggcggcggcc  75900
aggtccagcg ccacgcttcc gatcgcgcgc cgcgcgtcgg cccggagggc gtccaggcga  75960
tcgcggatat ccacgtactc ggcgtagccc ttttgaaaaa acggcacgta ctggcgcagg  76020
gccggcacgc cccccaagtc ttccgacagg tgtaggacgg cctcgtggta gtcgataaac  76080
ccgtcgttcg cctgggcccg ctccagcagc ccccccgcca gccgcagaag ccgcgccagg  76140
ggctcggtgt ccacccgaaa catgtcggcg tacgtgtcgg ccgcggcccc gaaggccgcg  76200
ctccagtcga tgcggtgaat ggctgcgagc ggggggagca tggggtggcg ctggttctcg  76260
ggggtgtatg ggttaaacgc aagggccgtc tccagggcaa gggtcaccgc cttggcgttg  76320
gttcccagcg cctgttcggc ccgctttcgg aagtcccggg ggttgtagcc gtgcgtgccc  76380
gccagcgcct gcaggcgacg gagctcgacc acgtcaaact cggcaccgct ttccacgcgg  76440
tccagcacgg cctccacgtc ggcggcccag cgctcgtggc tactgcgggc gcgctgggcc  76500
gccatcttct ctctgaggtc ggcggtggcg gcctcaagtt cgtcggcgcg gcgtcgcgtg  76560
gcgccgatga cctttcccag ctcctgcagg gcgcgcccgc tgggggagtg gtccccggcc  76620
gtcccttcgg cgtgcaacag gcccccgaac ctgccctcgt ggcccgcgag gctttcccgc  76680
gcgccggtgg tcgcgcgcgt cgcggcctgg atcagggagg catgctctcc ctccggttgg  76740
ttggcggccc ggcgcacctg gacgacaagg tcggcggcag ccgaccctaa ggtcgtgagc  76800
tgggcgatgg ccacccgcgc gtccagggcc aaccgagtcg ccttgacgta tcccgcggcg  76860
ctgtcggcca tggccgctag gaaggccagg ggggaggccg ggtcgctggc ggccgcgccc  76920
agggccgtca ccgcgtcgac caggacgcgg tgcgcccgca cggccgcatc caccgtcgac  76980
gcagggtctg ccgttgcgac ggcggcgctg ccggcgttga tggcgttcga gacggcgtgg  77040
gctatgatcg gggcgtgatc ggcgaagaac tgcaagagaa acggagtctc tggggcgtcg  77100
gcgaacaggt tcttcagcac caccacgaag ctgggatgca agccagacag agccgtcgcc  77160
gtgtccggag tcgggtgctc cagggcatct cggtactgcc ccagcagccc ccacatgtcc  77220
gcccgcagcg ccgccgtaac ctcagggggc gccccccgaa cggcctcggg gaggtccgac  77280
cagcccgccg gcagggaggc ccgcagggtc gccaggacgg ccggacaggc ctttagcccc  77340
acaaagtcag ggagggggcg caggaccccc tggagtttgt gcaagaactt ctcccgggcg  77400
tcgcgggcca ccttcgcccg ctcccgcgct ccctcgagca ttgcctccag ggagcgcgcg  77460
cgctcccgca aacgggcacg cgcatcgggg gcgagctctg ccgtcagctt ggcggcatcc  77520
atggcccgcg cctgccgcag cgcttcctcg gccatgcgcg tggcctctgg cgacagcccg  77580
ccgtcgtcgg ggtagggcga cgcgccgggc gcaggaacaa aggccgcgtc gctgtccagc  77640
tgctggccca gggccgcatc tagggcgtcg aagcgccgca gctcggccag acccgagctg  77700
cggcgcgcct gttggtcgtt aatgtcgcgg atgctgcgcg ccagctcgtc cagtggcttg  77760
cgttctatca gcccttggtt ggcggcgtcc gtcaggacgg agagccaggc cgccaggtcc  77820
tcgggggcgt ccagcgtctg gccccgctgg atcagatccc gcaacaggat ggccgtgggg  77880
ctggtcgcga tcgggggcgg ggcgggaatg gcggcgcgct gcgcgatgtc ccgcgtgtgc  77940
tggtcgaaga caggcaggga ctcgagcagc tggaccacgg gcacgacggc ggccgaagcc  78000
```

-continued

```
acgtgaaacc ggcggtcgtt gttgtcgctg gcctgtagag ccttggcgct gtatacggcc  78060
ccccggtaaa agtactcctt aaccgcgccc tcgatcgccc gacgggcctg ggtccgcacc  78120
tcctccagcc gaacctgaac ggcctcgggg cccagggggg gtgggcgcgg agccccctgc  78180
ggggccgccc cggccggggc gggcattacg ccgaggggcc cggcgtgctg tgagaccgcg  78240
tcgaccccgc gagcgagggc gtcgagggcc tcgcgcatct ggcgatcctc cgcctccacc  78300
ctaatctctt cgccacgggc aaatttggcc agagcctgga ctctatacag aagcggttct  78360
gggtgcgtcg gggtggcggg ggcaaaaagg gtgtccgggt gggcctgcga gcgctccaga  78420
agccactcgc cgaggcgtgt atacagattg gccggcgggg ccgcgcgaag ctgcagctcc  78480
aggtccgcga gttccccgta aaaggcgtcc gtctcccgaa tgacatccct agccacaagg  78540
atcagcttcg ccagcgccag gcgaccgatc agagagtttt cgtccagcac gtgctggacg  78600
aggggcagat gggcggccac gtcggccagg ctcaggcgcg tggaggccag aaagtccccc  78660
acggccgttt tccagggcag catgttcagg gtaaactcca gcagggcggc ggccgggccg  78720
gccaccccgg cctgggtgtg cgtccgggcc ccgttctcga tgagaaaggc gaggacgcgt  78780
tcaaagaaaa aaataacaca gagctccagc agccccggag aggccggata cggcgaccgt  78840
aaggcgctga tggtgagccg cgaacacgcg gcgacctcgc gggccagggc ggcggagcac  78900
gcggtgaact taaccgccgt ggcggccacg tttgggtggg cctcgaacag ctgggcgagg  78960
tctgcgcccg gggctcggg cgagcggcga gtcttcagcg cctcgagggc ctgtgaggac  79020
gccggaaccg tgggcccgtc gtcctcgccc gcctcggcga ccggcggccc ggccgggtcg  79080
gggggtgccg aggcgaggac aggctccgga acggaggcgg ggaccgcggc cccgacgggg  79140
gttttgcctt tgggggtgga tttcttcttg gttttggcag ggggggccga gcgtttcgtt  79200
ttctccccg aagtcaggtc ttcgacgctg gaaggcggag tccaggtggg tcggcggcgc  79260
ttgggaaggc cggccgagta gcgtgcccgg tgccgaccaa ccgggacgac gcccatctcc  79320
aggacccgca tgtcgtcgtc atcttcttcg gccgcctctg cggcgggggt cttgggggcg  79380
gagggaggcg gtggtgggat cgcggagggt gggtcggcgg agggtgggtc ggcggagggg  79440
ggatccgtgg gtggggtacc cttcagggcc accgcccata catcgtcggg cgcccgattc  79500
gggcgcttgg cctctggttt tgccgacgga ccggccgtcc cccgggatgt ctcggaggcc  79560
ctgtcgtcgc gacgggcccg ggtcggtggc ggcgactggg cggctgtggg cgggtgtggc  79620
cccgggcccc ctacccctc ccgggggccc acgccgacgc agggctcccc caggcccgcg  79680
atctcgcccc gcagggggtg cgtgatggcc acgcgccgtt cgctgaacgc ttcgtcctgc  79740
aggtaagtct cgctggcccc gtaaagatgc agagccgcgg ccgtcaagtc cgcaggagcc  79800
gcgggttccg ggcccgacgg cacgaaaaac accatggctc ccgcccaccg tacgtccggg  79860
cgatcgcggg tgtaatacgt caggtatgga tacatgtccc ccgcccgcac tttggcgatg  79920
aacgcggggg tgccctccgg aaggccgtgc gggtcaaaaa ggtatgcggt gtcgccgtcc  79980
ctgaacagcc ccatccctag ggggccaatg gttaggagcg tgtacgacag ggggcgcagg  80040
gcccacgggc cggcgaagaa cgtgtgtgcg gggcattgtg tctccagcag gcccgccgcg  80100
ggctccccga agaagcccac ctcgccgtat acgcgcgaga agacacagcg cagtccgccg  80160
cgcgccccctg ggtactcgag gaagttgggg agctcgacga tcgaacacat gcgcggcggc  80220
ccagggcccg cggtcgcgcg cgtccactcg cccccctcga ccaaacatcc ctcgatggcc  80280
tccgcggaca ggacgtcgcg agggcccaca tcaaatatga ggctgagaaa ggacagcgac  80340
gagcgcatgc acgataccga cccccccggc tccaggtcgg gcgcgaactg gttccgagca  80400
```

ccggtgacca cgatgtcgcg atcccccccg cgttccatcg tggagtgcgg tggggtgccc 80460
gcgatcatat gtgccctgct ggccagagac ccggcctgtt tatggaccgg acccccgggg 80520
ttagtgttgt ttccgccacc catgcccccg taccatggcc ccggttcccc tgattaggct 80580
acgagtcgcg gtgatcgctt cccaaaaacc gagctgcgtt tgtctgtctt ggtcttccac 80640
cccccccccc gcccgcccgc acaccataac accgagaaca acacacgggg gtgggcgtaa 80700
cataataaag ctttattggt aactagttaa cggcaagtcc gtgggtggcg cgacggtgtc 80760
ctccgggatc atctcgtcgt cctcgacggg ggtgttggaa tgaggcgccc cctcgcggtc 80820
cgcctggcgt gggccgtgcc cataggcctc cggcttctgt gcgtccatgg gcataggcgc 80880
ggggagactg tttccggcgt cgcggacctc caggtccctg ggagactccg gtccggctaa 80940
cggacgaaac gcggaagcgc gaaacacgcc gtcggtgacc cgcaggagct cgttcatcag 81000
taaccaatcc atactcagcg taacggccag cccctggcga gacagatcca cggagtccgg 81060
aaccgcggtc gtctggccca gggggccgag gctgtagtcc ccccaggccc ctaggtcgcg 81120
acggctcgta agcacgacgc ggtcggccgc ggggctttgc ggggggggcgt cctcgggcgc 81180
atgcgccatt acctctcgga tggccgcggc gcgctggtcg gccgagctga ccaagggcgc 81240
cacgaccacg gcgcgctccg tctgcaggcc cttccacgtg tcgtggagtt cctggacaaa 81300
ctcggccacg ggctcgggtc ccgcggccgc gcgcgcggct tgatagcagg ccgacagacg 81360
ccgccagcgc gctagaaact gacccatgaa gcaaaacccg gggacctggt ctcccgacag 81420
cagcttcgac gcccgggcgt gaatgccgga cacgacggac agaaacccgt gaatttcgcg 81480
ccggaccacg gccagcacgt tgtcctcgtg cgacacctgg gccgccagct cgtcgcacac 81540
ccccaggtgc gccgtggttt cggtgatgac ggaacgcagg ctcgcgaggg acgcgaccag 81600
cgcgcgcttg gcgtcgtgat acatgctgca gtactgactc accgcgtccc ccatggcctc 81660
ggggggccag ggccccaggc ggtcgggcgt gtccccgacc accgcataca ggcggcgccc 81720
gtcgctctcg aaccgacact cgaaaaaggc ggagagcgtg cgcatgtgca gccgcagcag 81780
cacgatggcg tcctccagtt ggcgaatcag ggggtctgcg cgctcggcga ggtcctgcag 81840
caccccccgg gcggccaggg cgtacatgct aatcaacagg aggctggtgc ccacctcggg 81900
gggcgggggg ggctgcagct ggaccagggg ccgcagctgc tcgacggcac ccctggagat 81960
cacgtacagc tcccggagca gctgctctat gttgtcggcc atctgcatag tggggccgag 82020
gccgccccgg gcggccggtt cgaggagggt gatcagcgcg cccagtttgg tgcgatggcc 82080
ctcaaccgtg gggagatagc ccagcccaaa gtcccgggcc caggccaaca cacgcagggc 82140
gaactcgacc gggcggggaa ggtaggccgc gctacacgtg gccctcagcg cgtccccgac 82200
caccagggcc agaacgtagg ggacgaagcc cgggtcggcg aggacgttgg ggtgaatgcc 82260
ctcgagggcg gggaagcgga tctgggtcgc cgcggccagg tggacagagg gggcgtggct 82320
gggctgcccg acggggagaa gcgcggacag cggcgtggcc ggggtggtgg gggtgatgtc 82380
ccagtgggtc tgaccataca cgtcgatcca gatgagcgcc gtctcgcgga gaaggctggg 82440
ttgaccggaa ctaaagcggc gctcggccgt ctcaaactcc cccacgagcg cccgccgcag 82500
gctcgccaga tgttccgtcg gcacggccgg acccatgata cgcgccagcg tctggcttag 82560
aacgcccccc gacaggccga ccgcctcgca gagccgcccg tgcgtgtgct cgctggcgcc 82620
ctggacccgc ctgaaagttt ttacgtagtt ggcatagtac ccgtattccc gcgccaaccc 82680
aaacacgttc gaccccgcga gggcaatgca cccaaagagc tgctggactt cgccgagtcc 82740

-continued

```
gtggccggtg ggcgtccgcg cggggacgcc cgccgccaga aacccctcca gggccgaaag  82800
gtagtgcgtg cagtgcgagg gcgtgaaccc agcgtcgatc agggtgttga tcaccacgga  82860
gggcgaattg gtattctgga tcaacgtcca cgtctgctgc agcagagcca gcagccgctg  82920
ctgggcgccg gcggagggct gctccccgag ctgcagcagg ctggagacgg caggctggaa  82980
gactgccagt gccgacgaac tcaggaacgg cacgtcggga tcaaacacgg ccacgtccgt  83040
ccgcacgcgc gccattagcg tccccggggg cgcacaggcc gagcgcgggc tgacgcggct  83100
gagggccgtc gacacgcgca cctcctcgcg gctgcgaacc atcttgttgg cctcgagcgg  83160
cggaatcatt atggccgggt cgatctcccg cacggtgtgc tgaaactgcg ccaacagggg  83220
cggcgggacc acagcccccc gctcgggggt cgtcaggtac tcgtccacca gggccaacgt  83280
aaagagggcc cgtgtgaggg gagtgagggt cgcgtcgtct atgcgctgga ggtgcgccga  83340
gaacagcgtc acccgattac tcaccagggc caagaaccgg aggccctctt gcacgaacgg  83400
ggcggggaag agcaggctgt acgccggggt ggtaaggttc gcgctgggct gccccaacgg  83460
gaccggcgcc atcttgagcg acgtctcccc aagggcctcg atggaggtcc gcgggctcat  83520
ggccaagcag ctcttggtga cggtttgcca gcggtctatc cactccacgg cgcactggcg  83580
gacgcggacc ggccccaggg ccgccgcggt gcgcaggccg gcggaatcca gcgcatggga  83640
cgtgtcggag ccggtgaccg cgaggatggt gtccttgatg acctccatct cccggaaggc  83700
ctggtcgggg gcctcgggga gagccaccac caagcggtgt acgagcaacc cggggaggtt  83760
ctcggccaag agcgccgtct ccggaagccc gtgggcccgg tggagcgcgc acaggtgttc  83820
cagcagcggc cgccagcagt cccgcgcgtc tgccggggcg atggccgttc ccgacaacag  83880
aaacgccgcc atggcggcgc gcagcttggc cgtggccaga aacgccgggt cgtccgcccc  83940
gtttgccgtc tcggccgtgg gggttggcgg ttggcgaagg ccggctaggc tcgccaatag  84000
gcgctgcata ggtccgtccg agggcggacc ggcgggtgag gtcgtgacga cgggggcctc  84060
ggacgggaga ccgcggtctg ccatgacgcc cggctcgcgt gggtggggga cagcgtagac  84120
caacgacgag accgggcggg aatgactgtc gtgcgctgta gggagcggcg aattatcgat  84180
cccccgcggc cctccaggac ccccgcaggc gttgcgagta ccccgcgtct tcgcggggtg  84240
ttatacggcc acttaagtcc cggcatcccg ttcgcggacc caggcccggg ggattgtccg  84300
gatgtgcggg cagcccggac ggcgtgggtt gcggactttc tgcggggcgg cccaaatggc  84360
cctttaaacg tgtgtatacg gacgcgccgg gccagtcggc caacacaacc caccggaggc  84420
ggtagccgcg tttggctgtg gggtgggtgg ttccgccttg cgtgagtgtc ctttcgaccc  84480
ccccccccct ccctcccccg ggtcttgcta ggtcgcgatc tggggtcgca atgaagacca  84540
atccgctacc cgcaacccct tccgtgtggg gcgggagtac cgtggaactc ccccccacaa  84600
cacgcgatac cgcgggacag ggcctgcttc ggcgcgtcct gcgccccccg atctctcgcc  84660
gcgacggccc agggctcccc agggggtcgg gaccccggag ggcggccagc acgctgtggt  84720
tgcttggcct ggacggcaca gacgcgcccc ctggggcgct gacccccaac gacgataccg  84780
aacaggccct ggacaagatc ctgcggggca ccatgcgcgg gggggcggcc ctgatcggct  84840
ccccgcgcca tcatctaacc cgccaagtga tcctgacgga tctgtgccaa cccaacgcgg  84900
atcgtgctgg gacgctgctt ctggcgctgc ggcaccccgc cgacctgcct cacctggccc  84960
accagcgcgc cccgccaggc cggcagaccg agcggctggg cgaggcctgg ggccagctga  85020
tggaggcgac cgccctgggg tcggggcgag ccgagagcgg gtgcacgcgc gcgggcctag  85080
tgtcgtttaa cttcctggtg gcggcgtgtg ccgcctcgta cgacgcgcgc gacgccgccg  85140
```

-continued

```
atgcggtacg ggcccacgtc acggccaact accgcgggac gcgggtgggg gcgcgcctgg  85200
atcgtttttc cgagtgtctg cgcgccatgg ttcacacgca cgtcttcccc cacgaggtca  85260
tgcggttttt cggggggctg gtgtcgtggg tcacccagga cgagctagcg agcgtcaccg  85320
ccgtgtgcgc cgggccccag gaggcggcgc acaccggcca cccgggccgg ccccgctcgg  85380
ccgtgatcct cccggcatgt gcgttcgtgg acctggacgc cgagctgggg ctggggggcc  85440
cgggcgcggc gtttctgtac ctggtattca cttaccgcca gcgccgggac caggagctgt  85500
gttgtgtgta cgtgatcaag agccagctcc ccccgcgcgg gttggagccg gccctggagc  85560
ggctgtttgg gcgcctccgg atcaccaaca cgattcacgg caccgaggac atgacgcccc  85620
cggccccaaa ccgaaacccc gacttccccc tcgcgggcct ggccgccaat ccccaaaccc  85680
cgcgttgctc ggctggccag gtcacgaacc cccagttcgc cgacaggctg taccgctggc  85740
agccggacct gcgggggcgc cccaccgcac gcacctgtac gtacgccgcc tttgcagagc  85800
tcggcatgat gcccgaggat agtccccgct gcctgcaccg caccgagcgc tttggggcgg  85860
tcagcgtccc cgttgtcatt ctggaaggcg tggtgtggcg ccccggcgag tggcgggcat  85920
gcgcgtgagc gtagcaaacg ccccgcccac acaacgctcc gcccccaacc ccttccccgc  85980
tgtcactcgt tgttcgttga cccgggcgtc cgccaaataa agccactgaa acccgaaacg  86040
cgagtgttgt aacgtccttt gggcgggagg aagccacaaa atgcaaatgg gatacatgga  86100
aggaacacac ccccgtgact caggacatcg gtgtgtcctt ttgggtttca ctgaaactgg  86160
cccgcgcccc acccctgcgc gatgtggata aaaagccagc gcgggtggtt tagggtacca  86220
caggtgggtg ctttggaaac ttgccggtcg ccgtgctcct gtgagcttgc gtccctcccc  86280
ggtttccttt gcgctcccgc cttccggacc tgctctcgcc tactcttctt tggctctcgg  86340
tgcgattcgt caggcagcgg ccttgtcgaa tctcgacccc accactcgcc ggacccgccg  86400
acgtcccctc tcgagcccgc cgaaacccgc cgcgtctgtt gaaatggcca gccgcccagc  86460
cgcatcctct cccgtcgaag cgcgggcccc ggttggggga caggaggccg gcggccccag  86520
cgcagccacc caggggggagg ccgccggggc ccctctcgcc cacggccacc acgtgtactg  86580
ccagcgagtc aatggcgtga tggtgctttc cgacaagacg cccgggtccg cgtcctaccg  86640
catcagcgat aacaactttg tccaatgtgg ttccaactgc accatgatca tcgacggaga  86700
cgtggtgcgc gggcgccccc aggacccggg ggccgcggca tcccccgctc ccttcgttgc  86760
ggtgacaaac atcggagccg gcagcgacgg cgggaccgcc gtcgtggcat tcgggggaac  86820
cccacgtcgc tcggcgggga cgtctaccgg tacccagacg gccgacgtcc ccaccgaggc  86880
ccttgggggc ccccctcctc ctccccgctt caccctgggt ggcggctgtt gttcctgtcg  86940
cgacacacgg cgccgctctg cggtattcgg gggggagggg gatccagtcg gccccgcgga  87000
gttcgtctcg gacgaccggt cgtccgattc cgactcggat gactcggagg acacggactc  87060
ggagacgctg tcacacgcct cctcggacgt gtccggcggg gccacgtacg acgacgccct  87120
tgactccgat tcgtcatcgg atgactccct gcagatagat ggccccgtgt gtcgcccgtg  87180
gagcaatgac accgcgcccc tggatgtttg ccccgggacc cccggcccgg gcgccgacgc  87240
cggtggtccc tcagcggtag acccacacgc gccgacgcca gaggccggcg ctggtcttgc  87300
ggccgatccc gccgtggccc gggacgacgc ggaggggctt tcggaccccc ggccacgtct  87360
gggaacgggc acggcctacc ccgtccccct ggaactcacg cccgagaacg cggaggccgt  87420
ggcgcgcttt ctgggagatg ccgtgaaccg cgaacccgcg ctcatgctgg agtacttttg  87480
```

-continued

```
ccggtgcgcc cgcgaggaaa ccaagcgtgt cccccccagg acattcggca gccccccctcg  87540
cctcacggag gacgactttg ggcttctcaa ctacgcgctc gtggagatgc agcgcctgtg  87600
tctggacgtt cctccggtcc cgccgaacgc atacatgccc tattatctca gggagtatgt  87660
gacgcggctg gtcaacgggt tcaagccgct ggtgagccgg tccgctcgcc tttaccgcat  87720
cctgggggtt ctggtgcacc tgcggatccg gacccgggag gcctcctttg aggagtggct  87780
gcgatccaag gaagtggccc tggattttgg cctgacggaa aggcttcgcg agcacgaagc  87840
ccagctggtg atcctggccc aggctctgga ccattacgac tgtctgatcc acagcacacc  87900
gcacacgctg gtcgagcggg ggctgcaatc ggccctgaag tatgaggagt tttacctaaa  87960
gcgttttggc gggcactaca tggagtccgt cttccagatg tacacccgca tcgccggctt  88020
tttggcctgc cgggccacgc gcggcatgcg ccacatcgcc ctggggcgag aggggtcgtg  88080
gtgggaaatg ttcaagttct ttttccaccg cctctacgac caccagatcg taccgtcgac  88140
ccccgccatg ctgaacctgg ggacccgcaa ctactacacc tccagctgct acctggtaaa  88200
cccccaggcc accacaaaca aggcgaccct gcgggccatc accagcaacg tcagtgccat  88260
cctcgcccgc aacgggggca tcgggctatg cgtgcaggcg tttaacgact ccggccccgg  88320
gaccgccagc gtcatgcccg ccctcaaggt ccttgactcg ctggtggcgg cgcacaacaa  88380
agagagcgcg cgtccgaccg gcgcgtgcgt gtacctggag ccgtggcaca ccgacgtgcg  88440
ggccgtgctc cggatgaagg gggtcctcgc cggcgaagag gcccagcgct gcgacaatat  88500
cttcagcgcc ctctggatgc cagacctgtt tttcaagcgc ctgattcgcc acctggacgg  88560
cgagaagaac gtcacatgga ccctgttcga ccgggacacc agcatgtcgc tcgccgactt  88620
tcacggggag gagttcgaga agctctacca gcacctcgag gtcatggggt tcggcgagca  88680
gatacccatc caggagctgg cctatggcat tgtgcgcagt gcggccacga ccgggagccc  88740
cttcgtcatg ttcaaagacg cggtgaaccg ccactacatc tacgacaccc agggggcggc  88800
catcgccggc tccaacctct gcaccgagat cgtccatccg gcctccaagc gatccagtgg  88860
ggtctgcaac ctgggaagcg tgaatctggc ccgatgcgtc tccaggcaga cgtttgactt  88920
tgggcggctc cgcgacgccg tgcaggcgtg cgtgctgatg gtgaacatca tgatcgacag  88980
cacgctacaa cccacgcccc agtgcacccg cggcaacgac aacctgcggt ccatgggaat  89040
cggcatgcag ggcctgcaca cggcctgcct gaagctgggg ctggatctgg agtctgccga  89100
atttcaggac ctgaacaaac acatcgccga ggtgatgctg ctgtcggcga tgaagaccag  89160
caacgcgctg tgcgttcgcg gggcccgtcc cttcaaccac tttaagcgca gcatgtatcg  89220
cgccggccgc tttcactggg agcgctttcc ggacgcccgg ccgcggtacg agggcgagtg  89280
ggagatgcta cgccagagca tgatgaaaca cggcctgcgc aacagccagt ttgtcgcgct  89340
gatgcccacc gccgcctcgg cgcagatctc ggacgtcagc gagggctttg ccccccctgtt  89400
caccaacctg ttcagcaagg tgacccggga cggcgagacg ctgcgcccca acacgctcct  89460
gctaaaggaa ctggaacgca cgtttagcgg gaagcgcctc ctggaggtga tggacagtct  89520
cgacgccaag cagtggtccg tggcgcaggc gctcccgtgc ctggagccca cccacccccct  89580
ccggcgattc aagaccgcgt ttgactacga ccagaagttg ctgatcgacc tgtgtgcgga  89640
ccgcgccccc tacgtcgacc atagccaatc catgaccctg tatgtcacgg agaaggcgga  89700
cgggaccctc ccagcctcca ccctggtccg ccttctggtc cacgcatata agcgcggact  89760
aaaaacaggg atgtactact gcaaggttcg caaggcgacc aacagcgggg tctttggcgg  89820
cgacgacaac attgtctgca tgagctgcgc gctgtgaccg acaaaccccc tccgcgccag  89880
```

gcccgccgcc actgtcgtcg ccgtcccacg ctctcccctg ctgccatgga ttccgcggcc 89940
ccagccctct cccccgctct gacggccctt acggaccaga gcgcgacggc ggacctggcg 90000
atccagattc caaagtgccc cgaccccgag aggtacttct acacctccca gtgtcccgac 90060
attaaccacc tgcgctccct cagcatcctt aaccgctggc tggaaaccga gcttgttttc 90120
gtgggggacg aggaggacgt ctccaagctt tccgagggcg agctcagctt ttaccgcttc 90180
ctcttcgctt tcctgtcggc cgccgacgac ctggttacgg aaaacctggg cggcctctcc 90240
ggcctgtttg agcagaagga cattctccac tactacgtgg agcaggaatg catcgaagtc 90300
gtacactcgc gcgtgtacaa catcatccag ctggtgcttt tccacaacaa cgaccaggcg 90360
cgccgcgagt acgtggccgg taccatcaac cacccggcca tccgcgccaa ggtggactgg 90420
ttggaagcgc gggtgcggga atgcgcctcc gttccggaaa agttcattct catgatcctc 90480
atcgagggca tctttttgc cgcctcgttt gccgccatcg cctaccttcg caccaacaac 90540
cttctgcggg tcacctgcca gtcaaacgac ctcatcagcc gggacgaggc cgtgcacacg 90600
acggcctcgt gttacatcta caacaactac ctcggcgggc acgccaagcc cccgcccgac 90660
cgcgtgtacg ggctgttccg ccaggcggtc gagatcgaga tcggatttat ccgatcccag 90720
gcgccgacgg acagccatat cctgagcccg gcggcgctgg cggccatcga aaactacgtg 90780
cgattcagcg cggatcgcct gttgggcctt atccacatga agccactgtt ttccgcccca 90840
ccccccgacg ccagctttcc gctgagcctc atgtccaccg acaaacacac caattttttc 90900
gagtgtcgca gcacctccta cgccggggcg gtcgtcaacg atctgtgagt gtcgcggcgc 90960
gcttctaccc gtgtttgccc ataataaacc tctgaaccaa actttgggtc tcattgtgat 91020
tcttgtcagg gacgcggggg tgggagagga taaaaggcgg cgcaaaaagc agtaaccagg 91080
tccgtccaga ttctgcgggc ataggatacc ataattttat tggtgggtcg tttgttcggg 91140
gacaagcgcg ctcgtctgac gtttgggcta ctcgtcccag aatttggcca ggacgtcctt 91200
gtagaacgcg ggtggggggg cctgggtccg caactgctcc agaaacctgt cggcgatatc 91260
aggggccgtg atatgccggg tcacgataga tcgcgccagg ttttcgtcgc ggatgtcctg 91320
gtagataggc aggcgtttca gaagagtcca cggcccccgc tccttggggc cgataagcga 91380
tatgacgtac ttaatgtagc ggtgttccac cagctcggtg atggtcatgg gatcggggag 91440
ccagtccagg gactctgggg cgtcgtggat gacgtggcgt cgcgggttgg ccacataact 91500
gcggtgctct tccagcagct gcgcgttcgg gacctggacg agctcgggcg gggtgagtat 91560
ctccgaggag gacgacctgg ggccggggtg gcccccggta acgtcccggg gatccagggg 91620
gaggtcctcg tcgtcttcgt atccgccggc gatctgttgg gttagaattt cggtccacga 91680
gacgcgcgtc tcggtgccgc cggcggccgg cggcagaggg ggcctggttt ccgtggagcg 91740
cgagctggtg tgttcccggc ggatggcccg ccgggtctga gagcgactcg ggggggtcca 91800
gtgacattcg cgcagcacat cctccacgga ggcgtaggtg ttattgggat ggaggtcggt 91860
gtggcagcgg acaaagaggg ccaggaactg ggggtagctc atcttaaagt actttagtat 91920
atcgcgacag ttgatcgtgg gaatgtagca ggcgctaata tccaacacaa tatcacagcc 91980
catcaacagg aggtcagtgt ccgtggtgta cacgtacgcg accgtgttgg tgtgatagag 92040
gttggcgcag gcatcgtccg cctccagctg acccgagtta atgtaggcgt accccagggc 92100
ccggagaacg cgaatacaga acagatgcgc cagacgcagg gccggcttcg agggcgcggc 92160
ggacggcagc gcggctccgg acccggccgt cccccgggtc cccgaggcca gagaggtgcc 92220

```
gcgccggcgc atgttggaaa aggcagagct gggtctggag tcggtgatgg gggaaggcgg  92280
tggagaggcg tccacgtcac tggcctcctc gtccgtccgg cactgggccg tcgtgcgggc  92340
caggatggcc ttggctccaa acacaaccgg ctccatacaa ttgaccccgc gatcggtaac  92400
gaagatgggg aaaagggact tttgggtaaa cacctttaat aagcgacaga ggcagtgtag  92460
cgtaatggcc tcgcggtcgt aactggggta tcggcgctga tatttgacca ccaacgtgta  92520
catgacgttc cacaggtcca cggcaatggg ggtgaagtac ccggccgggg ccccaaggcc  92580
ccggcgcttg accagatggt gtgtgtgggc aaacttcatc atcccgaaca aacccatgtc  92640
aggtcaattg taactgcgga tcggcctaac taaggcgtgg ttggtgcgac ggtccgggac  92700
acccgagcct gtctctctgt gtatggtgac ccagacaaca acaccgacac aagaggacaa  92760
taatccgtta ggggacgctc tttataattt cgatggccca actccacgcg gattggtgca  92820
gcaccctgca tgcgccggtg cgggccaacc ttccccccgc tcattgcctc ttccaaaagg  92880
gtgtggccta acgagctggg ggcgtattta atcaggctag cgcggcgggc ctgccgtagt  92940
ttctggctcg gtgagcgacg gtccggttgc ttgggtcccc tggctgccat caaaacccca  93000
ccctcgcagc ggcatacgcc ccctccgcgt cccgcacccg agaccccggc ccggctgccc  93060
tcaccaccga agcccacctc gtcactgtgg ggtgttccca gcccgcgttg ggatgacgga  93120
ttcccctggc ggtgtggccc ccgcctcccc cgtggaggac gcgtcggacg cgtccctcgg  93180
gcagccggag gagggggcgc cctgccaggt ggtcctgcag ggcgccgaac ttaatggaat  93240
cctacaggcg tttgccccgc tgcgcacgag ccttctggac tcgcttctgg ttatgggcga  93300
ccggggcatc cttatccata acacgatctt tggggagcag gtgttcctgc ccctggaaca  93360
ctcgcaattc agtcggtatc gctggcgcgg acccacggcg gcgttcctgt ctctcgtgga  93420
ccagaagcgc tccctcctga gcgtgtttcg cgccaaccag tacccggacc tacgtcgggt  93480
ggagttggcg atcacgggcc aggccccgtt tcgcacgctg gttcagcgca tatggacgac  93540
gacgtccgac ggcgaggccg ttgagctagc cagcgagacg ctgatgaagc gcgaactgac  93600
gagctttgtg gtgctggttc cccagggaac ccccgacgtt cagttgcgcc tgacgaggcc  93660
gcagctcacc aaggtcctta acgcgaccgg ggccgatagt gccacgccca ccacgttcga  93720
gctcggggtt aacggcaaat tttccgtgtt caccacgagt acctgcgtca cctttgctgc  93780
ccgcgaggag ggcgtgtcgt ccagcaccag cacccaggtc cagatcctgt ccaacgcgct  93840
caccaaggcg ggccaggcgg ccgccaacgc caagacggtg tacggggaaa atacccatcg  93900
caccttctct gtggtcgtcg acgattgcag catgcgggcg gtgctccggc gactgcaggt  93960
cggcgggggc accctcaagt tcttcctcac gacccccgtc cccagtctgt gcgtcaccgc  94020
caccggtccc aacgcggtat cggcggtatt tctcctgaaa ccccagaaga tttgcctgga  94080
ctggctgggt catagccagg ggtctccttc agccgggagc tcggcctccc gggcctctgg  94140
gagcgagcca acagacagcc aggactccgc gtcggacgcg gtcagccacg gcgatccgga  94200
agacctcgat ggcgctgccc gggcgggaga ggcgggggcc ttgcatgcct gtccgatgcc  94260
gtcgtcgacc acgcgggtca ctcccacgac caagcggggg cgctcggggg gcgaggatgc  94320
gcgcgcggac acggccctaa agaaacctaa gacggggtcg cccaccgcac ccccgcccgc  94380
agatccagtc cccctggaca cggaggacga ctccgatgcg gcggacggga cggcggcccg  94440
tcccgccgct ccagacgccc ggagcggaag ccgttacgcg tgttactttc gcgacctccc  94500
gaccggagaa gcaagccccg gcgccttctc cgccttccgg gggggccccc aaaccccgta  94560
tggttttgga ttcccctgac ggggcggggc cttggcggcc gcccaactct cgcaccatcc  94620
```

-continued

```
cgggttaatg taaataaact tggtattgcc caacactttc ccgcgtgtcg cgtgtggttc  94680
atgtgtgtgc ctggcgcccc caccctcggg ttcgtgtatt tcctttccct gtccttataa  94740
aagccgtatg tggggcgtga cggaaccacc ccgcgtgcca tcacggccaa ggcgcgggat  94800
gctccgcaac gacagccacc gggccgtgtc cccggaggac ggccagggac gggtcgacga  94860
cggacggcca cacctcgcgt gcgtgggggc cctggcgcgg gggttcatgc atatctggct  94920
tcaggccgcc acgctgggtt ttgcgggatc ggtcgttatg tcgcgcgggc cgtacgcgaa  94980
tgccgcgtct ggggcgttcg ccgtcgggtg cgccgtgctg ggctttatgc gcgcaccccc  95040
tcccctcgcg cggcccaccg cgcggatata cgcctggctc aaactggcgg ccggtggagc  95100
ggcccttgtt ctgtggagtc tcggggagcc cggcacgcag ccgggggccc cggccccggg  95160
cccggccacc cagtgcctgg cactgggcgc cgcctatgcg gcgctcctgg tgctcgccga  95220
tgacgtctat ccgctctttc tcctcgcccc ggggcccctg ttcgtcggca ccctggggat  95280
ggtcgtcggc gggctgacga tcggaggcag cgcgcgctac tggtggatcg gtgggcccgc  95340
cgcggccgcc ctggccgcgg cggtgttggc gggcccgggg gcgaccaccg ccagggactg  95400
cttttccagg gcttgccccg accaccgccg cgtctgtgtc atcaccgcag gcgagtctct  95460
ttcccgccgc cccccggagg acccagagcg acccggggtt cccgggcccc cgtccccccc  95520
gaccccccaa cgatcccacg ggccgccggc cgatgaggtc gcaccggcca gggtcgcgcg  95580
gcccgaaaac gtctgggtgc ccgtggtcac ctttctgggg gcgggcgcgc ttgccgtcaa  95640
gacggtgcga gaacatgccc ggggaacgcc gggcccgggc ctgccgctgt ggccccaggt  95700
gtttctcgga ggccatgtgg cggtggccct gacggagctg tgtcaggcgc ttccgccctg  95760
ggaccttacg gacccgctgc tgtttgttca cgccggactg caggtcatca acctcgggtt  95820
ggtgtttcgg ttttccgagg ttgtcgtgta tgcggcgcta gggggtgccg tgtggatttc  95880
gttggcgcag gtgctggggc tccggcgtcg cctgcacagg aaggaccccg gggacggggc  95940
ccggttggcg gcgacgcttc ggggcctctt cttctccgtg tacgcgctgg ggtttggggt  96000
gggggtgctg ctgtgccctc cggggtcaac gggcgggcgg tcgggcgatt gatatatttt  96060
tcaataaaag gcattagtcc cgaagaccgc cggtgtgtga tgatttcgcc ataacaccca  96120
aaccccggat ggggcccggg tataaattcc ggaaggggac acgggctacc ctcactatcg  96180
agggcgcttg gtcgggaggc cgcatcgaac gcacaccccc atccggtggt ccgtgtggag  96240
gtcgttttca tgcccggtct cgctttgccg ggaacgctag ccgatccctc gcgaggggga  96300
ggcgtcgggc atggccccgg ggcgggtggg ccttgccgtg gtcctgtgga gcctgttgtg  96360
gctcggggcg ggggtgtccg ggggctcgga aactgcctcc accgggccca cgatcaccgc  96420
gggagcggtg acgaacgcga gcgaggcccc cacatcgggg tcccccgggt cagccgccag  96480
cccggaggtc acccccacat cgaccccaaa ccccaacaat gtcacacaaa acaaaaccac  96540
ccccaccgag ccggccagcc ccccaacaac ccccaagccc acctccacgc ccaaaagccc  96600
ccccacgtcc acccccgacc ccaaacccaa gaacaacacc acccccgcca agtcgggccg  96660
ccccactaaa ccccccgggc ccgtgtggtg cgaccgccgc gacccattgg cccggtacgg  96720
ctcgcgggtg cagatccgat gccggtttcg gaattccacc cgcatggagt tccgcctcca  96780
gatatggcgt tactccatgg gtccgtcccc cccaatcgct ccggctcccg acctagagga  96840
ggtcctgacg aacatcaccg ccccacccgg gggactcctg gtgtacgaca gcgcccccaa  96900
cctaacggac ccccacgtgc tctgggcgga gggggccggc ccgggcgccg accctccgtt  96960
```

-continued gtattctgtc accgggccgc tgccgaccca gcggctgatt atcggcgagg tgacgcccgc 97020
gacccaggga atgtattact tggcctgggg ccggatggac agcccgcacg agtacgggac 97080
gtgggtgcgc gtccgcatgt tccgcccccc gtctctgacc ctccagcccc acgcggtgat 97140
ggagggtcag ccgttcaagg cgacgtgcac ggccgccgcc tactacccgc gtaaccccgt 97200
ggagtttgtc tggttcgagg acgaccacca ggtgtttaac ccgggccaga tcgacacgca 97260
gacgcacgag caccccgacg ggttcaccac agtctctacc gtgacctccg aggctgtcgg 97320
cggccaggtc cccccgcgga ccttcacctg ccagatgacg tggcatcgcg actccgtgac 97380
gttctcgcga cgcaatgcca ccgggctggc cctggtgctg ccgcggccaa ccatcaccat 97440
ggaatttggg gtccgcattg tggtctgcac ggccggctgc gtccccgagg gcgtgacgtt 97500
tgcctggttc ctgggggacg acccctcacc ggcggctaag tcggccgtta cggcccagga 97560
gtcgtgcgac caccccgggc tggctacggt ccggtccacc ctgcccattt cgtacgacta 97620
cagcgagtac atctgtcggt tgaccggata tccggccggg attcccgttc tagaacacca 97680
cggcagtcac cagcccccac ccagggaccc caccgagcgg caggtgatcg aggcgatcga 97740
gtgggtgggg attggaatcg gggttctcgc ggcgggggtc ctggtcgtaa cggcaatcgt 97800
gtacgtcgtc cgcacatcac agtcgcggca gcgtcatcgg cggtaacgca agaccccccc 97860
gttacctttt taatatctat atagtttggt ccccccctcta tcccgcccac cgctgggcgc 97920
tataaagccg ccaccctctc ttccctcagg tcatccttgg tcgatcccga acgacacacg 97980
gcgtggagca aaacgcctcc ccctgagccg ctttcctacc aacacaacgg catgcctctg 98040
cgggcatcgg aacacgccta ccggcccctg ggccccggga caccccccat gcgggctcgg 98100
ctccccgccg cggcctgggt tggcgtcggg accatcatcg gggagttgt gatcattgcc 98160
gcgttggtcc tcgtgccctc gcgggcctcg tgggcacttt ccccatgcga cagcggatgg 98220
cacgagttca acctcgggtg catatcctgg gatccgaccc ccatggagca cgagcaggcg 98280
gtcggcggct gtagcgcccc ggcgaccctg atcccccgcg cggctgccaa acagctggcc 98340
gccgtcgcac gcgtccagtc ggcaagatcc tcgggctact ggtgggtgag cggagacggc 98400
attcgggcct gcctgcggct cgtcgacggc gtcggcggta ttgaccagtt ttgcgaggag 98460
cccgcccttc gcatatgcta ctatccccgc agtcccgggg gctttgttca gtttgtaact 98520
tcgacccgca acgcgctggg gctgccgtga ggcgcgtgta ctgcggtctg tctcgtctcc 98580
tcttctcccc ttccctcccc ctccgcatcc caggatcaca ccggtcaacg agggttgggg 98640
gggtccggca cggacccaaa ataataaaca cacaatcacg tgcgataaaa agaacacgcg 98700
gtcccctgtg gtgtttttgg ttatttttat taaatctcgt cgacaaacag ggggaaaggg 98760
gcgtggtcta gcgacggcag cacgggcgga ggcgttcacc ggctccggcg tccttcgcgt 98820
ttaagcttgg tcaggagggc gctcagggcg gcgacgttgg tcgggccgtc gttggtcagg 98880
gcgttggctc gatggcgggc gaggacgggc gaggggctca acggcggggg cgggggcccg 98940
gtgcggcccg ggggggaaaa tagggcggat ccccccccagt cgtacagggg attttccgcc 99000
tcaatgtacg gggaggccgg cgctgcattc gccgtgttca cgcagacgtt ttcgtagacc 99060
cgcatccatg gtatttcctc gtagacacgc cccccgtcct cgctcaccgt ctcgtatatt 99120
gactcgtcgt cctcgtaggg ggcgtgccgt tcgcgggccg aggcggcgtg ggtggctttg 99180
cggcgggcgt cgtcgtcgtc gtcgtcggcc gtcagatacg tggcttccat ctggtcgggt 99240
tctccctccg gggcgggtcc ccacacccgt ggccgatcga ggctccccag agacgcgcgc 99300
cggacgagga gggggcacgt cgccgccggc ggtcgcctgt cgggtcccgc gacgttacgg 99360

-continued

```
gccgggaggc gcgggggcac ctcccccatg tgcgtgtaat acgtggccgg ctgtgtggcc  99420
gcagcggggg gctcggcgac cgggtcgttc gcatccggaa gcgggggccc cgcgccgtcc  99480
gcgcggcgcc tccggaacct ccgggtggac gcgggggtcg agtgtaggcg aggtcggggg  99540
aggggcgggg gctcgttgtc gcgccgcgcc cgctgaatct tttcccgaca ggtcccaccc  99600
cccgcgcgat gcccccccgg gccgctggcc atgtcgtccg gggaggcccc cgcggaccac  99660
gtcgtccggc gagacgccac gagccgcagg atggactcgt agtggagcga cggcgccccg  99720
ttgcggagca gatccgcggc cagggcggcc ccgaaccaag ccttgatgct caactccatc  99780
cgggcccagc tgggggcggt catcgtgggg aacagggggg cggtggtccg acagaaacgc  99840
tcctggctgt ccaccgcggc ccgcagatac tcgttgttca ggctgtcggt ggcccagacg  99900
ccgtacccgg tgagggtcgc gttgatgata tactgggcgt ggtgatggac gatcgacaga  99960
acctccaccg tggatacgac ggtatccacg gtcccgtacg taccgccgct ccgcttgccg 100020
gtctgccaca ggttggctag gcgcgtcagg tggcccagga cgtcgctgac cgccgccctg 100080
agcgccatgc actgcatgga gccggtcgtg ccgctgggac cccggtccag atggcgcgcg 100140
aacgtttccg cgggcgcctc cgggctgccg ccgagcggga ggaaccggcg attggaggga 100200
ctcagccggt gacatacgtg cttgtccgtc gtccacagca tccaggacgc ccaccggtac 100260
agcacggaga cgtaggccag gagctcgttg agccgcagtg cggtgtcggt gctggggcgg 100320
cttgggtccg ccgggcgcat aaagaacatg tactgctgaa tccgatggag ggcgtcgcgc 100380
aggccggcca cggtggcggc gtacttggcc gccacggccc cgctcttgaa cggggtgcgc 100440
gccagcagct ttggcgccag ggtgggccgc agcagcacgt gaaggctggg gtcgcagtcg 100500
cccacggggt cctcggggac gtccaggccg ctgggcacca ccgtctgcag gtacttccag 100560
tactgcgtga ggatggcgcg gctcaactgg ccgccgggca gctccacctc gcccagcgcc 100620
tgggtggcgg ccgaagcgta gtgccggatg tactcgtagt gcgggtcgct ggcgagcccg 100680
tccacgatca aactctcggg aaccgtgttg tgttgccgcg cggccaaccg gacgctgcga 100740
tcggtgcagg tcagaaacgc cggctgcgcg tcgtcggagc gctgccgcaa ggcgcccacg 100800
gccgcgctaa ggagcccctc cggggtgggg agcagacacc cgccgaagat gcgccgctcg 100860
ggaacgcccg cgttgtcgcc gcggatcagg ttggcaggcg tcaggcaccg cgccagccgc 100920
agggagctcg cgccgcgcgt ccggcgctgc atggtgacgc ccgttcggtc gggacccgcc 100980
ggtcggagtt atgccgcgtc cagggccatc ggggcgcttt ttatcgggag gagcttatgg 101040
gcgtggcggg cctcccagcc cggtcgcgcg cctccccgac acgtgcgccc gcagggcggc 101100
ggccccctcg tctcccatca gcagtttcct aaactgggac atgatgtcca ccacgcggac 101160
ccgcgggccc aacacggacc cgccgcttac gggggcgggg gggaagggct ccaggtcctt 101220
gagaagaaag gcggggtctg ccgtcccgga cacgggggcc cggggcgctg aggaggcggg 101280
gcgcagatcc acgtgctccg cggccgcgcg gacgtccgcc cagaacttgg cgggggtggt 101340
gcgcgcgtac aggggctggg tcgctcggag gacgcacgcg tagcgcaggg gggtgtacgt 101400
gcccacctcg ggggccgtga atccccgtc aaacgcggcc agtgtcacgc acgccaccac 101460
ggtgtcggca aagcccagca gccgctgcag gacgagcccg gcggccagaa tggcgcgcgt 101520
ggccgccgcg tcgtcccggc gccggtgcgc gtccccgcac gcccgggcgt actttaaggt 101580
cacggtcgcc agggccgtgt gcagcgcgta caccgcagcg cccagcacgg cgttgagccc 101640
gctgttggcg agcagccggc gcgctgcggt gtcgcccagc gcctcgtgct cggcccccac 101700
```

-continued gaccgcgggg cttcccaggg gcagggcgcg aaacagctcc tcccgcgcca cgtccgcaaa 101760
ggcggggtgg tgcacgtgcg ggtgcaggcg cgccccccacg accaccgaga gccactggac 101820
cgtctgctcc gccatcaccg ccagcacatc cagcacgcgc cccaggaagg cggcctcccg 101880
cgtcaaaacg caccggacgg cgtcgggatt gaagcgggcg agcagggccc cggtggccag 101940
gtacgtcatg cggccggcat agcgggcggc cacgcgacag tcgcggtcca gcagcgcgcg 102000
caccccgggc cagtacagca gggaccccag cgagctgcgg aacaccgcgg cgtcggggcc 102060
ggattggggg gacactaacc cccccgcgct cagtaacggc acggccgcgg ccccgacggg 102120
acgcaacgcc gtgaggctcg cgaactgccg cctcagctcg gccgccctgt cgtccaggtc 102180
agacccgcgc gcctccgcgt gaaggcgcgt cccgcacacc cacccgttga tggccagccg 102240
cacgacggca tccgccaaaa agctcatcgc ctgggcgggg ctggtttttg ttcgacgatc 102300
cgtcaggtca agaatcccat cgcccgtgat ataccaggcc aacgcctcgc cctgctgcag 102360
ggtttggcgg aaaaacaccg cggggttgtc gggggaggcg aagtgcatga cccccacgcg 102420
cgataacccg aacgcgctat ccggacacgg gtaaaacccg gccggatgcc ccagggctag 102480
ggcggagcgc acggactcgt cccacacggc aacctgaggg gccagtcgat ccaacgggaa 102540
tgccgcccgg agctccgggc ccggcacgcg tccctccaga acctccacct tgggcgggga 102600
acgggccccg ccgccgtcct ccggcccgac ggcttccggg tagtcgtcct cctcgtactg 102660
cagctcctct aggaacagcg gcgacggcgc cacccgcgaa ccgccgaccc gccccaaaat 102720
agcccgcgcg tcgacgggac ccaggtatcc cccctgccgg gcctgcggag gaccgcgggg 102780
aacctcatca tcatcgtcca ggcgaccgcg caccgactgg ctacgggccg catcgggccc 102840
ggggcgctgc cgggacgctc ggcgatggga tgtgggcggg gcttccgacg cgcgccgtcg 102900
tcgggctcgc gggccttccc gtcgacggcg cacgggcggc tcgtcgcccg ccatctcctc 102960
cagagcctct agctcgctgt cgtcatcccc gcggaacacc gcacgcaggt accccatgaa 103020
ccccacccca tcgcccgctg gctcgtccgc cacgggcgag gcgcgggggc gggtggatgc 103080
gcgcctcctg cgccccgcgg gttcgcgagc cgacatggtg gcgatagacg cgggttatcg 103140
gatgtccgct accccccaaa aaagaaaaag accccacagc gcggatggag gccggggtag 103200
gtgccgccgg accccctcgc gatgggaatg gacgggagcg acggggccgg cgcaaaaaaa 103260
cgcagtatct cccgcgaagg ctacccgccg ccccagcccc cggccaaatg cggaaacggt 103320
cccgcgctct cgcctttata cgcgggccgc cctgcgacac aatcacccgt ccgtggtttc 103380
gaatctacac gacaggcccg cagacgcggc taacacacac gccggcaacc cagaccccag 103440
tgggttggtt gcgcggtccc gtctcctggc tagttctttc ccccaccacc aaataatcag 103500
acgacaaccg caggttttgt aatgtatgtg ctcgtgttta ttgtggatac gaaccggtga 103560
cgggagggga aaacccagac gggggatgcg ggtccggtcg cgccccctac ccaccgtact 103620
cgtcaattcc aagggcatcg gtaaacatct gctcaaactc gaagtcggcc atatccagag 103680
cgccgtaggg ggcggagtcg tggggggtaa atcccggccc cggggaatcc ccgtccccca 103740
acatgtccag atcgaaatcg tctagcgcgt cggcatgcgc catcgccacg tcctcgccgt 103800
ctaagtggag ctcgtccccc aggctgacat cggtcggggg ggccgtcgac agtctgcgcg 103860
tgtgtcccgc ggggagaaag gacaggcgcg gagccgccag ccccgcctct tcgggggcgt 103920
cgtcgtccgg gagatcgagc aggccctcga tggtagaccc gtaattgttt ttcgtacgcg 103980
cgcggctgta cgcgtgttcc cgcatgaccg cctcggaggg cgaggtcgtg aagctggaat 104040
acgagtccaa cttcgcccga atcaacacca taaagtaccc agaggcgcgg gcctggttgc 104100
catgcagggt gggaggggtc gtcaacggcg cccctggctc ctccgtagcc gcgctgcgca 104160
ccagcgggag gttaaggtgc tcgcgaatgt ggtttagctc ccgcagccgg cgggcctcga 104220
ttggcactcc ccggacggtg agcgctccgt tgacgaacat gaagggctgg aacagacccg 104280
ccaactgacg ccagctctcc aggtcgcaac agaggcagtc aaacaggtcg ggccgcatca 104340
tctgctcggc gtacgcggcc cataggatct cgcgggtcaa aaatagatac aaatgcaaaa 104400
acaaaacacg cgccagacga gcggtctctc ggtagtacct gtccgcgatc gtggcgcgca 104460
gcatttctcc caggtcgcga tcgcgtccgc gcatgtgcgc ctggcggtgc agctgccgga 104520
cgctggcgcg caggtaccgg tacagggccg agcagaagtt ggccaacacg gttcgatagc 104580
tctcctcccg cgcccgtagc tcggcgtgga agaaacgaga gagcgcttcg tagtagagcc 104640
cgaggccgtc gcgggtggcc ggaagcgtag ggaaggccac gtcgccgtgg gcgcgaatgt 104700
cgatttgggt gcgttcgggg acgtacgcgt ccccccattc caccacatcg ctgggcagcg 104760
ttgataggaa tttacactcc cggtacaggt cggcgttggt cggtagcgcc gaaaacagat 104820
cctcgttcca ggtatcgagc atggtacata gcgcggggcc cgcgctaaag cccaagtcgt 104880
cgaggagacg gttaaagagg gcggcggggg ggacgggcat gggtggggag ggcatgagct 104940
gggcctggct caggcgcccc gttgcgtaca gcgggggggc cgccggggtg tttttgggac 105000
ccccggccgg gcgggggggc ggtggcgaag cgccgtccgc gttcatgtcg gcaaacagct 105060
cgtcgaccaa gaggtccatt gggtggggtt gatacgggaa agacgatatc gggcttttga 105120
tgcgatcgtc cccgcccgcc cagagagtgt gggacgcccg acggcgcggg aagagaaaac 105180
ccccaaacgc gttagaggac cggacggacc ttatgggggg aagtgggcag cgggaacccc 105240
gtccgttccc gaggaatgac agcccgtggt cgccaccacg catttaagca acccgcacgg 105300
gccgccccgt acctcgtgac ttccccccac attggctcct gtcacgtgaa ggcgaaccga 105360
gggcggctgt ccaacccacc ccccgccacc cagtcccggt ccccgtcgga ttgggaaaca 105420
aaggcacgca acgccaacac cgaatgaacc cctgttggtg ctttattgtc tgggtacgga 105480
agttttcact cgacgggccg tctggggcga gaagcggagc gggctggggc tcgaggtcgc 105540
tcggtggggc gcgacgccgc agaacgccct cgagtcgccg tggccgcgtc gacgtcctgc 105600
accacgtctg gattcaccaa ctcgttggcg cgctgaagca ggtttttgcc ctcgcagacc 105660
gtcacgcgga tggtggtgat gccaaggagt tcgttgaggt cttcgtctgt gcgcggacgc 105720
gacatgtccc agagctggac cgccgccatc cgggcatgca tggccgccag gcgcccgacc 105780
gcggcgcaga agacgcgctt gttaaagccg gccacccggg gggtccatgg cgcgtcgggg 105840
tttggggggg cggtgctaaa gtgcagcttt ctggccagcc cctgcgcggg tgtcttggat 105900
cgggttggcg ccgtcgacgc gggggcgtct gggagtgcgg cggattctgg ctgggccgat 105960
ttcctgccgc gggtggtctc cgccgccggg gccgcggggg ccttagtcgc cacccgctgg 106020
gttcgggggg cccgggggc ggtggtgggt gtgcgtccgg cccctccgga cccagcgggt 106080
ggcggaggcg cccgcgcagg ccccgggccg gacaaaaccg ccccggaaac gggacgccgc 106140
gtccggggga cctccgggtg ttcgtcgtct tcggatgacg agccccgta gagggcataa 106200
tccgactcgt cgtactggac gaaacggacc tcgcccctct ggcgcgagcg tgtctgtagg 106260
gcgccacggc gggaggtgtc aggcggacta tcgggactcg ccatacctga agacggggtg 106320
tagtacagat cctcgtactc atcgcgcgga acctcccgcg gacccgactt cacggagcgg 106380
cgagaggtca tggttccacg aacacgctag ggtcggatgc gcggacaatt aggcctgggt 106440

-continued tcggacggcg ggggtggtgc aggtgtggag aggtcgagcg ataggggcgg cccgggagag 106500
aagagagggt ccgcaaaacc cactggggat gcgtgagtgg ccctctgtgg gcggtggggg 106560
agagtcttat aggaagtgca tataaccaca acccatgggt ctaaccaatc cccaggggcc 106620
aagaaacaga cacgccccaa acggtctcgg tttccgcgag gaaggggaag tcctgggaca 106680
ccctccaccc ccacccctca ccccacacag ggcgggttca ggcgtgcccg gcagccagta 106740
gcctctggca gatctgacag acgtgtgcga taatacacac gcccatcgag gccatgccta 106800
cataaaaggg caccagggcc cccggggcag acatttggcc agtgttttgg gtctcgcacc 106860
gcgcgccccc gatcccatcg cgcccgccct cctcgccggg cggctccccg cgcgggcccg 106920
cgtctcccgc cgctaaggcg acgagcaaga caaacaacag gcccgcccga cagacccttc 106980
tggggggccc catcgtccct aacaggaaga tgagtcagtg gggatccggg gcgatccttg 107040
tccagccgga cagcttgggt cgggggtacg atggcgactg gcacacggcc gtcgctactc 107100
gcgggggcgg agtcgtgcaa ctgaacctgg tcaacaggcg cgcggtggct tttatgccga 107160
aggttagcgg ggactccgga tggccgtcg ggcgcgtctc tctggacctg cgaatggcta 107220
tgccggctga cttttgcgcg attattcacg cccccgcgct agccagcccc gggcaccacg 107280
taatactggg tcttatcgac tcggggtacc gcggaaccgt tatggccgtg gtcgtagcgc 107340
ctaaaaggac gcgggaattt gcccccggga ccctgcgggt cgacgtgacg ttcctggaca 107400
tcctggcgac ccccccggcc ctcaccgagc cgatttccct gcggcagttc ccgcaactgg 107460
cgcccccccc tccaaccggg gccgggatac gcgaagatcc ttggttggag gggcgctcg 107520
gggccccaag cgtgactacg gccctaccgg cgcgacgccg agggcggtcc ctcgtctatg 107580
ccggcgagct gacgccggtt cagacggaac acggggacgg cgtacgagaa gccatcgcct 107640
tccttccaaa acgcgaggag gatgccggtt tcgacattgt cgtccgtcgc ccggtcaccg 107700
tcccggcaaa cggcaccacg gtcgtgcagc catccctccg catgctccac gcggacgccg 107760
ggcccgcggc ctgctatgtg ttggggcggt cgtcgctcaa cgcccgcggc ctcctggtcg 107820
ttcctacgcg ctggctcccc gggcacgtat gtgcgtttgt tgtttacaac cttacggggg 107880
ttcctgtgac cctcgaggcc ggcgccaagg tcgcccagct cctggttgcg ggggcggacg 107940
ctcttccttg gatccccccg gacaactttc acgggaccaa agcgcttcga aactacccca 108000
ggggtgttcc ggactcaacc gccgaaccca ggaacccgcc gctcctggtg tttacgaacg 108060
agtttgacgc ggaggccccc ccgagcgagc gcgggaccgg gggttttggt tctaccggta 108120
tttagcccac agctttgggt tcgttccggg caataaaaaa cgtttgtatc gcatctttcc 108180
tgtgtgtagt tgtttatgtt ggatgcctgt gggtctatca cacccgcccc tccatcccac 108240
aaacacaaaa cacacgggtt ggatgaaaac acgcatttat tgacccaaaa cacacggagc 108300
tgctcgagat gggccagggc gaggtgcggt tggggaggct gtaggtctgg gaacggacac 108360
gcggggacac gattccggtt tggggtccgg gagggcgtcg ccgtttcggg cggcaggcgc 108420
cagcgtaacc tccgggggcg gcgtgtgggg gtgccccaag gagggcgcct cggtcacccc 108480
aatccccccc gaccgggttc ccccggcaac cccgaaggcg gagaggccaa gggcccgttc 108540
ggcgatggcc acatcctcca tgaccacgtc actctcggcc atgctccgaa tagcctggga 108600
gacgagcaca tccgcggact tgtcagccgc ccccacggac atgtacatct gcaggatggt 108660
ggccatacac gtgtccgcca ggcgccgcat cttgtcctga tgggccgcca cggccccgtc 108720
gatcgtgggg gcctcgaacc cggggtggtg gcgcgccagt cgttctaggt tcaccatgca 108780
ggcgtggtac gtgcgggcca aggcgcgggc cttcacgagg cgtcgggtgt cgtccaggga 108840

-continued ccccagggcg tcatcgagcg tgatgggggc gggaagtagc gcgttaacga ccgccagggc 108900
ctcctgcagc cgcggctccg cctccgaggg cggaacggcc gcgcggatca tctcatattg 108960
ttcctcgggg cgcgctcccc agccacatat agccccgaga agagaagcca tcgcgggcgg 109020
gtactggccc ttgggcgcgc ggacgcaatg gggcaggaag acgggaaccg cggggagagg 109080
cgggcggccg ggactcccgt ggaggtgacc gcgctttatg cgaccgacgg gtgcgttatt 109140
acctcttcga tcgccctcct cacaaactct ctactggggg ccgagccggt ttatatattc 109200
agctacgacg catacacgca cgatggccgt gccgacgggc ccacggagca agacaggttc 109260
gaagagagtc gggcgctcta ccaagcgtcg ggcgggctaa atggcgactc cttccgagta 109320
accttttgtt tattggggac ggaagtgggt gggacccacc aggcccgcgg gcgaacccga 109380
cccatgttcg tctgtcgctt cgagcgagcg gacgacgtcg ccgcgctaca ggacgccctg 109440
gcgcacggga ccccgctaca accggaccac atcgccgcca ccctggacgc ggaggccacg 109500
ttcgcgctgc atgcgaacat gatcctggct ctcaccgtgg ccatcaacaa cgccagcccc 109560
cgcaccggac gcgacgccgc cgcggcgcag tatgatcagg gcgcgtccct acgctcgctc 109620
gtggggcgca cgtccctggg acaacgcggc cttaccacgc tatacgtcca ccacgaggtg 109680
cgcgtgcttg ccgcgtaccg cagggcgtat tatggaagcg cgcagagtcc cttctggttt 109740
cttagcaaat tcgggccgga cgaaaaaagc ctggtgctca ccactcggta ctacctgctt 109800
caggcccagc gtctgggggg cgcgggggcc acgtacgacc tgcaggccat caaggacatc 109860
tgcgccacct acgcgattcc ccacgccccc cgccccgaca ccgtcagcgc tgcgtccctg 109920
acctcgtttg ccgccatcac gcggttctgt tgcacgagcc agtacgcccg cggggccgcg 109980
gcggccgggt ttccgcttta cgtggagcgc cgtattgcgg ccgacgtccg cgagaccagt 110040
gcgctggaga agttcataac ccacgatcgc agttgcctgc gcgtgtccga ccgtgaattc 110100
attacgtaca tctacctggc ccattttgag tgtttcagcc ccccgcgcct agccacgcat 110160
cttcgggccg tgacgaccca cgaccccaac cccgcggcca gcacggagca gccctcgccc 110220
ctgggcaggg aggccgtgga acaatttttt tgtcacgtgc gcgcccaact gaatatcggg 110280
gagtacgtca aacacaacgt gaccccccgg gagaccgtcc tggatggcga tacggccaag 110340
gcctacctgc gcgctcgcac gtacgcgccc ggggccctga cgcccgcccc cgcgtattgc 110400
ggggccgtgg actccgccac caaaatgatg gggcgtttgg cggacgccga aaagctcctg 110460
gtcccccgcg ggtggcccgc gtttgcgccc gccagtcccg gggaggacac ggcgggcggc 110520
acgccgcccc cacagacctg cggaattgtc aagcgcctcc tgagactggc cgccacggaa 110580
cagcagggcc ccacaccccc ggcgatcgcg gcgcttatcc gtaatgcggc ggtgcagact 110640
cccctgcccg tctaccggat atccatggtc cccacgggac aggcatttgc cgcgctggcc 110700
tgggacgact gggcccgcat aacgcgggac gctcgcctgg ccgaagcggt cgtgtccgcc 110760
gaagcggcgg cgcaccccga ccacggcgcg ctgggcaggc ggctcacgga tcgcatccgc 110820
gcccagggcc ccgtgatgcc ccctggcggc ctggatgccg gggggcagat gtacgtgaat 110880
cgcaacgaga tattcaacgg cgcgctggca atcacaaaca tcatcctgga tctcgacatc 110940
gccctgaagg agcccgtccc ctttcgccgg ctccacgagg ccctgggcca ctttaggcgc 111000
ggggctctgg ctgcggttca gctcctgttt cccgcggccc gcgtggaccc cgacgcatat 111060
ccctgttatt ttttcaaaag cgcatgtcgg cccggcccgg cgtccgtggg ttccggcagc 111120
ggactcggca acgacgacga cggggactgg tttccctgct acgacgacgc cggtgatgag 111180

-continued

```
gagtgggcgg aggacccggg cgccatggac acatcccacg atcccccgga cgacgaggtt 111240
gcctactttg acctgtgcca cgaagtcggc cccacggcgg aacctcgcga aacggattcg 111300
cccgtgtgtt cctgcaccga caagatcgga ctgcgggtgt gcatgcccgt ccccgccccg 111360
tacgtcgtcc acggttctct aacgatgcgg ggggtggcac gggtcatcca gcaggcggtg 111420
ctgttggacc gagattttgt ggaggccatc gggagctacg taaaaaactt cctgttgatc 111480
gatacggggg tgtacgccca cggccacagc ctgcgcttgc cgtattttgc caaaatcgcc 111540
cccgacgggc ctgcgtgcgg aaggctgctg ccagtgtttg tgatccccccc cgcctgcaaa 111600
gacgttccgg cgtttgtcgc cgcgcacgcc gacccgcggc gcttccattt tcacgccccg 111660
cccacctatc tcgcttcccc ccgggagatc cgtgtcctgc acagcctggg tggggactat 111720
gtgagcttct ttgaaaggaa ggcgtcccgc aacgcgctgg aacactttgg gcgacgcgag 111780
accctgacgg aggtcctggg tcggtacaac gtacagccgg atgcgggggg gaccgtcgag 111840
gggttcgcat cggaactgct ggggcggata gtcgcgtgca tcgaaaccca ctttcccgaa 111900
cacgccggcg aatatcaggc cgtatccgtc cggcgggccg tcagtaagga cgactgggtc 111960
ctcctacagc tagtccccgt tcgcggtacc ctgcagcaaa gcctgtcgtg tctgcgcttt 112020
aagcacggcc gggcgagtcg cgccacggcg cggacattcg tcgcgctgag cgtcggggcc 112080
aacaaccgcc tgtgcgtgtc cttgtgtcag cagtgctttg ccgccaaatg cgacagcaac 112140
cgcctgcaca cgctgtttac cattgacgcc ggcacgccat gctcgccgtc cgttccctgc 112200
agcacctctc aaccgtcgtc ttgataacgg cgtacggcct cgtgctcgtg tggtacaccg 112260
tcttcggtgc cagtccgctg caccgatgta tttacgcggt acgccccacc ggcaccaaca 112320
acgacaccgc cctcgtgtgg atgaaaatga accagaccct attgtttctg ggggccccga 112380
cgcacccccc caacgggggc tggcgcaacc acgcccatat ctgctacgcc aatcttatcg 112440
cgggtagggt cgtgcccttc caggtcccac ctgacgccat gaatcgtcgg atcatgaacg 112500
tccacgaggc agttaactgt ctggagaccc tatggtacac acgggtgcgt ctggtggtcg 112560
tagggtggtt cctgtatctg gcgttcgtcg ccctccacca acgccgatgt atgtttggcg 112620
tcgtgagtcc cgcccacaag atggtggccc cggccaccta cctcttgaac tacgcaggcc 112680
gcatcgtatc gagcgtgttc ctgcagtacc cctacacgaa aattacccgc ctgctctgcg 112740
agctgtcggt ccagcggcaa aacctggttc agttgtttga gacggacccg gtcaccttct 112800
tgtaccaccg ccccgccatc ggggtcatcg taggctgcga gttgatgcta cgctttgtgg 112860
ccgtgggtct catcgtcggc accgctttca tatcccgggg ggcatgtgcg atcacatacc 112920
ccctgtttct gaccatcacc acctggtgtt ttgtctccac catcggcctg acagagctgt 112980
attgtattct gcggcggggc ccggccccca agaacgcaga caaggccgcc gccccggggc 113040
gatccaaggg gctgtcgggc gtctgcgggc gctgctgttc catcatcctc tcgggcatcg 113100
cagtgcgatt gtgttatatc gccgtggtgg ccggggtggt gctcgtggcg cttcactacg 113160
agcaggagat ccagaggcgc ctgtttgatg tatgacgtca catccaggcc ggcggaaacc 113220
gtaacggcat atgcaaattg gaaactgtcc tgtcttgggg cccacccacc cgacgcgtca 113280
tatgcaaatg aaaatcggtc ccccgaggcc acgtgtagcc tggatcccaa cgaccccgcc 113340
catgggtccc aattggccgt cccgttacca agaccaaccc agccagcgta tccacccccg 113400
cccgggtccc cgcggaagcg gaacggggta tgtgatatgc taattaaata catgccacgt 113460
acttatggtg tctgattggt ccttgtctgt gccggaggtg gggcgggggc cccgcccggg 113520
gggcggaacg aggaggggtt tgggagagcc ggccccggca ccacgggtat aaggacatcc 113580
```

-continued accacccggc cggtggtggt gtgcagccgt gttccaacca cggtcacgct tcggtgcctc 113640
tccccgattc gggcccggtc gctcgctacc ggtgcgccac caccagaggc catatccgac 113700
accccagccc cgacggcagc cgacagcccg gtcatggcga ctgacattga tatgctaatt 113760
gacctcggcc tggacctctc cgacagcgat ctggacgagg acccccccga gccggcggag 113820
agccgccgcg acgacctgga atcggacagc agcggggagt gttcctcgtc ggacgaggac 113880
atggaagacc cccacggaga ggacggaccg gagccgatac tcgacgccgc tcgcccggcg 113940
gtccgcccgt ctcgtccaga agaccccggc gtacccagca cccagacgcc tcgtccgacg 114000
gagcggcagg gccccaacga tcctcaacca gcgccccaca gtgtgtggtc gcgcctcggg 114060
gcccggcgac cgtcttgctc ccccgagcag cacgggggca aggtggcccg cctccaaccc 114120
ccaccgacca aagcccagcc tgcccgcggc ggacgccgtg ggcgtcgcag ggtcggggt 114180
cgcggtggtc ccggggctgc cgatggtttg tcggaccccc gccggcgtgc ccccagaacc 114240
aatcgcaacc ctgggggacc ccgcccgggg gcggggtgga cggacggccc cggcgccccc 114300
catggcgagg cgtggcgcgg cagtgagcag cccgacccac ccggaggcca gcggacacgg 114360
ggcgtgcgcc aagcaccccc cccgctaatg acgctggcga ttgccccccc gcccgcggac 114420
ccccgcgccc cggccccgga gcgaaaggcg cccgccgccg acaccatcga cgccaccacg 114480
cggttggtcc tgcgctccat ctccgagcgc gcggcggtcg accgcatcag cgagagcttt 114540
ggccgcagcg cacaggtcat gcacgacccc tttgggggc agccgtttcc cgccgcgaat 114600
agcccctggg ccccggtgct ggcgggccaa ggagggccct ttgacgccga gaccagacgg 114660
gtctcctggg aaaccttggt cgcccacggc ccgagcctct atcgcacttt tgccggcaat 114720
cctcgggccg catcgaccgc caaggccatg cgcgactgcg tgctgcgcca agaaaatttc 114780
atcgaggcgc tggcctccgc cgacgagacg ctggcgtggt gcaagatgtg catccaccac 114840
aacctgccgc tgcgccccca ggaccccatt atcgggacga ccgcggctgt gctggataac 114900
ctcgccacgc gcctgcggcc ctttctccag tgctacctga aggcgcgagg cctgtgcggc 114960
ctggacgaac tgtgttcgcg gcggcgtctg gcggacatta aggacattgc atccttcgtg 115020
tttgtcattc tggccaggct cgccaaccgc gtcgagcgtg gcgtcgcgga gatcgactac 115080
gcgacccttg gtgtcggggt cggagagaag atgcatttct acctccccgg ggcctgcatg 115140
gcgggcctga tcgaaatcct agacacgcac cgccaggagt gttcgagtcg tgtctgcgag 115200
ttgacggcca gtcacatcgt cgcccccccg tacgtgcacg gcaaatattt ttattgcaac 115260
tccctgtttt aggtacaata aaaacaaaac atttcaaaca aatcgcccct cgtgttgtcc 115320
ttctttgctc atggccggcg gggcgtgggt cacggcagat ggcgggggtg ggcccggcgt 115380
acggcctggg tgggcggagg gaactaaccc aacgtataaa tccgtccccg ttccaaggcc 115440
ggtgtcatag tgcccttagg agcttcccgc ccgggcgcat cccccctttt gcactatgac 115500
agcgaccccc ctcaccaacc tgttcttacg ggccccggac ataacccacg tggccccccc 115560
ttactgcctc aacgccacct ggcaggccga aacggccatg cacaccagca aaacggactc 115620
cgcttgcgtg gccgtgcgga gttacctggt ccgcgcctcc tgtgagacca gcggcacaat 115680
ccactgcttt ttctttgcgg tatacaagga cacccaccac acccctccgc tgattaccga 115740
gctccgcaac tttgcggacc tggttaacca cccgccggtc ctacgcgaac tggaggataa 115800
gcgcggggtg cggctgcggt gtgcgcggcc gtttagcgtc gggacgatta aggacgtctc 115860
tgggtccggc gcgtcctcgg cgggagagta cacgataaac gggatcgtgt accactgcca 115920

-continued ctgtcggtat ccgttctcaa aaacatgctg gatgggggcc tccgcggccc tacagcacct 115980
gcgctccatc agctccagcg gcatggccgc ccgcgcggca gagcatcgac gcgtcaagat 116040
taaaattaag gcgtgatctc caacccccc atgaatgtgt gtaacccccc ccaaaaaaat 116100
aaagagccgt aacccaacca aaccaggcgt ggtgtgagtt tgtggaccca aagccctcag 116160
agacaacgcg acaggccagt atggaccgtg atacttttat ttattaactc acaggggcgc 116220
ttaccgccac aggaatacca gaataatgac caccacaatc gcgaccaccc caaatacagc 116280
atggcgccac accacgccac aacagccctg tcgccggtat ggggcatgat cagacgagcc 116340
gcgcgccgcg cgttgggccc tgtacagctc gcgcgaattg accctaggag gccgccacgc 116400
gcccgagttt tgcgttcgtc gctggtcgtc gggcgccaaa gcccccggacg gctgttcggt 116460
cgaacgaacg gccacgacag tggcataggt tggggggtgg tccgacatag cctcggcgta 116520
cgtcgggagg cccgacaaga ggtcccttgt gatgtcgggt ggggccacaa gcctggtttc 116580
cggaagaaac aggggggttg ccaataaccc gccagggcca aaactccggc gctgcgcacg 116640
tcgttcggcg cggcgccggg cgcgccgagc ggctcgctgg gcggcttggc gtgagcggcc 116700
ccgctccgac gcctcgccct ctccggagga ggttggcgga attggcacgg acaacagggg 116760
cccagcagag tacggtggag gtgggtccgt gggggtgtcc agatcaataa cgacaaacgg 116820
cccctcgttc ctaccagaca agctatcgta ggggggcggg ggatcagcaa acgcgttccc 116880
cgcgctccat aaacccgcgt cggttgcgc cgcctccgaa gccatggatg cgccccaaag 116940
ccacgactcc cgcgcgctag gtccttgggg taatggaaaa ggccctactc cccatccaag 117000
ccagccaagt taacgggcta cgccttcggg aatgggactg gcaccccggc ggattttgtt 117060
gggctggcat gcgtcgccca accgagggcc gcgtccacgg gacgcgcctt ttataacccc 117120
gggggtcatt cccaacgatc acatgcaatc taactggctc ccctctcccc ccctctcccc 117180
tctccccccc tctcccctct cccccctct cccctctccc cccctctccc ctctcccccc 117240
ctctcccctc tcccccctc tcccctctcc cccccctctcc cctctccccc cctctcccct 117300
ctccccccct ctcccctctc cccccctctc ccctctcccc tctgctcttt ccccgtgaca 117360
cccgacgctg ggggcgtggc tgccgggagg ggccgcggat gggcgggcct acttggtttc 117420
ccgccccccc cccccccccc cgaaccgccc cgccggcttt gccccccttt gatcccctgc 117480
tacccccaac ccgtgctggt ggtgcgggtt ggggggggat gtgggcgggg gtgcgcggga 117540
ggtgtcggtg gtggtggtgg tggtggtagt aggaatggtg gtgagggggg gggggcgctg 117600
gttggtcaaa aaagggaggg acgggggccg gcagaccgac ggcgacaacg ctccccggcg 117660
gccgggtcgc ggctcttacg agcggcccgg cccgcgctcc caccccccgg gccgtgtcct 117720
tgctttcccc ccgtctcccc cccccccgcc ttctcctcct cctcctcgtt tttccaaacc 117780
ccgcccaccc ggcccggccc ggcccggccc ggcccggcca ccgccgccca cccacccacc 117840
tcgggatacc cagccccggt cccccgttcc ccgggggccg ttatctccag cgccccgtcc 117900
ggcgcgccgc cccccgccgc taaaccccat cccgcccccg ggaccccaca tataagcccc 117960
cagccacacg caagaacaga cacgcagaac ggctgtgttt atttaaataa accaatgtcg 118020
gaataaacaa acacaaacac ccgcgacggg gggacggagg ggacggaggg agggggtgac 118080
gggggacggg aacagacaca aaaacaacca caaaaaacaa ccacccaccg acaccccccac 118140
cccagtctcc tcgccttctc ccacccaccc cacgccccca ctgagcccgg tcgatcgacg 118200
agcacccccg cccacgcccc cgcccctgcc ccggcgaccc ccggcccgca cgatcccgac 118260
aacaataaca accccaacgg aaagcggcgg ggtgttgggg gaggcgagga acaaccgagg 118320
ggaacggggg atggaaggac gggaagtgga agtcctgata cccatcctac acccccctgc 118380
cttccaccct ccggcccccc gcgagtccac ccgccggccg gctaccgaga ccgaacacgg 118440
cggccgccgc agccgccgca gccgccgccg acaccgcaga gccggcgcgc gcactcacaa 118500
gcggcagagg cagaaaggcc cagagtcatt gtttatgtgg ccgcgggcca gcagacggcc 118560
cgcgacaccc cccccccgcc cgtgtgggta tccggccccc cgccccgcgc cggtccatta 118620
agggcgcgcg tgcccgcgag atatcaatcc gttaagtgct ctgcagacag gggcaccgcg 118680
cccggaaatc cattaggccg cagacgagga aaataaaatt acatcaccta cccacgtggt 118740
gctgtggcct gtttttgctg cgtcatctca gcctttataa aagcgggggc gcggccgtgc 118800
cgatcgcggg tggtgcgaaa gactttccgg gcgcgtccgg gtgccgcggc tctccgggcc 118860
cccctgcagc cggggcggcc aaggggcgtc ggcgacatcc tccccctaag cgccggccgg 118920
ccgctggtct gttttttcgt tttccccgtt tcgggggtgg tgggggttgc ggtttctgtt 118980
tctttaaccc gtctggggtg tttttcgttc cgtcgccgga atgtttcgtt cgtctgtccc 119040
ctcacggggc gaaggccgcg tacggcccgg gacgaggggc ccccgaccgc ggcggtccgg 119100
gccccgtccg gacccgctcg ccggcacgcg acgcgaaaaa ggccccccgg aggcttttcc 119160
gggttcccgg cccggggcct gagatgaaca ctcggggtta ccgccaacgg ccggcccccg 119220
tggcggcccg gcccggggcc ccggcggacc caaggggccc cggcccgggg ccccacaacg 119280
gcccggcgca tgcgctgtgg tttttttttc ctcggtgttc tgccgggctc catcgccttt 119340
cctgttctcg cttctccccc ccccttctt cacccccagt accctcctcc ctcccttcct 119400
cccccgttat cccactcgtc gagggcgccc cggtgtcgtt caacaaagac gccgcgtttc 119460
caggtaggtt agacacctgc ttctccccaa tagagggggg ggacccaaac gacagggggc 119520
gccccagagg ctaaggtcgg ccacgccact cgcgggtggg ctcgtgttac agcacaccag 119580
cccgttcttt tcccccccctc ccacccttag tcagactctg ttacttaccc gtccgaccac 119640
caactgcccc cttatctaag ggccggctgg aagaccgcca gggggtcggc cggtgtcgct 119700
gtaacccccc acgccaatga cccacgtact ccaagaaggc atgtgtccca ccccgcctgt 119760
gtttttgtgc ctggctctct atgcttgggt cttactgcct gggggggggg agtgcggggg 119820
aggggggggtg tggaaggaaa tgcacggcgc gtgtgtaccc cccctaaagt tgttcctaaa 119880
gcgaggatac ggaggagtgg cgggtgccgg gggaccgggg tgatctctgg cacgcggggg 119940
tgggaagggt cgggggaggg ggggatggag taccggccca cctggccgcg cgggtgcgcg 120000
tgcctttgca caccaacccc acgtccccg gcggtctcta agaagcaccg ccccccctcc 120060
ttcataccac cgagcatgcc tgggtgtggg ttggtaacca acacgcccat cccctcgtct 120120
cctgtgattc tctggctgca ccgcattctt gttttctaac tatgttcctg tttctgtctc 120180
cccccccccc accccctccgc cccacccccc aacacccacg tctgtggtgt ggccgacccc 120240
cttttgggcg ccccgtcccg ccccgccacc cctcccatcc tttgttgccc tatagtgtag 120300
ttaacccccc ccgccctttg tggcggccag aggccaggtc agtccgggcg ggcaggcgct 120360
cgcggaaact taacacccac acccaaccca ctgtggttct ggctccatgc cagtggcagg 120420
atgctttcgg ggatcggtgg tcaggcagcc cgggccgcgg ctctgtggtt aacaccagag 120480
cctgcccaac atggcacccc cactcccacg cacccccact cccacgcacc cccactccca 120540
cgcaccccca ctcccacgca cccccactcc cacgcacccc cactcccacg cacccccact 120600
cccacgcacc cccactccca cgcaccccca ctcccacgca tccccgcgat acatccaaca 120660

-continued cagacaggga aaagatacaa aagtaaacct ttatttccca acagacagca aaaatcccct 120720
gagttttttt ttattagggc caacacaaaa gacccgctgg tgtgtggtgc ccgtgtcttt 120780
cacttttccc ctccccgaca cggattggct ggtgtagtgg gcgcggccag agaccaccca 120840
gcgcccgacc ccccctccc cacaaacacg gggggcgtcc cttattgttt tccctcgtcc 120900
cgggtcgacg ccccctgctc cccggaccac gggtgccgag accgcaggct gcggaagtcc 120960
agggcgccca ctagggtgcc ctggtcgaac agcatgttcc ccacgggggt catccagagg 121020
ctgttccact ccgacgcggg ggccgtcggg tactcggggg gcatcacgtg gttacccgcg 121080
gtctcgggga gcagggtgcg gcggctccag ccggggaccg cggcccgcag ccgggtcgcc 121140
atgtttcccg tctggtccac caggaccacg tacgccccga tgttccccgt ctccatgtcc 121200
aggatgggca ggcagtcccc cgtgatagtc ttgttcacgt aaggcgacag ggcgaccacg 121260
ctagagaccc ccgagatggg caggtagcgc gtgaggccgc ccgcggggac ggccccggaa 121320
gtctccgcgt ggcgcgtctt ccgggcacac ttcctcggcc cccgcggccc agaagcagcg 121380
cgggggccga gggaggtttc ctcttgtctc cctcccaggg caccgacggc cccgcccgag 121440
gaggcggaag cggaggagga cgcggccccg gcggcggaag aggcggcccc cgcgggggtc 121500
ggggccgagg aggaagaggc agaggaggaa gaggcggagg ccgccgagga cgtcaggggg 121560
gtcccgggcc caccctggcc gcgccccccc ggccctgagt cggagggggg gtgcgtcgcc 121620
gccctcttgg cccctgccgg cgcgaggggg ggacgcgtgg actgggggga ggggttttcc 121680
tggcccgacc cgcgcctctt cctcggacgc accgccgcct cctgctcgac agaggcggcg 121740
gaggggagcg gggcggcgcc ggagggggcg gcgccgcggg agggcccgtg cccaccctcc 121800
acgcccggcc cccccgagcc gcgcgccacc gtcgcacgcg cccggcacag actctgttct 121860
tggttcgcgg cctgagccag ggacgagtgc gactggggca cacggcgcgc gtccgcgggg 121920
cgggcggccg gctccgcccc gggggccggg gcgcgggggc cgggccccgg aggcggcgct 121980
cgcacgcacg gggccacggc cgcgcggggg cgcgcgggtc ccgacgcggc cgcggacgcg 122040
gggggcccgg ggcgggggc ggagcctggc atgggcgccg cgggggggcct gtggggagag 122100
gccgggggggg agtcgctgat cactatgggg tctctgttgt ttgcaagggg ggcgggtctg 122160
ttgacaaggg ggcccgtccg gcccctcggc cgccccgcct ccgcttcaac aaccccaacc 122220
ccaaccccaa cccccccgga ggggccagac gccccccgcg gcgccgcggc tcgcgactgg 122280
cgggagccgc cgccgccgct gctgttggtg gtggtgttgg tgttactgct gccgtgtggc 122340
ccgatgggcg ccgagggggg cgctgtccga gccgcggccg gctgggggc tgcgtgagac 122400
gccccgcccg tcacgggggg cgcggcggcg cctctgcgtg ggggggcgcg gggcgtccgg 122460
cgggggcgg gcggtacgta gtctgctgca agagacaacg gggggcgcga tcaggttacg 122520
ccccctcccc ggcccgccct ttcctcgccc gcccgcctat tcctccctcc cccccctcc 122580
tcctcctcct cccccagggt ccttgccgcc ccccgcctca ccgtcgtcca ggtcgtcgtc 122640
atcctcgtcc gtggtgggct ccgggtgggt gggcgacagg gccctcaccg tgtgcccccc 122700
cagggtcagg taccgcgggg cgaaccgctg attgcccgtc cagataaagt ccacggccgt 122760
gcccgccctg acggcctcct cggcctccat gcgggtctgg gggtcgttca cgatcgggat 122820
ggtgctgaac gacccgctgg gcgtcacgcc cactatcagg tacaccagct tggcgttgca 122880
cagcgggcag gtgttgcgca attgcatcca ggttttcatg cacgggatgc agaagcggtg 122940
catgcacggg aaggtgtcgc agcgcaggtg gggcgcgatc tcatccgtgc acacggcgca 123000
cacgtcgccc tcgtcgctcc ccccgtcctc tcgagggggg gcgcccccgc aactgccggg 123060

-continued gtcttcctcg cgggggggc tcccccccga gaccgccccc ccatccacgc cctgcggccc 123120
cagcagcccc gtctcgaaca gttccgtgtc cgtgctgtcc gcctcggagg cggagtcgtc 123180
gtcatggtgg tcggcgtccc cccgcccccc cacttcggtc tccgcctcag agtcgctgct 123240
gtccggcagg tctcggtcgc agggaaacac ccagacatcc ggggcgggct aaggggaaaa 123300 aagggggcg ggtaagaatg gggggggatt tcccgcgtca atcagcaccc acgagttccc 123360
cctctccccc ccccgcctca caaagtcctg cccccctgct ggcctcggaa gagggggag 123420 aaaggggtct gcaaccaaag gtggtctggg tccgtccttt ggatcccgac ccctcttctt 123480
ccctcttctc ccgccctcca gacgcaccgg agtcgggggt cccacggcgt cccccaaata 123540
tggcgggcgg ctcctcccca ccccccctaga tgcgtgtgag taaggggggc ctgcgtatga 123600
gtcagtgggg accacgcccc caacacggcg accccggtcc ttgtgtgttt gttgtggggg 123660
cgtgtctctg tgtatgagtc agggggtccc acggcgaccc cgggccctgc gtctgagtca 123720
aaggggccat gtgtatgtgt tgggggtctg tatatataaa gtcagggggt cacatggcga 123780
cccccaacag ggcgaccccg gtccctgtat atatagggtc agggggttcc gcacccccta 123840
acatggcgcc cccggtccct gtatatatag tgtcacgggg ttccacgccc cctaacatgg 123900
cgccccaaca tggcgcccgg ctcccgtgta tgagtggggg tcccccaaca tggcggccgg 123960
ttccagtgta agggtcgggg gtcccccaac atggcgcccc ccaatatggc gccccccaat 124020
atggcgcccc agacatggcg cccggcccct cacctcgcgc tgggggcggc cctcaggccg 124080
gcgggtactc gctccggggc ggggctccat gggggtcgta tgcggctgga gggtcgcgga 124140
cggagggtcc ctgggggtcg caacgtaggc ggggcttctg tggtgatgcg gagaggggc 124200 ggcccgagtc tgcctggctg ctgcgtctcg ctccgagtgc cgaggtgcaa atgcgaccag 124260
actgtcgggc cagggctaac ttataccca cgcctttccc ctccccaaag gggcggcagt 124320
gacgattccc ccaatggccg cgcgtcccag gggaggcagg cccaccgcgg ggcggccccg 124380
tccccgggga ccaacccggc gcccccaaag aatatcatta gcatgcacgg cccggccccc 124440
gatttggggg cccaacccgg tgtcccccaa agaaccccat tagcatgccc ctcccgccga 124500
cgcaacaggg gcttggcctg cgtcggtgcc ccggggcttc ccgccttccc gaagaaactc 124560
attaccatac ccggaacccc aggggaccaa tgcgggttca ttgagcgacc cgcgggccaa 124620
tgcgcgaggg gccgtgtgtt ccgccaaaaa agcaattagc ataacccgga accccagggg 124680
agtggttacg cgcggcgcgg gaggcgggga ataccggggt tgcccattaa gggccgcggg 124740
aattgccgga agcgggaagg gcggccgggg ccgcccatta atgagtttct aattaccata 124800
ccgggaagcg gaacaaggcc tcttgcaagt ttttaattac cataccggga agtgggcggc 124860
ccggcccatt gggcggtaac tcccgcccaa tgggccgggc cccgaagact cggcggacgc 124920
tggttggccg ggccccgccg cgctggcggc cgccgattgg ccagtcccgc ccccgaggcg 124980
gcccgccctg tgagggcggg ctggctccaa gcgtatatat gcgcggctcc tgccatcgtc 125040
tctccggaga gcggcttggt gcggagctcc cgggagctcc gcggaagacc caggccgcct 125100
cgggtgtaac gttagaccga gttcgccggg ccggctccgc gggccagggc ccgggcacgg 125160
gcctcgggcc ccaggcacgg cccgatgacc gcctcggcct ccgccacccg gcgccggaac 125220
cgagcccggt cggcccgctc gcgggcccac gagccgcggc gcgccaggcg ggcggccgag 125280
gcccagacca ccaggtggcg cacccggacg tggggcgaga agcgcacccg cgcgggggtc 125340
gcgggggtcg cgggggtcgc gggggtcgcg ggggtcgcgg ggggctccgg cgccccctcc 125400

-continued ccgcccgcgc gtcgcaggcg caggcgcgcc aggtgctccg cggtgacgcg caggcggagg 125460
gcgaggcgcg gcggaaggcg gaaggggcgc gagggggggt gggaggggtc agccccgccc 125520
cccgggccca cgccgggcgg tgggggcgg ggccgggggg cggcggcggt gggccgggcc 125580
tctggcgccg gctcgggcgg ggggctgtcc ggccagtcgt cgtcatcgtc gtcgtcggac 125640
gcggactcgg gaacgtggag ccactggcgc agcagcagcg aacaagaagg cgggggccca 125700
ccggcggggg gcggcggcgg ggcggccgcg ggcgcgctcc tgaccgcggg ttccgagttg 125760
ggcgtggagg ttacctggga ctgtgcggtt gggacggcgc ccgtgggccc gggcggccgg 125820
gggcggcggg ggccgcgatg gcggcggcgg cgggccatgg agacagagag cgtgccgggg 125880
tggtagagtt tgacaggcaa gcatgtgcgt gcagaggcga gtagtgcttg cctgtctaac 125940
tcgctagtct cggccgcggg gggcccgggc tgcccgccgc caccgcttta aagggccgcg 126000
cgcgaccccc ggggggtgtg ttttgggggg ggcccgtttt cggcgtctgg ccgctcctcc 126060
ccccgctcct ccccccgctc ctccccccgc tcctcccccc gctcctcccc ccgctcctcc 126120
ccccgctcct ccccccgctc ctccccccgc tcctcccccc gctcctcccc ccgctcctcc 126180
ccccgctcct ccccccgctc ctccccccgc tcctcccccc gctcctcccc ccgctcctcc 126240
ccccgctcct ccccccgctc ctccccccgc tcccgcggcc ccgcccccca cgcccgccgc 126300
gcgcgcgcac gccgcccgga ccgccgcccg cctttttttgc gcgcgcgcgc gcccgcgggg 126360
ggcccgggct gccacaggtg aaaccaacag agcacggcgc actccgcacg tcacacgtca 126420
cgtcatccac cacacctgcc caacaacaca actcacagcg acaactcacc gcgcaacaac 126480
tcctgttcct catccacacg tcaccgcgca cctcccgctc ctccagacgt accccggcgc 126540
aacacaccgc tcctgctaca caccaccgcc ccctccccag ccccagccct ccccagcccc 126600
agccctcccc ggccccagcc ctccccggcc ccagccctcc ccggccccag ccctccccgg 126660
ccccagccct ccccggcccc agccctcccc ggccccagcc ctccccggcg cgtcccgcgc 126720
tccctcgggg gggttcgggc atctctacct cagtgccgcc aatctcaggt cagagatcca 126780
aaccctccgg gggcgcccgc gcaccaccac cgcccctcgc cccctcccgc ccctcgcccc 126840
ctcccgcccc tcgccccctc ccgcccctcg ccccctcccg cccctcgccc cctcccgccc 126900
ctcgccccct cccgcccctc gccccctccc gcccctcgcc ccctcccgcc cctcgccccc 126960
tcccgcccct cgccccctcc cgcccctcgc cccctcccgc ccctcgcccc ctcccgcccc 127020
tcgccccctc ccgcccctcg ccccctcccg cccctcgccc cctcccgccc ctcgccccct 127080
cccgcccctc gccccctccc gcccctcgcc ccctcccgcc cctcgccccc tcccgcccct 127140
cgaataaaca acgctactgc aaaacttaat caggttgttg ccgtttattg cgtcttcggg 127200
tctcacaagc gccccgcccc gtcccggccc gttacagcac cccgtccccc tcgaacgcgc 127260
cgccgtcgtc ttcgtcccag gcgccttccc agtccacaac ttcccgccgc gggggcgtgg 127320
ccaagcccgc ctccgccccc agcacctcca cggcccccgc cgccgccagc acggtgccgc 127380
tgcggcccgt ggccgaggcc cagcgaatcc cgggcggcgc cggcggcagg gcccccgggc 127440
cgtcgtcgtc gccgcgcagc accagcgggg gggcgtcgtc gtcgggctcc agcagggcgc 127500
gggcgcaaaa gtccctccgc ggcccgcgcc accgggccgg gccggcgcgc accgcctcgc 127560
gccccagcgc cacgtacacg ggccgcagcg gcgcgcccag gccccagcgc gcgcaggcgg 127620
cgtgcgagtg ggcctcctcc tcgcagaagt ccggcgcgcc gggcgccatg gcgtcggtgg 127680
tccccgaggc cgccgcccgg ccgtccagcg ccggcagcac ggcccggcgg tactcgcgcg 127740
gggacatggg caccggcgtg tccgggccga agcgcgtgcg cacgcggtag cgcacgttgc 127800

-continued cgccgcggca caggcgcagc ggcggcgcgt cggggtacag gcgcgcgtgc gcggcctcca 127860
cgcgcgcgaa gacccccggg ccgaacacgc ggcccgaggc cagcaccgtg cggcgcaggt 127920
cccgcgccgc cggccagcgc acggcgcact gcacggcggg cagcagctcg cacgccaggt 127980
aggcgtgctg ccgcgacacc gcgggcccgt cggcgggcca gtcgcaggcg cgcacggtgt 128040
tgaccacgat gagccgccgg tcgccggcgc tggcgagcag ccccagaaac tccacggccc 128100
cggcgaaggc caggtcccgc gtggacagca gcagcacgcc ctgtgcgccc agcgccgaca 128160
cgtcgggggc gccggtccaa ttgcccgccc aggcggccgt gtccggcccg cacagccggt 128220
tggccagggc cgccagcagg caggacagcc cgccgcgctc ggcggaccac tccggcggcc 128280
cccccgaggc cccgccgccg gccaggtcct cgcccggcag cggcgagtac agcaccacca 128340
cgcgcacgtc ctcggggtcg gggatctggc gcatccaggc cgccatgcgg cgcagcgggc 128400
ccgaggcgcg caggggggcca aagaggcggc ccccggcggc cccgtggggg tgggggttat 128460
cgtcgtcgtc gccgccgccg cacgcggcct gggcggcggg ggcgggcccg gcgcaccgcg 128520
cggcgatcga ggccagggcc cgcgggtcaa acatgagggc cggtcgccag gggacgggga 128580
acagcgggtg gtccgtgagc tcggccacgg cgcgcgggga gcagtaggcc tccagggcgg 128640
cggccgcggg cgccgccgtg tggctgggcc ccgggggctg ccgccgccag ccgcccaggg 128700
ggtcggggcc ctcggcgggc cggcgcgaca cggccacggg gcgcgggcgg gcctgcgccg 128760
cggcggcccg gggcgccgcg ggctgggcgg gggcgggctc gggcccgggg ggcgtggagg 128820
ggggcgcggg cgcggggagg ggggcgcggg cgtccgagcc gggggcgtcc gcgccgctct 128880
tcttcgtctt cgggggtcgc gggccgccgc ctccgggcgg ccgggccggg ccgggactct 128940
tgcgcttgcg cccctcccgc ggcgcggcgg aggcggcggc ggccgccagc gcgtcggcgg 129000
cgtccggtgc gctggccgcc gccgccagca gggggcgcag gctctggttg tcaaacagca 129060
ggtccgcggc ggcggcggcc gcggagctcg gcaggcgcgg gtcccgcggc agcgcggggc 129120
ccagggcccc ggcgaccagg ctcacggcgc gcacggcggc cacggcggcc tcgctgccgc 129180
cggccacgcg caggtccccg cgcaggcgca tgagcaccag cgcgtcgcgc acgaaccgca 129240
gctcgcgcag ccacgcgcgc aggcggggcg cgtcggcgtg cggcggcggc ggggaagcgg 129300
ggcccgcggg tccctccggc cgcggggggc tggcgggccg ggccccggcc agccccggga 129360
cggccgccag gtcgccgtcg aagccctcgg ccagcgcctc caggatcccg cggcaggcgg 129420
ccaggcactc gacggccacg cggccggcct gggcgcggcg cccggcgtcg tcgtcggcgt 129480
cggcgtggcg ggcggcgtcg gggtcgtcgc cccccgcggg ggaggcgggc gcggcggaca 129540
gccgccccag ggcggcgagg atccccgcgg cgccgtaccc ggcgggcacc gcgcgctcgc 129600
ccggtgcggc ggcggcgacg gcggcgaccc cctcgtcatc tgcgccggcg ccggggctcc 129660
ccgcggcccc cgtcagcgcc gcgttctcgc gcgccaacag gggcgcgtag gcgcggcgca 129720
ggctggtcag caggaagccc ttctgcgcgc ggtcgtatcg gcggctcatg gccacggcgg 129780
ccgccgcgtg cgccaggccc cagccgaagc ggccggccgc catggcgtag cccaggtggg 129840
gcacggcccg cgccacgctg ccggtgatga aggagctgct gttgcgcgcg gcgcccgaga 129900
tccggaagca ggcctggtcc agcgccacgt ccccggggac cacgcgcggg ttctggagcc 129960
accccatggc ctccgcgtcc ggggtgtaca gcagccgcgt gatcagggcg tactgctgcg 130020
cggcgtcgcc cagctcgggc gcccacacgg ccgccggggc gcccgaggcc tcgaaccggc 130080
gtcgcgcctc ctccgcctcg ggcgcccccc agaggcccgg gcggctgtcg cccaggccgc 130140

-continued cgtacagcac ccgccccggg ggcgggggcc cggcgccggg ccacggctcc ccgctgacgt 130200
acccgtcgcg atagcgcgcg tagaaggcgc cggaggtcgc gtcggcgtcc agctcgaccc 130260
gccggggctg cccggccgtg aagcggcccg tggcgtcgcg gccggccacc gccgcgcggg 130320
cccggcggcg ctcgatgcgg cccgcggagg ccgcgggggt cctcgccgcc gcccggggct 130380
tgggcgcggc ctcggagagg gggggtggcc cgggcggggg cggcgtccgc ccgggggctg 130440
ccggcgccgc gctcgacgga ccccgcccga cggcccgcgc ctcgcgtgcg tggtcggccg 130500
cgtcgttgcc gtcgtcgtcc tcgtcctcgt cggacgacga ggacgaagag gatgcggacg 130560
acgaggacga ggacccggag tccgacgagg tcgatgacgc cgatggccgc caccggccgt 130620
gacgacgtct ccgcggcggc tgggccggcg ggcgcggcga caggcggtcc gtggggtccg 130680
gatacgcgcc gcgtagcggg gcctcccgtt cgcggccccg ggccggggcc cggtcgccgg 130740
cggcgtcggc tgcgtcgtcg tactcgtccc cgtcatcgtc gtcggctcga aaggcggggg 130800
tccggggcgg cgaggccgcg gggtcgggcg tcgggatcgt ccggacggcc tcctctacca 130860
tggaggccag cagagccagc tgtcgcggcg agacggcgtc cccggcgtcc tcgccggcgt 130920
cggtgcccgc cgcgggggcc ctcccgtccc gccgggcgtc gtcgaggtcg tgggggtggt 130980
cggggtcgtg gtcggggtcg tccccgccct cctccgtctc cgcgccccac ccgagggccc 131040
cccgctcgtc gcggtctggg ctcggggtgg gcggcggccc gtcggtgggg cccggggagc 131100
cggggcgctg cttgttctcc gacgccatcg ccgatgcggg gcgatcctcc ggggatacgg 131160
ctgcgacggc ggacgtagca cggtaggtca cctacggact ctcgatgggg ggagggggcg 131220
agacccacgg accccgacga cccccgccgt cgacgcggaa ctagcgcgga ccggtcgatg 131280
cttgggtggg aaaaaggaca gggacggccg atccccctcc cgcgcttcgt ccgcgtatcg 131340
gcgtcccggc gcggcgagcg tctgacggtc tgtctctggc ggtcccgcgt cgggtcgtgg 131400
atccgtgtcg gcagccgcgc tccgtgtgga cgatcggggc gtcctcgggc tcatatagtc 131460
ccaggggccg gcgggaagga ggagcagcgg aggccgccgg ccccccgccc ccccggcggg 131520
cccaccccga acggaattcc attatgcacg accccgcccc gacgccggca cgccgggggc 131580
ccgtggccgc ggcccgttgg tcgaaccccc ggccccgccc atccgcgcca tctgccatgg 131640
gcggggcgcg agggcgggtg ggtccgcgcc ccgccccgca tggcatctca ttaccgcccg 131700
atccggcggt ttccgcttcc gttccgcatg ctaacgagga acgggcaggg ggcggggccc 131760
gggccccgac ttcccggttc ggcggtaatg agatacgagc cccgcgcgcc cgttggccgt 131820
ccccgggccc cccggtcccg cccgccggac gccgggacca acgggacggc gggcggccca 131880
agggccgccc gccttgccgc ccccccattg gccggcgggc gggaccgccc caagggggcg 131940
gggccgccgg gtaaaagaag tgagaacgcg aagcgttcgc acttcgtccc aatatatata 132000
tattattagg gcgaagtgcg agcactggcg ccgtgcccga ctccgcgccg gccccggggg 132060
cgggcccggg cggcgggggg cgggtctctc cggcgcacat aaaggcccgg cgcgaccgac 132120
gcccgcagac ggcgccggcc acgaacgacg ggagcggctg cggagcacgc ggaccgggag 132180
cgggagtcgc agagggccgt cggagcggac ggcgtcggca tcgcgacgcc ccggctcggg 132240
atcgggatcg catcggaaag ggacacgcgg acgcgggggg gaaagacccg cccaccccac 132300
ccacgaaaca caggggacgc accccggggg cctccgacga cagaaaccca ccggtccgcc 132360
ttttttgcac gggtaagcac cttgggtggg cggaggaggg ggggacgcgg gggcggagga 132420
ggggggacgc gggggcggag gagggggggac gcgggggcgg aggagggggg acgcgggggc 132480
ggaggagggg ggacgcgggg gcggaggagg gggctcaccc gcgttcgtgc cttcccgcag 132540

-continued gaggaacgtc ctcgtcgagg cgaccggcgg cgaccgttgc gtggaccgct tcctgctcgt 132600
cgggcggggg gaagccactg tggtcctccg ggacgttttc tggatggccg acatttcccc 132660
aggcgctttt gcgccttgtg taaaagcgcg gcgtcccgct ctccgatccc cgcccctggg 132720
cacgcgcaag cgcaagcgcc cttcccgccc cctctcatcg gagtctgagg tagaatccga 132780
tacagccttg gagtctgagg tcgaatccga gacagcatcg gattcgaccg agtctgggga 132840
ccaggatgaa gccccccgca tcggtggccg tagggccccc cggaggcttg gggggcggtt 132900
ttttctggac atgtcggcgg aatccaccac ggggacggaa acggatgcgt cggtgtcgga 132960
cgaccccgac gacacgtccg actggtctta tgacgacatt cccccacgac ccaagcgggc 133020
ccgggtaaac ctgcggctca cgagctctcc cgatcggcgg gatggggtta tttttcctaa 133080
gatggggcgg gtccggtcta cccgggaaac gcagccccgg gcccccaccc cgtcggcccc 133140
aagcccaaat gcaatgctac ggcgctcggt gcgccaggcc cagaggcgga gcagcgcacg 133200
atggaccccc gacctgggct acatgcgcca gtgtatcaat cagctgtttc gggtcctgcg 133260
ggtcgcccgg gacccccacg gcagtgccaa ccgcctgcgc cacctgatac gcgactgtta 133320
cctgatggga tactgccgag cccgtctggc cccgcgcacg tggtgccgtt tgctgcaggt 133380
gtccggcgga acctggggca tgcacctgcg caacaccata cgggaggtgg aggctcgatt 133440
cgacgccacc gcggaacccg tgtgcaagct tccttgtttg gagaccagac ggtacggccc 133500
ggagtgtgat cttagtaatc tcgagattca tctcagcgcg acaagcgatg atgaaatctc 133560
cgatgccacc gatctggagg ccgccggttc ggaccacacg ctcgcgtccc agtccgacac 133620
ggaggatgcc ccctcccccg ttacgctgga aaccccagaa ccccgcgggt ccctcgctgt 133680
gcgtctggag gatgagtttg gggagtttga ctggaccccc caggagggct cccagccctg 133740
gctgtctgcg gtcgtggccg ataccagctc cgtggaacgc ccgggcccat ccgattctgg 133800
ggcgggtcgc gccgcagaag accgcaagtg tctggacggc tgccggaaaa tgcgcttctc 133860
caccgcctgc ccctatccgt gcagcgacac gtttctccgg ccgtgagtcc ggtcgccccg 133920
accccttgt atgtccccaa aataaaagac caaaatcaaa gcgtttgtcc cagcgtctta 133980
atggcgggaa gggcggagag aaacagacca cgcggacatg gggggtgttt gggggtttat 134040
tggcaccggg ggctaaaggg tggtaaccgg atagcagatg tgaggaagtc ggggccgttc 134100
gccgcgaacg gcgatcagag ggtcagtttc ttgcggacca cggcccggcg atgtgggttg 134160
ctcgtctggg acctcgggca tgcccataca cgcacaacac ggacgccgca ccggatggga 134220
cgtcgtaagg gggcctgggg tagctgggtg gggtttgtgc agagcaatca gggaccgcag 134280
ccagcgcata caatcgcgct cccgtccgtt tgtcccgggc agtaccacgc cgtactggta 134340
ttcgtaccgg ctgagcaggg tctccagggg gtggttgggg gccgcgggga acggggtcca 134400
cgccacggtc cactcgggca aaaaccgagt cggcacggcc cacggttctc ccacccacgc 134460
gtctggggtc ttgatggcga taaatcttac cccgagccgg attttttggg cgtattcgag 134520
aaacggcaca cacagatccg ccgcgcctac cacccacaag tggtagaggc gaggggggct 134580
gggttggtct cggtgcagca gtcggaagca cgccacggcg tccacgacct cggtgctctc 134640
caaggggctg tcctccgcaa acaggcccgt ggtggtgttt ggggggcagc gacaggacct 134700
agtgcgcacg atcgggcggg tgggtttggg taagtccatc agcggctcgg ccaaccgtcg 134760
aaggttggcc ggacgaacga cgaccggggt acccaggggt tctgatgcca aaatgcggca 134820
ctgcctaagc aggaagctcc acagggccgg gcttgcgtcg acggaagtcc ggggcagggc 134880
gttgttctgg tcaaggaggg tcattacgtt gacgacaaca acgcccatgt tggtatatta 134940
caggcccgtg tccgatttgg ggcacttgca gatttgtaag gccacgcacg gcggggagac 135000
aggccgacgc gggggctgct ctaaaaattt aagggcccta cggtccacag acccgccttc 135060
ccgggggggc ccttggagcg accggcagcg gaggcgtccg ggggagggga gggtgattta 135120
cgggggggta ggtcaggggg tgggtcgtca aactgccgct ccttaaaacc ccggggcccg 135180
tcgttcgggg tgctcgttgg ttggcactca cggtgcggcg aatggcctgt cgtaagtttt 135240
gtcgcgttta cgggggacag ggcaggagga aggaggaggc cgtcccgccg gagacaaagc 135300
cgtcccgggt gtttcctcat ggcccctttt ataccccagc cgaggacgcg tgcctggact 135360
ccccgccccc ggagaccccc aaaccttccc acaccacacc acccagcgag gccgagcgcc 135420
tgtgtcatct gcaggagatc cttgcccaga tgtacggaaa ccaggactac cccatagagg 135480
acgaccccag cgcggatgcc gcggacgatg tcgacgagga cgccccggac gacgtggcct 135540
atccggagga atacgcagag gagctttttc tgcccgggga cgcgaccggt ccccttatcg 135600
gggccaacga ccacatccct cccccgtgtg gcgcatctcc ccccggtata cgacgacgca 135660
gccgggatga gattggggcc acgggattta ccgcggaaga gctggacgcc atggacaggg 135720
aggcggctcg agccatcagc cgcggcggca agccccccctc gaccatggcc aagctggtga 135780
ctggcatggg ctttacgatc cacggagcgc tcaccccagg atcggagggg tgtgtcttttg 135840 acagcagcca tccagattac ccccaacggg taatcgtgaa ggcggggtgg tacacgagca 135900
cgagccacga ggcgcgactg ctgaggcgac tggaccaccc ggcgatcctg cccctcctgg 135960
acctgcatgt cgtctccggg gtcacgtgtc tggtcctccc caagtaccag gccgacctgt 136020
atacctatct gagtaggcgc ctgaacccac tgggacgccc gcagatcgca gcggtctccc 136080
ggcagctcct aagcgccgtt gactacattc accgccaggg cattatccac cgcgacatta 136140
agaccgaaaa tatttttatt aacacccccg aggacatttg cctgggggac tttggcgccg 136200
cgtgcttcgt gcagggttcc cgatcaagcc ccttccccta cggaatcgcc ggaaccatcg 136260
acaccaacgc ccccgaggtc ctggccgggg atccgtatac cacgaccgtc gacatttgga 136320
gcgccggtct ggtgatcttc gagactgccg tccacaacgc gtccttgttc tcggcccccc 136380
gcggccccaa aaggggcccg tgcgacagtc agatcacccg catcatccga caggcccagg 136440
tccacgttga cgagttttcc ccgcatccag aatcgcgcct cacctcgcgc taccgctccc 136500
gcgcggccgg gaacaatcgc ccgccgtaca cccgaccggc ctggacccgc tactacaaga 136560
tggacataga cgtcgaatat ctggtttgca aagccctcac cttcgacggc gcgcttcgcc 136620
ccagcgccgc agagctgctt tgtttgccgc tgtttcaaca gaaatgaccg ccccctgggg 136680
gcggtgctgt ttgcgggttg gcacaaaaag accccgatcc gcgtctgtgg tgtttttggc 136740
atcatgtcgc agggcgccat gcgtgccgtt gttcccatta tcccattcct tttggttctt 136800
gtcggtgtat cgggggttcc caccaacgtc tcctccacca cccaacccca actccagacc 136860
accggtcgtc cctcgcatga agcccccaac atgacccaga ccggcaccac cgactctccc 136920
accgccatca gccttaccac gcccgaccac acaccccccca tgccaagtat tggactggag 136980
gaggaggaag aggaggaggg ggccggggac ggcgaacatc ttgagggggg agatgggacc 137040
cgtgacaccc taccccagtc cccgggccca gccttcccgt tggctgagga cgtcgagaag 137100
gacaaaccca accgtcccgt agtcccatcc cccgatccca acaactcccc cgcgcgcccc 137160
gagaccagtc gcccgaagac accccccacc attatcgggc cgctggcaac tcgcccccacg 137220 acccgactca cctcaaaggg acgacccttg gttccgacgc ctcaacatac cccgctgttc 137280

-continued tcgttcctca ctgcctcccc cgccctggac accctcttcg tcgtcagcac cgtcatccac 137340
accttatcgt ttttgtgtat tggtgcgatg gcgacacacc tgtgtggcgg ttggtccaga 137400
cgcgggcgac gcacacaccc tagcgtgcgt tacgtgtgcc tgccgtccga acgcgggtag 137460
ggtatggggc gggggatggg gagagcccac atgcggaaag caagaacaat aaaggcggtg 137520
gtatctagtt gatatgcatc tctgggtgtt tttggggtgt ggcggacgcg gggcggtcat 137580
tggacggggt gcagttaaat acatgcccgg gacccatgaa gcatgcgcga cttccgggcc 137640
tcagaaccca cccgaaacgg ccaacggacg tctgagccag gcctggctat ccggagaaac 137700
agcacacgac ttggcgttct gtgtgtcgcg atgtctctgc gcgcagtctg gcatctgggg 137760
cttttgggaa gcctcgtggg ggctgttctt gccgccaccc atcggggacc tgcggccaac 137820
acaacggacc ccttaacgca cgccccagtg tcccctcacc ccagcccccct ggggggcttt 137880 gccgtccccc tcgtagtcgg tgggctgtgc gccgtagtcc tgggggcggc atgtctgctt 137940
gagctcctgc gtcgtacgtg ccgcgggtgg gggcgttacc atccctacat ggacccagtt 138000
gtcgtataat ttcccccccc cccccccttc tccgcgtggg tgatgtcggg tccaaactcc 138060
cgacaccacc agctggcatg gtataaatca ccggtgcgcc ccccaaacca tgtccggcag 138120
ggggatgggg gggcaatgcg gagggcaccc aacaacaccg ggctaaccag gaaatccgtg 138180
gccccggccc ccaataaaga tcgcggtagc ccggccgtgt gacactatcg tccataccga 138240
ccacaccgac gaatccccca agggggaggg gccattttac gaggaggagg ggtataacaa 138300
agtctgtctt taaaaagcag gggttaggga gttgttcggt cataagcttc agcgcgaacg 138360
accaactacc ccgatcatca gttatcctta aggtctcttt tgtgtggtgc gttccggtat 138420
ggggggggct gccgccaggt tgggggccgt gattttgttt gtcgtcatag tgggcctcca 138480
tggggtccgc agcaaatatg ccttggtgga tgcctctctc aagatggccg accccaatcg 138540
ctttcgcggc aaagaccttc cggtcctgga ccagctgacc gaccctccgg gggtccggcg 138600
cgtgtaccac atccaggcgg gcctaccgga cccgttccag ccccccagcc tcccgatcac 138660
ggtttactac gccgtgttgg agcgcgcctg ccgcagcgtg ctcctaaacg caccgtcgga 138720
ggccccccag attgtccgcg gggcctccga agacgtccgg aaacaaccct acaacctgac 138780
catcgcttgg tttcggatgg gaggcaactg tgctatcccc atcacggtca tggagtacac 138840
cgaatgctcc tacaacaagt ctctgggggc ctgtcccatc cgaacgcagc cccgctggaa 138900
ctactatgac agcttcagcg ccgtcagcga ggataacctg gggttcctga tgcacgcccc 138960
cgcgtttgag accgccggca cgtacctgcg gctcgtgaag ataaacgact ggacggagat 139020
tacacagttt atcctggagc accgagccaa gggctcctgt aagtacgccc tcccgctgcg 139080
catccccccg tcagcctgcc tctcccccca ggcctaccag caggggggtga cggtggacag 139140 catcgggatg ctgccccgct tcatccccga gaaccagcgc accgtcgccg tatacagctt 139200
gaagatcgcc gggtggcacg ggcccaaggc cccatacacg agcaccctgc tgcccccgga 139260
gctgtccgag acccccaacg ccacgcagcc agaactcgcc ccggaagacc ccgaggattc 139320
ggccctcttg gaggaccccg tggggacggt ggcgccgcaa atcccaccaa actggcacat 139380
accgtcgatc caggacgccg cgacgcctta ccatccccccg gccaccccga acaacatggg 139440
cctgatcgcc ggcgcggtgg gcggcagtct cctggcagcc ctggtcattt gcggaattgt 139500
gtactggatg cgccgccaca ctcaaaaagc cccaaagcgc atacgcctcc cccacatccg 139560
ggaagacgac cagccgtcct cgcaccagcc cttgttttac tagatacccc cccttaatgg 139620
gtgcgggggg gtcaggtctg cggggttggg atgggacctt aactccatat aaagcgagtc 139680
tggaaggggg gaaaggtgga cagtcgataa gtcggtagcg ggggacgcgc acctgttccg 139740
cctgtcgcac ccacagcttt ttttgcgaac cgtcccgttc cgggatgccg tgccgcccgt 139800
tgcagggcct ggtgctcgtg ggcctctggg tctgtgccac cagcctggtt gtccgtggcc 139860
ccacggtcag tctggtatca aactcatttg tggacgccgg ggccttgggg cccgacggcg 139920
tagtggagga agacctgctt attctcgggg agcttcgctt tgtgggggac caggtccccc 139980
acaccaccta ctacgatggg ggcgtagagc tgtggcacta ccccatggga cacaaatgcc 140040
cacgggtcgt gcatgtcgtc acggtgaccg cgtgcccacg tcgccccgcc gtggcattcg 140100
ccctgtgtcg cgcgaccgac agcactcaca gccccgcata tcccaccctg gagctcaatc 140160
tggcccaaca gccgcttttg cgggtccaga gggcaacgcg ggactatgcc ggggtgtacg 140220
tgttacgcgt atgggtcggt gacgcgccaa acgccagcct gtttgtcctg gggatggcca 140280
tagccgccga agggactctg gcgtacaacg gctcggccta tggctcctgc gacccgaaac 140340
tgcttccgtc ttcggccccg cgtctggccc cggcgagcgt ataccaaccc gcccctaacc 140400
aggcctccac cccctcgacc accacctcca ccccctcgac caccatcccc gctccctcga 140460
ccaccatccc cgctccccaa gcatcgacca cgcccttccc cacgggagat ccaaaaccac 140520
aacctcccgg ggtcaaccac gaacccccat ctaatgccac gcgagcgacc cgcgactcgc 140580
gatacgcgct aacggtgacc cagataatcc agatagccat ccccgcgtcc atcatagccc 140640
tggtgtttct ggggagctgt atttgcttta tacacagatg tcaacgccgc taccgacgct 140700
cccgtcgccc gatttacagc ccccagatgc ccacgggcat ctcatgcgcg gtgaacgaag 140760
cggccatggc ccgcctcgga gccgagctca aatcgcatcc gagcaccccc cccaaatccc 140820
ggcgccggtc gtcacgcacg ccaatgccct ccctgacggc catcgccgaa gagtcggagc 140880
ccgctggggc ggctgggctt ccgacgcccc ccgtggaccc cacgacaccc accccaacgc 140940
ctcccctgtt ggtataggtc cacggccact ggccgggagc accacataac cgaccgcagt 141000
ccctgagttg ggaataaacc ggtattattt acctatatcc gtgtatgtcg atttctttcc 141060
ccccctcccc ggaaaccaaa gaaggaagca aagaatggat gggaggagtt caggaagccg 141120
gggagagggc ccgcggcgca tttaaggcgt tgttgtgttg actttgcctc ttctggcggg 141180
ttggtgcggt gctgtttgtt gggctcccat tttacccgaa gatcggctgc tatccccggg 141240
acatggatcg cggggcggtg gtggggtttc ttctcggtgt ttgtgttgta tcgtgcttgg 141300
cgggaacgcc caaaacgtcc tggagacggg tgagtgtcgg cgaggacgtt tcgttgcttc 141360
cagctccggg gcctacgggg cgcggcccga cccagaaact actatgggcc gtggaacccc 141420
tggatgggtg cggcccctta cacccgtcgt gggtctcgct gatgcccccc aagcaggtgc 141480
ccgagacggt cgtggatgcg gcgtgcatgc gcgctccggt cccgctggcg atggcgtacg 141540
cccccccggc cccatctgcg accgggggtc tacgaacgga cttcgtgtgg caggagcgcg 141600
cggccgtggt taaccggagt ctggttattc acggggtccg agagacggac agcggcctgt 141660
ataccctgtc cgtgggcgac ataaaggacc cggctcgcca agtggcctcg gtggtcctgg 141720
tggtgcaacc ggccccagtt ccgaccccac ccccgacccc agccgattac gacgaggatg 141780
acaatgacga gggcgaggac gaaagtctcg ccggcactcc cgccagcggg accccccggc 141840
tcccgcctcc ccccgccccc ccgaggtctt ggcccagcgc ccccgaagtc tcacatgtgc 141900
gtggggtgac cgtgcgtatg gagactccgg aagctatcct gttttccccc ggggagacgt 141960
tcagcacgaa cgtctccatc catgccatcg cccacgacga ccagacctac tccatggacg 142020
tcgtctggtt gaggttcgac gtgccgacct cgtgtgccga gatgcgaata tacgaatcgt 142080
gtctgtatca cccgcagctc ccagaatgtc tgtccccggc cgacgcgccg tgcgccgcga 142140
gtacgtggac gtctcgcctg gccgtccgca gctacgcggg gtgttccaga acaaaccccc 142200
caccgcgctg ttcggccgag gctcacatgg agcccgtccc ggggctggcg tggcaggcgg 142260
cctccgtcaa tctggagttc cgggacgcgt ccccacaaca ctccggcctg tatctgtgtg 142320
tggtgtacgt caacgaccat attcacgcct ggggccacat taccatcagc accgcggcgc 142380
agtaccggaa cgcggtggtg gaacagcccc tcccacagcg cggcgcggat ttggccgagc 142440
ccacccaccc gcacgtcggg gcccctcccc acgcgccccc aacccacggc gccctgcggt 142500
taggggcggt gatgggggcc gccctgctgc tgtctgcact ggggttgtcg gtgtgggcgt 142560
gtatgacctg ttggcgcagg cgtgcctggc gggcggttaa aagcagggcc tcgggtaagg 142620
ggcccacgta cattcgcgtg gccgacagcg agctgtacgc ggactggagc tcggacagcg 142680
agggagaacg cgaccaggtc ccgtggctgg cccccccgga gagacccgac tctccctcca 142740
ccaatggatc cggctttgag atcttatcac caacggctcc gtctgtatac ccccgtagcg 142800
atgggcatca atctcgccgc cagctcacaa cctttggatc cggaaggccc gatcgccgtt 142860
actcccaggc ctccgattcg tccgtcttct ggtaaggcgc cccatcccga ggccccacgt 142920
cggtcgccga actgggcgac cgccggcgag gtggacgtcg gagacgagct aatcgcgatt 142980
tccgacgaac gcggaccccc ccgacatgac cgcccgcccc tcgccacgtc gaccgcgccc 143040
tcgccacacc cgcgaccccc gggctacacg gccgttgtct ccccgatggc cctccaggct 143100
gtcgacgccc cctccctgtt tgtcgcctgg ctggccgctc ggtggctccg gggggcttcc 143160
ggcctggggg ccgtcctgtg tgggattgcg tggtatgtga cgtcaattgc ccgaggcgca 143220
taaagggccg gtggtccgcc tagccgcagc aaattaaaaa tcgtgagtca cagcgaccgc 143280
aacttcccac ccggagcttt cttccggcct cgatgacgtc ccggctctcc gatcccaact 143340
cctcagcgcg atccgacatg tccgtgccgc tttatcccac ggcctcgcca gtttcggtcg 143400
aagcctacta ctcggaaagc gaagacgagg cggccaacga cttcctcgta cgcatgggcc 143460
gccaacagtc ggtattaagg cgtcgacgca gacgcacccg ctgcgtcggc atggtgatcg 143520
cctgtctcct cgtggccgtt ctgtcgggcg gatttggggc gctcctgatg tggctgctcc 143580
gctaaaagac cgcatcgaca cgcgcgtcct tcttgtcgtc tctcttcccc cccatcaccc 143640
cgcaatttgc acccagcctt taactacatt aaattgggtt cgattggcaa tgttgtctcc 143700
cggttgattt ttgggtgggt ggggagtggg tgggtgggga gtgggtgggt ggggagtggg 143760
tgggtgggga gtgggtgggt ggggagtggg tgggtgggga gtgggtgggt ggggagtggg 143820
tgggtgggga gtgggtgggt ggggagtggg tgggtgggga gtggcaagga agaaacaagc 143880
ccgaccacca gacagaaaat gtaaccatac ccaaaccgac tctgggggct gtttgtgggg 143940
tcggaaccat aggatgaaca aaccaccccg taccacccgc acccaagggt gcggtggctc 144000
atcggcatct gtccggtatg ggttgttccc cacccactcg cgttcggacg tcttagaatc 144060
atggcggttt tctatgccga catcggtttt ctcccccgca ataagacacg atgcgataaa 144120
atctgtttgt aaaatttatt aagggtacaa attgccctag cacaggggtg gggttagggc 144180
cgggtcccca cacccaaacg caccaaacag atgcaggcag tgggtcgagt acagccccgc 144240
gtacgaacac gtcgatgcgt gtgtcagaca gcaccagaaa gcacaggcca tcaacaggtc 144300
gtgcatgtgt cggtgggttt ggacgcgggg ggccatggtg gtgataaagt taatggccgc 144360
cgtccgccag ggccacaggg gcgacgtctc ttggttggcc cggagccact gggtgtggac 144420
cagccgcgcg tggcggccca acatggcccc tgtagccggg ggcgggggat cgcgcacgtt 144480
tgcagcgcac atgcgagaca cctcgaccac ggttcgaaag aaggcccggt ggtccgcggg 144540
caacatcacc aggtgcgcaa gcgcccgggc gtccagaggg tagagccctg agtcatccga 144600
ggttggctca tcgcccgggt cttgccgcaa gtgcgtgtgg gttgggcttc cggtgggcgg 144660
gacgcgaacc gcggtgtgga tcccgacgcg ggcccgagcg tatgctccat gttgtgggga 144720
gaaggggtct gggctcgcca ggggggcata cttgcccggg ctatacagac ccgcgagccg 144780
tacgtggttc gcggggggtg cgtggggtcc ggggctcccg gggagaccgg ggctcccggg 144840
gagaccgggg ctccctggga gaccggggtt gtcgtggatc cctggggtca cgcggtaccc 144900
tggggtctct gggagctcgc ggtactctgg gttccctagg ttctcggggt ggtcgcggaa 144960
cccggggctc ccggggaaca cgcggtgtcc tggggattgt tggcggtcgg acggcttcag 145020
atggcttcga gatcgtagtg tccgcaccga ctcgtagtag acccgaatct ccacattgcc 145080
ccgccgcttg atcattatca ccccgttgcg ggggtccgga gatcatgcgc gggtgtcctc 145140
gaggtgcgtg aacacctctg ggtgcatgc cggcggacgg cacgcctttt aagtaaacat 145200
ctgggtcgcc cggcccaact ggggccgggg gttgggtctg gctcatctcg agagccacgg 145260
gggggaacca ccctccgccc agagactcgg gtgatggtcg tacccgggac tcaacgggtt 145320
accggattac ggggactgtc ggtcacggtc ccgccggttc ttcgatgtgc cacacccaag 145380
gatgcgttgg gggcgatttc gggcagcagc ccgggagagc gcagcagggg acgctccggg 145440
tcgtgcacgg cggttctggc cgcctcccgg tcctcacgcc ccttttatt gatctcatcg 145500 cgtacgtcgg cgtacgtcct gggcccaacc cgcatggtgt ccaggaaggt gtccgccatt 145560
tccagggccc acgacatgct ccccccgac gagcaggaag cggtccacgc aacggtcgcc 145620
gccggtcgcc tcgacgagga cgttcctcct gcgggaaggc acgaacgcgg gtgagccccc 145680
tcctccgccc ccgcgtcccc cctcctccgc ccccgcgtcc cccctcctcc gcccccgcgt 145740 ccccctcct ccgcccccgc gtccccctc ctccgccccc gcgtcccccc tcctccgccc 145800
ccgcgtcccc cctcctccac ccccgcgtcc ccccctcctc cgcccaccca aggtgcttac 145860
ccgtgcaaaa aaggcggacc ggtgggtttc tgtcgtcgga ggcccccggg gtgcgtcccc 145920
tgtgtttcgt gggtggggtg ggcgggtctt tccccccgc gtccgcgtgt ccctttccga 145980
tgcgatcccg atcccgagcc ggggcgtcgc gatgccgacg ccgtccgctc cgacggccct 146040
ctgcgactcc cgctcccggt ccgcgtgctc cgcagccgct cccgtcgttc gtggccggcg 146100
ccgtctgcgg gcgtcggtcg cgccgggcct ttatgtgcgc cggagagacc cgccccccgc 146160
cgcccgggcc cgcccccggg gccggcgcgg agtcgggcac ggcgccagtg ctcgcacttc 146220
gccctaataa tatatatata ttgggacgaa gtgcgaacgc ttcgcgttct cacttctttt 146280
acccggcggc cccgcccct tggggcggtc ccgcccgccg gccaatgggg gggcggcaag 146340
gcgggcggcc cttgggccgc ccgccgtccc gttggtcccg gcgtccggcg ggcgggaccg 146400
gggggcccgg ggacggccaa cgggcgcgcg gggctcgtat ctcattaccg ccgaaccggg 146460
aagtcggggc ccgggccccg ccccctgccc gttcctcgtt agcatgcgga acggaagcgg 146520
aaaccgccgg atcgggcggt aatgagatgc catgcggggc ggggcgcgga cccacccgcc 146580
ctcgcgcccc gcccatggca gatggcgcgg atgggcgggg ccgggggttc gaccaacggg 146640
ccgcggccac gggcccccgg cgtgccggcg tcggggcggg gtcgtgcata atggaattcc 146700
gttcggggtg ggcccgccgg gggggcgggg ggccggcggc ctccgctgct cctccttccc 146760
gccggcccct gggactatat gagcccgagg acgccccgat cgtccacacg gagcgcggct 146820
gccgacacgg atccacgacc cgacgcggga ccgccagaga cagaccgtca gacgctcgcc 146880
gcgccgggac gccgatacgc ggacgaagcg cgggaggggg atcggccgtc cctgtccttt 146940
ttcccaccca agcatcgacc ggtccgcgct agttccgcgt cgacggcggg ggtcgtcggg 147000
gtccgtgggt ctcgcccccct ccccccatcg agagtccgta ggtgacctac cgtgctacgt 147060
ccgccgtcgc agccgtatcc ccggaggatc gccccgcatc ggcgatggcg tcggagaaca 147120
agcagcgccc cggctccccg ggccccaccg acgggccgcc gcccaccccg agcccagacc 147180
gcgacgagcg gggggccctc gggtggggcg cggagacgga ggagggcggg gacgaccccg 147240
accacgaccc cgaccacccc cacgacctcg acgacgcccg gcgggacggg agggcccccg 147300
cggcgggcac cgacgccggc gaggacgccg gggacgccgt ctcgccgcga cagctggctc 147360
tgctggcctc catggtagag gaggccgtcc ggacgatccc gacgcccgac cccgcggcct 147420
cgccgccccg gacccccgcc tttcgagccg acgacgatga cggggacgag tacgacgacg 147480
cagccgacgc cgccggcgac cgggccccgg cccggggccg cgaacgggag gccccgctac 147540
gcggcgcgta tccggacccc acggaccgcc tgtcgccgcg cccgccggcc cagccgccgc 147600
ggagacgtcg tcacggccgg tggcggccat cggcgtcatc gacctcgtcg gactccgggt 147660
cctcgtcctc gtcgtccgca tcctcttcgt cctcgtcgtc cgacgaggac gaggacgacg 147720
acggcaacga cgcggccgac cacgcacgcg aggcgcgggc cgtcgggcgg ggtccgtcga 147780
gcgcggcgcc ggcagccccc gggcggacgc cgcccccgcc cgggccaccc cccctctccg 147840
aggccgcgcc caagccccgg gcggcggcga ggacccccgc ggcctccgcg ggccgcatcg 147900
agcgccgccg ggcccgcgcg gcggtggccg gccgcgacgc cacgggccgc ttcacggccg 147960
ggcagccccg gcgggtcgag ctggacgccg acgcgacctc cggcgccttc tacgcgcgct 148020
atcgcgacgg gtacgtcagc ggggagccgt ggcccggcgc cgggccccg cccccggggc 148080
gggtgctgta cggcggcctg ggcgacagcc gcccgggcct ctgggggggcg cccgaggcgg 148140
aggaggcgcg acgccggttc gaggcctcgg gcgccccggc ggccgtgtgg gcgcccgagc 148200
tgggcgacgc cgcgcagcag tacgccctga tcacgcggct gctgtacacc ccggacgcgg 148260
aggccatggg gtggctccag aacccgcgcg tggtccccgg ggacgtggcg ctggaccagg 148320
cctgcttccg gatctcgggc gccgcgcgca acagcagctc cttcatcacc ggcagcgtgg 148380
cgcgggccgt gccccacctg ggctacgcca tggcggccgg ccgcttcggc tggggcctgg 148440
cgcacgcggc ggccgccgtg gccatgagcc gccgatacga ccgcgcgcag aagggcttcc 148500
tgctgaccag cctgcgccgc gcctacgcgc ccctgttggc gcgcgagaac gcggcgctga 148560
cgggggccgc ggggagcccc ggcgccggcg cagatgacga gggggtcgcc gccgtcgccg 148620
ccgccgcacc gggcgagcgc gcggtgcccg ccgggtacgg cgccgcgggg atcctcgccg 148680
ccctggggcg gctgtccgcc gcgcccgcct cccccgcggg gggcgacgac cccgacgccg 148740
cccgccacgc cgacgccgac gacgacgccg ggcgccgcgc ccaggccggc cgcgtggccg 148800
tcgagtgcct ggccgcctgc cgcgggatcc tggaggcgct ggccgagggc ttcgacggcg 148860
acctggcggc cgtcccgggg ctggccgggg cccggcccgc cagccccccg cggccggagg 148920
gacccgcggg ccccgcttcc ccgccgccgc cgcacgccga cgcgccccgc ctgcgcgcgt 148980
ggctgcgcga gctgcggttc gtgcgcgacg cgctggtgct catgcgcctg cgcggggacc 149040
tgcgcgtggc cggcggcagc gaggccgccg tggccgccgt gcgcgccgtg agcctggtcg 149100

-continued ccggggccct gggccccgcg ctgccgcggg acccgcgcct gccgagctcc gcggccgccg 149160
ccgccgcgga cctgctgttt gacaaccaga gcctgcgccc cctgctggcg gcggcggcca 149220
gcgcaccgga cgccgccgac gcgctggcgg ccgccgccgc ctccgccgcg ccgcgggagg 149280
ggcgcaagcg caagagtccc ggcccggccc ggccgcccgg aggcggcggc ccgcgacccc 149340
cgaagacgaa gaagagcggc gcggacgccc ccggctcgga cgcccgcgcc cccctccccg 149400
cgcccgcgcc cccctccacg cccccggggc ccgagcccgc ccccgcccag cccgcggcgc 149460
cccgggccgc cgcggcgcag gcccgcccgc gccccgtggc cgtgtcgcgc cggcccgccg 149520
agggccccga ccccctgggc ggctggcggc ggcagccccc ggggcccagc cacacggcgg 149580
cgcccgcggc cgccgccctg gaggcctact gctccccgcg cgccgtggcc gagctcacgg 149640
accacccgct gttccccgtc ccctggcgac cggccctcat gtttgacccg cgggccctgg 149700
cctcgatcgc cgcgcggtgc gccgggcccg cccccgccgc ccaggccgcg tgcggcggcg 149760
gcgacgacga cgataacccc cacccccacg gggccgccgg gggccgcctc tttggccccc 149820
tgcgcgcctc gggcccgctg cgccgcatgg cggcctggat gcgccagatc cccgaccccg 149880
aggacgtgcg cgtggtggtg ctgtactcgc cgctgccggg cgaggacctg gccggcggcg 149940
gggcctcggg ggggccgccg gagtggtccg ccgagcgcgg cgggctgtcc tgcctgctgg 150000
cggccctggc caaccggctg tgcgggccgg acacggccgc ctgggcgggc aattggaccg 150060
gcgcccccga cgtgtcggcg ctgggcgcac agggcgtgct gctgctgtcc acgcgggacc 150120
tggccttcgc cggggccgtg gagtttctgg ggctgctcgc cagcgccggc gaccggcggc 150180
tcatcgtggt caacaccgtg cgcgcctgcg actggcccgc cgacgggccc gcggtgtcgc 150240
ggcagcacgc ctacctggcg tgcgagctgc tgcccgccgt gcagtgcgcc gtgcgctggc 150300
cggcggcgcg ggacctgcgc cgcacggtgc tggcctcggg ccgcgtgttc ggcccggggg 150360
tcttcgcgcg cgtggaggcc gcgcacgcgc gcctgtaccc cgacgcgccg ccgctgcgcc 150420
tgtgccgcgg cggcaacgtg cgctaccgcg tgcgcacgcg cttcggcccg gacacgccgg 150480
tgcccatgtc cccgcgcgag taccgccggg ccgtgctgcc ggcgctggac ggccgggcgg 150540
cggcctcggg gaccaccgac gccatggcgc ccggcgcgcc ggacttctgc gaggaggagg 150600
cccactcgca cgccgcctgc gcgcgctggg gcctgggcgc gccgctgcgg cccgtgtacg 150660
tggcgctggg gcgcgaggcg gtgcgcgccg gcccggcccg gtggcgcggg ccgcggaggg 150720
acttttgcgc ccgcgccctg ctggagcccg acgacgacgc ccccccgctg gtgctgcgcg 150780
gcgacgacga cggcccgggg gccctgccgc cggcgccgcc cgggattcgc tgggcctcgg 150840
ccacgggccg cagcggcacc gtgctggcgg cggcgggggc cgtggaggtg ctgggggcgg 150900
aggcgggctt ggccacgccc ccgcggcggg aagttgtgga ctgggaaggc gcctgggacg 150960
aagacgacgg cggcgcgttc gagggggacg gggtgctgta acgggccggg acggggcggg 151020
gcgcttgtga gacccgaaga cgcaataaac ggcaacaacc tgattaagtt ttgcagtagc 151080
gttgtttatt cgaggggcgg gagggggcga ggggcgggag ggggcgaggg gcgggagggg 151140
gcgaggggcg ggagggggcg aggggcggga gggggcgagg ggcgggaggg ggcgaggggc 151200
gggagggggc gaggggcggg agggggcgag gggcgggagg gggcgagggg cgggaggggg 151260
cgaggggcgg gagggggcga ggggcgggag ggggcgaggg gcgggagggg gcgaggggcg 151320
ggagggggcg aggggcggga gggggcgagg ggcgggaggg ggcgaggggc gggagggggc 151380
gaggggcggg agggggcgag gggcgggagg gggcgagggg cggtggtggt gcgcgggcgc 151440
ccccggaggg tttggatctc tgacctgaga ttggcggcac tgaggtagag atgcccgaac 151500 cccccgagg gagcgcggga cgcgccgggg agggctgggg ccggggaggg ctggggccgg 151560
ggagggctgg ggccggggag ggctggggcc ggggagggct ggggccgggg agggctgggg 151620
ccggggaggg ctggggctgg ggagggctgg ggctggggag ggggcggtgg tgtgtagcag 151680
gagcggtgtg ttgcgccggg gtacgtctgg aggagcggga ggtgcgcggt gacgtgtgga 151740
tgaggaacag gagttgttgc gcggtgagtt gtcgctgtga gttgtgttgt tgggcaggtg 151800
tggtggatga cgtgacgtgt gacgtgcgga gtgcgccgtg ctctgttggt ttcacctgtg 151860
gcagcccggg ccccccgcgg gcgcgcgcgc gcgcaaaaaa ggcgggcggc ggtccgggcg 151920
gcgtgcgcgc gcgcggcggg cgtgggggc ggggccgcgg gagcgggggg aggagcgggg 151980
ggaggagcgg ggggaggagc ggggggagga gcggggggag gagcgggggg aggagcgggg 152040
ggaggagcgg ggggaggagc ggggggagga gcggggggag gagcgggggg aggagcgggg 152100
ggaggagcgg ggggaggagc ggggggagga gcggggggag gagcgggggg aggagcgggg 152160
ggaggagcgg ggggaggagc ggccagacgc cgaaaacggg cccccccaa aacacacccc 152220 ccgggggtcg cgcgcggccc tttaaagcgg tggcggcggg c 152261

<210> SEQ ID NO 110
<211> LENGTH: 154746
<212> TYPE: DNA
<213> ORGANISM: Human herpes virus strain 2

<400> SEQUENCE: 110
agtccccgtc ctgccgcgcg ggggcgggcg cgggaaaaaa gccgcgcggg ggcgcccgcg 60
ggaaggcagc cccgcggcgc gcggggggag gggcggcgcc cgcgggggag cggccggctc 120
cgggggaggg acggggaagg gggcgcgcgg ggctgccctg ccgcccgccc gccgccgccg 180
cccgccttcg cgcccccccc caaaaaacac ccccccggg ggttgactcc ccgggggaaa 240
agaggcgggg cgggagtccc cgtcctgccg ccgcccctta agagggcccg caacacggcc 300
cgggctgcgc acgccagccg ggacgggtga gttcgctagg caagcacgga ctggcggtta 360
cacgtgcatg cgtgccgagt gaactctccc gccccgacgc gctccggctc cgggcctacg 420
ccgagcccag ccgcccgcca tgtcccgccg ccggggtccc cgccgccggg gtccccggcg 480
ccggccgcgc cccggcgctc cagccgtgcc gcgccccggc gctccagccg tgccgcgccc 540
cggcgcgctc ccaaccgcag actcccaaat ggtccctgcg tacgactcgg gaaccgcggt 600
cgagagcgcg ccggccgcgt cctcgctcct gcggcgctgg ctgctggtgc cccaggcgga 660
cgacagcgac gacgcggact acgccggcaa cgacgacgca gagtgggcga acagcccccc 720
gagcgagggc ggggggaagg cgccggaggc cccgcacgcc gcgcctgccg ccgcctgccc 780
cccgccgccg ccgcgcaagg agcgcgggcc gcagcgcccc cttccgcccc acctggcgct 840
acggctgcgc accacgacgg agtacctggc gcgcctgagc ctgcgccggc ggcggccccc 900
cgcgtccccg cccgcggacg cgccgcgcgg gaaggtacgc ctcccctccg acccccctgac 960 gcccctccga ccccctgacg cccctccgac cccctgacgc ccctccgacc ccctgacgcc 1020
cctccgaccc cctgacgccc ctccgacccc ctgacgcccc tccgaccccc gtgtctcccc 1080
gcccgcaggt gtgcttctcg ccgcgcgtgc aggtgcgcca tctggtggcc tgggagacgg 1140
ccgcgcgcct ggcccgacgg gggtcctggg cgcgcgagcg ggccgaccgc gaccggttcc 1200
ggcgccgcgt ggcggcggcc gaggcggtca tcggaccgtg cctggagccc gaggcccgag 1260
ctcgggcccg agcccgagcc cgggcccacg aagacggcgg acccgcggag gaggaggagg 1320

```
cggcggcggc ggcgcgcggg tcctccgccg ccgcgggccc gggccgtcgg gcggtctagg   1380
gttgaaccgg cgagggcggc ctcggccggc ggagccccgg agctccgaag gtctgcgcga   1440
ggccgctctc cgaagagacg atgggagccc cgcgtatata tccgcgaggg cccggcgccg   1500
ccccgccgct ccgcccgccc caggggggcgg cgccggccaa ccgcgcgccg ccgcgcgggc   1560
ccggactccg ccccggcgac cgccccgcgc cggcttcccg gtatggtaat tagaaacttt   1620
taataggcgg tcccggccgc catccccgcg catggtaatt agcaactttt aatgggccgg   1680
cgttcccgct cgcggtaatt agcagctttt aacgggccgc cattcccgct tatggtaatt   1740
aaaaacgttc ggacggcccc tcgctccccg cgtaattact ccctcggggt tccgggttat   1800
gctgattact ttcttggcag aacacgcaga gcctcgcgcg ccgccgggtg ggtgggctga   1860
tcggccccta ttggtcccct gggcttccta gtatgctaat gaatttttcc ccgggggcgg   1920
gcaccactca gggccgcgcc ggcggggcgc cggggggact cccatctgcg tcggcggggg   1980
gcggcgcatg ctaatggggt tcttggagta cacccggttg gtccccgggg acggggccgc   2040
cccgagaggg ggggattccc tccctccgcc cccgccgggg cgcgcggcta ttgggggaat   2100
cgtaaatgcc gcccctttgg gggagtggat aggcgccggg tataaggcag ccccgtgtga   2160
cggtcgggcc gcattcgcac cccggcactg cgagcgacgg agcggcggcc cggcgggagg   2220
aggagacccg gagagacaga gactaaaacc cggcaagaga gagaccgcgg gccgccgtct   2280
cgagtctacc ctaccccggc tcatggaacc ccggcccggc acgagctccc gggcggaccc   2340
cggccccgag cggccgccgc ggcagacccc cggcacggtg agagggcgac ccccgggtct   2400
caggcccccc cttttccccg gaccacccgg ctgcgggttg gggtggtcg cgggcggtgg   2460
gctcggggc ggggacgctt gacggggccg acccccggcc cgcttaagcg gtcgggggac   2520
ccccgtgggc cgtgcgccgc cccccgaccc tctggggggg cgagggaggc agggaggagc   2580
ccgagagcgg gggacagggg gggagacgag gggtcggaat ccaaaggacg cagaccacct   2640
ttggttacgg accccttct cccccccttc cgaacaaaaa gcagcgggcg gggggccggg   2700
gtgagggagg gacacggggg acacggcgcg ggggtcccgc ctcacgcccc gcgccctcta   2760
aatccccccc gttgctttgt caagcagccc gccgccccgc acgcctgggg gatgctcaac   2820
gacatgcagt ggctcgccag cagcgactcg gaggaggaga ccgaggtggg aatctctgac   2880
gacgaccttc accgcgactc cacctccgag gcgggcagca cggacacgga gatgttcgag   2940
gcgggcctga tggacgcggc cacgccccccg gcccggcccc cggccgagcg ccagggcagc   3000
cccacgcccg ccgacgcgca gggatcctgt gggggtgggc ccgtgggtga ggaggaagcg   3060
gaagcgggag gggggggcga cgtgtgtgcc gtgtgcacgg acgagatcgc ccccgcccctg   3120
cgctgccaga gttttccctg cctgcacccc ttctgcatcc cgtgcatgaa gacctggatt   3180
ccgttgcgca acacgtgtcc cctgtgcaac accccggtgg cgtacctgat agtgggcgtg   3240
accgccagcg ggtcgttcag caccatcccg atagtgaacg acccccggac ccgcgtggag   3300
gccgaggcgg ccgtgcgggc cggcacggcc gtggacttta tctggacggg caacccgcgg   3360
acggccccgc gctccctgtc gctgggggga cacacggtcc gcgccctgtc gcccaccccc   3420
ccgtggcccg gcacggacga cgaggacgat gacctggccg acggtgaggg cgggcggggg   3480
tcgggcgggg ggcgggcggg ggtcgggcgg gggtcgggcg ggggtcgggc gggggtcggg   3540
cgggggtcgg gcgggggtcg ggcgggggtc gggcgggggt cgggcggggg tcgggcgggg   3600
gtcgggcact aaccgggggc tcccgtctct gtctccctct gcagtggact acgtcccgcc   3660
cgccccccga agagcgcccc ggcgcggggg cggcggtgcg ggggcgaccc gcggaacctc   3720
```

```
ccagcccgcc gcgacccgac cggcgccccc tggcgccccg cggagcagca gcagcggcgg   3780
cgccccgttg cgggcggggg tgggatctgg gtctgggggc ggccctgccg tcgcggccgt   3840
cgtgccgaga gtggcctctc ttccccctgc ggccggcggg gggcgcgcgc aggcgcggcg   3900
ggtgggcgaa gacgccgcgg cggcggaggg caggacgccc cccgcgagac agccccgcgc   3960
ggcccaggag ccccccatag tcatcagcga ctctccccg ccgtctccgc gccgccccgc   4020
gggccccggg ccgctctcct ttgtctcctc ctcctccgca caggtgtcct cgggccccgg   4080
gggggaggt ctgccacagt cgtcggggcg cgccgcgcgc ccccgcgcgg ccgtcgcccc   4140
gcgcgtccgg agtccgcccc gcgccgccgc cgcccccgtg gtgtctgcga gcgcggacgc   4200
ggccgggccc gcgccgcccg ccgtgccggt ggacgcgcac cgcgcgcccc ggtcgcgcat   4260
gacccaggct cagaccgaca cccaagcaca gagtctgggc cgggcaggcg cgaccgacgc   4320
gcgcgggtcg ggagggccgg gcgcggaggg aggacccggg gtcccccgcg gcaccaacac   4380
ccccggtgcc gccccccacg ccgcggaggg ggcggcggcc cgcccccgga agaggcgcgg   4440
gtcggactcg ggccccgcgg cctcgtcctc cgcctcttcc tccgccgccc cgcgctcgcc   4500
cctcgccccc cagggggtgg gggccaagag ggcggcgccg cgccgggccc cggactcgga   4560
ctcgggcgac cgcggccacg ggccgctcgc cccggcgtcc gcgggcgccg cgcccccgtc   4620
ggcgtctccg tcgtcccagg ccgcggtcgc cgccgcctcc tcctcctccg cctcctcctc   4680
ctccgcctcc tcctcctccg cctcctcctc ctccgcctcc tcctcctccg cctcctcctc   4740
ctccgcctcc tcctcctccg cctcttcctc tgcgggcggg gctggtggga gcgtcgcgtc   4800
cgcgtccggc gctggggaga gacgagaaac ctccctcggc ccccgcgctg ctgcgccgcg   4860
ggggccgagg aagtgtgcca ggaagacgcg ccacgcggag ggcggccccg agcccggggc   4920
ccgcgacccg gcgcccggcc tcacgcgcta cctgcccatc gcgggggtct cgagcgtcgt   4980
ggccctggcg ccttacgtga acaagacggt cacgggggac tgcctgcccg tcctggacat   5040
ggagacgggc cacatagggg cctacgtggt cctcgtggac cagacgggga acgtggcgga   5100
cctgctgcgg gccgcggccc ccgcgtggag ccgccgcacc ctgctccccg agcacgcgcg   5160
caactgcgtg aggccccccg actacccgac gcccccgcg tcggagtgga acagcctctg   5220
gatgaccccg gtgggcaaca tgctctttga ccagggcacc ctggtgggcg cgctggactt   5280
ccacggcctc cggtcgcgcc acccgtggtc tcgggagcag ggcgcgcccg cgccggccgg   5340
cgacgccccc gcgggccacg gggagtaggg ggagctaaca ctcggcttgc tgcccgaagg   5400
aagccgcccc ccaccggacc accggccgag gcgcctcggg ggcaggggga ggtgggggg   5460
gggaaagacg gggaggagac aggaagtggg ggtgggagtg gggggggggg acggacacgg   5520
ccccgaacag caacacacac cagcattttg ttatggactt tctggccttg ttgaaaactt   5580
gaggaaaaaa aaaactttat atttataaaa attttacaat aaagttttgt gatgcttttg   5640
acacactttg ttgttggcct ttgatgcagc tcccccgcgc agggggccg gggatggggg   5700
ggaagggagg aggaggaggg ggggcgggca cgagaagccg cccccacccc cgaggcctgt   5760
tggtctttat catagaacag agccggggcc cggcctcgtt ctggctccct gtcttggtgg   5820
gtgggcgggc tggctggcgg gtaaaaaaag agtgtgtccg tgttgacagg gaggggggcc   5880
cgatcgtgca gagcacgcac gtctggccgg ccagaccctg ggggtggtgg gcaggagtgg   5940
gagggcgcct ggctcgggga gggaggaggg ggggggtcag ccgcaccacc ggcgcgaagc   6000
caggggccag ggaactttga tagagagggg ggaaagtggg gcgggggcga gggcggttga   6060
```

-continued

```
atcacaacgc atgcacgccc tctgcccccg gggacgggtg ggaggaagga ggagggagaa   6120
gagaagaccc gaggcatgca cccgcactta cgcccgtgcc cacccccgcc ccggcgccca   6180
ccccgcccgc acacctgccc gccacgcccg cccctcctca ccctggctgg gagaaaggag   6240
gaggagcagg aagaggagac ccgaggcatg caaccgcact caccccaccc cgcccgcaca   6300
cctgcccgcc acgcccgccc ctccttaccc tggctgcggg gagactccca tcggggcgag   6360
ggggctcgcg cgttcgcaac accacaccac accacacggc ccaccacaac acggcccacc   6420
acgacacaac acgacacgac gcgttttgcg gggcatgcaa gtcgacacac cgcgcgcgtg   6480
cctacctttc cctagcggcc ccggcccccg gcccgtttcc ttccgccacc actaccacca   6540
cccccccgcc cgcgcccacg cggtagagga aggggacggg cgccacaccc acggctgtgg   6600
ccgggcacgc gcctttgggg ttgttggggg ggggtgaccg gcgcgtgggg gcggtgggcg   6660
tacgggcccg acccgcgcct gcccccccgg gaacgacgac gggggggggg gaaacggggg   6720
tgggtggaag ggaagaggaa ggagaaaggg ggggtggatc cgaacacgcc ggatccgcga   6780
aaataataac aaaacaaaca aaaacagaaa caaaaacaaa aacacctaga aaaaaaggat   6840
acgggttggc tcgcgggcgg tgcggctgac ctgcctgccc tttctgggac ccccgcctcg   6900
tgtttcttga aagggggagg aagaacagtt ctcccccaac ccctgctctc ttctctcttc   6960
cgcccgcccc ccccccctct ccccgccgcc tcagcagaag ctcacctgta cgaccctaaa   7020
cctacctgcg agaacgcgcg gcgttcgagg ggcgcgctct ctcacacgag acacacgcag   7080
gcgccccccc cccccggagc ctgggtcccc cggcggacgg ctcacgcggc gcggcgtctc   7140
ggtgggacgc gggcaaaggg cggcggcggc gggggggggg gggggaaatg tgaggagagc   7200
gagacagaga gagagaagga agagggaagg ggcgcggcgg gacgggggaa gacgaggaga   7260
agggaagggg cgagggtcgg gcccgggagc ggggcggccc gggagggaga agaaacggaa   7320
cgcggaaacg ccgccggcgc ggcccggggc cccggggccc ccgcgctccg ccgggggccc   7380
gggccggacc gccgggcggg ggacgccttc cgcccggcgc cgggcggcta cccgggaccc   7440
ccggccggga atcgaaaaaa gcctccgggg gcccctttcg cgcctttcgc gaacgcgcgg   7500
cgccggaggg ggcggccgcc gaggtgcggg ggcccctccg gccggggcgc acctcggcgg   7560
ccaagccccg gcccgcccgg gggtccccga ggcaagaggc ggaccctcgg aggcgcggaa   7620
gaagacggga ggcgggggaa aaaaggggga agagaggggg aggtagggag gggagaggag   7680
aagggcgcgc cggtgcgcgg agcagccttc cttctccgga gtccctctcg atcggcggcg   7740
ggcccctgcg ttcgttgctg ccgcgccccc ggttttataa agacagggat gacgcagcag   7800
aaatgcccac agcaacacgc gggcggggct cgggctctcc ggcggcttaa tggatctccg   7860
ggcacggcgc ccgcaaccgc agagcactca gctggcgcgc cccccccccaa cgtgggagtg   7920
tttaatggaa gggcgtgggg ccggccgccg gatgcccgcg ggggcctaat gcggcgggag   7980
gcgtgggccg ctggcgccgc ggcccgtctg ctggcccgcg gcccgtctgc tggcccgcgg   8040
ccacgtaaac aatgacacag gggttctctc cgccgcggcc ggcgcggggc gttgccggcc   8100
cggcccggcc ccggagcccg cggcgctgct cggctgcggc cgcgggctcc gggggctccg   8160
cactctgccc ggctcgcccc gtccccccctc ttgctgcttt tccgcgcgcc tctctttccc   8220
gttgctttcc ctctcccccc cccccccctct ctctctctct ctctctctct ccgccatcct   8280
cccgcccggc cgcccactcc ccgctcggcc tctccggctg cggtgcttgg gtctccttcg   8340
tcgggcggcg gggggggggc gtcgggactc gcggagggcc ggagaatgga aggcgagggg   8400
atgcaggagg aggatcggga ctccccatct tctgcccttc catcctccgt tttccgctt    8460
```

-continued

```
tccaccgccg ccgccaccac ccccccttcc ttcgcccgcc cgcctcgccc cggacccctc   8520
ccccccgtgt tccccccatc gttcaccacc acgcccccca ccgcgccttg gctgtttggg   8580
gggtggcggc ggtggtcggc gtgctgccgg aggctgcggg cgcggggtag gtgggtgggc   8640
gggtggtggg ggggggcccg gctgcgtctc gccgcgatcc cgccggtggg gcgcggcggc   8700
ggtcggggtg gggggagagt gtcgtgggtg tgttttcgtg tcccccacca ccactcccac   8760
cccgaccgcc gccgcgcccg cgtttctgcc gcccgcgcgc tcctgtgtgg accccggggt   8820
gggcggcggg ggggggtgcc gtgggtgtgg cggcggggcg cgggccgggg ccggggctcg   8880
ctggtccgcc gaagtaaaga aaagatcgcc accgtgtgtt cgtctgtgtg ttctgcgcgg   8940
cgccggggcc cccctgccgg gcggggcggt ggggcggggt cggggtcgcg gcggggaagg   9000
aaggaaagac cccggaagcg ccgggagggg gcgccggcgc gacgcgggcg gccgggcggg   9060
ggcgcgcggc ggccgggcgg gggcgcgcgg cggccgggcg ggggcgcgcg gcggccgggc   9120
gggggcgcgc ggcggccggg cgggggcgcg cggcggccgg gcgggggcgc gcggcggccg   9180
ggcgggggcg cgctttcccc gcgtcgcccc tcgggttccc aagacctatc acgtgtgcgc   9240
aggggagggg aggacgcggg ggaggggagg acgcggggga ggggaggacg cgggggatat   9300
ataaagcggt agaaagcgcg ggaatgggca tattggaccc gcgtgattcg gttgctcgcg   9360
gttgtcttgt ttggacgttt tttatgcggg aacaaggggg cttaccggtt acactgtccg   9420
ctcgctatgg ggttcgtctg tctgtttggg cttgtcgtta tgggagcctg gggggcgtgg   9480
ggtgggtcac aggcaaccga atatgttctt cgtagtgtta ttgccaaaga ggtgggggac   9540
atactaagag tgccttgcat gcggaccccc gcggacgatg tttcttggcg ctacgaggcc   9600
ccgtccgtta ttgactatgc ccgcatagac ggaatatttc ttcgctatca ctgcccgggg   9660
ttggacacgt ttttgtggga taggcacgcc cagagggcgt atctggttaa ccccttctc   9720
tttgcggcgg gatttttgga ggacttgagt cactctgtgt ttccggccga cacccaggaa   9780
acaacgacgc gccgggccct ttataaagag atacgcgatg cgttgggcag tcgaaaacag   9840
gccgtcagcc acgcacccgt cagggccggg tgtgtaaact ttgactactc acgcactcgc   9900
cgctgcgtcg ggcgacgcga tttacggcct gccaacacca cgtcaacgtg ggaaccgcct   9960
gtgtcgtcgg acgatgaagc gagctcgcag tcgaagcccc tcgccaccca gccgcccgtc  10020
ctcgcccttt cgaacgcccc cccacggcgg gtctccccga cgcgaggtcg gcgccggcat  10080
actcgcctcc gacgcaacta gccacgtctg catcgcaagc caccctgggt cgggagcagg  10140
acagccgacc cgtctagcgg ccgggtcggc tgtccagcgt cgtcgcccta gaggctgtcc  10200
gccgggcgtg atgttttccg catctacgac ccccgaacag cccctggggc tgtcgggcga  10260
tgcgacgccg cccctgccga cttccgtgcc cctggactgg gccgcgtttc ggcgcgcgtt  10320
tctgatcgac gacgcctggc ggcccctgtt ggagccggag ctcgcgaacc ccctaaccgc  10380
gcgcctcctc gcggagtatg accgtcggtg ccagaccgaa gaggtgctgc cgccgcggga  10440
ggatgtgttc tcctggacgc ggtattgtac ccccgacgac gtgcgcgtgg ttatcatcgg  10500
gcaggacccg taccaccatc ccggccaggc gcacggcctg gcgtttagcg tgcgtgcgga  10560
tgtgccggtg cctccgagtc tacggaacgt gctggcggcg gttaaaaatt gttaccccga  10620
cgcgcgcatg agcggccgcg gctgcctgga aaagtgggct cgcgacggcg tgctgttgtt  10680
gaacacgacc ctgaccgtca agcgcggggc ggcggcgtcc cactccaagc ttggatggga  10740
ccgttttgtg ggcggggtgg tccaacggct ggccgcgcgc cgcccgggcc tggtctttat  10800
```

gctctggggc gcccatgccc agaacgcgat caggcccgac cctcgccaac actacgtcct 10860
caagttttct cacccgtcgc ccctctccaa ggtcccgttt gggacgtgcc agcatttcct 10920
cgccgcgaat cgctacctcg aaacccggga cattatgccg atcgactggt cggtataaga 10980
tgccgacatc cggggtcttg atttacgagg gggcaattaa taaagactgt tgatggttaa 11040
atctcgggtc tcataccggt ccgtgatgtc gggcgtgggg gaagagaggg tcccctctgc 11100
gtttactatc cttgcctcgt ggggctggac gtttgcaccc cagaaccatg atcctggcgc 11160
gtcgccgaat acgacgccca tagagtcgat tgcggggacc gcaccggacg cgcacgtggg 11220
gcctctcgac ggagagccgg accgggatgc gatctccccg cttacgtcga gcgtggccgg 11280
cgacccgccg gggggcggacg gcccctacgt cacctttgat actctgttta tggtatcttc 11340
gatcgacgaa ctggggcgcc gccagctcac ggatacgatc cgtaaggacc tgcggctgtc 11400
gctggccaag ttcagcatcg cgtgtaccaa gacctcgtcg ttttcgggga cggccgcgcg 11460
ccagcgcaag cgcggagcac cgccgcaacg cacatgcgta ccacgcagca acaagagcct 11520
ccagatgttc gttttgtgca agcgcgccaa cgccgcgcag gtgcgcgagc agctgcgggc 11580
ggttattcgg tcgcgcaagc cgcgcaagta ttacacgcgg tcctcggatg ggcggctctg 11640
cccggccgtc cccgtgtttg tacacgagtt tgtttcgtcc gaacccatgc gcctccatcg 11700
agataacgtc atgctgtcta cggaaccaga ctaagcaccc ccgccgtccc ctttcttttc 11760
cccctaccct tcccccgtta ctgatgtgtt gtacgtttca ataaataaca cgtagcttat 11820
tttgttggat gatggattga ttgattttat tgaccgttcg ttcgcccggc ggtgccgtcg 11880
ccgcgcgcag agggaatatg caagcgggcg gggtggggag gaaagaaggt ttcaggttcc 11940
gggggttggg tctgcgtcgt ccagggtggg gctgatctga atttcccgca gaacctcgac 12000
cagtaggtct gttgtgtttg ctgggaactc gcccgccgtt ggggatacgg gggcgggggg 12060
tgtggtcggg cggacgtcca ggggtgcgtt atcgcacccc cgcgccgcct cgggggccgt 12120
cccgtagatc gttgcggtga tgtagatggt gtccggggtc cacaccaccg tcaggatgcc 12180
ggccgtcgca ctccggacgc tttcgccgtg cgatgagctg acccaggagt caaaggggta 12240
cgcgtacata tgggcgtccc accagcgctc cagcctctgg gtactagcgc gtcctataaa 12300
gcggtatgcg caaaattcgg cacgacagtc gataatcacc agcagcccga tgggggtgtg 12360
ttgtatcacc acgcctccgc ggggcaggcg gtcctggcgc gctcgacccc gcgtcagaac 12420
cgcgcgcgtc cctgactcaa acacgtgcac cacctgtgcc gcgtccggca gcgcgctcgt 12480
tagcgacgcc ctggggtgat gtaggctgta cgcgatggtc gtctgggggt tccccatgtc 12540
tcgggggggt gggggtgaat gtcacccggc ccgggtgcgg tgggaacgcg agggaatgga 12600
gggttaatag acaatgacca cattcggatc gcgtagagca gatagtatgt gctcgctaat 12660
gacgtcatcg cgttcgtggc gctcccggag cgggtttaga ttcatgtgca ggaactcgga 12720
tgaggtggtg cgggacatgg ctacgtacgc gctgtttagg cgcaggtttc cgggcgtgaa 12780
gcatatggcg accttgtcca gactgagccc ctgggagcgc gtgatggtca tcgcgagttt 12840
ggagctgatg ccgtagtcgg cgttgatggc catggccagc tccgtggagt cgatcgactc 12900
gacaaactca ctgatgttgg tattgacgac agacatgaag ccgtgctggt cccgcaggac 12960
gatgtagggc aggggggact cctccaagaa ctcggccacg ccggccgtcg cgtgccgccg 13020
ccgcagctcc tccgcgaacg cgaacacccg ggtgtacgtg taccccatca gcgtgtagtt 13080
gtccgtctgc agggccacgg acatcagccc cccgcgcggc gagccggtca gcagctcgca 13140
gccccggaaa atgacattgt ccacgtaggt gctgaagggg gcgctctcaa acacctcccc 13200
gaagagctcc cgtaggataa ggtatcgccc cagaaaggcc ctcttcagga gcccaaactg 13260
ggcgtggacg gccgcggtgg tctcaggctc ttcgagggcg tagtggcagt agaacacgtc 13320
cagctgctgt tcgtccagcc cggcgaagat aacgtcaagg tcgtcgtcgg ggaagtcgtc 13380
cgggcccccg tcccgcgggc ccaggtgctt aaaattgaac gcacgctccc ccggagagcg 13440
gtcgctggtg tcggcggccc tggttgccga tgcgccggcg gcgtcccggc gtagcgacag 13500
gagttctgcc gtcagctccc ctaggcggcc gtaggccagg gtcctctggg tcgcgtccag 13560
gccggggcgc tggagaaagt tgtaaaagtg aatcagcccg ccgaacatga gccgcgacag 13620
gaaccggtag gcgaactcca ccgaggtctc cccctgggtc ttcacgaagc tgtcgtcgcg 13680
cagcacagcc tcgaaggtcc gaaacgtccc gtcgaaccca aacaccatct ttcggaggcg 13740
cgcggtcacc gcgacctggc tgttgaggac gtacgtgatg tcgttccggg ccacgactag 13800
ctgttgcttg ctgtgcacct cacagcgcac gtgccccgcg tcctggtcct gactctggga 13860
gtagttggtg atgcgactgg cgttggccgt gatccacttt tccatggtca gcgtgggttg 13920
ctgcgtgagc cgtcgatact cgtcaaactc tttgaccgac acaaacgtga gcacggggag 13980
ggtaaacaca acaaactccc cctcgcgagt cacctttagg taggcgtgga gcttggccat 14040
gtacgcgctg acctccttgt gggacgagaa cagccgcgtc caccccggaa ggttggccgg 14100
gttggtgatg taactttccg ggacgacaaa gcggtccaca aactgcatgt gctcctcggt 14160
gatgggaagg ccgtactcca gcaccttcat gaggttcccg aactcgtgct ccacacatcg 14220
cttgttgtta atgaaaatgg cccagctgtg cgagaggcgc gtgtactcgc gtagggtgcg 14280
gttgcagatg aggtacgtga gcacgttttc gctctgccgg acggagcatc gcagtttttg 14340
gtgttcgaag gtggactcca gcgaggccgt ctgggtcggc gaccccacgc acaccagcac 14400
cggccgcagg cggcccgcgt actgggggt gtggtacagg gcgttaatca tccaccagca 14460
atacaccacg gtcgtgagta ggtgccgccc caggagcccg gcctcgtcga tgacgataat 14520
gttgctgcgg gtgaaagccg gcagcgcccc gtgtgtgacc gaggccaggc gcgtgagggc 14580
accctggccc agccccaaag tctgctctag ggcggtgagg gcgtggaact cgtttcgcgc 14640
gtcttcgccc ccgtgcgccg ccagggcccg cttggtgatg tcgaggatca cctcccagta 14700
gtacgtcagg tctcgccgct gcaggtcttc cagcgaggcg gggctgctgg ccagggtgta 14760
cgggtgctgc cccagctggg cctggacgtg attcccgcga aacccgaact cgtgaaagat 14820
ggtgttgatg ggtcgactca gaaacgcccc cgagagctta acgtacatgt tctgcgccgc 14880
gattcgcgtg gcgcccgtga ccacgcagtc caggacctcg ttgagggtct gcacgcacgt 14940
actctttccg gatccggcgt tgccggtgat gagatacgcc gcgaacggaa actcccggag 15000
cggcaggccg gtcgggacct ccaaggccgc cacgtcccgg aaccactgca ggcgcggcac 15060
ctgcgtgacg tcgagctgct gctgcgagag ctctcggatg cgtgcgatga ttggttggac 15120
cccgtgcatg gacgtaaaat ttaaaaacgc ctcgtccctg aaccgcacgg cgggtctggc 15180
cccgggctgc tgtgggggcg gacctggtgc ccggacgtcc cgcgagccct ccccgccgga 15240
cgccgccatg gccgcacagc gcgcgcgggc gccggcgatg cggacgcggg gcggcgacgc 15300
ggcgctatgc gcccccgagg acggctgggt gaaggttcac cccacccccg ggacgatgtt 15360
gttccgcgag attctcctcg ggcagatggg gtacaccgag ggtcaggggg tgtacaacgt 15420
cgtccggtcc agcgaggccg ccacccgaca gctgcaggcg gcgatcttcc acgcgctcct 15480
caacgccacg acgtaccggg acctggagga ggactggcgc cgccacgtgg tggcccgcgg 15540

-continued cctccagccg cagcggctgg ttcgcaggta ccggaacgcc cgggagggcg atatcgccgg 15600
ggtggccgag cgggtgttcg acacgtggcg atgcacgctc aggacgacgc tgctggactt 15660
tgcccacggg gtggtagact gctttgcgcc gggcggccca agcggaccga ccagcttccc 15720
caaatatatc gactggctga cgtgtctggg gctggttccc atattgcgca agacgcgcga 15780
gggggaggcg acgcagcgcc tgggggcgtt tctcaggcag cacacgctgc cccggcagct 15840
ggccacggtc gccggggccg cggagcgcgc cggcccgggg cttctggatc tggccgtcgc 15900
gttcgactcc acgcgcatgg cggaatacga ccgcgtgcac atctactaca accatcgccg 15960
gggggagtgg ctggtgcgcg acccggtcag cgggcagcgc ggcgagtgcc tggtgctgtg 16020
cccccccctg tggaccggcg accgcctggt cttcgattcg cccgttcagc ggctgtgccc 16080
cgagatcgtc gcgtgccacg ccctccggga acacgcgcac atctgccgtc tgcgcaacac 16140
cgcgtccgtc aaggtgctgt tggggcgcaa gagcgacagc gagcgcgggg tggctggcgc 16200
cgcgcgggtc gtcaataagg cgctggggga ggatgacgag acgaaggccg gctcggccgc 16260
ctcgcgtctc gtgcggctca tcatcaacat gaagggcatg cgccacgtgg gcgacatcaa 16320
cgacacggta cgcgcctact tggacgaggc ggggggggcac ctgatcgaca cccccgccgt 16380
cgaccacacc ctccctgggt tcggcaaggg cggcaccggc cgcgggtcgc gcccccagga 16440
cccgggggcg cgaccgcagc agcttcgcca ggcgtttcag acggccgtgg tcaacaacat 16500
caacggcatg ctggagggct atatcaataa tctctttgga accatagaac gcctgcgaga 16560
gacgaacgcg ggtctggcga cccagctgca ggcgcgcgac cgcgagctgc ggcgcgccca 16620
ggcgggggcg ctggagcggg agcagcgcgc ggcggaccgg gcggccgggg gaggcgcggg 16680
ccgcccggcg gaggcggatc ttctccgggc cgactacgac attatcgacg tcagcaagtc 16740
catggacgac gacacgtacg tggccaacag tttccagcac cagtacatcc ccgcgtacgg 16800
ccaggacctc gagcgcctgt cgcgcctctg ggagcacgag ctggtgcgct gcttcaagat 16860
tctgcgccac cgcaacaagc agggccagga aacgtcgatc tcgtactcta gcggggcgat 16920
cgcctccttc gtggccccgt atttcgagta cgtgcttcgc gccccccgag cgggcgcgct 16980
catcaccggc tccgatgtca tcctagggga ggaggagtta tgggaggcgg tctttaagaa 17040
aacccgcctg cagacgtacc tgacagacgt cgcggccctg ttcgtggcgg acgtacagca 17100
cgcggctctg ccccggcccc cctccccaac ccccgccgat ttccgggcga gcgcgtcccc 17160
gcggggcggg tcccggtccc ggacccggac ccgatcccgg tcgcccggga gaacgccgag 17220
gggtgcgccg gaccagggct ggggcgtcga acgcagggat ggccgacccc acgcccgccg 17280
atgagggaac ggccgccgcc atcctcaaac aggccatcgc cggggaccgc agtctggtcg 17340
aggtggcgga ggggatcagc aaccaggcgc tgctgcgcat ggcctgcgag gtgcgccagg 17400
tcagcgatcg ccagccgcgg tttaccgcga ccagcgtcct gcgcgttgac gtcaccccca 17460
gggggcggtt gcggttcgtt ctggacggga gttccgacga cgcgtacgtg gcgtcggagg 17520
attactttaa gcgctgcggg gaccagccga cgtatcgcgg ttttgcggtc gtcgtcctca 17580
cggccaacga ggaccacgtg cacagcctgg ccgtgccccc cctcgttctg ctgcaccggc 17640
tctccttgtt tcgccccacg gacctccggg acttcgagct cgtctgcctg ctgatgtacc 17700
tggagaactg tccccggagc cacgccacgc cctcgctgtt cgtcaaggtg tcggcgtggt 17760
tgggggtcgt ggcccgccac gcgtctccct tcgagcgcgt ccgctgcctt ctcctccgca 17820
gctgccactg gatcctgaac acgctaatgt gcatggcggg cgtgaagccc ttcgacgacg 17880
agctagtcct gccccactgg tacatggccc actacctgct ggccaacaat ccgccccccg 17940

```
tcctctcggc cctgttttgc gccaccccgc agagctctgc gttgcagttg cccgggcccg  18000
tcccccgcac ggactgtgtg gcctataacc cggccggcgt catgggaagc tgctggaatt  18060
ccaaggacct gcgttcggct ctggtgtatt ggtggctttc ggggagcccc aaacgacgga  18120
cctcgtcgct tttctatcgg ttttgctaac tccggaaaat aaacgtgttt tttatggaac  18180
gttccccacc tgtcgtgtca tctctcgggg gatggtggtg ggcctgtgtg tgtgtcttgt  18240
gcaccgaagg aggaaagtgg gggggtggtg gtgctggtgg tggaaagaca tgatagaggg  18300
aacaaagaaa tagaagaaaa ccacaaccgg cgcgtgccag taaatacgga cgcgcgcaca  18360
cgcggggggt aagttggagc acggggcccc ggtttattga ccaaattcag ggaaacagaa  18420
accgaatctt ttcatcgaaa gggtacacaa agctcccgcc ctcgccccac acgccttcca  18480
gaacccccgt aaacaccagt tgaatctcgc gcaggatctc gcgcaggtga tgggcgcagt  18540
ccacgggggg gagcaccaag ggccgcgggt acagatccac ggggacgccg accgactccc  18600
cgcccccggg acatacgcgc acgacgcgtc tccagtattg ctccgcgtcc agcagggcgc  18660
ctccgcggaa ggccgtttgg ggcagggggt cgtcggcctc gcctgggggg gtcagaacgc  18720
tccagtactc cgcgtccaga cgcctcccga aggcatccag gacaaagcgg tcacaggcgt  18780
cctccatgac gccccgggcc gcgcacacgg cctcctccgg cgggccggcg gccggccgcc  18840
ggaggattcg tctcagcgcg tcgcgcataa cctcggccgc cgcggcgtac gcggccccgc  18900
ggagaggaaa tccctgcagg aagtcggtgt catcgcggga gttccagaac cacgccccgg  18960
tctggctcca ggtgacgacg tgggtgtaga cgccctctgg cgccagggag gggggcgaggc  19020
gcgggcgtat gccgttggcc gaaagtacgg cgcgcacgga cgcctcgagg gcccggcggg  19080
cgtcctggat cgcgccgtgc gcggcgtccg cgtccccggg gtccacgttg aacagccccc  19140
agaacgcagc cccggtgccg ccgcagaccg caaacttcac cgagctggcc gtctgctcga  19200
tctgcaggca gacggcggcc atgaccccgc cgagcagctg ccggagcgcg gggcaggcgt  19260
cgcacgcgtc cggcaccagg cgctccagca cggcccgggc ccagggctcc gagggggcgg  19320
ccgccaccag cgcgtccagc ctttccaggc ccgcccgccc ccgggcttcc ggcagcccgg  19380
cctccccgag gcccgcgagg gcggccagga gctgggcctg gagcccggag aaacaaaacc  19440
gcgccgtcca gaccggcccg acggccgccg gggggtcgag tagttggatg gtggtggccg  19500
tggggtgcca ccgcgcgacc gcttcccgaa aggcgggcag gaggcggccg gccgcctccg  19560
aggccacggc cggccatgcc cgcgggggca ggacgaccct ggcgcccacc gcgggccagg  19620
cccccaggca cgcggcatgg gtggccgcgg cgccccgcac caggtcacgc gccgactcgg  19680
cggcggcggc ggccggcacg gtaaacgtgg gccagcccgg aaatcccagc acggcaaagt  19740
attggacggg ccctccccgg acctcaaacc cgggccccag aaaagcgaag acgggggcca  19800
gggctccggg ggcggcgtgg accgtggtat gccactgccg gaagagggcg accagcgccg  19860
gggcggagaa cccgtcgccg gcgctcacga agtagtcgta gccgcgcggc agcagcaccc  19920
gcgccgtgac ccgctgcggg tgtccgcggg gccgcaggcc gacctcgcac acctcgacca  19980
ggtccgcgaa ggcgccctcc ttcctggtcg gcggaaacgc cagggtggtg tattcgcgcg  20040
caaaacgcgc ggtcctcgtc gtgatggtga cggcgagcga ggcggaggac gcgcactggg  20100
ggctgtcgcg aatggcggcc aggcgcgccc acgccaaccg cgcgccgggg tgctcggcga  20160
cgcgcgcgga cagggccagc gggtcgacgt cgaccttggc ctccacgtcc aggagggcgg  20220
cgcgaggagc ggccggcggg ccccacgacg ccctttcgac cctcacgacc agacccgtct  20280
```

-continued gcgggtccca gcccaggcgc agcgggacga agagggccca ccggcccgtc tggcgctcca 20340
gggccgccag aacgcacgca tacagcgccc gccacagggt cgggtccccc aggggctcca 20400
gcggggaggc ggccggggcc gtcgcggcgc gggcggccgc gacggccccg ggggccgaga 20460
cgtcggggga gccgtagaag tcctgcaggt cggacgaacc aacggacacc tccgcgaagc 20520
gcgcgcgcgc ctcccccgcg gcgtcgcgac agaccagata cagcagggcg tggaggcagt 20580
cgcgcgtgcg cgggggcagc cataccgcgt atagggtaat ggcgctgacg ctctcctcca 20640
cccaaacgat gccgggggct tccatgccac gacgcccggg ggttgccgtg tatcgaacga 20700
gcgcggcccc agacttatag ggtgctaaag ttcaccgccc cctgcatcat gggccaggcc 20760
tcggtgggaa gctccgacag agccgcctcg agaatgatgt cagtgttggg ctgggcgccg 20820
gaggcgtgcg tgcgcaagca gcgcccccac gcgggcgcgc gcagcttgaa gcgcgcgccc 20880
gcaaactccc gcttatgggc catcagcagc gcgtacagct gtctgtgcgt ccggcaggcg 20940
ctgtggtcga tgcggtgggc gtccagcagc tccacgatgg ctcgcttggt gaggttttta 21000
acgcgccccg ccccgggaaa cgtctgcgtg ctcttggcca gctgcacccc gaacagttcg 21060
ccccagatga tcttgaacag cgacagcgcg tgctccgtct cgctcacgga cccgcgcggg 21120
gggcagccgc tcagggcgtc ggccacgcgc ttaaccgcgt cctccgacag caaggggccg 21180
tcggtcacgt tacagtggcc cagttcgaac accagctgca tgtagcggtc gtagtggggg 21240
ttcagcagct ccagcacgtc ctcggggcta aaggttcgcc ccgacccccc ggccatcgag 21300
tcccactgca ggcacgcggc catggtgctg cacagacgga acagctccca gacgggggcg 21360
acgtttaggg tggggtgtag ggccacaagc tccagctctc cggcggcgtt gatcgtgggg 21420
atgacgcccg tggcgtagtg gtcgtaaagc cgccggaaga tggcgctgct atgggcggcc 21480
atggggacgc gaagacaggc ctccagcagc accaggtaga tgaaccgcgt gcggccgacc 21540
aggctgttga ggccgcgcat gagcgcgacc acctcggccg gcgcgacgtc cggccggagg 21600
tacttttcga cgaaaaggcc cacctcctcc gtctcggcgg cctgggccga cagggacgtg 21660
tcggggtcct ggcagcgcag ctcccgcaga tcccgctggg ccctcagggc atcaaaatgt 21720
atcccccgca aaaacagaca aaagttcctc ggggtcagcg cggcgtcgtg gccccagaac 21780
cgcacgtgca tgcagttgag ggtcagaagc atgtggagga tgttaagact gtccgcgagg 21840
cacgccagcg tgcacctctc gaagtagtgc ttgtaccgga atttgctgta gatgcgcgac 21900
ccccgcgcct gcgccgcgtc ggcgtgcgac gcgtcgcagc gccctttgaa ccggcggcac 21960
aacaggttcg tcacctggga aaactgtgcc ggccactgcc cgctggcgct caccacgtgg 22020
ttgagcagca tgggcgtaaa gacgggctcc gagcgcgccc cggacccgtc catgtagatc 22080
agcagctccc ccttgcggag agtccgtacc cgccccagcg actggtacac ggacaccatg 22140
tccggcccgt agttcatggg tttcacgtag gcgaacatgc tgtcaaagtg cggcggatcg 22200
aagctaaggc ccaccgtcac gaccgttgtg tagatgacca cccggtaccg gccccatgtg 22260
gtcacgtcgc cgggcggggt gagcgagtgg agcagcagca cgcggtccgt aaactgccgg 22320
cagaacctgg caacgacctc cgcgaaggag accgtcgacg agaagatgca gacgttatct 22380
ccgccggcca ggcgcgcctc cagctccccg aagaaggtgg cgtccggggg ggcgtccggg 22440
gggggcgccc cgcccgccgg cccccggcgg cgcagggccg cctgcaggac ctcgggcccc 22500
aggcgcggga gaaacagaca acggcgcgcc gaaaatccgg gcatggcgta ctccccgatg 22560
accacgtgaa cgttcttttc gccccggagg ctgcacagaa agtccaccag ctgcgcgttg 22620
gcggtggcgt ccatggcgat gatccgcggg cacgtgcgca gcaggcgcag catcaacgcg 22680

```
tcgacgcggc ccagctgctg catcgtcggc gagtacagtt ggcccaacgt cgacatgact  22740
tcgtccagga cgagcacgtc gtagttgttc aacaggttcg ggcccacgcg atgaagactt  22800
tccacctgca cgatgagacg gtggaagggg cggtcgttca tgatgtaatt ggtggatgag  22860
aagtaggtga cgaagtcggg caaccctgac tcagcgaacc gcgtcgccag ggtctgagta  22920
aaactccgac gacaggagac gaccagcaca ctcgtgtccg gagagtggat cgcttccccc  22980
aaccagcgga tcagcgcggt agtttttccc gagcccattg gcgcgcggac cacagttacg  23040
caccgggccg tcggggcgct cgcgtccggg aaggtgacgg gtccgtgttg ctgccgctcg  23100
atcgttgttt tcgggtggac ccggggaacc cactcggcca aatccccccc gtaaagcatc  23160
cgcgccagcg atacactcga cgtgtactgc tcgcactcgt catccccgat gggacgccgg  23220
gcccccaggg gatcccccga ggccgcgccg ggcgccgacg tcgcgcccgg ggcgcgggcg  23280
gcgtggtggg tctggtgtgt gcaggtggcg acgttcatcg tctcggccat ctgcgtcgtg  23340
gggctcctgg tgctggcctc tgtgttccgg gacaggtttc cctgccttta cgccccccgcg  23400
acctcttatg cgaaggcgaa cgccacggtc gaggtgcgcg gggtgtagc cgtccccctc  23460
cggttggaca cgcagagcct gctggccacg tacgcaatta cgtctacgct gttgctggcg  23520
gcggccgtgt acgccgcggt gggcgcggtg acctcgcgct acgagcgcgc gctggatgcg  23580
gcccgtcgcc tggcggcggc ccgtatggcg atgccacacg ccacgctaat cgccggaaac  23640
gtctgcgcgt ggctgttgca gatcacagtc ctgctgctgg cccaccgcat cagccagctg  23700
gcccaccttta tctacgtcct gcactttgcg tgcctcgtgt atctcgcggc ccatttttgc  23760
accagggggg tcctgagcgg gacgtacctg cgtcaggttc acggcctgat tgacccggcg  23820
ccgacgcacc atcgtatcgt cggtccggtg cgggcagtaa tgacaaacgc cttattactg  23880
ggcaccctcc tgtgcacggc cgccgccgcg gtctcgttga acacgatcgc cgccctgaac  23940
ttcaactttt ccgccccgag catgctcatc tgcctgacga cgctgttcgc cctgcttgtc  24000
gtgtcgctgt tgttggtggt cgagggggtg ctgtgtcact acgtgcgcgt gttggtgggc  24060
ccccacctcg gggccatcgc cgccaccggc atcgtcggcc tggcctgcga gcactaccac  24120
accggtggtt actacgtggt ggagcagcag tggccggggg cccagacggg agtccgcgtc  24180
gccctggcgc tcgtcgccgc ctttgccctc gccatggccg tgcttcggtg cacgcgcgcc  24240
tacctgtatc accggcgaca ccacactaaa tttttcgtgc gcatgcgcga cacccggcac  24300
cgcgcccatt cggcgcttcg acgcgtacgc agctccatgc gcggttctag gcgtggcggg  24360
ccgcccggag acccgggcta cgcggaaacc ccctacgcga gcgtgtccca ccacgccgag  24420
atcgaccggt atggggattc cgacggggac ccgatctacg acgaagtggc ccccgaccac  24480
gaggccgagc tctacgcccg agtgcaacgc cccgggcctg tgcccgacgc cgagcccatt  24540
tacgacaccg tggaggggta tgcgccaagg tccgcggggg agccggtgta cagcaccgtt  24600
cggcgatggt agccgtttcg ttcgttttaa taaaccgacg ttgtgcgttt caccatactt  24660
cggcgcgcgt gtgtgtgtgt ttttttttt gtggtgttta ttttcccccc accccttcct  24720
tttctttcgg ccaccacccc cctcctcccc cgtactatac aacaaaaaat accacacata  24780
cgaccaaata cggacaatca tttctgtctt tattcgctat cagagagtgg gggcgtgagc  24840
gtggcaggag ggcgggccac gtcggggtcc cgccgtctgg tgtgacgcga tggggggtcc  24900
gatgcgcgcc ggtactgggg ccccggcgcc cgggtgacca cgcgcacgtc ggggggcacg  24960
tagaagttac cctcttcttc ggactcgatg tccacgacgt caaattcgtg ggcggtcagc  25020
```

-continued

```
gagacgacct ccccgccgtc ggtggtgatg acgttgtgtc ggcagcagca gggccgcgcc  25080
ccggagaacg cgaggcccat aacttggcga gcgtatcgtc gaaggccagg cggctgtttc  25140
gccggatgtc ccggtagatc cccggctcga cgcggacggg ggtgatgatc agggcgatcg  25200
gaacggcctg gtccgggagg atcgatgcct tggcgggtcc gggggccccg ccaggcccgg  25260
cgggcgctcc gcggccgtcc tccaggcgga acgtcacgcc ctcctccgcg cccgcgcggt  25320
gcctgccgag gaacgtcacc aggtgcggtt gcagggggca gtcgggaaag tggctgtcga  25380
ggacgtatcc ctgcaccaag atctgtttga agttcgggtg gcgggggttg gcgaagatgg  25440
gctcgcggcg aaccagctcc ccggagctcc aggccacggg agagatggtg cgacgctcaa  25500
ggtcggggac gccaaacaga agcacctccg agacaacgcc gctatttaac tccaccagcg  25560
cccgatccgg ggcggagcat cgcctttttt cgccggcggc gcgggaatcg agccagtccc  25620
ggtcttgggt gacgagcgcc tcctccgggc ccggaacgcg cccgggcgcg aagtagcgca  25680
cgccggggtt ggggatggac cggatgaacg cccggaacgc ctccggcgat cgccgcgcca  25740
tcaggtcctc gtacgcggag gccgcggggg cgccggggtc cgcggggtcg aacgcgtact  25800
tggctcggca cttaacctcg tagaaggcca ggggggtctg gggggcgggg gccaggtagc  25860
cgtgagggtc cctggggcac acgaggatgt ccagggacgc ccccaccatg cccgtgtggc  25920
cgtccatgag gaccccgcac gcgtgcacgt tctcctcggc gaggtccccg ggttggtgaa  25980
agacgaagcg cccggcgtcg gcgtcgtcgt tgacgcccgc gtccgcgcgg cccacgcagt  26040
agcgaaacag caggtttcgg gccgtcggct cgttcacccg cccgaacatc accgccgacg  26100
actgggcgtc cagccgcagg ctggcgttgt gggtgagcca ctgggacgag aagcacggac  26160
cctgcgcgcc ccaccgcagc gtggaggcgg tcgtcaggcc ccgccgaagc agggcccaga  26220
gctggcagtc ggcctggttt tgcgtcgccg cctcgtaaaa tcccataagc gggcgggggg  26280
cgacggcttc ggcggcggac gggggggcgc ggcgcgtcag gcgccagagg tgccggccga  26340
gcccgcggtc caccatgccg gccgcctcca gcgacacgac gagggagcac agatagtcca  26400
ggcgagccca caggggcccg atggccagag gggagcggac gccgcgcagc aggccgcgca  26460
ggtggcgctc gaacgtttcc gccaagatat gggggggcag tgcgttgggg atcgccgacg  26520
ccgaccacat cgggtcgggg tccgggggac cggggctgca gtccgggtcg atggcgtgtg  26580
cgccccccgg cgagaggggga atgtcggggg ttggcgggcc ggatgaggcc tcagagaggg  26640
ccggggacgc gggccgggcc ttttcgcccg gggccccgcc gtcgggttgc ccacgtgggg  26700
ggctctgggg ccaatgggaa cccggggccc ccggtgacgt ggggcggggt ggggcggggc  26760
ggggcccaaa gacggtcgcc agatctaggc tgttgggtcg gggccgcttc gggggactat  26820
cggggtcgcg ggcggggtcc gcggggcgct tggcgccggg tgttgcggcg gccgccattt  26880
ttacgagcag ccgaagagct cgagggcgga agggatcctc acgacagaga gtggcgcgcg  26940
gccgggttgg cgtgacagag gcgggagacc agcaccagca gcggcctcag ctcgggcggc  27000
agcgacaccg acgacaggac ggccttgtgc gtgcgctggt aatttataca ctgctccgtg  27060
aacgcgcgcc gaatcttggg attgcgaagg tggcgccgga tgccctccgg cacgtcatac  27120
gccaggccgt gggtgttggt ctcggccgag ttgacaaaga gggcggggtg cagaacgcag  27180
cgataggcga ggagggccac ggcaaagtcc ggcgagagct ggttgttaaa gtactggtag  27240
cccgggacgc gggtcacggg gacgcccagg ctcggggcca cgtacacgct aaccagcagc  27300
tccagcagcg tctgccccag ggcgtagaga tcgaccgcca gcccgacgtc gtgcttcagg  27360
gggcggttgt taaactcggc ccgctcgttg ttgaggtact ttaccgagag ctccggtggc  27420
```

```
tggttgtacc cgtgccccac cagagtgtga aagttggccg tggtcagggc ggcgggcatc  27480
ccaaaccccc ggggggactc gaggtccggc tcctggaggc aaaactggcc ccgggatatc  27540
gtggagttgg agttcagggt caccaggcta aagtcggcca ggacggccgg ccggagcgac  27600
accgcgtccg atcgcagcat cacgaggacg ttggcgcact tgatgtccag gtggctgatc  27660
ccgcacctgg tgttcaggaa caccacggcg cgcgccaggt ctgtgaagca gtggtggagg  27720
gccgtcgcga cggagggggt ggtcgcgcgc agggacgcca gctggccgat gtacttgccg  27780
aggtccatgt cgtacgcggg gaacacgatc tggcgctgct gcagcgagaa cccgagcggg  27840
gtgataaagc cgcggatgtc gtgggtgcgg ccgccgcgaa gagcgcactc ccccacgagc  27900
agggtcgcga cgagctccac ggcaaaccac tctttttccc ggatggtctt cacggcgagc  27960
ttgtgttcgc gaatcaactg cacctcgccg taccccccg agcccccgaa gctgcgggcc  28020
ccggggatct ccagggtcgt gtagcggagg gcggggttga cggcgaatac ggggatgcat  28080
agcttgtgga tgcgcgcgag ggacaggatg tgcgaggggg gcgacggggg cgaggtcatg  28140
gccgtctcgg acctgcgcag gggcgggcgc cttagcttgg ccgcagggcc gggggcctcg  28200
ggggacgagc ggcgacgaga cgagcggctc actcgccatc gggacagtcc cgcgcgaagc  28260
cgctcccgga agctggatcg gcggcgggac ccggggcggg ctccggagac ggcgccgtct  28320
cggggggagg ggccgcttgg gcgtccggac gcccggcggc tgagggagtg tatgtaggac  28380
gcgagccagg ccttgaagga gcgtcggtgt gcaccttggg ggctgatgtc agctgccaca  28440
tgactagcag gtcgctgtcg cccggactca tccatccgtc cgccaggtcg ccgtcccccc  28500
acagagacgc gttcgccgcg gcctcttcga gctgctcctc ctggtccgca agacgatcgt  28560
ccgccgcgtc caggcgctcg ctaagcgcgg gatcgaggta ccgtcggtgt gcggttagaa  28620
aatcacgtcg cgccgcttgc tcttccacgc gaattttaac acaggtcgct cgctgtcgca  28680
tcatctctaa gcgcgcgcgg gactttagcc gcgcctccaa ttccaagtgg gccgccttgg  28740
cggccataaa ggcgccaaca aacctaggat cttgtgtact cacgccctcc cggtgtagct  28800
gcagggtctg gtccctgtac acctcggccc ggaggtgcgt ctcggccaaa cgtcggcgca  28860
gggccgcgtg gctggcgtct cggctcatct cgccgccccc gcgcgcgccc gacgtcggac  28920
tccttcgccc cgaccccct gacctcagcc gcccccgcct cgcccgcgat gtttggccag  28980
cagctggcgt ccgacgtgca gcagtacctg gagcgcctgg agaaacagag gcaacagaag  29040
gtgggcgtcg acgaggcgtc ggcgggcctg acgctcggcg gcgatgcgct gcgcgtccct  29100
tttttggatt ttgccaccgc gacgcccaag cgccaccaga ccgtggtccc gggcgtcggg  29160
acgctccacg actgctgcga gcactcgccg ctcttctcgg ccgtcgcgcg gcggttgctg  29220
tttaatagcc tggtgccggc gcaactcagg gggcgtgact ttgggggcga ccacacggcc  29280
aagctggagt tcctggcccc cgagctggtg cgggcggtgg cgcgcctgcg gtttcgggag  29340
tgcgcgccgg aggacgccgt gccccaacgc aacgcctact acagcgtcct gaacacgttt  29400
caggccctgc accgctccga agcctttcgg cagttggttc acttcgtgcg ggacttcgcc  29460
cagttgttga aaacctcgtt ccgggcctct agtctcgcgg agactacggg ccccccgaag  29520
aaacgggcca aggtggacgt ggccacccac gggcagacgt acggcacctt ggagctcttc  29580
cagaaaatga tactaatgca cgcgacctac tttctggccg ccgtgctgct cggggaccac  29640
gcggagcagg tcaacacgtt cctgcggctc gtgttcgaga tccccctgtt tagcgacacg  29700
gccgtgcggc acttccgcca gcgcgccacc gtgtttctag tccccaggcg ccacggaaag  29760
```

acctggtttt tggtgcccct catcgcgctg tcgctcgcgt ccttccgggg gatcaagata 29820
ggctacacgg cccacatccg caaggcgacc gagcccgtgt ttgatgagat cgacgcctgc 29880
ctgcggggct ggtttggctc gtcccgggtg gaccacgtca agggggaaac catctcgttc 29940
tcgttcccgg acggctcgcg cagcacgatc gtgtttgcct ccagccacaa cacgaacgta 30000
agtacgcctt cctcccgcgg tgcctgtttc cccggtgccg ccctccccga gatcgaccga 30060
cagacaaaca cagccagacg cgagtgtggg acgacacgcc cgcagccccc cccccgccat 30120
ggcggggggg aagccttact gtttatttgt aatcggacga tgaggctctg gccacggccc 30180
gcgcgaccgc ggggcagctc gttgcaaaca ggcggctggt atacgatgac agaacgcaga 30240
ggcgccaccc ggcgctggtc gggcggatga cgctttccgc gccgtcccgg cccacgacga 30300
cctcgtgcag gtgggccgtg atgcgcgggc ggcgggtcgc ctgccgcagg ataaccgcgt 30360
ccacggggtg cccgaagagg agctgacaca ggctcgcgtc cccccggacg gccagggtgc 30420
gctgggccat attggaccac atgcacgggg cgacgcaggg acaggcctcc gccacggcgg 30480
gggcgcgcca cagcgcgttg gcggaatcga tgtgggccgt cggggcgcag gcgccgcctc 30540
ctcccggggg gtcggtaatc ctggatagca gccatcctaa atggcgggcc cggctgcccg 30600
ggggacagag cgaccccagg tcatcatcca tggcccagca gtatatgcgg ccgccgggga 30660
ggtgccacca ggcccccgga cccagggcac agcacgcccc ggattcgggg gccgtgtccg 30720
tgggtaccag gtaggcgccg tcgagctcgt gggccacggg ctcgtccgcg agctgttcgg 30780
cggcggggtc gggggtttcc tccggggggg aggcagcttc caggtggccg aaggctaggg 30840
tgcacagcag cggggtccgg gggtgcgtta cgctgcggag gtggacggtg gcgcagtagc 30900
ggcgctcgcg gttaaagaag aaaatggcaa agaacgtgtt cgaaggcagg cgcagcgcct 30960
tgggccgcgt caggtacagg aagatctcgc agaaaagggc acgctcgggg tcggggtccg 31020
gaagggccac ctggcacagc ggctcggtga ggaccgtgag gcaccgaaaa atcttaagcc 31080
gctcgtcccc ccgaacgacg cgccacacga agacagagtt ggcgatgcgc gcgacgaggt 31140
cggcttcggg ccccgggtcg ggggcgcgcg cgtcgggggg ggcgccccgg tgacccggcg 31200
gggccgcggc tcccgggggg cctggcgtcg cctggggacg ccagagtgcc cgctgtgcca 31260
ggttggtggt ggggaaggga ccggagacgc accaaaagca gaggggccag cgcgtgtatg 31320
agttgggggg ggggtgggtg agcggtggaa caaaagcacg cgtcagcgga caaggccggg 31380
tcccgtagcc gccccgcgac agaaccggag tccgacggca cgcgcgacgg ggtctgcgag 31440
gctgaggtac gccgcggtgt taatggtaaa cgcaaagcct cccggaaaga ccactagccc 31500
gcagaggcgg cgattgaacc caaggcagag gtacgcgtag ctctctcccg gaaggtattg 31560
ctcgcagacc ctgtgtgggg cagtggaggg gctgccctcc atgaagcgac atttactctg 31620
ctcgcgtcca ttgacgtcac cgtcaatcac cactgcgatt ggacggttgg tgaggcgcag 31680
cgtgtctccg ctggtgctgt agtagtcaaa cgcgtagtgg gcgtcggagt cggcgaagcg 31740
ggcggggatg tcgtcgctga gagggacgag ccgccgccgc cgcccccgac cgccctggcc 31800
gcccagatgc gccagcacgg ccagggcgta cgcggtgtga aagaacgcgt cgggggcggt 31860
cccctcgagg gcgcgcatca ggttctccag gagcacgggg aagcgccgcg tcacctcccc 31920
tagccactcg ctctggtggg ggccaaagtc gtagcgcagg cgctggaaga tgcgcgggcc 31980
gccttggagc gcggcccgga tagagtggcc cagggcccgc agacacgcga tctggatgcg 32040
cgcgacgaag gccacctcgg ccgcgatgtc aaagggctgc agcacggggc gcgggtggcg 32100
caggggtccc tcgagcgcgg gaaagcgacg cagcagcgcc gtctgggccg cgggggacag 32160

-continued ctggtggggg cgcacgacgc gctcggcggc acaggcctcc gtcagggccg tggccagctc 32220
ggaggacagc cgcggggggc gggcgcgtcg cccgccccac gccaccgaat tctcgtagga 32280
gacgacgacg aagcgctgct tggtcccgta gtgatggcgc aggaccacgg agatggagcg 32340
acggctccac agccagtcgg gccggtcgcc gccggccaga gcttcccacc cgcggtccag 32400
ccactcgacc agcgatcgcg gcttggcggt ccccggcacg agggtgagca cgtcgttgag 32460
gacgtcctcg cccgcggccc gggggccccc ccggctggca aagcgccccc cgccgggcgg 32520
ctccaggccc gccagcaccg cctccgcgtc cgacgcgccc agggctcccc cgctgacggc 32580
ctggtggacc agggcgccct ggcggagccc cgaggcgacg ccggaggccg cgtgcttggg 32640
gcgcgcgcgg accgggtggc ggcgggtgac gtcctgcacg gcccgctgga ccagcgcgag 32700
gatctcctcg ttctcttgcg tgatggacac gtcctccgcg gtggccgtgt cgcctcccgg 32760
ggccgtgagc tgctcctccg gggagatggg ggggtctggg gtgccgacaa cggccggccc 32820
ggccccgccc gagaccgagg acgcctgggg agtgggggtg ccgctttccc ccatccccag 32880
ggacaggtgg gccgccgcct ccgtcgcggc ggcgggagcc gcggccccca gccgcgcgac 32940
gtagcgacaa aagtggcgac agaggcgcat gaggcgcgcg ccgtcggccg cgtatcgcgt 33000
gtttggcggg acgagctcgt cgtaactgaa caggagcacg cgggcacagg tcgcccacgg 33060
gccccacgcc aggcgcagcg ccgcgaccgt gtacgggtcg tacacgcctt gggcgtcgca 33120
cgcgaccggc agggagacga acagcccgcc cgcgctgggg acgcgcggca ggaggtccgg 33180
gtgcgccggg atgacggggg ctaggatcgc ccccaccgca tccgccggca cgtaggcggc 33240
aaacgccgaa cgccacgggg tgcagtcgcc ggtcgcgtgg gcccgggtct gggtttcgac 33300
ccggaagttc gcggccgccc caccgtcggg gcggccgcgc acgagggcgg acagcgggac 33360
ccccgccgcc gccaggcact cgctggagat gatgacgtga atcagcgagg cggggctgct 33420
cgggtcccgg gtgagatcgt attggacctc gttggcaaag tgcgcgttca tggcccggcc 33480
ggcggtgcga gcccttcccg gtgccggaag gggcgtgggt ggggggtgcg tgtgcgcgtc 33540
ctcggggccc gcgggcgcac gtgcgcttat acgctgtgtg tttcgtctgt ccccagggaa 33600
tccggggcca ggactttaac ctgcttttcg tcgacgaggc caactttatt cgcccggatg 33660
cggtccagac gattatgggc tttctcaatc aggccaactg caagatcatc ttcgtctcgt 33720
cgaccaacac cgggaaggcc agcacgagct ttttgtacaa cctccgcggg gccgccgacg 33780
agctgctcaa cgtggtcacc tatatatgcg acgaccacat gccgcgggtg gtgacgcaca 33840
ccaacgccac ggcctgttcc tgctatatcc tgaacaaacc cgtgtttatc acgatggacg 33900
gcgccgttcg ccggacggcc gatctgtttc tgcccgactc cttcatgcag gagatcatcg 33960
gggggcaggc ccgcgagacc ggcgacgacc ggcccgtcct aacaaagtcg gcgggggagc 34020
ggtttctgct gtaccgcccc tccaccacca ccaacagcgg cctgatggcc cccgagctgt 34080
acgtgtacgt ggacccggcg ttcacggcca acacgcgcgc ctccggcacc ggcatcgcgg 34140
tcgtcgggag gtaccgcgac gatttcatta tcttcgccct ggagcacttt ttcctccgcg 34200
cgctcacggg atcggccccc gcggacatcg cccgctgcgt cgtgcacagc ctcgcccagg 34260
tgctggcgct gcaccccggg gcgtttcgca gcgttcgcgt ggcggtcgag ggcaacagca 34320
gccaggactc ggccgtggcc atcgccacac acgtgcatac cgagatgcac cgcatcctgg 34380
cctcggcggg ggccaacggc ccggggcccg agctcctctt ctatcactgc gagccgcccg 34440
gcggcgcggt attgtacccc ttctttctgc tcaacaaaca gaagacgccc gccttcgaat 34500
actttatcaa aaagttcaac tccgggggcg tcatggcgtc ccaggagctc gtctccgtga 34560
cggtgcgcct gcagaccgac ccggtcgagt atctgtccga gcagctcaac aacctcatcg 34620
aaaccgtctc tcccaacacc gacgtccgca tgtactccgg aaaacgcaac ggtgccgcgg 34680
acgacctcat ggtcgcggtc atcatggcca tttacctggc ggccccgacc gggatccccc 34740
cggccttttt tccgatcacg cgcacgtctt gagtctttct tgccgtttct tttgtttctc 34800
tttctttccc cccctctctc cgcaataaac gccttcccgg aactgtgttt ccccccctac 34860
aacagtgttg tccgttggtt gggtggttgg ggtgcggggg tgggcggggg aagcaagaaa 34920
acggtcggcg aacacaacat cgggaaaacg gattcccgca cgtgcgtctt cccagattcg 34980
acacacacac ccccccttctc cttaaataaa cacaaaccac acgctcgttg gttggttaat 35040
gccagcgctt tatttacgtc ttgttttttt tgcgtttcct ccgcgggtcc cttcccaaca 35100
cgcctgcccc cgcctcaggg gtagcggata accggggcca tgtcgccgga ttgcacaacg 35160
gcggcgccgt cgaacgtaca cacccgaacc gccggggcca gggccaggat gtccccgagt 35220
tggcccgcgt gcgccagcca ggcgaccagc gcctcgtaaa gcggcagcct gcgttcgccg 35280
tcctgcatca gcatgggggc ttcggggtgg atgagctggg cggcttctcg cgtgacgctc 35340
tgcatctgca ggagcgcgtt cacgtatccg tcctgggcgc tcagcgcgag cagccggggg 35400
atgagcgtga ggatgagggt ggttccttcg gttatggagt agaccatgtt gaggacgagc 35460
gaccgcagct cggtgtttac ggaggcgagt tgctggacgt cggccacgag cgagagacgg 35520
gccccgttgt aatacagcac gttgaggtcg gggagctccc cgggcgtccg ggggtcgggg 35580
ttgaggtccc ggatgccccg ggcgaccagc cgcgcgacta tctcgcgggc caggggcgtt 35640
gggagcggga ccggaaaccg cagcgtgagg tccagcgact ccaggcgcac gtccgtcgcc 35700
tggccctcga agacgggcgg gacgaggctg acgggatccc cgttgcagag gtcgacgggg 35760
gaggtgttgc ggagattgac ggtgccggcg tgcgtgagcc ccaggtccac ggggcaggcg 35820
acgattcgcg tgggcagcac ccgcgtgatt accgcgggga agcgcctgcg gtacgccagc 35880
aacaacccca acgtgtcggg actaactcct ccggagacga acgattcgtg cgccacgtcc 35940
gcgagcgcca gctggcggcg gatggtcggc agaaagacca ctcgaccctc gcaccgctgc 36000
agcgccgcgg catcggggcg cgagataccc gaggggatcg cgatgtctgc ttcgaaacaa 36060
tccgtgatca tggcgccggg ccgcgagaca ccggaacgcg ggggtgcggg agggccggaa 36120
agcgcaacgc aaccgggacg atgatgaaac agagatgggg ggcaccgacc gtgtgggaga 36180
gggggcgggg cagggctcag cagcacgcac ggggaggtct gtcgtgcgca ggagccccag 36240
gtgagaatca gtcccccgga gctcgggtct gggttttatt gggacctgcc ctcggaatcg 36300
cggctcccag tccaagcccc cctggggggg gcggggacag ggggtgtgtg tgggtaaaag 36360
caacgtcgga aaatcaaacc caatgcccca aacaggaaaa aaaaagacgg gcgggtggag 36420
ggaaagctgg ggaagaagaa gccaatttta cagagacagg ccctttagcg gggaggcgtc 36480
gtagatgaga tactgcgtaa agtgggtctc tcgcgcgtgg gcctccccat cgcgggcgct 36540
gcgtagcagg gcggggtcgc tggcgcaggt gatcgggtag gcttcctgaa acaggccgca 36600
cgggtcttcc acgagctcgc ggcaccccgg cgggcgctta aactgcacgt cgctggcagc 36660
ggtggccgtg gataccgccg atcccgtttc cacgatgaga cgctccaggc agcgatgttt 36720
ggccgtgatg tcggccgcgg tgaagaactt gaagcagggg ctgaggacgg gcgaggcccc 36780
gttgaggtga taggccccgt tgtacagcag gtccccgtac gagaaccgct gcgacgccca 36840
cgggttggcc gtggccgcga agggccgcgc cgggtcgctc tggccgtggt cgtacatgag 36900

-continued

```
ggctatgacg tccccctcct tgtcccccgc gtacacgccg ccggccgcgc gtccccgcgg  36960
gttgcagggc cggcgaaagt agttgatgtc cgtggccacg gggtggcga tgaactcaca  37020
cacggcatcc tgcccgtggt ccatgccggc gcgccgcggc acctgggcgc agccaaagac  37080
cgggaggggc tgggccggcc ccagccggtt tcccgccacg accgcgttgc gcaggtacac  37140
ggcggccgcg ttgtctagca gcgggggggc cccgcggccg aggtaaaagt tttgggggag  37200
gttgcccatg tccgtaacgg ggttgcggac ggtgcccgtg gccgcgacgg cggtgtagcc  37260
cacacccagg tccacgtttc cgcgcggctg ggtgagcgtg aagttgaccc ccccgcccgt  37320
ttcgtggcgg gccacctgga gctggcccag aaagtacgcc tccgacgcgc gctcggaaaa  37380
cagcacgttc tcggtcacga agcggtcctg ccgcacgacg gtgaacccga acccggggtg  37440
gaggcccgtc ttgagctggt gatacagggc cacggggctc atcttgaagt accccgccat  37500
gagcgcgtag gtcagcgcgt tctcccccgc cgcgctctcg cgggcgtgct gcaccacggg  37560
ctggcggatg gaggagaagt agttggcccc cagggccggg gggaccaggg ggacgtcgcg  37620
cgccaggtcg cgcagggccg gggggaagtt gggcgcgttg gccacgtggt cggcgcccgc  37680
aaacagcgcg tggacgggca ggacgtagaa gtattcgcca ttttggatgg tgtggtccag  37740
gtgctggggg gccatgagca gcacgccggc gtgcagcgcc ccgtcgaaga tgcgcatgtt  37800
ggccgtcgac gcggtgttgg cgcccgcgtc gggcgccgcg gagcacagca gcgccgtcgt  37860
gcgctcggcc atgttgtgcg ccagcacctg cagcgtgagc atggcgggcc cgtcgacgac  37920
gacgcgcccg ttgtggaaca tgcgcttgac cgtgttggcc accagattgg cgggatgcag  37980
cgggtgggcg gggtcggtca cgggatcgct cgggcactcc tcaccggggg cgatctccgg  38040
gaccaccatg ttctgcagcg tggcgtacac gcggtcgaag cggacccccg cggtgcagca  38100
gcgcccccgc gagaaggccg gcaccagcac gtaatagtag attttgtggt ggacggtcca  38160
gtcggccggc cggtgcggcc ggtcgtcggc ggcgtcggcc gcgcgggcct gggtgttgtg  38220
cagcagccgg ccgtcgttgc ggttaaagtc ggccgtcgcc acgttgcacg ccgccgcgta  38280
gacgggctcg tgcccccccg cgtcaatccg gcagtctcgg tggcggtcca gggccgcgtg  38340
tcgcataagg ccgtcgcagt cccacacgag gggcggcagc agcgccgggt cgcgcatcag  38400
gtgattcagc tcggcctgag cctgcccgcc cagctccggg cccggcaggg taaagtcgtc  38460
caccagctgg gccagggcct cgacgtgggc caccaggtcc cgatacacgg ccatgcactc  38520
ctcggggagg tcgcccccga ggtaggtcac gatgtacgag accagcgagt agtcgttcac  38580
gaacgccgcg catcgcgtgt tgttccagta gctggtgatg cactgagtca cgagccgcgc  38640
cagggcgcag aacacgtgct cgttgccgtg aatcgcggct tgcagcaggt aaaacaccgc  38700
cgggtagctg cggtcctcga acgccccgcg gacggcggct atggtagccg gcgccatggc  38760
gtggcggcca acgccgagct ccaggccccg ggcgtcacga aacgccaccg gacacagcgc  38820
caggggcagg ttgccgttga ccacgcgcca ggtggcctgg atcgccccccg gaccggccgg  38880
ggggacttcg ccgccgggaa gctcgacgtc ggccacgccc gcgaagaagt cgaacgcggg  38940
gtgcagctcc agagccaggt tggcgttgtc gggctgcatg aactgctccg cggtcatctg  39000
gcactcggcg acccaccgga cccggccgtg ggcgaggcgc tgccgccagg cgttcagaaa  39060
acgctgctgc atgtccgcgc cggggccggc cggggccgcg acgtacgccc cgtacggatt  39120
cgcggcctcg acggggtcgt ggttcacgcc cccgacggcc gcgtcgatgt tcatgagcga  39180
aggatgacac acggtcccga ccgcgttctc catggacagc cgcagaacct ggtggtcctt  39240
```

-continued

```
tccccaaaaa aacagctgcc ggggagggaa cgcgcggggc tccgggtggc cgggggcggg  39300
caccaggtcc ccggcgtgcg cggcgaagcg ctccatggcc gggttgaaca gccccagggg  39360
caggacgaac gtcaggtcca tggcgcccac cagggggtag ggcacgttgg tggcggcgta  39420
gatgcgtctc tccagggcct ccaggaagac cagcctgtcg cctatggcca ccagatccgc  39480
gcgcacgcgc gttgtctggg gggcgctttc gagttcatcc agcgtctccc ggttcgcctc  39540
gagttgctcc tcctgcatat ccagcaggtg gcggcccacg tcgtccaggc tccgcacggc  39600
cttgcccatc accagcgccg tgacgaggtt ggccccgttc aagaccatct cgccgtaggt  39660
caccggcacg tcggcctcgg tgtcctccac cttcaggaag gactgcagga ggcgctgttt  39720
gatggcggcg gtggtgacca gcaccccgtc gaccggccgc ccgcgcgtgt cggcgtgcgt  39780
caggcggggc acggccacgg acggctgcgt cgccgtggtc aggtccacga gccaggcctc  39840
gatggcctcg cggcgatggc ccgccttgcc caggaagaag ctcgtgtcgc aaaagctccg  39900
cttcagctcg gcgaccaggg tcgcccgggc aaccctggtc gccaggcgcc cgttgtcgag  39960
atatcgttgc atgggcaaca gcagggccag gggaggcgcc ttctccaaca gcacgtgcag  40020
catctggtcg gccgtgccgc gctcaaacgc ccccaggacg gcctggacgt tgcgcgcgag  40080
ctgctggatg gcgcgcagct ggcgatgcag gctaatgccc gtcccgtcca gggcctcccc  40140
cgtgagcagg gcaatggcct cggtggccag gctgaaggcg gcgttcaggg cccggcggtc  40200
gatgaccttc gtcatgtaat tatgcacggg ctgctcgacg gggtgcgggc cgtcgcgggc  40260
gatgaggggc tggtggacct cgaactgcac acgcccttcg ttcatgtaag ccagctccgg  40320
gaacttggtg cacacgcacg ccacggacag gccgagctcc agaaagcgca cgagcgacag  40380
ggtgttgcag taggacccca gcagggcgtc aaactctacg tcatacaggc tgttttcgtc  40440
ggagcgcacg gcggcgaaaa aatcaaagag tctgcggtgg gacgccacct cgatcgtact  40500
caggatggag ccggtgggca ggatggccgc ggcgtaccgg taacccgggg ggtcgcgggc  40560
aggagcggcc attgggttcc ttgggggatt cgcaggctcc atcaagccga gctcgggaag  40620
gccaagcccc tcccgcacaa cgcctcaccg ccggcggacg cgactaacaa cccacgggcc  40680
gccaaaaccc caaggggcaa cccgaccaac aacaggcgag gggaggaaag gcgtaaaggg  40740
ggcgttggga ggcaaaaaga aagaaaacac ccagacgtag gcccgaggac cggccggcgt  40800
cctctgtccc cgagcaccca ctgtgcccaa caggcacggg ggcgagctgc ccctgcctta  40860
tatacccccc cgccacaccc ccgttagaac gcgacgggtg ccttcaagat ggccctggtc  40920
caaaagcgtg ctagaaaaaa gttggtaaag gcggcaaagc agtccgccgc cgccacccac  40980
atggcggcgc cggccgcgca ggcgattccc agagaacggg cgcggagggg atccgtgcgg  41040
ggcagcagct ggctggcggt gatccaatgg aaaagcccgt cgggactgaa cgtctcatgg  41100
gcggccgcca ccagggcgca cagggccgcg ccgcccatga tcacgcacaa cccccaaaac  41160
acgggtggcg acaacggcag gcgatcccgt ttgatgttca cgtacaggag gagcgcccgt  41220
gccagccacg tgacatagta ggcgaggacg gcggctataa tacatgccgg cgccaccgcc  41280
cgtccggtcc acccgtaata catgcccgcg gccaccagct ccagcggctt gaggaccagg  41340
aacgaccaag caaacatcac cacccgcttg gaaaagaccg gctgggtgtg gggcggaaga  41400
cgcgagtagg ccgaactgac aaaaaaatca gacgtgccgt acgaggacag cgaaaactgt  41460
tcatcgagcg gcagttctcc gtcctccccg ccacacgcgg cctcgtctac cagctcgcga  41520
tccaacaaag gaacatcatc ccgcattgtc atggtcggtg cggggagccg gcgaggcagc  41580
aaaaccgaaa gtagtgctgg cggcgcgggc ccgggtccgg acccaagctt cagggatggg  41640
```

```
gggcggaggc caaaatcaaa caagcaccgc gcgggttcta cacacaaccc ccacccgggt  41700
agtatccgcg gatgcgagtg cctggcgaag tcacgtccca gcaggatata aacctcggcc  41760
gttgggcccg gaacccccga aattcacacc cacgccctga cgcccaaatc atgggtggat  41820
gtggttcgcg agccgcacat ccgtgcgtcc gccctccccc gcgggctgat gacgtggcgg  41880
ttagtcagtg ggaaggcagg gggaaagatg ggttggggga ggaaacgaag aaaacaccca  41940
gagggccacg tcgggaatgc gcccggagtt gtccttaaaa ggccggccgt gcgtgacgga  42000
agccgtcgtt tgcccaagca ccgacgccgc gatccacagt ggggggagtt cctccgtccg  42060
gccacaaccc tacgcgcggg cggcacgcgc gagagcaacc cacgggtccc gttcgcgcca  42120
ccgccagccc ttgctcccac caccctcctc ccaccacccc actattcccc cccccaagtc  42180
cgccccgtgg ctcgccggcc atggagctca gctatgccac caccctgcac caccgggacg  42240
ttgtgtttta cgtcacggca gacagaaacc gcgcctactt tgtgtgcggg gggtccgttt  42300
attccgtagg gcggcctcgg gattctcagc cgggggaaat tgccaagttt ggcctggtgg  42360
tccgggggac aggccccaaa gaccgcatgg tcgccaacta cgtacgaagc gagctccgcc  42420
agcgcggcct gcgggacgtg cggcccgtgg gggaggacga ggtgttcctg gacagcgtgt  42480
gtctgctaaa cccgaacgtg agctccgagc gagacgtgat taataccaac gacgttgaag  42540
tgctggacga atgcctggcc gaatactgca cctcgctgcg aaccagcccg ggggtgctgg  42600
tgaccggggt gcgcgtgcgc gcgcgagaca gggtcatcga gctatttgag cacccggcga  42660
tcgtcaacat ttcctcgcgc ttcgcgtaca ccccctcccc ctacgtattc gccctggccc  42720
aggcgcacct cccccggctc ccgagctcgc tggagcccct ggtgagcggc ctgtttgacg  42780
gcattcccgc cccgcgccag cccctggacg cccgcgaccg gcgcacggat gtcgtgatca  42840
cgggcacccg cgcccccaga ccgatggccg ggaccggggc cgggggcgcg ggggccaagc  42900
gggccaccgt cagcgagttc gtgcaagtga agcacatcga ccgtgttgtg tccccgagcg  42960
tctcttccgc ccccccgccg agcgcccccg acgcgagtct gccgcccccg gggctccagg  43020
aggccgcccc gccgggcccc ccgctcaggg agctgtggtg ggtgttctac gccggcgacc  43080
gggcgctgga ggagccccac gccgagtcgg gattgacgcg cgaggaggtc cgcgccgtgc  43140
atgggttccg ggagcaggcg tggaagctgt ttgggtcggt gggggctccg cgggcgtttc  43200
tcggggccgc gctggccctg agcccgaccc aaaagctcgc cgtctactac tatctcatcc  43260
accgggagcg gcgcatgtcc cccttccccg cgctcgtgcg gctcgtcggt cggtacatcc  43320
agcgccacgg cctgtacgtt cccgcgcccg acgaaccgac gttggccgat gccatgaacg  43380
ggctgttccg cgacgcgctg gcggccggga ccgtggccga gcagctcctc atgttcgacc  43440
tcctcccgcc caaggacgtg ccggtgggga gcgacgcgcg ggccgacagc gccgccctgc  43500
tgcgctttgt ggactcgcaa cgcctgaccc cggggggggtc cgtctcgccc gagcacgtca  43560
tgtacctcgg cgcgttcctg ggcgtgttgt acgccggcca cggacgcctg gccgcggcca  43620
cgcataccgc gcgcctgacg ggcgtgacgt ccctggtcct gaccgtgggg gacgtcgacc  43680
ggatgtccgc gtttgaccgc gggccggcgg gggcggctgg ccgcacgcga accgccgggt  43740
acctggacgc gctgcttacc gtttgcctgg ctcgcgccca gcacggccag tctgtgtgag  43800
atatcccaat aaagtgcagt cgttttctaa cccacggatg ccgttgtatg cctatacggg  43860
ggactatggg gggggaaagg aaaggaaaca ggaatggaga agggaaagga acagaggcgg  43920
tagcggacgc acggcggaca caataacaaa cagaccgcgg acacggaggg agtcggttgg  43980
```

-continued gttgggcgtg gacgccgctg cgtccacaca cccgtttatt cgcgtctcca caaaaatggg 44040
acgcacgttc ggaccaccct aaggatgccc gccagggccg cggtaatcat aacgaccccc 44100
agcgcggacg cggccagaaa cccgggggcg atggtggcga tgggcagcgt gtcaaaggcc 44160
agcagatgaa tcacagttcc gttggggaac aacaacaggg ccacggacgg cacgtcgctg 44220
gaaaacacgt tcggggtgcc cgccaccggc ccctgggcca gctgctgttg ggtggcatcc 44280
gtgtccacca gcagcaccga catgacctcc ccggccgggg tgtagcgcag aaacacggcc 44340
cccacgaggc cgaggtcgcg ccggttttcg gtgcgcacca gccgcttcgg ctcaatctcc 44400
cgcgcgtgcc cttcgcaggt ggcggtgaga taggtgataa acagcgggcg gcggacgtca 44460
acgcccgtaa gcttgtatcc gatcccgcgg ggcaaggggg tgtgggtgac gacgtagctg 44520
gcgttgtggg tgatgggcac gaggatccgg ggctccgcgt tgtgcgacgg gccgctacac 44580
tggtgggtgg cctccgggac gaaggcgcgg atcagggcgt tgtagtgcgc ccagcgcgtg 44640
agaacggagg ccacgccgcg ggtctgttgt gccatgacgt ccgccgggat gtcggatcgg 44700
gtggccatgg ccagcgcgtc caggatgaac ccgccctcgg cgagatcgaa gcgcagggaa 44760
gctgcgcatg gggaaaagtg gtccgggagc cagaagaggt ttttctggtg gtcggtcctg 44820
gctagcgcgg cccggagatc ggcgtgggtc gccgcggcga cgtcggacgt acacagggcc 44880
gtggttatga ggaggccccg gcgggcgcgt tcccgctgct cggccgaggg cgcgcccgcc 44940
aggaacggcg cccggaggac ggccgtggcg taaaacagcg ctcggcggac catcggggcg 45000
gttagcgcgc ggccgccgag aaactcggcg tacagggcgt cgatcaggcg ggccgcgctc 45060
ggggccaccg cgccataggc cgcggggctg tccaacacga acgccagctg atagcccagc 45120
gcgtgcgcca ccaggctctg ctctcgctcg aggatcgcgg ccaccagatg cccgaggcgc 45180
gcctccagcc gcaggcgggc cgccgggtcc aacacggaca cgttcaggaa caccgagtcg 45240
gccgcgcagc ccgctgctcc ccgggcggcc aggccggcca gcacgcgcga gtgggccaaa 45300
aagcccagca ggtcggagag gcgaatcgcg tcgtgggcgt gggccgcgtt gacgaacgca 45360
aaccccgacg aggcgagcag ccccgcgagg cgccagaaca gggacggacg cgcgtccgtg 45420
ccggagcccg ggtcctcccc caaaaactcc gcataggccc gcgacatata ctgggcgtag 45480
ttcgtgctct cctcggggta gccggccacc cgccggaggg cgtccagcgc cgagccgttg 45540
tcggcgggcg tcggggcccc caggacaaag acgcgatacc tggggccggc cggaggcccg 45600
gggagcaccg cgggggcgtt ttcgtcggtc ggatttccga cccgagcgag ggtcttgtcc 45660
gcaggcacca ctatgatctc ggccggaggg ctgtcccgca tcgatatcac gagccccatg 45720
aagcccttcc cgtatcgcgc gcgcacgagc gcggcgtcgc acccgaacgc cagcccgccc 45780
gtcgtccaga cgcccacggg ccacgtcgag gccgacgggg agaggtacac gtaccgaccc 45840
ggagtccgta gcaggcccct ggcggccagc caggtcacgg atgcgttgtg cagatgcgcg 45900
atgctcaggt tcgtcgtcgg atgcctcggt gtccccgcgg gcggccccgg gggcggcgcg 45960
ttgcgtcggc cgtccgggtg cctctcggtc gccccgtcgt ctccccgcgg gaacgtaagc 46020
ccctcgcggt ccggcgcggc cgcgaatgtt acccaggccc gggaccgcaa cagcgcggag 46080
gcgccggggt tgtgcgacag tcccttgagc tgggtcacct cggcgggggg acgggacgtg 46140
ggccccgcct cggggagctc gggcaggctc gcgttccgag gccggccgag cagataggtc 46200
tttgggatgt aaagcagctg cccggggtcc cgaggaaact cggccgtggt gaccaacacg 46260
aaacaaaagc gctcggcgta ccaccgaagc atgggcacgg atgccgtagt caggttgagt 46320
tcgcccgggg gcgccaagcg tccgcgctgg gggtcgctgg cgtcgggggt gttgggcaac 46380

-continued

```
cacagacgcc cggtgtttgt gtcgcgccag tacgtgcggg ccaaccccag accgtgcaaa  46440
aaccacgggt cgatttgctc cgtccagtac gtgtcatggc cccggcaac gcccaccagg  46500
acccccatca ccacccacag accggggccc atggtcgtcg tcccggctgc cagtccgcag  46560
atgggggggg gtgtccgtac ccacggccca aagaggctcc gcacctcgga ggctatcgga  46620
ggccctttgt tgccgtaagc gcgggccaaa ggatggggtg gggtgagggt aaaagcacaa  46680
agggagtacc agaccgaaaa caaggacgga tcggcccgct ccgtttttcg gtggggtgct  46740
gatacggtgc cagccctggc cccgaacccc cgcgcttatg gacacaccac acgacaacaa  46800
tgccttttat tctgttcttt tattgccgtc atcgccggga ggccttccgt tcgggcttcc  46860
gtgtttgaac taaactcccc ccacctcgcg ggcaaacgtg cgcgccaggt cgcgtatctc  46920
ggcgatggac ccggcggttg tgacgcgggt tgggatcatc ccggcggtga ggcgcaacag  46980
ggcgtctcga cacccgacgg gcgactgatc gtaatccagg acaaatagat gcatcggaag  47040
gaggcggtcg gccaagacgt ccaagaccca ggcaaaaatg tggtacaagt ccccgttggg  47100
ggccagcagc tcgggaacgc ggaacagggc aaacagcgtg tcctcgatgc ggggcagaga  47160
ccccgcgccg tcctcggggt cggggcgcgg ggtcgccgcg gcgacccccg tcagccggcc  47220
ccagtcctcc cgccacctcc cgccgcgctg caggtaccgc accgtgttgg cgagtagatc  47280
gtagacacgg cgaatggcgg acagcatggc caggtcaagc cgctcgcccg ggcgttggcg  47340
tctggccagg cggtcggcgt gttcggcctc cggaaggaca cccaggacca ggttcgtgcc  47400
gggcgcggtc gggggcatga gggccacgaa cgccaacacg gcctgggggg tcatgcttcc  47460
catgaggtac cgcgcggccg ggtagcacag cagggaggcg atagggtgcc ggtcgaaaac  47520
aagggtgagg gccgggggcg gggcttgcgg gcccacagcc tccccccga tatgaggagc  47580
caaaacggcg tccgtcgccg cataaggcgt gctcattgtt atctgggcgc tggtcattac  47640
caccgccgcc tccccggccg atatctcgcc gcggtccaga cggtgctgcg tgttgtagat  47700
gttcgtcagg gtctcggagg cccccagcac ctgccagtaa gtcatcggct cggggacgta  47760
gacgatattg tcgcgcggcc ccagggcctc catcagctgc gcggaggtgg tggtcttccc  47820
caccccgtgg ggtccgtcta tataaacccg cagcagcgtg ggcagctccg gatccccgcg  47880
ggctccggag gccccctggc gatggctagg acgggacgcc gcgcggccgt cggtaggccc  47940
gctcgcacga gcagcctgac cgaacgcagg cgcgtgctgt tggccggcgt gagaagccat  48000
acccgcttct acaaggcgtt cgcccgagag gtgcgggagt tcaacgccac caggatttgt  48060
ggaacgctgc tgacgctgat gagcgggtcg ctgcagggtc gctcgctgtt cgaggccacg  48120
cgcgtcacct taatatgcga agtggacctc gggccgcgcc gcccagactg catctgcgtg  48180
ttcgaattcg ccaatgacaa aacgttggga ggtgtgtgcg tcatcctgga gctaaagaca  48240
tgcaaatcga tttcttccgg ggacacggcc agcaaacgcg aacagcggac cacgggcatg  48300
aagcagctgc gccactccct gaagctgctg cagtcgctcg cgcctccggg ggacaaggtc  48360
gtctacctgt gtcctatttt ggtgtttgtc gcgcagcgta cgctgcgcgt cagccgcgtg  48420
acccggctcg tcccgcaaaa gatctccggc aacatcaccg cggccgtgcg gatgctccaa  48480
agcctgtcca cgtatgccgt gccgccggaa ccgcagaccc ggcggtcgcg gcgccgggtc  48540
gccgcgaccg ccagaccgca aaggcccccc tccccgacac gtgacccgga aggcacggcg  48600
ggtcatccgg ccccaccaga gagcgacccc ccctccccag gggtcgtagg cgtcgctgcg  48660
gagggtgggg gtgtgcttca gaaaatcgcg gcgctttttt gcgtgccggt ggccgccaag  48720
```

-continued

```
agcagacccc ggaccaaaac cgagtgaggt tctgtgtgtt gttttttttt ttttttttcc  48780
tcgttttgtt ttctcttctt tccccccccc ctcccccgct tctggccaag catcctcacc  48840
tgcttaagcg gaacccgcgg gcgcgcgggg actcatttgt cgccggcgac acccacccga  48900
caacagcccc tgggtgtcga ccgctgtcgc ccccgtctgt cgcctctccc tttttttcccc  48960
ccctcaaaga acgtggtgtt gggcgccggc caattcttcc cggagcgccg tcgtcgcccg  49020
cccgccgccc tcgaacatgg acccgtacta ccctttcgac gcgctggacg tttgggaaca  49080
caggcgcttc atcgtcgccg actccaggag cttcatcacc cccgagttcc cccgggactt  49140
ctggatgttg cccgtgttca acatcccccg ggagacggcg gcggagcggg cggcagtgct  49200
gcaggcccag cgcaccgcgg ccgcggcggc cctggagaac gccgccctcc aggccgccga  49260
gctgcccgtc gacatcgagc gccggatacg cccgatcgag cagcaggtgc atcacatcgc  49320
cgacgccctg gaggcgctgg agaccgcggc ggccgcggcc gaagaggcgg atgccgcgcg  49380
ggacgccgag gcgagggggg agggcgctgc ggacggggca gcgccgtcgc ccaccgcggg  49440
ccccgccgcc gcggagatgg aggttcagat cgtacgcaac gacccgccgc tacgatacga  49500
taccaacctc cccgtggatc tgctacacat ggtgtacgcg ggccgcgggg ccgcgggttc  49560
gtcgggagtc gtctttggta cctggtaccg cacgatccag gaacgcacca tcgcggactt  49620
ccccctgacc acccgcagcg ccgactttcg agacgggcgc atgtccaaga ccttcatgac  49680
cgcgctggtc ctgtctctgc agtcgtgcgg ccggctgtac gtgggccagc gccactattc  49740
cgccttcgag tgcgccgtgc tgtgtctgta tctgctgtac cgaaccaccc acgagtcctc  49800
ccccgatcgc gatcgcgctc ccgttgcgtt cggggacctg ctggcccgcc tgccgcgcta  49860
cctggcgcgt ctggccgcgg taatcggcga cgagagcgga cgcccgcagt accgctaccg  49920
cgacgacaag ctgcccaaag cgcagttcgc ggcggccggc ggccgctacg agcacggggc  49980
cctggccacc cacgtcgtga tcgccacgtt ggtgcgccac ggggtgctac cggcggcccc  50040
gggcgacgtt ccccgagaca ccagcacccg cgtgaacccc gacgacgtgg cccaccgcga  50100
cgacgtcaac cgcgccgccg ccgcgttttt ggcacgcggc cacaacctct tcctgtggga  50160
ggaccagacg ctgctgcggg cgaccgccaa caccattacg gccctggccg tgcttcggcg  50220
gctcctcgcg aacggcaacg tgtacgcgga ccgcctcgac aaccgcctgc agctgggcat  50280
gctgatcccg ggagccgtcc cggcggaggc catcgctcgg ggggcgtccg gattggactc  50340
gggcgccata aaaagcggcg acaacaacct ggaggcgctg tgcgttaact atgtacttcc  50400
gctgtatcag gcagacccca cggtcgagct gacccagttg tttccggggc tggccgccct  50460
gtgcctggac gcccaggcgg ggcggccact ggcgtcgacg aggcgcgtgg tggatatgtc  50520
gtcgggcgcc cgccaggcgg cgctcgtgcg cctcaccgcg ctggagctca tcaaccgcac  50580
ccgcacaaac accaccccctg tgggggagat tattaacgcc cacgatgcct tggggataca  50640
atacgaacag gggcctgggc tgctcgccca gcaggcacgc atcggcttgg cgtcaaacac  50700
caagcgattc gccacgttca acgtgggcag cgactacgac ctgttgtact ttttgtgtct  50760
cgggttcatt ccccagtacc tgtccgtggc ctagggaagg gtgggggtgg tggtggtggg  50820
gtgtttttct gttgttgttt ctggtccgcc tggtcacaaa aggcacggcg ccccgaaacg  50880
cgggctttag tcccggcccg gacgtcggcg gacacgcaac aacggcgggc cccgtgggtg  50940
ggtaagttgg ttcgggggca tcgctgtatt cccttgcccg cttccacccc cccccccctt  51000
cccgttttgt ttgtttgtgc gggtgcccat ggcgtcggcg gaaatgcgcg agcggttgga  51060
ggcgcctctg cccgaccggg cggtgcccat ctacgtggcc gggtttttgg ccctgtacga  51120
```

cagcggggac ccgggcgagc tggccctgga cccagacacg gtgcgtgcgg ccctgcctcc 51180
ggagaacccc ctgccgatca acgtagacca ccgcgctcgg tgcgaggtgg gccgggtgct 51240
cgccgtggtc aacgaccctc gggggccgtt ttttgtgggg ctgatcgcgt gcgtgcagct 51300
ggagcgcgtc ctcgagacgg ccgccagcgc cgctattttt gagcgccgcg gacccgcgct 51360
ctcccgggag gagcgtctgc tgtacctgat caccaactac ctgccatcgg tctcgctgtc 51420
cacaaaacgc cggggggacg aggttccgcc cgaccgcacc ctgtttgcgc acgtggccct 51480
gtgcgccatc gggcggcgcc ttggaaccat cgtcacctac gacaccagcc tagacgcggc 51540
catcgctccg tttcgccacc tggacccggc gacgcgcgag ggggtgcgac gcgaggccgc 51600
cgaggccgag ctcgcgctgg ccgggcgcac ctgggccccc ggcgtggagg cgctcacaca 51660
cacgctgctc tccaccgccg tcaacaacat gatgctgcgt gaccgctgga gccttgtggc 51720
cgagcggcgg cggcaggccg ggatcgccgg acacacgtac cttcaggcga gcgaaaaatt 51780
taaaatatgg ggggcggagt ctgcccctgc gccggagcgc gggtataaaa ccggcgcccc 51840
gggtgccatg gacacatccc ccgccgcgag cgttcccgcg ccgcaggtcg ccgtccgtgc 51900
gcgtcaagtc gcgtcgtcgt cttcttcttc ttcttttccg gcaccggccg atatgaaccc 51960
cgtttcggca tcgggcgccc cggcccctcc gccgcccggc gacgggagtt atttgtggat 52020
ccccgcctct cattacaatc agctcgtcac cgggcaatcc gcgccccgcc acccgccgct 52080
gaccgcgtgc ggcctgccgg ccgcggggac ggtggcctac ggacaccccg gcgccggccc 52140
gtccccgcac tacccgcctc ctcccgccca cccgtacccg ggtatgctgt tcgcgggccc 52200
cagtcccctg gaggcccaga tcgccgcgct ggtgggggcc atcgccgccg accgccaggc 52260
gggtgggctt ccggcggccg ccggagacca cgggatccgg gggtcggcga agcgccgccg 52320
acacgaggtg gagcagccgg agtacgactg cggccgtgac gagccggacc gggacttccc 52380
gtattacccg ggcgaggccc gccccgagcc gcgcccggtc gactcccggc gcgccgcgcg 52440
ccaggcttcc gggccccacg aaaccatcac ggcgctggtg ggggcggtga cgtccctgca 52500
gcaggaactg gcgcacatgc gcgcgcgtac ccacgccccc tacgggccgt atccgccggt 52560
ggggccctac caccaccccc acgcagacac ggagaccccc gcccaaccac cccgctaccc 52620
cgccaaggcc gtctatctgc cgccgccgca catcgccccc ccggggcctc ctctatccgg 52680
ggcggtcccc ccaccctcgt atcccccagt tgcggttacc cccggtcccg ctcccccgct 52740
acatcagccc tcccccgcac acgcccaccc ccctccgccg ccgccgggac ccacgcctcc 52800
ccccgccgcg agcttacccc aacccgaggc gcccggcgcg gaggccggcg ccttagttaa 52860
cgccagcagc gcggcccacg tgaacgtgga cacggcccgg gccgccgatc tgtttgtgtc 52920
acagatgatg gggtcccgct aactcgcctc caggatccgg acttgggggg ggtgtgtgtt 52980
ttcatatatt ttaaataaac aaacaaccgg acaaaagtat acccacttcg tgtgcttgtg 53040
tttttgtttg agaggggggg gtggagtggg ggggaaagtg ggccgaatga cacaaaaatt 53100
aggtcggagg ggtgaggggg gggggctagg agccgaaccg atggccccca cacgcgacgg 53160
aaggcccgga agactaccac ggggaggggg tgtggaaagc gaccggtcgc agggagacgg 53220
ggttggtttg gggttggttt ggggttggtt ttcccgttag cacatgtctg catttgtttt 53280
tctagtcaca cgcccccccc cccccaaata aaaaccaagg caaaacaata ccagaagtca 53340
tgtgtatttt tgaacatcgg tgtcttttta tttatacaca agcccagctc ccctcccctc 53400
ccttagagct cgtcttcgtc tccggcctcg tcctcgttgt ggagcggaga gtacctggct 53460
ttgttgcgct tgcgcagaac catgttggtg accttggagc tgagcagggc gctcgtgccc 53520
ttctttctgg ccttgtgttc cgtgcgctcc atggccgaca ccaaagccat atatcggatc 53580
atttctcggg cctcggccaa cttggcctcg tcaaacccgc ccccctccgc gccttcctcc 53640
ccctccccgc ccacgccccc ggggtcggaa gtcttgagtt ccttggtggt gagcggatac 53700
agggccttca tgggattgcg ttgcagttgc aggacgtagc ggaaggcgaa gaaggccgcg 53760
accaggccgg ccaggaccag cagccccacg gcaagcgccc cgaaggggtt ggacataaag 53820
gaggacacgc ccgagacggc cgacaccacg ccccccacta ctcccatgac taccttgccg 53880
accgcgcgcc ccaagtcccc catcccctcg aagaacgcgc acagccccgc gaacatggcg 53940
gcgttggcgt cggcgcggat gaccgtgtcg atgtcggcaa agcgcaggtc gtgcagctgg 54000
ttgcggcgct ggacctccgt gtagtccagc aggccgctgt ccttgatctc gtggcgcgtg 54060
tagacctcca ggggcacaaa ctcgtggtcc tccagcatgg tgatgttcag gtcgatgaag 54120
gtgctgacgg tggtgacgtc ggcgcgactc agctggtgag agtacgcgta ctcctcgaag 54180
tacacgtagc ccccgccgaa gatgaagtag cgccggtggc ccacggtgca cggctcgagc 54240
gcgtcgcggg tgaggcgcag ctcgttgttc tcgcccagct gcccctcgat cagcgggccc 54300
tggtcttcgt accgaaagct gaccaggggg cggctgtagc acgtccccgg ccgcgagctg 54360
acgcgcatcg agttctgcac gatcacgttg tccggggcga cgggcacgca cgtggagacg 54420
gccatgacgt ctccgagcat gcgcgcgctc acccgccggc cgacggtggc ggaggcgatg 54480
gcgttggggt tgagcttgcg ggcctcgttc cagagagtca gctcgtggtt ctgcagctcg 54540
caccacgcga cggcgatgcg ccccagcatg tcattcacgt ggcgctgtat gtggttatac 54600
gtaaactgca gccgggcgaa ctcgatcgag gaggtggtct tgatgcgctc cacggacgcg 54660
ttggcgctgg gcgcctcccg cagtggcgcg ggcgtggcat tccggggctt gcggtcctgc 54720
tcccgcatgt actcccgcac gtacagctcg gcgagcgtgt tgctgaggag gggctggtac 54780
gcgatgagga agcccccgt ggccaggtag tactgcggct ggcccacctt gatgtgcgtg 54840
gcgttgtact tgcgcgcaaa catgcggtcg atggcctcgc gggcatcccg gccgatgcag 54900
tcgcccaggt cgacgcgcga gagcgagtac tcggtcaggt tggtggtgaa ggtggtcgag 54960
atggcgtcgg aggagaagcg gaaggagccg ccgtactcgg cgcggagcat ctcgtccacc 55020
tcctgccact tggtcatggt gcagaccgcc ggtcgcttcg gcacccagtc ccaggccacg 55080
gtaaacttgg gggtcgtcag caagttgcgg gtcgtcggcg acgtggcccg ggccttcgtg 55140
gtgaggtcgc gcgcgtagaa gccgtcgacc tgcttgaagc ggtcggcggc gtagctggtg 55200
tgctcggtgt gcgacccctc ccggtagccg taaaacgggg acatgtacac aaagtcgccc 55260
gtcgccagca caaactcatc gtacgggtac accgaccgcg cgtccacctc ctcgacgatg 55320
cagttgaccg tcgtgccgta ccgatggaac gcctccaccc gcgaggggtt gtacttgagg 55380
tcggtggtgt gccacccccg gctcgtgcgc gtggcgacct tcgccggctt gagctccatg 55440
tcggtctcgt ggtcgtcccg gtgaaacgcg gtggtctcca tgttgttccg cacgtacttg 55500
gccgtggagc ggcagacccc cttggtgtta atcttgtcga tcacctcctc gaagggaacg 55560
ggggcgcggt cctcgaatat ccccataaac tgggagtagc ggtggccgaa ccacacctgc 55620
gacacggtca cgtctttgta gtacatggtg gccttgaatt tgtacggggc gatgttctcc 55680
ttgaagacca ccgcgatgcc ctccgtgtag ttctgcccct ccgggcgcgt cgggcagcgg 55740
cgcggctgct caaactgcac caccgtggcg cccgtcgggg gcgggcacac gtaaaactgg 55800
gcatcggcgt tctcgacctt gatttcccgc aggtgcgcgc gcagcgtggc gtggccggcg 55860

-continued gcgacggtcg cgttggcgtc ggggggcggg gtcgcctcgg gccgcttggg cggctttttg 55920
gttttccgct tccgggcctt ggtggtcgcg gggctcggga cggggggcgg ccgggaggcg 55980
ggacccccgt tcgccgcgac ggtcgcggcc acgccgcccg aggcgcgggg ggccgccggg 56040
gccgccgggg ccgccgacgc caccgcggcc accagcgccc ccacgaccag cgcgcaaatc 56100
aagccccccc cgcgcatggc gggcctacgg gggcgcgtcg ctcccgccgc ccgctagtct 56160
gggggcgagg tgctgcagga ccgagtagag gatggaaaaa acgtctcggt cgtaaaccac 56220
gaccgagcgg ggtccgatgc agccgtcggg gccgctctcg acgatggcca ccagcggaca 56280
gtcggagttg tacgtgaggt acacgcccgg cgggtagcgg tacagacctt cggaggtcgg 56340
gcggctgcag tcggggcggc gcaactcaag ctccccgcac cggtagaccg acgcaaagag 56400
tgtggtggcg ataatgagct cgcgaatata tcgccaggcg gcgcgctggg tgggcgtgat 56460
tccggaaaca ccgtcaaaac agtagaactt ttgaaactcg ctgacggccc aatcagcgcc 56520
cgaacccccc gcgcccatga tgaagcgggc gagttcctcc ttgaggtgcg gcaggagccc 56580
cacgttctcg acgctgtagt acagcgcggt gttgggggc tgggcgaagc tgtgggtgga 56640
gtggtcgaac aggggcccgt tgacgagctc gaagaagcga tgggtgatgc tggggagcag 56700
ggccgggtcc acctggtggc gcagcagcga cgctcgcatg aaccggtgcg cgtcaaacac 56760
gcccggggcg gcgcggttgt cgatgaccgt gcccgcgccc gccgtcaggg cgcagaagcg 56820
cgcgcgcgcc gcgaagccgt tggcgaccgc ggcgaaggtc gcgggcagca cctcgccgtg 56880
gacgctgacc cgcagcatct tctcgagctc cccgcgctgc tcgcgcacgc agcgcccgag 56940
gctggccagc gaccgcttgg tcaggcggtc cgcgtacagc cgccggcgct cccgcacgtc 57000
cgcggcggcc cgcgtcgcga tgtcgcccca gctctccggc ccctgcgccc ctggctcggg 57060
gccgcgctcc ccgtcctcgc tcgcgggcgt ccccgcgcca cgcctccgcc ccccctcctc 57120
cgcggcggcc cggggctctt cctcctcggc ccccccggtc gcgccgccgg cccccagccg 57180
cgccagcacg cggcgcagcg cctcctcgtc gcactgctcg gggctgacga gccgccgcag 57240
cagcggcgtc gtcaggtggt ggtcgtagca cgcgcgtatc agcgcctcga tctgatcgtc 57300
gggcgacgtc gcctggccgc cgatgatcag ggcgtccacc atgtccagcg ccgccaggtg 57360
gcccccgaac gcgcgatcga agtgctccgc ccgccgcccg aacagcgcca gctccacggc 57420
caccgcggcg gtctcctgct gcagctcgcg ctgcgccagc gcgttcaggt tgtcggcgaa 57480
ggcgtccatg gtggagtggc gggcgcgatc gccggacgcc agccagaagc gcagctcgct 57540
gatggcgtac aggccgggcg tagtggcctg aaacacgtca tgcgcctcca gcagggcgtc 57600
ggcctcctcg cggacagaag agctatcggc gggcggcggg ccggccctgg ccccgccgcc 57660
cgccgcggtc cgcgccagcg cctggtccag cacacagagc gctcgcgcgc gggcggcgtc 57720
cgacagcccg gcggcgtggg gcaggtaccg tcgcagctcg ttggcgtcca gccgcacctg 57780
ggcctgttgg gtgacgtggt tacagatgcg gtccgccagg cggcgggcga tggtcgcccc 57840
ttggttcgcg gtgacgcaca gctcctcgaa acagaccgcg cacgggtggg acgggtcgct 57900
cagctccggg ggcacgatga ggcccgaccc caccgccgcc accataaact cccggacgcg 57960
ctccagcgcg gccgtggcgc cgctcggggg ggtgatgagg tggcagtagt tcagctgctt 58020
gagaaaattc tcgacatcat gcaggaagca cagctccatg cggacgtccc cgccgtacgt 58080
ctgcagccgg atctgctggt ggtacggaca gggtcgggcc agacccatgg tctcggtgaa 58140
aaaggcagag acgtcacccg tggtcgcgaa cgtttccagg tggcccagga gccgctcccc 58200
ctcgcgccac gcgtactcca ggagcaactc cagggtgacc gacagcgggg tgagaaaggc 58260
ggcggcctga gcctccagcc ccggccgcag gtgccgccgc agcacgcgca cctggagcgc 58320
gttgagtttt agctgggcga gcttccccag gccgatctgg gggtcgcatc gtcgaagcag 58380
ctctagctga aaaacgtacg tctgtacctg cccgagcagg gccaacagtt tctgtcgggc 58440
cgcagtgggc tcggaaaccg cggccggggg cgcggccgcc atggcgagtc acccggccgt 58500
gctgtggttt agttaaggtt tggggggggg tgggtcagag gcgcgccccg cgcggactga 58560
tgcggcggcg ggcccctgac atcccctctt tatgcccgtc gcccgcccgc ccgccccgcc 58620
ggtgtgccgt gattcgcgga gtcggggcct tgtgtttctt tctttccccc ccgaatccgt 58680
tctttcttcc tcaccccccc ctccccacac acccacccag gactcgccac cacaaggagg 58740
cgagagcccg tcgctaaccc aaagacacag tcacgagaca cgatatcgac tgtagttgcg 58800
atcgtttatt ttatacacaa caccaacctt tccttcgacc ccccccaccc ccgcccctag 58860
agcatatcca acgtcaggtc ctttttctcc ggtggtccct ccccaaacgg atcgtcgccg 58920
tgaaacgccc gctttcgggc gacgccggcc gcccccgccg ccgccgccaa accgccgaac 58980
gacgccgcgt ggtcatcctc gtcgccgaaa tccccaaagt taaacacctc cccggcggcg 59040
ccgagctggc tgaccagggc ctccgcctcg tgggccacct ccagggccgc gtcggtcgac 59100
cactcgccat gcccgcgctc cagggcgcgg gtggtaaact ccatcatttc ctcgctcagg 59160
tactcgtcct ccagcagcgc cagccagtcc tcgatctgca gctgctgggt gcgggggccc 59220
aggctcttga cggtcgccac aaacacgctg ctggcgaccg ccgccccgcc ctccgcaatg 59280
atgccccgga gctgctcgca cagcgaatgc tcgtgggccc cgcccccgag actcgacgcc 59340
gcgcacacaa acccggccct ggggcaggcc aggacaaact tgcgggtgcg gtcaaagatc 59400
agcagcgggc acgcgttttt gccgcccagc aggctggccc agttcccggc ctgaaacacg 59460
cggtcgttgc cggccatgcc gtagtatttg ctgatgctga ggcccagcac gaccatcggg 59520
cgcgcggcca tcacgggccg cagcaggttg cagctcgcga acatggacgt ccaggcgccg 59580
gggtgcgcgt cgagggagtc catcagcgcg cgggccccgg cctccaggcc cgcgccgccc 59640
tgcggggccc aggcggccgc cgcctgcacg ctggggggac ggcgggaccc ggcgatgacg 59700
gccgtgaggg tgtttatgaa gtacgtcgag tggtcgcagt acctcaagat ctggttggcc 59760
atgtagtaca tggccagttc gctcacgtta ttgggggcca ggttgataaa gttaatcgcg 59820
ccgtagtcca gggagaacct cttaatgaac gcgatggtct ctatgtcctc gcgcgacaag 59880
agccgggcgg ggagctggtt gcgctggagg gcggtccaga accactgcgg gttcggctgg 59940
ttcgaccccg ggggcttgcc gttgggaaag atgaccgcgt ggaactgctt cagcaggaag 60000
cccagcggtc cgaggaggat gtccacgcgc ttgtcgggct tctggtaggc gctctggagg 60060
ctggcgaccc gcgccttggc ggcctcggac gcgttggcgc tcgcgcccgc gaacaacacg 60120
cggctcttga cgcgcagttc cttgggaaac ccaagggtca cgcgggcaac gtcgccctcg 60180
aagctgctct cggcgggggc cgtctggccg gccgttaggc tgggggcgca gatagccgcc 60240
ccctccgaga gcgcgaccgt cagcgtcttc gccgacagga acccgttgtt gaacaggtcc 60300
atgacgcgcc gccgcagcac cggttggaat tgattgcgaa agttgcgccc ctcgaccgac 60360
tgcccggcga acaccccgtg gcactggctc agggccaggt cctggtacac ggcgaggttg 60420
gaccgccgcg cgaggagctg cagcaggggg cacggcccgc aggtgtacgg gtccagcgac 60480
agcgacatgg cgtggttggc ctcggccaga ccgtcgcgga acttaaagtt gcgcccctcg 60540
atcaggttgc gcatcagctg ttccacctcg cgatccacca gctgcttgat gttgttcacc 60600
accgtgtgca gggcctcgcg gttgccgata atcgtctcca gcctccccag ggccgtgggc 60660
accgcctggt ccacgtactg cagggcctcg agctcggcca tgacgcgctc ggtggccgcg 60720
cggtacgtct cctgcatgat ggtccgggtg ttctcggacc cgtccgcgcg cttcagggcc 60780
gagaaggcgg cgtagttccc cagcacgtcg cagtcgctgt acgcgctgtt catcgttccg 60840
aagaccccaa tggcccccg ggcggcgctc gcgaacttgg ggtggcgggc ccgcagccgc 60900
atcagcgtcg tgtgcgcgca ggcgtggcgg gtctcgaagg tacacaggtt gcagggcacg 60960
tcggtctggc ccgagtccgc gacgtagcga aacacgtcca tctcctggcg cccgacgatg 61020
actccgccgt cgcagcgctc caggtaaaac agcatcttgg ccagcagggc cggagagaac 61080
ccgcacagca tggccaggtg ctcgccggcg aactcctggg ttccgccgac gaggggcgcc 61140
gtggggcgcc cctcgtaccc gggcaccacg tggccctcgc ggtccagctg cgggttggcc 61200
gccacgtgcg tgccgggcac gagaaagaag cggtaaaagg agggcttgct gtggtccttg 61260
gggtccgccg gcccggcgtc gtccacctcg gtcaggtgga gggccgaatt ggtgctgaac 61320
accatggcgc ccacgaggcc cgcggcgcgc gccaggtacg ccccgacggc gccggcgcgg 61380
gccgcgggcg tttcctggcc ctcaagcagg ggccacgtgg tgatgtcggg gggcggctcg 61440
tcaaagaccg ccatcgacac gatggactcc agggccaggg cggcgtcgcc cgccatcacc 61500
gaggccaggc gctgctcaaa cccgcccgcc gggcccttgt tcccggcgtc gcgcgcgccc 61560
cgctggggct taccctggct ggcctcgaag gccgtgaacg taatgtcggc ggggagggcc 61620
gcgccctcgt ggttttcgtc gaacgccagg tgggcggccg cgcgggccac ggcgtccacg 61680
ttccgggcac gcagggccac ggcggcgggc ccgacgaccg cctcgaacag caggcgggcg 61740
agggggcggt tgaaaaacgg aagggggtag ttgaaattct ccccgatcga tcggtggttg 61800
cagttaaacg gatcggcgat gacccggcta aaatccggca taaacatctg cagcggatac 61860
acggggatgc ggtgaacctc cgcgtccccg atggttacct tgtccatccc gcccagatgc 61920
aggaaggtgt tgctgatgca cacggcctcc cggaagccct ccgtgatcac cagatacagc 61980
aaggcccggt ccgggtccag tccgagccgc tcgcacagcg cgtcccccgt cgtctcgtgc 62040
tttaggtcgc agggccgggg cgcgtagtcc gcgaagccaa aatgcgggcg cgcccgctcg 62100
cagagccgcg tcaggttggg ggcctgggtg ctgggggcca ggtggcggcc gccgtgaaag 62160
acgtaaacgg acgggctgta gtgcgagggc ataagcttga gggacaccgc ggtcccccca 62220
aggcccgtcg tgcgggaccc gacgaccgcg gccacgttgg cctcaaaccc gctctccacg 62280
gtcaggccga cgatgagggg cgcgacggcg acgtccgcgt cgccgctgcg cgccgacagt 62340
agcgacagca gctccaggcc ttcggccgga caggcgcggc catacacgta ccccatcggc 62400
cccggaggaa ccttgacggt ggtcgtcgtt ttgggcttgg tgtccatggc tttcgggaga 62460
tcggcgaccg gcaggaacgg gggcccggca agacgaccgg gggcagacgg gggaggccgc 62520
gcgtggtcga cggctgctgc ccgccgtcgt ctctccgatg gggtcgaatg ccggcgctgg 62580
gggtggggtc tacacccgcc cgttcgccga gcggcccctg gtgggggtgg gatgggtggg 62640
atggggtggg cgagaatggc ccgccaccgg atcgcgccgg acgggggggc ccggggttgg 62700
gcaaggtttg ggcgcaaggc tccagcggcg attcgagagg cctgcggatg gcggcccaga 62760
gctgggtatg ctcggccggg gcggccggta tatgtacggc gtgctgggag gggcggcgtc 62820
gggccccgcc cacggtccgc cacgccccgc gcgtcatcgg cagggggcgt ggccgccctt 62880
ctaaaaaaag tgagaacgcg aagcgttcgc actttgtcct aataatatat atactattag 62940
gacaaagtgc gaacgcttcg cgttctcact ttttttagaa gggcggccac gccccctttg 63000
acgtcacgct cacccgggcg gccggccgcc cataagcgcg gcctgccggg ccgataaaaa 63060
gaaaccgcgg cgcccccgcg gacaccacac actggctctc gaaccccgga cgcgcagaag 63120
ggacccgggc gcgggtccgc cggtaagagc cggggggaac atcggcaccg ccatcccacc 63180
ccgagctgtt gggtgggcgg gtgggggggc tggtgaggcg gtggtgggag ggggcggcgt 63240
atagcaggac aacgaccggc ggcgatgttt tgtgccgcgg gcggcccggc ttcccccggg 63300
gggaagccgg cggctcgggc ggcgtctggg ttttttgccc cccacaaccc ccggggagcc 63360
acccagacgg caccgccgcc ttgccgccgg cagaacttct acaaccccca cctcgctcag 63420
accggaacgc agccaaaggc cctcgggccg gctcagcgcc atacgtacta cagcgagtgc 63480
gacgaatttc gatttatcgc cccgcgttcg ctggacgagg acgcccccgc ggagcagcgc 63540
accggggtcc acgacggccg cctccggcgc gcccctaagg tgtactgcgg gggggacgag 63600
cgcgacgtcc tccgcgtggg cccggagggc ttctggccgc gtcgcttgcg cctgtggggc 63660
ggtgcggacc atgcccccga ggggttcgac cccaccgtca ccgtcttcca cgtgtacgac 63720
atcctggagc acgtggaaca cgcgtacagc atgcgcgccg cccagctcca cgagcgattt 63780
atggacgcca tcacgcccgc cgggaccgtc atcacgcttc tgggtctgac ccccgaaggc 63840
catcgcgtcg ccgttcacgt ctacggcacg cggcagtact tttacatgaa caaggcggag 63900
gtggatcggc acctgcagtg ccgtgccccg cgcgatctct gcgagcgcct ggcggcggcc 63960
ctgcgcgagt cgccgggggc gtcgttccgc ggcatctccg cggaccactt cgaggcggag 64020
gtggtggagc gcgccgacgt gtactattac gaaacgcgcc cgaccctgta ctaccgcgtc 64080
ttcgtgcgaa gcgggcgcgc gctggcctac ctgtgcgaca acttttgccc cgcgatcagg 64140
aagtacgagg ggggcgtcga cgccaccacc cggtttatcc tggacaaccc ggggtttgtc 64200
accttcggct ggtaccgcct caagcccggc cgcgggaacg cgccggccca accgcgcccc 64260
ccgacggcgt tcggaacctc gagcgacgtc gagtttaact gcacggcgga caacctggcc 64320
gtcgaggggg ccatgtgtga cctgccggcc tacaagctca tgtgcttcga tatcgaatgc 64380
aaggccgggg gggaggacga gctggccttt ccggtcgcgg aacgcccgga agacctcgtc 64440
atccagatct cctgtctgct ctacgacctg tccaccaccg ccctcgagca catcctcctg 64500
ttttcgctcg gatcctgcga cctccccgag tcccacctca gcgatctcgc ctccaggggc 64560
ctgccggccc ccgtcgtcct ggagtttgac agcgaattcg agatgctgct ggccttcatg 64620
accttcgtca agcagtacgg ccccgagttc gtgaccgggt acaacatcat caacttcgac 64680
tggcccttcg tcctgaccaa gctgacggag atctacaagg tcccgctcga cgggtacggg 64740
cgcatgaacg gccggggtgt gttccgcgtg tgggacatcg gccagagcca ctttcagaag 64800
cgcagcaaga tcaaggtgaa cgggatggtg aacatcgaca tgtacggcat catcaccgac 64860
aaggtcaaac tctccagcta caagctgaac gccgtcgccg aggccgtctt gaaggacaag 64920
aagaaggatc tgagctaccg cgacatcccc gcctactacg cctccgggcc cgcgcagcgc 64980
ggggtgatcg gcgagtattg tgtgcaggac tcgctgctgg tcgggcagct gttcttcaag 65040
tttctgccgc acctggagct ttccgccgtc gcgcgcctgg cgggcatcaa catcacccgc 65100
accatctacg acggccagca gatccgcgtc ttcacgtgcc tcctgcgcct tgcgggccag 65160
aagggcttca tcctgccgga cacccagggg cggtttcggg gcctcgacaa ggaggcgccc 65220
aagcgcccgg ccgtgcctcg gggggaaggg gagcggccgg gggacgggaa cggggacgag 65280
gataaggacg acgacgagga cggggacgag gacggggacg agcgcgagga ggtcgcgcgc 65340
gagaccgggg gccggcacgt tgggtaccag ggggcccggg tcctcgaccc cacctccggg 65400
tttcacgtcg accccgtggt ggtgtttgac tttgccagcc tgtaccccag catcatccag 65460
gcccacaacc tgtgcttcag tacgctctcc ctgcggcccg aggccgtcgc gcacctggag 65520
gcggaccggg actacctgga gatcgaggtg gggggccgac ggctgttctt cgtgaaggcc 65580
cacgtacgcg agagcctgct gagcatcctg ctgcgcgact ggctggccat gcgaaagcag 65640
atccgctcgc ggatccccca gagcaccccc gaggaggccg tcctcctcga caagcaacag 65700
gccgccatca aggtggtgtg caactcggtg tacgggttca ccggggtgca gcacggtctt 65760
ctgccctgcc tgcacgtggc cgccaccgtg acgaccatcg gccgcgagat gctcctcgcg 65820
acgcgcgcgt acgtgcacgc gcgctgggcg gagttcgatc agctgctggc cgactttccg 65880
gaggcggccg gcatgcgcgc ccccggtccg tactccatgc gcatcatcta cggggacacg 65940
gactccattt tcgttttgtg ccgcggcctc acggccgcgg gcctggtggc catgggcgac 66000
aagatggcga gccacatctc gcgcgcgctg ttcctccccc cgatcaagct cgagtgcgaa 66060
aaaacgttca ccaagctgct gctcatcgcc aagaaaaagt acatcggcgt catctgcggg 66120
ggcaagatgc tcatcaaggg cgtggatctg gtgcgcaaaa acaactgcgc gtttatcaac 66180
cgcacctcca gggccctggt cgacctgctg ttttacgacg ataccgtatc cggagcggcc 66240
gccgcgttag ccgagcgccc cgcagaggag tggctggcgc gacccctgcc cgagggactg 66300
caggcgttcg gggccgtcct cgtagacgcc catcggcgca tcaccgaccc ggagagggac 66360
atccaggact ttgtcctcac cgccgaactg agcagacacc cgcgcgcgta caccaacaag 66420
cgcctggccc acctgacggt gtattacaag ctcatggccc gccgcgcgca ggtcccgtcc 66480
atcaaggacc ggatcccgta cgtgatcgtg gcccagaccc gcgaggtaga ggagacggtc 66540
gcgcggctgg ccgccctccg cgagctagac gccgccgccc caggggacga gcccgccccc 66600
ccagcggccc tgccctcccc ggccaagcgc ccccgggaga cgccgtcgca tgccgacccc 66660
ccgggaggcg cgtccaagcc ccgcaagctg ctggtgtccg agctggcgga ggatcccggg 66720
tacgccatcg cccggggcgt tccgctcaac acggactatt acttctcgca cctgctgggg 66780
gcggcctgcg tgacgttcaa ggccctgttt ggaaataacg ccaagatcac cgagagtctg 66840
ttaaagaggt ttattcccga gacgtggcac cccccggacg acgtggccgc gcggctcagg 66900
gccgcggggt tcgggccggc gggggccggc gctacggcgg aggaaactcg tcgaatgttg 66960
catagagcct ttgatactct agcatgagcc ccccgtcgaa gctgatgtcc cgcatcttgc 67020
aataaatgtc tgcggccgac acggtcggaa tttccgcgtc cgctggtttc tctgcgttgc 67080
gtctgaccac gagcacaaac gtgctctgcc acacgtgggc ggcgaaccgg tagccggggc 67140
acgcggtcag catccgatcg atgagccggt agtgcaggtg ggccgacgtg ccggggaaga 67200
tgacgtacag catgtggccc ccgtacgtgg ggtccgggta aaaaagaaac cgggggtcgc 67260
acgccccccc tccgcgcagg atcgtgtgca cgaaaaagag ctcgggctgg ccgagcgtat 67320
cggccaggag gtcctggagg ggggtgctgt ggcggtcggc cagcacgacc agggaggcca 67380
gaaaggtgcg gtgctcaaag atcgtattga tctgctgcac gaaggccagg atgagggcct 67440
cgcggctgac ggtggccagc cgcccgtcgc ccgcgctgca cgcggggcag cagcccccga 67500
tccccaggta gtagcccatg cccgagaggg tcaggcagtt gtcggccacg gtctggtcca 67560
ggctgaaggg gagcgacacg gggggtcgtct tcaccagggg cacggagagc gagcgcacga 67620
tggcgatctc ctcggagggc gtctgggcga gggcggcgaa gaagccgcgg tagcgacggc 67680

-continued

```
gctcgtgcag gcagagctcc agcctgcgcg cgtgcgacgg caggctcttg cgggaggccc  67740
ggcgctccac gccggggttc ccggcggcgg aaaagcgcga ccgccgccgg gtcttgtcgc  67800
ggccgggccc gggccgggag ccggagcgac ggggggcgat gtcatacata ggtacagagg  67860
gtgtgctcca gggacaggag agagatcgag tgtcgtctga gcagcgcgcc ggcctcgcgg  67920
acaaatgtgg ccagcgcggt gggcttcggc acaaatacct ggtacgtctt gaaggtgtag  67980
atgagggccc gcagggctat acagacccgc ccctcgaact cgttgccgca ggccaacttg  68040
gccttgtgaa gctgcagctc gtcgcgatgg tcggcgcggg ggtggccaaa caggacccag  68100
gggtcgactt ccatctccgt gatggcgcac atcggatcgc agaacatgtg cttgaagatg  68160
gcctcggggc ccgcggcccg aagcaggctc acgaaccggc ccccgtcccc gggctgcgcc  68220
tcggggtccg cctcgagctg gtccacgacc ggcactatgc agtcgaagag gctggtgttg  68280
ttctccgagt agcggacgac ggacgccctc aggcgtcgca tggccagcca gtaggcccgc  68340
accagcaaca gattgcacag caggcattcc ccgccggtgc gcccgcgccc ccggccgtgc  68400
ttcagcacgg tggccatcag cgggcccagg tccaggtcgg gctggggctg gggctcggcg  68460
aactgcgcaa aacgcggggc cgcgtcgcgc atgcgcgccc cgcggtgcgc ttcccaggac  68520
tcgctgaccg cggcgcggcg ggcgtccgcg gcggcgcgca gccggggccc cgactcccag  68580
acggcggggg tgccggcgag cagcagcagg atcaggtcgg cgtacgccca cgtctccggc  68640
tcaccccct gcgccagcgc cccggcggcg gcctcgaact ccccgttgcg ggcggcggcg  68700
cgcgtgcagc agctgtctcc gcccccgcgc ttgccctcgg tgcagtcgag caggcgggcg  68760
cagtccttcc agttcatcag ggcggtggtg agggagggtt gcgttcccga gcccccgccc  68820
gcccccgccc ccgccccgtc atcgcccccg gaggccaggg tcccgatgag ggcccgggtt  68880
gcggactgcg cgaggaagga atagttggag tactgcacct tggcggcgcc cggggagggc  68940
gtcggcctgg gttgcttctg ggcgtggcgc ccgggcaccc cgccgtcggt ccggaagcag  69000
cagtggagaa agaaatgccg gtggatgtcg ttgatggtca gggcgaagcg cgcgaaggag  69060
ccgacaaggg tcgccttctt ggtgcgcagg aagtggtggt ccatgacgta gacgaactcg  69120
aaggcggcca cgaagatgct cgcggcgcag tggggcgcgc ccaggcactt ggcgcagagg  69180
aacgcgtaat cggccaccca ctggggcgag aggcggtagg cctgcttgta cagctcgatg  69240
gtgcggcaga ccagacaggg gcggtccagc gcgaaggtgt cgacggacgc cgcggcgaag  69300
ggccccgtgt ccaagagtcc ctctgccgtg gggtctgcgg gcgggccgcg ggcggacccc  69360
ggcccccgcc cccccgaagc ctcgcgcgcg gccccgcgcg gccgcggggg ggcgggcgcg  69420
acgtcgctct ccacgtcctc gtcgagcgcg ctcgcgggcg gcacgcctac cacgtgacag  69480
gccgccagga gctcggcgca cagggcctcg ttaagagcca gaaggtcggg atcgaaggcc  69540
acatacggac gctcgaacgc gccctccttc cagctgctgc ccggcgactc ttcgcgcacg  69600
gcggcgctcg acggcacccc cggggcggac gtcgccatgg ccggtcgagc ggggcgcacg  69660
cgtccgcgaa cgttacggga cgcgatcccc gactgcgcgc tgcggtccca gaccctggaa  69720
agtctagacg cgcgctacgt ctcgcgagac ggcgcggggg acgcggccgt ctggttcgag  69780
gacatgaccc ccgccgaact agaggttata ttcccgacca cggacgccaa gctgaactac  69840
ctctcgcgga cgcagcggct ggcctccctc ctgacgtacg ccgggcctat aaaagcgccc  69900
gacggccccg ccgccccaca tacgcaggac accgcgtgcg tgcacggcga gctgctcgcc  69960
cgaaagcgcg aacggttcgc ggcggtcatt aaccggttcc tggacctgca ccagatcctg  70020
cggggctgac gcgcgcttcg gcggggcacc ggcaccggga ccgacttgtt ttacataaca  70080
```

gtagggggtg ggggaacgcg caccettgcc cggtcgcgat ggcggggatg gggaagccct 70140
acggcggccg cccgggggac gcgttcgagg gtctcgttca gcgcatcagg ctcattgttc 70200
ccgccacgct gcgcggcggg ggtggggagt cgggccccta ctcgccatcc aacccgccct 70260
cgagatgtgc cttccagttc cacggccagg atgggtccga cgaggccttc ccgatcgagt 70320
acgtcctgcg gctcatgaac gactgggccg atgtgccctg caacccctac ctgcgcgtgc 70380
agaacaccgg cgtttcggtg ctgtttcagg ggttttttaa ccggccccac ggcgccccgg 70440
ggggcgcgat cacggcggag cagaccaacg tgattctgca ctccaccgag acgacgggac 70500
tgtccctcgg agacctggac gacgtcaagg ggcgcctcgg cctggacgcc cggccgatga 70560
tggccagcat gtggatcagc tgctttgtgc gcatgccccg ggtgcagctc gcgtttcggt 70620
tcatgggccc cgaggacgcc gttcgcacgc ggcggatcct gtgtcgcgcc gccgagcagg 70680
ccctcgcccg tcgccgccgg tccaggcggt cccaggatga ctacggggcg gtggtggtgg 70740
cggcggcgca ccactcttcc ggagcgcccg ggccgggggt cgccgcctcg ggcccgccag 70800
cgccgcccgg acggggaccg gcccgtccgt ggcatcaggc cgtgcagttg ttccgggccc 70860
cgcgtccggg ccccccggcg cttctgttgc tggcggcggg gctgtttctg gggggccgcta 70920 tctggtgggc ggttggcgcg cgcctatgaa agggggcgag ccaccgtccc gcccgccagt 70980
gcatcccaga cgcccgcgag ccgcacatcc cctccgctcc cgcctccggc ccgattctta 71040
cggcgcgacc caaggtcccg atggccgccc cgcagtttca ccgccccagc accattaccg 71100
ccgacaacgt ccgggcgctc ggcatgcgcg ggctcgtgtt ggccaccaac aacgctcagt 71160
tcatcatgga taacagctac ccgcatccgc acggaacgca gggtgcggtg cgagagtttc 71220
ttcgcgggca ggccgcggcg ctgacggacc tcggggtgac ccacgccaac aacacgttcg 71280
ccccgcagcc tatgttcgcg ggcgacgccg cggccgaatg gctgcggccc tcgttcggtc 71340
ttaagcgcac gtattccccc tttgtcgttc gcgaccccaa gacccccagc accccgtgag 71400
tcctcggcgg gtccctccgc ggccgtctct cgttgccccc ctttcccccct tcccgggtgg 71460 ttcaataaaa aacaccaaca tacgatattc gcgtttgata cgtttattgg ggggggtgta 71520
gggcccaacg atcggcgatt aacaacacca aacaatcgag cgcgtctaac ccagtaacat 71580
gcgcacgtga tgtaggctgg tcagcacggc gttgctgcgc tgaaacagcg ccctgcgggt 71640
ccgctgcagc tgttgttgta tgcggcggca tgcgcggatc aaaaccgcca gggcgctacg 71700
accggtgctt cgtacgtagc gtcgcgacaa gacggcattt gcctgtacgg gcaaggggcc 71760
aaattgcgag tgtggtgact ggaggtggtc ggcggccaat gggccgggtg gttcgtcggc 71820
ggggggcaag tgcggttccg gtgggagggg gtcgagcgcc tcggtatcat ccgagtccga 71880
gaaacgcagg gagtctgcgt cggagtgttc atcatcggag gagatgtgca gcgtctgaag 71940
cagcgatgcg ggtgggggcg cggagtcgac gtgaagcgcg agagaggaag cccacgaagt 72000
cacagcggac actgggaggt gggtgtttgt atgtgtggga gactcgggcg tcgggaccga 72060
gtctcggctc tggggtgtaa gcgtccgagt tacgggcggc aggggcggct ggggcagggg 72120
cggctggggc aggggcggct ggggcagggg cggctggggc aggggcggct ggggcagggg 72180
cggctggggc aggggcggct ggggcagggg cggctggggc aggggcggct ggggcagggg 72240
cggctggggc aggggcggct ggggcaccga gcgcgcgcgg atgcgcgtcc gcgcggcggg 72300
tttggtcgcg ggtgactggg gtggggggcg gcgggcaacc gggcctccgg gcacgaccca 72360
accgcacaaa ggctcgctcg ggcaaccgg gcctggggcc aaaggcgggg ggctggtctg 72420
gacggcggag gtcggggggg caaggcccgg agaaggcggc actgccgccg ctgcggcgga 72480
aaccgcggcc gcgtggtcgg ctgggtcccg gggagagggg agggagttca acgaggccga 72540
gagcgaggcg accgcggggc gcgtgaggcg ccggggtggg ccggccgcgg ggccccgggg 72600
gggtgtcggc gagggacccg ctgttgtctg gcggcggccg cggcggcggt cgcccccggg 72660
gacgaccgct ccttcggcgg gcggaggcgg gatgggcgcg agcgtggggg cgggaaaggc 72720
cccgcgagcc gaggcggggc cggcggaag gggcaaagca gaaacccaag ccgggggcgc 72780
ggactccggg gtgggcggct ggtcgggagg acgcgcggaa gcggcgaccg gggcgaccgg 72840
ggcggggagt gccggcggac gccacccctc ggggggggcg gaggcccggg gcgcgcgcga 72900
tttggcacgc gtccggcggg acctgcgcac gcgcggcacg gcggcggaga aagcggcggc 72960
agagccggaa aaggccgggg gaggaagcgc ggcatccgcg gggggactcg gtgtgggtgg 73020
cgagggccgt gggtcgtcgc gaggggccac gggcacgcgc cccgtgtttt gttgaggcgg 73080
gacactcggt cgtgtttcgc gagccgtagc tgccggcccg atgggccgcg gtgcgtactg 73140
ggacgtgggg acggactgat cggtggcggg ggggggaaga agggccgggg ccggattggg 73200
cgtggggccg ccggcgtcgt cggacgccag ctcctccagg ccgtggatcc aggcccacat 73260
gcgagggggg acgggctcgc cggtggtggc gtcggtgagg agagtggggg cgaggacccc 73320
cgggtccgcc tgccgtgcgg ggggggcagc ggggtcctcg ggacccgatc cgccatcccc 73380
ccccgcaagg tcccgcgggt cgcgggcggc ggtcggggca gagggacctg cctcgtcggc 73440
gagggggcgc tggtaaaccg ggtgtcccgg gaacagctcc cccgtcagga gggaggcgtc 73500
gaagggccgc ccgaggatgg cccgcgcgaa gaaggggtcc gcgtcggcgg cgctcgccgc 73560
gagaacgtcc cccgcggtag ccacaaacgg aagctcctcg gtggcctcgc tgcccacaaa 73620
ccgcacgtca ggggggccgg ggggctccgg ggcttcccac aagaccgcga ccggggtcat 73680
ggagatgtcc acgaggacca ggcacggggg cccgtcggcg agagggcgct cggcgatgag 73740
cgccgacagg cgcgggagct gcgccgccag acacgcgttt tcgatcgggt tgagatcggt 73800
gtggaggagg ccgacggccc acgtctcgat gtcggacgac acgacgtcgc gcagggcggc 73860
gtccggcccg ccggggcgcg agtcgaagag cgtcaggcac agttccagtt ccgactcgcg 73920
ggagaaggcc gtggtgttgc ggagcgccac cacgacgggc gcgccgagga gcaccgcggc 73980
cagaaccagg tccatggccg taacgcgcgc ggcgggggtg cggtgggtcg cggcggccag 74040
cacggccacg tgctggcccg tgggtcggta gagggcgtgg ggggcctcgg ggagggacgc 74100
ctcgcgcccc cccgccgggc cgagcgtctg gccagactcc aggcgtgcgg ccaggagggc 74160
gtcgaagctg tcgtactcgg tgtagtcgtc gggaaacatg caggtccaca gcgcggccaa 74220
agcggcgctc ggcagacaca tgcgcccgag gacgctcacc gccgccaggg cctgggccgg 74280
actgagcttc ccgagcgccg ggacgtcccg gcgctgggtc ccgagctcca aggccgagcg 74340
ccagggcgcc agcgggtcgg tttcggacag cttgccccgg cgccagtcgg ccagccgcgt 74400
gccgaacagg aggccccggg tcgggggggcc tccgtccaaa aacgtcggca acacgcggat 74460
gcgggcgtcg ggatgcgggg tcaggcgctg gacgaacagc atggactccg ctgcgtcctc 74520
gaacgcgcgt tcgagggtga ggtgcatgta ctcgtgctgg cgaacgaggt ccaggcgcca 74580
gaagttgtag atgtgttccg gaacgccggc caccagcgcg accagcacgt cgttctcgtt 74640
gaaggcgacg cagtggcgct gggacccccg ggggcccggc ggcggacgcg gcgccgccgc 74700
tccggacgcc cagcccagct gggcccagcg acacccaaac tcgcgcgtga gggtggtggc 74760
gacgagggcg acgtacagct cggccgccgc gtccatcgag gcgccccacg tcgcctggcg 74820
atggcgcacg aagcgaccga acagctgaaa gttggcggcc tgggcgtcgc tgagggccag 74880
ctggagccgg ttcacgacgg tcagcacgta catggccgtg accgtcgggg ccgattcgag 74940
gacgtccgtc ggaagcgggg gccgcacgca ggccgcctcg ggacgcatca gcagcgcgcc 75000
gagtttgtcg gtgacggccg ggaagcatag cgcgtactgc agcggcgttc cgtccggggc 75060
caaaaagctg gtggcgaacg gcagatccag agcgctgacg gcctcacgca gcaccagggg 75120
ccccgggtct ccgccggcgc gcagatacgc ctcgccccgg cggcgcagca gctgcgggtc 75180
gacctcgtgg ccctcggggg aagaagaggc ccgggcgcgg gcgtcgaggg cgcgaagatc 75240
aacgagcagg ggcgcgggcg cggactccgc gcccgcgccc gtctggccgc cggccctggc 75300
gtacgcgcta tataagccca tgcggtattg gatgagttcc cgcgcgcccc ggaactcctc 75360
caccgcccac ggggccaggt ccgcggccgc cgcgtcgaac tccgccagca ggccccccag 75420
ggcgtcaaag ttcatctccc agggcaccct gcgcaccacc tcatcccgca gccgggcgca 75480
cagggcggtg tgcttggtga cgcgcgcgcc cagctcctcc acggcctccg cgcgctcggc 75540
gcccttggcg cccaggacgc cctggtacct ggcggaaagg cgctcgtagg ccggctgggc 75600
ccgcagcccc gacaccgtgt tggtggtgtc ctgcagggcg cgcagctgct cgtgcatggc 75660
gcggaacccc tcgggggact tccaggcgcc cccccggacg cggccaaagc gaccccagac 75720
ctcgtcccac tccgcctcgg cctcctccag ggacctccgc agggcgtcga cgcggcgccg 75780
agtatcaaag agcgccccca ggcggccggc gtgccgcgcc agggggccgg ggccgtcgcc 75840
gcgggcggcg cttagcgggt gcgtctcgaa ggtgcgctgg gcgtgctcta gccagataac 75900
cgcgggcacg tcgagctcgc gcgttttctc ggtctgatcc aacagaacct cgacctggtc 75960
ggcgatctcc gccaccgagc gcgcctggtc gagcgtcttg gccacggtcg ccgggacggc 76020
gaccaccttc agcatggtct tgaggttggc caggccctcg gcctcgatct gggcccggcg 76080
ctcgcgcgcg gccagcgcct cccgcaggcc cgccatgacc cgctcggtgg cctccgcgcg 76140
ctgctgtttg gcgcgcacca ctgcgtcctt ggtctcggcc gtgtcctgcc gggtcacgaa 76200
ggcgacatac tcggcgtacg ccgtgttctt cacggggctc tggtccacgc gctccaacgc 76260
cgccgcgcac gcgaccagcg cgtcctcgct gggacacggc agggtgaccc cggtccggac 76320
cagctccgcg gtggcctccg ggtcattccg ggccgcggat atctgctccg cggcggccgc 76380
caggtccagg ggcacgccgc cgagcgcccg gtgcacgtcg gcccggatgg cgtccaggcg 76440
atcgcggagc tccacgtagt cggcgtagcc atgttggaag aacggcacgt accggcgcag 76500
gccgggcacg ctcgtcatgt cgtccgccag gcgccccacg gcctcgtggt agtcgataaa 76560
cccgtcgccc gcctgggcca tttccaggag cccctccgcg atgcgcagca gccgcgccag 76620
gggctcggcg tcgacccgaa acatgtcggc gtaggtttcg gcggcggcgt ggaacgccgc 76680
gctccagccg aggcggtgga tggcggcgag cggggggagc atggggtggc gctggttctc 76740
gggggtgtag gggttaaacg cgaaggccgt atccagggcg agggtgaccg cctcggcgtt 76800
ggccgcgagc gcctgctcgg cgcgcttgcg gaagtcccgg gggttgtagc cgtgcgtgcc 76860
cgccagcgcc tgcaggcggc gcagctcgac cacgtcgaac tcggcgcggt tctcgacgcg 76920
gtccagcgcc gcctcgacgc cggcggccca gcgctcgctg ctgccccggg cgcgctgggc 76980
cgccatcttc gccgtcaggt cggcgacggc ggcctcaagt tcgtcggcgc ggcgtcgcgt 77040
ggcgccgatg accttgccca gctcctgcag ggcgcgcccg ctgggggaat ggtccccggc 77100
cgtcccttcg gcgtgcagca ggcccccgaa cccagcctcg tgccccgcga ggctttcccg 77160

-continued agcagcggtc gtcgcgcggg ccgcggcatc gatgagggcg gcatggtccc cctccggctg 77220
ggcgcaggcc cggcgcgcct ggactaccag gtcggcggcc gccgacccca gggtcgtgag 77280
ctcgtcgatg gccccccgcg cctccagggc cagccgagtc gcctttacat accccgcggc 77340
gctatcggcc agcaccgcga ggaaggacag gggcgaggcc gggtcgcggg cggccgcgcc 77400
cagggccgac accgcgtccg ccagggcgcc atgcgcccgc acggccgcgt ccaccgtcgc 77460
cgcgggactt gccgtcgcga cggcggcgct cccggcgttg atggcgtttg acacggcttt 77520
ggcgattgtg gggcgtgat cggaaaagaa ctgcacgagg accggcgtct cgggggcgtc 77580
ggcgaacagg gtcttcagca ccaccacgaa ggcgggatgc aggccggcca gagccgtcgc 77640
ggtatccggg gtcgggtgtt ccagggcctc ccggtactgc cccagcagcc cccacaggtc 77700
cgcccgcagc gccgccgtga cttccggggg ggggccccgg acggcatcgg ccaggtcggt 77760
ccaccccgcg ggcagggagg cccgcagggt cgccagcacg gccggacacg cctttagccc 77820
cacaaagtcc gggaggggcc gcaggacccc ttggagtttg tgcaggaact tctcccgggc 77880
gtcgtgggcc accttggcgc gctcccgcgc gtcgttgagc atcgcctcca gggcgtgggc 77940
gcgctcccga agccgggagc gcgcctccgg agcgagctcc gccgtcatct tggccgcctc 78000
catggccctc gcctgccgca gcgcgtcttc ggccatgcgc gtggcctcgg gggacagccc 78060
gcccccgtcg acgtacggcg cggggccggt cgccgggacg aaggccgcgt cgctgtccag 78120
ctgctgcgcg agcgccgcgt cgagggcgtc gaagcgctgc agttcggcca gccccgagct 78180
gcgccgcgcc tgctggtcgt tgatgccgtg gatgctgcgc gccagctctt ccaggggctt 78240
gcgttcgatg agcccctggg tcgcggcgtc ggtcaggacc gagagccagg ccgccaggtc 78300
ctcgggggca tctaggggct ggccccgctg gagcaggtcc cgcagcagga tggcctgggg 78360
gctggtggcg aggggggcg ggggggggag cgcggcgcgc tgagcgacgt cccgcgtgtg 78420
ttggtcaaag gccggtagcg attccagcaa ctggaccatg ggcacgaccg cggccgaggc 78480
cacgtgaaac cgacagtcgt ggctgtcgct ggcctgcagg gccttcgcgc tgtatacggc 78540
tccccggtgg aagtactcct tgaccgcgct ctcgatcgcc cggcgggcct ggatccgcac 78600
gtcctccagc cgcgcctgga tggcctcggg gcccagggcg ggcgggcacg gggccctgcc 78660
gccggcgccc ggggcggcgg gcacgggcat cacggtcagg ggcccggcgc gctgcgagac 78720
cgagtcgacc ccgcgggcga gggcgtctaa ggcctcgcgc atctcgcggg cctccgcctc 78780
gacccgcatc tcttcgcccc gggcaaactg ggccagcgcc tggatccgat ggagaagcgg 78840
ctccgggtgc gtcggggtgg cgggggcgaa cagggtgttc gggtgggcgc gcgagcgctc 78900
caggagccac tctccgaggc gtgcgtacag attggccggc ggggcggcgc gcagctgcag 78960
atccaggtcc gcgaggtccc cgtaaaaggc gtccgtctcc cgaataacgt ccctggcgac 79020
caggaccagc ttagcgaggg ccaggcgccc gatctgcgaa ttttcgtcca gcacgtgctg 79080
gatgaggggc cggtgggcgg ccacgtccgc caggctcatg cgcgtggacg ccaggaagtc 79140
cccgacggcc gttttgcggg gcagcatgcg cagggtgaag tccagcaggg ccgcggccgg 79200
gccggccacc ccggcctgcg tatgcgtgcg ggccccgttc tcgatcaaaa aggcgaggac 79260
gcgctcaaag aagaagatga cgcagagctc caacagcccc gggtgcgccg ggtacggcga 79320
ccgcagggcg ttgatggtga gctgcgaaca cgcggccacc tcgcgggcca gggcggcatc 79380
gcgcgccgcg agccggaccg ccgtggcggc cacattgggg tggacctcga acagctgcgc 79440
caggtcggcg ccggggggct ccggggggcg gcgggccccc agcgtctcga gcacggacgg 79500
cgacgacggg ctcgcgggcc cgtcgtcgcc gccgccctgc ccggactgcg ggggggtatc 79560
cggtgcggga gggaccgtgg cggctatggg cgtcggggag gaggcgggga cctcggcggc 79620
gacgggggcc ttcttcttgg gcgcggactt cttcttggcc ttggcgggcg gggccttggg 79680
ggcgggcctc tcgcccgagg tcagatcctc cacgctggac ggtggggtcc aggtgggccg 79740
gcggcgcttg ggcaagccgg tagaatagcg cgcccggtgg cgacccaccg gcactgcccc 79800
cacctccagg acccgcaggt cctcggcttc ttcggccgcg tccccggcgg gtgtctgcgg 79860
gggcggggcg gcgtgcggtg gacccgaggc cgcggcgtcc ggggccgagg gcttcgcggg 79920
cggggtcccc tccagggctg ctgcccacac atcatcgggg gggcggtttg ggtgccccgc 79980
ctgcggtgtg tcgggtgggc ccgaggcccc ccgggggggcc tcggggggcc ggtcggcccc 80040
aggggtctgg acgtgggtgg gcgcggggag cgcggggacg accgggcccg agccttctcc 80100
gtccccccctg gggaccacac cgacaaagag cgccccgagc cccccgatct cgccccgcag 80160
ggggtgggtg atggccacgc gccgctcgac gaacggttcg tcctgcaggt aagtctcgct 80220
ggccccgtag aggtgcaggg ccgcggcggt caggtccgcc ggcgccacgg cccccgggcc 80280
ggagggcaca aaaaacacca tggcgcccgc ccaccgcacc ttggggcggt cgtgggcgta 80340
atacgtcagg tacgggtaca cgtcgcccgc ccgcaccttg gcgataaacg cgggcgttcc 80400
cgcgggcagg ccgtgcgggt caaacagata ggccgtgtcg ccgtcccggt agagccccat 80460
gcccaggggg ccgatggtca ggagcgtgta ggacagcggc cgcatggccc aggggccggc 80520
gaagaacgtg tgcgcggggc attgcgtctc cagcagcccc gccgtgggct ccccgaagaa 80580
gcccacctcg ccgtacaccc gcgaaaacac gcaacgcagg ccgccgcgcg ccgccgggta 80640
ctccaggaag ttggggagct cgataatgga acacatgcgc ggcggcccgg agcccgcggc 80700
cgcgcgcgtc cactcgcccc cctccaccag acatccctcg atggcctccg cggacagcac 80760
gtcgcggggc cccacgtcga aaagaagact gagaaacgac agggacgagc gcatgcacga 80820
taccgacccc cccggctcca gatcggtcgc gaactggttc cgaacaccgg tgaccacgat 80880
atcgcgatcc ccctggcgct tcatcgtggg gtgaggtagc gcggccggaa tcatgtgtgc 80940
cgcgcccgcc acgagcgggg cctgtttatg ggccgggcgt cccgatgagt actgttgttt 81000
ccgccgcccg aacccccccg cccatcaacc gcctgttcgt cccccctaacc acacacccgg 81060
tatcgcgtgt gtgtggtttc ccgggaagac acatcccacc ccatgaagtt ttgccctttt 81120
tttccgtccc gcactacgcc acctttccac cccccccaa aaaaacaaca accaactccc 81180
agatggatgg gtgcgataat aaagctttat tattgtttaa ccaaaggcga gtcctacggg 81240
tgtaccggtg gtgtctcctg cggcgtcatc tcgtcgtcct ccacgggggt gttgggccaa 81300
gggaccgtct cgcggcccgc cgggcgcgtc gacggcgcgc gggcctgcgt gtcctgtggg 81360
ccgggtgtcg tgggttcggg ggtgctaccg ccggcatctt gggcctccag gtccccgggg 81420
gcccccgggc cggcggaagg ccgaaacgcc gaggcgcgaa acacgccgtc ggtgacctgc 81480
aggagctcgt ttattaatag ccagtccatg ctcagcgtag cggccagccc ctggggagac 81540
aggtccacgg agtccggaac caccgtcggc tgacccaggg gccccaggct gtagtccccc 81600
caggccccca ggtcatgacg gttcgtgagc acgacgaggt ctgcggccgg gctgggggc 81660
gcgtcctcgg tcgcgtgggc catcacctcc tgaatggctg cggtgcgctg atcggccgag 81720
ctggcgaagc gcgccacgac cagcgcgcgc tccgtctgca ggcccttcca cgtgtcgtgg 81780
agttcctgaa cgaactcggc cacccgctcg gggcccgtgg ccgcgcgtgc ggcctgatag 81840
ccggccgaga ggcgccgcca gcgcgccagg aactgactca tgtaacagaa cccggggacc 81900

-continued

```
tggtcccccg acatcaactt tgacgccctg gcgtggatgc ccgacacgat ggccaggaac  81960
ccgtggattt cccgccgcac gacggccagc acgttaccct cgtgcgagac ctgggccgcc  82020
agctcgtcgc ataccccgag gtgcgccgtc gtctcggtga cgacggaccg cagccccgcg  82080
agggacgcga ccagcgcgcg cttggcgtcg tgatacatgc cgcagtactg gctcaccgcg  82140
tcgcccatgg cctcggggcg ccagggcccc aggcgctcgt gggcgtctgc gaccacggcg  82200
tacaggcggt gcccgtcgct ctcgaaccgg cactcaaaga aggcggcgag cgtgcgcatg  82260
tgcagccgca gcagcacgat cgcgtcctcc agctggcgga ccagggggtc ggcgcgctcg  82320
gcgagctcct gcagcacccc ccgggccgcc agggcgtaca tgctgatcag cagcaggctg  82380
ctgcccacct cgggaggctg ggggggaggc agctggaccg cgggccgcag ctgctcgacg  82440
gcccccctgg cgatcacgta cagctcgcgc agcagctgct cgatgttgtc ggccatctgc  82500
atcgtgggcc cgacgccggc ccgggtggcc ggttcgagga gggtgatcag cgcgcccaat  82560
tttgtgcggt gcccctcgac ggtggggaga tagcccaggc cgaagtcgcg cgcccaggcc  82620
agcacccgca gggcaaactc gatggggcgg ggcaggtagg cagcgttgca cgtggccctc  82680
agcgcgtccc cgaccaccag ggccagcacg taagggacga accccgggtc ggcgaggacg  82740
ttggggtgga tgccctccag ggccgggaag cggatcttgg tggccgcggc caggtgaacc  82800
gagggggcgt ggctaggcgg cccgacgggg agcagcgcgg acagcggcgt ggccggggtg  82860
gtgggggtca ggtcccagtg ggtctggccg tacacgtcga gccagatgag cgccgtctcg  82920
cgcaggaggc tgggctggcc ggcgctgaag cggcgctcgg ccgtctcaaa ctcccccacg  82980
agcgtgcgcc gcaggctcgc caggtgttcc gtcggcacgg ccgggcccat gatgcgcgcc  83040
agcgtctggc tgaggacgcc gcccgacagg ccgaccgcct cacagagccg cccgtgcgtg  83100
tgctcgctgg cgccctggat ccgccggaac gttttcacgt agccggcgta gtgcccgtac  83160
tcccgcgcga gcccgaacac gttcgccccc gcaagggcaa tgcacccaaa gagctgctgg  83220
atctcgctga gcccgtggcc ggggggcgtc cgcgcgggca cccccgccac caaaaacccc  83280
tccagggccg atatgtactg ggtgcagtgc gcgggcgtga accccgcgtc ggtaagcgtg  83340
ttgatcacca cggagggcga gttgctgttc tggaccaaag cccacgtctg ctgcagcagc  83400
gcgaggagcc gttgctgggc cccggcggag ggcggctccc ctagctgcag caggccggtg  83460
acggccggac ggaagatggc cagcgccgac gcactcagaa acggcacgtc ggggtcgaag  83520
acggccgcgt ccgtccgcac gcgcgccatc agcgtccccg ggggcgcgca cgccgaccgc  83580
gggctgacgc ggcttagggc ggtcgacacg cgcacctcct cgcgactgcg aaccattttg  83640
gtggcctcga ggggcgggat catgatagcc gggtcgatct cccgcaccgt gtgctgaaac  83700
tgggccagca gcggcggcgg gaccaccgcg ccccgatcgg gggtcgtcag gtagtcgtcc  83760
accagcgcca gcgtaaacag ggcccgcgtg aggggggtca gggcggcgtc gtcgatgcgc  83820
tgtaggtgcg ccgagaacag cgtcacccaa ttgctgacca gggccaagaa ccggagaccc  83880
tcttgcacga tcggggacgg gaagagcagg ctgtacgccg gggtggtcag gttggcgccg  83940
ggttgcccca ggggaaccgg ggacatctta agcgacatct ccccgagggc ctccagggag  84000
gtccgcgggt tcatggccag gcagctctgg gtgacggtcc gccagcggtc gatccactcc  84060
acggcacact ggcggacgcg caccggcccc agggccgccg tggtgcgcag cccggcggcc  84120
tccagcgcgt gggtcgtgtc ggagccggtg atcgccagga ccgtgtcctt gatgacgtcc  84180
atctcccgga aggccgcctc gggggtctcg gggagcgcca ccgccatgcg gtgcaccagc  84240
agcccgggga ggttctcggc caagagcgcc gtctccggaa gcccgtgggc ccggtgcaag  84300
```

gcgcacagtt gctccaggag cgggtgccag cacgcccgcg cctccgccgg gccgaccgcc 84360
gcgcccgaca acagaaacgc cgccgtggcg gcgtgcagtt tggccgcgga cagaaacgcc 84420
ggctcgtccg cgctgcccgc cggctcgctc gagggggagg gcggccggcg gaggttggtc 84480
aggctcccca acaggacctg caacggtccg tttgggggtg gagcggacgg gggggtcatg 84540
ccggcgggcg ccgggacctg gagcgcgctg tccgacatgg cgaccggcgt gcgcgctcgg 84600
cgacgcggcg cggagaccgc gggcccaaac gggaatgact gccgccgccc tatacggagg 84660
ggctaagtat cgcccgggga cccttcgaaa ccccgggcgt gtcgcaagta cgccgcgaag 84720
gcgcggcgtg ttatacggcg cgttatgtcc cggcattccg ttcgtgggtt cgggcccggg 84780
tgctgtcggg tgggagtgtg tgtggggggg ggcggcgcga cggcggcccg gaccaagtgt 84840
atcgcggccg ttccgtgggg cggcccaaca ggccctttaa acatttgcgt atgcaccggc 84900
ccagccagtc ggacaccgga acccaccaga ggcggaagcc gccttcgccc gtgagggtgc 84960
gtgtgttttc tggtggcgtg tttttccttt ccgccctcct ccctccccac ctccaccacc 85020
cccccccaca actcgcccgt tggcgatcgg cgggaaaacc atgaaaacca agccactccc 85080
gacagccccg atggcgtggg ccgagagtgc cgtggaaacc accaccagcc cgcgcgagct 85140
cgcgggccac gccccgctcc ggcgcgtcct gcgcccgccc atcgctcgcc gcgacggccc 85200
ggtgcttttg ggggacaggg cccccaggag gacggccagt acgatgtggc tgctggggat 85260
cgaccccgcg gagtcgtctc cgggaacgcg cgctacccga gacgataccg agcaggccgt 85320
ggacaagatc ctcaggggag cccggcgcgc gggagggctg accgtccccg gcgccccccg 85380
ctatcacctg acccgccagg taaccctgac ggatctctgc caaccaaacg cggagccggc 85440
cggggcgctc cttttggccc tgcggcaccc caccgacctc ccccacctgg cccgccatcg 85500
ggctccgccc ggccggcaga ccgagcgact ggccgaggcc tggggccagc tcctggaggc 85560
ctccgccctg gggtccgggc gggccgagag cggctgcgcg cgcgcgggcc ttgtgtcgtt 85620
taactttctg gtggccgcgt gcgccgccgc ctacgatgcg cgcgacgccg ccgaggcggt 85680
ccgggcccac atcacgacca actacggcgg gacgcgggcc ggggcgcggc tggaccggtt 85740
ttccgaatgc ctgcgcgcca tggtccacac gcacgtgttt ccccacgagg tcatgcggtt 85800
tttcgggggg ctagtgtcgt gggtcacaca ggacgagctg gctagcgtca ccgccgtctg 85860
cagcggaccc caggaggcca cacacaccgg ccacccgggc aggccccgtt cggccgttac 85920
catcccggcc tgcgccttcg tggacctgga cgccgagctg tgcctggggg gcccctgggg 85980
ggcgttcctg tacttggtct tcacctaccg acagtgccgg gaccaagagc tctgttgcgt 86040
gtacgtggtc aagagccagc tccccccgcg cggactggag gcggccctcg agcggctgtt 86100
cgggcgcctc cggataacca acacgattca cggggccgag gacatgacgc cccctccccc 86160
gaaccgaaac gttgactttc cgctcgccgt cccggccgcg agctcgcaat ccccgcggtg 86220
ctcggcgagc caagtcacga acccccagtt tgtcgacagg ctgtaccgct ggcagccgga 86280
tctgcggggg cgccctaccg cacgcacctg cacatacgcc gccttcgcag agctgggtgt 86340
catgccagac gacagccccc gctgtctgca ccgcaccgag cggtttgggg cggtcggcgt 86400
tccggttgtc atcctggagg gcgtggtgtg gcgcgcggcg gggtggcggg cctgcgcgtg 86460
atcgtctatt gacgacggcc gcccaacccg agcgaccttc ccctcccact tccccccccc 86520
tacacaccaa ctccgccctc gccgtcttgg ccgtgcgcgg ccccgtgcgt ccgtctcaat 86580
aaagccaggt taaatccgtg acgtggtgtg tttggcgtgt gtctctgaaa tggcggaaac 86640

-continued

```
cgacatgcaa atgggattca tggacatgtt acaccccccct gactcaggag ataggcatat  86700
cctccttaga ttgactcagc acacgatcgc accccacccc tgtgtgccgg ggataaaagc  86760
caacgcgggc ggtctgggtt accacaacag gtgggtgctt cggggacttg acggtcgcca  86820
ctctcctgcg agccctcacg tcttcgccca ccgattcctg ttgcgttcct gtcggccggt  86880
gctgtcctgt cgacagattg ttggcgactg cccgggtgat tcgtcggccg gtgcgtcctt  86940
tcggtcgtac cgcccacccc gcctcccacg ggcccgccgc tgtttccgtt catcgcgtcc  87000
gagccaccgt caccttggtt ccaatggcca accgccctgc cgcatccgcc ctcgccggag  87060
cgcggtctcc gtccgaacga caggaacccc gggagcccga ggtcgccccc cctggcggcg  87120
accacgtgtt ttgcaggaaa gtcagcggcg tgatggtgct ttccagcgat ccccccggcc  87180
ccgcggccta ccgcattagc gacagcagct ttgttcaatg cggctccaac tgcagtatga  87240
taatcgacgg agacgtggcg cgcggtcatt tgcgtgacct cgagggcgct acgtccaccg  87300
gcgccttcgt cgcgatctca aacgtcgcag ccggcgggga tggccgaacc gccgtcgtgg  87360
cgctcggcgg aacctcgggc ccgtccgcga ctacatccgt ggggacccag acgtccgggg  87420
agttcctcca cgggaaccca aggacccccg aaccccaagg accccaggct gtcccccccgc  87480
cccctcctcc cccctttcca tggggccacg agtgctgcgc ccgtcgcgat gccaggggcg  87540
gcgccgagaa ggacgtcggg gccgcggagt catggtcaga cggcccgtcg tccgactccg  87600
aaacggagga ctcggactcc tcggacgagg atacgggttc ggagacgctg tctcgatcct  87660
cttcgatctg ggccgcaggg gcgactgacg acgatgacag cgactccgac tcgcggtcgg  87720
acgactccgt gcagcccgac gttgtcgttc gtcgcagatg gagcgacggc cccgcccccg  87780
tggcctttcc caagccccgg cgccccggcg actcccccgg aaaccccggc ctgggcgccg  87840
gcaccgggcc gggctccgcg acggacccgc gcgcgtcggc cgactccgat tccgcggccc  87900
acgccgccgc accccaggcg gacgtggcgc cggttctgga cagccagccc actgtgggaa  87960
cggaccccgg ctacccagtc cccctagaac tcacgcccga gaacgcggag gcggtggcgc  88020
ggtttctggg ggacgccgtc gaccgcgagc ccgcgctcat gctggagtac ttctgtcggt  88080
gcgcccgcga ggagagcaag cgcgtgcccc cacgaacctt cggcagcgcc ccccgcctca  88140
cggaggacga ctttgggctc ctgaactacg cgctcgctga gatgcgacgc ctgtgcctgg  88200
accttccccc ggtccccccc aacgcataca cgccctatca tctgagggag tatgcgacgc  88260
ggctggttaa cgggttcaaa cccctggtgc ggcggtccgc ccgcctgtat cgcatcctgg  88320
gggttctggt ccacctgcgc atccgtaccc gggaggcctc ctttgaggaa tggatgcgct  88380
ccaaggaggt ggacctggac ttcgggctga cggaaaggct tcgcgaacac gaggcccagc  88440
taatgatcct ggcccaggcc ctgaacccct acgactgtct gatccacagc accccgaaca  88500
cgctcgtcga gcgggggctg cagtcggcgc tgaagtacga agagttttac ctcaagcgct  88560
tcggcgggca ctacatggag tccgtcttcc agatgtacac ccgcatcgcc gggtttctgg  88620
cgtgccgggc gacccgcggc atgcgccaca tcgccctggg gcgacagggg tcgtggtggg  88680
aaatgttcaa gttctttttc caccgcctct acgaccacca gatcgtgccg tccacccccg  88740
ccatgctgaa cctcggaacc cgcaactact acacgtccag ctgctacctg gtaaaccccc  88800
aggccaccac taaccaggcc accctccggg ccatcaccgg caacgtgagc gccatcctcg  88860
cccgcaacgg gggcatcggg ctgtgcatgc aggcgttcaa cgacgccagc cccggcaccg  88920
ccagcatcat gccggccctg aaggtcctcg actccctggt ggcggcgcac aacaaacaga  88980
gcacgcgccc caccggggcg tgcgtgtacc tggaaccctg gcacagcgac gttcgggccg  89040
```

```
tgctcagaat gaagggcgtc ctcgccggcg aggaggccca gcgctgcgac aacatcttca  89100
gcgccctctg gatgccggac ctgttcttca agcgcctgat ccgccacctc gacggcgaga  89160
aaaacgtcac ctggtccctg ttcgaccggg acaccagcat gtcgctcgcc gactttcacg  89220
gcgaggagtt cgagaagctg tacgagcacc tcgaggccat ggggttcggc gaaacgatcc  89280
ccatccagga cctggcgtac gccatcgtgc gcagcgcggc caccaccgga agccccttca  89340
tcatgtttaa ggacgcggta aaccgccact acatctacga cacgcaaggg gcggccatcg  89400
ccggctccaa cctctgcacc gagatcgtcc acccggcctc caagcgatcc agtggggtct  89460
gcaacctggg aagcgtgaat ctggcccgat gcgtctccag gcagacgttt gactttgggc  89520
ggctccgcga cgccgtgcag gcgtgcgtgc tgatggtgaa catcatgatc gacagcacgc  89580
tacaacccac gccccagtgc acccgcggca acgacaacct gcggtccatg ggcattggca  89640
tgcagggcct gcacacggcg tgcctcaaga tgggcctgga tctggagtcg gccgagttcc  89700
gggacctgaa cacacacatc gccgaggtga tgctgctcgc ggccatgaag accagtaacg  89760
cgctgtgcgt tcgcggggcg cgtcccttca gccactttaa gcgcagcatg taccgggccg  89820
gccgctttca ctgggagcgc ttttcgaacg ccagcccgcg gtacgagggc gagtgggaga  89880
tgctacgcca gagcatgatg aaacacggcc tgcgcaacag ccagttcatc gcgctcatgc  89940
ccaccgccgc ctcggcccag atctcggacg tcagcgaggg ctttgccccc ctgttcacca  90000
acctgttcag caaggtgacc agggacggcg agacgctgcg ccccaacacg ctcttgctga  90060
aggaactcga gcgcacgttc ggcgggaagc ggctcctgga cgcgatggac gggctcgagg  90120
ccaagcagtg gtctgtggcc caggccctgc cttgcctgga ccccgcccac cccctccggc  90180
ggttcaagac ggccttcgac tacgaccagg aactgctgat cgacctgtgt gcagaccgcg  90240
ccccctatgt tgatcacagc caatccatga ctctgtatgt cacagagaag gcggacggga  90300
cgctccccgc ctccaccctg gtccgccttc tcgtccacgc atataagcgc ggcctgaaga  90360
cggggatgta ctactgcaag gttcgcaagg cgaccaacag cggggtgttc gccggcgacg  90420
acaacatcgt ctgcacaagc tgcgcgctgt aagcaacagc gctccgatcg gggtcaggcg  90480
tcgctctcgg tcccgcatat cgccatggat cccgccgtct cccccgcgag caccgacccc  90540
ctagataccc acgcgtcggg ggccggggcg gccccgattc cggtgtgccc cacccccgag  90600
cggtacttct acacctccca gtgccccgac atcaaccacc ttcgctccct cagcatcctg  90660
aaccgctggc tggagaccga gctcgtgttc gtgggggacg aggaggacgt ctccaagctc  90720
tccgagggcg agctcggctt ctaccgcttt ctgtttgcct tcctgtcggc cgcggacgac  90780
ctggtgacgg aaaacctggg cggcctctcc ggcctcttcg aacagaagga cattcttcac  90840
tactacgtgg agcaggaatg catcgaggtc gtccactcgc gcgtctacaa catcatccag  90900
ctggtgctct ttcacaacaa cgaccaggcg cgccgcgcct atgtggcccg caccatcaac  90960
cacccggcca ttcgcgtcaa ggtggactgg ctggaggcgc gggtgcggga atgcgactcg  91020
atcccggaga agttcatcct catgatcctc atcgagggcg tctttttttgc cgcctcgttc  91080
gccgccatcg cgtacctgcg caccaacaac ctcctgcggg tcacctgcca gtcgaacgac  91140
ctcatcagcc gcgacgaggc cgtgcatacg acagcctcgt gctacatcta caacaactac  91200
ctcgggggcc acgccaagcc cgaggcggcg cgcgtgtacc ggctgtttcg ggaggcggtg  91260
gatatcgaga tcgggttcat ccgatcccag gccccgacgg acagctctat cctgagtccg  91320
ggggccctgg cggccatcga gaactacgtg cgattcagcg cggatcgcct gctgggcctg  91380
```

-continued

```
atccatatgc agcccctgta ttccgccccc gcccccgacg ccagctttcc cctcagcctc  91440
atgtccaccg acaaacacac caacttcttc gagtgccgca gcacctcgta cgccggggcc  91500
gtcgtcaacg atctgtgagg gtctgggcgc ccttgtagcg atgtctaacc gaaataaagg  91560
ggtcgaaacg gactgttggg tctccggtgt gattattacg caggggaggg gggtggcggc  91620
tggggaaagg gaaggaacgc ccgaaaccag agaaaaggac caaaagggaa acgcgtccaa  91680
ccgataaatc aagcgccgac cagaaccccg agatgcataa taacgatttt attactctta  91740
ttattaacag gtcgggcatc gggaggggat gggggcgcgc gtttcctccg ttccggctac  91800
tcgtcccaga atttagccag gacgtccttg taaaacgcgg gcgggggcgc gtgggcccac  91860
agctgcgcca gaaaccggtc ggcgatgtcc ggggcggtga tatgccgagt cacgatggag  91920
cgcgctaaat cttcgtcgcg gaggtcctga tagatgggca gtctttttag aagagtccag  91980
ggtccccgct ccttggggct gataagcgat atgacgtact tgacgtatct gtgctccacc  92040
agctcggcga tggtcatcgg atcgggcagc cagtccaggg cctccggggc gtcgtggatg  92100
acgtggcggc gacgtccggc gacatagccg cggtgttccg cgacccgctg cgcgttgggg  92160
acctgcacga gctcgggcgg ggtgagtatc tccgaggagg acgaccgggc gccgtcgcgc  92220
ggcccaccgg cgacgtccgg gggctggagg ggggggtctt cttcgtagtc gtcctcgccc  92280
gcgatctgtt gggccagaat ttcggtccac gagatgcgcg tctcgaggcc gaccggggcc  92340
gcggtcagcg taggcatgct ctccagggag cgcgagttgg cgcgctcccg ccgggccgcc  92400
cggcgggcct gggatcggct cggggcggtc cagtgacact cgcgcagcac gtcctcgacg  92460
gacgcgtagg tgttattggg gtgcaggtct gtgtggcagc ggacgaacag cgccaggaac  92520
tgcgggtaac tcatcttgaa gtactgcagc aggtcgcggc agtgaatcgt cggaatgtag  92580
ccggtgctga tgtccaacac gatatcgcag cccatcagca ggagatcggt atccgtggta  92640
tgcacgtacg cgaccgtgtt ggtatgatag aggttcgcgc aggcgtcgtc ggcctccagc  92700
tgacccgagt tgatgtaggc gtaccccagc gcccgcagaa cgcggataca gaacaggtga  92760
gccaggcgca gggccggctt cgagggcgcg cccgaggggg ccgccgggcc tgggccggcg  92820
gcccgcgttc cccggtcccc cggggcgaag gcgtgcccgc ggcggcgcat gttggaaaag  92880
gcgaaactgg gcctggagtc ggtgatgggg gaaggcggcg gcgaggcgtc tacgtcactg  92940
gcctcctcgt ccgtgcggca ctgggccgtc gtgcgggcca ggatcgcctt ggccccgaac  93000
acaaccggct cggtacactc gaccccgcga tcggtcacga agatggggaa cagggacttt  93060
tgggtaaaca cccgtaacat actacagaga cagtgtagcg tgattgcctc gcggtcgtaa  93120
cttgggtagc ggcgctgata tttaaccacc agggtataca tgacattcca caggtccacg  93180
gcgatggggg taaagtagcc ctccggggcc cggaggcccc ggcgcttcac cagatggtga  93240
gtctgggcaa acttcatcat gccaaacaga cccattccgg cacgattgta ggtgcggata  93300
ggtctctcta cagagctgta taggtgtgac ggtccgggac acccaagccc gccgcccctg  93360
tgtacagtgg ctgcggcgac gaccccgctc caacaagacg ctatcccggg aaaggcacgc  93420
tctttataat tctttttat ttcccatcta cgtgcggatt ggtgcaaccg ccggcgcgcg  93480
ccggtgcagg ccgaccatct ctctcttccc cccctccccc tcccccgagc cctcaaagag  93540
ggtgtggcct aactagcgga aggcgtattt aaccagacta gggcggcggg tccgccgtag  93600
tccttggctc gggtagccac tgctctgtgg ctcgggtccc ccggcccccc taacccccat  93660
ccggtccgcg tcatccgccc cctccgcctg cgacacaaac ggccgcgcct ccgggcccgg  93720
tgacacgacg cgcctcgtct ctgcggattg tcccgggagc gtcgcggcat ggctcatctt  93780
```

-continued

```
cccggcggtg cggccgccgc ccccctttcg gaggacgcga tcccgtcgcc gcgcgagcgg  93840
acggaagact ggccgccctg ccagatagtg ctgcagggcg ccgagctgaa cgggatcctg  93900
caggcctttg cgccgcttcg cacgagcctt ttggactcgc tcctggtcgt gggcgaccga  93960
ggcatccttg tacataacgc gattttcggc gagcaggtgt ttctgcccct cgaccattcg  94020
cagttcagtc gctatcgatg gggcggaccc accgcggcgt tcctgtctct cgtggaccag  94080
aagcgatccc tgctgagcgt gtttcgcgcc aaccagtacc ctgacctgcg gcgggtggag  94140
ctgacggtca cgggccaggc cccgtttcgc acgctggtgc agcgcatatg gacgaccgcg  94200
tccgacggag aggccgtgga gcttgccagc gagacgctca tgaaacgcga gttgacgagc  94260
ttcgcggtac tactccccca gggcgacccc gacgtccagc tgcgcctcac gaagccccag  94320
ctcacgaagg tggtgaacgc cgtcggggac gagaccgcca aacccaccac gttcgagctc  94380
ggccccaacg gcaagttttc cgtgtttaac gcgcgcacct gcgtcacctt tgccgcccgc  94440
gaggagggcg cgtcgtccag caccagcgcc caggtccaga ttctgaccag cgcgctgaag  94500
aaggcgggcc aagcggccgc caacgccaag acggtctacg gggaaaacac acaccgcaca  94560
ttctcggtgg tcgtcgacga ctgcagcatg cgggcggtcc tccggcggct ccaggtcggc  94620
ggggggaccc tcaagttctt cctcacggcc gacgtcccca gcgtgtgtgt caccgccacc  94680
ggccccaacg cggtgtcggc ggtgtttctt ttaaaacccc agcgggtctg cctgaactgg  94740
ctcggccgga gcccgggttc ctcgaccggg agcttggcgt cccaggactc tcgggccggc  94800
ccgaccgaca gccaggactc ctcctccgag ccggacgcgg gcgaccgcgg cgccccagaa  94860
gaagaaggcc tcgagggcca ggcccgggta ccgcccgcgt tcccggaacc gccgggaacc  94920
aagcggaggc accccggggc cgaagttgtc cccgcggacg acgccaccaa gcgcccgaag  94980
acgggcgtgc ccgccgcccc cacgcgagcc gagtcgcccc ccctctccgc gagatacgga  95040
cccgaggcgg cggagggtgg tggggacggc ggccgctacg cgtgctactt tcgcgacctc  95100
cagaccggcg acgcgagccc cagccccctc tccgccttcc ggggtcccca aagaccccca  95160
tacggctttg ggttgccctg acggcaacgg gtggtggccg aacgcctcac cgcgcccggg  95220
cacgcggggt gcgttgtgtt aaaaaaataa ataaatgggg tagtgtgtcc ccccccccctc  95280
caaccaatat ggctgtcgtg tgtggttccg ggttgcgcct ccgtcctttc caccccccctt  95340
ccccctcctt ttttgttttg cgtgcgctta taagagcggg cccggggccc ttcgcagctt  95400
caccgagagc gccgtcgggc cccgggtgcg ggatgtgtcg cggggacagc cccggggtcg  95460
cgggcgggag cggcgaacac tgcctcggag gggatgatgg ggacgacggg cgcccccgcc  95520
tcgcctgcgt gggtgccatc gctcgggggt tcgcgcatct ctggctccag gccgccacgc  95580
tgggcttcgt ggggtctgtc gttctgtcgc gcggcccgta tgcggacgcc atgtcggggg  95640
cgttcgtgat cgggagcacc ggcctggggt tcctccgcgc cccccccgcg ttcgcccggc  95700
cgccgacgcg tgtgtgcgcg tggctgaggc tggtcggcgg gggagcggcc gtggccctgt  95760
ggagcctcgg ggaggccggc gcgcctccgg gggttccggg cccggcgacc cagtgcctgg  95820
cgctcggggc cgcctacgcg gcgctgctgg tgctggccga cgacgtccat cccctttcc  95880
tcctcgcccc gcggcccctg tttgtcggca ccctgggggt tgtcgtcggc gggctgacga  95940
taggcggcag tgcgcgctac tggtggatcg acccccgcgc cgccgcggcc ctgacggcgg  96000
cggtggtggc gggcctcggg acaaccgccg ccggggacag cttttccaag gcctgtcccc  96060
gccaccgccg cttttgcgtc gtctccgcgg tcgagtctcc cccgccccga tacgccccgg  96120
```

-continued

```
aggacgccga gcggccaaca gaccacggac ccctgttacc gtcgacgcac caccagcgat  96180
ctccgcgggt ctgcggcgac ggggccgcac ggcccgaaaa catctgggtt cccgtggtga  96240
cctttgcggg cgcgctcgcg ctggccgcct gcgccgcgcg agggtctgac gcggctccgt  96300
caggcccggt cctgccgctg tggccccagg tgtttgtcgg gggccacgcg gcggcgggcc  96360
tgacggagct gtgtcagacc ctcgcgcccc gggacctcac ggacccgctg ctgtttgcgt  96420
acgtcggatt ccaggtcgtg aaccacgggc tgatgtttgt ggtccccgac atcgccgtat  96480
acgcgatgct gggggcgcc gtgtggatct cgctgacgca ggtgcttggg ctccggcgcc  96540
gccttcacaa ggacccagac gccgggccct gggcggccgc gaccctgcgg ggcctctttt  96600
tctccgtcta cgcattgggg tttgcggcgg gggtgctggt gcggccgcgg atggcggcga  96660
gccggcggtc ggggtgatcg ccatttcaaa taaaaggcac gagttccccg aataccaccg  96720
gcgtgtgatg atttcgccct accgctccga tccccggggg gaggggggaa ggaaatgggg  96780
gcgggggtgc cgtggacggg tataaaggcc agggggcag gcgggcccat cactgttagg  96840
gtgttaggtt gggaggtggc acaaaaagcg acactcccgt gttgtagttg tccgcgggag  96900
gcggtggttt ccggcaaccc tcctcgctgc gccgggcgcg cccaccggtc cttcgcgggg  96960
gccggggctc ttctggtcat ggcccttgga cgggtgggcc tagccgtggg cctgtggggc  97020
ctgctgtggg tgggtgtggt cgtggtgctg gccaatgcct cccccggacg cacgataacg  97080
gtgggcccgc gggggaacgc gagcaatgcc gccccctccg cgtccccgcg gaacgcatcc  97140
gccccccgaa ccacacccac gcccccccaa ccccgcaagg cgacgaaaag taaggcctcc  97200
accgccaaac cggccccgcc ccccaagacc gggcccccga agacatcctc ggagcccgtg  97260
cgatgcaacc gccacgaccc gctggcccgg tacggctcgc gggtgcaaat ccgatgccgg  97320
tttcccaact ccacccgcac ggagttccgc ctccagatct ggcgttatgc cacggcgacg  97380
gacgccgaga tcggaacggc gcctagctta gaggaggtga tggtaaacgt gtcggccccg  97440
cccgggggcc aactggtgta tgacagcgcc cccaaccgaa cggacccgca cgtgatctgg  97500
gcggagggcg ccggcccggg cgccagcccg cggctgtact cggtcgtcgg gccgctgggt  97560
cggcagcggc tcatcatcga agagctgacc ctggagaccc agggcatgta ctactgggtg  97620
tggggccgga cggaccgccc gtccgcgtac gggacctggg tgcgcgttcg cgtgttccgc  97680
cctccgtcgc tgaccatcca cccccacgcg gtgctggagg gccagccgtt taaggcgacg  97740
tgcacggccg ccacctacta cccgggcaac cgcgcggagt tcgtctggtt cgaggacggt  97800
cgccgggtgt tcgatccggc ccagatacac acgcagacgc aggagaaccc cgacggcttt  97860
tccaccgtct ccaccgtgac ctccgcggcc gtcggcggcc agggcccccc gcgcaccttc  97920
acctgccagc tgacgtggca ccgcgactcc gtgtcgttct ctcggcgcaa cgccagcggc  97980
acggcatcgg tgctgccgcg gccaaccatc accatggagt ttacgggcga ccatgcggtc  98040
tgcacggccg gctgtgtgcc cgagggggtg acgtttgcct ggttcctggg ggacgactcc  98100
tcgccggcgg agaaggtggc cgtcgcgtcc cagacatcgt gcgggcgccc cggcaccgcc  98160
acgatccgct ccaccctgcc ggtctcgtac gagcagaccg agtacatctg ccggctggcg  98220
ggatacccgg acggaattcc ggtcctagag caccacggca gccaccagcc cccgccgcgg  98280
gaccccaccg agcggcaggt gatccgggcg gtggaggggg cggggatcgg agtggctgtc  98340
cttgtcgcgg tggttctggc cgggaccgcg gtagtgtacc tcacccacgc ctcctcggtg  98400
cgctatcgtc ggctgcggta actccggggc cgggcccggc cgccggttgt cttcttttcc  98460
accccttccg tcccccgtac ccaccacacc ccaccccacc cccccgccgt cccccgggcg  98520
```

```
ttataagccg ccgcactcgc ttttcccacc ggaaaatcct cggcccgatc cgaacggcgc  98580
acgccgcgtg ggctccaaac gcctccggaa gagagcgccc cgccccgata ttcaagcccg  98640
cggtggtgct atggctttcc gtgcttcggg acccgcctac cagcccctcg cccccgcggc  98700
ctccccggcg cgggctcgtg ttccggccgt ggcctggatc ggcgtcggag cgatcgtcgg  98760
ggcctttgcg ctcgtcgccg cgttggttct cgtacccccct cggtcctcgt ggggactctc  98820
gccgtgcgac agcggctggc aggaattcaa cgcgggatgc gtcgcgtggg accccacccc  98880
cgtcgagcac gagcaggcgg tcggcggctg cagcgcgccg gccacccttta tcccccgtgc  98940
ggccgccaag cacctggccg ctctgacacg cgtccaggcg gagagatcgt cgggttactg  99000
gtgggtgaac ggagacggca tccggacctg tctgagactc gtcgacagcg tcagtggcat  99060
cgacgagttt ttcgaggagc tcgcgatccg catatgctac tacccacgaa gccccggcgg  99120
gtttgtccgc ttcgtaactt cgatacgtaa cgccctgggg ttgccgtgag gcgcgcgtcc  99180
gacggtcccg cttctcgcct ctcttcttcc cccaccccac ccaccgacca acgacggcgt  99240
ttggccaata ccctcctttt ttctttttct cttccccccc ccccaaaaaa aacaataaac  99300
agctaattgc gtacgacaaa ccatgcggaa ctcgctgttt tttttctctg tttgttactt  99360
tttattgaaa cagacatacg gggaaagggg ccggaaaccg agacggtggg gccggcggtc  99420
gcattttttt aatggctctg gtgtcggccg cgtttgagct tcgtcaacag ggcgctgagg  99480
gcggcgacgt tcgtcgggcc gtcgttggcc agcgcgttgg tccgggggcg ggcgggcatg  99540
ggcgacaggc ttagtcccgg gtccggggcg cgtgtggccc gccgagggga gaagagggca  99600
gacccgcccc agtcgtacag gggattttcc gcctcgatgt acggggagtc cggggcgtct  99660
cccggcaggg cggccccgcc ggcaagacgc cggcgagggc agatgttttc gtatacccga  99720
acccagggga tctcctcgta gacgcgcccc ccatcctcgc ccaccgactc gtaaatggaa  99780
tctgcgtcct cggagggggc gcggggggcg tggctttcgg ccggccaggc ggcggcggcg  99840
gtggtgtcgg cggcgggggt ggcgccaagc ccgacgcccg cgggcatggc ggcgtcatcg  99900
tcgggcagca gatacgtgtt ttccatctgg tccggttcgg cctccgcgtc cggcccccag  99960
gtccgcaccg cgtcgtagac cccggcggcc tcgcgctgag ccgcgagcgg gcgcgccgcg 100020
gctgccggcc gctgctcggg gggcgcgggg ttgcggggcg ggaggcgcgg gggcgccccg 100080
gccatatgcg tgtaatacgt ggccggccgg ccggcgcagg gctcgggacc ccggtcggcc 100140
gcgtcgacgt gcgggggctc ggggaggtcc tcgcggtggc gcctgcacct ccgaggggcc 100200
gcgggggtcg agtgggggcg agcccggggg agcggcgggg gtgcgttgtc gcgccgggtc 100260
cgttgtatct tgtcccggca gctcccgccg accgcgccgc ggccccccgg tgggccggac 100320
gccgcgaggc gcaggatgga ctcgtagtgg ggcgacgggg ttccgctccg aagcaggtcc 100380
ggggccaggg cggccccgaa ccaggacttg atgctgagtt ccatccgggc ccagctcggg 100440
gcggtcatcg tggggaacag gggggcggcg gtcctgcaga agcgctcctg gctgtccacc 100500
gccgccgtaa ggtactcgtt gttcaggctg tcggaggccc agacgacata cccggtaagc 100560
gtcgcgttaa ttatatactg ggcgtggtgg tggactatgg atagaacctc gacggtcgag 100620
acgatggcgt ccacgatccc gtacgtgccg ccgctgcgct tgccggtctc ccacaggtgg 100680
gccaggcgcg tcaggtggcc caggacgtcg ctgaccgccg cccgcagggc catgcactgc 100740
atcgagcccg tggtgccgct gggcccgcgg tccaggtggc gcgcaaacgt ctccgcgggc 100800
gcctccagac tcccgctgag cgccacgaac cggcgatcgg cggggcccag gcggcgacac 100860
```

-continued acgtacttgt ccgccgtcca cagcatccac gaggcccaat ggtacaacac ggagacgtag 100920
gccaggagct cgctcagccg cagtgcggtg tccgtgctcg gccggctcgg gtctgcgggg 100980
cgcataaaga acatgtactg ctggagcctg tgggccgcgt cgcgcaaccc cgccaccgcg 101040
gcggcgtact tggccgcggc ggccccgctc ttgaacgggg cgcgcaccag cagcttcggg 101100
agcagggtgg gccgcagcag cacgtgcagg ctggggtcgc agtcgcccgc cgggtcgtcg 101160
gggatgtcca ggccgctggg cacgaccgtc tggaggtact tccagtactg cgctaggatg 101220
gcgcggctca gctggccgcc cgacagctcc acctcgccga gcgcctgctt ggcggccgac 101280
gcgtagtgcc ggatgtagtc gtagtgcggg tcgctggcga gcccgtctac gatcaggctc 101340
tcggggacgg tgttatggtg ccgcgccgcc agccggacgc tgcgatcggc gccggtcaga 101400
aacgccggct gcaggtcgtc ggcgcgctgc cgcaggacgc ccacggccgc gctgaggagc 101460
ccctccgggg tggggagcag acacccggcg aagatgcgcc gctcggggac gcccgcgttg 101520
gcgccgcgga tgaggttggc cggcgtcagg caccgcgcca gccgcaggga gctcgcgccg 101580
cgcgcccggc gttgcatggc ggagaccgtt cggtcggggg ccccgccggt cggaggtatg 101640
ccgcgtcccg ggatataggg ttgcttttta tggggaggcg cctatgggcg tggcgggccg 101700
cccagcccgg tcgcgcgcct cccggacacg tgcgcccgga gggcggcggt ctcctcgtcg 101760
cccatgagca gtttccgaaa ctgcgccatg atgtccacga cgcggacccg cggccccagc 101820
acggactcgc tattcagggg ggcggggggg aaggccgcca ggtcttcgag caggaaggcg 101880
gggtctgccg tcccgctcac gggcgcccgg ggcgccgagg acgcggggcg aaggtccacg 101940
tgttccgcgg cggcgcgcac gtccgcccaa aatttggcgg gggtggtccg cgcgtacagg 102000
ggctgggtcg cgcggaggac gcacgcgtag cgcagggggg tgtacgtgcc cacctcgggg 102060
gccgtcgacc cgccgtcaaa cgcggccagg gccacgcacg cgaccaccgt gtcggccagg 102120
cccagcagcc gctgcaggat gagccccgtc gccagcacgg cgcgcgcggc cgccgcgtcg 102180
tccctgcgcc ggcgcgcgtc cccgcaggcc agggcgtatt tcagggtaac ggtcgccagg 102240
gccgtgtgca gcgcgtacac ggccgcgccc agcacggcgt tcagcccgct ggtggcgagc 102300
aggcggcgcg ccgcggtgtc gcccagcgcc tcgtgctcgg ccgccacgac cccggggctg 102360
cccaggggca gggcgcgaaa cagcgcctcc tgctccacgt ccgcaaacgc ggggtgggcg 102420
gagtgcgggt gcaggcgcgc ccccacgacc accgagagcc actggaccgt ctgctccgcc 102480
aggaccgcca gcacgtccag gacgcgcccc gcaaacgcgg cctcccgcgg gagcacgcat 102540
ttgacggcgc cggggttgaa gcgggcgagc agagccccgg tggcgatgta cgtcatgcgc 102600
cccgcgtagc gggcggccac gcgacagtcg cgccccagga gcgcgcgcac cccgggccag 102660
tacagcaggg accccagcga actgcgaaag accgcggcgt cggggccggg gtgggggggc 102720
gcggcccctc ccgcgctgag cagcggcacg gcggcggccc ccacgggccg caacgccgtg 102780
aggctcgcga actgccgtcg gagctcggcc gccctgtcgt cgagctccga gccgcgcccc 102840
tccgtgtgca ggcgcgtccc gcagacccac ccgttgatcg ccacccgcac gatggcgtcc 102900
accagaaaac ccatcgcgcg ggaggggctg gtttttgccc gccgatccgt caggtcgagg 102960
atcgcgtcgc ccgtgacgta ccaggccagc gcctcgccct gctgcagcgt ctggcggaaa 103020
aacacctttg ggtcggccgg ggaggcaaag tgcatgaccc ccacgcgcga cagcccgaac 103080
gcgctatccg gacacgggta gaacccggcc ggatgtccca gggccagggc cgagcgcacg 103140
gactcgtccc acgcggcgac tcggggggtc aggcggtcca gggggaatgc cgcctgcagc 103200
tccgggcccg acacgcggcc cgcgagaatc tcgaccgtcg cggaaggccg cgccccgggg 103260
ccgtcatcgt gcgcgacggc ggcggggtag tcgtcctcct cgtagttgag ctcgtccagg 103320
aacagcggcg agggcaccac ccgcgaaccg cccacccgcc ccaaaacgtc gcgtgggtcc 103380
atcgggccca ggtagcctcc ccgcggggcc cgcgtgatgg cgctgtcccg gcgtccgcga 103440
acggactggc tcctggccgt aacggacctg gggcgcggaa aggacgcccg gcgggggggc 103500
gccgccgccc gggcctcgga cgcgcgtcgg gacccggggt gaccgcgggc ctcccggcga 103560
cggcgcgggg gcggctcttc gctcgccatc tcccccgcgg cctcgacctc gctgtcgtcg 103620
tccacgttaa acaccgcccg caggtacccc attaacccga ctccaccgcc ctcgggctcg 103680
tcctccacgg gcgagtcggc gcgatgcgcg gacggggcat gggaccgggt ggaggcgcgc 103740
ctccggcgta cggcatgccc gcgcacggac atggtggccg gaggcccgat tttttacaca 103800
cgccctcccc gcagacggac gaggaaaggg gtggtgcgag gggggaggcc caaacgggga 103860
ggtgggggt agggggcggt cccagggagc ggggggtagg aaccggcacg acgggaacag 103920
agaaaacgcg accgctccaa caagggtggg ggggtgggcc tcgtccccac gcagacccgc 103980
gggcaaatgc gagaacggga cccgcgcgcc tgcctttata cgcggacccc agcaccacga 104040
gccgttctgt gacgcgaatc tacacgaccg cgggctcgta ggcgcgacta acgcccaacc 104100
caacggcaca caccccccac cccgcgcgta accccatttc tttcatggtc ccgtaataaa 104160
cagccaacgc acgccgcgta tgatgagttg cttgccaatg tttattgctg tggttgcgaa 104220
ccctctatcg cgatacagac ggaggtgagg cggggcggtg gtgggggggg ggcgcgccgc 104280
ccggtcgcac atcctacccc ccaaagtcgt caatgcccat ggcatcggta aacatctgtt 104340
caaactcaaa atcgtccacg tccaaagccc catacgagac ggggtcgtgg gtcattcccg 104400
gggaggggga ctccacgtcc cccagcatct ccaagtcgaa gtcgtccagg gcgtcggcgg 104460
gcgtcatatc cacctcctcg ccgtccaggc ggagttcgtc tcccaggctg acgtcggtaa 104520
tgggggcggt ggtggacagt ctgcgggggc gttgtcccgc ggagagaaac gacatgcgcg 104580
gcgccaccag cccggcctcc gcaggagcgt catcgtcgtc cgggaggtcg agcaggccct 104640
cgattgtcga tccgtaattg tttctggtcc gcccgcggct atacgcgtgc tcccgcatga 104700
cggactcgcc ctccgaggtc gcgacgctgg agtacgagtc caacttggcc cggatcagca 104760
gcataaagta cccagaggag cgggcctggt tgccctgcag gacgggcggg gtcgtgaggg 104820
gcgccccggg ttcctccgcc gccgcacttc gcaccagcgg gaggttcagg tgctcgcgaa 104880
tgtggtttag ctcccgcagt cgccgggcct ccacgggaac tccccgcacg gtgagcgatc 104940
cgttgataaa catcaggggc tgaaacagac acgccaactg gcgccagctc tccaggtcgc 105000
agcagaggcc gtcgaacaga tcgggccgca tcatctgctc ggcgtacgcg gcccatagga 105060
tctcgcggct cagaaagagg tatagatgca gaaacaggac gcgcgccagg cgcgcggtct 105120
cgcggtagta cctgtccgcg atcgtggtgc gcagcatctc ccgcaggtcg cggttgcggc 105180
cccgcatgtg tgcctggcgg tgtagctgcc gaacgctggc gcgcaggtac cggtacaggg 105240
ccgagcaaaa atttgccaac acggtccggt agctctcctc ccgcgcccgc agctcaccgc 105300
ggaaaaactg cgccatggcc tcgtagtacg aaggcagctc gtcgcgggtg gcgggcaggg 105360
tggggaacgc cacgtcgccg tgggcgcgaa tgtcgatcgg ggagcgctcg gggacgtgcg 105420
catcccccca gtcgatcacg tcgctgggca gcgtcgacag aaacttgcac tcccggtaca 105480
tgtcggcgtt ggtcgggaac ccagagaaca ggtcctcgtt ccaggtatct agcatggtac 105540
acagcgcggg acccgcgctg aagcccagat cgtcgaggag acggttaaac agggccgcgg 105600

-continued gggggacggg catgggcggc gagggcatca gctgggcctg actcagccga ccggtggcgt 105660
acagcggagg ggcggctggg gtgttcttgg gacccccggc tggcctgggg ggcggtggcg 105720
aaaccccgtc cgcgtccgca aacagatcgt cgaccaacag gtccatgggg gcggttgggt 105780
ccgggaataa cgatctcgag aggcgaatga gacgtgcccg agcgcccggc ggcggagagg 105840
gggggaggga tccgggaccc gcgacagaaa aaggccgggg ccctcgcgaa gggaatcgcc 105900
gggggtgccg tgcgtccccg aggactgaca tctcgcgtcc accaccccgc atttaagtat 105960
caccccagtg ccgccccaaa cctcgtgact tccccaccgc tccgggcggc ccgtcccccg 106020
cgctcggaag ggaggcgtgt ccttcctccc gcccctcccg cccctcccgc ccctcccgcc 106080
cctcccgccc ctcccgcccc tcccgcccct cccgcccctc ccgcccctcc cgcccctccc 106140
gcccctcccg cccctcccgc ccctcgccac aaacgcgtgc tgacagcgaa gtggttaaat 106200
cgaccgtgat gctttattgt ctgtcgtctg aacgcggtcg gggtcgctac tcgagggggc 106260
ggcggggacg ggaagccgag cgggcggggg cccgtgcggt cgcggcggca cgccccgcgg 106320
ggcggccccg ggcggccgcg gtcgcgtcga cgtcctgcgc cgcgtcggga ttcaccaact 106380
cgttcgcgcg ctgcaggagg ttcttgccct cgcagaccgt cacgcgaatg gtggtgaggt 106440
cgaggagctc gttgaggtct tcgtcggtgt gcggccgcga catgtcccac agctgtaccg 106500
ccgccagccg ggcgtgcgtg gccgccaggc gcccgaccgc ggcgcagaag acgcgcttgt 106560
tgaacccggc cacccggggg gtccacggcg ccgtggggct cggtggggcg gtgctgaagt 106620
gcagcttctt ggccagtccc tgggcgggtg tcttggttct tcccgaggcc gtgggagcgg 106680
gggcgtctag gagcacggcg gagtcggcct gggcgggtcg cctgccgcgg gcggggtcgg 106740
tcgccggggt cgcggaggcc ttaggcgccc cgcgcgtcat tttgggggtc cgcgcgggag 106800
gggcgtgcga gcgcccgccg gcgcccacgg ggcccccggg gggtggagga gcgcgcgcgg 106860
ggccggggcc gtgagagccc gcgacggacg ccgaacgacg cggtcgcgcg gtatcccggg 106920
actcgtcgtc gtccgaagac gagtcccggt agagggcata cccagcctcg tcataatgga 106980
gaaagcgaac ctcgcccctc gggcgcgcgc gcatcgggcc agcgccgcgg cggaagtcgt 107040
cgcgcggact ctctgggtcc gccggggaga ccgggccata gtacagctcc tcgtgggtcc 107100
cgcgcggcgc ttcccgcgga cacgacttga cggagcggcg agaggtcatg gtctatcgga 107160
gacaccgggg acgcccgtgc ggatcacagg gaaggcgtcg gcgaaggagg cagagagcgt 107220
cggaaggcgg cgagggaggg aaagagggag accggcgggg tacgggagag cagcgagggc 107280
ctgcgtaacc cacgggggcc gcgggagtgg ctccctgcgg gttgcggggg agagtttata 107340
ggaagtggat ataaccgcag gcgacgggac taaccaatcc ccgggggggc aacggacaga 107400
cacgccccga acaggcccga cttccgcgag gaagcaaagg ccgggggccg cccaacgaca 107460
cgcccacccc ttcccaacag ggcgggctca ggctgacccg gcggccagtg cccgctgaca 107520
tatctgatac acgtgcgcga tcatacatac gcccatcgag gtcatgccta gataaaaggg 107580
caccaggacc cccgggacgg acaccacacc ggcgctgtcg ccccggcatt gcgcgtcccc 107640
gataacgccg cgtgcgcctg ccgcgttcgg cggctccccg ggcacgcccg cgacgagcgc 107700
gacgaacaac agcaccaccc agcggcccag tcttgcgggt ttccccgtca tcgcggcgat 107760
gagtcagtgg gggcccaggg cgatccttgt ccagacggac agcaccaacc ggaatgccga 107820
tggggactgg caagcggccg tagctattcg cgggggcgga gtcgttcaac tgaacatggt 107880
caacaaacgc gccgtggatt ttaccccggc agaatgcggg gactccgaat gggccgtggg 107940
ccgcgtctct ctgggcctgc gaatggcaat gccgcgggac ttctgcgcga ttattcacgc 108000
ccccgcggta tccggccccg ggccccacgt gatgctcggt ctcgtcgact cgggctaccg 108060
cggaaccgtc ctggccgtgg tcgtagcccc gaacgggacg cgcgggtttg cccccggggc 108120
cctccgggtc gacgtgacgt ttctggacat ccgggccacc cccccgaccc tcaccgagcc 108180
gagctccctg caccggtttc cgcagttggc gccgtccccg ctggcagggt tacgagaaga 108240
tccttggttg gacggggcgc tcgcgaccgc cggggggggcg gtggccctgc cggccagacg 108300
gcgcggggga tcgctggtct acgcgggcga gctaacgcag gtgaccaccg agcacggcga 108360
ctgcgtgcac gaggcgcccg cctttctgcc aaagcgcgag gaggacgcag gctttgacat 108420
tctcatccac cgagccgtga ccgtcccggc caacggcgcc acggtcatac agccgtccct 108480
ccgcgtattg cgcgcggccg acggaccaga ggcctgctat gtgctggggc ggtcgtcgct 108540
caatgccagg ggcctcctgg tcatgcctac gcgctggccc tccgggcacg cctgtgcgtt 108600
tgttgtatgt aacctgaccg gagtcccggt gaccctacaa gccgggtcca aggtcgccca 108660
gctgctcgtc gcggggaccc acgccctccc ctggatcccc cccgacaaca tccacgagga 108720
cggcgcattc cgggcctacc ccagaggggt tccggacgcg accgccaccc cccgagaccc 108780
gccgattttg gtgtttacga acgagtttga cgcggacgcc cccccaagca agcgggggggc 108840
cggggggttt ggctccactg gcatctagac cgcgcctcgc gtcgggccag atggggcccc 108900
ggtcaataaa gagctctgtt tcgcatatgc cctggtgttg gcggtttttt tttgttgtct 108960
gtctgcccgg cgctcggttg tccgttctgt cgtcgctatc acatacgcac aaacacacgg 109020
gtagagtgga accgaaaccg gtcgacgttt attcaccaca cagaaacaca agctaagcga 109080
gaaggagggg ggcctcggtc gacgaggcct ggcgtttggg ggcggacgtg cgatgacgtg 109140
ggtccggtgt agggtccgcg gggggcacgg gcccggggcg aacgggggat ctgtcgccgg 109200
cgtgggtgac tgggaccgac gcaacctccg gggcttgtgc cctcgtaggc ccgggggggg 109260
cctcggtcgc tccaagcccc gcggtgcggg tccctccggc cagagccgag gtggagagac 109320
caagggcccg ctccgcgatc gccacgtcct ccatgaccac gtcgctctcg gccatgctcc 109380
gaatggcctg ggagacgagc acgtccgccg acttgtccgc ggccccccacc gacatgtaca 109440
tctgcaggat ggtggccatg cacgtgtccg ccaggcggcg catcttgtcc cgatgcgccg 109500
caacggcccc gtcgatggtg gagccctcga gtcccgggtg gtggcgcgcc agcctctcga 109560
ggttgaccat gcaggcgtgg tatgtgcggg ccagggcgcg cgccttcacg aggcgccggg 109620
tgtcgtccag cgactctagg gcgtcgtcga gcgtgatggg ggcgggcaaa agcgcattga 109680
ccaccgccag ggcctcctgc agccgcggct ccgcctccga gggcggagcc gcggcccgaa 109740
tcatctcata ttgttgttcc tcggggcgcg ttccccaacc gcacagcacc ccgagcaggg 109800
acgccatccc ggaacacgcg cgcggctctg cgccggcttt cccccacccc accccctccg 109860
ggttcgcagg ggcgatgggg acggaagact gcgatcacga agggcggtcg gttgcggctc 109920
ccgtggaggt tacggcgctg tatgcgaccg acgggtgcgt tatcacctcc tcgctcgccc 109980
tcctcacaaa ctgcctgctg ggggccgagc cgttgtatat attcagctac gacgcgtacc 110040
ggtccgatgc gcccaatggc cccacgggcg cgcccaccga acaggagagg ttcgagggga 110100
gccgggcgct ctaccgggat gcgggggggc taaatggcga ttcatttcgg gtgacctttt 110160
gtttattggg gacggaagtg ggcgtgaccc accacccgaa agggcgcacc cggcccatgt 110220
ttgtgtgccg cttcgagcga gcggacgacg tcgccgtgct ccaagacgcc ctgggccgcg 110280
ggaccccatt gctcccggcc cacgtcacag caactctgga cttggaggcg acgtttgcgc 110340
tccacgctaa catcatcatg gctctcaccg tggccatcgt ccacaacgcc cccgcccgca 110400
tcggcagcgg cagcaccgcc cccctgtatg agcccggcga atcgatgcgc tcggtcgtcg 110460
ggcgcatgtc cctggggcag cgcggcctca ccacgctgtt cgtgcaccac gaggcgcgcg 110520
tgctgggggc gtaccgccgg gcgtattatg ggagcgccca aagccccttt tggtttctga 110580
gcaaattcgg cccggacgaa aagagcctgg tgctggccgc taggtactac ctactccagg 110640
ctccgcgctt ggggggcgcc ggagccacgt acgatctgca ggccgtgaaa gacatctgcg 110700
cgacctacgc aatcccccac gacccacgcc ccgacaccct cagtgccgcg tccttgacct 110760
cgttcgccgc catcactcgg ttctgttgca cgagccagta ctcccgcggg gccgcggccg 110820
ctgggtttcc gctgtatgtg gagcgccgca tcgccgccga cgtacgcgag accggcgcgc 110880
tggagaagtt catcgcccac gatcgcagct gcctgcgcgt gtccgaccgg gaattcatta 110940
cgtacatcta cctggcccac tttgagtgct tcagcccccc gcgcctggcc acgcatctcc 111000
gggccgtgac cacccacgac cccagccccg cggccagcac ggagcagccc tcgcccctgg 111060
gtcgggaggc ggtggaacag ttcttccggc acgtgcgcgc ccagctgaac atccgcgagt 111120
acgtaaagca aaacgtcacc cccagggaaa ccgccctggc gggagacgcg gccgccgcct 111180
acctgcgcgc gcgcacgtat gccccggcgg ccctcacgcc cgcccccgcg tactgcgggg 111240
tcgcagactc gtccaccaaa atgatgggac gtctggcgga agcagaaagg ctcctagtcc 111300
cccacggctg gcccgcgttc gcaccaacaa cccccgggga cgacgcgggg ggcggcactg 111360
ccgcccccca gacctgcgga atcgtcaagc gcctcctcaa gctggccgcc acggagcagc 111420
agggcacgac gcccccggcg atcgcggctc tcatgcagga cgcgtcggtc caaacccccc 111480
tgcccgtgta caggattacc atgtccccga ccggccaggc gtttgccgcg gcggcgcggg 111540
acgactgggc ccgcgtgacg cgggacgcgc gcccgccgga agcgaccgtg gtcgcggacg 111600
cggcggcggc gcccgagccc ggcgcgctcg gccggcggct cacgcgccgc atttgcgccc 111660
ggggccccgc gctcccccccg ggcggcctgg ccgtcggggg ccagatgtac gtgaaccgca 111720
acgagatctt caacgccgcg ctggccgtta cgaacatcat cctggatctg gacatcgccc 111780
tgaaggagcc cgtccccttt ccccggctcc acgaggccct gggtcacttt aggcgcgggg 111840
cgctggcggc ggttcagctg ttgtttcccg cggcccgcgt agaccccgac gcctatccct 111900
gttatttttt caaaagcgcc tgtcggcccc gcgcgccgcc cgtctgtgcg ggcgacgggc 111960
cctcggccgg tggcgacgac ggcgacgggg actggttccc cgacgccggt ggtcccggcg 112020
acgaggagtg ggaggaggac acggacccca tggacacgac ccacggcccc ctcccggacg 112080
acgaggccgc gtacctcgac ctgctacacg aacagatacc agcggcgacg cccagcgaac 112140
cggactccgt cgtgtgttcc tgcgccgaca agatcgggct gcgcgtgtgc ctaccggtcc 112200
ccgccccgta cgttgtgcac ggctccctga cgatgcgtgg ggtggcgagg gtgatccagc 112260
aggcggtgct gttggaccgc gacttcgtgg aggccgtagg gagccacgta aagaactttt 112320
tgctgatcga tacgggcgtg tacgcccacg gccacagcct gcgcttgccg tatttcgcca 112380
agatcggccc cgacggctcc gcgtgcggcc ggttattgcc cgtcttcgtg atcccccccg 112440
cgtgcgagga cgttccggcg ttcgtcgccg cgcacgccga cccgcggcgc ttccactttc 112500
acgccccgcc catgttttcc gcggccccgc gggagatccg cgtcctccac agcctgggcg 112560
gggactatgt cagctttttc gagaagaagg cgtcgcgcaa cgccctggag cactttgggc 112620
gacgcgagac cctgacggag gttctgggcc gctacgatgt gcggcccgac gccggggaga 112680
ccgtggaggg gttcgcgtca gaactgctgg ggcgaatagt cgcgtgcatc gaggctcact 112740
ttcccgagca cgcgcgggaa tatcaggccg tgtccgttcg ccgggccgtc attaaggacg 112800
actgggtcct gctgcagctg atccccggcc gcggcgccct gaaccaaagc ctctcgtgtc 112860
tgcgcttcaa gcacggcagg gcaagtcgcg cgacggcccg gacctttctc gcgctgagcg 112920
tcgggaccaa caaccgccta tgcgcgtccc tgtgtcagca gtgctttgcc actaaatgcg 112980
ataacaaccg cctgcacacg ctgtttaccg tcgatgcggg cacgccatgc tcgcggtccg 113040
ctccctccag cacctcacga ccgtcatctt cataacggcc tacggcctcg tgctcgcgtg 113100
gtacatcgtc tttggtgcca gtccgctcca ccgatgtatt tacgcggtgc gccccgccgg 113160
ggcgcacaac gataccgccc tcgtgtggat gaagataaac cagacgctgt tgtttctggg 113220
cccgccgacc gcccccccg gcggggcatg gaccccccac gcccgcgtct gctacgccaa 113280
tatcatcgaa ggtcgggccg tgtccctccc ggccatcccc ggcgccatga gccgccgggt 113340
catgaacgtg cacgaggccg taaactgctt ggaggccctc tgggacaccc agatgcgcct 113400
ggtggtcgtc ggttggtttc tgtatctagc gttcgtcgcc cttcaccaac gacgatgcat 113460
gttcggcgtc gtgagtcccg cgcacagcat ggtggccccg gcgacctatc ttttgaacta 113520
cgccggccgc atagtgtcga gcgtgttctt gcaataccc tacacgaaaa tcacccgcct 113580
cctctgcgag ctatccgttc aacgccagac cctggtgcag ctgttcgagg cggatccggt 113640
caccttcttg taccaccgcc cggccattgg cgtcatcgtg ggctgcgagc tgctgctccg 113700
cttcgtggcc ctcggtctca tcgtcggcac cgctctcatc tcccggggcg cctgcgcgat 113760
cacacacccc ctgtttctaa caatcaccac ctggtgtttc gtgtccatca tcgccctgac 113820
ggagctgtat ttcatcctgc ggcggggctc ggccccaaa aacgcggaac cagcggcccc 113880
cagggggcgc tccaaagggt ggtcgggcgt ctgcgggcgc tgctgttcca tcatcctctc 113940
cggtatcgcc gtgcgcctgt gctatatcgc cgtcgtggcc ggggtggtgc tcgtggcgct 114000
tcgctacgaa caggagattc agcggcgcct gtttgatctg tgacgtaacg cctcttccgt 114060
tggaagaggc ggacccagtc gcccatacaa attaaataca cgacccgcct cgggcctacg 114120
caccctcgca cgtcgcatgc aaattaaaat cgtgcacaga gccgatccgg cctcgggtct 114180
gcttgcccct cccccggccc agcacaggca ggctcgtccg acttccgcat acaccccacc 114240
ctaccgcgtg cttccgcacc cccgcctacg cgtgtacgcg aaggcggacc cagacctgcc 114300
gtatgctaat taaatacata aaacccaccc tcggtgtccg attggtttct ggggacggcg 114360
ggggcggggg cggtgacgcc cgacggggag ggacaaggag gagtttcgga aagccggccc 114420
cggtcgtgcg ggtataaggg cagccaccgg cccactgggc gctgtgtgct gccgtgtgcc 114480
gaccccggtt gcgcgtcggt gccgctcctc gattcggacc cggccactct cttccgacac 114540
gcgccccctc ggaggacacc cgccatccca gccccggcga cctacaacat ggctaccgac 114600
attgatatgc taatcgacct aggattggac ctgtccgaca gcgagctcga ggaggacgct 114660
ctggagcggg acgaggaggg ccgccgcgac gaccccgagt ccgacagcag cggggagtgt 114720
tcctcgtcgg acgaggacat ggaagacccc tgcggagacg gaggggcgga ggccatcgac 114780
gcggcgattc ccaaaggtcc cccggcccgc cccgaggacg ccggcacccc cgaagcctcg 114840
acgcctcgcc cggcagcgcg gcggggagcc gacgatccgc cacccgcgac caccggcgtg 114900
tggtcgcgcc tcgggaccag gcggtcggct tccccccggg aaccgcacgg ggggaaggtg 114960
gcccgcatcc aacccccgtc gaccaaggca ccgcatcccc gaggcgggcg gcgaggtcgc 115020
cgccggggcc ggggtcgata cggccccggc ggcgccgact ccacaccaaa accccgccgg 115080

-continued cgcgtctcca gaaacgccca caaccaaggg ggtcgccacc ccgcgtcggc gcggacggac 115140
ggccccggcg ccacccacgg cgaggcgcgg cgcggagggg agcagctcga cgtctccggg 115200
ggcccgcggc cacgaggcac gcgccaggcc ccccctccgc tgatggcgct gtccctgacc 115260
cccccgcacg cggacggccg cgccccggtc ccggagcgaa aggcgccctc tgccgacacc 115320
atcgaccccg ccgttcgggc ggttctgcga tccatatccg agcgcgcggc ggtcgagcgc 115380
atcagcgaaa gctttggacg cagtgccctg gtcatgcaag accccttttgg cgggatgccg 115440
tttcccgccg cgaacagccc ctgggctccc gtgctggcca cccaagcggg ggggtttgac 115500
gccgagaccc gtcgggtttc ctgggaaacc ctggtcgctc acggcccgag cctctaccgc 115560
acattcgcag ccaacccgcg ggccgcgtcg acagccaagg ccatgcgcga ctgcgtgctg 115620
cgccaggaaa atctcatcga ggccctggcg tccgcggatg agacgctggc gtggtgcaag 115680
atgtgcattc accacaatct gccgctccgc ccccaggacc ctatcatcgg aacggcggcc 115740
gccgtgctgg aaaacctcgc cacgcgcctg cgcccctttc tgcagtgcta cctgaaggcc 115800
cgaggcctgt gcgggctgga cgacctgtgc tcgcggcgac gcctgtcgga cattaaggat 115860
attgcctcct ttgtgttggt catcctggcc cgcctcgcca accgcgtcga gcgcggcgtg 115920
tcggagatcg actacacgac cgtgggggtt ggggccggcg agacgatgca cttttacatc 115980
ccgggggcct gcatggcggg tctcattgaa atactggaca cgcaccgcca ggagtgttcc 116040
agtcgcgtgt gcgagctgac ggccagtcac actatcgccc ccttatatgt gcacggcaaa 116100
tacttctact gcaactccct attttaggca agaataaaca tattgacgtc aacccaagtg 116160
gttccgtgtg atgttcttgg cgcgcgcggc gggtggggcg gagactccgg ggcgatgccg 116220
gcgtgcgcgt gggaggaggg cgatgaccca ccggataaat gtggggcccc ggcccggccc 116280
gcttcatagc gcgtccagga actcacggca gacgcgtatt caccgacccc cccctcgcaa 116340
catgacaacg acgcccctct cgaacctgtt tttacgggcc ccggacatca cccacgtcgc 116400
ccccccgtac tgtctgaatg ccacgtggca ggccgaaaac gccctgcaca cgaccaaaac 116460
ggaccccgcg tgcctggccg cgcggagtta tttagtccgc gcctcctgct cgaccagcgg 116520
ccccatccac tgttttttct ttgcggtgta caaggactcg cagcactccc ttccgctggt 116580
taccgagctc cgcaacttcg cggacctggt caaccacccg cccgtcttgc gcgaactaga 116640
ggataagcgt ggggggcggc tgcggtgcac gggcccattc agctgcggaa ccatcaagga 116700
cgtctccggt gcatcccccg cgggggaata cacgataaac ggtatcgtgt accactgtca 116760
ctgtcggtat ccgttctcca aaacctgctg gctcggggca tccgcggccc tacaacacct 116820
tcgctctata agctcaagcg gcacggccgc tcgcgcggca gaacagcgac gccacaaaat 116880
caaaatcaaa atcaaggtat aacccacccc cttccctccg agtccgtatg caacctcatt 116940
aataaagagt gagaaccaac caaaacagac gcggtgtgag tttgtgggtt ataggaaccc 117000
ggtaaatacc acgcgacgaa ccagcatgtg tgttaacgca acttttattc gttgtatcgc 117060
gggagggggg aagcttaccg ccaaaggaag gccaagatga taacgacgac caccgcgacc 117120
accccaaaaa ccgcatgacg acacgtcccg ccacaccacc ctggggcttg gggcgtgtcg 117180
gagctcgacg cacagcgggc cgcgcgttgg gcccggtaca gctctcgcga attgacaagc 117240
gggggtcgcc acgtgcgcga gctttgcacg cggggttggt cggccggccc cacggacccg 117300
cccggtggct cggtcggaca tgcggccatg accatggcgt aggtgggggg gcgatccgag 117360
gtcgcctctg cgtaagtagg gaggcccgac gggaggtcgc ctcccacgcc agggtgggcc 117420
ccaatcatag tttccggtag aaacaggggg gtctccacaa acaacccccc tgggccaaag 117480
ctccggcgcc gcgcccgtcg ttcggcgcgg cgcctggcgc gccgagcggc ccgccaggcg 117540
gcgcggcgcg agcggccacg ctcacacacc tcgccgtcac cggaagaagc cggtgaaaca 117600
agcccaaccg gcgacgtccc tgcagagtac ggtggaggcg agtccgtggg ggtgtcgata 117660
tcaataacga caaactggcc cgcgctcgcg ccggccacac tctcgtatgg gggcggggcg 117720
tcaatcacgc tatcatctcc gtcatccctg catgcgtggg catgcccagc ccccaacgcc 117780
atggtgggga ttcgcggctc agaagcctgc atgtcgtgtg gtcggtcgta gtccaacgtg 117840
cctcccccac ccaccacaca gccggtcccc acgccgacca ctagaccgca gacgtcgccc 117900
aaccgaggtc cccgtgcaca gaccgcgcct tttatagccc caggggttgc taattaacgc 117960
acgcatgcag acgcaattta ttttgctccc ccgcgtcctc ccctcccctg cgcacacgtg 118020
ataggtcttg ggaacccgag gggcgacgcg gggaaagcgc gcccccgccc ggccgccgcg 118080
cgcccccgcc cggccgccgc gcgcccccgc ccggccgccg cgcgcccccg cccggccgcc 118140
gcgcgccccc gcccggccgc cgcgcgcccc cgcccggccg ccgcgcgccc ccgcccggcc 118200
gcccgcgtcg cgccggcgcc ccctcccggc gcttccgggg tctttccttc cttccccgcc 118260
gcgaccccga ccccgcccca ccgccccgcc cggcaggggg gccccggcgc cgcgcagaac 118320
acacagacga acacacggtg gcgatctttt ctttacttcg gcggaccagc gagccccggc 118380
cccggcccgc gccccgccgc cacacccacg gcaccccccc ccgccgccca ccccggggtc 118440
cacacaggag cgcgcgggcg gcagaaacgc gggcgcggcg gcggtcgggg tgggagtggt 118500
ggtgggggac acgaaaacac acccacgaca ctctccccccc accccgaccg ccgccgcgcc 118560
ccaccggcgg gatcgcggcg agacgcagcc gggccccccc ccaccacccg cccacccacc 118620
taccccgcgc ccgcagcctc cggcagcacg ccgaccaccg ccgccacccc ccaaacagcc 118680
aaggcgcggt ggggggcgtg gtggtgaacg atggggggaa cacggggggg aggggtccgg 118740
ggcgaggcgg gcgggcgaag gaaggggggg tggtggcggc ggcggtggaa agcggaaaaa 118800
cggaggatgg aagggcagaa gatggggagt cccgatcctc ctcctgcatc ccctcgcctt 118860
ccattctccg gccctccgcg agtcccgacg cccccccccc gccgcccgac gaaggagacc 118920
caagcaccgc agccggagag gccgagcggg gagtgggcgg ccgggcggga ggatggcgga 118980
gagagagaga gagagagaga gagggggggg gggggagagg gaaagcaacg ggaaagagag 119040
gcgcgcggaa aagcagcaag agggggggacg gggcgagccg ggcagagtgc ggagcccccg 119100
gagcccgcgg ccgcagccga gcagcgccgc gggctccggg gccgggccgg gccggcaacg 119160
ccccgcgccg gccgcggcgg agagaacccc tgtgtcattg tttacgtggc cgcgggccag 119220
cagacgggcc gcgggccagc agacgggccg cggcgccagc ggcccacgcc tcccgccgca 119280
ttaggccccc gcgggcatcc ggcggccggc cccacgccct tccattaaac actcccacgt 119340
tggggggggg cgcgccagct gagtgctctg cggttgcggg cgccgtgccc ggagatccat 119400
taagccgccg gagagcccga gccccgcccg cgtgttgctg tgggcatttc tgctgcgtca 119460
tccctgtctt tataaaaccg ggggcgcggc agcaacgaac gcaggggccc gccgccgatc 119520
gagagggact ccggagaagg aaggctgctc cgcgcaccgg cgcgcccttc tcctctcccc 119580
tccctacctc cccctctctt ccccctttt tcccccgcct cccgtcttct tccgcgcctc 119640
cgagggtccg cctcttgcct cggggacccc cgggcgggcc ggggcttggc cgccgaggtg 119700
cgccccggcc ggaggggccc ccgcacctcg gcggccgccc cctccggcgc cgcgcgttcg 119760
cgaaaggcgc gaaaggggcc cccggaggct tttttcgatt cccggccggg ggtcccgggt 119820
agccgcccgg cgccgggcgg aaggcgtccc ccgcccggcg gtccggcccg ggcccccggc 119880
ggagcgcggg ggccccgggg ccccgggccg cgccggcggc gtttccgcgt tccgtttctt 119940
ctccctcccg ggccgccccg ctcccgggcc cgaccctcgc cccttccctt ctcctcgtct 120000
tcccccgtcc cgccgcgccc cttccctctt ccttctctct ctctgtctcg ctctcctcac 120060
atttcccccc cccccccccg ccgccgccgc cctttgcccg cgtcccaccg agacgccgcg 120120
ccgcgtgagc cgtccgccgg gggacccagg ctccgggggg ggggggcgcc tgcgtgtgtc 120180
tcgtgtgaga gagcgcgccc ctcgaacgcc gcgcgttctc gcaggtaggt ttagggtcgt 120240
acaggtgagc ttctgctgag gcggcgggga gagggggggg gggcgggcgg aagagagaag 120300
agagcagggg ttgggggaga actgttcttc ctcccccttt caagaaacac gaggcggggg 120360
tcccagaaag ggcaggcagg tcagccgcac cgcccgcgag ccaacccgta tccttttttt 120420
ctaggtgttt ttgtttttgt ttctgttttt gtttgttttg ttattatttt cgcggatccg 120480
gcgtgttcgg atccaccccc cctttctcct tcctcttccc ttccacccac ccccgtttcc 120540
cccccccccg tcgtcgttcc cgggggggca ggcgcgggtc gggcccgtac gcccaccgcc 120600
cccacgcgcc ggtcaccccc ccccaacaac cccaaaggcg cgtgcccggc cacagccgtg 120660
ggtgtggcgc ccgtcccctt cctctaccgc gtgggcgcgg gcgggggggt ggtggtagtg 120720
gtggcggaag gaaacgggcc gggggccggg gccgctaggg aaaggtaggc acgcgcgcgg 120780
tgtgtcgact tgcatgcccc gcaaaacgcg tcgtgtcgtg ttgtgtcgtg gtgggccgtg 120840
ttgtggtggg ccgtgtggtg tggtgtggtg ttgcgaacgc gcgagccccc tcgccccgat 120900
gggagtctcc ccgcagccag ggtaaggagg ggcgggcgtg gcgggcaggt gtgcgggcgg 120960
ggtggggtga gtgcggttgc atgcctcggg tctcctcttc ctgctcctcc tcctttctcc 121020
cagccagggt gaggaggggc gggcgtggcg ggcaggtgtg cgggcggggt gggcgccggg 121080
gcgggggtgg gcacgggcgt aagtgcgggt gcatgcctcg ggtcttctct tctccctcct 121140
ccttcctccc acccgtcccc gggggcagag ggcgtgcatg cgttgtgatt caaccgccct 121200
cgcccccgcc ccactttccc ccctctctat caaagttccc tggcccctgg cttcgcgccg 121260
gtggtgcggc tgaccccccc cctcctccct ccccgagcca ggcgccctcc cactcctgcc 121320
caccaccccc agggtctggc cggccagacg tgcgtgctct gcacgatcgg gccccccctcc 121380 ctgtcaacac ggacacactc tttttttacc cgccagccag cccgcccacc caccaagaca 121440
gggagccaga acgaggccgg gccccggctc tgttctatga taaagaccaa caggcctcgg 121500
gggtgggggc ggcttctcgt gcccgccccc cctcctcctc ctcccttccc ccccatcccc 121560 ggccccccctg cgcgggggag ctgcatcaaa ggccaacaac aaagtgtgtc aaaagcatca 121620
caaaacttta ttgtaaaatt tttataaata taaagttttt tttttcctca agttttcaac 121680
aaggccagaa agtccataac aaaatgctgg tgtgtgttgc tgttcggggc cgtgtccgtc 121740
cccccccccc actcccaccc ccacttcctg tctcctcccc gtctttcccc ccccccacct 121800
ccccctgccc ccgaggcgcc tcggccggtg gtccggtggg gggcggcttc cttcgggcag 121860
caagccgagt gttagctccc cctactcccc gtggcccgcg ggggcgtcgc cggccggcgc 121920
gggcgcgccc tgctcccgag accacgggtg gcgcgaccgg aggccgtgga agtccagcgc 121980
gcccaccagg gtgccctggt caaagagcat gttgcccacc ggggtcatcc agaggctgtt 122040
ccactccgac gcggggggcg tcgggtagtc ggggggcctc acgcagttgc gcgcgtgctc 122100
ggggagcagg gtgcggcggc tccacgcggg ggccgcggcc cgcagcaggt ccgccacgtt 122160
ccccgtctgg tccacgagga ccacgtaggc ccctatgtgg cccgtctcca tgtccaggac 122220
gggcaggcag tcccccgtga ccgtcttgtt cacgtaaggc gccagggcca cgacgctcga 122280
gacccccgcg atgggcaggt agcgcgtgag gccgggcgcc gggtcgcggg ccccgggctc 122340
ggggccgccc tccgcgtggc gcgtcttcct ggcacacttc ctcggccccc gcggcgcagc 122400
agcgcggggg ccgagggagg tttctcgtct ctccccagcg ccggacgcgg acgcgacgct 122460
cccaccagcc ccgcccgcag aggaagaggc ggaggaggag gaggcggagg aggaggaggc 122520
ggaggaggag gaggcggagg aggaggaggc ggaggaggag gaggcggagg aggaggaggc 122580
ggaggaggag gaggcggcgg cgaccgcggc ctgggacgac ggagacgccg acgggggcgc 122640
ggcgcccgcg gacgccgggg cgagcggccc gtggccgcgg tcgcccgagt ccgagtccgg 122700
ggcccggcgc ggcgccgccc tcttggcccc cacccccctgg ggggcgaggg gcgagcgcgg 122760
ggcggcggag gaagaggcgg aggacgaggc cgcggggccc gagtccgacc cgcgcctctt 122820
ccgggggcgg gccgccgccc cctccgcggc gtggggggcg gcaccggggg tgttggtgcc 122880
gcgggggacc ccgggtcctc cctccgcgcc cggccctccc gacccgcgcg cgtcggtcgc 122940
gcctgcccgg cccagactct gtgcttgggt gtcggtctga gcctgggtca tgcgcgaccg 123000
gggcgcgcgg tgcgcgtcca ccggcacggc gggcggcgcg ggcccggccg cgtccgcgct 123060
cgcagacacc acgggggcgg cggcggcgcg gggcggactc cggacgcgcg gggcgacggc 123120
cgcgcggggg cgcgcggcgc gccccgacga ctgtggcaga cctccccccc cggggcccga 123180
ggacacctgt gcggaggagg aggagacaaa ggagagcggc ccggggcccg cggggcggcg 123240
cggagacggc gggggagagt cgctgatgac tatggggggc tcctgggccg cgcggggctg 123300
tctcgcgggg ggcgtcctgc cctccgccgc cgcggcgtct tcgcccaccc gccgcgcctg 123360
cgcgcgcccc ccgccggccg cagggggaag agaggccact ctcggcacga cggccgcgac 123420
ggcagggccg cccccagacc cagatcccac ccccgcccgc aacggggcgc cgccgctgct 123480
gctgctccgc ggggcgccag ggggcgccgg tcgggtcgcg gcgggctggg aggttccgcg 123540
ggtcgccccc gcaccgccgc ccccgcgccg gggcgctctt cggggggcgg gcgggacgta 123600
gtccactgca gagggagaca gagacgggag cccccggtta gtgcccgacc cccgcccgac 123660
ccccgcccga cccccgcccg acccccgccc gacccccgcc cgacccccgc ccgacccccg 123720
cccgaccccc gcccgacccc cgcccgaccc ccgcccgccc cccgcccgac ccccgcccgc 123780
cctcaccgtc ggccaggtca tcgtcctcgt cgtccgtgcc gggccacggg ggggtgggcg 123840
acagggcgcg gaccgtgtgt ccccccagcg acagggagcg cggggccgtc cgcgggttgc 123900
ccgtccagat aaagtccacg gccgtgccgg cccgcacggc cgcctcggcc tccacgcggg 123960
tccgggggtc gttcactatc gggatggtgc tgaacgaccc gctggcggtc acgcccacta 124020
tcaggtacgc caccggggtg ttgcacaggg gacacgtgtt gcgcaacgga atccaggtct 124080
tcatgcacgg gatgcagaag gggtgcaggc agggaaaact ctggcagcgc aggggcgggg 124140
cgatctcgtc cgtgcacacg gcacacacgt cgcccccccc tcccgcttcc gcttcctcct 124200
cacccacggg cccacccccca caggatccct gcgcgtcggc gggcgtgggg ctgccctggc 124260
gctcggccgg gggccgggcc gggggcgtgg ccgcgtccat caggcccgcc tcgaacatct 124320
ccgtgtccgt gctgcccgcc tcggaggtgg agtcgcggtg aaggtcgtcg tcagagattc 124380
ccacctcggt ctcctcctcc gagtcgctgc tggcgagcca ctgcatgtcg ttgagcatcc 124440
cccaggcgtg cggggcggcg ggctgcttga caaagcaacg ggggggattt agagggcgcg 124500
gggcgtgagg cgggaccccc gcgccgtgtc ccccgtgtcc ctccctcacc ccggcccccc 124560

-continued gcccgctgct ttttgttcgg aaggggggga gaaaggggtc cgtaaccaaa ggtggtctgc 124620
gtcctttgga ttccgacccc tcgtctcccc ccctgtcccc cgctctcggg ctcctccctg 124680
cctccctcgc ccccccagag ggtcgggggg cggcgcacgg cccacggggg tcccccgacc 124740
gcttaagcgg gccgggggtc ggccccgtca agcgtccccg cccccgagcc caccgcccgc 124800
gaccaccccc aacccgcagc cgggtggtcc ggggaaaagg gggggcctga gacccggggg 124860
tcgccctctc accgtgccgg gggtctgccg cggcggccgc tcggggccgg ggtccgcccg 124920
ggagctcgtg ccgggccggg gttccatgag ccggggtagg gtagactcga gacggcggcc 124980
cgcggtctct ctcttgccgg gttttagtct ctgtctctcc gggtctcctc ctcccgccgg 125040
gccgccgctc cgtcgctcgc agtgccgggg tgcgaatgcg gcccgaccgt cacacggggc 125100
tgccttatac ccggcgccta tccactcccc caaaggggcg gcatttacga ttcccccaat 125160
agccgcgcgc cccggcgggg gcggagggag ggaatccccc cctctcgggg cggccccgtc 125220
cccggggacc aaccgggtgt actccaagaa ccccattagc atgcgccgcc ccccgccgac 125280
gcagatggga gtcccccogg cgccccgccg gcgcggccct gagtggtgcc cgcccccggg 125340
gaaaaattca ttagcatact aggaagccca ggggaccaat aggggccgat cagcccaccc 125400
acccggcggc gcgcgaggct ctgcgtgttc tgccaagaaa gtaatcagca taacccggaa 125460
ccccgaggga gtaattacgc ggggagcgag gggccgtccg aacgttttta attaccataa 125520
gcgggaatgg cggcccgtta aaagctgcta attaccgcga gcgggaacgc cggcccatta 125580
aaagttgcta attaccatgc gcggggatgg cggccgggac cgcctattaa aagtttctaa 125640
ttaccatacc gggaagccgg cgcggggcgg tcgccggggc ggagtccggg cccgcgcggc 125700
ggcgcgcggt tggccggcgc cgccccctgg ggcgggcgga gcggcggggc ggcgccgggc 125760
cctcgcggat atatacgcgg ggctcccatc gtctcttcgg agagcggcct cgcgcagacc 125820
ttcggagctc cggggctccg ccggccgagg ccgccctcgc cggttcaacc ctagaccgcc 125880
cgacggcccg ggcccgcggc ggcggaggac ccgcgcgccg ccgccgccgc ctcctcctcc 125940
tccgcgggtc cgccgtcttc gtgggcccgg gctcgggctc gggcccgagc tcgggcctcg 126000
ggctccaggc acggtccgat gaccgcctcg gccgccgcca cgcggcgccg gaaccggtcg 126060
cggtcggccc gctcgcgcgc ccaggacccc cgtcgggcca ggcgcgcggc cgtctcccag 126120
gccaccagat ggcgcacctg cacgcgcggc gagaagcaca cctgcgggcg gggagacacg 126180
ggggtcggag gggcgtcagg gggtcggagg ggcgtcaggg ggtcggaggg gcgtcagggg 126240
gtcggagggg cgtcaggggg tcggaggggc gtcagggggt cggaggggcg tcagggggtc 126300
ggaggggagg cgtaccttcc cgcgcggcgc gtccgcgggc ggggacgcgg ggggccgccg 126360
ccggcgcagg ctcaggcgcg ccaggtactc cgtcgtggtg cgcagccgta gcgccaggtg 126420
gggcggaagg gggcgctgcg gcccgcgctc cttgcgcggc ggcggcgggg ggcaggcggc 126480
ggcaggcgcg gcgtgcgggg cctccggcgc cttccccccg ccctcgctcg gggggctgtt 126540
cgcccactct gcgtcgtcgt tgccggcgta gtccgcgtcg tcgctgtcgt ccgcctgggg 126600
caccagcagc cagcgccgca ggagcgagga cgcggccggc gcgctctcga ccgcggttcc 126660
cgagtcgtac gcagggacca tttgggagtc tgcggttggg agcgcgccgg ggcgcggcac 126720
ggctggagcg ccggggcgcg gcacggctgg agcgccgggg cgcggccggc gccggggacc 126780
ccggcggcgg ggaccccggc ggcgggacat ggcgggcggc tgggctcggc gtaggcccgg 126840
agccggagcg cgtcggggcg ggagagttca ctcggcacgc atgcacgtgt aaccgccagt 126900
ccgtgcttgc ctagcgaact cacccgtccc ggctggcgtg cgcagcccgg gccgtgttgc 126960

-continued

```
gggccctctt aaggggcggc ggcaggacgg ggactcccgc cccgcctctt ttcccccggg 127020
gagtcaaccc ccgggggggg tgttttttgg gggggggcgc gaaggcgggc ggcggcggcg 127080
ggcgggcggc agggcagccc cgcgcgcccc cttccccgtc cctcccccgg agccggccgc 127140
tcccccgcgg gcgccgcccc tccccccgcg cgccgcgggg ctgccttccc gcgggcgccc 127200
ccgcgcggct tttttcccgc gcccgccccc gcgcggcagg acggggacta gcaggctgtg 127260
ccgcagacca ccacacactc ccaagctccc cgcccccccg aagacgccag tcgcaccacc 127320
gctcgccctc gcagaccaga cagttgcacc aagcacccgc ccgcccgcac acggttcccc 127380
gccaccccct ccctcccctc catcccgccg agctcgcggc agcccctccc ccccgcgcgc 127440
cacggggctg cggtcccgcg gccgcctccc ccgcggccgc ctcccccgcg ccccgccccg 127500
ggggcttccc ccgcccctcc ccccgcgccc gcggccccga gctcgcagca gcccctccct 127560
cccgcgcccc gtgccttccc tcccgctcct gcgggggggc tcgggccacc tgaccttcgt 127620
aacctgcact caggtcagag ccccagaccc cccgcgggcg cgggagacgt gccgcccgcc 127680
cgacccccgc ccgcccgacc cccgcccgcc cgacccccgc ccgcccgacc cccgcccgcc 127740
cgacccccgc ccgcccgacc cccgcccgcc cgacccccgc ccgcccgacc cccgcccgcc 127800
cgacccccgc ccgcccgacc cccgcccgcc cgacccccgc ccgcccgacc cccgcccgcc 127860
cgacccccgc ccgcccgacc cccgcccgcc cgacccccgc ccgcccgacc cccgaataaa 127920
ccacacaagg cggtacgttt tcgtctgtct cgttctttat ttctcacaca cgcgcgcggc 127980
catcgccgcg tctgtcttaa aggcgcacag acgcccgatt ccttccccct ctccccatct 128040
cccccctccc ccgctcccgg aagtttcccc ccccgtcact ccccaaacag tccgtcgtcg 128100
tcgtcctcca gctccgcgtc catgtccacg ggctcgcgcc tcggcggcgt ggccagcccc 128160
gcggcggtcc ccaccacctc cacgccgccg cccgccgcgg ccagcaccgt ccccgcgcgg 128220
cccgcggccg acgcccagcg tatctgcggg ggcgggcccg cgtccgcgtc gtcgcgcagc 128280
accagcgggg gcgcgtcgcc gtcgggctcg agcagcgccc gcgcgcagaa ctcccgccgc 128340
ggcccgcgca gctccgccgg gccgccgcgc acggcgtcgc gccccagcgc cacgtagacg 128400
ggccgcagcg gcgcgcccag gccccagcgc gcgcaggcgc ggtgcgagtg cgcctcgtcc 128460
tcgcagaagt ccggcgcgcc gggcgccatg gcgtcgcccg cgcccgaggc ggcggcccgg 128520
ccgtccagcg ccgggagcac ggcgcggcgg tactcgcgcg gggacatggg caccagcgtg 128580
tcggggccga agcgcgtgcg cacgcggtac cgcacgttgg ccccgcggca gaggcgcagc 128640
ggcggcgcgt cggggtacag gcgcgcgtgc gcggcctcca cgcgcgcgaa gacccccggc 128700
ccgaacacgc ggccggaggc cagcacggtg cggcgcaggt cccgcgccgc cggccagcgc 128760
acggcgcact gcacggcggg cagcacctcg caggccaggt aggcgtgctg ccgcgagacc 128820
acgggcccgt cggcgggcca gtccgcggcg cgcacggcgt tgacgacgat gaggcggcgg 128880
tcgcaggcgc cggccagcag ccccaggaac tccacggcgc cggcgaaggc caggtcccgc 128940
gtggacagca gcagcacgcc ctgcgcgccc agcgccgaga cgtcgggggc gccggtccag 129000
ttgcccgccc aggcggccgt ggcgggcccg cagagccggt tgcccagggc cgccagcagg 129060
caggacagcc cgccgcgctc ggcggaccac tccggggggg gcccgccccc ggcgcggccc 129120
gcggccaggt cctcgcccgg cagcggcgag tagaggatca ccacgcgcac gtcctccggg 129180
tcgggcacct ggcgcatcca ggccgccgcg cggcgcagcg ggcccgaggc gcgcagcggg 129240
ccgaaggcgg cgggcgcgcc gccgggggc ggggcggcgc agcgcgcggc cagcgaggcc 129300
```

agcgcgcgcg ggtcgaacat gagggccggg cgccacggcg cggggaagag cgggtggtcc 129360
gtgagctcgg ccacggcccg cggggcgcag taggcctcca gggcggcggc cgagggcgcc 129420
ggcgtgtggc tgggccccgg cggctggcgg cgccagccgc cctgcgggtc ggggccctcg 129480
gcgggccggc gggtcagcgc cgcggggcgc ggcggccgcg gcggcggcgt cggcggggcg 129540
gggggcgcgg cccccgcggg aggggcggcc gcggggcggg gggcgtccgc gcggctcttc 129600 ttcgggggc gcggggcgcc gcccggcggc gccctggccg gggcggggct cttgcgcttg 129660
cgcgcctccc gcggcgcgga ggcgggcgcg gcgagcgagt cggccgcggc gacggtgtcg 129720
gccagcaggg ggcgcaggct ctggttctgg aagagcaggt ccgcggcggc ggcggcggcg 129780
gagctcagca ggcgcgggct ccgcggcagc gccgggccca gggcccggc gaccaggctc 129840 acggcgcgca cggcggccac ggcggcctcg ctgccgccgg ccacgcgcag gtccccgcgc 129900
aggcgcatca gcaccagcgc gtcgcgcacg aaccgcagct cgcgcagcca ggcgcgcagg 129960
cggggcgcgt cggcgtgcgg cggggcggcc gcgcccgcgg gccccgggcg cgggggcgcg 130020
gcgggccggg ctccggccag ccccggcacg gccgccaggt cgccgtcgaa gccctccgcc 130080
agcgcctcca ggatcccgcg gcaggcggcc aggcactcca cggccacgcg gcccgcctcc 130140
gcgcgccggc cgccgccacc accgccggcg ccgtcgtcgt cgtcgtcgtc gtcggccccg 130200
gccggcgcgg aggcgggcgc ggcgctcagg cgccccaggg cggcgagcac ccccgcggcg 130260
ccgtagccgg cgggcaccgc gcgctcgtcg gccggcgacg ccgccgccga cggcaacggg 130320
gcggcggcgg cggcgggctt cccgcgggcg tcgtcgccgt cgtggcggtt ggcgtcgccg 130380
ccgtcgtcgg gggttcgcgc cccggtcagc gccgcgttct cgcgcgccag caggggcgcg 130440
taggcgcggc gcaggctggt cagcaggaag cccttctgcg cgcggtcgta gcggcggctc 130500
atggccacgg cggccgccac gtgcgccagg ccccagccga agcggcccgc cgccatggcg 130560
taccccaggt ggggcacggc ccgcgccacg ctgccggaga tgaaggagct gctgttgcgc 130620
gccgcgcccg agatccggaa gcaggcctgg tccagcgcca cgtccccggg cgccacgcgc 130680
gggttctgga gccaccccat cgcctccgcg tccggcgtgt acagcagccg cgtgatcagg 130740
gcgtactgct gcgccgcgtc gcccagctcg ggcgcccaca cgggcgccgg ggcgcccgag 130800
gcctcgaacc gggcccgcgc ctcctccgcc tcgggcgccc cccagaggcc ggggcggctg 130860
tcgcccagcc cgccgtacag cacgcgcccc gggggcgggg ggccggcccc gggccacggc 130920
tccccgctga cgtacccgtc gcggtagcgc gcgtagaagg cgccggaggc cgcgtcggcg 130980
tccagctcga cccgccgggg ccgcccggcc gtgaagcggc ccgtggcgtc gcggccggcc 131040
accgccgcgc gggcccggcg gcgctccagg cggcccgcgg tcgccgcggg ggtccgggcc 131100
ggggcgggct cggccctggg cgggctcggc cggggcgccg cccccggggc cctcgcgggc 131160
acccccgcct cctcgtcgtc cgcgccgagg gtcccgcccg cggcgtggtc tgcggcgctg 131220
gcgggggcgc gggcggcgtc gtcgtcgtcg tcgtcgtcag acgaggaggc ggatgcagac 131280
gaggaggagg aggcggagga ggaggcggag gacgccgacg acgaggatcc ggattttgat 131340
gagtcagagg cggccgagcg ccggcggggg gcgcgccggc ggcggtggtg gtggtggtgg 131400
tggtgtcggc ggggcgccgg gggtcgcggc gacaggctgg ccatggggtc cgggtacgcc 131460
ccgcggaccg cggacgtcgt ctccggtccg cggacccagc ggcccgcgtc gcggtcgtcg 131520
tcatcgtcgt cgtcgtcgtc gtcgtcgttc tcctcgccat aatcggcgcg catggagggg 131580
gtccgcggcg gagaaggcga gcgggccgct tcttcttgcg cgccgtcgcg ctccgggggg 131640
ggcgacggga tcgtgcgaac ggcctcgtcc accatcgagg ccagcagggc cagctgccgc 131700
ggcgagacga cgccgtccgc ggcaggctcg tcgacggcct ccccggacgc cggggccgcc 131760
tcgtcggcat cggcatcggc ggcggcgtcg tcggcctcgt cttcgttctc ctccggccca 131820
ccgtgccacc cgaacccggg ccgcgcggcg gggcgacggt ccgggttcgg ggtgggcggc 131880
ggtccgtcgg ctggatccgg agatccgggg ccgccggtcg tctccgccgc ggcccggaga 131940
cgtccccgt cctcgtccgc catcgcgacc tcggccccgc ggccctgcgt cgtcgtcgtc 132000
gtcttcttct tcttccgctg ctccgccgac atcgcctccg accggggtgt gcgggggggg 132060
ggtcttcttc ttcttcttca ggggcggcag tgggggggg tggttggcag tctctctccc 132120
ccccgtgcgg tgcgtgcgtg tgcctgtgtc ttttcgcctc tccgcgccga tcgggtagat 132180
cctggcggcc gcgtcggtag ccgcgctccg tgtggacgat cgccccgtcg cctggctgat 132240
atagtcctcg gggcgcgcgg ggcgggggga aaggaggagg acgcggagga ggagcgatcg 132300
acgccgccgc gccccggctc gccggggttc cgcccccagg tggaaccgca ttatgcgcgg 132360
ccccgccccg acgcccgcgc gtccgcgtcc gtggcggcgg cccgttggtc gcgccgccgc 132420
cgctccgccc gcgcggcatc tcattagcgc ccggcgcggg cggcttccgc ttccgcccgc 132480
gatgctaatg agaccctcgt cgcgggcggg ctcgctcccc tgcccttccg ggttcgtggt 132540
aatgagatgc cggccccgcg ctcccgttgg cccccgccgg ccccaaaggg gccggcgagg 132600
tcgccccgtt ggtccgcggg cggctccgcc ccaaaggggg cggggccgca gggtaaaaga 132660
agtgagaacg cgaagcgttc gcacttcgtc ctaatagtat atatattatt agggcaaagt 132720
gcgagcgctg gcgccctgcc cggggcccgc gtcatcccgc gctccgcccc aaagggggcg 132780
gggccgcagg gtaaaagaag tgagaacgcg aagcgttcgc acttcgtcct aatagtatat 132840
atattattag ggcaaagtgc gagcactggc gccctgcccg gggcccgcgt catcccgcgg 132900
gctccgcccc gaggcgggcc cggacggggg gcgggccgtt cctcgcgcac ataaagggcc 132960
ggcgtcccgg tcgccgccgc accaggggca caccggctgc gcggcggaga ccgggacggc 133020
agcggcggca tcgcgaaggg ggccacagcg agacagagac gccggcggcg agcggggcac 133080
cgacgcaccc ggatcggatc ggatacagag acgcgggcgc atcggttcct tttcgttctg 133140
cctttccctc cccccccccc ccccccaccc tgtacgtacc gcgaggaccc atccacccac 133200
tgcagcctta tcgcaggtac ggtgacccgg ggggccggcc gggggggacgg gcgggggacg 133260
gggggacggg ccggggggac gggccggggg gacgggccgg ggggacgggc cgggggggacg 133320
ggccgggggg acgggccggg gggacgggcc ggggggacgg gccgggggga cgggccgggg 133380
ggccgggggg ccggggggcc ggggggccgg ggggacgggg ggacgggggg acgggggggac 133440
ggggggacgg ggggacgggg ggacgggggg acgggggggac ggggggacgg ggggacgggg 133500
ggacgggggg acggggggac ggggggacgg ggggacgggg ggacgggccg gggggacggg 133560
gggacgggcc ggggggacgg ggggacgggc cggggggacg gggggacggg ccggggggac 133620
ggggggacgg gccgggggga cggggccccg atcccaacat ccgcgctttc tcgcaggccg 133680
ggcgccgcct tcgtggacgg gacaccggtg tggtaactgg cgacaaggcg ttgccactat 133740
ggcagacatc cccccggacc cgcccgcgct caacacgacg cctgcgaatc atgctccccc 133800
atccccaccc ccgggttcac ggaagcgcag acgccccgtc ctccccagct cgtcggaatc 133860
tgagggtaag cccgacacag aatcggaatc ctcctcgacc gagtcgtccg aggatgaggc 133920
gggagaccta cgcggcgggc gccgtcgctc ccccgcggag ctcgggggga ggtatttttt 133980
ggatctgtcg gcagaatcga ccacggggac ggaatcggag ggaacggggc cgtcggacga 134040

-continued cgatgatgat gatgcgtcag acggctggtt ggttgacaca cccccccgca aatccaagcg 134100
accccgaatc aacctgcgat taacgagctc ccccgaccgg cgtgcgggtg tggttttccc 134160
cgaggtgtgg agaagcgaca gacctatccg cgcggcgcaa ccccaggccc cggccagtct 134220
tccggggatc gcgcacgcgc accggcgctc tgctcgccag gcccagatgc ggagcggagc 134280
cgcctggacg cttgatctgc attacatacg ccagtgcgtc aaccagctct ttcggatcct 134340
gcgtgccgcc ccgaacccgc ccggcagcgc caaccgcctg cgccacctgg tgcgagactg 134400
ctacctcatg ggctactgcc ggacccgcct ggggccgcgc acgtggggcc gcctgctgca 134460
gatctcgggc ggaacctggg acgtgcgcct gcgaaacgca atccgggagg tcgaggcgca 134520
ttttgaaccc gccgccgagc ccgtgtgcga gctgccctgt ctgaacgcca ggcgttacgg 134580
ccccgagtgt gatgttggca atctcgagac caacggcggc tcgacgagcg atgatgagat 134640
atcggatgcg acggactcgg acgataccct cgcgtcccat tccgacacgg aggggggcc 134700 ctccccggcc ggccgggaga acccggaatc cgcgtccggc ggggctatcg cggctcggct 134760
ggagtgtgag tttgggacgt ttgactggac gtccgaggag ggctcccagc cctggctgtc 134820
cgcggtggtc gccgatacca gctccgccga acgctctggc ctacccgccc cgggcgcgtg 134880
tcgcgcaacg gaagccccag aacgcgagga cgggtgccga aaaatgcgct tccccgccgc 134940
ctgcccctat ccctgcggcc acacatttct ccggccatga gcgcgggacc cccagcccgg 135000
tgtgtttgcc aaacgaaaaa taaacgccct acaagaaagc ttttgtgtct gagtgtctgg 135060
tttttctggg ggtggaggaa ggaacgacaa aaaaaagaaa caaacgcgac accgctcgta 135120
cgtgtaatgg ggccgcagtg ttttttatta gcatcggggg gggttagagg ttggtgattg 135180
gatagcaaac gtgggatgac ggaggccact cgtcgccaac ggccagcggg ggcccggggt 135240
tctgggggtc atcgtccccc gtctgccagg agggctcatc gggaatctcg ggtcgcccca 135300
tgcacgtaaa acacgggcgc tgcgtggggt gggtcgccgg atgcgggcgg gatgatgcgg 135360
ggcggggttt gttgtgagga gccacgaggg accgtagcca gcgaagacag ctgcgttccc 135420
ggtcgccggg caccaccacg ccgtattggt attcgtatcg gctaaggaga ttttccaggg 135480
ggtgattagg cgctgcgggg aacggggtcc acgacacggt ccgctcgggc aaaaaccgat 135540
cgggcagggg ccacggttcc cccacccacg cgtcgttggt cttcgtggcg atgaagcgaa 135600
accccagccg ggttttttgt gcgtactcga aaaacggcac acacaggtcc gccgccccga 135660
ccacccacag gtggtatagc cggtgggggc cggggcgctc ttgatgcagg agccgaaaac 135720
acgcaggggc atccagaatc tcgatgcttt ccagggggtc gtcctccgca aacaggcccg 135780
tcgtggtgtt tgggggacag cgacaggagc gggttcgcac gatcggtcgg gtgaatttgg 135840
gcaagtccat cagaggctcg gccagcctgc gaaggttcgc cgggcgaacc accaccgggg 135900
ttcccagagg ctcggaggcc aggatccggc attgccgaag cagaaaactc cacagagccg 135960
ggcttgcgtc agcggaagtc cgcggcaggg cgtttcgttg gtctaggagg gtaaccacac 136020
ttacaacaac aacgcccatg tcggtatatt aggcccgtgg tccgatcttc actcactcgc 136080
ctgtctgcgg acctatgcac ggcgggacgg cgcgcggacc cggggggggct gcttgctatc 136140 acacggcccg ttcgcacgtt cgatttttttc agccttgttt ggttggctag gtatcccgga 136200
taatctgacg ttccggatat agggggcggg gggtagtggg gggtgtgtcg acaaactgcc 136260
gcttcttaaa acaccggggc ccgtcgctcg gggtgctcgt tggttggcac gcgcgacgcg 136320
gcaaatggcc tgtcgtaagt tctgtggggt ctaccgtaga cccgacaaga gacaggaggc 136380
gtccgtcccg ccggagacaa acacggcccc ggccttcccg gcgagcacct tttatacccc 136440
cgcggaggat gcgtacctgg cccccgggcc cccggaaacc atccaccctt cccgcccacc 136500
gtcccccggc gaggctgcgc gcctgtgtca gctgcaggag atcttggccc agatgcacag 136560
cgacgaggac taccccatcg tggacgccgc gggtgcggag gaggaagacg aggccgacga 136620
tgacgccccg gatgacgtgg cctacccgga ggactacgcg gaggggcgtt ttctgtccat 136680
ggtttcggcc gccccccctgc ccggagccag cggccatcct cctgttccgg gccgcgcagc 136740
cccccccgac gtccggacct gcgacacggg taaggtgggg gccacggggt tcaccccgga 136800
agagctcgac accatggacc gggaggcact tcgggccatc agccgcgggt gcaagccccc 136860
ttcgaccctg gcaaaactgg tgaccgggct gggattcgcg atccacggag cgctcatccc 136920
ggggtcggag gggtgtgtct ttgatagcag ccacccgaac taccctcatc gggtaatcgt 136980
caaggcgggg tggtacgcca gcacgagcca cgaggcgcgg ctgctgagac gcctgaacca 137040
ccccgcgatc ctacccctcc tggacctgca cgtcgtttct ggggtcacgt gtctggtcct 137100
ccccaagtat cactgcgacc tgtataccta tctgagcaag cgcccgtctc cgttgggcca 137160
cctacagata accgcggtct cccggcagct cttgagcgcc atcgactacg tccactgcaa 137220
aggcatcatc caccgcgata ttaagaccga gaacatcttc atcaacaccc ccgagaacat 137280
ctgtctgggg gactttgggg cggcgtgctt tgtgcgcggg tgtcgatcga gccccttcca 137340
ttacgggatc gcaggcacca tcgatacaaa cgcccccgag gtcctggccg gggatccgta 137400
cacccaggta atcgacatct ggagcgccgg cctggtgatc tttgagaccg ccgtccacac 137460
cgcgtccttg ttctcggccc cgcgcgaccc cgaaaggcgg ccgtgcgaca accagatcgc 137520
gcgcatcatc cgacaggccc aggtacacgt cgacgagttt ccgacgcacg cggaatcgcg 137580
cctcaccgcg cactaccgct cgcgggcggc cgggaacaat cgtccggcgt ggacccgacc 137640
ggcgtggacc cgctactaca agatccacac agacgtcgaa tatctcatat gcaaagccct 137700
tacctttgac gcggcgctcc gcccaagcgc cgcggagttg ctgcgcctgc cgctatttca 137760
ccctaagtga ccccgctccc cccgggggc gtggaggggg gggctggttg gatgtttttg 137820
cacaaaaaga cgcggccctc gggctttggt gtttttggca ccttgccgcc cggcgtcatg 137880
cacgccatcg ctcccaggtt gcttcttctt tttgttcttt ctggtcttcc ggggacacgc 137940
ggcgggtcgg gtgtccccgg accaattaat ccccccaaca gcgatgttgt tttcccggga 138000
ggttcccccg tggctcaata ttgttatgcc tatccccggt tggacgatcc cgggcccttg 138060
ggttccgcgg acgccgggcg gcaagacctg ccccggcgcg tcgtccgtca cgagcccctg 138120
ggccgctcgt tcctcacggg ggggctggtt ttgctggcgc cgccggtacg cggatttggc 138180
gcacccaacg caacgtatgc ggcccgtgtg acgtactacc ggctcacccg cgcctgccgt 138240
cagcccatcc tccttcggca gtatggaggg tgtcgcggcg gcgagccgcc gtccccaaag 138300
acgtgcgggt cgtacacgta cacgtaccag ggcggcgggc ctccgacccg gtacgctctc 138360
gtaaatgctt ccctgctggt gccgatctgg gaccgcgccg cggagacatt cgagtaccag 138420
atcgaactcg gcggcgagct gcacgtgggt ctgttgtggg tagaggtggg cggggagggc 138480
cccggcccca ccgccccccc acaggcggcg cgtgcggagg gcggcccgtg cgtccccccg 138540
gtccccgcgg gccgcccgtg gcgctcggtg cccccggtat ggtattccgc ccccaacccc 138600
gggtttcgtg gcctgcgttt ccgggagcgc tgtctgcccc cacagacgcc cgccgccccc 138660
agcgacctac cacgcgtcgc ttttgctccc cagagcctgc tggtggggat tacgggccgc 138720
acgtttattc ggatggcacg acccacggaa gacgtcgggg tcctgccgcc ccattgggcc 138780
cccggggccc tagatgacgg tccgtacgcc cccttcccac cccgcccgcg gtttcgacgc 138840
gccctgcgga cagaccccga gggggtcgac cccgacgttc gggccccccg aaccgggcgg 138900
cgcctcatgg ccttgaccga ggacacgtcc tccgattcgc ctacgtccgc tccggagaag 138960
acgcccctcc ctgtgtcggc caccgccatg gcaccctcag tcgacccaag cgcggaaccg 139020
accgcccccg caaccactac tccccccgac gagatggcca cacaagccgc aacggtcgcc 139080
gttacgccgg aggaaacggc agtcgcctcc ccgcccgcga ctgcatccgt ggagtcgtcg 139140
ccactccccg ccgcggcggc ggcaacgccc ggggccgggc acacgaacac cagcagcgcc 139200
tccgcagcga aaacgccccc caccacacca gcccccacga cccccccgcc cacgtctacc 139260
cacgcgaccc cccgccccac gactccgggg ccccaaacaa cccctcccgg acccgcaacc 139320
ccgggtccgg tgggcgcctc cgccgcgccc acggccgatt ccccccctcac cgcctcgccc 139380 cccgctaccg cgccggggcc ctcggccgcc aacgtttcgg tcgccgcgac caccgccacg 139440
cccggaaccc ggggcaccgc ccgtaccccc ccaacggacc caaagacgca cccacacgga 139500
cccgcggacg ctccccccgg ctcgccagcc cccccacccc ccgaacatcg cggcggaccc 139560
gaggagtttg agggcgccgg ggacggcgaa cccccccgagg acgacgacag cgccaccggc 139620
ctcgccttcc gaactccgaa ccccaacaaa ccaccccccg cgcgccccgg gcccatccgc 139680
cccacgctcc cgccaggaat tcttgggccg ctcgccccca acacgcctcg cccccccgcc 139740
caagctcccg ctaaggacat gccctcgggc cccacacccc aacacatccc cctgttctgg 139800
ttcctaacgg cctcccctgc tctagatatc ctctttatca tcagcaccac catccacacg 139860
gcggcgttcg tttgtctggt cgccttggca gcacaacttt ggcgcggccg ggcggggcgc 139920
aggcgatacg cgcacccgag cgtgcgttac gtatgtctgc cacccgagcg ggattagggg 139980
gtgggggtgg ggggcgagaa acgatgaagg acgggaaagg gaacagcgac caaatgtcac 140040
gataagaaca ataaacctgt gacgtcaatc agatatgtga gtttggttgt gttttgtggg 140100
actgggggcg gggggtggga ggtatcagtg ggtgacagag tcttttaaaa gacgtgtccc 140160
ggggccctcg agatgcgcaa cttttggcca cacagagaaa ggcccccaga cgaagtcacc 140220
cgggtccccg aacaaaaaca aaaaccttga ccgccgccgg ggggcgtgcc tgttgttttg 140280
gtctcaatgg atcggtatgc cgttcggacc tgggggattg tgggaatcct cgggtgtgct 140340
gctgttgggg ccgcacccac cggccccgcg tccgatacaa caaacgcgac cgcacgcctc 140400
cccacgcacc ccccactcat ccgttccggg ggctttgccg tccccctcat cgtggggggg 140460
ctgtgtctca tgattctggg gatggcgtgt ctactcgagg tcctgcgtcg cctgggtcgc 140520
gagttggcga ggtgctgccc ccacgcgggc caatttgccc catgattttt cgcctttctg 140580
gccttgcccc caccccatcg ccccgattgt gtgtcgggtg cccggggtac agcagctatg 140640
gagcggtcgg taatataact ttggttgtcg ccacacgccc cgtgccgggc atgggttgtg 140700
cgggaaggac gaaataatcc ggcgatcccc aagcgtacca actggggggg gggggggggg 140760
ggaaaagaaa ctaaaaacac atcaagccca caacccatcc cacaatgggg gttatggcgg 140820
acccaccgca ccaccatact ccgattcgac cacatatgca accaaatcac ccccagaggg 140880
gaggttccat ttttacgagg aggaggagta taatagagtc tttgtgttta aaacccgggg 140940
tcggtgtggt gttcggtcat aagctgcatt gcgaacgact agtcgccgtt tttcgtgtgc 141000
atcgcgtatc acggcatggg gcgtttgacc tccggcgtcg ggacggcggc cctgctagtt 141060
gtcgcggtgg gactccgcgt cgtctgcgcc aaatacgcct tagcagaccc ctcgcttaag 141120
atggccgatc ccaatcgatt tcgcgggaag aaccttccgg ttttggacca gctgaccgac 141180
cccccggggg tgaagcgtgt ttaccacatt cagccgagcc tggaggaccc gttccagccc 141240
cccagcatcc cgatcactgt gtactacgca gtgctggaac gtgcctgccg cagcgtgctc 141300
ctacatgccc catcggaggc cccccagatc gtgcgcgggg cttcggacga ggcccgaaag 141360
cacacgtaca acctgaccat cgcctggtat cgcatgggag acaattgcgc tatccccatc 141420
acggttatgg aatacaccga gtgcccctac aacaagtcgt tgggggtctg ccccatccga 141480
acgcagcccc gctggagcta ctatgacagc tttagcgccg tcagcgagga taacctggga 141540
ttcctgatgc acgcccccgc cttcgagacc gcgggtacgt acctgcggct agtgaagata 141600
aacgactgga cggagatcac acaatttatc ctggagcacc gggcccgcgc ctcctgcaag 141660
tacgctctcc ccctgcgcat ccccccggca gcgtgcctca cctcgaaggc ctaccaacag 141720
ggcgtgacgg tcgacagcat cgggatgcta ccccgcttta tccccgaaaa ccagcgcacc 141780
gtcgccctat acagcttaaa aatcgccggg tggcacggcc ccaagccccc gtacaccagc 141840
accctgctgc cgccggagct gtccgacacc accaacgcca cgcaacccga actcgttccg 141900
gaagaccccg aggactcggc cctcttagag gatcccgccg ggacggtgtc ttcgcagatc 141960
cccccaaact ggcacatccc gtcgatccag gacgtcgcgc cgcaccacgc ccccgccgcc 142020
cccagcaacc cgggcctgat catcggcgcg ctggccggca gtaccctggc ggtgctggtc 142080
atcggcggta ttgcgttttg ggtacgccgc cgcgctcaga tggcccccaa gcgcctacgt 142140
ctcccccaca tccgggatga cgacgcgccc ccctcgcacc agccattgtt ttactagagg 142200
agtttccccg ctcccgtgta cctctgggcc cgtgtgggag ggtggctggg gtatttgggt 142260
gggacttgga ctccgcataa agggagtctc gaaggaggga aactaggaca gttcataggc 142320
cgggagcgtg gggcgcgcac cgctgtcccg acgattagcc accgcgccca cagccacctc 142380
gacccgtccg atcccggtat gcccggccgc tcgctgcagg gcctggcgat cctgggcctg 142440
tgggtctgcg ccaccggcct ggtcgtccgc ggccccacgg tcagtctggt ctcagactca 142500
ctcgtggatg ccggggccgt ggggccccag ggcttcgtgg aagaggacct gcgtgttttc 142560
ggggagcttc attttgtggg ggcccaggtc ccccatacaa actactacga cggcatcatc 142620
gagctgtttc actaccccct ggggaaccac tgcccccgcg ttgtacacgt ggtcacactg 142680
accgcatgcc cccgccgccc cgccgtggcg ttcaccttgt gtcgctcgac gcaccacgcc 142740
cacagccccg cctatccgac cctggagctg ggtctggcgc ggcagccgct tctgcgggtt 142800
cgaacggcaa cgcgcgacta tgccggtctg tatgtcctgc gcgtatgggt cggcagcgcg 142860
acgaacgcca gccggtttgt tttgggggtg gcgctctctg ccaacgggac gtttgtgtat 142920
aacggctcgg actacggctc ctgcgatccg gcgcagcttc ccttttcggc cccgcgcctg 142980
ggaccctcga gcgtatacac ccccggagcc tcccgaccca cccctccacg gacaacgaca 143040
cccccgtcct ccccccgaga cccgaccccc gcccccgggg acacagggac gcccgcgccc 143100
gcgagcggcg agatagcccc gcccaattcc acgcgatcgg ccagcgaatc gagacacagg 143160
ctaaccgtag cccaggtaat ccagatcgcc ataccggcgt ccatcatcgc ctttgtgttt 143220
ctgggcagct gtatctgctt catccataga tgccagcgcc gatacaggcg cccccgcggc 143280
cagatttaca accccggggg cgtttcctgc gcggtcaacg aggcggccat ggcccgcctc 143340
ggagccgagc tgcgatccca cccaaacacc ccccccaaac cccgacgccg ttcgtcgtcg 143400
tccacgacca tgccttccct aacgtcgata gctgaggaat cggagccagg tccagtcgtg 143460
ctgctgtccg tcagtcctcg gccccgcagt ggcccgacgg ccccccaaga ggtctaggtc 143520
caagcgggcc gttcggcagg cccgccccac cgccccccatc gtggttattt cccccccccc 143580
ccccccaata aaccgatgtt atttgcctat atgcgtgtgt tggatccctt tgtgatcgtt 143640
cgtcattccc cggatggcat gggaggcggg taatggatgg gcggggcccg gggggaggaa 143700
aaagaataaa gggggtagtg tcggagaggc ccgccgcgca tttaaggagt cgccgccccg 143760
actctgtgtc ttcgggtgac ttggtgcgcc gccgtcagct agtctccgat ctgccccgac 143820
cgacggctcc tgccacccga acatggctcg cggggccggg ttggtgtttt ttgttggagt 143880
ttgggtcgta tcgtgcctgg cggcagcacc cagaacgtcc tggaaacggg taacctcggg 143940
cgaggacgtg gtgttgcttc cggcgcccgc ggaacgcacc cgggcccaca aactactgtg 144000
ggccgcggaa cccctggatg cctgcggtcc cctgcgcccg tcgtgggtgg cgctgtggcc 144060
cccccgacgg gtgctcgaga cggtcgtgga tgcggcgtgc atgcgcgccc cggaaccgct 144120
cgccatagca tacagtcccc cgttccccgc gggcgacgag ggactgtatt cggagttggc 144180
gtggcgcgat cgcgtagccg tggtcaacga gagtctggtc atctacgggg ccctggagac 144240
ggacagcggt ctgtacaccc tgtccgtggt cggcctaagc gacgaggcgc gccaagtggc 144300
gtcggtggtt ctggtcgtgg agcccgcccc tgtgccgacc ccgacccccg acgactacga 144360
cgaagaagac gacgcgggcg tgacgaacgc acgccggtca gcgttccccc cccaaccccc 144420
cccccgtcgt ccccccgtcg cccccccgac gcaccctcgt gttatccccg aggtgtccca 144480
cgtgcgcggg gtaacggtcc atatggagac cctggaggcc attctgtttg cccccgggga 144540
gacgtttggg acgaacgtct ccatccacgc cattgcccac gacgacggtc cgtacgccat 144600
ggacgtcgtc tggatgcggt ttgacgtgcc gtcctcgtgc gccgatatgc ggatctacga 144660
agcttgtctg tatcacccgc agcttccaga gtgtctatct ccggccgacg cgccgtgcgc 144720
cgtaagttcc tgggcgtacc gcctggcggt ccgcagctac gccggctgtt ccaggactac 144780
gcccccgccg cgatgttttg ccgaggctcg catggaaccg gtcccggggt tggcgtggct 144840
ggcctccacc gtcaatctgg aattccagca cgcctccccc cagcacgccg gcctctacct 144900
gtgcgtggtg tacgtggacg atcatatcca cgcctggggc cacatgacca tcagcaccgc 144960
ggcgcagtac cggaacgcgg tggtggaaca gcacctcccc cagcgccagc ccgagcccgt 145020
cgagcccacc cgcccgcacg tgagagcccc ccatcccgcg ccctccgcgc gcggcccgct 145080
gcgcctcggg gcggtgctgg gggcggccct gttgctggcc gccctcgggc tgtccgcgtg 145140
ggcgtgcatg acctgctggc gcaggcgctc ctggcgggcg gttaaaagcc gggcctcggc 145200
gacgggcccc acttacattc gcgtggcgga cagcgagctg tacgcggact ggagttcgga 145260
cagcgagggg gagcgcgacg ggtccctgtg gcaggaccct ccggagagac ccgactctcc 145320
ctccacaaat ggatccggct ttgagatctt atcaccaacg gctccgtctg tataccccca 145380
tagcgagggg cgtaaatctc gccgcccgct caccaccttt ggttcgggaa gcccgggccg 145440
tcgtcactcc caggcctcct atccgtccgt cctctggtaa ggcgtcttcc gacgacgcgg 145500
acgtcggcga tgaactgatt gccatcgcgg acgcacgcgg ggacccgcca gagaccctgc 145560
cccccggcgc gggcggcgcc gcgcccgcgt gccgcagacc acctcgcggc ggctcccccg 145620
cggcctttcc cgtggccctc cacgccgtgg acgccccctc ccaattcgtc acctggctcg 145680
ccgtgcgctg gctgcggggg gcggtgggtc tcggggccgt cctgtgcggg attgcgtttt 145740
acgtgacgtc aatcgcccga ggcgcataaa ggtccggcgg ccaccccgcc gcagctcata 145800
aaaatcgtga gtcacggcaa ccccaccttc gcctccgccc tccgccagcg cccttccgcg 145860
tccgcgatga cctcccggcc cgccgaccaa gactcggtgc gttccagcgc gtcggtgccg 145920
ctttaccccg cggcctcgcc cgtcccggca gaagcctact actcggaaag cgaagacgag 145980
gccgccaacg acttcctcgt gcgcatgggc cgccagcagt cggtcctaag gcgccgacgg 146040
cggcgcacgc ggtgcgtcgg gctggttatc gcctgtctcg tcgtggccct cctatctgga 146100
gggttcgggg cacttttggt gtggctgctc cgctaaatga cgcctcgatg tatggcgcct 146160
tcttcgcccc cacccctcgc cgcgacccac gtccgtatgt taattgcaat aaagtggttg 146220
attgtcatta cggtctacta ggttgtcttt tttttttggg gggggggag gaaatgcaga 146280 aaagggtaag aaattctcgg aatttcaccc ccgggggggg gcaagtgcag taacccagtt 146340
cctcagtgtt tgggaaatct attgaactct cccggctcct ccgtgttagg gaagtctctt 146400
ggggaaatct attgacctct cgcccccccc cccccaggag gggggcagtg cagtacccca 146460
gttcctccgt gctggggaaa tctctctgcc gggtacgggc tccagacgaa ggacccatac 146520
atttccccat ccgcacccca catctggcgt tctagagtca cgacgcattt gcccccgtcc 146580
ccgcagcaac acacaaagcg atttcaattt tcacgatttt attattaatt acaccaacca 146640
ccctgtcccc gggacgtggt caggaccggg ggtccgcacc caaacgcacg aaacaaatgc 146700
tggcagtgtg ccgaatataa ccccgcgtag gaacacgtcg acgcgtgcgc caaacagcac 146760
cagaaggcgc atgccatcag caggtcgtgc atatggcgat gtgtttggac gcagggcgca 146820
gccgcggcga taaaattcat ggcggccgtc cgccagggcc acagcggcga ggactccctg 146880
ttggcccgaa gccattgggt atgaaccagc tgcgcctcct gtccgaccct ggctcccgcc 146940
agcgggggcg gtgggtcgtg ggtgttgaga gcacacaggc gggacacctc gatcaccgtc 147000
cgaaaaaagg cccggtggtc cgcgggcagc atctgcaggt gcgccagggc ctgggcgttg 147060
agagggtaca actcggagcc gggggactcc gggggccggt ccgcgcggtg ccgcgagttg 147120
gcacgctttg gggcccgggt gtcggacgcg ggcgcgttat ggatcccgac gcggggcaga 147180
acgtacgtgc gttggcgcgg cgatgagggg tccgggctgc cgaggggggc gtaggggacc 147240
gggctaggca agcccgcggg ttgcgcgggg ttcccgtggg ggtctaggct ccctgggcac 147300
ccgtgggggt cgtgggggtc gcgggtccct gggtatgcgc gggaccctgg gttctctggg 147360
agatcgtgga actcgcggtt ccctgggctc tcggggaacc cggggctccc tggggacacg 147420
tggtgccctg ggaattcttg atggtcggac ggcttcagat ggcttcggga tcgagagggc 147480
cgcacagact cgtagtagac ccgaatctcc acgtttcccc gccgccggat catggtcgcc 147540
gccccggtgc gggggcccgt cggtcggaag cgagtgccct tcaagcgtgt ccgctcctct 147600
gggctgcatg ccgtcggatg gggtgccttt taaggaaagg tctcggctgc ccgccccaac 147660
cggggtttgg gggtgggccg gggaaacccc ggatgccatg ggggggtcac accctaagcg 147720
ccggcgcgct ggttgggtgg gggtagaggg gagtccccgg tcgacgagat cgtatcaagg 147780
ggccagcacg cgatcctgcc gctcgttcga tctagcacac ccacgggtct gctgtgtggg 147840
atttcgactc gcgggatccg atcgcacgtc cggaggacac agcagcggga gctccgggtc 147900
ggtcaccgca gttctggccg cctctcggtc ctcccgttcc cttttatgga tctccgcgca 147960
gacatcgcca tacgtccggt gtgtgcaccg cgaagaatcc agaaacatgt ccgtcgtttt 148020
cagggcccaa gacatggtgt cccgtccacg aaggcggcgc ccggcctgcg agaaagcgcg 148080
gatgttggga tcggggcccc gtccccccgg cccgtccccc cgtccccccg gcccgtcccc 148140
ccgtcccccc ggcccgtccc cccgtccccc cggcccgtcc ccccgtcccc ccggcccgtc 148200
cccccgtccc cccgtccccc cgtccccccg tccccccgtc cccccgtccc cccgtccccc 148260 cgtcccccg tccccccgtc cccccgtccc cccgtccccc cgtccccccg tccccccgtc 148320
cccccgtccc cccggccccc cggcccccg gccccccggc cccccggccc gtcccccgg 148380 cccgtccccc cggcccgtcc ccccggcccg tccccccggc ccgtcccccc ggcccgtccc 148440
cccggcccgt cccccggcc cgtcccccg gcccgtcccc ccgtcccccg cccgtccccc 148500
cggccggccc cccgggtcac cgtacctgcg ataaggctgc agtgggtgga tgggtcctcg 148560
cggtacgtac agggtggggg gggggggggg ggagggaaag gcagaacgaa aaggaaccga 148620
tgcgcccgcg tctctgtatc cgatccgatc cgggtgcgtc ggtgccccgc tcgccgccgg 148680
cgtctctgtc tcgctgtggc cccccttcgcg atgccgccgc tgccgtcccg gtctccgccg 148740
cgcagccggt gtgcccctgg tgcggcggcg accgggacgc cggcccttta tgtgcgcgag 148800
gaacggcccg cccccgtcc gggcccgcct cggggcggag cccgcgggat gacgcgggcc 148860
ccgggcaggg cgccagtgct cgcactttgc cctaataata tatatactat taggacgaag 148920
tgcgaacgct tcgcgttctc acttctttta ccctgcggcc ccgccccctt tggggcggag 148980
cgcgggatga cgcgggcccc gggcagggcg ccagcgctcg cactttgccc taataatata 149040
tatactatta ggacgaagtg cgaacgcttc gcgttctcac ttcttttacc ctgcggcccc 149100
gccccctttg gggcggagcc gcccgcggac caacggggcg acctcgccgg cccctttggg 149160
gccggcgggg gccaacggga gcgcggggcc ggcatctcat taccacgaac ccggaagggc 149220
aggggagcga gcccgcccgc gacgagggtc tcattagcat cgcgggcgga agcggaagcc 149280
gcccgcgccg ggcgctaatg agatgccgcg cgggcggagc ggcggcggcg cgaccaacgg 149340
gccgccgcca cggacgcgga cgcgcgggcg tcggggcggg gccgcgcata atgcggttcc 149400 acctggggc ggaaccccgg cgagccgggg cgcggcggcg tcgatcgctc ctcctccgcg 149460
tcctcctcct ttccccccgc cccgcgcgcc ccgaggacta tatcagccag gcgacggggc 149520
gatcgtccac acggagcgcg gctaccgacg cggccgccag gatctacccg atcggcgcgg 149580
agaggcgaaa agacacaggc acacgcacgc accgcacggg ggggagagag actgccaacc 149640 acccccccc actgccgccc ctgaagaaga agaagaagac cccccccccg cacaccccgg 149700
tcggaggcga tgtcggcgga gcagcggaag aagaagaaga cgacgacgac gacgcagggc 149760
cgcggggccg aggtcgcgat ggcggacgag gacgggggac gtctccgggc cgcggcggag 149820
acgaccggcg gccccggatc tccggatcca gccgacggac cgccgcccac cccgaacccg 149880
gaccgtcgcc ccgccgcgcg gcccgggttc gggtggcacg gtgggccgga ggagaacgaa 149940
gacgaggccg acgacgccgc cgccgatgcc gatgccgacg aggcggcccc ggcgtccggg 150000
gaggccgtcg acgagcctgc cgcggacggc gtcgtctcgc cgcggcagct ggccctgctg 150060
gcctcgatgg tggacgaggc cgttcgcacg atcccgtcgc cccccccgga gcgcgacggc 150120
gcgcaagaag aagcggcccg ctcgccttct ccgccgcgga ccccctccat gcgcgccgat 150180
tatggcgagg agaacgacga cgacgacgac gacgacgatg acgacgaccg cgacgcgggc 150240
cgctgggtcc gcggaccgga gacgacgtcc gcggtccgcg gggcgtaccc ggaccccatg 150300
gccagcctgt cgccgcgacc cccggcgccc cgccgacacc accaccacca ccaccaccgc 150360
cgccggcgcg cccccgccg gcgctcggcc gcctctgact catcaaaatc cggatcctcg 150420
tcgtcggcgt cctccgcctc ctcctccgcc tcctcctcct cgtctgcatc cgcctcctcg 150480
tctgacgacg acgacgacga cgacgccgcc cgcgcccccg ccagcgccgc agaccacgcc 150540
gcgggcggga ccctcggcgc ggacgacgag gaggcggggg tgcccgcgag ggccccgggg 150600
gcggcgcccc ggccgagccc gcccagggcc gagcccgccc cggcccggac ccccgcggcg 150660

-continued accgcgggcc gcctggagcg ccgccgggcc cgcgcggcgg tggccggccg cgacgccacg 150720
ggccgcttca cggccgggcg gccccggcgg gtcgagctgg acgccgacgc ggcctccggc 150780
gccttctacg cgcgctaccg cgacgggtac gtcagcgggg agccgtggcc cggggccggc 150840
cccccgcccc cggggcgcgt gctgtacggc gggctgggcg acagccgccc cggcctctgg 150900
ggggcgcccg aggcggagga ggcgcgggcc cggttcgagg cctcgggcgc cccggcgccc 150960
gtgtgggcgc ccgagctggg cgacgcggcg cagcagtacg ccctgatcac gcggctgctg 151020
tacacgccgg acgcggaggc gatggggtgg ctccagaacc cgcgcgtggc gcccggggac 151080
gtggcgctgg accaggcctg cttccggatc tcgggcgcgg cgcgcaacag cagctccttc 151140
atctccggca gcgtggcgcg ggccgtgccc cacctggggt acgccatggc ggcgggccgc 151200
ttcggctggg gcctggcgca cgtggcggcc gccgtggcca tgagccgccg ctacgaccgc 151260
gcgcagaagg gcttcctgct gaccagcctg cgccgcgcct acgcgcccct gctggcgcgc 151320
gagaacgcgg cgctgaccgg ggcgcgaacc cccgacgacg gcggcgacgc caaccgccac 151380
gacggcgacg acgcccgcgg gaagcccgcc gccgccgccg ccccgttgcc gtcggcggcg 151440
gcgtcgccgg ccgacgagcg cgcggtgccc gccggctacg gcgccgcggg ggtgctcgcc 151500
gccctggggc gcctgagcgc cgcgcccgcc tccgcgccgg ccggggccga cgacgacgac 151560
gacgacgacg gcgccggcgg tggtggcggc ggccggcgcg cggaggcggg ccgcgtggcc 151620
gtggagtgcc tggccgcctg ccgcgggatc ctggaggcgc tggcggaggg cttcgacggc 151680
gacctggcgg ccgtgccggg gctggccgga gcccggcccg ccgcgccccc gcgcccgggg 151740
cccgcgggcg cggccgcccc gccgcacgcc gacgcgcccc gcctgcgcgc ctggctgcgc 151800
gagctgcggt tcgtgcgcga cgcgctggtg ctgatgcgcc tgcgcgggga cctgcgcgtg 151860
gccggcggca gcgaggccgc cgtggccgcc gtgcgcgccg tgagcctggt cgccggggcc 151920
ctgggcccgg cgctgccgcg gagcccgcgc ctgctgagct ccgccgccgc cgccgccgcg 151980
gacctgctct tccagaacca gagcctgcgc cccctgctgg ccgacaccgt cgccgcggcc 152040
gactcgctcg ccgcgcccgc ctccgcgccg cgggaggcgc gcaagcgcaa gagccccgcc 152100
ccggccaggg cgccgccggg cggcgccccg cgccccccga agaagagccg cgcggacgcc 152160
ccccgccccg cggccgcccc tcccgcgggg gccgcgcccc ccgccccgcc gacgccgccg 152220
ccgcggccgc cgcgccccgc ggcgctgacc cgccggcccg ccgagggccc cgacccgcag 152280
ggcggctggc gccgccagcc gccggggccc agccacacgc cggcgccctc ggccgccgcc 152340
ctggaggcct actgcgcccc gcgggccgtg gccgagctca cggaccaccc gctcttcccc 152400
gcgccgtggc gcccggccct catgttcgac ccgcgcgcgc tggcctcgct ggccgcgcgc 152460
tgcgccgccc cgccccccgg cggcgcgccc gccgccttcg gcccgctgcg cgcctcgggc 152520
ccgctgcgcc gcgcggcggc ctggatgcgc caggtgcccg acccggagga cgtgcgcgtg 152580
gtgatcctct actcgccgct gccgggcgag gacctggccg cgggccgcgc cgggggcggg 152640
ccccccccgg agtggtccgc cgagcgcggc gggctgtcct gcctgctggc ggccctgggc 152700
aaccggctct gcgggcccgc cacggccgcc tgggcgggca actggaccgg cgccccegac 152760 gtctcggcgc tgggcgcgca gggcgtgctg ctgctgtcca cgcgggacct ggccttcgcc 152820
ggcgccgtgg agttcctggg gctgctggcc ggcgcctgcg accgccgcct catcgtcgtc 152880
aacgccgtgc gcgccgcgga ctggcccgcc gacgggcccg tggtctcgcg gcagcacgcc 152940
tacctggcct gcgaggtgct gcccgccgtg cagtgcgccg tgcgctggcc ggcggcgcgg 153000
gacctgcgcc gcaccgtgct ggcctccggc cgcgtgttcg ggccgggggt cttcgcgcgc 153060
gtggaggccg cgcacgcgcg cctgtacccc gacgcgccgc cgctgcgcct ctgccgcggg 153120
gccaacgtgc ggtaccgcgt gcgcacgcgc ttcggccccg acacgctggt gcccatgtcc 153180
ccgcgcgagt accgccgcgc cgtgctcccg gcgctggacg gccgggccgc cgcctcgggc 153240
gcgggcgacg ccatggcgcc cggcgcgccg gacttctgcg aggacgaggc gcactcgcac 153300
cgcgcctgcg cgcgctgggg cctgggcgcg ccgctgcggc ccgtctacgt ggcgctgggg 153360
cgcgacgccg tgcgcggcgg cccggcggag ctgcgcgggc cgcggcggga gttctgcgcg 153420
cgggcgctgc tcgagcccga cggcgacgcg cccccgctgg tgctgcgcga cgacgcggac 153480
gcgggcccgc ccccgcagat acgctgggcg tcggccgcgg gccgcgcggg gacggtgctg 153540
gccgcggcgg gcggcggcgt ggaggtggtg gggaccgccg cggggctggc cacgccgccg 153600
aggcgcgagc ccgtggacat ggacgcggag ctggaggacg acgacgacgg actgtttggg 153660
gagtgacggg gggggaaact tccgggagcg ggggaggggg gagatgggga gagggggaag 153720
gaatcgggcg tctgtgcgcc tttaagacag acgcggcgat ggccgcgcgc gtgtgtgaga 153780
aataaagaac gagacagacg aaaacgtacc gccttgtgtg gtttattcgg gggtcgggcg 153840
ggcgggggtc gggcgggcgg gggtcgggcg ggcgggggtc gggcgggcgg gggtcgggcg 153900
ggcgggggtc gggcgggcgg gggtcgggcg ggcgggggtc gggcgggcgg gggtcgggcg 153960
ggcgggggtc gggcgggcgg gggtcgggcg ggcgggggtc gggcgggcgg gggtcgggcg 154020
ggcgggggtc gggcgggcgg gggtcgggcg ggcgggggtc gggcgggcgg cacgtctccc 154080
gcgcccgcgg ggggtctggg gctctgacct gagtgcaggt tacgaaggtc aggtggcccg 154140 agccccccccg caggagcggg agggaaggca cggggcgcgg gagggagggg ctgctgcgag 154200
ctcggggccg cgggcgcggg gggaggggcg ggggaagccc ccggggcggg gcgcggggga 154260
ggcggccgcg ggggaggcgg ccgcgggacc gcagccccgt ggcgcgcggg ggggaggggc 154320
tgccgcgagc tcggcgggat ggaggggagg gagggggtgg cggggaaccg tgtgcgggcg 154380
ggcgggtgct tggtgcaact gtctggtctg cgagggcgag cggtggtgcg actggcgtct 154440
tcgggggggc ggggagcttg ggagtgtgtg gtggtctgcg gcacagcctg ctagtccccg 154500
tcctgccgcg cgggggcggg cgcgggaaaa aagccgcgcg ggggcgcccg cgggaaggca 154560
gccccgcggc gcgcgggggg aggggcggcg cccgcggggg agcggccggc tccgggggag 154620
ggacggggaa gggggcgcgc ggggctgccc tgccgcccgc ccgccgccgc cgcccgcctt 154680
cgcgcccccc cccaaaaaac accccccccg ggggttgact ccccggggga aaagaggcgg 154740
ggcggg 154746

<210> SEQ ID NO 111
<211> LENGTH: 124884
<212> TYPE: DNA
<213> ORGANISM: Human herpes virus strain 3

<400> SEQUENCE: 111
aggccagccc tctcgcggcc ccctcgagag agaaaaaaaa aagcgacccc acctccccgc 60
gcgtttgcgg ggcgaccatc ggggggggatg ggattttttg ccgggaaacc cccccccgcc 120
agcctttaac aaaacccgcg ccttttgcgt ccacccctcg tttactgctc ggatggcgac 180
cgtgcactac tcccgccgac ctgggacccc gccggtcacc ctcacgtcgt cccccagcat 240
ggatgacgtt gcgaccccca tcccctacct acccacatac gccgaggccg tggcagacgc 300 gccccccccct tacagaagcc gcgagagtct ggtgttctcc ccgcctcttt ttcctcacgt 360

-continued

```
ggagaatggc accacccaac agtcttacga ttgcctagac tgcgcttatg atggaatcca    420
cagacttcag ctggcttttc taagaattcg caaatgctgt gtaccggctt ttttaattct    480
ttttggtatt ctcaccctta ctgctgtcgt ggtcgccatt gttgccgttt ttcccgagga    540
acctcccaac tcaactacat gaaactactg tccggaaggg gaaggtattt attctcgctt    600
gcagcttgtc gcgcgtgtat gcacaacaaa agctatatat gtcaccaaag ccaacgtcgc    660
catctggagt actacaccca gtacgttgca taacctgtcc atttgcattt tcagttgcgc    720
ggacgccttt ctccgggatc gtggccttgg gacatcaacc agtggaataa gaaccgccgg    780
tggtcttgtt tgaacgacga gtggcgacgc gttgttctgc ataagctctg tatgctgata    840
cataaacaca gagtctgtat cgctatcaga ttcccgaaca ccttccggta ccccatactc    900
cgataccctg gacattgcgg atcccaaaaa tataatatta acaggatttg cttatacttt    960
gctacagctt atataaattt atgtgcgata catcttaagt gcatccgtac gttatttata   1020
cattgcctgt cacgtgaaaa gactgtgtta cccaataaag gttctacaaa aaatgcttta   1080
ttgggtgttt gtttaatagc tattatcgta acccaccccc gtaaaatcat aaaatgcatg   1140
taatttctga gacacttgca tatgggcatg ttcccgcatt tattatgggc tccactctgg   1200
tgcgtcccag tttaaacgcc accgccgagg aaaatcccgc gtcagaaacg cgatgtttat   1260
tacgagtgct tgcggggaga actgtagacc tgccaggcgg aggaacgtta cacattacct   1320
gtaccaaaac ctatgtaatt attggcaaat atagcaaacc cggcgaacgt cttagccttg   1380
cccgtctaat agggcgtgca atgacgcctg gaggtgcaag gacatttatt attttggcga   1440
tgaaggaaaa gcgatccaca acgcttgggt atgaatgtgg tacgggcttg catttactgg   1500
ctccatctat gggtacattt ctccgcacac acggtttaag taacagagat ctctgtttat   1560
ggcggggtaa tatttatgat atgcatatgc aacgtcttat gttttgggag aatatcgcgc   1620
aaaataccac tgaaacacct tgtataacgt cgacgttaac atgcaacttg acagaagact   1680
ctggtgaagc cgcacttacc acgtcagacc gacccactct cccaacccta acagcccaag   1740
gaagaccaac agtttccaac attcgtggaa tattgaaagg atccccccgt caacagccgg   1800
tctgtcaccg ggttagattt gccgaaccta cggagggcgt attgatgtaa tcactaaata   1860
aaatacacct tttttcgatt gtacgtattt ttatttaaat gtgtagttca tagtccgccg   1920
acagccgctc gggcttttcc cccacataca acatgatcgt atgcctcgga tgcaccggtc   1980
caacactccg ccgagaaggg ggatttacaa tgacagtgat acccaatagc cgccagatgt   2040
acacccagct gtccggactc cagcatcatc tgctgagttg cggcgctgaa gggtgcatcg   2100
catagggtgt tataattagc catttccggt aacagtcgtt gggaatttag gaggctgcaa   2160
aacggctgta ggtcaacata cattggggat tcagatggtt tatctcgacg tccaagtcca   2220
atcaaaaaag cgtgtaaatc atcagcccgg ccgcatgttg ctcgaagagc acataacctc   2280
ttaacaccgt acagagggga tggcgtcggt gcatgtgagt tggcagggca tgtccacgtt   2340
gtttccaacg ccagtggcgg tataacttgt gtaaacgacg ccaacgggtc aggtttaaga   2400
ttcactcgga tgggttgact gctttcggaa gctcccgttg tatccattaa ttaaacgttc   2460
ggtacacgtc tggtgtgtgt tttacccgaa tcagagacgg aattgcaaag atattggttt   2520
gaaagcaatg taatcccgcc catatatccc caacgtcgcc ttaaaaactc ccacaatatt   2580
acatttttat tagtctttta ttaatataga atcacataaa caattgataa aatcaagggg   2640
tggtgtataa tgattaaaaa tataaattga tatgttttac aagcatgaaa taggtattta   2700
```

-continued

```
ctattctaac aggtaaatat gcttaatgat taaaaataca aattagtatg ttttgacaag   2760
catgaaaaag gtatttttta ttttagcagt taaaggtact acacttaaaa tatttaccgt   2820
atggacgggc gtcagaaaga tgcccggccc aagttgagag ggtacattca acacgaccac   2880
actcgcgttg gtgggtgatt agggcctcta aaacaccggc cagacatgac ccgggtgtat   2940
attcttgtaa cacttgaacg ttacaactga tatcatcata ttccacaaat ttagagccac   3000
ggacaactat attagcaatg cggcaatca taacaaacat ataagtagta atacacgtga   3060
tatcactaaa acgttgctgg cgcaacagtt cggggagagt acgagacccc aaatcgttgt   3120
ccctgtttag aagaagacat cttacaaaag gccccagctt taactttaaa ttctccaaaa   3180
gtgacttcga ggttgcaaca atgggattat ttgtgtagat gggcaagttt tttgccgcta   3240
acattttaat ccacgttaac agttcatccg cagactccaa cgcttcaatc aaagattctc   3300
cacgtatgac tctctcacgc aacgcgcggg caatacgtga gtccatttta tatgactcaa   3360
aggtacgata aagttcatgt ccgtacaaca tcaactccgg ccaagatgtg ttttgtttta   3420
tccccggaaa acatccaccg gaagcccatg aatcaccctc ttgtattgtg gcatatcgga   3480
ctaccagttt ttcaattgtt tcatctaaat ggcgtaccga gtcaatggtc acgctggctc   3540
ccgcggtgga gacgacttca atagcacggc ccgtaattcg atcgaccggg atatcatact   3600
cttttcgaat acgctctcgg cgggcgtctc tcttggaaaa tcgcaacctg tacgattcgt   3660
catgtgtctg atcatttctt tctcccgtgg tcattgcagg aggcgttgta ggacgccgtc   3720
ttcgatttga cagggatcga tcacggtgtt ttcttgaact ttgagtgtta taagatctgg   3780
atgatcgtcg atgtccccgt tcgatgcgtg catatccagt ctccacgtct cttcctccat   3840
gatggtttga atcgggtaat acaacaacca aagttttcgg gcgattgtgg tggtagcttt   3900
cacgccttcc gtgccttcgt ttggaatacc gtggattata tgctgtatct gcagtacgct   3960
ccacatacac agttctagac gttgtggagt cctcgcctgg agtggagcca atagcttcat   4020
catttgccca atcggtgact tccaatgcaa agtcatccga aggttcgtct ggtagcaaat   4080
tcataaagtc ttcacaaata gtagacacgt ctgggtcggt tggaattgaa gcagaggcca   4140
tggctgcaaa atatctgaca attgcgtgtt tgcagttgcc tgtatcttcc gccaatgttg   4200
tagaatttat aggctcaccc aaccccgcaa tgggcgtgtt tagtcacatg attaatgctt   4260
ctgggagttt tcactttccc caaacaagct tacctgcacc ctttgttcgt aatgcataaa   4320
aataaccact gctatagcaa atatgacgat ataaaaacat tttatagcaa ggccggacat   4380
tactgtagcg caacatgttg tgcatatacc acgtattccc cccgtattga tatgatttaa   4440
atgattatcc ttggttggtt ttggtctaac ataagatata agctctacta tagcgagcgt   4500
gcatacaaca acccaggcca gaatccgaat gtatgtgggg tataataacg cgcatggtgt   4560
atatgcaacg ccaagcgtta aaagcacaat acatccagat gatatatgag cgataacctc   4620
caaaagcatc aataacgtaa cacctttatg catatataaa aaacttatag ggtcagcatt   4680
aaatacttta ctcataccat cccgtcgcat ggaaacatca cataacaacc ttgccaactt   4740
tgtatatggg taaccaagaa gaatgttcga aataacccgt gttacgtaat tcagtgaata   4800
tgatgtgggg gatattaact cacaggatga tcggaatggc ccaaacatac gacgtattcg   4860
tcgaaattgt aaatacatac catatacaaa ccatgcaaaa aaaatcattt ttagctgcac   4920
gcaccaaaaa taagcgtgac aattacgtgt tcccagaaca attcgaattt tgtcatgcaa   4980
aggtgtagaa atagcggttt ttaccatagt atctcctgat aatagatttt cccggcagct   5040
gtaatcgtat ccagataggc catccaaaaa cgttgagtgg tttacaaacg ttacatatat   5100
```

aagagagttg ttataagacc cccatacaac cggtccacca ttaatcaccg tggttgcata 5160
cacacactca tgttcaaact ttacacgagc ggtataccat agggtaaaaa cagcatgtcc 5220
gctaagtaga cacataatta taaaatgttc tgtcttgatt cctaaagcct gcatgacccg 5280
tggaagatgg caattcaagc acgatgtagt atcacacggt tggtgttaac tcgaagttaa 5340
atttggataa ttaggtactt ctagagtaaa gattgtatgc atgcgattgc tatcgcactt 5400
tgtagcaaaa cattgttgtg caagcgaaat acacaaacgg ttgtgatgat ccactcgcag 5460
agacacaaat gtccggggag ccgttcttcc tccgcgatgg ggatatcgaa gacaagtgaa 5520
cccttttgtt ccgcatatga gctgaaataa cacccagtcc cttttgatgg cgatacactt 5580
tgatgatgtt aaggtatatt cgcgatcacg cccggggaaa tgaacagcaa tatgctccac 5640
aatagattct aatattgtgc tgtcgacaaa ggcctccagt gtaaatgcgt ccagacaagt 5700
taccccgcgc tcttttagag cctttgttaa agatatttgc ggggagctaa atatttgttt 5760
attacgcgca accttacgtt caaaaaactc tgcgtattcc cccccaaggt tatgtaaaat 5820
aaattgcact ggaacattcg actgcggtct tgaatgaaaa tgaaagtttg ccgggtttct 5880
atgtgatgtc acaaacgcta atatatcaat acactgctca ggtacaacat aaaatgggag 5940
tagttgtcca accgccgtcc ctgtggttgt tactttggag aaaaaaggca gtcttaaact 6000
atgtccgtgg ctataaacac cagtatctat aaacgaaaag tcccgtaaat acggaccaat 6060
atattcaaca aattcccgtt ccagcaacac cgcttgctgt aatatttgtg caaacccctt 6120
taaagtggaa gaccccacta acgcataggg atttgggatt ggtacgcata ccctgaaacc 6180
tattttctct ttacagttac agggtagagt ttcatgcaag ttttcattgt ttgatacatc 6240
ggcgtgtgta tggacttcag acgttgtctg tgtatcaaaa aaccatacat cctctgtata 6300
attctcttct acacacgtgt ataattcgcc attttctatg taaaaatcga tgtcagaatg 6360
gctggttata tccaataaat tatcatcatc caacacctca acggtaggtt caggacatgc 6420
agttttataa aaataacatg ggtctttgtt agggtttacc acggcctttg gaaaaagtaa 6480
ttgcatggcc gttaaaatac catgacgaaa tgctcgcatg ccggcatgta aaatacccaa 6540
tgggatgggt tttcttatat gaaagtctac atcaagtatg aggtttgtga ttataagatt 6600
tgtattaaat agctcattcc tgtttatata aagctgatct ttgggtatgt ttgatgaaat 6660
tttagaaacg tttttaacag acgtagataa tagtaaagtc aactgcatat ctcgtagtga 6720
agcggcaaca aaattacatg gattaatttg tttaaggtcc tccgcaatta atcgagcctc 6780
gtgcggtaaa gtgtaacggt ttgttattga tgaccacgta tcattagcaa taacagcaaa 6840
tgcttgggcg ccgtgaggca aggctacccg atatacaggc attggtccag ttacctcaga 6900
atggccgatg agggcttcta atggagtttt ataactcagg atggatacat catgtgtggc 6960
tatcccagtg gcagcagaga aaaacagtaa tagttttgta atccccgggc tcgtatcaaa 7020
accagtacga ccactttggt taggtgtatc gtttgcaaag ttggctgctc gtaacgcctc 7080
cgcggaaaca cccgaatcct caaaattaga caattcgtca aaaccgggtg gatttgaggg 7140
aatagtggag gaccatccat atggactaaa ttgtttttca atgttttcca cacgacgagt 7200
tagcgttgta gctaggtcac atacgcctat aaacttgcta ggttttgcgg catacgtaag 7260
acttaaagta tatgttttag taattgtata tttatgtcca atctcaggtc caagttcagt 7320
gacatcacaa attacgttct tttttatata gtcacgcatg ttgagacgag aacgtacatg 7380
attaaaaaaa ttagcagtag ctctttttcc caggttggat gattttaaga ggaccggttt 7440

-continued attcacaaaa tctgagtatg taaccgcttg taggtggtct gcgatctgtt tccgattgaa 7500
acattcaaaa tgtgccagat aaatataatc aacaaattca cggtctggaa ctttaaggcc 7560
ttttctatcg ttggtaatat actccgatac tgcgtgtatt tccgttgtgt ctgtatgtat 7620
tcgctgtaaa atgtacgata gagcattttt ggctgtcaaa cctcgtgtat atgttgagga 7680
acaacaaaac atggaaagtt tatcaaaaga caacaagtcc gaaatattgt acccactaca 7740
attaggtaat gccgggactt ggtaagttaa aaacaaatct ttaattgcct gtaagtcata 7800
taagggggtt tccaacgtat tgtaacttgt gtccgtttgt aacaagtaat agcgtgtagc 7860
caacactagc gttttttcag agggtccaaa tcgaacaata taccaaaacg gcgagcatcc 7920
atacccccag tagagtcgtc gatatgcagc caatacttga cgttcgtaat gggcatataa 7980
tgatgttagc tcctgacgac caacggattt tttaactaac ttgcagagtg ttgcctctgt 8040
gatgcatagg ccgttgtccg ataatccctt tcggtttaaa tggtgtgttg ttaccatcag 8100
agtttgtata acttccgagt gaatgtcaaa cgtctccgat atacataggg tatcagatat 8160
tatatgcgga tttaggggtg ctccatacca taacgcctta tataaagctt taaaatcagt 8220
ttgggtttta aaacaacaaa aaaatatagg ccagacccgg gatcgtacat ctccagttga 8280
aaatccacca attaaataaa aaataacgtt gacgtcccta ctacaaaata aatgcattat 8340
ttggttttct tcatcgtttt cagttacttc acgtgggcgt ttagttggga ttacttgcgt 8400
gatctcttcc ctcccatttt tgacaaagac gtcatctaag tcgggagtcc aagtataact 8460
caccacatac agaggttctg tgcttatctg cccggtaagc aacaacagcg agtgggagat 8520
tgcacatccc tttgtggcaa ataataaccg aatcgtcggt ttggaggatt tatccatagt 8580
tcaatacgtt ggaaagccag tcaatcatgc agacggtgtg tgccagctta tgtggatatg 8640
ctcgaatacc aactgaagag ccatcttatg aagaggtgcg tgtaaacacg cacccccaag 8700
gagccgccct gctccgcctc caagaggctt taaccgctgt gaatggatta ttgcctgcac 8760
ctctaacgtt agaagacgta gtcgcttctg cagataatac ccgtcgtttg gtccgcgccc 8820
aggctttggc gcgaacttac gctgcatgtt ctcgtaacat tgaatgttta aaacagcacc 8880
attttactga agataacccc ggtcttaacg ccgtggtccg ttcacacatg gaaaactcaa 8940
aacggcttgc tgatatgtgt ttagctgcaa ttacccattt gtatttatcg gttggcgcgg 9000
tggatgttac tacggatgat attgtcgatc aaaccctgag aatgaccgct gaaagtgaag 9060
tggtcatgtc tgatgttgtt cttttggaga aaactcttgg ggtcgttgct aaacctcagg 9120
catcgtttga tgtttcccac aaccatgaat tatctatagc taaaggggaa aatgtgggtt 9180
taaaaacatc acctattaaa tcggaggcga cacaattatc tgaaattaaa cccccactta 9240
tagaagtatc ggataataac acatctaacc taacaaaaaa aacgtatccg acagaaactc 9300
ttcagcccgt gttgacccca aaacagacgc aagatgtaca acgcacaacc cccgcgatca 9360
agaaatccca tgttatgctt gtataaatat tgaaataaaa actaaaaacg tttctggtgt 9420
atgtttttat tttgtatata aaattaaaac attgctggct ggcgtggtta ttacatttaa 9480
tgttttagta gaaaatcgac atcgtttgtt tctttatcag ttgaaccaaa tccacgcgtt 9540
ccccgttcgc tgggtgtggc tattagatct aacgttttag taaaatacca ttgtacaccc 9600
ggtatgccac atttaccgcg gatagcataa ggaaatgcaa tattacttaa aacgttgtgt 9660
tttaagtgta tttgggtgtt gtgatctatt aacaggacct gtgcaagacg atctcccgtt 9720
tttatacgta tgtcatcacc cgtgagatta tatacgtaga atttacagtg ttctcctgca 9780
ggccatgccg ttggacacac gataatgcct gatcggcttt tcgatgatct tccaaaaata 9840

-continued

```
taagcgttta tactcggatg ttgtaagtcc cagtctctta taatcggtaa gacaattttt   9900
ataaattcat tcctttttaa atataggtta tatggtacac aaatatcata tcccgcgtct   9960
tcttggcgtt ttggattgat gatatgtttg taggttaagg gaacatcgat atggtattct  10020
gcagaatccc tatgtaaagg ttgcccctgc tgtaccgtgg aaatatcagc aaattcaggt  10080
ataacgggtt tttcataatt tgacggcgag tttgataagg gttgaacttg tatcgattta  10140
aaaattggat ccagatgttt aagaacgttt tttgggagaa ggcgactttg tcttaatttt  10200
accgggaaca agtagattgt taaatgtccg ggtaaaataa cggttactcc tggccggtaa  10260
tacaaaaggg ctgaaattac tcctctgtaa cccgcatcaa taactccgtt ggcgacaaaa  10320
aaattgtctt catcagcaag ggcagtatct ttgcattgaa ttaacaacag tgcgtattca  10380
ttgggaggcg ccgacttaac caacagctcc aactgctgca tataaaaacc gccccgtgtt  10440
acagattttt cagatggcag ttcgagtttc ttgtggttcc ggagtaacaa cggttgatgt  10500
cgacttactt tatcgtctaa cacgcattgc agcgtatctg cacattcagg ttgaacttct  10560
attaaaattg tatcttttaa acaccgattc ggaatagttt ggctacaaaa catatcacct  10620
gtatttactg ccgtttccaa gatgggatca attaccgctt cgttcatatt aataacgatg  10680
caaattttat ttttttgtga agacagcagt ggggagccaa actttgcaga acggaatttt  10740
tggcatgcca gctgttcggc tcgtggagtt tatatcgacg gatcaatgat caccaccctt  10800
ttcttctacg catccctttt gggggtgtgt gtagccctta tttcgttagc ttatcatgcg  10860
tgtttccggt tatttactcg ttctgtatta cgcagcacgt ggtaaacccg tttgcctata  10920
aaaggggcag gcgtgtataa gagggcccct gtttaatacg cggtctgccg tgtttggata  10980
tttcacgacc ctatcgttta tttacgtaat ggcatcttcc gacggtgaca gactttgtcg  11040
ctctaatgca gtgcgtcgta aaacaacgcc tagttattcc ggacaatatc gaaccgcgcg  11100
gcgaagtgtg gtcgtaggac cccccgatga ttcagacgac tcgttgggtt acattaccac  11160
agttggggcc gattctcctt ctccagtgta cgcggatctt tattttgaac ataaaaatac  11220
gacccctcgc gtacatcaac caaacgactc cagcggatcg gaagatgact ttgaagacat  11280
cgatgaagta gtggccgcct ttcgggaggc ccgtttgaga catgaactgg ttgaagatgc  11340
tgtatatgaa aacccgctaa gtgtagaaaa accatctaga tcttttacta aaaatgcggc  11400
ggttaaacct aaattagagg attcaccgaa gcgagctccc ccgggagcag gcgcaattgc  11460
cagcgggaga ccaatttcct tcagcactgc accaaaaacc gcaacaagct cgtggtgcgg  11520
tcctacgcca tcatataaca aacgcgtctt ttgtgaagcg gtccggcgcg tagccgccat  11580
gcaggcacaa aaggctgccg aagcggcttg gaatagtaat cccccaagga ataacgccga  11640
attagaccgt ttgttaaccg gagccgttat tcgtattacg gtgcatgagg gtttaaattt  11700
aatacaagcc gctaatgaag cagacctagg tgaaggagca tcggtatcca aacgtggaca  11760
taatcgaaaa actggagatt tacagggggg catgggtaat gaacctatgt acgcacaagt  11820
tcgtaagcca aaaagtcgaa cggatacaca aacgactggg cgtataacta atcgaagtag  11880
ggcccgttct gcatcaagaa ctgatacgcg aaaataggga tataattacg cagtaacggt  11940
ttacccggta ttatgtataa taaataaacg tataaaagac agtcgtggtt tgtgtttatt  12000
ataaatgtgt attatatgtc acatattata aactgtttaa atagtaccac gtggtattat  12060
gaacagttta taatcagttg ctaccaaaca aaccccatta gacggcgggt tttgataaag  12120
ggaatcgctt atttaaacta aagattttac tctataagta tggagtgtaa tttaggaacc  12180
```

-continued

```
gaacatccta gtacagatac gtggaatcgt agtaaaacgg aacaagcggt tgtggacgca  12240
tttgatgaat cgttgtttgg tgatgtagca tcggatattg gatttgaaac gtcgttatat  12300
tcacatgcag ttaaaactgc tccgtctccg ccttgggtag ctagccctaa aattttatat  12360
caacagttaa tacgggatct tgatttttca gaagggccgc gtttactatc atgtcttgaa  12420
acctggaacg aggatttatt ctcatgtttt cctattaatg aggacctata ttccgatatg  12480
atggttttat ccccggatcc agatgacgtt atctcaaccg tttcaaccaa agaccatgtt  12540
gaaatgttta atttaacaac ccggggttcc gttcgattgc ctagtccacc aaagcaaccg  12600
acggggcttc cagcttacgt tcaggaggtc caggattcgt ttaccgtaga actacgcgcc  12660
cgggaagaag catacacaaa actactagtt acttattgta aatcgattat acgttatctc  12720
caaggaacgg cgaaaaggac gacaataggt cttaatatac aaaaccctga ccagaaagct  12780
tacacgcaac tcaggcaaag tattctactt agatattatc gtgaggtggc aagtttggcg  12840
cgtcttctgt acctacattt atatttaacc gtaacgcgtg aattttcctg gcgtttgtac  12900
gccagtcaat ctgcacaccc ggacgtgttt gcggctttaa aattcacctg gaccgaacgt  12960
cgacagttca cgtgtgcgtt tcatcctgta ttatgcaacc acggcattgt gttattagaa  13020
gggaaaccac taacagcgtc tgccttgagg gaaataaatt accgccgccg agaactggga  13080
ctgcctctag ttagatgtgg tcttgttgaa gaaaacaaat ctccgttggt tcaacaaccc  13140
tcattttcgg ttcatttacc acggtcggtg ggttttctta cccaccacat taagcgtaag  13200
ttagacgcat atgcggtcaa acatcctcaa gaaccgagac atgtacgagc ggatcatcct  13260
tacgcaaaag ttgttgaaaa tagaaactac ggtagtagca tcgaagctat gattttagca  13320
cctccgtccc catccgagat cctgccgggg gacccaccac gcccacccac gtgtgggttt  13380
ttaacgcgtt aaacgtcatt ggggtagagg gtgtaaataa attacgaaaa cgtgcatgcg  13440
ttttttattt ttacaatgcg ccgtatatgg tatgtctgtc atgtgctcta aagtcccata  13500
tataaaagaa gccccaacga gtgtatgcgt attgcgtacc gcgaccctgg gatgttttac  13560
aggcgcgttt gtttgtctcg gttataagta tgcagtcggg tcattataac cggaggcaat  13620
cccgccgaca gcggatatcg tctaatacca cagactcccc ccgtcacaca cacggaacac  13680
gttatcggtc aaccaattgg tatacacacc caccccagat attgtccaat tcagaaacat  13740
tagttgcggt tcaagaacta ctgaactccg agatggatca ggacagcagt tctgacgcat  13800
cggatgattt tccgggatac gccttacatc attctacata taatggatcc gaacaaaata  13860
catcaacttc cagacatgaa aatcgcatat ttaaattaac ggagagggaa gctaatgagg  13920
aaatcaacat caatacggac gcgatcgacg acgagggaga ggcggaggag ggagaggcgg  13980
aggaggacgc gatcgacgac gagggagagg cggaggaggg agaggcggag gaggacgcga  14040
ttgacgacga gggagaggcg gaggagggag aggcggagga ggacgcgatt gacgacgagg  14100
gagaggcgga ggagggagag gcggaggagg gagaggcgga ggagggagag gcggaggagg  14160
acgcgatcga cgacgaggga gaggcggagg aggacgcggc ggaggaggac gcgatcgacg  14220
acgagggaga ggcggaggag gattattttt ctgtaagtca agtttgcagt cgagacgcgg  14280
atgaggttta ttttacgtta gacccggaaa taagttacag taccgatctt cgcattgcaa  14340
aggttatgga gcctgcggta tcaaaggaac ttaatgtatc aaaacgttgt gttgaacctg  14400
ttaccctaac aggctctatg ttagcgcata atgggtttga tgagtcctgg tttgctatgc  14460
gcgaatgtac ccgtcgcgaa tatattacgg tccaaggatt atacgaccca attcatttac  14520
ggtatcagtt tgatacttcc cggatgacac ccccacagat tttgagaact ataccagccc  14580
```

```
ttcctaacat gacacttggt gaacttttat tgatttttcc tattgaattt atggcccagc  14640
caatttctat agaacgtatt ttagttgaag atgtattttt agataggcgg gcttccagta  14700
aaacacataa atacggcccg cgttggaatt ccgtctacgc acttccatat aatgcgggta  14760
aaatgtatgt acaacacatt cctgggtttt atgacgtgtc cttacgtgct gtgggccaag  14820
gaacggccat ttggcatcac atgatattat ccacagcagc atgcgctatt tctaatcgca  14880
tttcacatgg agatggatta ggatttttgt tagacgcggc aattcgtatt agcgcaaact  14940
gtattttttt gggacgtaac gataattttg gcgtggggga tccatgttgg ttagaagacc  15000
atcttgccgg attaccacga gaagccgtac ccgacgtact ccaagtgaca cagttggttt  15060
tgccaaatcg gggtccaacg gttgccatta tgcgtggttt ttttggggcg ttggcatatt  15120
ggcccgaact aagaattgct ataagtgaac catctacatc tttggtgcga tatgctaccg  15180
gtcacatgga acttgccgaa tggtttttat tttcacgtac acatagttta aagccacaat  15240
ttaccccaac ggaacgggaa atgttagcgt catttttttac gttgtatgtt actcttggtg  15300
gaggaatgtt gaactggatc tgtagagcaa ctgcaatgta tttagctgct ccttaccatt  15360
cccgttcggc ttacatcgcg gtctgtgaat ctctgcccta ttactatatc ccggttaata  15420
gtgacctgtt atgtgattta gaggtattac tgttaggcga ggtcgacctc ccaactgttt  15480
gtgaatccta cgcaactatt gcacacgaat taaccggata tgaggctgtt cgcacagcag  15540
ccacaaattt tatgatagag tttgccgatt gttataagga aagtgagacc gatttaatgg  15600
taagcgcgta cctgggggcc gttttattgt tacaacgggt gttgggtcat gcaaatcttc  15660
ttttgttgct tctctccggt gctgcgttgt acggaggatg ttcaatttac atcccccgag  15720
gtattttaga tgcatataat actttaatgt tggcagcaag tcctctttac gctcaccaaa  15780
ctttaacatc cttttggaaa gaccgcgatg atgcaatgca aactttgggg attcgaccga  15840
caacggacgt tttacccaaa gagcaagaca ggatagttca ggcatcacct atagagatga  15900
acttccgttt tgtgggattg gagaccatct atccccgaga acagcccatt ccctccgtgg  15960
acctagccga aaatcttatg caatacagga atgaaattct gggtttggat tggaaaagcg  16020
tagccatgca tttactacga aaatattaag ggttgtgatt tttttcatta ggatgaaaag  16080
aacgtttcct agccacaccc acaaaggagt ttgtaaaata aaatctctgt ttagacctta  16140
aaatttgttg tgtgtgttgt gtggggggtc cgtgaggatc gacctttaca agatataatt  16200
tgtccatatc gcaatgtttt ctcggtttgc gcgttccttt tccagcgatg atagaacgcg  16260
taaatcttat gatggtagtt accaaagttt taatgccggc gaacgtgatt tgcccacacc  16320
tacccgggac tggtgttcta tttcccaacg cataaccagc gagcgcgtga gggatggatg  16380
tcttattcca acgcccggcg aggctttgga gacggcggta aaggctttat ctgaaaagac  16440
cgacagccta acatcgccgg ttttacaaag taccgaaaga cacagtgttc tgcttggatt  16500
acaccataat aatgttcctg aatcgttggt ggtctcgtgt atgtctaacg atgttcatga  16560
cgggtttatg cagcgttata tggaaacaat tcaaagatgt ttggatgacc tgaaactttc  16620
tggggatgga ctttggtggg tttatgaaaa tacatattgg cagtatctca aatacaccac  16680
aggagccgag gtaccggtga cttcagagaa ggtaaataaa aagtctaaat ccacggtttt  16740
gttgttttca tccgtagttg ccaataaacc aatatccaga catcctttta aatctaaagt  16800
tataaattcg gattaccggg gaatatgtca ggagctacgt gaggcgttag gagctgtgca  16860
aaagtatatg tattttatgc gtccagatga tcctacaaac cccagcccgg atacaagaat  16920
```

-continued

```
acgtgtacaa gaaattgcgg cttacacggc tactggctac gggtggatgt tatggttctt  16980
ggacgttgtg gacgccaggg tatgtcgcca tctcaaactt caatttcgac ggattcgagg  17040
gccgcgcgcg tctgttattc cagatgattt gcttagacga catttaaaaa cgggtcctgc  17100
ggtctcagcg ggcacaggag ttgcgtttat tttagcagca acaactgcca gcgctcttac  17160
tgcgcttttg cgtattagtg tattatggcg aaaggaagag tggcgggatg gtttaaatgg  17220
aaccgcagct gcaattgttg cggcggttga acttattacg cttttgcacc accattttca  17280
atacttaatt aatatgatgc ttattggata tgcatgttgg ggggatgggg gattaaacga  17340
tccttatata ttaaaggcgc tacgtgccca gggacggttt ttatattttg cgggtcagtt  17400
ggtcagaaca atgtcaacac acagttgggt tgtgttagag accagcaccc atatgtggtt  17460
ttcccgggcc gtggcgcaga gtattttagc acatgggggt aaacccacaa agtattatgc  17520
tcaggttctt gccgccagta aacggtatac tccgttacat ttaagacgta tatccgaacc  17580
atcgagtgtg tctgatcagc cgtatattcg ttttaatcga ctgggatctc caatagggac  17640
aggtataggg aatttggaat gtgtctgttt aacgggaaat tatttatctg acgacgtaaa  17700
tgcaagttcg catgtaatta atacagaagc accgttaaac agtatagcac ccgatacaaa  17760
tagacagcgg acttctcgcg ttttagttcg tccagacacg ggtttggatg taactgtccg  17820
aaaaaaccac tgtctggaca taggccatac ggacggtagt ccagttgacc caacgtatcc  17880
tgatcattac acccggataa aggcggaata tgaaggtccg gttcgggatg aatcaaacac  17940
aatgtttgac caaagatcgg atttacgtca catagaaacc caagcatctt taaatgatca  18000
cgtatatgaa aatataccac ccaaggaagt gggttttaac tcatcttcag acctggatgt  18060
ggatagcctt aacgggtaca cctccggaga catgcataca gacgatgact tatcaccaga  18120
ttttataccc aacgacgttc ccgttagatg taaaaccacg gttacgttta ggaaaaatac  18180
gcctaagagt catcattaag tacagcggtt aatagatagt tatggactag gcactttggc  18240
ggtcatttcc acaaccaggt taaaattggg ggatttggga gaaaatagtc tattgcgtat  18300
tttctgttca ataattggac tgcgttattt aaaggtctga ttggttgatt gggttataaa  18360
aggaattact cctttaaatt ttacttaatg tacccacaat atcaagtggt cgtttgtatt  18420
taacgattat taccggtacc atgggagact tgtcatgttg gacaaaggtg ccgggtttta  18480
cgttaaccgg cgaacttcag tacttaaaac aagtggatga tattttaagg tatggagttc  18540
ggaaacgcga tcgaacagga atcggaacgt tatctttatt tggaatgcaa gctcgataca  18600
atttgcgaaa tgaatttcct cttttaacta caaagcgtgt tttttggagg gccgtcgtgg  18660
aagagttgtt atggtttatc cgcgggtcaa ccgattccaa agaactcgcc gctaaagata  18720
tacacatatg ggatatatac ggatcgagca aatttctaaa taggaatggc ttccataaaa  18780
gacacacggg ggaccttggc cccatttacg gcttccagtg gagacatttt ggagcggaat  18840
ataaagactg tcaatcaaac tatttacagc aaggaatcga tcagctgcaa actgttatag  18900
atacaattaa aacaaaccca gaaagccgac gaatgattat atcgtcttgg aatccaaagg  18960
atatcccctt aatggtacta cctccatgtc acacgttatg tcagttttac gttgcaaacg  19020
gtgaattatc ctgccaagta taccagagat cgggggatat gggccttggg gtaccgttca  19080
acattgctgg atatgcactt cttacctaca tagtagcgca tgttacagga cttaaaaccg  19140
gagatttaat tcatacaatg ggggatgcac atatttactt gaatcatata gatgctttaa  19200
aagtgcagct agctcgatcc ccaaaacctt ttccttgcct taaaattatt cgaaatgtaa  19260
cagatataaa cgactttaaa tggacgattt ttcagcttga tggatataat ccacaccccc  19320
```

ccctaaaaat ggaaatggct ctttaatgga tttttaaatg ttgtcaagac agtagatgtg 19380
ttgcgaatgt aataaaatga tatacacaga cgcgtttggt tggtttctgt ttatgaacag 19440
caacggatgc atagggttgc gataactgcg ataagaccca atgtcccaag gatagatatc 19500
acaccaatta taactgctac aacggaaaat gtagtggcgt aggtagatgc atcgtaggta 19560
taaacggccg aaaacggagg gaattttta gggtaaccat ctagatgaca cgaataggtg 19620
ataggtccgt cgagttccga tgttggacaa gaactttgca tgtttacaaa ccgtttgttt 19680
tgatcacaca ccccagtaat ctcactgttt tcgtggttaa tgggagaatc gttaacccac 19740
catacgaaat gtacaacgcc acgtggcaca catttgccg tacatactat gtgtccatca 19800
ataataccta tagacacgtt gggaaatgga tagacgtcag gggtaacgac agcagaatat 19860
ttcatattag agacgccatc ccgaatccat aaaacattac attggatggc tgggggtggg 19920
taatccattt gtttttgctg tggaattcgt accgccgaaa cataactaaa taatccattg 19980
gcatattctt gtattgcatc ggttataaaa ttttttccga tgttaccaaa ccttgaagtc 20040
caccgaacac gtaccgagtg cggtggataa tactttgata cgttacagta ggctgcgtat 20100
gtctgtccgg ttaagactgg atcgccgaca acggtaatat ttggacgata atacgttgta 20160
actgtaatac tgtgttccga tatgacgttc ttagtttttg tattaacgac tcgccaaata 20220
tacgttccct ccgtggtagc atccatagat aaaattgtta cagaaaaatc agacgttgtt 20280
ttaacatctg gtattacata attttcctta gcgtgtgtaa atatctcagg gttgtttatt 20340
aagtttaaat cggcactgtt gctatataac ataaccggta aatctggcat gcgtattaac 20400
gcattgccca gttgacggtg cggatctata aggtgacgcg taaaccaaac ttcaatatga 20460
agatcggggc gtataagcga cttccacctt gttatatttg aaccttccgg atctaaagaa 20520
tattgttcat atgtttttg ttgctgctta aaggccgcct gttgtccggt cgttagacgc 20580
atgtaacaag gcatgataaa tgtgtgaaaa tagggtatgg attgtattcc gccgtgaacg 20640
cattgtatat tttcatatag aaaaggtggt tgtgaatgtt gggtgttggc tgcgggatcg 20700
ggctttcggg aagcggccga ggtgggcgcg acggcgggat cgggctttcg ggtagcggcc 20760
gaggtgggcg cgacggcggg atcgggcttt cgggaagcgg ccgaggtggg cgcgacggcg 20820
ggatcgggct ttcgggtagc ggccgaggtg ggcgcgacgg cgggatcggg ctttcgggaa 20880
gcggccgagg tgggcgcgac ggcgggatcg ggctttcggg aagcggccga ggtgggcgcg 20940
acggcgggat cgggctttcg ggaagcggcc gaggtgggcg cgacggcggg atcgggcttt 21000
cgggtagcgg ccgaggtata taattcagtt atacttacgg gtgtgggttg agattcagtc 21060
gataattgta tacacgcgat cgttaaaatt aaatttattt gtatccgctt catcctggtt 21120
tttattgaca catccacgct ccccttaaat aaaagattaa aacacccacc gcggaattta 21180
aatgatggaa acgtttttt cgacattggg aataataaaa acggcttttg caactttaaa 21240
aactttattt atctcgatta cgatacatat gtaccacata gatagcatag atttattata 21300
atataaacac acacgtgata tactttagtg atatgagatg ccataaaaca gtcaataggt 21360
ttaacgctta gtctcatcat ctgaatacac gtcaaacccg ccgcaactgt tgatgttaga 21420
attataatag ctccccatga aatgccggca aatgttacag ctatacccgt caccgaggtc 21480
gttgtatata atacaattac ccataggttt tttttttctt gatataaaac ggcaaaaccc 21540
tgtaacccaa atgctataat atgacctcct attgaaactg ctaacgttac ttgtgtaagt 21600
ttgataaaat gatttaattt aattatatgt gagattgccc acattaatgg ggtaactata 21660

```
tataacaccg ggggtataac agacattata cgaattcctt taaacacgcg tttaagggtc  21720
cgggaacttt ctcgatggtc acatactctc ccgcggtcat tttgtgtata tacaacggca  21780
aaacctaaat ctgtataagt gtttaattgc ttatggcgat ttttacgata tatacacgta  21840
tcttgcaaat cggtggcggc atcgacaatt gaaactagtg tgacaataga tatacacaat  21900
ccaataagaa cctcatattt actgacatac atatataaaa taacggttag taaacctccc  21960
aacccagttc ccaacatcat aacataaaaa taaatatgcg gtccattgaa tgtcgtaaca  22020
aagttgtagt aatggatatg cacagcagcc actgttccgg taatcgcgga tatggaaatt  22080
cccagtaatt ctacaaatgg aagatcccgg gatattgggc aaccaaccgc ccataacaca  22140
gcaaaaccca acacgaccac cgtctgcaaa catcgtccca attttgctaa tgtgcgtaga  22200
aatttcacgg atgttggcca taaccccgaa acgacgatca accccataat agttgcattg  22260
acggcagctt cgcagacgtg atattgtaaa attaacccgg acgtgataac gcttgcttgt  22320
agtcccacga gaaacaaccg cgatgctgag gttattgcac acgaattaca ttcttgaggg  22380
tttccgacac atccttggat tgattgagcg cggattaatt ctctgtctaa cacacccagg  22440
ttttcatcat ggacagctct ttcaccattc acggccatgt cttaagttta ataattcaaa  22500
acaaataaaa atgtgttcat ctatggtaca cacaagtttg tatgtaaaat ataagcaaaa  22560
gttgcactta tttaactgta catattacgt cagattcacg tgataattca gaataatcca  22620
gggttcctgc agggtccact ggaggagcca cacaatattc gcgaattccg attccctcct  22680
gccatgtggt ttcggggagt ttcccccccca ttttatttcc ggtatttttt tcgtttcttt  22740
ttgttaataa attgcgtctt ttttttaatg gtggttcatc cttcacagat tccatgttcg  22800
caaataattg catcgaggtt aatttttctt taaggtcttt gggacttaag aacgttgcat  22860
aaaaaaaaga atgcacgggt gcggaacgtt ggatatacaa tccaaccatg ggggagttag  22920
ttaaggcgag ataaaaatta atataacacg tctcatcccg tgttaactta agattttgta  22980
cggcagaacg gaatccactg tgtgtttcca ataatactcc aaattcacgc atactcccgc  23040
tgccataaac aacattatta aggatccttt ttgaatttgt gattgagcgt attaaattat  23100
atggtgtagg cttgcttccg tttatatcca aggaaacatt aaatgagata aaaccacccc  23160
cggcggtctg gatgtacata tccgtggctg ttagaatgaa gcatgttgta aacccaaaag  23220
ttttaagtag tcgctgtaaa cgggtgaatt gatcgcgttt taagcaaatg cttatatctg  23280
gagttagatt tggaaacatc attgtataac aagcgagttc acgttttaca acttgtttgt  23340
aacattgtac ttgatcatct ggaccacaat cacccgggcg ttgccatacc atcgtttgga  23400
taatactccg ctcgggggt tgtccggtaa atttaaaata taaccgtgtt ggggtcgacg  23460
gatcttttgt atggcgaaac gcgtcaataa gcgaggaccg tccctccgtt gccgcgagta  23520
caaccattct cggcccagtc caattatact ggtcaaacat atttgccggt ataggaatat  23580
acagttgttc tgtttccaaa ctacagtgaa taattaatcc ttcgtcgctg aatattaaaa  23640
tagaatccct tagtctatta accagaggtg atatagacga aattaaacca gtaagcgttt  23700
tttccgttaa aacagctctg gcgatttctg gggcgtcaaa acccgcatgc aattccatgt  23760
ccaaagcatc gtctgtacgc gacctcaaat ccataattta ctacttaaaa tgtttactat  23820
agaaaaagta atcatatgta aacacacgag tttcgttaat atgtttgttt aacccgatcc  23880
ggtgacttaa gtacataaac aggcatgata tttgaatagt acggcccatg ggagggaaca  23940
tttccacgtg ttccaataca gggggtgttc cttaataggg actgtgcaat aaaatacgta  24000
agaagttacc agatttgatg taatgtttgt cataaaaaat atgtacatca ttatatacgt  24060
```

-continued

```
ctgtaattaa cacaagatca catcgaagaa ttactgaagc cgctgtgaaa cctttcacaa  24120
gacgatataa acttggttaa gtgtattgat ggggctcttt ggactgacac gctttatcca  24180
tgaacataaa ctggttaaac ccagcatcat ttcaacgcca cccggagttt taacccccgt  24240
ggcggtagac gtatggaacg tcatgtacac attgttggaa cgtttatacc ctgtgggtaa  24300
acgcgagaat ttacacggac catctgtaac gatacattgt cttggagtct tattgcggct  24360
attaacacaa cggtcatact atccgatatt tgtattggaa cgttgtacag acggcccatt  24420
atcacgtgga gccaaggcaa ttatgtcacg ggccatgaac cacgatgaaa ggggaacctc  24480
ggacttaacc cgtgttctac tatcatccaa cacatcatgt tctatcaagt ataacaaaac  24540
atcggaaaca tatgacagtg tgtttcgaaa ctcttccacg agttgtattc ctagcgaaga  24600
aaacaaatcc caggatatgt ttttggacgg ttgtccacga caaactgaca agacgatctg  24660
cctgcgcgac caaaacgtat gcagtcttac ctctacaatg ccatcccgag gacatcctaa  24720
ccatcgatta tatcacaaat tgtgtgcaag tcttattaga tggatggggt atgcatacgt  24780
cgaggcggtt gacattgagg cggacgaggc atgtgcaaac ttatttcata cgcgtacagt  24840
ggctttggtt tatacgacag atactgattt actcttcatg ggctgtgata ttttgttaga  24900
tgcaattcct atgtttgctc cagtagtacg atgtcgcgat ttgcttcaat atttaggaat  24960
tacataccct gaatttttgg ttgcctttgt tcgctgtcag accgatttgc atacaagtga  25020
caacctaaaa tctgttcagc aagttattca ggataccggc ctgaaagttc cacatcaaat  25080
ggacacttca acgcgctccc ccacttacga ctcgtggaga catggcgagg ttttcaaaag  25140
tcttaccgta gccacgtcgg gtaaaacaga aaacggagtg tccgtttcca aatatgcatc  25200
taaccgatcg gaggtgacag tagacgccag ttgggcttta aaccttctgc caccctcatc  25260
ctccccattg gataatttgg aacgcgcatt tgttgaacat ataatcgccg tggtaactcc  25320
attgacccgc ggtcgcctaa agttaatgaa acgtgtaaat attatgcaaa atacggcaga  25380
cccatatatg gttattaaca ccttatatca taacttaaag gggaaaaaaa tggctcgcca  25440
atacgcacgt atttttaaac agtttattcc tactccactc ccactaaaca ctgtattaac  25500
aaaatattgg aattaaaaca cacataagag cgacttaatg gttcattgtt ttattttgct  25560
cgtatataca tgttataaat cgtttatcac tgtgcccgca taagatgtac tgtgtctctc  25620
aaaaaaattt gtgtttttat ctgcaatcat aaatgcaagt ggaaagtccg aatcgggagg  25680
tggggtgtta aatagttttg gtacattaat cgctgataaa agcctgtccg cgctgaattt  25740
cacgtattgt gtaattgcat cgacgttcac caaacgggtt ttgggtgcat gggattttaa  25800
aaacgcacac tcgatttcaa cggcttccga aaacagttga tgtattctgg tgatagcggg  25860
tttttcgggt acatagttat tgtatataca acacgatgcg ctggtatgta tggcttcatc  25920
tcggcttata aggtcgttaa attgacaagt tacaacaaat agtccgttat tgcgtaaata  25980
tgcaatagcc gcgaacgatg atacaaaaaa aatgccctct ataagaatca ttagtatata  26040
tttttctgca acggatgggt tgtcccgtac cttttcttcc aaccattgta ctttttgttg  26100
gatcgacgga ttattaatag tgacatttac gtattgtacc cgcaacgatt catcccctct  26160
gaacaacatt agttgaattt gactatagac acgcgcgtgg acaacctcga tgcactcttg  26220
ttcaatgtag taatggtgaa tatccttttg ggaaaagagt tgggttagag agcccaaatt  26280
aacatttacc agatcatctg ccgccgataa aaatgtaaaa ataaatctgt agaatattag  26340
ttcatcttcc gttaaacagt ccaagtattg ataatcatct tcaatgataa aatcgctttc  26400
```

-continued

```
taaccaacga ttcgaaatgc tcagggcacg taaattgttt atatctggac actccggcct  26460
gtaaaaaaaa tgactgcaat ctttctgatc cattttggaa tagtttcccg tgtaaattta  26520
taaagcacaa ctggtacagg ttaattcgcc tcccgcaaac agtccgctgt tcgtagcttt  26580
acgaatttta cagtagtaca tacccgtttt aaggccggct ttataggcac gtataagcaa  26640
attcattatt ttggaggcgg gaattgtccc gtctgggcgt tcctcaataa ataaagtcat  26700
tgattgactt tggtcaataa atggcgccct ttctgcacac atatcaacga gatcctcttg  26760
ctcatattca aacgctgttt tatattttaa gagtgggtga ctattagata aacagccaaa  26820
cgaacgtatt actgaccatt ggtttttctc aagtatgttt ataacttcca gtcgtttttc  26880
ttcacatgaa tacatatctc ttagttcgtc cataaggtct aagttgggtc taagtaactc  26940
acccgaggtg gtgaccttac taaacatatt attataaatt ggagagaaac cctcactgca  27000
ctccgttacc tgtgcagatg aaactgtggg cattaacgct aagaactgcg agttgtataa  27060
cccataagcg caaatatcat ctcgcagggt acaccatggt aaatctaaat aacttatcgt  27120
agaaaaccca tcttggtgta accatccctt agcatattta ctttcggtaa aacccttaaa  27180
cggggctaag ccgccaatct tacacatttc catgcttgtt ttcattgtct catacaacat  27240
taactccgct atttgtacat ttaaccgtct agctggttgg gaagttaaat caaatcctaa  27300
gcggagacaa gttgtatgta acccttgtat gccaatgcca agtgatcggt tgtttttttac  27360
acctttacat gattttttac atggaaagtt cccagccgcc aggaccccgt ttaaaaaaat  27420
aacagtcgtt cttgctgtca attgaaggtc gtttaaatta aatgacactg ggcctttgga  27480
taagcacgtt gtaagattta tgctggcaag attacatacg ccatgttgat gagcgtctgc  27540
cttttgaaca atttccgtac acaaatttga ccccgtgata gcatttcctt gggtattcat  27600
atgataatta cgattacagg catctttgaa cattaaaaag gggcttcctg ttacagcagc  27660
actgcgtatg attgtgaatg cgatatcttg aatgggaaca gaagaaacgc ctaatccttc  27720
tctctctaaa cgtaaatagg ttgaagtgaa tgcctccccg tgtaatgttc gaaggatatc  27780
ggctctgtta tcaaaaagag tccactgaac attactagcc ccttttagat agcttaggta  27840
tctttcaaaa aataaatctg gggtccataa acaacaaaat atgttatcac atcgaaatat  27900
ttcatcacga accaacattc cacgtgtggc caaaacagtt tgtagatcga cgtgccatgg  27960
ttctatgtaa acacaaactc cagttggtcg ttcacaatca ctgttaattg ccataaccat  28020
gcaatctaaa agttttaaaa ctgcaagaag acctttcgtt tgattttccg taggtattaa  28080
attcagactc tgtagagaaa ttcccactcc acctcgactt tgtaataccg ttcccacatc  28140
gcctgtgata gctcgaacag ctctcccaac agtgatggat tccgggtcca ttaaataaca  28200
actggccgtt gccccggtct ctcgacctaa aaacatcata accggtgtag ccgggacaat  28260
tttctgacat gccaacgctg tgaaaaatac ccgacagaca tcagtccatg tataaccatc  28320
atttattccg ggaataagag ttgcgatttt aggcaggttt acgatttctg ttgtcacggt  28380
ggccgccagt cttaaaaaga attggcaaag cgactctaat ttaccttcct ctaacttagt  28440
taaataaaag tcttcgtact ttaaagcaga ctgtagtcca agggtagcta aagcggggta  28500
ttgatctttc aaaaacggtt ctaatatagc ccgacgaatt tcgtccctcc gcccttcaat  28560
tgcttggcgg actcggggag ttaaacagag aattggggaa gtcaaccacg tttccatgga  28620
aacggatcgt aggttaatac ggcaatggat aagttctcca caacatcggt acactcgctc  28680
atcttgtcgc gtcaccgcct taagttttga gacgatagtg ctaatatact ccattaattc  28740
caccggtgtg gttgattcgg gcggaatgat gtattccttg tagccatgtt gacataatcg  28800
```

-continued gtttataatg tcatgaaccg tattaaaaat tcttttgaac tccataacgg ataacgtatt 28860
taggctccgg aataaacctt taaaccctaa actcacagct gagttagttc tacaatattg 28920
tagactccct tatatatggt tacgtacagc ctgcccctcc ccagtatata atatcacgca 28980
aaacccacgc tatgttaaat tcagtttatt ttacatacat gctttaataa taacattcgt 29040
tccatgtatt tgtacccccc cacacaaccc cctctaacca aatagttggc acgttataac 29100
ctccgaaccg ttccatgcgt cttgtataac gcacagactc tgatggaatt gttccaatta 29160
acgtatatgc cgcatacatg caggataatt gtgtgggaag tccccgaaaa tcgccggtcc 29220
attgatacaa tcgctgtcta gccaagttcc aatttactcc tgtaatttcg ccaatactac 29280
atcgagggct tgtcgggtca ttggataact gcacaagcgg caacgccctt gtgttatatg 29340
gctggtgggt atttgcaacc ccttcagtcc cccaggcggc attttcagct cgtatgcgtc 29400
ctaacaggaa gccaatacca cgaccaaaac attgttcgtt tagttggctt aatgcaagat 29460
gcagtcttac accttctcgt tggcgtcgct gtgtatatac aaaaaccaag aacacatgct 29520
tcagtccgtc cgcggaaaga tgtaaatctt tgtcaacgtc ccaaaatacg caggccggga 29580
tgttggctgt gaccctgcga gttgaagttt tgtctgtacg tgcagcttct tggggacctt 29640
tggccacggc ggttatattg cataaattat cctgaatggt atattccagc agggacccaa 29700
aaaaacttat aaatcgatgt ggaaatacat gacattgtac catcgcacgt aaacactccg 29760
aaaaccttat gagccgcgtt tccatacgac tgcatcccata ggcagaaaca attgctgttc 29820
tgttggcatc cgctgcctgt ttatccgtat attcttctgc ccggcatgcg gcgatgaaac 29880
ttaatgacgt tacatatgct ctaagccccc caccttctcc aacggtccaa ggagccgtgc 29940
aggcattgaa taggtttcgt aaaccctcta gtagtacatc ggggtcacgt ccagcctgtg 30000
taagtgtatt agcttctcca atcatgtcag atggatgacg aaggattaag acgattgacc 30060
cagcatgctc aatgtccgga cgaaaaaaat cggttaatga cacttgttgg attagctgtg 30120
tcgttgattt aaaattattt aacgggagtc taatggtaac ttgcgggtta ccaattgaag 30180
ttggatttat ttgaatgttg ttcatacgat taataacaat tgaacggggg gttacttgaa 30240
tagacgcggt ttctgtacgt tttggtggta catgtatcgg ttgtttgttc agacctccaa 30300
agcgagggcc aattgttaaa tcgcgactcc aatttccgaa gaagcccgga gcataagtca 30360
tatgaagccc gttccctatt tgaataaaac ggttatttcc taaaagactg atattagttc 30420
cacatagcgt ttgttcgttt aaagtaaaat gcgagttggt tggttgactc cccatagctg 30480
aggggttaaa ttcacacaat gcaatcgtga cgtggtacta tctgaaatgt tgcctggggt 30540
atgtgtacac attatacagt cgtagtaccg tttatataat gttaggtagg aggagcctat 30600
aaaaatattt tgattggcgt taaaaggttc ttcaacttac cgtgacgtcc tttttattaa 30660
catgcgtttt tattgatgtt acatttatgt cttttcattc cggacggatg tagctttttc 30720
atatcacgtt ataaagttaa gtcagcgtag aatataccat ggaagaacca atttgttatg 30780
atacacaaaa acttttggat gatttaagta acttgaaagt acaagaagcg gacaacgaaa 30840
gaccatggtc accagagaaa acagaaatcg ccagagttaa ggtagttaag tttttacgat 30900
ctacccagaa aattccagct aaacatttta ttcagatatg ggaacccctg cattctaata 30960
tctgttttgt atattccaat acatttttgg cggaggctgc tttcacggcc gaaaatttac 31020
ccggactgtt gttttggaga ctagatctag actggacgat agaggagcca ggtaatagct 31080
taaaaatttt aacccagcta tcaagtgtag tacaagattc cgagacgtta catcgtttat 31140

-continued

```
cggccaataa attacgaacc tcgtctaaat ttggacccgt ttcgatacac ttcattataa  31200
cggactggat aaatatgtac gaggtcgcct taaaggatgc aacaacagcc attgaatcac  31260
cattcactca cgctcgtatt ggaatgttgg aaagcgccat tgcagcttta acacaacata  31320
aatttgcgat catttacgat atgccatttg ttcaagaggg gattcgtgtt ttaacacaat  31380
atgcaggatg gcttcttccg tttaatgtta tgtggaatca gattcaaaat agctcactca  31440
ctcctctaac acgagccctt tttataatct gtatgattga tgaatatctc acggaaacgc  31500
cagtacatag catatcagaa ttatttgcag atactgtaaa tttaattaaa gatgaggcgt  31560
tcgtatccat cgaagaagcg gtaacgaatc cacgaacggt gcacgagtca cgaatttcct  31620
cagctctggc ttatcgagac ccttatgttt ttgagacatc cccgggaatg cttgctagga  31680
gacttagatt agacaatggt atatgggaaa gcaacctctt atcgttgtcc acccccggaa  31740
ttcatattga ggcgctgtta catttactaa actccgaccc ggaagcggaa accacatctg  31800
gaagtaatgt agcagaacac acccgtggca tttgggaaaa ggttcaggct agtacatcgc  31860
ctagtatgtt aataagcacc cttgccgaat ccgggtttac aagattttca tgcaaattgc  31920
tacgtcggtt tattgctcac cacacactcg ccggttttat tcacggaagc gttgtagcag  31980
acgagcatat tacagatttc caacaaacac taggatgtct cgctttagtg ggtggactgg  32040
cataccaatt agtggaaacg tacgctccta ctaccgagta tgtgttaaca tatacacgga  32100
cagtaaacga gaccgaaaaa cggtatgaaa cgctattacc cgccttagga ttaccaccgg  32160
gaggcctggg acaaattatg cggcgctgtt ttgctccacg accccttatt gaaagtatac  32220
aagcgacacg cgtaatacta cttaatgaaa tttcacatgc agaagctaga gagacaacat  32280
attttaagca aacacataat caatcctcag gtgcgttatt accacaagca ggacaaagtg  32340
ccgtacgcga agccgtacta acctggtttg acctacgtat ggattcaaga tggggtatta  32400
ctcccccggt ggatgtgggt atgacacctc ctatttgtgt tgatccaccg gctacagggt  32460
tggaagctgt catgataaca gaagcactaa agattgcata tcctaccgaa tataatcgct  32520
ctagcgtgtt tgtggaaccg tcgtttgtgc cttatattat tgcaacaagc acgcttgatg  32580
ccctttcggc aacaatagct ttgtcttttg atacacgggg aatacagcaa gccttgtcta  32640
ttcttcagtg ggctcgcgat tatggatccg gaaccgtgcc caatgcagat ggatatcgca  32700
caaaactatc tgctcttata acaatattag aacctttttac ccgtacacac cccccagtac  32760
ttttaccatc tcacgtttct actatagatt cccttatatg cgaacttcat cggactgttg  32820
gcattgccgt tgacctgctt ccccagcacg tccgtccttt ggttcctgac cgtccttcta  32880
ttacaaatag cgttttttta gcaactctct attatgatga actttacggt cgttggaccc  32940
gactggataa aacatcgcag gcgttggttg aaaattttac atccaacgcg ttagtggttt  33000
ctcggtacat gttaatgtta caaaaatttt ttgcgtgtcg tttttatcca acgccagatc  33060
ttcaggctgt tggtatctgt aacccaaagg ttgaacgcga tgaacaattt ggggtatggc  33120
gtttaaacga tcttgctgat gcggttggtc atattgttgg gacaatacaa ggaatccgaa  33180
cgcaaatgag agtgggaata tccagcctgc gcacaattat ggccgatgct tcctcagccc  33240
ttagggaatg tgaaaattta atgactaaaa cctccacttc tgctattggg cctcttttttt  33300
caacgatggc ttcccggtat gcacggttta cacaggatca aatggacatt ttaatgcgtg  33360
ttgacaaact aacaacagga gaaaatatac ccggtcttgc aaatgtagag atttttttaa  33420
ataggtggga acgaatagca acagcttgta ggcatgccac ggcagtcccg tcggccgaat  33480
ctattgcaac cgtgtgtaat gaattgaggc gcggtttaaa aaatatacaa gaggatcgtg  33540
```

-continued

```
taaatgcccc aacctcatat atgagtcacg cccgaaatct ggaagatcac aaggcagcag  33600
tttcattcgt tatggactcc aggcaacagt ttattgtgga ttctggacct cagatgggcg  33660
cggttttaac ttcacaatgt aatataggaa catgggagaa tgtaaatgca acgtttttac  33720
atgataatgt taaaataacg acaacggtca gagacgtaat ttcagaggct ccgacgctga  33780
taataggaca aagatggctt cgtccagatg agattttatc taatgtagat ttgcgtcttg  33840
gcgtacccgg gaatacaagt gggagtgacc cttaatataa aacaggcgtg tttatgtaca  33900
ttaaagtatt tgtggttttt attgactggg cgtttcgttt gtataacgct gttgttgcta  33960
gtattttcat aacctcctag gtttttggag ctacacgtgc ttattcaacg ctctttggga  34020
tttgaatcat cgtaaacgta gcgtccctac cagttgagcg cgtaattttc gtaagcaata  34080
aaatggatat aattccgcct atagctgtca ctgttgcggg agtgggaagc cgtaatcaat  34140
ttgacggtgc cctgggaccg gcgtcaggtc tgtcatgttt aagaacatct ttatcgtttt  34200
tgcatatgac atatgcgcat ggaattaatg caaccctgtc atcagacatg attgatggat  34260
gtttacaaga gggtgcagca tggactacgg atctgtctaa tatggggagg ggtgtcccag  34320
atatgtgtgc tcttgttgat ctccccaatc gaatttcata tattaaactg ggggacacta  34380
ccagtacgtg ctgcgttttg tctagaatat acggcgatag ccattttttt accgttccag  34440
acgagggttt tatgtgcaca caaattcccg ctagagcgtt tttcgatgat gtgtggatgg  34500
gacgtgaaga gtcgtataca attataactg tagactcaac gggaatggcc atctatcgtc  34560
agggaaacat atcttttatt tttgatccac atggccatgg gactatagga caggctgtag  34620
ttgttcgggt gaataccacg gatgtgtact cttatatcgc atcggagtat acccaccgcc  34680
ccgataacgt agaatcccaa tgggccgctg cattagtttt ttttgtcacc gcaaacgacg  34740
gtcccgtaag cgaagaagcg ctatcttcgg cagtaacgct tatatacgga agctgtgata  34800
catattttac agatgaacaa tattgcgaaa aactggttac agctcaacat ccgttgcttc  34860
tttcacctcc taattccacg acaattgtgc ttaataaatc gtctatagta cctcttcacc  34920
aaaacgttgg tgaaagtgta tccttggaag caaccctaca ttcaacgtta accaacacgg  34980
ttgcactgga ccctagatgt agttacagcg aggttgatcc ttggcatgcg gttctagaaa  35040
caacctcgac tgggtctggc gttttggatt gtcgtcgtag acgccgtcct tcatggactc  35100
ctccttcaag cgaggaaaat ttagcttgta tcgacgatgg cttggtaaat aatacacatt  35160
ccacggataa tttacataaa cccgctaaaa aggttctcaa atttaaacca actgtagacg  35220
tgccggataa aacacaagtg gcacatgtat taccccgcct acgagaagtt gctaacaccc  35280
cagacgttgt gttaaatgta tccaatgtag atacgcctga atccagtccc actttttcac  35340
ggaacatgaa tgtaggaagc agtttgaaag atcggaagcc atttctattt gaacagagtg  35400
gtgatgtcaa catggttgtc gaaaaactac tacaacatgg gcatgaaatt agcaatggat  35460
acgtacaaaa tgcggtgggt acgttggata ctgttattac cggtcataca aatgttccca  35520
tttgggtaac aaggcccttg gttatgccag acgaaaagga tccattggag ctttttatta  35580
acctcaccat tttgcgttta acgggatttg tggtggaaaa tggaacacgt acacatcatg  35640
gtgctacaag cgttgtatca gactttatag gtccccttgg ggaaatttta acaggatttc  35700
cctccgccgc ggaacttata cgcgttacaa gtttgatatt aacaaacatg ccgggggcgg  35760
aatatgctat taaaactgtt ctccggaaaa aatgtacaat tggcatgctc attatcgcta  35820
agtttggtct agttgccatg cgggttcagg atacaaccgg cgctttacat gccgaactag  35880
```

-continued

```
atgtgttaga agcggatcta ggaggttcgt cgcccataga cctctattct agactgtcga  35940
caggtcttat aagtatacta aattcgccta ttatttctca tcccggactt tttgccgagc  36000
ttattccaac ccgtacaggg tccctgtctg aacgaatacg tcttctttgt gaattagtct  36060
cggcccggga gacacgctat atgcgtgaac acaccgcgct tgtttctagt gtaaaggctt  36120
tagagaatgc attacggtct acccgcaata aaattgatgc cattcaaata ccagaagttc  36180
cccaggaacc cccggaagaa accgacattc cacccgaaga gttaattcgg cgtgtatatg  36240
agatacgatc cgaagttaca atgctattga cctcggctgt tacagaatac ttcacccgcg  36300
gagtgttata tagcacacgg gccttgatcg ctgaacaatc ccctaggcgt tttcgggtcg  36360
cgaccgcaag tacggcaccc attcaacggc ttttagattc tcttccggaa ttcgacgcta  36420
aattaacggc aatcatatcg tccctgtcta tacaccctcc tcctgagact atacaaaatc  36480
tccccgtcgt atctctgtta aaagagctta ttaaagaagg ggaagattta aacacagaca  36540
cggctctcgt atcgtggtta tctgtagtcg gggaagctca aaccgcaggt tacttatcca  36600
gacgagagtt cgatgaatta tcacgtacaa ttaaaaccat taatacacgc gcaacgcaac  36660
gggcttccgc ggaagcagag ttgtcttgct ttaatacgct aagcgcggcc gtagaccaag  36720
ccgtaaagga ctatgaaaca tataacaatg gtgaggtcaa gtatcctgaa ataacacggg  36780
atgatttatt agcaacaatt gtacgtgcta cagacgattt ggtgcgacag ataaaaattt  36840
taagtgatcc aatgatccaa tccggtttac aaccttcgat taaaagacga ttggaaacaa  36900
ggcttaaaga ggttcagacg tatgcaaacg aggcccgaac cacacaggac acaataaaga  36960
gtcgaaaaca ggcggcatat aataaactcg gggggttact tcgcccggta accggttttg  37020
tgggacttag ggctgcagta gatttattac cggaacttgc ttctgagtta gatgtccaag  37080
gagccctggt aaatctcagg accaaagtct tagaggcgcc ggtagagatc cgttctcaac  37140
ttacgggtga tttctgggcg ttatttaacc aatatcgaga cattttagaa catcccggaa  37200
acgcacgcac atctgtctta ggaggactgg gagcttgttt tacagctatt atcgaaattg  37260
tgccgatacc tacggagtat agaccatcat tgcttgcgtt ttttggtgac gtggcagatg  37320
tgcttgcatc cgacatcgcg accgtatcta ctaacccgga aagtgagtcc gccataaacg  37380
ctgttgttgc aactcttagt aaagcgacgt tagtttcatc tacagtgcca gccttatcct  37440
ttgtgttgtc gttatataaa aaatatcagg ctttacaaca agaaattacg aatacccata  37500
agttgactga attacaaaaa caacttggag atgacttctc caccctagct gtctcatctg  37560
gacacttgaa gtttatatca tcttcaaatg tagatgatta tgaaataaac gatgcgatat  37620
tatcaataca aacaaatgtg cacgccctaa tggatacggt taaacttgtt gaagttgaac  37680
tgcaaaagct acccccccat tgtattgctg ggacatctac cttatctcga gtagtaaagg  37740
atcttcataa actcgtcaca atggcacatg agaagaagga acaggcaaaa gtgttaatta  37800
ccgattgtga acgtgcacat aaacaacaaa cgactcgggt tttgtatgag cgttggacac  37860
gtgatattat agcatgtctg gaggcaatgg aaacgcgcca tatatttaac gggacagaac  37920
tggcacggtt gcgagatatg gccgctgcgg gagggtttga tatacacgca gtttacccac  37980
aagcacgtca ggttgtagcg gcatgtgaaa ctacagccgt tacggcatta gatactgtgt  38040
ttcgccacaa tccatatacc cccgaaaata caaatattcc accacctttg gctttgttaa  38100
gagggttaac atggtttgat gatttttcga ttacggctcc cgtattcacc gttatgtttc  38160
caggtgttag tattgaggga ctccttctgc ttatgcgtat tcgcgcggtt gtgttattat  38220
ccgccgatac gtctattaat ggaataccta actaccgaga tatgatatta cgaacctcgg  38280
```

gggatctatt acaaataccc gcattggctg ggtatgttga tttttacaca cggtcttatg 38340
atcagtttat aaccgaaagt gtaacgttaa gtgaacttag agcagacatc agacaggctg 38400
ccggggctaa acttacagaa gcaaataagg ctttggagga agtaactcat gttcgggcac 38460
acgaaacggc taaacttgca cttaaagaag gtgtcttcat tacattacca agcgaaggtt 38520
tattgattcg ggctatagag tattttacaa ctttcgatca taaacgattt ataggaacgg 38580
catatgaaag agttttacaa acaatggtag accgcgatct aaaggaggcc aacgcagagc 38640
ttgcacagtt tcgtatggtg tgtcaggcaa caaagaaccg tgcaatacaa attttacaaa 38700
acattgttga tacggccaat gccactgagc aacaagaaga cgtggatttc actaacctga 38760
agacgttatt aaaactaacc ccccctccca aaacaattgc attggccatt gatagatcta 38820
cttccgttca ggacattgtc acgcagtttg cattgctgtt agggcgtctg gaagaagaaa 38880
ctggtacgtt ggacattcag gcggttgact ggatgtacca agctcgcaat attattgact 38940
cccatccact aagtgtgcgt atagacggta ccggccccct gcatacttat aaagataggg 39000
tggataaact ttatgcgtta cgaactaaat tagatctcct acgacgacga atagaaaccg 39060
gtgaggttac gtgggacgat gcatggacaa catttaaaag agaaacgggg gatatgttgg 39120
catcggggga cacgtacgct acttccgtag atagtataaa ggcactccag gcatcggcgt 39180
ctgtggttga catgctttgt tccgaacccg aatttttttt attgcctgtg gaaacgaaaa 39240
accgtctcca aaaaaagcaa caggaacgta aaacggcgtt ggatgttgtg ttgcaaaaac 39300
aaagacagtt tgaagagacc gcgtctcgct tacgagcttt aattgaacgt attccaacgg 39360
agagtgacca tgacgttctt cgtatgttat tacgtgattt cgatcaattt acacatttgc 39420
ctatatggat aaaaacacag tatatgacat ttcgaaattt actcatggta cggttaggct 39480
tgtatgcaag ttatgctgag atttttccac ccgcgtctcc aaacggagta tttgctccta 39540
ttcccgccat gtcgggtgta tgtctagaag accaatcccg atgcattcgc gcgcgggtgg 39600
ccgcgtttat gggggaggcg tctgtggtgc aaacgtttag ggaagccaga tcttctatag 39660
acgctttgtt tggaaaaaat ttaacctttt acttggatac tgatggggtt ccacttcgat 39720
atagagtgtg ttataaatca gttggggtta aacttggaac catgctatgc agtcagggtg 39780
gattatcttt acgaccggca cttcccgatg aaggtattgt ggaagaaact acactatcgg 39840
cattacgcgt ggccaatgag gtcaatgagc tacgcattga atacgaatcc gctataaaat 39900
ccgggttttc tgccttttcc acctttgtta ggcatcgcca cgccgaatgg ggtaaaacca 39960
acgcacgcag agccattgca gagatatacg ccggccttat aacaacaaca ttgacacgac 40020
aatacggggt tcattgggac aagcttattt attcttttga aaaacaccac ctaacttctg 40080
taatgggcaa tggactaact aaaccaatcc agagaagggg tgatgtacgc gtattagagt 40140
taaccctatc tgatattgta actattttgg ttgccacaac cccggtacat cttctcaatt 40200
ttgctagatt ggatttaatt aaacagcatg agtatatggc ccgtaccctc agacccgtaa 40260
tcgaggccgc atttagaggt cgtttactcg ttcgctcatt ggatggagac ccgaaaggca 40320
atgcccgggc ctttttttaat gccgccccat ccaaacataa actcccgtta gctcttggat 40380
caaaccaaga tcctaccggc gggagaatat ttgcatttcg gatggcagat tggaaacttg 40440
ttaaaatgcc acagaaaata acggatcctt ttgcgccatg gcaactttcc cccccccccg 40500
gggtaaaggc caatgtcgat gcagttaccc gtataatggc aacagatcgt cttgcgacca 40560
ttactgtact tgggcgcatg tgtctcccgc caatttcctt agtgtcaatg tggaatacgc 40620

-continued

```
tgcaaccgga ggaattcgca tacagaacac aagatgatgt ggacattata gttgatgcga  40680
gactggattt gtcatccacg cttaatgcaa gatttgatac cgctcccagc aataccacgt  40740
tagagtggaa tacagaccgt aaagtaatta cagatgctta tattcaaacc ggggcaacga  40800
cagtttttac agtaacgggg gcggcaccaa ctcacgtttc taatgtaaca gcgtttgaca  40860
tagcaactac ggctatttta tttggggctc ctttggttat tgccatggaa cttacatccg  40920
tttttcaca aaattccgga cttactttgg ggttaaaatt attcgattcc cggcatatgg  40980
ctacagattc gggtatatcc tcagccgtat ctcccgatat tgtttcttgg gggttacgtt  41040
tactgcatat ggatcctcac ccaattgaaa atgcatgttt aattgtccaa ctagaaaaac  41100
tgtccgcgct cattgcaaac aaacctctta caaacaatcc cccgtgttta ctgctattgg  41160
acgaacatat gaatccctct tatgttttat gggaacgaaa agactcgatt ccagctccgg  41220
attatgtggt cttttggggg ccagaatctc ttattgattt gccgtacatc gactccgatg  41280
aggactcttt cccctcgtgt cccgatgatc cattttactc gcaaattatt gccggttatg  41340
cgccccaagg ccccccaaac ctcgacacaa ctgattttta cccaacggag ccactattta  41400
agtctcccgt tcaagttgtt agaagttcca aatgtaaaaa aatgcccgtc cggcccgcgc  41460
agcccgcgca gcccgcgcag cccgcgcagc ccgcgcagac cgtccagccc gcgcagccca  41520
tagaaccggg cacacaaata gtggtacaaa attttaagaa accccaaagc gtaaaaacaa  41580
cccttagcca aaaagatatt cccttgtatg tggaaaccga atcagaaacg gctgtgctta  41640
tacctaagca attaaccacc tccattaaaa caaccgtttg taaaagtatt accccaccaa  41700
ataaccaatt gtcggattgg aaaaataatc cacagcaaaa ccaaacgtta aaccaagcgt  41760
tcagtaaacc aatacttgag attacctcca ttccgacaga tgactcgata tcttaccgga  41820
cttggattga aaaatcaaat caaacacaaa aacggcatca aaatgaccct cgaatgtata  41880
actccaaaac agtattccac cctgtaaata accaattacc ttcttgggtt gacacggcag  41940
ccgatgcccc ccaaacggac ctattgacaa actataaaac aagacagccg tcgccaaact  42000
ttccgcggga cgtacacaca tggggcgtat cttctaaccc gtttaactca ccgaacagag  42060
acctatatca aagtgatttt agtgaacctt ctgacggcta tagcagtgag agtgaaaatt  42120
ctatcgtact aagtctcgac gaacatcggt catgtcgcgt tcctaggcac gtacgcgttg  42180
ttaatgccga tgtagtcacc ggtcgacgtt atgtccgagg gaccgccttg ggagcactgg  42240
cactgttaag ccaggcatgt cggcgtatga tcgacaacgt tagatataca cgtaaacttt  42300
taatggacca cacggaagat atatttcaag gcctggggta tgttaaattg ttattagatg  42360
gaacatatat ataaagtagc gcctattaaa gaaaaaaaaa aaacaacgat tattttctgt  42420
gtatttttat ttacacccta cgacttcttg aagcgtttcc agattgtccc gtgtgtgaca  42480
aggtctgtcc cttacccccc tggggggtat tttgggttgg gggcggggta gactgtggca  42540
cgccttgggc cgcgggcggt gatccggttg ttggctggac agtgcttgac tgtgctccct  42600
gttgcggttg ttgtccagaa gaccccgaca ccacgtgttg ctgttgtcca acggatgccg  42660
acgtcgtttg aggtgggggg tgttgcgggg atgatcccga aaacgccaac gcggcgggct  42720
gttgtaaagc agactgatcg gcgctctgtg ttttttgcgg caatatagta ggccccgaga  42780
ttcccaaact catggatgga tttgggggtt gtggtcgtat aatacgcggg ttaaacgtac  42840
gttttaagcc aaccgttggt cttaaccatg tcatagggtc agtctcggca aacatggccg  42900
ttcggcgtat cgtatttgca ttatggttag cgcgtgcacg cgcggcactg gccgcggctc  42960
ccacggtgta aatgcttctg gcatcagcga tgtccacacg gtgaccaggt tgcaaaggtc  43020
```

```
cactggcgtt taaaagtcgt attaaagcaa cgggggtgta agccgcaatt gcttccaccg  43080
aaaatgtggt ggggttgctg ggatcaaaga ctacacgaga cgatgcgggt tgtgtcatcg  43140
tttattagtt tacgggacaa tcgataacag catacacgta catctgcgca ggatatgtac  43200
ggaaaggcaa tttatttcca gaaaagcacc gcccctaata caactaccag tacaattaca  43260
atgaacaggg catatgtcac gttagctacg ggtagagcaa gtttccagac acgcgtagtt  43320
tgggtatcgg gtaacgcagg tttaatgtca ctttgcattt gaacagacgt gtttggactt  43380
ccgttctcgg gtggggatct gaatgaaggc cgccagcgta tatattcatc caaattattg  43440
ccagtttcct tatacatgta tgcatccgtg gcgcgggcca taagtttaat ggtgcgagat  43500
ggatcttccg gtcccataaa acgaaaggat aactgaacat atggcattcg cacaaagcag  43560
ttcacccaca ttaaagcctg gagaggtcgg cggtcaatac ccccacctcg tttaattgat  43620
tccaaagcag ataggttgat accggtactt aacgttgaac taagaatcac gttattactg  43680
tcaatggaca cttcagccac tggtgcgtta gtcggacgaa aaaaaaaacc ttgaaatagc  43740
acagacaccc ccgtattttg aatttttatg taagggtcac aatctacttg cgcccaattc  43800
gccattaaac gcataatata ctctaccgga aaggcttcgg atacgttgtc ttcgccgtta  43860
aactgaaaaa cacaacgggc ggggggcgt tgtggatcaa atattggaag atccccatcg  43920
caacattgaa gagcgcttgg taccaccaac cgaatacgtt gtaaaagatt atctccgcaa  43980
cccctcctgc gttcactccg tacatacgtt ctccgtgaca tattgatcta aggttgcaaa  44040
ccaaggcaca cgcgtgaagt atttagacca tttatcgtgg gatataggag gagtttggag  44100
tgatccaccc cctgacgact tattaatgcg tttattttcc ccatgtatta agcatccttc  44160
aatatttcat gcaaatctag aaatttggcc atgactcccg caaagcgttc acggcgacgg  44220
gtcacgctgg cactatgttc acatggaaca acataagcag atttttctga atcgttactt  44280
tctttatgtt ttaaaacgga cgccaggcga ctggtaaatg atatataatt taattgagcg  44340
tcagttgtag gtagaattgc ttctatttcc gggggaatta aattttcaaa ccaaacggaa  44400
agagtaaagg tgctatcagc aggaaaatac tttgactcca gtgcatcgat atttaataga  44460
ttaacatcgg tgtctgtaat taaatcgcgg gccctcatcc cagagatgga tcgggtagaa  44520
tcagaagaac ccatggatgg attcgaatcg cccgtattct ccgaaaatac atcttctaat  44580
tccggatggt gttccgacgc attttccgat tcgtacatcg cttataatcc agcccttctg  44640
ctaaaaaacg atttgttatt ttcagaattg ttatttgcct cccacttaat aaatgttccc  44700
cgtgcaatag aaaacaacgt cacttatgag gcctcttcgg cggtaggtgt ggataatgaa  44760
atgacctcaa gtaccactga atttatagaa gaaattggag acgttttggc gttagacaga  44820
gcctgtttgg tctgcagaac gcttgatttg tataaacgta aatttggact gacaccggaa  44880
tgggttgcgg actacgccat gttatgtatg aaaagtctgg catccccgcc ctgtgcagtt  44940
gtcactttta gcgctgcctt tgaatttgtg tatcttatgg atcgttacta cctgtgccgt  45000
tataacgtta ctttggttgg gtcctttgcc aggcgcacgc tttccctgtt agatatacaa  45060
agacattttt ttttgcatgt atgttttcgt accgatggag ggttaccagg tatacgaccg  45120
ccccccggta aggaaatggc caacaaagta agatattcca attactcctt ttttgtacag  45180
gcggtagtta gggctgcatt actatcgatc agcacgtctc gtttagacga aaccgaaacg  45240
cgtaagtcat tttactttaa tcaggacgga ctgactggag gccctcaacc tttagcggcc  45300
gccttggcta attggaaaga ttgcgcgcgg atggttgact gttcatcatc ggaacatcgc  45360
```

-continued acaagtggga tgattacctg cgcggaacgt gcattaaaag aggatataga gtttgaagat 45420
atattaatag acaaacttaa aaaatcgtct tacgtagaag cagcttgggg ttacgcagac 45480
ttggctttat tattactgag tggggttgct acttggaatg tagacgagcg tacaaattgt 45540
gctatagaaa ctcgcgttgg atgtgttaaa tcatactggc aggcgaaccg gattgaaaac 45600
tccagggacg ttccaaaaca attttccaaa tttacgagcg aggatgcctg tcccgaagta 45660
gcatttgggc ctattttgtt aactacctta aaaaacgcaa agtgccgtgg tcgcacgaat 45720
accgaatgca tgttatgttg tttattaacc atagggcact attggatcgc tttgcggcag 45780
tttaaaaggg atatattagc atactcagca aataacacaa gtttatttga ctgtatcgaa 45840
cctgtaatca atgcatggag cctagataac cccattaaac ttaaatttcc atttaatgat 45900
gagggtcgat tcataaccat tgtaaaagca gcaggttccg aggccgtata taaacattta 45960
ttttgcgatc tcctatgcgc tctctcggaa ttacagacaa accctaaaat tttatttgcc 46020
catcctacaa ccgcggataa ggaagtgttg gagttatata aagcccaact ggctgcacaa 46080
aacagatttg aaggtcgtgt atgtgctggc ctgtggacat tggcgtatgc atttaaagcc 46140
taccagattt ttccacgcaa accaaccgcc aatgccgcat tcatacgaga tggaggactt 46200
atgcttcgac gacatgcaat atcgctggtc tccctcgaac acaccctatc gaagtatgtc 46260
taggcgatat aaatccgtat ctcggagcgg gccttcgatg cgtgtacgct ccagaacgcc 46320
atgccgccgt caaaccattc gaggaaaact tatgtcaaag gagcggtctg tgtaccgcca 46380
ttattttaat tacatcgcaa ggtccccccc agaagaacta gctaccgtta gaggcttaat 46440
cgtgccaatt attaagacga cccctgtcac ccttccgttt aacttgggtc agacagtggc 46500
ggataactgc ctgtcgttat ccggaatggg ttatcattta ggtctcggag gttattgtcc 46560
gacatgcact gcatctggag aaccgcgtct atgtcgaacc gatcgggcgg ctctgatact 46620
agcatatgtt cagcagctta acaacatata cgaatatcgt gtgtttcttg catccatttt 46680
ggcgctatca gaccgagcca acatgcaagc agcgtccgct gaacccctat tgtcgagcgt 46740
attggcacaa ccggaattat tttttatgta tcatattatg agggaggggg gcatgcgaga 46800
tatacgcgta ctttttttatc gtgatggaga tgccggaggg tttatgatgt atgttatatt 46860
tccggggaaa tctgttcacc tccattacag actaatcgat catatacagg ccgcgtgtcg 46920
ggggtataaa atagtcgcac acgtttggca gacaacattt ttactgtcgg tatgtcgcaa 46980
cccagaacaa caaacagaga ctgtggtgcc atccattgga acatcggacg tttactgtaa 47040
aatgtgtgac cttaactttg atggagaatt gcttttggaa tacaaaagac tctacgcatt 47100
atttgatgac tttgttcctc ctcggtgatt tcagcttcag tgttcatttt attatcccag 47160
cacggggcgt gtatacaaac aaagcctgcc gcctgcaagc ggtttagcat tttaacgtta 47220
acaactcgtg tctctggaat aaaacgtttt aaaagccgtt ctgtgagttt agtgtcgttt 47280
ccaaataacg ccttaaaagt tacactcgcc gtcccaatga gatgagaaaa ataatagtca 47340
atgtttaaag acagcccgtg tgatgttacg tgaatgggat cttccgctaa gtcagatatt 47400
attaacttac gctttgcttc cccacaccgt ttacctgcgg tattctgtaa aggatctcca 47460
cgtagcaaag ctacactttt tgcatcagcc tccacttcgt ctgtgggggc cacaataaca 47520
taagggatgc gttctcgaac gtttgggatt tgaccctgtc tcattactaa tttataaatat 47580
actgttaagt gagccaagcg acggtttatg taggcggatg gtggacgact aagctcggcc 47640
gtcataacaa acttattaat atccaatttg ggtgatgtaa tctggcgatg tgcatctgca 47700
attatgcgtc caaacccggc catcccagac ggcatggccc gtctattcca ttcagcaatg 47760

```
gaaacacacg acgcctccgc cgcagcacgc gagacggtgt cgtcatataa caacagttct  47820
acaagtttgc gggcataatc gttaataaat tgacagttgt tttttctaac caagtcgact  47880
cccttcatta aaacctttcc gccgtaaatt accccaatgt actttttctt tgttataagc  47940
aaaagtttta taaaagtttt ttcacactcc aactttatag gaggacaaaa cagagccgtt  48000
gaaattatat gtgccatttt ctcgccgatt ttagctatcc cctcaacact aacacccttg  48060
aatcggataa acacagaatc cgtatctcca tatataacct ttacctcgta cgctttttgg  48120
gagagaacgc tactttcaat gtctggaaac gctgtaataa aacgttcaaa tgcggcccag  48180
ttattatgaa tataatctct ggtacttaat aacatttgac ggccaattgt agtgacagtg  48240
gccgctacgt ataaacatgg cagaaatccc tgcgcaactc cagtaaaacc gtacacggaa  48300
ttacaaacta cttttatcgc ggcttgttgt ttgtctaata acactgcttc atctgaagaa  48360
cttccgggta tgcgcgctct aatagccttg cgcatagcca accagtcttt taaaagaaca  48420
cccagcagac tttctcgaac gttagagcgc acaaaaaaaa gacgttttcc tccaactgta  48480
aaggtggcat aatcggatgg attcaaacgt ttaaccgtct caaaatttaa cgttagcgtg  48540
gtaaaacata agttatgggc ctgaattata cttggatata aacttgcaaa atccaatacg  48600
accaccggat cgatataaaa tcccgtatca gggtcaaaaa ccctggctcc tttatatcct  48660
acatttcgcc cacttgacgt accagtggga gaaacgctct cgtcttcatc catctcttcc  48720
tcaacatccc cgacatcggg aataacatcc ttatattcaa aagtagctgg gtatccccca  48780
tcgggtaaaa taaatcctcg agacgaagcc agtcctaata aacaggtgta aatcctaacc  48840
tgctgtccgt cgtaaatagc cttggttaaa gtaattctag ctagccttgc aaccgcggat  48900
aactcaaggt gtggtaaata tttaaaaaac agtttcccca caagagccga gtcttgtata  48960
caatattcac caataattcc tcgtgtattc ggtccactag cgtaatatcc cggaatgtct  49020
ttgtagggca aatctctctt ggactcattt agagcttcac gtgcaaccga atctaattta  49080
taactcgaga gttttaattt ttcagttgca attgcataca tatccagaga tatgagaccg  49140
ttgatcttta ccttgcttcg tcgctgaaat ccggatttgc caacatccca tatcttaaac  49200
agacccccac ggtttatact gccataacca tcaagcttga gactgtatat agaattaagt  49260
ttctccataa taaacgccca atcaaaatta acaatgttat aacctgtggc aaactcggga  49320
gcgtactgtt ttacgagggt cataaatgca attaatagct cgaattcact atcaaactcc  49380
agcacagtcg gctccggtaa ccccgcgtcc ttcatttctt gtacatacct ttgtggtaag  49440
tcacaagagc caagggaaaa cagtaaaatg tgttctaaag actgtcgagg gattgaatat  49500
aatagacaag aaatttggat tacaagatcc tccagatgtg ttgcatcggg aaacgccagc  49560
tcattagatc ctcctgattt acattcaata tcgaaacata acaacttgta gtcaggccat  49620
gagtcatcgt ttggtatagc ctgcagatta tccgacatgc agtcaatttc aacgtcgctt  49680
aacgttaatt ggcgacttgc cggtcgaact cgaacacgtt ccccatcaac tccaggtttt  49740
agttgatacc aaccaaaact aacaaagccg ggattatcca ttagaaaacg agtggtagcg  49800
tctacccgac cttcatactt tttcaactcc gggtgaaagt tatcacaaag ataatttgta  49860
aatttagatg agggagaata caccctgtaa aacgcacatg gctgtgtatc gtagtaataa  49920
acatctgtgc gctcaataac ctcaacgcga aagctttctg gagatgcgct tttaaacgag  49980
gtaccatgaa aagcgttctt gtctccattt aacgttgcat cattttgtgt tatcatagaa  50040
ctgcgtaaac actcggcaag taatacagat aactcgctac cggaacgtat gccacaagcg  50100
```

-continued

```
gtatccacct cggctttgtt tatataaaaa tattgacaga tgccgtatac atgaactgcc  50160
acccttttc cacatcggga catgccaagt aaagtaataa cggtaccaag cggtcgtgtt  50220
gcagttgcaa accgggatac atctccatta gacgcggctt ctgttgtttc gacaatatca  50280
tatacatgga atgtgttaaa gcgggggtca aacttatccc cacgaaagtc gatttccccc  50340
caaatattca cgcgtctagg ccaggggctg gaacaacgaa aatccagaat cggaacttct  50400
tttccattac agtaaacttt aggcggtcga ctaagtgtac cgacgtgaac cccctttcgt  50460
tcttccatgg gcacatcttc atctaaacat ttaggggcca aaaattgaaa cgatgacatg  50520
gtagttttgt aactatgaag aaattctctg ttactaccgc gcccggttct tgggttatat  50580
ttaatccctg atgcttgggt taaaaaggga ttacaaaacc ccgttctgat cgccatttta  50640
tgttaacgat tgataatctt gtaaaaagcc agtgttactg agtaacacaa ccccacgccc  50700
ttctaataca taaagtgtaa tcacgtgatt tgttgtggtt tccgcatatg taatacccgt  50760
ttaaaagcct ctcttcttaa tgtatcgaca gactgggttt tgggtggtca tttgaccctg  50820
ccaacaaccc cccattatta cgagtacttc accaaaatgg aaaatactca gaagactgtg  50880
acagtgccca cggggcccct gggttacgtt tatgcgtgcc gggttgaaga tttggatctg  50940
gaggaaattt catttttggc cgctcgtagc acggactctg atttggcttt attacctttg  51000
atgcgtaatt tgaccgtgga aaaaactttt acatccagcc tggcggtggt ttctggagca  51060
cgcactacgg gtcttgccgg agctggtatt accttaaaac tcactaccag tcatttctat  51120
ccatctgtct ttgtctttca cggaggcaaa cacgttttac ccagctccgc ggccccaaat  51180
ctcacacgcg cgtgtaacgc ggctcgagaa cggtttgggt tttcacgctg ccaagggcct  51240
cctgttgacg gtgctgttga gacgaccggc gctgagatat gcacccgcct tggattagag  51300
ccagaaaata caatattata cttggtggtc acggcattgt ttaaggaagc cgtatttatg  51360
tgcaacgtgt ttctgcatta tggaggactc gatattgttc atattaacca tggggatgtt  51420
atacgtatac cgttatttcc ggtacaactt ttcatgcccg atgttaaccg tctggtaccc  51480
gacccattca acactcatca caggtctatc ggagagggtt ttgtataccc aacacccttt  51540
tataacaccg ggttgtgcca tttaatacat gactgtgtta ttgctcccat ggccgttgcc  51600
ttgcgcgtca gaaatgtaac tgccgtcgcc cgaggagcgg cccaccttgc ttttgatgaa  51660
aatcacgagg gggcagtact cccccctgac attacgtaca cgtattttca gtcctcttca  51720
agtggaacca ctaccgcccg tggagcgcgt cgaaacgatg tcaactccac gtctaagcct  51780
agcccatcgg gggggtttga aagacggttg gcgtctatta tggccgctga cacagccttg  51840
cacgcagaag ttatattcaa cactggaatt tacgaagaaa ctccaacaga tatcaaagaa  51900
tggccaatgt ttataggcat ggagggcact ttgccaaggc taaacgctct ggggtcatat  51960
accgctcgtg tggccggggt cattggtgcg atggttttca gcccaaattc tgcgttgtat  52020
ctaactgagg tggaggatag cgggatgacc gaagccaagg atgggggacc gggtccatca  52080
tttaatcgat tttaccagtt tgccggacct catttagctg cgaatcccca aacagatcga  52140
gatggccacg ttctatccag tcagtctacg ggttcatcaa acacagagtt tagcgtggat  52200
tatttggcac tcatttgtgg atttggagca cccctgttgg cgcgactgct tttttatcta  52260
gaacgctgtg acgctggtgc gtttacaggg ggtcacgggg atgcgttaaa atatgttacg  52320
gggacctttg actctgaaat tccatgtagt ttatgtgaaa aacacacgcg gccggtatgc  52380
gctcacacaa cagtacaccg acttagacaa cgcatgccgc gatttggaca agccacccgt  52440
caacctattg ggtgtttgg aacaatgaac agccaatata gcgactgcga tcctctagga  52500
```

aactatgctc catatttaat ccttcgaaaa cccggggatc aaacggaagc agcaaaggca 52560
accatgcagg acacttatag ggctacacta gaacgcttgt ttatcgatct agaacaagag 52620
cgactactgg atcgcggtgc cccatgttct tccgagggac tatcgtctgt cattgtggat 52680
catccaacgt ttcgtcgcat attagacaca ctgcgtgcgc gtatagaaca gacaacaaca 52740
caatttatga aagtgttggt tgagacccgc gattataaga tccgtgaagg attatccgaa 52800
gccacccatt caatggcgtt aacgtttgat ccatactcag gagcattttg tcccattacc 52860
aatttttag ttaaacgaac acacctagcc gtggtacaag acttagcatt aagccaatgt 52920
cattgtgtat tttacggaca gcaagttgag gggcggaact ttcgtaacca attccaacct 52980
gttttgcggc ggcgttttgt tgacctgttt aatggggggt ttatatcaac acgctctata 53040
accgtaacat tatctgaagg tcctgtatcc gccccaaatc cgacattggg acaagacgcg 53100
cccgcggggc gtacctttga tggggattta gcgcgcgtaa gcgtggaagt tattcgggat 53160
atacgagtta aaaatagggt cgttttttca ggtaactgta caaatctctc tgaggcagcc 53220
cgggcaaggc ttgtaggcct tgcaagtgcg taccaacgcc aagaaaaaag agtggatatg 53280
ttacacgggg ccctagggtt tttgcttaaa cagtttcacg gcctgttatt tcctcggggt 53340
atgccaccaa acagtaaatc ccccaacccg cagtggtttt ggaccctgtt acaacgcaac 53400
cagatgccgg cagataaact tacacacgaa gagattacca ctattgcagc tgttaaacgg 53460
tttaccgagg aatatgcagc aataaacttt attaatctac ccccaacctg cataggagaa 53520
ttagcccagt tttatatggc aaatcttatt cttaaatact gcgatcattc acagtacctt 53580
ataaatacct taacttctat aattacgggt gccaggcgcc cgcgtgaccc atcatccgtt 53640
ttgcattgga ttcgtaaaga tgtcacgtcc gccgcggaca tagaaaccca agcaaaggcg 53700
cttcttgaaa aaacggaaaa cttaccggaa ttatggacta cggcttttac ttcaactcat 53760
ttagtccgcg cggccatgaa tcaacgtccc atggtcgttt taggaataag cattagtaaa 53820
tatcacggag cggcaggaaa caaccgcgtc tttcaggcag ggaattggag cggtttaaac 53880
gggggtaaaa atgtatgccc gctatttaca tttgatcgca ctcgccgttt tataatagca 53940
tgtcctagag gaggttttat ctgccccgta acaggtccct cgtcgggaaa tcgagaaacc 54000
accctatccg accaagttcg cggtataatt gtcagtggcg gggccatggt tcaattagcc 54060
atatacgcca cggttgtgcg tgcagtgggc gctcgagcac aacatatggc atttgacgac 54120
tggttaagtc ttacagacga tgagttttta gccagagact tggaggagtt acacgaccag 54180
attatccaaa ccctggaaac gccctggacc gtagaaggcg ctctagaagc agtaaagatt 54240
ctagatgaaa aaacgacagc gggagatggg gaaacccccca caaacctagc atttaatttt 54300
gattcttgtg aaccaagcca tgacaccaca tctaacgtat taaacatttc agggtcaaac 54360
atttcagggt caactgtccc tggtcttaaa cgaccccccg aagatgacga actctttgat 54420
cttagtggta ttcccataaa acatgggaac attacaatgg aaatgattta acctccctct 54480
ttatccaatt aaagcccaca cgcgggtgag tgtacgtaat aaacaagtca atattacata 54540
ttctgttgtg ttttcttttt ttgtgtgtag tccttaccca tatgacctgt aatatagtgt 54600
gtctccaacc attcagctta cagtccagtg gacagtaaca gcccgataac atggaattgg 54660
atattaatcg aacattgttg gttctactgg gtcaagttta tacgtacatc tttcaggttg 54720
aactgctacg tcgatgtgat ccaagggtgg cgtgtcgctt tttatatcgg ttagcggcta 54780
actgtttgac agttcgttat ttattaaagc tgtttctccg gggatttaat acccagctaa 54840

-continued

```
aatttggaaa cactcccacg gtttgtgcac tgcattgggc attatgttat gtaaagggag  54900
aaggtgagcg tttgtttgag ttgctacaac attttaaaac gcgttttgtt tatggtgaga  54960
ctaaagactc aaactgtatc aaagattact ttgtctcagc gtttaactta aaaacctgcc  55020
aatatcacca tgagctgtcg ttaacaacat acggaggtta cgtatcgagt gaaattcagt  55080
ttttacacga cattgagaat tttttaaaac agcttaatta ctgctatatt atcacgtctt  55140
ctcgtgaggc gctaaacaca ttggaaaccg tgacgcggtt tatgacagat actataggaa  55200
gcggtctaat accacccgtg gagttgtttg atccggcgca tccatgtgct atatgttttg  55260
aagaattatg tataacagct aaccaaggtg agaccttaca tcgtagatta ttaggatgta  55320
tctgcgatca cgttactaag caagttcggg ttaacgtgga tgttgacgat attattcggt  55380
gtttaccata tatccctgat gtaccggata tcaaacgtca atccgccgtt gaagcgttac  55440
gaacacttca aaccaagacg gtagtcaatc ccatgggagc aaagaacgat acgtttgacc  55500
aaacatacga aattgcgagc accatgcttg attcttataa tgtttttaaa cctgcccctc  55560
ggtgtatgta cgccatcagc gagcttaaat tctggttaac gtctaattcc actgaaggac  55620
cccaacgtac tttagacgtg tttgttgata atttggatgt attaaacgaa catgaaaaac  55680
acgcagaact tacagccgta acggttgagt tggcgttatt tggaaaaact cccatacact  55740
ttgatagggc gttttctgaa gaactcggat ctctggatgc aattgatagt attttggttg  55800
gcaatcgctc atcctcacca gacagtcaga tagaagcatt aattaaagcc tgttatgccc  55860
atcatctatc gtcgcctctc atgcgtcaca tttctaaccc gagtcatgat aacgaagccg  55920
ccttacgcca acttttagaa agagttgggt gtgaggatga tttaaccaaa gaggcgagtg  55980
acagcgctac agcatccgaa tgtgatctga acgatgatag tagcataact tttgctgttc  56040
atggatggga aaacctgtta tccaaagcaa aaattgacgc tgcggaaaga aaacgagtat  56100
atcttgaaca tctgtctaag cgctctctaa ccagcctcgg tagatgtatc cgcgaacagc  56160
gccaagagct agaaaaaaca ctcagggtaa acgtttatgg agaggcctta ttgcagacat  56220
ttgtttcgat gcaaaatggg tttggggcac gaaacgtgtt tttagctaag gtttcccagg  56280
cagggtgtat tatcgacaat cgcattcagg aagcggcctt tgatgcacat agatttataa  56340
ggaatacctt agttcgacat acagtagatg cggctatgtt acctgcactt acacataaat  56400
tttttgagtt ggtcaacggc ccattgttta atcacgatga acaccgtttt gcacaacccc  56460
ctaacaccgc cttatttttt accgtggaaa acgttggcct atttccgcac ttaaaagagg  56520
aattggcaaa gtttatgggc ggtgtcgttg gttccaactg gcttctcagt ccatttaggg  56580
gcttttattg cttttctggg gtagaaggcg ttacttttgc acagagactt gcctggaaat  56640
atattaggga gcttgtgttt gcaaccacac tattcacctc tgttttccat tgtggggagg  56700
tgcggttatg tcgcgttgac cgtctaggta aggatccacg cgggtgcacg tctcaaccta  56760
aaggtatagg cagttcccac ggacccttag acggcattta tttaacgtac gaagaaacat  56820
gtccccttgt ggctattatt caaagtggag aaacagggat cgaccagaat accgtcgtaa  56880
tctacgattc agacgttttt tctcttctat acaccctaat gcagcggctg gctccggatt  56940
caacggaccc ggcgttttca taacctccgt tacgggggtg tggttatgct ttttatgcat  57000
attttctatg tttgttacgg cggttgtgtc ggtctctcca agctcgtttt atgagagttt  57060
acaagtagag cccacacaat cagaagatat aacccggtct gctcatctgg gcgatggtga  57120
tgaaatcaga gaagctatac acaagtccca ggacgccgaa acaaaaccca cgttttacgt  57180
ctgcccaccg ccaacaggct ccacaatcgt acgattagaa ccaactcgga catgtccgga  57240
```

-continued

```
ttatcacctt ggtaaaaact ttacagaggg tattgctgtt gtttataaag aaaacattgc  57300
agcgtacaag tttaaggcga cggtatatta caaagatgtt atcgttagca cggcgtgggc  57360
cggaagttct tatacgcaaa ttactaatag atatgcggat agggtaccaa ttcccgtttc  57420
agagatcacg gacaccattg ataagtttgg caagtgttct tctaaagcaa cgtacgtacg  57480
aaataaccac aaagttgaag cctttaatga ggataaaaat ccacaggata tgcctctaat  57540
cgcatcaaaa tataattctg tgggatccaa agcatggcat actaccaatg acacgtacat  57600
ggttgccgga acccccggaa catataggac gggcacgtcg gtgaattgca tcattgagga  57660
agttgaagcc agatcaatat tcccttatga tagttttgga ctttccacgg gagatataat  57720
atacatgtcc ccgttttttg gcctacggga tggtgcatac agagaacatt ccaattatgc  57780
aatggatcgt tttcaccagt ttgagggtta tagacaaagg gatcttgaca ctagagcatt  57840
actggaacct gcagcgcgga actttttagt cacgcctcat ttaacggttg gttggaactg  57900
gaagccaaaa cgaacggaag tttgttcgct tgtcaagtgg cgtgaggttg aagacgtagt  57960
tcgcgatgag tatgcacaca attttcgctt tacaatgaaa acactttcta ccacgtttat  58020
aagtgaaaca aacgagttta atcttaacca aatccatctc agtcaatgtg taaaggagga  58080
agcccgggct attattaacc ggatctatac aaccagatac aactcatctc atgttagaac  58140
cggggatatc cagacctacc ttgccagagg ggggtttgtt gtggtgtttc aacccctgct  58200
gagcaattcc ctcgcccgtc tctatctcca agaattggtc cgtgaaaaca ctaatcattc  58260
accacaaaaa cacccgactc gaaataccag atcccgacga agcgtgccag ttgagttgcg  58320
tgccaataga acaataacaa ccacctcatc ggtggaattt gctatgctcc agtttacata  58380
tgaccacatt caagagcatg ttaatgaaat gttggcacgt atctcctcgt cgtggtgcca  58440
gctacaaaat cgcgaacgcg ccctttggag cggactattt ccaattaacc caagtgcttt  58500
agcgagcacc attttggatc aacgtgttaa agctcgtatt ctcggcgacg ttatctccgt  58560
ttctaattgt ccagaactgg gatcagatac acgcattata cttcaaaact ctatgagggt  58620
atctggtagt actacgcgtt gttatagccg tcctttaatt tcaatagtta gtttaaatgg  58680
gtccgggacg gtggagggcc agcttggaac agataacgag ttaattatgt ccagagatct  58740
gttagaacca tgcgtggcta atcacaagcg atattttcta tttgggcatc actacgtata  58800
ttatgaggat tatcgttacg tccgtgaaat cgcagtccat gatgtgggaa tgattagcac  58860
ttacgtagat ttaaacttaa cacttcttaa agatagagag tttatgccgc tgcaagtata  58920
tacaagagac gagctgcggg atacaggatt actagactac agtgaaattc aacgccgaaa  58980
tcaaatgcat tcgctgcgtt tttatgacat agacaaggtt gtgcaatatg atagcggaac  59040
ggccattatg cagggcatgg ctcagttttt ccagggactt gggaccgcgg gccaggccgt  59100
tggacatgtg gttcttgggg ccacgggagc gctgctttcc accgtacacg gatttaccac  59160
gtttttatct aacccatttg gggcattggc cgtgggatta ttggttttgg cgggactggt  59220
agcggccttt tttgcgtacc ggtacgtgct taaacttaaa acaagcccga tgaaggcatt  59280
atatccactc acaaccaagg ggttaaaaca gttaccggaa ggaatggatc cctttgccga  59340
gaaacccaac gctactgata ccccaataga agaaattggc gactcacaaa acactgaacc  59400
gtcggtaaat agcgggtttg atcccgataa atttcgagaa gcccaggaaa tgattaaata  59460
tatgacgtta gtatctgcgg ctgagcgcca agaatctaaa gcccgcaaaa aaaataagac  59520
tagcgccctt ttaacttcac gtcttaccgg ccttgcttta cgaaatcgcc gaggatactc  59580
```

-continued ccgtgttcgc accgagaatg taacgggggt gtaaatagcc agggggtttg ttttaattta 59640
ttaataaaaa tgtgtattac gttactcatg tgtctccatt acgcatcaca gggggtattt 59700
atacccgata atatacaaaa cgcgttttgt acctctaccg cacccgatat cttaacgggg 59760
ttattatgga atcgtctaac attaacgcgc tacaacaacc gtcgtctatc gcacatcatc 59820
cgtccaaaca gtgcgcttca agtctcaatg aaacagtaaa agattctccc cccgcgattt 59880
atgaagatag gttagaacac acgccggtac aattaccccg cgacggtaca ccccgagacg 59940
tatgttctgt gggacagcta acctgtcgag catgtgcaac gaaacctttt cgccttaacc 60000
gcgacagcca atacgactac ttaaacacat gtccaggggg ccgtcatatt tcactggcac 60060
tggagattat aacgggtcga tgggtttgca tcccgcgtgt gtttccggat accccagagg 60120
aaaaatggat ggcgccatat attattccag accgagaaca accatcatca ggggatgaag 60180
attctgacac cgattaaatt taacttaaat aaaaccttac cacccataaa aacgccttct 60240
gtttgtttaa cacgacaccg cttaacaaaa aaaaaaaaac caaacacgcc ttttatgaat 60300
gtaatacttt tatttgttgg ttaacaccgc cccaccatca tctgatttgc aaacatatcg 60360
gcgtcgtctg ccgtggaccc ctgtattaaa ggggccttgg aactcgcctc cactgcattt 60420
acatcttgtc caactgtatc tgtatgtggg gtgcttgttg tattttggga tgagcataga 60480
cccgaaacgc tttgaagctg ttttaataaa atcgatattc gaggatcccg tgtcccctct 60540
ggtatatttg tatggtgcga caaaggcatt tgtgtcccat tttgtgattt tagctctgta 60600
acctcctgtt gcagttttgc cacaacccca gcaagctctt cgtgctgacc attagaaact 60660
ctgtgtctcc tctgccaata tgatggagaa actcgacgtc tccgatgcgt tatatacgtt 60720
ggttcaccgg gaaaatatat atttgaggga aactctccgt ccatttgaga ctccccacta 60780
taaaaagaat ccaattccct ttgatccatg ctcttgaaat cccgttttcc tggacgacgg 60840
acatcggttt tgtctggaaa atttacacac ggggtctgca agtcaatacc ccgttcggcg 60900
gccaatgcgt tcataaatgc ggacatttgc atttccaaac gattgggtgg tggatatccc 60960
ggaaacccgt acggtccccc gaagtgtccc ggagggcaac cataaccccc tgtattaggt 61020
gggaaggcag gcgggtgtgg agatccatat ggcccgacga tatactgtcc gttatttgga 61080
gctccaattg atacctgcgg atttttagtc tgcccggtta acagctgtga ataatacgcg 61140
gtaggtatca gtacaaattc ccctccggtt ggaacgcccg acgggggctg tggtgagata 61200
ttactagcgt tacctgctac agaagccata tcgctgtcgt tcctacacaa ctgcgtaacc 61260
tttaaatgcg gaacagtctt ttcacaatct tcatttgatt ccccaacacc caacgcgaga 61320
tcgtatatgg gcccgccggg gtggaatgtg gcgtttataa cacccgcgtt gggtaattta 61380
gactccaccc cattaacgtt ggttatccga gcaagtccat atccggtgct agcctgaaga 61440
taaacgtgac ccataattcc ggcttcgcgt ctacgttttg caaccacgtc ccatctatct 61500
cttaaaagca tattgttcac ggctgtggat aataacacct tggcgagttt atcttcgcta 61560
accttccata ctttatttaa acccgcgtag tctttaacca gcgacaataa ccgcgcttta 61620
ctttccatcg ataaaacccg gaatggttca attgaagatt ccggggtaca gtcataattg 61680
accactgttc caacgcgtct tccaacaaca cataacgcaa catgggtaaa aaaattaccg 61740
tctggtatct cattcgggga caatcgtttt gaagacaggg atacggaggg taagtaattt 61800
gtgaccaagt ataacgcacg ttctagcgga gataatacag aatctctatt tccaaaaaaa 61860
ttcgaatggg ccgcttcaaa cagcaccgca tgtagttgag ggcatctaac gatacccaaa 61920
aaaaaaggtc cgcgtatgtc ctcaatgatt gcgattactt cacccacgac acagtctttt 61980

```
cgatgatcga tgtttattgg tattttacta gtaggcggca aagcggaccg cacaatctct  62040
ggggtaatat ttaattcccc ttcgtccttt gaatataagg ctaaataccc agccacgtat  62100
aacgcttcac agttctcttc gtcagcttca gcagccatta taaacacccc acggaccgga  62160
tagtgaatac tcacggtgtg gaggcaaact gaggaatgac acccaaacag acaaaatata  62220
gaagatcata gtcactgtta acgttgaact gcgcaaggcg gcgactttct tccaatgccg  62280
cccttacacg cggttggtgc attaacattc caagtccccg ttcatattgc aacataacac  62340
tgtcatgtat tgataccacg gcggctatgg gtagggatgt aacattttgt cggcggtgtt  62400
ctaattccaa tgcaattaag cttatgagcc gatcttggta ctgtccagaa gaaatatcta  62460
ttacggttct tcctaaactt ccacgactaa gctgggtatg cgcgtctaaa caaagagcaa  62520
ctaatccagg aaacatttca gtcagctctg tggtccgatt taacgtatac agtggtgcta  62580
tatatcgttc acataaaaat tgaaagttat tattaccgct tttaaacttc ccatcaaacc  62640
ccgtcgctcc gcgcaagatt acattgttgg taggggttcc tgttgcttct gacacaatca  62700
aacccagttg aaaattattt tttagtttat ctccgtatac gttcccgttc cataataagc  62760
gccttaataa taataacgcc gtaatcgtgt caattgttaa ccttaataga gtttggtctt  62820
ccataagaaa cacgttttgg gcccgttcta aatacgccgc ggccgcctgt tgaatcttgt  62880
ccacatatgc ggtatgattg cgatcaataa tgtcattaac cccaggatta aactgtccag  62940
gtgcaggcgg taggacctgc aaccgtataa gcgcatccat aacagaatgt gacgttaagg  63000
cgccttgatc ataccgcccc ccacgagcat gaaactggtc gcgtggtaga cgatcatagc  63060
aaaattgata actgttttta ttttcgtgtg ttgtcatata attcacaaat gtctcagtat  63120
attccggtag gtgctctata aggttcccga aggacgaaac ttgaggttcg tggacactat  63180
tagatgtcct atacattaaa tataaacata ataccgcaca ctcgaacgcg gagtacgctc  63240
tatctccaac atacattctc ccggcggact gtagacatgt taccgttgtg ttcataaacg  63300
tacgggaaat gcgcccgtct ttacaatcaa ctccgcgtgc agctacgggc ctatctaaca  63360
caagccgttc ctgcagagta cgataccatg gcccgaaaac aatccctgga gagttattgc  63420
cccttgccct tcccaagtac accagggtga taaaatccac ttgaaagttt gtatcgtact  63480
gcaacggtgc atcatttttg gcaatctgta cctcggggtg tatagactca ttgcgtatta  63540
tttctgtacg tgtacattcc tcagattgtg catctgcttc ttccgcctcg gcagcagccg  63600
tctccaggga atccaaaacc ttggccatgc gcgttagttg ttcttcgagg ggctttaaac  63660
gacgatctat ttccgttggt aacgtaatcg tttccccgcg aaggttgtct aatgcggcaa  63720
cggccgccgc attttttaac gttaacgtat ttttttccaa atcgggattc atacgccctc  63780
ttaactcaaa cgcgggagcc gtccagtagt gtatggggaa gttgggggct ataaagttct  63840
tagtggtaga caaaaatatc ccacatttat tcggaaacga gatagatccg aacccatatc  63900
tcgccgtcat ggtgtctgca gcaaacaaag tcaactggcg tgaatataaa ccggtactgc  63960
tttaaaagct gttttcttac ccatgggaaa acatcccggt tatactttgt aaaattccac  64020
cacaagcacc taaagaaggc cttctaaggg gtaaatccac cccacaagct gcattttctt  64080
caaactttgt taaagcggaa cgatggcatg atttcgcacg ctttttcgca agagaacata  64140
cgtgaatttt ctttttgcat agacgtcttc gctctctaac ggaccttatc ggggggggtat  64200
attccgctac attctccaaa tgcgacgcta gcataacaag gtttccatga atcacctttg  64260
ggggtaaccg agttacctgt aacaggttca gaccccgttg agatacaaac acaaggaggg  64320
```

-continued

```
gggtcaccat tatttcatca gatcccgtgg gtgtggtttc ctttattaaa gccatggtat  64380
ccctcagctg gcgcataccc tcgcaaaact ggtgatactt agtaggggta tgtatattag  64440
cgctaaaacg gcaagatttt aattccacta taaaacaaac ggtctttccg gcaccactgg  64500
attccgtttg tataatacaa acacaatcgg ggcgtcggcg tcccaaattt acttcaaacg  64560
acattgatat gcgtacagcc ctttgaacat ccacgtggga taacggcgac aggagttttg  64620
ccagcctcgg gttgaacgcg tccgcgaaac ctcgacgtac gttatcaata tcctttttga  64680
gtacatcgta aaaacgagtg tggcaacgtt gtcccaaacg aaaacacttg gcccgaattc  64740
gactagcgga catatttgaa gttccgtccc agaagataac ctaagacgcg tttgtctaca  64800
ataaacatgt caacggataa aaccgatgta aaaatgggcg ttttgcgtat ttatttggac  64860
ggggcgtatg gaattggaaa aacaaccgcc gccgaagaat ttttacacca ctttgcaata  64920
acaccaaacc ggatcttact cattggggag cccctgtcgt attggcgtaa ccttgcaggg  64980
gaggacgcca tttgcggaat ttacggaaca caaactcgcc gtcttaatgg agacgtttcg  65040
cctgaagacg cacaacgcct cacggctcat tttcagagcc tgttctgttc tccgcatgca  65100
attatgcatg cgaaaatctc ggcattgatg gacacaagta catcggatct cgtacaagta  65160
aataaggagc cgtataaaat tatgttatcc gaccgacacc caatcgcctc aactatatgt  65220
tttcccttgt ccagatactt agtgggagat atgtccccag cggcgcttcc tgggttattg  65280
tttacgcttc ccgctgaacc ccccgggacc aacttggtag tttgtaccgt ttcactcccc  65340
agtcatttat ccagagtaag caaacgggcc agaccgggag aaacggttaa tctgccgttt  65400
gttatggttc tgagaaatgt atatataatg cttattaata caattatatt tcttaaaact  65460
aacaactggc acgcgggctg gaacacactg tcattttgta atgatgtatt taaacagaaa  65520
ttacaaaaat ccgagtgtat aaaactacgc gaagtacctg ggattgaaga cacgttattc  65580
gccgtgctta aacttccgga gctttgcgga gagtttggaa atattctgcc gttatgggca  65640
tggggaatgg agaccctttc aaactgctca cgaagcatgt ctccgttcgt attatcgtta  65700
gaacagacac cccagcatgc ggcacaagaa ctaaaaactc tgctacccca gatgaccccg  65760
gcaaacatgt cctccggtgc atggaatata ttgaaagagc ttgttaatgc cgttcaggac  65820
aacacttcct aaatatacct agtatttacg tatgtaccag taaaaagatg atacacattg  65880
tcatactcgc gtgtacgtgt ttttcttttt tatatatgcg tcatttatta ccacatcctt  65940
taatcccgcc tttatctccc taaaacggag tggtaatatt aaaagccgcc aagcctgttg  66000
gtgggtgagg aggggtaaag gcacgctgtg tgcataacgt tgcggtgata ttgtagcgca  66060
agtaacagcg actatgtttg cgctagtttt agcggtggta attcttcctc tttggaccac  66120
ggctaataaa tcttacgtaa caccaacccc tgcgactcgc tctatcggac atatgtctgc  66180
tcttctacga gaatattccg accgtaatat gtctctgaaa ttagaagcct tttatcctac  66240
tggtttcgat gaagaactca ttaaatcact tcactgggga aatgatagaa aacacgtttt  66300
cttggttatt gttaaggtta accctacaac acacgaagga gacgtcgggc tggttatatt  66360
tccaaaatac ttgttatcgc cataccattt caaagcagaa catcgagcac cgtttcctgc  66420
tggacgtttt ggatttctta gtcaccctgt gacacccgac gtgagcttct ttgacagttc  66480
gtttgcgccg tatttaacta cgcaacatct tgttgcgttt actacgttcc caccaaaccc  66540
ccttgtatgg catttggaaa gagctgagac cgcagcaact gcagaaaggc cgtttggggt  66600
aagtctttta cccgctcgcc caacagtccc caagaatact attctggaac ataaagcgca  66660
ttttgctaca tgggatgccc ttgcccgaca tacttttttt tctgccgaag caattatcac  66720
```

caactcaacg ttgagaatac acgttcccct ttttgggtcg gtatggccaa ttcgatactg 66780
ggccaccggt tcggtgcttc tcacaagcga ctcgggtcgt gtggaagtaa atattggtgt 66840
aggatttatg agctcgctca tttctttatc ctctggacca ccgatagaat taattgttgt 66900
accacataca gtaaaactga acgcggttac aagcgacacc acatggttcc agctaaatcc 66960
accgggtccg gatccggggc catcttatcg agtttattta cttggacgtg ggttggatat 67020
gaatttttca aagcatgcta cggtcgatat atgcgcatat cccgaagaga gtttggatta 67080
ccgctatcat ttatccatgg cccacacgga ggctctgcgg atgacaacga aggcggatca 67140
acatgacata aacgaggaaa gctattacca tatcgccgca agaatagcca catcaatttt 67200
tgcgttgtcg gaaatgggcc gtaccacaga atattttctg ttagatgaga tcgtagatgt 67260
tcagtatcaa ttaaaattcc ttaattacat tttaatgcgg ataggagcag gagctcatcc 67320
caacactata tccggaacct cggatctgat ctttgccgat ccatcgcagc ttcatgacga 67380
actttcactt ctttttggtc aggtaaaacc cgcaaatgtc gattatttta tttcatatga 67440
tgaagcccgt gatcaactaa agaccgcata cgcgctttcc cgtggtcaag accatgtgaa 67500
tgcactttct ctcgccaggc gtgttataat gagcatatac aaggggctgc ttgtgaagca 67560
aaatttaaat gctacagaga ggcaggcttt attttttgcc tcaatgattt tattaaattt 67620
ccgcgaagga ctagaaaatt catctcgggt attagacggt cgcacaactt tgcttttaat 67680
gacatccatg tgtacggcag ctcacgccac gcaagcagca cttaacatac aagaaggcct 67740
ggcatactta aatccttcaa aacacatgtt tacaatacca aacgtataca gtccttgtat 67800
gggttccctt cgtacagacc tcacggaaga gattcatgtt atgaatctcc tgtcggcaat 67860
accaacacgc ccaggactta acgaggtatt gcatacccaa ctagacgaat ctgaaatatt 67920
cgacgcggca tttaaaacca tgatgatttt taccacatgg actgccaaag atttgcatat 67980
actccacacc catgtaccag aagtatttac gtgtcaagat gcagccgcgc gtaacggaga 68040
atatgtgctc attcttccag ctgtccaggg acacagttat gtgattacac gaaacaaacc 68100
tcaaaggggt ttggtatatt ccctggcaga tgtggatgta tataacccca tatccgttgt 68160
ttatttaagc agggatactt gcgtgtctga acatggtgtc atagagacgg tcgcactgcc 68220
ccatccggac aatttaaaag aatgtttgta ttgcggaagt gtttttctta ggtatctaac 68280
cacgggggcg attatggata taattattat tgacagcaaa gatacagaac gacaactagc 68340
cgctatggga aactccacaa ttccaccctt caatccagac atgcacgggg atgactctaa 68400
ggctgtgttg ttgtttccaa acggaactgt ggtaacgctt ctaggattcg aacgacgaca 68460
agccatacga atgtcgggac aataccttgg ggcctcttta ggaggggcgt ttctggcggt 68520
agtggggttt ggtattatcg gatggatgtt atgtggaaat tcccgccttc gagaatataa 68580
taaaatacct ctgacataaa aaacatgtat aataaaaagt cactataaac gtattctcta 68640
caatacttta ttcgcgaata atacacacta cctttgggtt tttttcccgt ccccaaatgg 68700
tgtttggtgc actctaccaa aaaatagagc gcctaaatat gctatataac gcctcccagc 68760
aaaatacggt tcaaaggcat tacccgatat tgtattgtag tacagggcaa tgggaattga 68820
tgatcccaat aaacggcata gacgcacagc gccgttatag caggggtctc cagagtacag 68880
ggtatctaag taccgggata tctcatactc atgcctttcc gtgacagaaa catcaaccgg 68940
aacagtatcc gataaaccaa ctcctgtttt tgcaaggcgt aaaattcgca caccttcctt 69000
ttttgcaaga tgtgacgttt ccttgtaaca gggaagctgg gggagtggta agaacaacaa 69060
agtttcagcc aacgtgccaa taaagcccac ttccctcaag aggctgtttg ctgtatccac 69120
aatggtccgt attaaatctt gagcaacttg atccgtgtca tcatcactgg gtaacgcgtt 69180
aacataacta cgcgttaaat cttcaataac ggcataacaa ttaaacgctt cccaccgaga 69240
cagtatatat tgaacaatca cgaaccgttg acaggacgtc agatcacgtc cgtaagcatg 69300
cccgaaaaat ggaagttccc cccgttcgcc atataccgca acaactgcag tatatatcgt 69360
ctcacgggct tcattaagtt catcttcaag tccaggccat tttctggctt taaatataac 69420
ctcgtccgca aaaaaaaccg cacatgataa cgcgcggata caatgagtag tggctttatg 69480
gcgaggatcc caaatgtcca ttacccgggg gatggtccta atctgtacaa agttacttag 69540
tgtaatatga tcggacttct tacgccgtct aggctgtttc tcagaatacg gttcacccga 69600
aatcggcaca tcatctgctt ttacgtcttc cgtaaccaca tcagcagcgc gccgactaac 69660
aattatactt gtttttcat cgtcgttact tccgttaagc gcgtctcgta tctcgggcgt 69720
cccgtcgaat aatccactca ctagctcctg caaactttct ggtaactcca acatacgcat 69780
atacaccaat gaaaaactgg cttcgtttgg tacgtacata aagccatttg tggtattaat 69840
ggcggtgggt gttggaaaca attttagctt attctcgcgc gtaacatcta cccccgccac 69900
caatgttaaa tgcgtcacgg ggagggacac gagataatct gcgagcgtag ggtcctccac 69960
ttcaacatca aatgttccgc aaaggtcgcg atccaccgcc cccgatcccg ctgcaagtaa 70020
ggccactcga tccaaaaaca cgcagttatt attggatgat accgcccatg tcttcccggt 70080
gcgattgagc tcacttcgaa cgtaactggc aacagatctg tcaccgggtc cgaccccgcg 70140
aacaacatgt ccaaattttg cgatctcgcc tccatgtttg cggggtatgg aaattaagca 70200
tcccccgcat ataaaatacg ccctggtagc acgctcgtta aaataaaacg ttacgccgtt 70260
ataagatacg gttgaatgat atggaaattc catattaaag cgtttatcgg aacattaacc 70320
tcgaacttgc cgtcccgtga tcgtgtgatc gccaacctta ggtccacacc gaatatgaga 70380
aatatataac tacacgcaaa cattcaaaac accgtggtat cattaacgtc atatgaaaag 70440
atccaatcaa tccaatcaac cacacctcct accgtttagc acgtcagcta tgtgacatgc 70500
tccaaacata cgtaaacatt tagagagggt gttataacag tctgtcaggc ggggtatatt 70560
ctacataata caaggatcgg ctttaacttt gtcaacattt ttactttgga ctataaactg 70620
cgactgaacg ttatgaaccc accccaagcc cgcgtctcgg aacagacaaa ggacttgctt 70680
agcgttatgg ttaaccagca ccccgaagag gacgcaaaag tgtgtaaatc cagtgataat 70740
tcaccgcttt ataacaccat ggttatgtta tcgtatgggg gtgatacgga cttactatta 70800
agctctgcat gtacccgcac atctaccgta aacaggtcgg cgtttacgca acactccgtg 70860
ttttatatta tatccacggt gttgattcaa ccaatatgtt gtatcttctt tttttttac 70920 tataaagcga cacgctgtat gctcttattc acagccgggt tacttctgac gattctacat 70980
cactttcgac ttattattat gttattgtgt gtctacagaa atatacgatc agacctgcta 71040
cccttatcta catcccagca actgctgctt ggaattattg ttgtgactcg aacaatgcta 71100
ttttgtatta cggcgtatta tactcttttt atagacaccc gggtgttctt tttgattacc 71160
ggacacttgc aaagtgaggt tatttttcca gatagcgttt caaaaatact tcctgtgtcg 71220
tggggtccaa gtccagccgt gttactggta atggcggcag ttatttacgc tatggactgt 71280
ttggtggaca cggtatcctt tattgggcca agggtgtggg tccgtgttat gttaaaaaca 71340
tctatttcgt tttagtccat ttcaataaat gtactataat tgttcagtct aaaaataatg 71400
ttgggtattt ataattaccg cccccgtgtt acttggaaac acccatacat atgttccact 71460
ctacatcaaa cttctcgcag ttttcttgtt cccgcacacg tttacacgtc cggattcaag 71520
tcgcaacgct gctgacaaaa tgacaacggt ttcatgtccc gctaacgtga ttactacaac 71580
ggaatctgat cgtattgctg ggttatttaa catcccagcg gggatcattc caactggaaa 71640
tgtgctgtca accatagagg tgtgtgcaca ccgttgcatt tttgattttt ttaaacaaat 71700
acgatcagat gataacagcc tttactcggc tcaattcgat attcttttgg ggacatactg 71760
caatacatta aactttgtgc gttttctaga acttggactg tctgtcgctt gcatctgtac 71820
taaatttccg gagctggctt acgtgcgaga tggcgttatt caatttgagg tacaacaacc 71880
catgatagca cgtgatggcc cacatcccgt cgatcagcct gttcataatt atatggttaa 71940
gcggatacac aagcgttcgt taagcgctgc gtttgcaatt gcatcggaag cgttgagttt 72000
gttaagtaac acatatgtcg atgggacaga gattgactca tcgttacgta taagagctat 72060
ccaacagatg gctcgtaatt tacgcaccgt tttggactca tttgaacgag gcactgccga 72120
tcaacttctt ggtgttctat tggagaaagc cccaccgcta tcgctgcttt caccaattaa 72180
taaattccaa cccgagggac atctaaatcg tgttgcacgc gcggccctac tttcggacct 72240
caaacgtaga gtctgtgcgg atatgttttt tatgacccga cacgccaggg aacctaggct 72300
gatctctgcg tatctgtcgg atatggtttc gtgcacccaa ccatcggtga tggtatcacg 72360
aataactcat acaaacactc gcggacggca ggttgacggt gtgttggtaa caacagcaac 72420
cttaaaacgg caactattac agggaatttt acaaattgac gacaccgccg ctgacgtacc 72480
agtaacatat ggcgaaatgg ttctacaggg gacaaacttg gtaaccgccc ttgtgatggg 72540
aaaggccgtc cgcggaatgg atgatgtagc ccgccatctc cttgatataa ccgaccctaa 72600
cacgttaaac ataccgtcta tacccccaca atccaactcc gattcaacga cagctgggct 72660
tccggttaac gcccgtgttc ctgcggattt agtgattgtt ggggataaac ttgtattctt 72720
agaagcatta gaacggcggg tctaccaagc tacgcgcgtt gcctaccctc ttattggaaa 72780
tatagatatt acgtttatca tgccaatggg agtgtttcag gcaaactcca tggacagata 72840
tacacgacac gccggcgatt tttcaactgt atccgaacag gatccacgtc aatttccacc 72900
ccaagggatt tttttttata ataaagatgg gatattaaca cagttgactc ttcgtgatgc 72960
aatgggtacc atctgccaca gttcattgct tgatgtcgag gccacacttg ttgccctccg 73020
ccaacaacat ttagatcgtc agtgttattt tggtgtatac gtggccgagg gtacagagga 73080
cacattggat gttcaaatgg ggaggtttat ggaaacgtgg gcagatatga tgcctcatca 73140
ccctcattgg gtaaacgaac atttaacaat tctacagttt atagctccga gcaacccgcg 73200
tctaaggttt gaattaaacc ccgcctttga ttttttttgtt gcaccggggg acgtagacct 73260
tcccggaccg cagcgtcccc cggaagccat gccaaccgtt aacgcaacat tacggattat 73320
caacggaaac attcccgtgc ctctatgtcc catttcattt cgagactgtc gcggaaccca 73380
actcggtttg ggaagacata caatgacccc ggcaaccatt aaagccgtaa aggatacatt 73440
tgaagaccgc gcatacccaa ctattttcta catgctagag gctgttattc atggaaacga 73500
aagaaacttc tgtgcgttac tgcgactgtt aacacagtgt attcgcgggt attgggagca 73560
atcccacagg gtggcatttg taaataactt tcacatgtta atgtacataa ctacatatct 73620
cggaaacggt gagcttcccg aagtctgtat taatatatat cgggatttac tgcagcatgt 73680
aagagcatta cgccaaacta taaccgattt tacaatacaa ggagagggcc ataacggcga 73740
gacctcggaa gcgctaaata acatccttac ggatgacacg tttattgcac ctattctatg 73800

```
ggattgtgat gcgttaatat accgtgatga agccgcccga gaccgactcc ccgcaattcg  73860
tgtaagcggg cgaaacggat accaagccct tcactttgtg gatatggccg ggcataactt  73920
ccaacgacgc gataatgtgt taatccacgg gagacccgtt cggggagaca cgggtcaggg  73980
tattcccatt actccacacc atgaccgtga atggggtatt ctctccaaga tttactacta  74040
tattgtcatt cctgcatttt cccgcggttc ctgttgtaca atgggcgtgc gttatgatcg  74100
cctataccct gcgttacagg cagttatcgt tccggaaatt cccgctgatg aagaagcccc  74160
aactacccca gaagatccaa gacaccctct tcacgcacac caactcgttc cgaactctct  74220
taacgtttac ttccataatg cacacctaac cgttgatggt gatgcattgc tcacactaca  74280
agagttaatg ggagatatgg ctgaacgaac gacggccatt ttagtatcaa gcgcccccga  74340
tgcgggagcc gccacggcaa caaccagaaa tatgagaata tatgacggag cgctttacca  74400
tggccttatt atgatggcat atcaggcgta cgatgaaacc attgcaacgg gtactttttt  74460
ttatcccgtt ccggtcaacc ctctgtttgc atgtccggaa catttggcat cattgcgtgg  74520
aatgacaaat gctaggcggg ttttggcaaa aatggtacca ccaatccctc cttttctggg  74580
agccaaccac cacgcaacta tacgccaacc cgttgcctac catgtaacgc atagtaagtc  74640
ggattttaat actcttacat attctcttct tggagggtat tttaagttta caccaatatc  74700
tcttacacat caactacgaa cgggatttca ccccgggatt gcctttaccg tagtgcgcca  74760
ggatcgcttt gccacagagc aacttttata tgccgagcgt gcttctgaat cgtactttgt  74820
cggacaaatc caagtacacc atcatgatgc tattgggggg gtaaacttta ccctaaccca  74880
acccagagct cacgtggacc tgggagtcgg gtatacagct gtatgtgcca cagcagccct  74940
gcgatgccct ctcacggata tggcaatac tgcccaaaat cttttttttt cacgaggagg  75000
agtgccaatg ttacatgata acgttaccga atcgttgcgt cgtataacag catcgggggg  75060
tcgcttaaat cccaccgaac ccctacccat cttcggcgga ctacgtcctg ctacatcggc  75120
aggaattgca cgagggcaag cctctgtgtg tgagtttgtg gccatgccgg tgtccactga  75180
cctacaatat tttagaactg catgcaatcc tagaggtcga gcatctggaa tgttatatat  75240
gggtgaccgt gacgccgaca tagaggctat aatgtttgat cacacacaat cggatgttgc  75300
ttatacagat cgagcaactc ttaacccatg ggcatcacaa aaacattcat acggtgacag  75360
gctatacaac ggaacataca accttacagg cgcttctcct atctacagcc catgctttaa  75420
gtttttaca ccagcggagg ttaacactaa ttgtaataca ctggatcggc ttctaatgga  75480
ggcaaaggct gtggcgtcgc aaagctccac cgacactgaa tatcaattta aacgccctcc  75540
cggttctacc gaaatgacac aggatccgtg tggccttttt caagaagcat atccaccact  75600
atgctcaagc gatgcggcca tgttacgaac ggctcacgcg ggagaaaccg gggcagatga  75660
agttcactta gcccaatatc tgattcgaga cgcgtcgccc cttaggggat gtcttcctct  75720
tccgcgataa tttcaccacg cccacatacc cactcccaat aaaagccctg tagagcgcat  75780
tggcatctta cttgagattt ggatacgctc ggccgacttg gtctgtttca cgcttcctta  75840
aacaacatgg ctatgccatt tgagatagag gtattgttac caggagaact atccccggcg  75900
gaaacatctg cattacagaa atgtgaggga aaaattatta ccttctcaac cctgcgtcat  75960
cgagcttcac tggtggatat agcgctgtcg tcatattaca ttaacggtgc tccaccagac  76020
acgctctcgc tgttagaggc ataccgaatg cgattcgcgg cagttataac acgggtcatc  76080
ccgggaaagt tgttggcgca tgccattggc gtgggtactc ctacacccgg gttgtttatt  76140
caaaatacat cccccgttga tctttgtaat ggcgattaca tctgcttact tcctccggtt  76200
```

```
ttcgggtccg cagactcaat tcgcttggac tctgtaggac tggaaattgt tttcccttta  76260
accatccccc agaccttaat gcgagaaatc atcgccaaag tggttgcacg ggccgttgag  76320
cgcacggccg cgggtgctca aattttaccc cacgaagttc tacgaggcgc ggatgtcatt  76380
tgttacaatg gaaggcgtta tgaactcgaa acaaatttac aacatcggga cggatcggat  76440
gcggctattc gcacattggt tttaaatcta atgttttcca taaacgaggg atgtctgctt  76500
ttattggcgc tgattccaac tttgttagtc caaggagcac acgacggtta tgtaaattta  76560
ttgatacaaa cggccaattg cgttagagaa accggccagt taattaatat accgccaatg  76620
ccgcggattc aagacggcca tcgccgattt cccatatatg aaactatttc atcttggata  76680
tcaacatcat ctagactggg ggataccttg ggaactcgcg caattttacg cgtctgtgtg  76740
tttgatggac cctctactgt tcatccggga gaccgcacgg ccgtgattca agtgtaaaca  76800
ggtgttaata aaaacacaac cagtctagtt acatttcacg cgtcttgttt ttatttaata  76860
ggcataaaca cggaatccgg tatacatgaa ctgccaatat acacggacat aattaatgca  76920
accatcagat catctgacat tgttcccgtg gtacctttac ccgtgtaagt ttttgtgtct  76980
agattaccca taccgccttt aattacctct gtcaggttat ccaactgttt acatagatac  77040
tccacggggt ctacacctaa ctttactgtt agggatacaa gctcctgtga ggctattata  77100
tttccggagt taaatcgttt aacaaaatag tctacggccg gcgttttttg tttttgtaat  77160
aaaaaaaaag ggtacgccac gctacatccg ggaggtatgg aatgataaaa cagtaacact  77220
ggagcggaag atagcacgtt tcccttttcg aggacagcaa actgttgtgc tatagccaac  77280
gatatggcaa ctgcagaatc ctggctgctg tttccctcta tagaaacgtg tacgtttgta  77340
aatgtattgg ggtgtaaagc gagtatgtgg cctaagcatt gagtaacgca acgccctatc  77400
tcactggaag acgtgccagt taaagctcta agaaaaaagt gctccaatcc aaatataatc  77460
caatccgact tataacgacc aacaatcgct acaccagtac cagacgctcg tgtatttgag  77520
gtaaatgcag ggtctacgta aacgtacaac actgacgata atatagcaca attcgcaacg  77580
gttgacggcc gatataaaat aaacctctca cgggcagttt ttgtaaataa tggccggtca  77640
aaccccacac ccccagaatt ctgtttacgc ccacctacaa tttcctgcac gaaggagtcg  77700
gccataaata aatctgcagt gcgccgcatg gctccatcca ttgtgatgaa aaccggctta  77760
tttaatacat aacacgaaca agctgtgaca tcgctatgtg ctaaaacacg cggcatgtga  77820
tcgtcgcata catatgtaac aacgtttaac aactgatccg acgatccacg taagttatac  77880
aaaaaacttg tacttgcttt tccggtattt gttgatgaaa caaaaataat tttacaattg  77940
gtttgattta aaaatccgac tatagtttgt acagcatcag gtcgaataaa attagcttca  78000
tccacaaaca gaagattaaa atcttgacct cggataccct ggaacgatag aaagatatat  78060
agttacccca ccaaagttta aatgtatcct taaataccac gtacgtaaaa aatgtttgaa  78120
tacgtacata tttctttttt ttttccagta caaccatatc cggtgtataa tggaagccca  78180
tttggcaaat gaaaccaaac atgcactttg gcataatgat cacacaaaag gattactaca  78240
cgttgtgata cctaacgcgg ggcttattgc ggccggaata gatcccgcat tactgatttt  78300
aaagaaaccc ggacaacgct tcaaggttga agtacaaaca agatatcatg ctacaggtca  78360
atgcgaaccg tggtgtcaag ttttcgccgc gtacattccc gataacgcct taacaaatct  78420
cttaatacca aaaacggaac catttgtttc acacgttttt tcggccacgc ataattcagg  78480
gggattgatt ttatcattgc ctgtttatct tagccccggt ttattctttg atgcatttaa  78540
```

-continued cgttgtagcg atacgaataa atactggaaa ccgcaagcac cgtgatattt gtattatgta 78600
tgcagaacta atcccaaacg gaacgcgtta ttttgctgat ggacaacggg tacttttatt 78660
atgcaaacag ctgattgcgt atatccgatg cacccctcgt cttgcatcgt ctataaaaat 78720
atacgcagag catatggtgg cagccatggg tgaatcacac acgtcaaatg gggacaatat 78780
tggacccgtt tcatccataa tcgatcttga tcgacagtta acttctggag gtattgatga 78840
ctcccctgct gaaacacgca tacaggaaaa taatcgggac gtccttgagc taataaaacg 78900
ggccgtaaac attgttaact ccaggcaccc cgtccgacct tctagttccc gcgttgcatc 78960
tgggttgctt caaagtgcaa agggccacgg agcgcaaact tccaacacag atccgatcaa 79020
taacggttcc tttgatggcg tccttgagcc gcctggacaa gggcgattta cgggaaagaa 79080
aaacaattcg tccgccagca tcccaccttt acaagacgtt ctattgttta ccccagcttc 79140
gacagaaccc caaagtctta tggaatggtt cgacatctgt tatgcccaat tagttagcgg 79200
ggacactcca gcagatttct ggaaacggcg tcccctatca attgtaccgc gacattacgc 79260
agaatccccc agtccgttga ttgtagtatc ttacaacgga tcctctgcct ggggaggacg 79320
tattaccgga agtccaattt tatatcactc tgcacaggct attattgatg ctgcgtgtat 79380
aaatgcccgg gttgacaatc cccaaagcct acatgtgaca gctcgccaag agctagtcgc 79440
gcgtttaccg tttttggcta acgtcctaaa taatcaaacc cccttacccg cctttaaacc 79500
aggcgccgaa atgtttttaa accaggtatt taaacaagcg tgtgtgacat cgctaaccca 79560
aggtcttata acggagttac aaacgaaccc gactctacaa caactcatgg aatatgatat 79620
tgcagattct tcccaaacgg ttattgatga aattgtagcc cgcacaccag acctgattca 79680
gactatagtt tcggtgttaa cggaaatgtc aatggatgcg ttttataaca gctccttgat 79740
gtatgcggtt ttggcgtatc tgtcatctgt atatacacga ccacaaggtg gggggtatat 79800
accctacctt cacgcttcct tcccatgctg gttaggtaat cgttctatat atttatttga 79860
ctattataat tcaggagggg aaatacttaa gctttccaag gtccccgttc ccgtagcctt 79920
agaaaaggtt ggtattggta attccacaca actgaggggt aaatttatac gcagcgcgga 79980
tattgttgat attggaattt gttctaagta tttacccggt caatgttacg cgtacatttg 80040
tctaggattt aaccagcaat tacaatccat tttagtttta ccgggggggat ttgcggcatg 80100 tttttgtatt accgataccc tacaggcagc actacctgca tcgttaatcg gacctattct 80160
agacagattc tgcttctcta ttcccaaccc ccataaataa attagtgtca ctataaaaac 80220
ataacaccag aatctcttca tatgtaattt tacgtcattt ctcccgtttc cacccccctct 80280 taaaatataa aataaccggg tgggtggcat taaacccaca agtacccggg cggcaatccg 80340
ctagactgtt tttctgctca tggaattaca acgcatattt ccgctgtaca ccgctacggg 80400
tgcagcgcgc aaattaaccc ccgaggcagt tcagagactc tgcgatgcat taacgctgga 80460
tatgggatta tggaagtcca tcctgaccga tccccgggtg aaaataatgc gatcaactgc 80520
ttttataact ttaaggatcg ctccgtttat ccccccttcaa acggatacta ctaatattgc 80580
cgttgttgta gccacaattt acatcacgcg cccacgtcag atgaacttac ctccgaagac 80640
ttttcatgta attgtaaatt ttaattacga ggtctcgtac gcaatgacgg cgactttaag 80700
aatttatccg gttgaaaaca tagaccatgt ttttggagca acgtttaaga acccgatcgc 80760 gtacccccctt ccaacatcta ttccggatcc tcgagcagat cccaccccccg cagatcttac 80820 accaacgcca aacttaagca actacttaca acccccgcgg cttccgaaaa atccatacgc 80880
atgtaaagtt atttctccgg gagtgtggtg gtcagacgaa cgaaggcgtt tatatgtact 80940
ggctatggaa cctaatttaa tagggctatg tcccgccgga tggcatgctc ggatacttgg 81000
ctctgtatta aatcgactcc tcagccatgc ggacggatgt gatgaatgta atcatagagt 81060
tcacgtgggg gcactgtatg cgttacccca tgtcacaaat catgcggaag gttgtgtgtg 81120
ttgggctccg tgtatgtgga gaaaggccgg tcagcgggaa ttaaaagtgg aggtagacat 81180
tggcgccacg caggttcttt ttgtagatgt caccacctgc attcgaatta cgagtactaa 81240
aaatcctcgc attaccgcaa atcttggcga cgttatagcg ggaaccaacg ccagtggtct 81300
ctctgtacca gtaaattcat ctgggtggca gctttatatg tttggagaaa cattaagccg 81360
ggctattatt aacggctgtg gtctgcttca gcgaatttgc ttccccgaga cacaaagatt 81420
atcgggtgaa ccggaaccta caaccaccta gtatacctta actcaaccgc cgttgtggaa 81480
aggtatatgt caacatttac agtaatatat taaaggttaa atttataaaa cactcacgtt 81540
tgtgttgtga cttgacgcga acaccgctgt gctgtaagac ccgtcggtaa atgaaaacgt 81600
aatagattcg ccttttacat gatccacgta atttgcccca aaccactgtt ccaggcgaga 81660
cttgataccc tcaaacacgg gttccgttgc tttgcgtata tgagccgtat aacccacttt 81720
aattcctcta aacgtggcca ttactaaagc tattaatggt acaagaaacc atgttttccc 81780
atgtctacgt ggtaccaaaa acacagttga tttttgtttg aagtgttcta aaacactgtc 81840
agaaacactt ggcgtgttaa acactgtacg cagaaagcag tcaactctgt cggcatgatc 81900
gcccaatagc accgatgaaa taaaatgcgt ggtgtgcatg aggatcattt tttgaaacag 81960
ttccaacgtc cccttatatc tgccatagat tggaacgtca acctttgcgc gtttgccatg 82020
acttccacac tcttcaatac tctcaaaaga tgtttccaca aggtacgaaa accgttgtgt 82080
aaaggtagac aactgacaga aactatccga cagagaaaac gcgcgaaatg tgttcataac 82140
accgctatac gcatttcgat gaggtgctgc ttcttccggt gaatattcat aaaactgtac 82200
actactgaca gcctttttta attcagggct tacgtttgca tttaccgaat atcgccatgg 82260
tttcaaaact acattggggg tacagttgta ccctgttgac gatagaaacg cgccaaacat 82320
tgcccgtcga gcagtagccg agaacagtgg aatatattca caacagttgt gaagcgttcc 82380
aattccggga ataacggcct gatgacgtcg ggttacatct atagcaaaat tcagaaacgg 82440
gatttgggtt gcgtttccca gagacccttg ccgcgtggaa cacggggtag gggactccaa 82500
cgtcccaaag cgttcatccc tacgacgctt tagacgttca aaatatctta cagattcttc 82560
accaagcgta cgaccaaaca ttatcaatga catttaacat caattcacgg aatccgcctc 82620
atctcttgta agcagtaaaa caggaagccg cgtcatctta cgtactcgtt acgtatatat 82680
cataaacatt ttcagggccg cattcattca ctttggtcat gtcaggccac actccaacct 82740
acgcttctca taggcgtaac cgtgtcaaac tagttgaggc gcataaccgc gcggggttat 82800
ttaaagaacg gaccctcgat ctaatccgtg ggggtgcgag tgtacaagat ccagcatttg 82860
tgtatgcctt tactgctgca aaagaggcct gcgccgattt aaataaccag ctccgctctg 82920
cagctcgcat agcttcagtt gaacagaaga ttcgtgatat acaatccaag gttgaggaac 82980
aaacaagtat tcaacagatt ttaaatacaa acagacgcta tatagcaccc gattttattc 83040
gcggtttgga taaaacagaa gacgataata ccgataatat agacagactg gaagacgcgg 83100
taggaccgaa catcgaacac gaaaatcata cttggtttgg agaagacgac gaagcgttac 83160
ttacacaatg gatgctgacg acacaccccc caacctccaa atatctccaa ctgcaggacc 83220
tttgcgttcc caccacaata ccgacggaca tgaaccaaat gcaaccgcag ccgatcagca 83280
agaacgagaa tccaccaacc ccacacacgg atgtgtaaat catccatggg ccaatccgtc 83340
aactgcaaca tgcatggaat caccagaacg atcacaacag acaagcttat ttttattaaa 83400
gcacggctta acgagagatc caatacatca acgcgaaagg gtggacgttt ttccacaatt 83460
taacaaaccc ccatgggttt ttagaatttc caaattatcc cgtttaattg tacccatctt 83520
cacgctcaat gaacagttat gtttttctaa attacagatt cgagatagac ccaggtttgc 83580
gggacgggga acgtatgggc gtgttcatat atacccatcg tcaaaaatag ctgtaaaaac 83640
catggacagt cgtgttttta atagagagtt aattaacgcg attttagcga gtgagggttc 83700
tatacgagca ggggaaaggc taggtatttc tagcatagtt tgccttttag gtttttcgtt 83760
acaaaccaaa cagctactgt ttccggcata cgacatggat atggatgaat acattgttcg 83820
cctgtccaga cggttgacaa tacctgatca catagacaga aaaattgccc atgtattttt 83880
agatttggct caagcgttga cgtttttaaa tcgaacgtgc ggcctgaccc acctagatgt 83940
gaaatgtggc aatatttttc ttaacgtcga caactttgcc tcgttggaaa taaccacagc 84000
agtaatcgga gactatagcc tagtaacatt aaatacgtat tccctttgta ctcgagcgat 84060
atttgaagtt ggaaatccat cccacccgga gcacgtacta cgcgtacccc gggatgcatc 84120
gcagatgtca tttcgtttgg tgttgagtca tggaacaaac caaccccctg aaatcttgct 84180
tgattatatt aatggaacgg gccttactaa atatactgga accttgcccc aaagagttgg 84240
acttgcgatt gatctttatg cattgggcca agcactctta gaagttatcc tgctaggacg 84300
tcttcccgga caactgccca tttcagtaca tcggaccccg cattatcact actacggtca 84360
taagttatca ccagatttgg cgcttgatac gctggcatat cgatgtgtcc tggcgccata 84420
tatactccca tctgacatcc ccggggactt aaattataat ccctttatac acgccggaga 84480
gctgaacacc cgtatttccc ggaattcttt acgccggata ttccagtgtc acgcagtgcg 84540
ttacggcgta acgcactcaa agcttttcga aggcatacgc attccggcct cattataccc 84600
agccactgtt gttacatcgt tgttgtgtca cgataattca gaaatacgct cggatcaccc 84660
tttattatgg cacgatcggg attggatagg atcgacataa gcccccagcc agccaaaaaa 84720
attgcccgtg tgggaggtct acagcaccct tttgtaaaaa cggatattaa cacgattaac 84780
gttgaacacc attttataga cacgctacag aagacatcac cgaacatgga ctgtcgcggg 84840
atgacagcgg gtatttttat tcgtttatcc cacatgtata aaattctaac aactctggag 84900
tctccaaatg atgtaaccta cacaacaccc ggttctacca acgcactgtt ctttaagacg 84960
tccacacagc ctcaggagcc gcgtccggaa gagttagcat ccaaattaac ccaagacgac 85020
attaaacgta ttctattaac aatagaatcg gagactcgtg gtcagggcga caatgccatt 85080
tggacactac tcagacgaaa tttaatcacc gcatcaactc ttaaatggag tgtatctgga 85140
cccgtcattc cacctcagtg gttttaccac cataacacta cagacacata cggtgatgcg 85200
gcggcaatgg cgtttggaaa aaccaacgaa ccggcggcac gagcgatagt tgaagcattg 85260
tttatagatc cggctgatat ccgtactcct gatcatttaa cgccagaagc tacaactaag 85320
ttttttaatt ttgacatgct caataccaaa tctccaagtc tccttgtggg tacaccaaga 85380
atcggaacgt atgaatgtgg acttttaatc gacgttcgaa cgggacttat aggcgcgtcg 85440
ttggacgttc ttgtatgtga cagggaccct ttaactggca ccctaaatcc ccaccctgca 85500
gaaaccgaca tttcattttt tgaaattaaa tgtcgtgcta aatacctctt tgatccagat 85560
gacaaaaata acccgctcgg tcggacgtac accacgttaa taaatagacc tacaatggca 85620
aatctacggg actttttata tactataaaa aacccatgtg taagcttctt tggaccctca 85680
gcaaacccaa gtacacgcga ggccttaata acggatcacg ttgaatggaa acgtttagga 85740
tttaaaggtg ggagggccct tacagaactc gacgcccatc atttgggcct caatcggaca 85800
atctcatccc gagtgtgggt atttaatgat ccggacatac aaaaggggac aattacaacc 85860
attgcatggg ccactggaga tacggctctt caaattcctg tatttgccaa tccgcggcac 85920
gctaacttta aacaaattgc cgtacaaacc tatgtattat ccggttactt tccagcgcta 85980
aaactacggc ccttccttgt cacctttata ggacgtgtgc gccgaccaca cgaggtggga 86040
gtcccattgc gcgtcgatac acaagcggct gccatttacg aatataactg gccgactatc 86100
ccaccccact gtgcggttcc ggttatagcc gttctaacgc ctatcgaagt tgatgtgcct 86160
agagtgacac aaatacttaa agacacagga aacaacgcga ttacatcagc attgcggtca 86220
ttgcgatggg acaatcttca tccagcggtc gaggaggaat ctgtggattg tgcaaacggt 86280
acaacgagct tgttacgtgc aacggagaaa ccgttgcttt gaactcagag ttctttgaag 86340
actttgactt tgatgagaat gtaacagagg acgccgataa atccacacaa cgccgcccac 86400
gagtgatcga tgtaacacca aaacgaaaac cttcgggaaa gagctcccat tccaaatgcg 86460
caaaatgtta aaccctgata aaccctgata aacgttctaa taaaaacatc aaatcatggt 86520
tggttactgt gaatgtttgt tttattgctt gggggtttac aagtacaacc cacgctactc 86580
ccacccactg tttgatcgct cgtataacag ctcatcctcg cggtccgttt catatgttga 86640
gtcattttca tagacgtagc cgtagccttg tgatgggtaa tttgtgcggc gagaatttct 86700
atgtgcaggt tttacttttc gtatgtatcc ccgtacccgc tcgggtactc ttcttacggc 86760
accgtagaac cgactgcgtt tctgtcgatg atacacatat gcacgcatca atctgagaag 86820
caacatgaca acggaaaaca cggccaggca agccaaggtt ccccgagttg tgggaattaa 86880
ccgtggagat tgaaccgata tagggtcata taatcggtcc atatacgagt gcgcggcggt 86940
tcccaacgta gcacaggcca cgagcgttcc cagggacggt cctattaaca cgtgtatata 87000
atgcgccaaa attaattctg atactataag atatacaact gacaatgtac taaatgtaga 87060
catggccacg gacaccgatg accacagtcc cgtatgtaga tgattcgcca ccacaagttc 87120
cagcattaat gatacaaata ggatacatat cgccatcaac gcagccatca aattcacgaa 87180
cactgcgcgc gtaggccccg caaggcgata taaaaagacg ctctgctgtc gtaaatttgc 87240
gaccgctttt atgttcgttt cgtccaattt tccgcgtcca caaaaatacg ttgtaaatat 87300
tacacttgtc gcaaaatgtc caagatataa tgtagcagcc acgccgattt gcttgtaagc 87360
taataataac acaacggcgt ttaataacca caatgacaaa agaccccaaa aaagtgttgt 87420
gggatctaca actaaccatg caacaccgga gctttgccgg acacgttgat ttttcgtttc 87480
tcggtgtata atcgcggccg tgatcagtgt atataccgcc atggccattg ccgttaaagc 87540
cgtgtagtaa gtaaatgcca caacgctatg tggttccaaa aacaaaaccg gggcgctgta 87600
tccacctcta tttccggacc atacccccc atctagggtg gcgttaaata actcataatc 87660
aactacggca gcataaaaac aagggatccc ggtatattca gaagaggcgg caattaacgt 87720
agccaggagc attaccgcac ccaaagtgaa catcatcacc tgaattatcc aaattcgcca 87780
attaagcgta tccatttgat gatctaacgc ttccacctcg ggtgtcgtgg tgtcgtacgg 87840
cgagactttt tcagaacgcg gccccttctt ttgagttccc atgtctccca acaccgggga 87900
gagcaacgcc gccgtctatg cgtccagtac acagctcgcg cgggcgttat atggagggga 87960
tctggtttcg tggattaaac acacccaccc gggaattagc ctggaactgc aattggatgt 88020

-continued

```
tccagtaaaa ctaataaaac ctggtatgtc acaaactcgc ccggtaaccg tcgtacgtgc  88080
ccctatgggc tctggtaaaa caacagcctt gcttgagtgg cttcaacacg cgttaaaggc  88140
agatattagc gtactggttg tctcatgtcg ccgtagcttt acccagacgt tgattcaacg  88200
gtttaacgat gcaggcctct ccggattcgt aacatatttg acatccgaga catatattat  88260
gggttttaaa cgtttgattg tgcaacttga aagcctacac cgcgtatcca gcgaagctat  88320
cgacagctac gacgtattaa tactggatga ggtaatgtca gtgattggac aattatactc  88380
ccccacaatg agacgtcttt ccgcggttga tagcctatta tatcgtcttt taaatcgctg  88440
ttctcaaatt atcgcgatgg atgctacagt aaactcgcag tttattgatt taatctccgg  88500
attgcgtgga gatgaaaaca tacacacaat tgtgtgtaca tacgcgggag ttgggttctc  88560
cggaagaact tgcacgatcc tgcgtgatat gggcatcgac acgcttgtgc gagtcattaa  88620
acgatctcct gaacacgagg atgtacgtac catacaccaa ctacgtggaa catttttga  88680
cgaactagca ctacgattac aatgtgggca taacatctgt atattttcat caactttatc  88740
gttttcggag ctagttgctc agttttgtgc aatatttaca gactctattc ttattttaaa  88800
ctcaactcgg cccctatgta atgtaaacga atggaaacat tttcgcgtgt tggtgtacac  88860
taccgtcgtg accgttggat tgagttttga catggctcat tttcatagca tgtttgctta  88920
cataaagcca atgtcatatg ggccggatat ggtatcggtc taccagtcat tagggcgtgt  88980
acgtttattg ctacttaatg aagttttgat gtacgtcgat ggctcaagga ccagatgcgg  89040
acccctgttc tcgccaatgt tactaaactt taccatcgca aataaatttc aatggtttcc  89100
tacacacacc caaataacta acaaactgtg ctgtgcattt aggcaacgat gtgcaaatgc  89160
atttacacgc tcgaacaccc atctcttctc aagatttaaa tacaaacacc ttttcgagag  89220
atgctctctt tggagtttag ccgatagcat taatatctta caaactcttt tggcctctaa  89280
ccaaattttg gttgtattgg atggcatggg tccaataacg gacgtttccc cagttcaatt  89340
ttgtgcattt atacacgatc tcagacatag cgctaacgcc gtagcttcct gtatgcgttc  89400
tcttagacag gacaatgaca gctgcttgac cgattttggc ccttccggat ttatggccga  89460
taacattacc gcgtttatgg aaaagtatct tatggagtca attaataccg aagaacaaat  89520
taaagtattt aaagcccttg catgtccaat agaacagcct agactagtca atacggcaat  89580
attgggggcg tgtatacgaa tacctgaagc gttggaagca tttgacgtat ttcaaaaaat  89640
atacacgcac tacgcttccg gttggtttcc cgtcctggac aaaaccgggg aatttagcat  89700
cgcgactata actaccgccc caaatttaac cacacattgg gagctgtttc gccgttgtgc  89760
ctatattgca aaaacactca agtggaatcc gtccaccgaa ggctgtgtaa cacaagtttt  89820
ggatacggac attaatacac ttttcaatca acacggggat tcgctggctc aactaatatt  89880
tgaggttatg cgctgtaacg ttactgacgc taagattata ttaaaccgcc cggtttggcg  89940
aacaaccgga ttcttagatg gatgccataa tcaatgcttc cgtccaatcc ctacaaaaca  90000
cgaatataac attgctctat ttcgtttaat ttgggaacaa ttatttggcg cccgcgtaac  90060
taaaagtacc cagacctttc cgggaagtac tcgtgtgaaa aacctaaaaa aaaaagatct  90120
agaaacttta cttgattcaa ttaacgtgga tcgttctgca tgtcgtacct accgccagtt  90180
gtataacctg cttatgagcc agcgccattc gttctctcaa cagcgttaca aaattactgc  90240
ccccgcttgg gcacgccacg tgtattttca agcacatcaa atgcacttgg ccccgcatgc  90300
cgaagccatg ctacaattag cgctatcgga actgtccccg ggatcgtggc cgcggataaa  90360
cggggcggta aattttgaaa gtttataacc cgttaatacc atatatggac atccataggg  90420
```

ggggttacat aaatactaag cctctgtaca acacaaaggg cctctaacaa tgcactgaac 90480
cacaaccaag ctatggacgc aacgcagatt accttggtta gagaaagcgg acacatttgt 90540
gccgcaagca tatacacatc ctggacacag tccggacaat taacacagaa cggtctttcc 90600
gtgttatact acttattatg caaaaactca tgtgggaaat acgtccctaa gtttgccgaa 90660
attaccgtac aacaagagga tttatgtcgc tactccaggc atggggggag tgtttctgcg 90720
gcaacgtttg cgtctatctg cagggcggcg tcctcggctg cgttagacgc ctggcccctt 90780
gaaccactgg gtaacgcaga cacctggcgt tgtctccatg gcactgccct ggccacttta 90840
cggcgcgtat tagggtttaa atcgttttat tcgccagtaa cattcgagac tgatacgaat 90900
acaggtcttc tgttaaaaac aatccccgat gaacacgcgt tgaataatga caacacgcca 90960
tctaccggag tattgagggc taattttccc gtggccattg atgtttcagc agtcagcgca 91020
tgtaacgccc acacgcaagg tacgtcgcta gcctacgccc gcctgaccgc acttaaatct 91080
aacggtgaca cccagcaaca aacaccttta gacgtggagg taattacacc aaaggcctac 91140
atacgtcgga aatataagtc tacgttttcc ccccctatag agcgggaagg ccaaacctcc 91200
gatttgttta accttgaaga acgccgcttg gttcttagtg gcaatcgcgc aattgtggta 91260
agggtactct taccgtgtta ttttgactgt ttaacaacgg attccaccgt tacatcttcc 91320
ctttcaatat tagcaacata tagactgtgg tacgcggcgg cgtttggaaa acccggggtt 91380
gtccgtccaa tctttgcgta tttaggcccg gaactcaatc cgaagggtga agacagagac 91440
tacttttgta ctgtcggatt tcccggatgg accactcttc ggacacaaac tccagccgtc 91500
gaatctattc gcacggctac ggagatgtac atggaaacgg atgggttgtg gccagtaacc 91560
ggtattcagg cctttcatta tctagccccc tggggacagc atcccccctt acctccgcgg 91620
gtgcaggatc ttattgggca aatccctcaa gatactggac atgcagatgc aactgtcaat 91680
tgggacgcgg gccggatatc taccgtcttc aaacagcctg tacaactaca agatcgttgg 91740
atggcaaagt ttgatttcag cgcctttttt cccacgatat actgcgctat gttccccatg 91800
cattttagat taggcaaaat cgtcctggct agaatgcgtc gaggaatggg gtgcctaaaa 91860
cccgcgttgg tgtctttttt tggggggtta cggcacatac tcccgagtat atacaaagct 91920
attattttta tagccaatga aattagcctt tgcgtcgaac aaacggcctt ggaacagggc 91980
tttgctatat gtacttatat aaaagatgga ttttggggaa tcttcaccga tttacatacg 92040
cgcaatgtat gttcagatca ggcacgttgt tcggccttaa atttagcggc cacctgcgaa 92100
agagcagtca cgggcttatt acgaattcaa ctaggtctta actttacacc cgccatggaa 92160
ccggtactcc gggtcgaggg tgtgtacact cacgcattta cctggtgtac cacgggaagc 92220
tggctgtgga atttacaaac aaacacgcct ccggatttag ttggcgtgcc atggcgaagt 92280
caggcggcgc gagatttaaa ggagcgtctt tcaggactcc tatgtaccgc aacaaaaatt 92340
cgagaacgga tacaggaaaa ttgcatatgg gaccatgtcc tatacgacat atgggccgga 92400
caagttgtgg aggctgccag aaaaacatac gtcgattttt ttgaacatgt ttttgatcgc 92460
cgttatactc cggtatactg gagtcttcag gagcaaaatt cggaaacaaa agcaataccg 92520
gcatcttatc tgacatacgg acacatgcaa gataaggatt ataaaccaag acagataatt 92580
atggttcgta atcccaaccc acatggacct cctactgttg tttactggga attgctacca 92640
tcgtgtgcct gtattccccc catagactgc gctgctcatc tcaagcccct tatacacacg 92700
tttgtcacta ttattaacca tcttctagat gctcataatg atttttcaag tccatcattg 92760

-continued

```
aaatttactg acgatcccct tgcttcatat aacttcttgt ttttatgaca aaaaaacacg  92820
ccgcaacaac ccatccttaa aataaaaggt ttatttactt tacaacccgt ggtgaatttt  92880
tatacgtttc aaataactga acatttttcg gtgttaccat ggtgcgattt aaccaccaaa  92940
aatatacgct cttctgatat tccgaatctc gtaaaggtcc atttaacaat cccgggggta  93000
cttgcaccac accatctgga cagggggggg ttccgtgggg caggtcaaaa cgctgaccca  93060
ccccacatga atatatagcc tttataatat tgggggccgt tccaggctga gggttcagta  93120
acttaacaaa catataatgc ggcaatacgc gggtttttgt aaaggggttg ttatcaacga  93180
catacattag agtgtttaac aaccataaaa ctccctcata taaaaaccga cgcatttttt  93240
ccaaaggtcc tatttgacac tcaacgcgtc taagatatac agacaattgt acaaacagcg  93300
atggagatgc cccggagggc ccaatgcctt ccagatacat taaaataaca cataaggtaa  93360
aatctaggac attatccggg cggaatagag tcatccgata gattaacagg cgcggaggca  93420
cccccaccgt atacacccta tcttcaaccg cagttaatac ggaaaaaata aatccgcgga  93480
acgctggttg agtaacacac tccatgtagt aacgatcaca ggacacctca cttgaatcac  93540
cattcaacac tactaaaacg gtctcttggt gttccggttt tacgcgcagt gatacaacag  93600
agtttgccaa aaagcgtggc ttcaaaccgg ttacctcccg cgcctcgcat acgaatcttg  93660
gtattgcttg tattctaaga tcttcgatca cgtcgctcac atccaacccc tcttcggctc  93720
gtgttagtaa gttgtcgatc gttacgctgc aacctaaaat gctgggtata tttattccgg  93780
acatcccatc ggccatcccc gcgcctccgg tttgctcgaa ttttatccag taaggtcgaa  93840
tccgctgcat ttaccttgtg tacccgtaac ctctcagggg ggtgtccttt cataaaatgg  93900
gataggtttt tatatccaac atgcatgtat tggttattta ttttattggg ttccgggatt  93960
ctttcgtcat cttctgtagg gtcaggcaaa ccccaggaag gacttggtgt tctccgtggg  94020
ccccgtttta ttacctctgc gcgaacctgc atttcatata atattcggat ttgggataaa  94080
taggactctg ttctcgcctt tttaaaaata gcctggcata actcttcctc tgacctatgt  94140
acctcgcttt gagttaccaa gaatcctaat cgggtggccc gtaatatgaa tgaaaaatac  94200
ggcgcaacta gtaatgagat tgacgcattt gaatatgata cagaaatttc ctggccttga  94260
ttattgttta cccggtgaag cttaaaacag cgaacaagtt cctgtttcca tagctcagac  94320
aaacgtttta tatcatctcc ataagggggg atataacgag attgaaaact attggcaata  94380
tatgcatcat cccctattat gccggtaaga tctataacct cgtgatttaa atcggcaata  94440
cgtgtttctt ctgccattgt aatatgtgac cctttagatg gctttatttt taccctctct  94500
tcccgtaacc gtttcagctc tccttctttg aactggagcc tttcggtcag atcgctgttc  94560
acatccttga gaccctcaat ggttttgaat aaattattca cataaccctc gagcatgccg  94620
ttgatactgt taaccaccga agttttaaac gcactttgaa cgtttgttgt tccggacatt  94680
gccccccccgt taaaggattg gttggccttg ccaaaccccg gttgtgatgt gtccaccgat  94740
ccacttcctt ccagaatgtg attgcccgtt tcttctagat aggaacgtac ggtttcggta  94800
atatctccaa catgtctcat gttttttaag ttaactatta gctttacaag tctagacgcg  94860
gccgatccag cccgtgttgt atcgttctcg cccattatac gatcaaccgc acgtgtgctg  94920
tgagatctat catcttcatt ccggcgacct attaacacgc gcaaaggggc tgtatttaaa  94980
acttggcaga cgcgagcatg ttcacgtaat gcataacagg ccaacacctc cccagaaagc  95040
cgctgtaagg gtgagtcaaa tactacaccc tccccacata caacgggcgg ccacacgacc  95100
aaacactctc ccttcatgcc cgttacatca tcctttgcca taattaatct tcggttataa  95160
```

-continued

```
ttataataaa gacgcgtcct atcataatcc ataatagcaa cattttgcat acactcaact  95220
aggcttgtga caaccgccgc tcctctggcc aacgttgcat cggcaacttt taacatctgg  95280
gacagttctg ccgcttgacc catatacgta tttaatggtg caggggttcc attctgttct  95340
gatcgtacct ttcttacaac gggcacaata cctacacagg ctatccagtc cacgtatttg  95400
gcaaaaccga cccttccatt taaaccactg gtatagagac aaccggttat tccacgcaga  95460
aactcaagta acgatgactg taatgtttga cgccaggttt caaaaacctg atgtgcaagc  95520
cgtacggctt ctgattctcc acatagccca taacgttccg ctagagcccc ggcatgcagg  95580
ttacattgtt ggatgtggtg ttcccaatct gctgctaggt cctcataccg agttgcatcc  95640
aacgcgttca tcaaaacggt tgcctgaact tggcgaatta cagtttccgt agaccgtaca  95700
gcgctatata tgccttgtcc atcggtatat ccaaagtcac cggctaggat ttttcgaaac  95760
aacatacttt gcgtggttgg gtgtattaac atccagccat cttcctccgg aaatgtacaa  95820
aaccctatat ccggggcgta ctcattccag tatatatcga acatgttctt gtattggtca  95880
tttgggttac ttccattcaa gccctggtca atagaaacag aacttgctat ccttttttct  95940
tcactaccgg aactgttatt aaaaagagac gttatttcgg ccattgaaaa ccacgatgaa  96000
aagatcaatt tctgtagaca gttcttcacc caaaaacgtt tttaatccag agacgcccaa  96060
tggatttgat gacagtgtat atttaaactt cacctctatg catagcattc aacctatcct  96120
ctcacggatt cgagaacttg ccgcaattac gattccaaaa gaacgtgttc cgcggttgtg  96180
ttggtttaaa cagttactcg aactgcaagc gcctcctgaa atgcagagga atgagctccc  96240
cttctccgtt tatttaatta gcggaaatgc cggctccgga aaaagcacgt gtatccaaac  96300
gcttaacgaa gctatcgatt gcattattac cggatccacc agggttgctg cccaaaatgt  96360
tcatgctaag ttatcaacgg cttatgcgag tcgtccgata aacacaatct ttcatgaatt  96420
tggttttcgc ggaaatcaca ttcaggctca gctgggccgt tacgcatata actggactac  96480
gacccccccct tctattgagg acctgcaaaa aagagatatt gtatactact gggaagtttt  96540
aattgatata acaaaacgag tgtttcaaat gggggacgac ggtcgcggag gaacatcgac  96600
atttaaaacc ctgtgggcaa ttgaacgttt gcttaataaa cctacaggct caatgtccgg  96660
aaccgcgttt atcgcatgcg gttcccttcc ggcttttacc cggagcaacg ttattgttat  96720
tgatgaagca ggattgctag ggcgtcatat tctcacggcc gttgtttact gttggtggct  96780
tttgaatgct atatatcaaa gccctcagta cataaacggt cgaaaaccgg tcatagtatg  96840
cgtcggttcg cccacccaaa ctgactcgtt agaatctcat tttcaacatg acatgcagcg  96900
ttcacacgta actcctagtg aaaatatact cacgtatata atctgcaatc aaactctgcg  96960
tcaatatact aacatctcac ataactgggc aatctttatt aataacaaac gatgtcaaga  97020
ggacgatttt ggaaatcttt taaaaacgct tgagtacggg ctacctatta ccgaagcaca  97080
tgcgcgtctg gtcgatacat ttgttgtacc tgcatcctat attaacaatc ctgctaatct  97140
tcccggatgg acgcgtctgt attcgtcgca taaggaggtg agcgcgtata tgagtaagtt  97200
acacgcgcat ttaaaactat cgaaaaatga ccatttttct gtgtttgcct taccgactta  97260
tacattcatc cggctaacgg catttgatga ataccgcaaa ttaacgggac aacccggact  97320
ttctgttgaa cattggatac gggcaaactc cggtcgtttg cacaattatt cccaaagccg  97380
agatcatgac atgggaacag ttaaatacga aacacattca aatcgcgact taattgtagc  97440
ccgtacagac atcacttacg tgctaaatag tctcgtagtt gtaaccacaa gactacgtaa  97500
```

-continued

```
gttagttatt ggattcagtg gtacatttca atcgtttgca aaggttttac gtgacgactc  97560
ctttgtgaag gctcgaggag agacatccat cgaatatgct taccggtttc tgtcaaacct  97620
aatctttgga ggcttgatta acttttacaa ttttttgtta aataaaaacc tacatcccga  97680
taaggtatcg ttagcataca aacggttagc tgccttaacc ctggagttat tgtctggaac  97740
aaacaaagcc cccttacacg aagcagcggt taatggggcg ggtgccggga ttgactgtga  97800
tggtgcagct acttctgccg ataaagcctt ctgctttacc aaagcccccg agtccaaagt  97860
aacggcctcc atacccgaag acccggatga tgtaattttt acggcactta acgacgaggt  97920
tattgacttg gtatactgcc agtacgaatt ttcctatccc aaatcatcca atgaggtcca  97980
tgctcagttt ctgttaatga aagctattta cgatggtcga tatgccatat tagcagagct  98040
tttcgaaagc agctttacaa ccgccccctt tagcgcgtat gtcgataatg ttaatttcaa  98100
cggaagcgag cttttgatcg gcaatgtgcg gggggggctg ttatctttgg cattacaaac  98160
agatacgtat acccttttgg ggtatacttt tgcacccgtg ccagtctttg tagaggaact  98220
gacccgaaaa aagctgtacc gcgaaactac cgaaatgtta tatgctctac acgtacctct  98280
tatggtctta caggatcaac atgggtttgt gtccatcgta aacgctaacg tatgtgaatt  98340
taccgagtct atagaggatg cagaattggc aatggccacc acggtggact atggccttag  98400
ttctaaacta gccatgacaa ttgcacgctc acagggtctg agtttagaga aggtagctat  98460
ctgttttacg gcggataaac tgcgcctaaa tagtgtgtat gttgccatgt cgcgtacggt  98520
ctcctctagg ttcttaaaaa tgaatctaaa ccctctacgg gaacgatatg aaaaatccgc  98580
agaaattagc gatcacattc ttgccgctct acgtgatccc aacgtacacg ttgtgtatta  98640
aagcattgta taaaaacacg catgcgggct tgctgttctc atttctaggt tttgtcttaa  98700
atacacccgc catgagcatc tctggacccc caacgacgtt tattttatat aggttacatg  98760
gggttaggcg ggttcttcac tggactttac cggatcatga acaaacactc tacgcattta  98820
cgggtgggtc aagatcaatg gcggtgaaga cggacgctcg atgtgataca atgagcggtg  98880
gtatgatcgt ccttcaacac acccatacag tgaccctgct aaccatagac tgttctactg  98940
acttttcatc atacgcattt acgcaccggg atttccactt acaggacaaa ccccacgcaa  99000
catttgcgat gccgtttatg tcctgggtcg gttctgaccc aacatctcag ctgtacagta  99060
atgtgggggg ggtactatcc gtaataacgg aagatgacct atccatgtgt atctcaattg  99120
ttatatacgg tttacgggta aacagacctg acgatcagac cacaccaaca ccaaccccgc  99180
accagtatac atcgcaaagg cggcagcctg aaaccaactg tccttcttca ccacaaccgg  99240
cctttttcac atcagacgac gacgttcttt cgttaatatt acgggacgcc gcaaacgcgt  99300
aaagacagat tcaagactaa catttatccc aactgattac atttcatacg cgaataaacg  99360
acacaaaaaa tttatattta acggctttta atttgaagac acctatcctc ttaacgttga  99420
tgagccttgc aggttgggtg ccgcgcttca ccggtattat acataaccga tttaccgtgt  99480
ttacggcagt ctgaccattt accagtgtat gtctgtaata cgacgttgtt gtgtcccgac  99540
aaaattaact cgcgtacaaa tttctgatgt tcccccggcg tggcaacgct ggcatttcca  99600
aacacattac gttctcgtac gtccatgacc gctattttca gtattaattg gttggtcggt  99660
caaagtattt tccttatgta aaaggacacg atctaaagcc gtaaactcat acacaaacac  99720
tggtaccaac ggacgcgatt ttccgtccgt tgagcgggtg taatatcggc gaggtcttct  99780
tgcacgaata ctctcgtaca gtaggtttct gacacggggt gcatgggttt tttgacacaa  99840
cacaaacatt tgcaggctct tatgactgga tggattgaat ttatttttag atagggtcac  99900
```

```
gtgtttttgt cgtgacacgc ctcgaccaga aaaggctgcg gttttcgtac acgcgaccgt  99960
tatttcacag gcgttcataa ccaagctgcg gcggatggtg tcggttaatt gtctccgccc 100020
aagttcgtca atagatgata ccatgaacaa cgtatcaaat ggtacatagt cgtctttggt 100080
tttctcaata cagcccgcgt gcccaatcgg aaatttttca tttgcatcaa cgctattttc 100140
tgtaaaatcg ttctgaacac tgtgttggct ggctacctgt ttaaaatttg ggatcgaaca 100200
cggtccacga tgcaatcccc aaccccattg aagcaatgcc gtcggtacgg aaggaggcaa 100260
ctccgaaaac attatggtac gcaagagggt cgattggagt gttatataac actccaatcg 100320
atctcgggtt cgcctttacg cgtaaaatac tcattggctt gaacgaaatg tcgacaattc 100380
cgaaatggaa cacgggacaa tggcgacgga tgcgcgtgtg ttagcaccag atgacatctt 100440
gaattcggtt gggttgtctt ctgtgcatgc gcaccccaca gcataaaaac taaccctgta 100500
cggttctcgc ataacctctg tagcacgcgt tgcaccagcc gcccccagcc taagtataca 100560
tgcgaccccg gagtcccgcg acgaaccgta agcgtggtat tcagcaataa cacccccctgc 100620
cttgcccaac tctccaggca tccgtgagtg ggcggagtca tatttgggta tgattccatg 100680
agggccgcaa aaatattttt aagactagac ggtggtgtta tgccacgttt tacactaaac 100740
gctagcccat gtgcatgtcc cgcggtaggg tatggatctt gaccaataat tacaacgcga 100800
atgctctggg gtccgcaaaa tcgcgtccat gcaaaaatat cgcctgtaga tggaagtatt 100860
tcttcccctg aatttaaaag acgattgtat tctaaaaaaa tacctttcgc gtacggctct 100920
ttaagttcgt ccgacaacag gtcataccac tcaggggaaa tgttaaactt gctgaaaact 100980
tcaaccgaat ccagttgcga agagacgggg gtgaacgttt ccgtgtcgta atgatgtgac 101040
atgttattta acttgaaggt tgggggggtct agcttaaccc ccaaaggcag cccgcggggt 101100
cgcttgcggg tttttttggt aaccggatgg gccaaaacat aaatgtcctt tgaatccgat 101160
agtttcattt cattggcata cgcgttggaa caaacggtcg gctccccaga cacatccatt 101220
ttccgggata tttgtggaag atggagtaga gtctacccat acaccggaaa gggcatccaa 101280
caaagcatcg cgtatgtccc cgcttttatg ttcttcacca acagattgtg ccagcccctt 101340
taaggtgacg tatggatttg tccagtacgc catttgtttg tctttaaacc aaagtataac 101400
ttccggtact ggacattttg tcttaaccac gattcccgat agcgcctcgc tgaggtttga 101460
taccgggggt gccgcatagt cccacgcctc atataccgat gacacgcacg gttccgttat 101520
aatcaaactc acatccgata gcggtttggc tccaaaaaac aacggagtgt cgtcttggag 101580
atgaagacaa tacgcgattg tgatagtttt taaaaaaact atctgcagta accatttatg 101640
tgatgccatg acgcttgtgt tttcccttca ctacgacgtt gtcgtatcct ttgaaaaact 101700
tgaccactct aatggaagca tggacaagta tgagttttat atatacagtt ggcctttagt 101760
taaactcttg gtgtcatatc tcattttcct aaaaagggcg atcttaatat gtcaaacgtc 101820
acggcgtgcc gacaaagcga atttccatgc aagatttgga tgtagtattt atacacccaa 101880
tcacatgtca cgtattaagc tttacagtcc cccgttatct gatataatca cttttcttaa 101940
cacgtcatcg ggaaaacaga tgtttatatt atacctctcg cggtcattta cggcaaatac 102000
ttagaccgtt ttcaagcgga ctgaaaacgc tcaaattgcc ttttggaggc ctgcccaacg 102060
gccattatcc cttggatcta agattgattt gcggtaacgt ttgccaatca agctttaaaa 102120
acgtacccca aacttaaaac gctcaaattg ccttttggag gcctgcccaa cggccattat 102180
cccttggatc tgagattgat ttacggtaac gtttgccaaa cccacgcatt tcagtttaaa 102240
```

tatttctaag cattcttagt gcgtacttgg cagcgtgctt aaaatatcaa ccaatatcca 102300
ttatgctaca cgtttccttc tatccgtttc aatccattaa aagtccatta acaaaaatga 102360
tgcatcatac ctaattcacc taaaaacctg actcattgca gcagcgtttc ctccttgcag 102420
actatccagt tggcatttta aacgggtccg gctgcctaaa ccgaaaacac cgttgccttt 102480
actgtaagta caaaactaaa atttatattt gcgtgcgtat tttgtaacat atatgccttt 102540
tatccccccg caagtttgct ttaccctcgc cttcaccacc cccgccacct tccggccatt 102600
ttaataactt taattgctat aagacatacc caaaccggat gatttttgcc gctggaaaaa 102660
cagcttctaa ttttcccgtc tcaactcggc cttggttgca tctccaagta tacctttagt 102720
ttgctcccgt agaggtgtat aaatacaaac ggtgacaagt attgagcgta atctcaaatt 102780
tttgtaattt agggcggagc gcttacgaca gcacatgcgt actgttagac tgttatgttt 102840
attgtatttg cagagcagga tgccccggtt actccgagac cggattgcgg gcattccgaa 102900
tcgtgtacgg acttaccagg gggcagtatt tacaccttgg gttccagata taccaaccct 102960
tacgaccaat agcaacactc aggtattttt aaaatgcacg tttaatgatc ataatttaca 103020
tacagttggt aataaagcag actgtggatg tttaaggcat ttccttcccc ctcccaacaa 103080
actaggactt cttcatcttg tttggaatac ctttacccgc tttaccggca gagctttttt 103140
tggtaaggtg tttcagtgaa cctgatgttg atccggaggt ggagggggta ttggactccc 103200
cctgtggaga ggcaactttg cgggttttac ttcccttaca tgccgaatca gactcagatg 103260
tcaggtctat tgttaagcat cgtttaacgt ctctgccggt atgaaataaa cggcgcttag 103320
caccccttgc gcttcccggt ttaatccccg gtaacacaga aaaaagcctg actttttggg 103380
gtgtatttac caatcgggta tccctttcat cgccacgaga ggtctccccg gttgaggtgg 103440
tttctggtct tacaattgga cctgtaatta gttggatggc tgtatctttc caggtccagg 103500
tttgcatggt taggcgggtt ggatcggtac atcgatccaa caagaataac atgtttgtta 103560
caaacggtcc tgttgaatca tgcaaaagac aacgcaggga tgtttttaat cccgcctcat 103620
cacgcccgta aatacctata tagtttaata tcaacatttt tgtaggctct acaatttcgg 103680
gttgatacag ttccgcaagt tgatcatcaa gccatccgag taaaggttgc atgtaacacg 103740
ggaatctcgc gtttccctct gttcctctat ccgtggctcg aaaaggcagt ctgtccatgg 103800
ttcgtgggtc ttgattaatt cccacagata ctggacgatc acggtagtcc tgccccccgg 103860
tccggggttg ctgtgcagat tcaatcgagc catacaccac cggggtcgcc gatcgaacag 103920
caggttggtc tttaaaaaat accttccgta aaaatgatgc ggtagagcat gttttggtta 103980
caccagggct cgagtctcgg gtcggtggtt gtatagaatc ctgttgagag tcacttggtg 104040
actctgctgt gggctctcta gccgacgatt gaaggggccc agggtttggt gattgaatgg 104100
gctcccgact cgatcttgat gttggctgtt ggatggactc ccgactcggt cctgggcttg 104160
gtggcagaag atctatgaca tctcccggta ggatgtcgat ggaatcttca aatgacggct 104220
cagaaaaacc atcgtcgtcg gatgggtgca cttcatattc cttgtaactt gtatcactta 104280
cgatcttatg caggatggat tgcactggac accggcagag aggacactgg acgctggtgg 104340
aggtccatgc ccgaatacaa acaaagcaga agtcgtgcaa acacggcatg gtttttccga 104400
gatcggaaac ggtgctcatg catatggtgc aggtattatc cgaagcgtcg gaggtgccgc 104460
taccgcccgc taatatggta tccatggtaa caactggctg tattctaatg tccgggcatc 104520
caaacacgta gcagaactgc catgcgttct aaattgtgag ttgtggcgag tacattttta 104580
taattggtac caacgaagac acacccctat atccctccac ccatttcttt taagtcccac 104640
ccactaaaac gtgggtataa aatgtgtatt ggggtaggcg gacagtccca acaaacaggg 104700
aagttgattg gtataacctt gggccgggta tacagctaag tgacatttta gattctgtct 104760
ttatttagat aaagagcgat acgaagacat ttctccaccc ccctgtaata cccgtaaata 104820
aaggtaagtc cacaaacaaa agcactgtat ataggaagtc gggtgtattg ggacagttac 104880
tccattagag gcgtacaaac aatactggga tagggtaatg caagtccccc ccgatggtcg 104940
ccccgcaaac gcgcggggag gtggggtcgc ttttttttt ctctctcgag ggggccgcga 105000
gagggctggc ctcctctccc ggggtccgcc gggcgcccag aaaccggggg ggggttattt 105060
tcgggggggg gtccgaccag cccgcccgtc gcccgcccgc acagacagac agacactttt 105120
ttcataaaaa ccgttccgct tttattaaca acaaacagtc cgcgcgccag tggcgctcac 105180
gagaaaagga ggggactccg tcacccccga ctctgcgggg ggctcctccc cccgcgccct 105240
ccccacacat cgtcctcgtc ctcggaggac gaggacgagg acaacagctc caccttgacc 105300
gccgggcgca aacccacccg gcggtctcgc agcacacccg gggccaccga cacgatgctc 105360
accccaaagg atgaccccgg tgcgtccccg tcgtccccgc ccccctcctc gctgtcccac 105420
gcgtcttcac accccacctc ccaatcgtcc agctccaaag cgtgttctct gtcgtctgcg 105480
gtgcgccgct gtcgccccgc ctgggtttct gacggccgtt ccgagccccc gtggtgtccg 105540
aacacgaacc gtgttccgtc gctcccctcc aacaccgtct ccgcggcccc aaaaccgggc 105600
ggccacatta ctctgggaat cggggggagg gcattccgag cctcgtccgc cgacgcatac 105660
agcgccaccg accgaccggc cacgggtgga agcacgagtg gttctgcggc agggtcgggt 105720
tccagcaggg cgtggcggca aaacaccctc gcccaggtgg gtacgtcgcc ggcctccggc 105780
ccggcggccc ccggtctccg tccctcggga aggaagacgg gtcgaagcgc ggcacccagg 105840
ccccatcggt ttgctgcgcg gtggctatgt gccgcctcgt ccacaaagtc ggctgccccg 105900
agccccagac cccgagactg tcgcgcgagg tccttgcaac cgtcaaaacc cggcagcacg 105960
tactgccggt attcacgggg cgacaggggg acgcgggtct tggggcccgc gcgggtacac 106020
acggtgtatg cgacgttccc accgcggcac aaacacaggg gttgttcgcc cgggtacagg 106080
ttggcaaacg cagtctcgat acgagcaaaa ctcgctggcc caaaggtgcg cgacgatgca 106140
aacacggccc gggcgagtcc ttctgtgacc gccgagtctg gccatcggac gacggcctgg 106200
gcgtccggtc gcgccggggc ccggacgtac acgtgatact gagacaaagc gggtccatcc 106260
ctgggccacc tctcgagggc caccgcgtcc aacaccagca accggcgccg ggcagaggcc 106320
aaccgcgagc ctagatactc gacggccccg gcaaaggcca ggtctcgggt cgacagtaat 106380
aaaacgcccc gggcgttcaa agcggacacg tccggcgggc cggtccagtt cccggcccag 106440
gcatgagtgc tcggcaggca caaccggtta ctcagggctg ccaggaccac agacagtccc 106500
cctcgggatg gactccatga cggtcccgga tctgtcgcga gggtgctctc gagggggccg 106560
ttgatgtcct ctccgggcaa cggatcgtag atgatcagaa gcctcacatc ctccgggtct 106620
gggatctgcc gcatccaggc gcacctccgt cgcagcgcct ccactccgct gggtggacca 106680
aaccgtcggt ctcctccgcc cggacgccga gcggcgattt ccgccaaggc gccgggatca 106740
aagcttagcg cagggcgcca ggccgtggga aacaatgggt cgtcgaccag acgggcgatg 106800
gtttcggggg tacagtacgc cttgcgagcc tggtccgacg ggaccggggt atgcagggcc 106860
ccccggggaa tacgccgaaa tcccccgttt ggggccggtc cgtcaagtgg catcgttatt 106920
acggcggggg gatccaccac agggcccgag gtgatggtca cgggctcgga tacccgcctc 106980

-continued ttggccttgg aaaccacatg atcgtctgca acccgggcgt ccgcgacggg tgtctcccta 107040
atcttgtcga ggaggcttct gctctcgact ggctgggact tgcgcttgcg cggagttcgt 107100
aaacgatcat ccggtggaca cacagaaaga gagcgtgcgg cggccgacgg ctgagggtcg 107160
ggagcctgtg tggccggggt tgttggagaa gggtgaccgc gggagatccg cgccgccgga 107220
ctggagcccg ttgcctcggg gtatgccatg ctggcaaagg ctctgcggag actctgtagg 107280
ataaagtgtt tttgggcccg gtcgtatcga cggctcatag ccacggccgc ggccgcgtgg 107340
gggagagccc agagggcctc ccccgtggcc atggcttcgc ctacatgcgg aacgggagac 107400
gctacgctcc ccgtaacggc ggtacccgcc cgtcccggtg gcaacagctt ttggtagaac 107460
tggttcaggg ccgagttgac accggtcagc ttggggttct ggagccatgc tatagggtct 107520
ctgtctggac agtagatcag gttaatcagc gcgcggtact gtctagccgg atctcccaac 107580
tccggcacgt aaagcggcac gggttccgtt gaggcctcgt aacgagcccg cgccgctctc 107640
acagcctcat cctcccagtg accctctctg gtctccccgg acggtccaaa ccgcaccctg 107700
ttggatggga ggggtgccga tccgggccaa gggcttccgt cgggcatcat gagcggcccc 107760
gacaccgggg gaattatcgg ggttctggat cgcggcaggg aaaatgattt ctgtctctgg 107820
cgccccggtt cccccgcaag acgtttggtc ttacgaatcc tcggatcggg accgctgatg 107880
gatcgatatc ccggttggat attttgtttc gtcgacccac catcatttga gtccgaatca 107940
tccgaatttg acggggaagg ggcgtgttcg cgtccggacc tgctgcctgt agtttcactt 108000
cccaccgaaa cgcgccgggg ttcatcgtct tcatcctccg atgacgatcc ccacgacgag 108060
gaagaggatg aagacgaaac aaactcacga ctctttggct ttttctccac tgggctgtca 108120
tcctcaatcg ggtctggtgc gtgggatctt cccggcaggg ccaaaaaacgc tctaggtttg 108180 ccccccgacg aacgtccagg gacgcgaggt gttatacccc gggcatcatg tttccttggg 108240
cgggtatcat cggtctcaaa cggcaggtcc gcctttgccc ccttagcggg aacgctgtcc 108300
gaaaggacgt ggtacaattg ctcaaccggg ccgggtacag gtccaccggg tttccgcgcc 108360
gggagtggga ccttaacctt caaagtcttt ttcttcgggc tctttccctg agcgggccgt 108420
tgagttttct ggagaactac tccgtccccc gatgcatgcg catgacccgc ttgctcatcg 108480
cccggctttt tacccgagat ggactgagtt tgtctgtctc gatggaccac cgacggcaaa 108540
cctggtgaat ttcctctcgt cgtttgtcgg ggtatagacc gctggtcttc ccgttgatcg 108600
ttcccggcgg cgtctccaac aggagacgcg ggggatacag gggagaaggc ctgcgggaac 108660
ggaggggtcg tacctctgcc cgtttcccca tcgttcatcg gtggttttgg agacctagca 108720
agcttcgttc cgagagagac tgtctcaagg gagcgatcgg ctcctgttgg ttctcgcgcg 108780
ccggcctccg agaatcgggt gtggaagacc tcggccagcg ggattacagg cgagcccatt 108840
agatcctgac cgtcctcgca tacgtagtcg tcttgtgtta gctcttcgcc aacatcttcc 108900
gttctgggtt ctggttgaag tcccgatacg gagggaattg aaacgatctc gtgttcccgt 108960
cccaccatga ccccgttctc tccaaatagt agatcgtcag gctgactcga ggtgaccacc 109020
cgggccctgt gttcggcggc cgccgcggcc gcgtccaaca ggtccattaa ctccaaagta 109080
tcaggcgacc ccgcgcgttg gggtgtagag cgctgcatcg gcggcgtatc catcgcactg 109140
gggtgaattt agacgtaccc gagttttcca aacgctctcg cagccttcaa aggattgcga 109200
ttgcggttgg tgagggagtt ccaacagtac ttaaaacgtg ttgtgccccc ccctcgaccg 109260
catatttcct ccccgtgtcg tcaccgtgta aatattctta atgataagac gatgtagtga 109320
ttggacgaga ctcgaggcgg gaagttcatg gaccatagta tgcgtttaag gagagaccgc 109380

-continued tggttggcga tgtacgcccg gtgtctattt ccgcatacct tacaacatca taacaaggga 109440
taccagacat gtgaatttca tttacatatg tttaaataac aaccaatcat cgtgtgtcta 109500
cagacgatat ataatataca taaacacaat tggggttgtc tcacatgcaa aacatcttat 109560
ataacacggg ttgtttccac ccatccggca tctagttaat caaatgcacg tcgacggtgt 109620
gtttgggtcc ctctccgtcg tcattacgtt cgcgcaatca acaagcgtat acaccaccac 109680
ccctcccaac gattatgtca ggcggcacga agcccgcgat aacccataaa atacacacgg 109740
ggttgtggtg ttcacgtaac cccccgccga tggggagggg gcgcggtacc ccgccgatgg 109800
ggagggggcg cggtaccccg ccgatgggga gggggcgcgg taccccgccg atggggaggg 109860
ggcgcggtac cccgccgatg gggagggggc gcggtacccc gccgatgttt ataaccataa 109920
ttctctaaac cgttgtagaa aatcacaaaa aaatttattc aaaaacaagt cgaagaactt 109980
catatctgag gcatgtaaac ccgttcgcac ttcctggggt ggaatggggt ggggtggggg 110040
ggtgaaaaag gggggggtt aaattgggcg tccgcatgtc tgtggtgtac gccaatcgga 110100
tacactcttt tgatctgcat tcgcacttcc cgtttttca ctgtatgggt tttcatgttt 110160
tggcatgtgt ccaaccaccg ttcgcacttt ctttctatat atatatatat atatatatat 110220
atatatagag aaagagagag agtttcttgt tcgcgcgtgt tcccgcgatg tcgcggtttt 110280
atggggtgtg ggcgggcttt tcacagaata tatatattcc aaatggagcg gcaggctttt 110340
taaaatcgat ttgacgtgat aaaaaaaaac acacggggcc cccccctttt tttggtgtta 110400
taaaggcaac ccaatcgaag gtctcccgcc ccggaatccc ccattgccat tttacccaag 110460
tagccttatt catagatgta aacgtttggg tgtgtgtttt gttgtgcagg gttcgtccga 110520
ttcataacgc gacagcgtcg agtcggtttt aagggaaaag gttactacgg ccccaaggac 110580
atgttttgca cctcaccggc tacgcggggc gactcgtccg agtcaaaacc cggggcatcg 110640
gttgatgtta acggaaagat ggaatatgga tctgcaccag gacccctgaa cggccgggat 110700
acgtcgcggg gccccggcgc gttttgtact ccgggttggg agatccaccc ggccaggctc 110760
gttgaggaca tcaaccgtgt ttttttatgt attgcacagt cgtcgggacg cgtcacgcga 110820
gattcacgaa gattgcggcg catatgcctc gacttttatc taatgggtcg caccagacag 110880
cgtcccacgt tagcgtgctg ggaggaattg ttacagcttc aacccaccca gacgcagtgc 110940
ttacgcgcta ctttaatgga agtgtcccat cgaccccctc gggggaaga cgggttcatt 111000
gaggcgccga atgttccttt gcataggagc gcactggaat gtgacgtatc tgatgatggt 111060
ggtgaagacg atagcgacga tgatgggtct acgccatcgg atgtaattga atttcgggat 111120
tccgacgcgg aatcatcgga cggggaagac tttatagtgg aagaagaatc agaggagagc 111180
accgattctt gtgaaccaga cggggtaccc ggcgattgtt atcgagacgg ggatgggtgc 111240
aacaccccgt ccccaaagag accccagcgt gccatcgagc gatacgcggg tgcagaaacc 111300
gcggaatata cagccgcgaa agcgctcacc gcgttgggcg agggggtgt agattggaag 111360
cgacgtcgac acgaagcccc gcgccggcat gatataccgc ccccccatgg cgtgtagtct 111420
ttataaataa atacaatggt ttggctcgtg tcttttttg atgtctgtct gtgggggagt 111480
ggggtgttgt ggatattaga gggtagaggg tgctggtttg aacgtctcca ttaacccacg 111540
gggtccccac acgggccgtg tggtatgaat ctctgcggat cccgcggtga gcacccgggc 111600
ggtgaatatg ccggacttta ctgcacacga cacgataccc ccgcgcacca ggctctcatg 111660
aacgacgccg aacggtactt cgccgccgcg ctatgcgcca tatctaccga ggcctacgag 111720

-continued gcttttatac acagcccctc cgagagaccg tgcgcgagtt tgtgggggag ggcaaaggac 111780
gccttcggac ggatgtgcgg ggagctcgca gcggatagac aacgtccacc ctcggttccg 111840
ccgatccgca gagcggtgtt atcgttatta cgcgagcaat gcatgccgga tccacaatcg 111900
catctggagc tcagcgagcg gctgatattg atggcatatt ggtgctgttt gggacacgcc 111960
ggacttccga ctattggatt gtcgcccgat aataaatgca tccgcgccga attatatgac 112020
cgccccgggg gaatttgtca caggcttttt gacgcgtacc tgggctgcgg gtcccttgga 112080
gtcccaagaa cctacgagag atcctgacac cccatccctt tatatagaaa aaaaaaataa 112140
atttaaaaca tacaccggat aaaagcgtac tgttttttat ttaaatttac acgctcggcg 112200
ttgccccggt tcggtgatca ccgggtctta tctatataca ccgtgtaact cgaacccccg 112260
tgactccctc caatcgcgtt accaaactct tcttccgtat ccgtagattc cgagtcctcg 112320
aaatcgtcca cttatccaac aaattgtgac gttatatatc ccaaggcaaa ggccgctccc 112380
gtcatagcaa atacaaagac aattattagc gtaatataac agaatttttt acgatgatat 112440
attttatgtt gatattttcc aattcgacgc aaaaattcat ctgccgtttc attttcgcta 112500
tcactataat aacacttttc agccgaacgg ctcggttgta tggctgttat cgttgtatta 112560
tttggttgcg ctcgcggggt taccaccgct tccatcagta aggccacggc ctcaccctcc 112620
atggtgtttt gtccggccat agaaatccag attgtaaggc cagcaggcta gtttaaaagt 112680
gtttaatacc acaccttttg atatttatat acatgcaaga ttctagatta ttcatcaata 112740
ggtcgtttaa agcgcgtttt cataaacgtt gtcagctata ccgacattct cacaaagagg 112800
taaagttacc ttacgttatt attaaataaa acatgtagac attattaata atcctaggaa 112860
caatcaaatc catatttgta agttatgttt aacccctccc ctttttgtca ttatctccgc 112920
cctcttataa tcggatcact ttataagtgt gtcggtgagt atattttgta cagttgttgg 112980
acaacaggtt tttggttcat taacactatc aacataagtc ggggtataca agtataatga 113040
acgacgttga tgcaacagac acctttgttg gacaaggaaa gttccgtggc gccatctcaa 113100
catcaccgtc acatattatg caaacatgtg ggtttataca acagatgttt ccagttgaaa 113160
tgtcgcccgg catagaatct gaggatgatc ccaattatga cgttaacatg gatatacagt 113220
cttttaatat atttgatggt gtacacgaaa ctgaagccga agcctctgtg gcattgtgcg 113280
cagaagcacg cgttggaatt aataaagcgg gatttgtaat attaaaaacg tttacaccag 113340
gggcggaagg ttttgcgttt gcgtgtatgg acagtaaaac atgtgaacat gtggtcatta 113400
aagcgggtca acgtcaagga acggccaccg aggcaaccgt gttaagagcg ttaacccacc 113460
catccgttgt acagcttaaa ggaacgttta cgtataacaa aatgacatgt cttatattac 113520
cacgttaccg aacagattta tactgctatc tagctgcaaa gcgcaacctc cccatatgtg 113580
acattttagc aattcagcga tctgtattac gcgcgttaca gtatcttcat aataacagta 113640
ttattcaccg tgatataaaa tctgaaaata tatttattaa ccacccaggt gatgtttgtg 113700
tgggagactt tggagcagcg tgtttccccg tggatattaa tgccaacagg tattatggct 113760
gggctggaac aatcgccaca aactctcctg agttattggc tagagatcca tatggacctg 113820
ccgtggacat atggagtgcc gggattgtat tatttgaaat ggctacagga cagaactcgt 113880
tatttgaacg agacggttta gatggcaatt gtgacagtga gcgtcaaatt aaacttatta 113940
tacgacgatc tggaactcat cccaatgaat ttcccattaa ccctacatca aatcttcgtc 114000
gacaatacat tggtttggca aaacggtctt ctcgaaaacc cggatccagg ccattgtgga 114060
caaatctata tgagttgcca attgatttgg agtatttgat atgtaagatg ttatcgtttg 114120
acgcacgtca tcgaccatca gcagaggtgt tgcttaacca ctctgttttc caaactcttc 114180
ccgatccata tccaaatcca atggaagttg gagattaaaa ttcattaagc ctgttaataa 114240
aatattgtat aaattgtgtt tataacgtat aacccgttaa ggcaaatagg gtacaaacgc 114300
gcaatgtttt gaaatactaa tataaataac ataaccaata gaaacttaat acagagtcac 114360
gccccattac aacaaggata aaacacggga tcattttctt aacattgtag tagcgctgaa 114420
aagcgtcccc tcccccggct cacagagctg ctcttcggtg tagttgggta tactggtgcg 114480
cctcatttaa tcgcgatgtt tttaatccaa tgtttgatat cggccgttat attttacata 114540
caagtgacca acgctttgat cttcaagggc gaccacgtga gcttgcaagt taacagcagt 114600
ctcacgtcta tccttattcc catgcaaaat gataattata cagagataaa aggacagctt 114660
gtctttattg gagagcaact acctaccggg acaaactata gcggaacact ggaactgtta 114720
tacgcggata cggtggcgtt ttgtttccgg tcagtacaag taataagata cgacggatgt 114780
ccccggatta gaacgagcgc ttttatttcg tgtaggtaca aacattcgtg gcattatggt 114840
aactcaacgg atcggatatc aacagagccg gatgctggtg taatgttgaa aattaccaaa 114900
ccgggaataa atgatgctgg tgtgtatgta cttcttgttc ggttagacca tagcagatcc 114960
accgatggtt tcattcttgg tgtaaatgta tatacagcgg gctcgcatca caacattcac 115020
ggggttatct acacttctcc gtctctacag aatggatatt ctacaagagc ccttttttcaa 115080
caagctcgtt tgtgtgattt acccgcgaca cccaaagggt ccggtacctc cctgtttcaa 115140
catatgcttg atcttcgtgc cggtaaatcg ttagaggata acccttggtt acatgaggac 115200
gttgttacga cagaaactaa gtccgttgtt aaggagggga tagaaaatca cgtatatcca 115260
acggatatgt ccacgttacc cgaaaagtcc cttaatgatc ctccagaaaa tctacttata 115320
attattccta tagtagcgtc tgtcatgatc ctcaccgcca tggttattgt tattgtaata 115380
agcgttaagc gacgtagaat taaaaaacat ccaatttatc gcccaaatac aaaaacaaga 115440
aggggcatac aaaatgcgac accagaatcc gatgtgatgt tggaggccgc cattgcacaa 115500
ctagcaacga ttcgcgaaga atcccccccca cattccgttg taaacccgtt tgttaaatag 115560
aactaattat cccggatttt atattaaata aactatatgc gttttattta gcgttttgat 115620
tacgcgttgt gatatgaggg gaaggattaa gaatctccta actataagtt aacacgccca 115680
catttgggcg gggatgtttt atgaagcctt aaaggccgag ctggtataca cgagagcagt 115740
ccatggtttt agacctcggg cgaattgcgt ggttttaagt gactatattc cgagggtcgc 115800
ctgtaatatg gggacagtta ataaacctgt ggtgggggta ttgatggggt tcggaattat 115860
cacgggaacg ttgcgtataa cgaatccggt cagagcatcc gtcttgcgat acgatgattt 115920
tcacaccgat gaagacaaac tggatacaaa ctccgtatat gagccttact accattcaga 115980
tcatgcggag tcttcatggg taaatcgggg agagtcttcg cgaaaagcgt acgatcataa 116040
ctcaccttat atatggccac gtaatgatta tgatggattt ttagagaacg cacacgaaca 116100
ccatggggtg tataatcagg gccgtggtat cgatagcggg gaacggttaa tgcaacccac 116160
acaaatgtct gcacaggagg atcttgggga cgatacgggc atccacgtta tccctacgtt 116220
aaacggcgat gacagacata aaattgtaaa tgtggaccaa cgtcaatacg gtgacgtgtt 116280
taaaggagat cttaatccaa aaccccaagg ccaaagactc attgaggtgt cagtggaaga 116340
aaatcacccg tttactttac gcgcaccgat tcagcggatt tatggagtcc ggtacaccga 116400
gacttggagc tttttgccgt cattaacctg tacgggagac gcagcgcccg ccatccagca 116460
tatatgttta aaacatacaa catgctttca agacgtggtg gtggatgtgg attgcgcgga 116520
aaatactaaa gaggatcagt tggccgaaat cagttaccgt tttcaaggta agaaggaagc 116580
ggaccaaccg tggattgttg taaacacgag cacactgttt gatgaactcg aattagaccc 116640
ccccgagatt gaaccgggtg tcttgaaagt acttcggaca gaaaaacaat acttgggtgt 116700
gtacatttgg aacatgcgcg gctccgatgg tacgtctacc tacgccacgt tttggtcac 116760
ctggaaaggg gatgaaaaaa caagaaaccc tacgcccgca gtaactcctc aaccaagagg 116820
ggctgagttt catatgtgga attaccactc gcatgtattt tcagttggtg atacgtttag 116880
cttggcaatg catcttcagt ataagataca tgaagcgcca tttgatttgc tgttagagtg 116940
gttgtatgtc cccatcgatc ctacatgtca accaatgcgg ttatattcta cgtgtttgta 117000
tcatcccaac gcaccccaat gcctctctca tatgaattcc ggttgtacat ttacctcgcc 117060
acatttagcc cagcgtgttg caagcacagt gtatcaaaat tgtgaacatg cagataacta 117120
caccgcatat tgtctgggaa tatctcatat ggagcctagc tttggtctaa tcttacacga 117180
cgggggcacc acgttaaagt ttgtagatac acccgagagt ttgtcgggat tatacgtttt 117240
tgtggtgtat tttaacgggc atgttgaagc cgtagcatac actgttgtat ccacagtaga 117300
tcattttgta aacgcaattg aagagcgtgg atttccgcca acggccggtc agccaccggc 117360
gactactaaa cccaaggaaa ttacccccgt aaaccccgga acgtcaccac ttctacgata 117420
tgccgcatgg accggagggc ttgcagcagt agtactttta tgtctcgtaa tatttttaat 117480
ctgtacggct aaacgaatga gggttaaagc ctatagggta gacaagtccc cgtataacca 117540
aagcatgtat tacgctggcc ttccagtgga cgatttcgag gactcggaat ctacggatac 117600
ggaagaagag tttggtaacg cgattggagg gagtcacggg ggttcgagtt acacggtgta 117660
tatagataag acccggtgat caccgaaccg gggcaacgcc gagcgtgtaa atttaaataa 117720
aaaacagtac gcttttatcc ggtgtatgtt ttaaatttat tttttttttc tatataaagg 117780
gatggggtgt caggatctct cgtaggttct tgggactcca agggacccgc agcccaggta 117840
cgcgtcaaaa agcctgtgac aaattccccc ggggcggtca tataattcgg cgcggatgca 117900
tttattatcg ggcgacaatc caatagtcgg aagtccggcg tgtcccaaac agcaccaata 117960
tgccatcaat atcagccgct cgctgagctc cagatgcgat tgtggatccg gcatgcattg 118020
ctcgcgtaat aacgataaca ccgctctgcg gatcggcgga accgagggtg gacgttgtct 118080
atccgctgcg agctccccgc acatccgtcc gaaggcgtcc tttgccctcc cccacaaact 118140
cgcgcacggt ctctcggagg ggctgtgtat aaaagcctcg taggcctcgg tagatatggc 118200
gcatagcgcg gcggcgaagt accgttcggc gtcgttcatg agagcctggt gcgcgggggt 118260
atcgtgtcgt gtgcagtaaa gtccggcata ttcaccgccc gggtgctcac cgcgggatcc 118320
gcagagattc ataccacacg gcccgtgtgg ggaccccgtg ggttaatgga gacgttcaaa 118380
ccagcaccct ctaccctcta atatccacaa caccccactc ccccacagac agacatcaaa 118440
aaaagacacg agccaaacca ttgtatttat ttataaagac tacacgccat ggggggggcgg 118500
tatatcatgc cggcgcgggg cttcgtgtcg acgtcgcttc caatctacac ccccctcgcc 118560
caacgcggtg agcgctttcg cggctgtata ttccgcggtt tctgcacccg cgtatcgctc 118620
gatggcacgc tggggtctct ttggggacgg ggtgttgcac ccatccccgt ctcgataaca 118680
atcgccgggt accccgtctg gttcacaaga atcggtgctc tcctctgatt cttcttccac 118740
tataaagtct tccccgtccg atgattccgc gtcggaatcc cgaaattcaa ttacatccga 118800
tggcgtagac ccatcatcgt cgctatcgtc ttcaccacca tcatcagata cgtcacattc 118860
cagtgcgctc ctatgcaaag gaacattcgg cgcctcaatg aacccgtctt ccccccgagg 118920
gggtcgatgg gacacttcca ttaaagtagc gcgtaagcac tgcgtctggg tgggttgaag 118980
ctgtaacaat tcctcccagc acgctaacgt gggacgctgt ctggtgcgac ccattagata 119040
aaagtcgagg catatgcgcc gcaatcttcg tgaatctcgc gtgacgcgtc ccgacgactg 119100
tgcaatacat aaaaaaacac ggttgatgtc ctcaacgagc ctggccgggt ggatctccca 119160
acccggagta caaaacgcgc cggggccccg cgacgtatcc cggccgttca ggggtcctgg 119220
tgcagatcca tattccatct ttccgttaac atcaaccgat gccccgggtt ttgactcgga 119280
cgagtcgccc cgcgtagccg gtgaggtgca aaacatgtcc ttggggccgt agtaaccttt 119340
tcccttaaaa ccgactcgac gctgtcgcgt tatgaatcgg acgaaccctg cacaacaaaa 119400
cacacaccca aacgtttaca tctatgaata aggctacttg ggtaaaatgg caatggggga 119460
ttccggggcg ggagaccttc gattgggttg cctttataac accaaaaaaa ggggggggcc 119520
ccgtgtgttt ttttttatca cgtcaaatcg attttaaaaa gcctgccgct ccatttggaa 119580
tatatatatt ctgtgaaaag cccgcccaca ccccataaaa ccgcgacatc gcgggaacac 119640
gcgcgaacaa gaaactctct ctctttctct atatatatat atatatatat atatatatat 119700
agaaagaaag tgcgaacggt ggttggacac atgccaaaac atgaaaaccc atacagtgaa 119760
aaaacgggaa gtgcgaatgc agatcaaaag agtgtatccg attggcgtac accacagaca 119820
tgcggacgcc caatttaacc cccccccttt ttcacccccc caccccaccc cattccaccc 119880
caggaagtgc gaacgggttt acatgcctca gatatgaagt tcttcgactt gtttttgaat 119940
aaattttttt gtgattttct acaacggttt agagaattat ggttataaac atcggcgggg 120000
taccgcgccc cctccccatc ggcggggtac cgcgcccccct ccccatcggc ggggtaccgc 120060
gccccctccc catcggcggg gtaccgcgcc ccctccccat cggcggggta ccgcgccccc 120120
tccccatcgg cggggggtta cgtgaacacc acaaccccgt gtgtatttta tgggttatcg 120180
cgggcttcgt gccgcctgac ataatcgttg ggaggggtgg tggtgtatac gcttgttgat 120240
tgcgcgaacg taatgacgac ggagagggac ccaaacacac cgtcgacgtg catttgatta 120300
actagatgcc ggatgggtgg aaacaacccg tgttatataa gatgttttgc atgtgagaca 120360
accccaattg tgtttatgta tattatatat cgtctgtaga cacacgatga ttggttgtta 120420
tttaaacata tgtaaatgaa attcacatgt ctggtatccc ttgttatgat gttgtaaggt 120480
atgcggaaat agacaccggg cgtacatcgc caaccagcgg tctctcctta aacgcatact 120540
atggtccatg aacttcccgc ctcgagtctc gtccaatcac tacatcgtct tatcattaag 120600
aatatttaca cggtgacgac acggggagga aatatgcggt cgaggggggg gcacaacacg 120660
ttttaagtac tgttggaact ccctcaccaa ccgcaatcgc aatcctttga aggctgcgag 120720
agcgtttgga aaactcgggt acgtctaaat tcaccccagt gcgatggata cgccgccgat 120780
gcagcgctct acaccccaac gcgcggggtc gcctgatact ttggagttaa tggacctgtt 120840
ggacgcggcc gcggcggccg ccgaacacag ggcccgggtg gtcacctcga gtcagcctga 120900
cgatctacta tttggagaga acggggtcat ggtgggacgg gaacacgaga tcgtttcaat 120960
tccctccgta tcgggacttc aaccagaacc cagaacggaa gatgttggcg aagagctaac 121020
acaagacgac tacgtatgcg aggacggtca ggatctaatg ggctcgcctg taatcccgct 121080
ggccgaggtc ttccacaccc gattctcgga ggccggcgcg cgagaaccaa caggagccga 121140
tcgctccctt gagacagtct ctctcggaac gaagcttgct aggtctccaa aaccaccgat 121200

-continued gaacgatggg gaaacgggca gaggtacgac ccctccgttc ccgcaggcct tctcccctgt 121260
atcccccgcg tctcctgttg gagacgccgc cgggaacgat caacgggaag accagcggtc 121320
tataccccga caaacgacga gaggaaattc accaggtttg ccgtcggtgg tccatcgaga 121380
cagacaaact cagtccatct cgggtaaaaa gccgggcgat gagcaagcgg gtcatgcgca 121440
tgcatcgggg gacggagtag ttctccagaa aactcaacgg cccgctcagg gaaagagccc 121500
gaagaaaaag actttgaagg ttaaggtccc actcccggcg cggaaacccg gtggacctgt 121560
acccggcccg gttgagcaat tgtaccacgt cctttcggac agcgttcccg ctaaggggc 121620
aaaggcggac ctgccgtttg agaccgatga tacccgccca aggaaacatg atgcccgggg 121680
tataacacct cgcgtccctg gacgttcgtc ggggggcaaa cctagagcgt ttttggccct 121740
gccgggaaga tcccacgcac cagacccgat tgaggatgac agcccagtgg agaaaaagcc 121800
aaagagtcgt gagtttgttt cgtcttcatc ctcttcctcg tcgtggggat cgtcatcgga 121860
ggatgaagac gatgaacccc ggcgcgtttc ggtgggaagt gaaactacag gcagcaggtc 121920
cggacgcgaa cacgcccctt ccccgtcaaa ttcggatgat tcggactcaa atgatggtgg 121980
gtcgacgaaa caaaatatcc aaccgggata tcgatccatc agcggtcccg atccgaggat 122040
tcgtaagacc aaacgtcttg cgggggaacc ggggcgccag agacagaaat cattttccct 122100
gccgcgatcc agaaccccga taattccccc ggtgtcgggg ccgctcatga tgcccgacgg 122160
aagcccttgg cccggatcgg cacccctccc atccaacagg gtgcggtttg gaccgtccgg 122220
ggagaccaga gagggtcact gggaggatga ggctgtgaga gcggcgcggg ctcgttacga 122280
ggcctcaacg gaacccgtgc cgctttacgt gccggagttg ggagatccgg ctagacagta 122340
ccgcgcgctg attaacctga tctactgtcc agacagagac cctatagcat ggctccagaa 122400
ccccaagctg accggtgtca actcggccct gaaccagttc taccaaaagc tgttgccacc 122460
gggacgggcg ggtaccgccg ttacggggag cgtagcgtct cccgttccgc atgtaggcga 122520
agccatggcc acgggggagg ccctctgggc tctcccccac gcggccgcgg ccgtggctat 122580
gagccgtcga tacgaccggg cccaaaaaca ctttatccta cagagtctcc gcagagcctt 122640
tgccagcatg gcataccccg aggcaacggg ctccagtccg gcggcgcgga tctcccgcgg 122700
tcacccttct ccaacaaccc cggccacaca ggctcccgac cctcagccgt cggccgccgc 122760
acgctctctt tctgtgtgtc caccggatga tcgtttacga actccgcgca agcgcaagtc 122820
ccagccagtc gagagcagaa gcctcctcga caagattagg gagacacccg tcgcggacgc 122880
ccgggttgca gacgatcatg tggtttccaa ggccaagagg cgggtatccg agcccgtgac 122940
catcacctcg ggccctgtgg tggatccccc cgccgtaata acgatgccac ttgacggacc 123000
ggccccaaac gggggatttc ggcgtattcc ccggggggcc ctgcataccc cggtcccgtc 123060
ggaccaggct cgcaaggcgt actgtacccc cgaaaccatc gcccgtctgg tcgacgaccc 123120
attgtttccc acggcctggc gccctgcgct aagctttgat cccggcgcct tggcggaaat 123180
cgccgctcgg cgtccgggcg gaggagaccg acggtttggt ccacccagcg gagtggaggc 123240
gctgcgacgg aggtgcgcct ggatgcggca gatcccagac ccggaggatg tgaggcttct 123300
gatcatctac gatccgttgc ccggagagga catcaacggc cccctcgaga gcaccctcgc 123360
gacagatccg ggaccgtcat ggagtccatc ccgaggggga ctgtctgtgg tcctggcagc 123420
cctgagtaac cggttgtgcc tgccgagcac tcatgcctgg gccgggaact ggaccggccc 123480
gccggacgtg tccgctttga acgcccgggg cgttttatta ctgtcgaccc gagacctggc 123540
ctttgccggg gccgtcgagt atctaggctc gcggttggcc tctgcccggc gccggttgct 123600

-continued

```
ggtgttggac gcggtggccc tcgagaggtg gcccagggat ggacccgctt tgtctcagta 123660

tcacgtgtac gtccgggccc cggcgcgacc ggacgcccag gccgtcgtcc gatggccaga 123720

ctcggcggtc acagaaggac tcgcccgggc cgtgtttgca tcgtcgcgca cctttgggcc 123780

agcgagtttt gctcgtatcg agactgcgtt tgccaacctg tacccgggcg aacaacccct 123840

gtgtttgtgc cgcggtggga acgtcgcata caccgtgtgt acccgcgcgg gccccaagac 123900

ccgcgtcccc ctgtcgcccc gtgaataccg gcagtacgtg ctgccgggtt ttgacggttg 123960

caaggacctc gcgcgacagt ctcggggtct ggggctcggg gcagccgact ttgtggacga 124020

ggcggcacat agccaccgcg cagcaaaccg atggggcctg ggtgccgcgc ttcgaccccgt 124080

cttccttccc gagggacgga gaccgggggc cgccgggccg gaggccggcg acgtacccac 124140

ctgggcgagg gtgttttgcc gccacgccct gctggaaccc gaccctgccg cagaaccact 124200

cgtgcttcca cccgtggccg gtcggtcggt ggcgctgtat gcgtcggcgg acgaggctcg 124260

gaatgccctc cccccgattc ccagagtaat gtggccgccc ggttttgggg ccgcggagac 124320

ggtgttggag gggagcgacg gaacacggtt cgtgttcgga caccacgggg gctcggaacg 124380

gccgtcagaa acccaggcgg ggcgacagcg gcgcaccgca gacgacagag aacacgcttt 124440

ggagctggac gattgggagg tggggtgtga agacgcgtgg gacagcgagg aggggggcgg 124500

ggacgacggg gacgcaccgg ggtcatcctt tggggtgagc atcgtgtcgg tggccccggg 124560

tgtgctgcga gaccgccggg tgggtttgcg cccggcggtc aaggtggagc tgttgtcctc 124620

gtcctcgtcc tccgaggacg aggacgatgt gtggggaggg cgcgggggga ggagcccccc 124680

gcagagtcgg gggtgacgga gtcccctcct tttctcgtga gcgccactgg cgcgcggact 124740

gtttgttgtt aataaaagcg gaacggtttt tatgaaaaaa gtgtctgtct gtctgtgcgg 124800

gcgggcgacg ggcgggctgg tcggaccccc ccccgaaaat aacccccccc cggtttctgg 124860

gcgcccggcg gaccccggga gagg                                       124884
```

INSULATED HERPESVIRUS-DERIVED GENE EXPRESSION CASSETTES FOR SUSTAINED AND REGULATABLE GENE EXPRESSION

The present application is a United States nationalization of PCT International Patent Application PCT/US2005/005461, filed Feb. 17, 2005, which claims priority from provisional application Ser. No. 60/545,375, filed Feb. 17, 2004, the entire contents of which are specifically incorporated herein by reference in their entirety.

The United States government has certain rights in the present invention pursuant to NIAID grant R01-AI48633 from the National Institutes of Health.

1.0 BACKGROUND OF THE INVENTION

1.1 Field of the Invention

The present invention relates generally to the fields of molecular biology and virology, and in particular, to genetic expression cassettes, and vector comprising them useful for the delivery of nucleic acid segments encoding selected therapeutic constructs (including for example, peptides, polypeptides, ribozymes, and catalytic RNA molecules), to selected cells and tissues of vertebrate animals. In particular, these genetic constructs are useful in the development of gene therapy vectors, including for example, HSV, AV, and AAV vectors, for the treatment of mammalian, and in particular, human diseases, disorders, and dysfunctions. The disclosed compositions may be utilized in a variety of investigative, diagnostic and therapeutic regimens, including the prevention and treatment of a variety of human diseases. Methods and compositions are provided for preparing viral vector compositions comprising these genetic expression cassettes for use in the preparation of medicaments useful in central and targeted gene therapy of diseases, disorders, and dysfunctions in an animal, and in humans in particular.

1.2 Description of the Related Art

Currently, viral vectors show the greatest efficiency in gene transfer (reviewed in Anderson, 1998; Verma and Somia, Nature, 1997). For correction of genetic diseases such that persistent gene expression is required, herpesvirus, retrovirus, lentivirus, adenovirus, or AAV based vectors are desirable due to the integrating nature of the viral life cycle.

In considering transgene expression, there are many known situations where a transferred gene(s) is capable of a short period of expression however followed by a decline to undetectable levels without the loss of the expression construct. These expression constructs may sustain transgene expression for periods of time up to 2 weeks and on rare occasions 2 months (Palmer et al., 2000). Unfortunately, despite claims of sustained expression up to 2 months, the over-ruling factor is that one can anticipate an eventual decline of transcript levels often to near zero levels. As a result, this presents an additional variable to transgene expression; the predictability or probability of transgene expression. For the purposes of gene therapy, transgene expression kinetics must be predictable to achieve safe and reliable therapeutic effects.

The mechanisms responsible for transcript loss have been attributed to elaborate defense mechanisms used by eukaryotic cells to protect both the structure of their genomes and to oppose expression of abnormal transcription units (Bestor, 2000). These mechanisms include, but are not limited to, DNA methylation, multi-copy repeat-induced transgene silencing, post-transcriptional gene silencing (PTGS) mediated by RNAi, position effects that impose histone methylation/deacetylation. These host defense mechanisms represent a formidable barrier to many forms of gene therapy. Current gene therapy applications often depend on a construct or recombinant virus with the ability to express an agent of interest (protein or RNA) in a particular tissue. However, cells can detect alterations within their genome due to multi-copy transgene insertions or to abnormal transcripts and elicit a strong and heritable silencing effect. A common example of multi-copy transgene silencing is in the generation of transgenic animals. It had previously been found that transgene copy number was inversely proportional to the level of gene expression in some lines of transgenic mice. It is thought that end-to-end ligation of the expression construct and/or homologous recombination between construct molecules generates transgene concatemers (often 5-50 copies) that integrate at a single site within the genome (Dobie et al., 1997). Unfortunately, the tandem repeats appear to contribute to a phenomenon similar to position effect varigation (PEV). PEV may be the result of position-dependent inactivation of the expression construct mediated by the surrounding heterochromatin environment and results in the heritable maintenance of the transcription “off” state (Dobie et al., 1997).

2.0 SUMMARY OF THE INVENTION

The present invention overcomes limitations inherent in the prior art by providing genetic constructs comprising nucleic acid sequences derived from Herpes Simplex Virus type I (HSV-I) that are capable of facilitating persistent/long-term and regulatable transgene expression in selected host cells. An important feature of these new gene expression cassettes is that the cassette is bounded by control elements that protect and insulate the gene expression portion of the cassette from the influence of DNA and chromatin structure that lie outside of the cassette, when the cassette is inserted into a viral vector or a cellular genome. These control elements effectively maintain the expression cassette in an accessible and transcriptionally-responsive conformation. The expression cassettes of the present invention facilitate predictable and sustained expression of a transgene regardless of where the cassette was inserted. For example, the cassette may be used to insert a transgene into a viral vector (including, for example, but not limited to adenovirus, adeno-associated virus (AAV), retrovirus (Lentivirus), or Herpesviruses), or into the genome of a eukaryotic cell, including mammalian cells such as human cells.

Following appropriate delivery or insertion of the genetic constructs into suitable recipient cells, the cassette is specifically engineered to express a gene of interest in a regulated manner for the duration of the cell’s life. Importantly, this invention addresses a common and presently intractable problem associated with the failure of many gene therapy vectors or transgenic animals to express genes at predictable and sustained levels due to the repressive effects of the surrounding chromatin.

Another important aspect of the present invention is that by employing selected control elements within the genetic constructs that contain particular nucleic acid sequences, it is possible to confer cell-type specific expression. For example, in an illustrative embodiment, the expression cassette may contain the components from HSV-1 that allow regulation of the control elements in neurons. By modifying these elements, however, one may alter the cell type and tissue specificity to allow the cassette to function in other cell types such as, for example, in the liver or in lung tissue.

In one embodiment, the cassette employs a defective form of HSV-1 vector as the vehicle to carry the gene expression cassette for ex vivo gene transfer to the central and peripheral nervous systems. This illustrative delivery system comprises two parts: (1) the insulated gene expression cassette and (2) a defective HSV-I based virus vector to deliver the transgene to the CNS. The ability of this cassette to maintain persistent, long-term gene expression, in a highly regulated manner, represents a powerful tool in the fields of gene therapy, basic gene expression assays, and in the development of animal disease models.

In one embodiment, the invention provides an isolated polynucleotide that comprises at least a first isolated HSV LAT enhancer element, at least a first isolated LAT insulator/boundary region operably positioned upstream of the isolated LAT enhancer element, and at least a second isolated LAT insulatory/boundary region operably positioned downstream of the isolated LAT enhancer element. The LAT enhancer element may comprise, consist essentially of, or consist of a contiguous nucleotide sequence from an HSV LAT 5' exon. In preferred embodiments, the LAT enhancer element may comprise, consist essentially of, or consist of, a contiguous nucleotide sequence from about nucleotide 118,975 to about nucloetide 120,471 of an HSV LAT 5' exon, or more preferably a contiguous nucleotide sequence from about nucleotide 118,975 to about nucloetide 120,471 of an HSV LAT 5' exon, or more preferably still, a contiguous nucleotide sequence from about nucleotide 118,975 to about nucloetide 120,471 of an HSV LAT 5' exon. In certain embodiments, an even smaller LAT enhancer element may be preferred, and in such conditions, the enhancer element may comprise, consist essentially of, or consist of, a contiguous nucleotide sequence from about nucleotide 118,975 to about nucloetide 120,471 of an HSV LAT 5' exon. Exemplary human HSV genomes have been illustrated in SEQ ID NO:109, SEQ ID NO:110, and SEQ ID NO:111, which represent the complete genomic sequences of the human HSV 1, 2, and 3 virus, respectively.

In certain embodiments, the isolated expression cassettes of the invention may, in addition to the polynucleotides described above, further comprise a nucleic acid segment that comprises at least a first promoter region operably positioned upstream of the LAT enhancer element, and downstream of the first LAT insulator/boundary region. Exemplary promoter regions include, but are not limited to, an HSV LAP1 promoter. In certain embodiments, the HSV LAP1 promoter comprises, consists essentially of, or consists of, a sequence region of from about nucleotide 117,938 to about 118,843 of the HSV genome.

The first LAT insulator/boundary region of the disclosed expression cassette, may comprise, consist essentially of, or consist of, a contiguous nucleotide sequence from an HSV insulator region or an HSV boundary region. Exemplary sequences for such a first LAT insulator/boundary region include sequence regions that comprise, consist essentially of, or consist of, a contiguous nucleotide sequence from about nucleotide 8365 to about nucleotide 9273 of the human HSV genome, and in particular, from the HSV 1 genome as identified in SEQ ID NO:109.

The second LAT insulator/boundary region of the disclosed expression cassette may comprise, consist essentially of, or consist of, a contiguous nucleotide sequence from an HSV insulator region or an HSV boundary region. Exemplary sequences for such a second LAT insulator/boundary region include sequence regions that comprise, consist essentially of, or consist of a contiguous nucleotide sequence from about nucleotide 120,208 to about nucleotide 120,940 of the human HSV genome, and in particular, from the HSV 1 genome as identified in SEQ ID NO:109.

The disclosed polynucleotides may also optionally further comprise at least a first multiple cloning region operably positioned downstream of the first LAT insulator/boundary region and upstream of the LAT enhancer element. This multiple cloning region may also further comprise a nucleic acid sequence that encodes at least a first promoter or at least a first enhancer sequence that can be used to express a selected gene operably placed under its control in a suitable mammalian host cell.

The disclosed polynucleotides may also optionally further comprise at least a second multiple cloning region operably positioned upstream of the second LAT insulator/boundary region and downstream of the LAT enhancer element. This second multiple cloning region may also optionally further comprises at least a first nucleic acid sequence that encodes a heterologous peptide, polypeptide, or enzyme, and preferably, one that encodes a heterologous therapeutic agent, including for example, antibodies, antigen binding domains, peptides, polypeptides, enzymes, ribozymes, or even antisense polynucleotides.

Exemplary therapeutic agents include, but are not limited to, peptides or polypeptides such as an antibody, a growth factor, a neurotrophic factor, a transcription factor, an anti-apoptotic factor, a proliferation factor, an enzyme, a cytotoxin, a transcription factor, an apoptotic factor, a tumor suppressor, a kinase, a cytokine, a lymphokine, a protease, or other therapeutic polypeptide that may be beneficial when expressed in a mammalian host cell.

When it is desirable to express two or more therapeutic agents in a host cell, the second multiple cloning region may also optionally further comprise at least a second distinct nucleic acid sequence that encodes at least a second distinct therapeutic agent. As in the case of the first therapeutic agent, the second agent may also be selected from the group consisting of a peptide, an antibody, a protein, a polypeptide, a ribozyme, a catalytic RNA molecule, an antisense oligonucleotide, and an antisense polynucleotide.

When a catalytic RNA molecule is selected as the therapeutic agent, this ribozyme will preferentially and specifically cleave a first mRNA molecule encoding, for example, a transcription factor, an anti-apoptotic factor, an enzyme, a proliferation factor, a receptor, a growth factor, an oncogenic peptide, a signaling polypeptide, or a growth factor polypeptide. Exemplary catalytic RNA molecules include, for example, hammerhead and hairpin ribozymes.

The expression cassettes of the invention typically will be on the order of about 1000 to about 10,000 nucleotides in length, and more preferably, of from about 2000 to about 9000 nucleotides in length, or of from about 3000 to about 8000 nucleotides in length, of from about 4000 to about 7000 nucleotides in length, although larger or smaller expression cassettes are contemplated to be useful in certain embodiments.

Another embodiment of the invention concerns vectors that comprise one or more of the disclosed expression cassette polynucleotides. Exemplary vectors include plasmids, with one such vector, Insulated Viral Artificial Chromosome vectors (IVACs) being particularly preferred. In illustrative embodiments, one such plasmid vector is described in detail hereinbelow and show in FIG. 12A and FIG. 12B. This vector has been designated pIVAC_1.0.

Another embodiment of the invention concerns viral vectors, virions, or viral particles that comprise one or more of the disclosed expression cassette polynucleotides. Such vectors will preferably comprise a retroviral, adenoviral, adeno-associated viral, or a herpes viral vector. Exemplary vectors include gutless HSV vectors, gutless AV vectors, gutless AAV vectors, recombinant HSV vectors, recombinant AV vectors, and recombinant AAV vectors that comprise, consist essentially of, or consist of, one or more of the disclosed expression cassettes. Pluralities of such viral particles, as well as host cells comprising them also represent important embodiments of the invention. Preferred host cells include animal cells, with mammalian host cells, and human host cells in particular, being preferred.

The compositions of the present invention when used in therapy of mammals, and in therapy of humans in particular, may also further optionally comprise one or more pharmaceutical excipients, diluents, buffers, or such like, and may optionally further comprise a lipid, a liposome, a lipofection complex, a nanoparticle, a nanocapsule, or other component to facilitate improved cellular adhesion, infection, or uptake. Preferably compositions of the present invention will be formulated with pharmaceutical excipients that are designed for administration to a human host cell through suitable means, such as injection.

In another embodiment, the invention concerns therapeutic, diagnostic, and prophylactic kits. Such kits are often suitable for commercial sale, and typically will comprise in suitable container means: (a) one or more components polynucleotides, plasmid vectors, viral vectors, virions, or viral particles, host cells, or compositions that comprise them; and (b) instructions for using the kit.

In another embodiment, the invention concerns the use of the polynucleotides, expression cassettes, viral vectors, and compositions comprising them in the manufacture of medicaments and in methods for treating, preventing, or ameliorating the symptoms of a disease, disorder, defect, or dysfunction in an animal, preferably mammals, and in particular, humans. Such polynucleotides and expression vectors are contemplated to be particularly useful in the manufacture of medicaments and in methods for preventing, treating, or alleviating the symptoms of one or more mammalian diseases, including, but not limited to, cancer, diabetes, autoimmune disease, kidney disease, cardiovascular disease, pancreatic disease, liver disease, cystic fibrosis, muscular dystrophy, neurological disease, neurosensory dysfunction, stroke, ischemia, an enzyme deficiency, a psychological deficit, a neuromuscular disorder, an eating disorder, a neurological deficit or disease, a neuroskeletal impairment or disability, Alzheimer's disease, Huntington's disease, Parkinson's disease, pulmonary disease, a skin disorder, a burn, or a wound, or such like. The vectors and pharmaceutical compositions of the invention are also contemplated to find utility in the manufacture of medicaments and methods for administering genetic constructs to selected human cells for use in various treatment modalities, including for example, ex vivo, in situ, in vitro, or in vivo gene delivery. The use of such compositions in the development of viral gene therapy vectors, such as recombinant AV, AAV, and/or HSV vectors, is particularly envisioned by the present inventors.

3.0 BRIEF DESCRIPTION OF THE DRAWINGS

The following drawings form part of the present specification and are included to further demonstrate certain aspects of the present invention. The invention may be better understood by reference to the following description taken in conjunction with the accompanying drawings, in which like reference numerals identify like elements, and in which:

FIG. 1 shows an illustrative gene expression cassette of the present invention. The therapeutic gene of interest may be cloned into the multiple cloning site 3' of the LAT enhancer, while the MCS upstream of the LAT promoter may be utilized to facilitate introduction of one or more additional promoter elements for expression of the selected gene of interest. HSV type I strain 17syn+ neuronal-specific DNA boundary element; Cell-type specific boundary elements may be swapped in/out. HSV type I strain 17syn+ insulator element capable of protecting and maintaining the gene expression portion of the cassette in highly responsive transcriptional state. Multiple cloning sites represented by a cluster of restriction enzyme sites that may be used to facilitate cloning of the gene of interest and/or an additional promoter element. HSV type I strain 17syn+ latency associated transcript (LAT) core promoter. HSV type I strain 17syn+ latency associated transcript (LAT) 5' exon DNA exhibiting enhancer function. The element is bound by Splice Donor (SD) and Splice Acceptor (SA) sites to facilitate splicing of the transcript's 'artificial' intron from the desired downstream gene of interest transcript. Splicing also promotes nuclear export of desired transcript.

Figure 2:
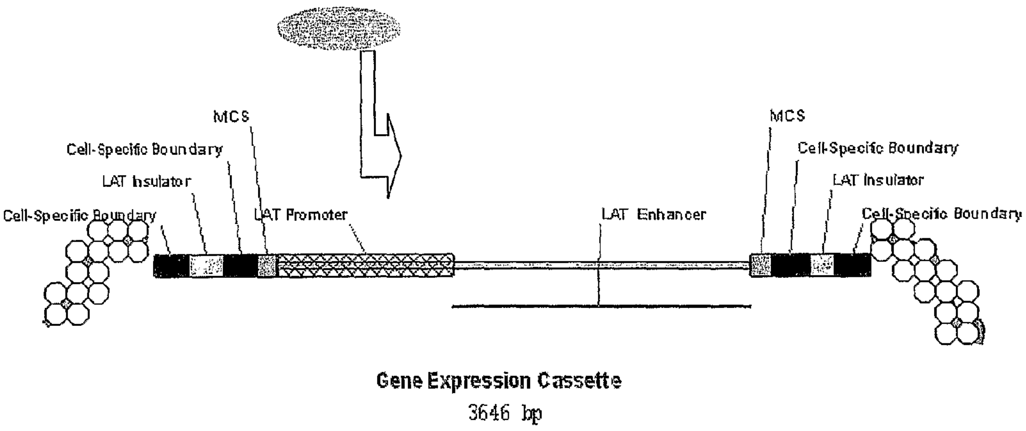

FIG. 2 shows another an illustrative gene expression cassette of the present invention. The therapeutic gene of interest may be cloned into the multiple cloning site 3' of the LAT enhancer, while the MCS upstream of the LAT promoter may be utilized to facilitate introduction of one or more additional promoter elements for expression of the selected gene of interest. HSV type I strain 17syn+ neuronal-specific DNA boundary element; Cell-type specific boundary elements may be swapped in/out. HSV type I strain 17syn+ insulator element capable of protecting and maintaining the gene expression portion of the cassette in highly responsive transcriptional state. Multiple cloning sites represented by a cluster of restriction enzyme sites that may be used to facilitate cloning of the gene of interest and/or an additional promoter element. HSV type I strain 17syn+ latency associated transcript (LAT) core promoter. HSV type I strain 17syn+ latency associated transcript (LAT) 5' exon DNA exhibiting enhancer function. The element is bound by Splice Donor (SD) and Splice Acceptor (SA) sites to facilitate splicing of the transcript's 'artificial' intron from the desired downstream gene of interest transcript. Splicing also promotes nuclear export of desired transcript. Transcriptionally repressed regions of DNA located outside of the insulated cassette.

Figures 3A, 3B, 3C:
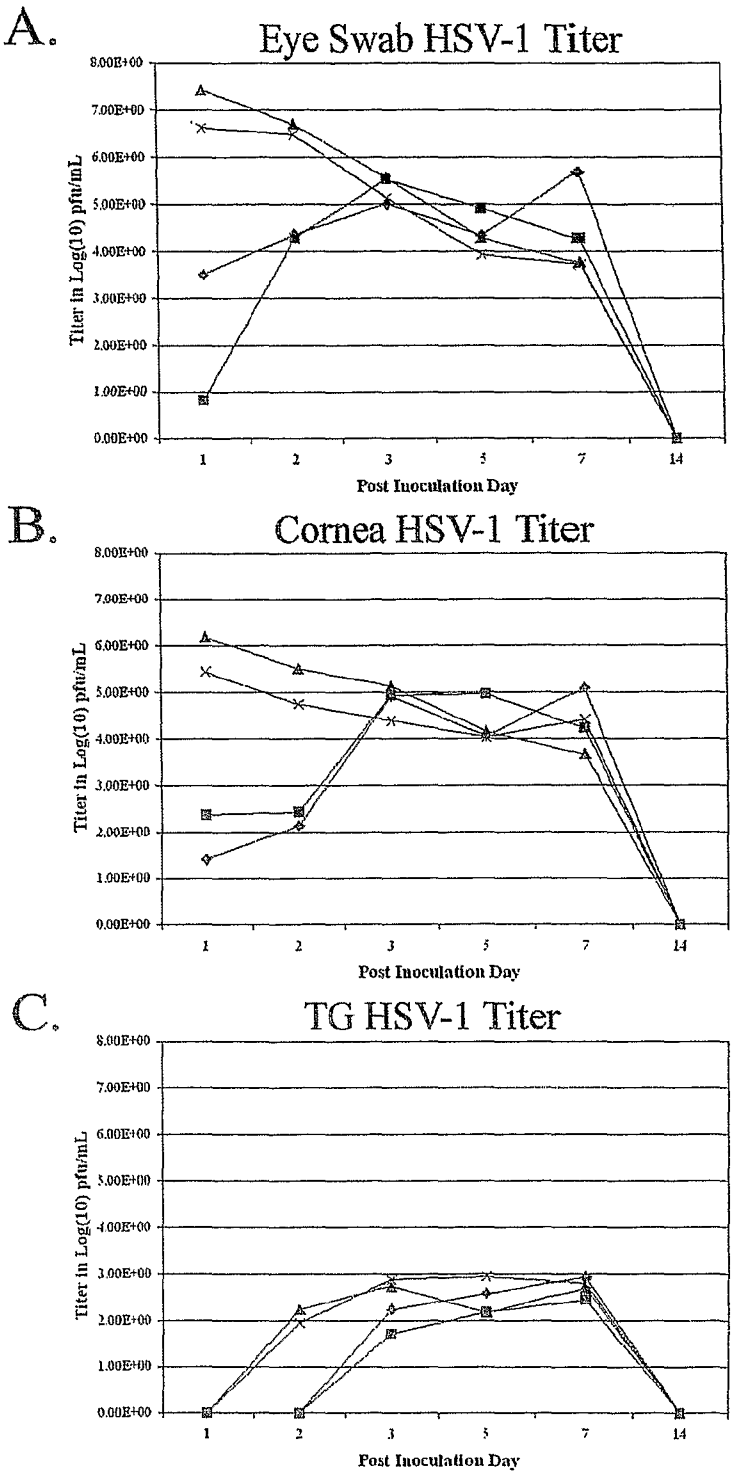

FIG. 3A, FIG. 3B and FIG. 3C show titers of infectious virus detected in eye swabs, corneas, and TG during acute infections following inoculation with high and low doses of $LAT^+$ and $LAT^-$ viruses. Rabbits were inoculated with 500,000 or 500 PFU of either 17ΔPst ($LAT^-$) or 17ΔPstR ($LAT^+$). At the indicated times, eye swabs were taken, the rabbits were sacrificed, and corneas and TG were dissected. Virus titers were determined by standard plaque assays and are expressed as the log titer of infectious virus present in the eye swabs (FIG. 3A), corneas (FIG. 3B), and TG (FIG. 3C). Diamonds, 17ΔPst (500 PFU); squares, 17ΔPstR (500 PFU); triangles, 17ΔPst (50,000 PFU); X's, 17ΔPstR (50,000 PFU).

Figure 4:
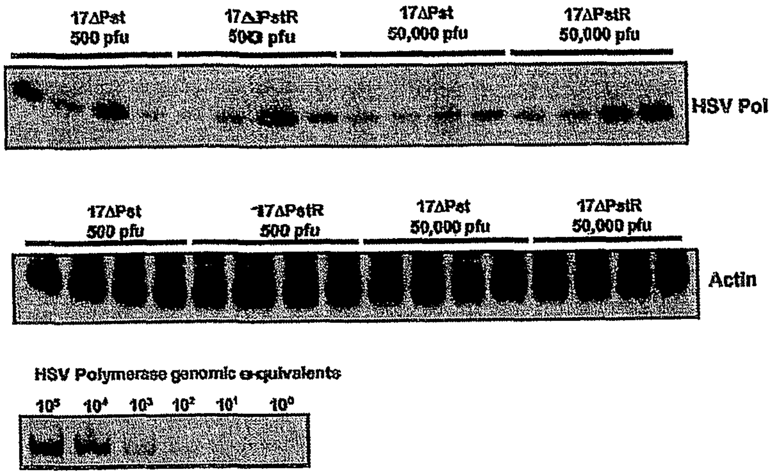

FIG. 4 shows HSV-1 DNA detected in the TG of rabbits 30 days after infection with high and low doses of $LAT^+$ and $LAT^-$ viruses. Total TG DNA was isolated from rabbits infected with 50,000 or 500 PFU of either 17ΔPst or 17ΔPstR, and HSV-1 DNA was detected by PCR™ analysis. HSV-1 DNA was detected using primers specific for the HSV-1 DNA polymerase gene, and primers specific for the rabbit β-actin gene were used as an internal control. A titration mixture of dilutions of a cloned target plasmid containing the HSV-1 DNA polymerase target sequences was spiked into DNA extracted from an uninfected rabbit TG to generate a standard curve.

Figure 5:
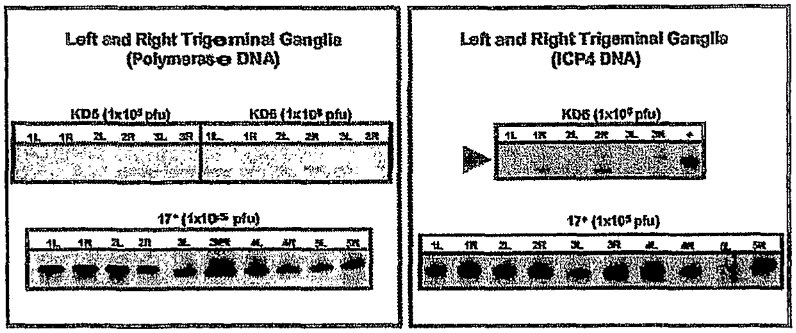

FIG. 5 shows HSV-1 DNA detected in the TG of rabbits 14 days after infection with a nonreplicating HSV-1 recombinant. Total TG DNA was isolated from rabbits infected with 500,000 PFU of either KD6, a nonreplicating ($ICP4^-$) recombinant, or wild-type 17syn+. The left panels show HSV-1 DNA samples obtained using primers specific for the HSV-1 DNA polymerase gene and primers specific for the rabbit β-actin gene as an internal control. The right panels show PCR™ analysis of the same samples using primers specific for the ICP4 gene and β-actin as the internal control. The dash indicates the location of the ICP4-specific product. L, left TG; R, right TG.

Figures 6A, 6B:
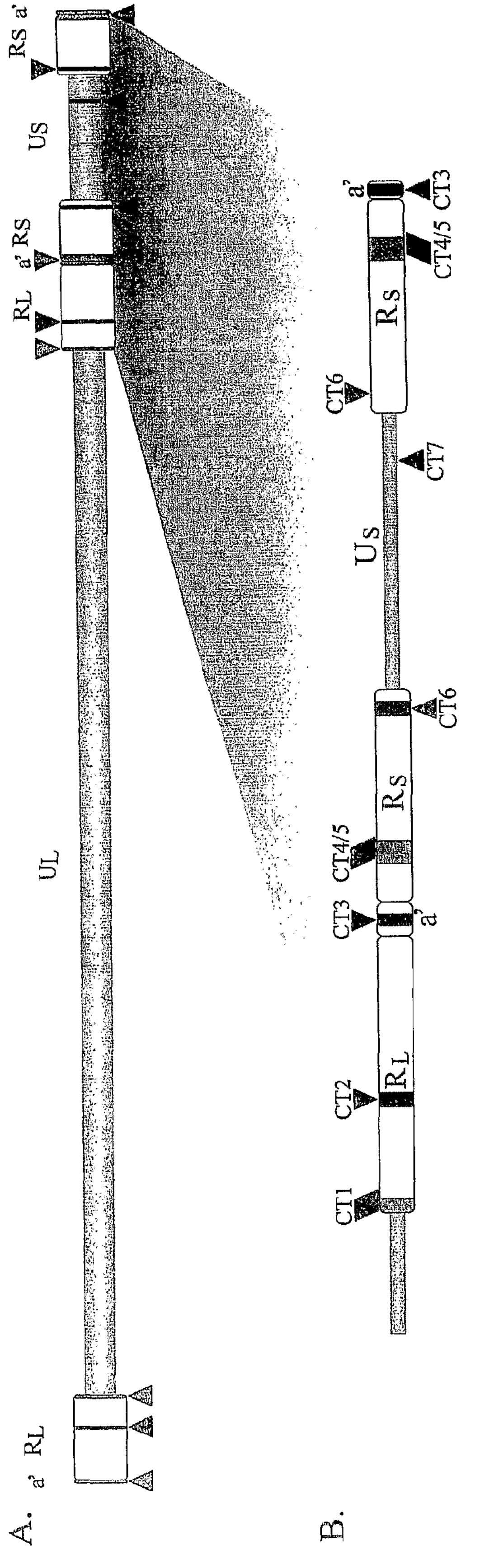

FIG. 6A and FIG. 6B show an expanded view of a portion of the HSV-1 UL, internal RL and RS, US and terminal RS regions illustrating the location of tandem CTCF motifs (FIG. 6A). FIG. 6B shows a linear diagram of a portion of the genome labeled with relative locations of CTCF clusters and immediate-early genes. The sequences of the motifs are shown in Table 10.

Figures 7A, 7B, 7C:
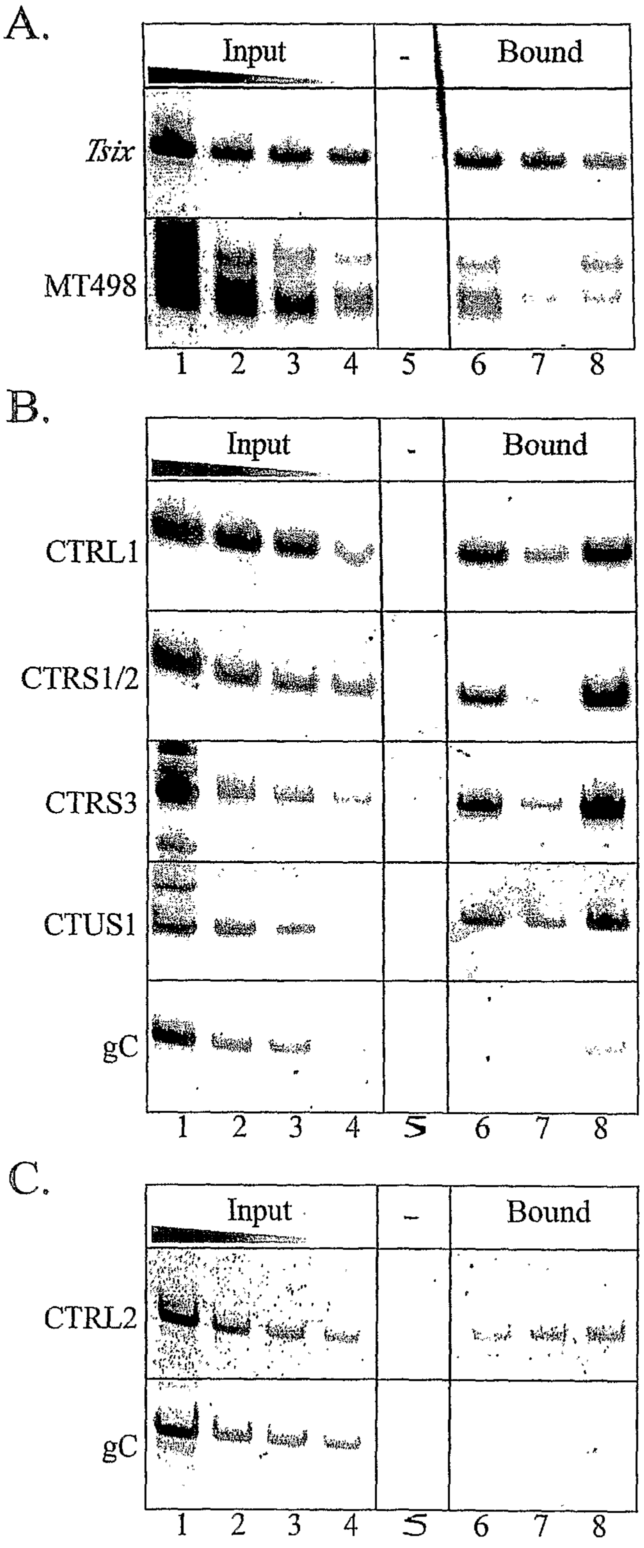

FIG. 7A, FIG. 7B and FIG. 7C show ChIP analysis of identified CTCF motif clusters within latent HSV-1 DNA using antiserum specific for anti-CTCF. DRG from mice latently infected with HSV-1 strain 17syn+ were processed and subjected to ChIP analysis as described. The relative enrichment of CTCF at respective motif clusters was determined by PCR™ analysis of the ChIP fraction (Lane 6-8) relative to dilutions of the input material (Lane 1-4). Lane 5 is the no-input control. In FIG. 7A, ChIPs were validated using results published by Chao et al. (2002) by performing PCRs on titrated input and 1/10 dilution of bound ChIP sample with primers to cellular target Tsix imprinting/choice center CTCF-site A (positive control) and MT498 (negative control). FIG. 7B shows PCRs performed with the same titrated input and bound ChIP sample with primers to the CT1, CT4/5, and gC viral targets. FIG. 7C shows PCRs performed with titrated input and 1/100 dilution of bound ChIP sample with primers to the CT2 and gC viral targets. Band intensities of PCR™ products generated with ChIP-precipitated DNA were quantitated with respect to two-fold dilutions of input and used to demonstrate fold enrichments.

Figures 8A, 8B:
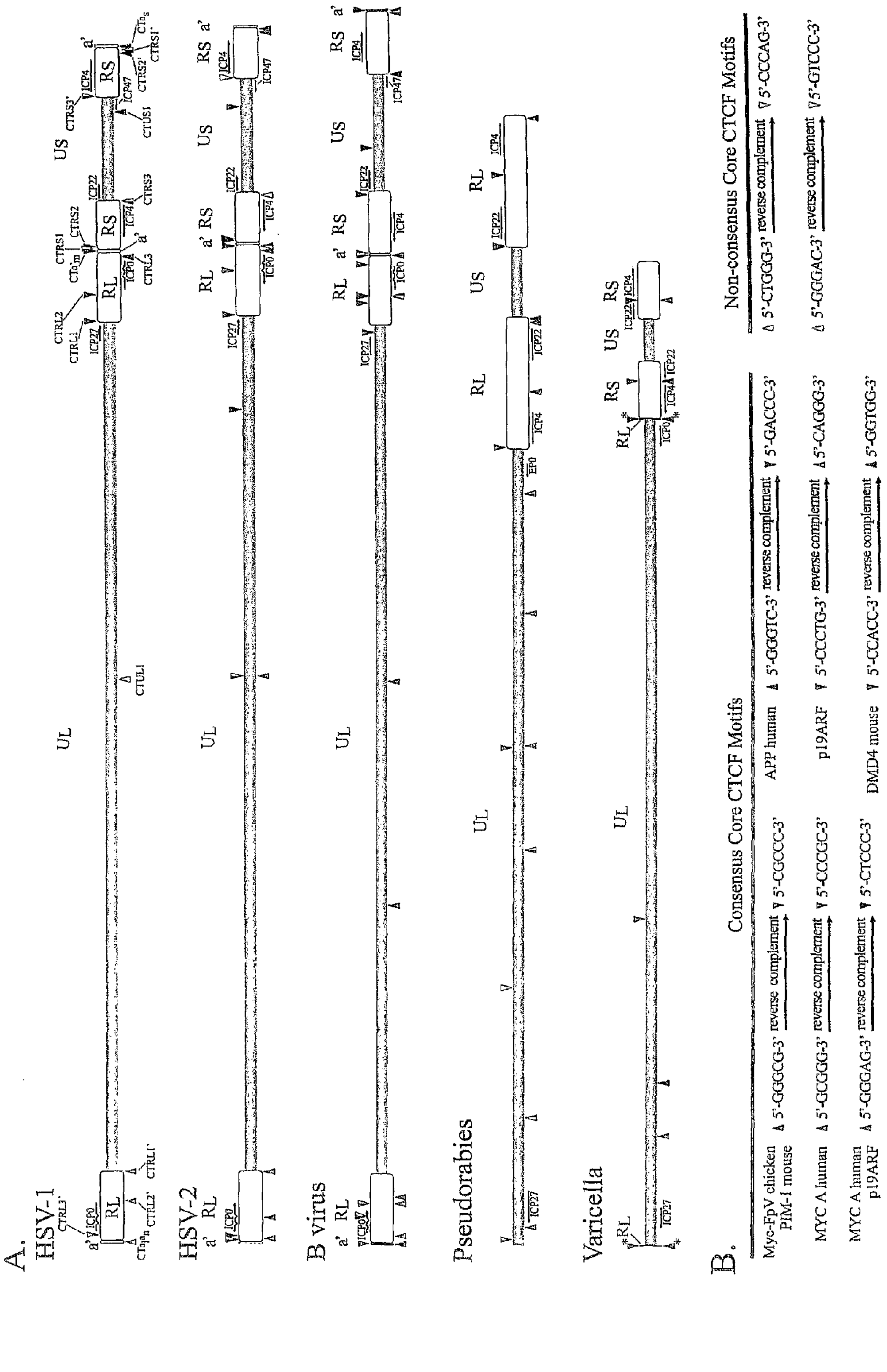

FIG. 8A and FIG. 8B show clustered CTCF binding sites are conserved across the Alphaherpesvirus family and bound the immediate-early genes. Sequence analysis was performed using a tandem repeats finder program to analyze DNA sequences (Benson, 1999). Analyses include HSV-1 strain 17syn+, HSV-2 strain HG52, Cercopithecine herpesvirus 1 (monkey B virus), Suid herpesvirus 1 (pseudorabies virus), and Human herpesvirus 3 strain Dumas (varicella-zoster virus). Solid black triangles represent consensus CCCTC or CTCCC clusters. Open white triangles represent nonconsensus CCCGC, CGCCC, CCCTG, or GTCCC clusters. Partial solid/open triangles represent clusters composed of interleaved consensus and non-consensus motifs. The pointed end of each triangle reflects the DNA strand direction (direct or complement).

Figure 9A:
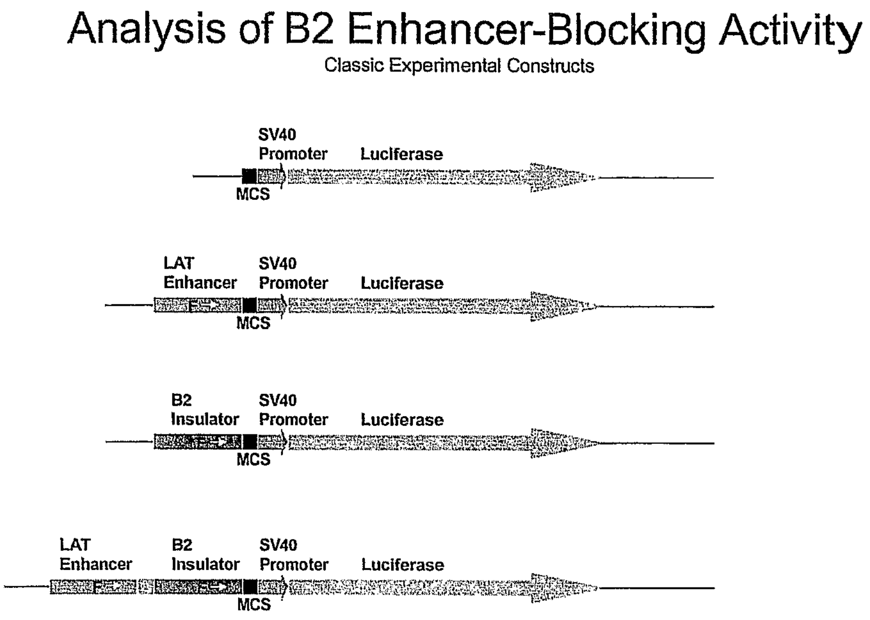
Figure 9B:
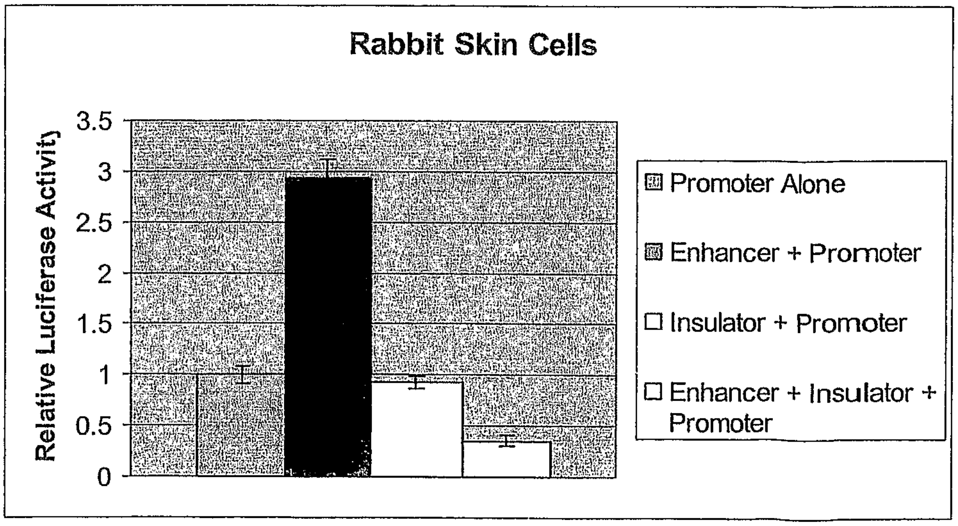

FIG. 9A and FIG. 9B. FIG. 9A. Diagram of the expression cassettes of 4 transient assay plasmids that were constructed to evaluate the enhancer-blocking activity of the HSV-1 B2 insulator. All constructs employed the luciferase gene as the reporter, and the SV40 promoter. The first construct was used to test the basal level of transcription of the SV40 promoter. The second construct contains the LAT enhancer (LTE) to assess the level of enhancement of the SV40 promoter by the LTE. The third construct contains the B2 insulator to assess any effect of the insulator region alone on SV40 promoter activity, and finally the forth construct places the B2 insulator between the enhancer and the SV40 promoter to assay for enhancer-blocking activity. FIG. 9B. Results of the enhancer-blocking assay. The constructs were each transfected (along with a second plasmid containing a renilla luciferase expression cassette to control for transfection efficiency) into rabbit skin cells. The results show the normalized luciferase activity (relative to the SV40 promoter-alone construct) and indicate that B2 insulator is capable of strongly blocking the activity of the LAT enhancer FIG. 10A and FIG. 10B. Schematic Diagram of Additional Insulator Elements within the HSV-1 Genome. FIG. 1A. Linear depiction of the location of the insulators in the $R_L$, $R_S$ and $U_S$ regions of the HSV-1 genome. Locations of the insulators are indicated by the triangles. Insulators B1 and B2 are shown larger (and in bold). Additional insulators are numbered B3-B8. FIG. 10B. Circular depiction of the genome (as exists naturally during latency) shows the potential of the additional insulators to partition the genome into separate, independently regulated chromatin domains.

Figure 11:
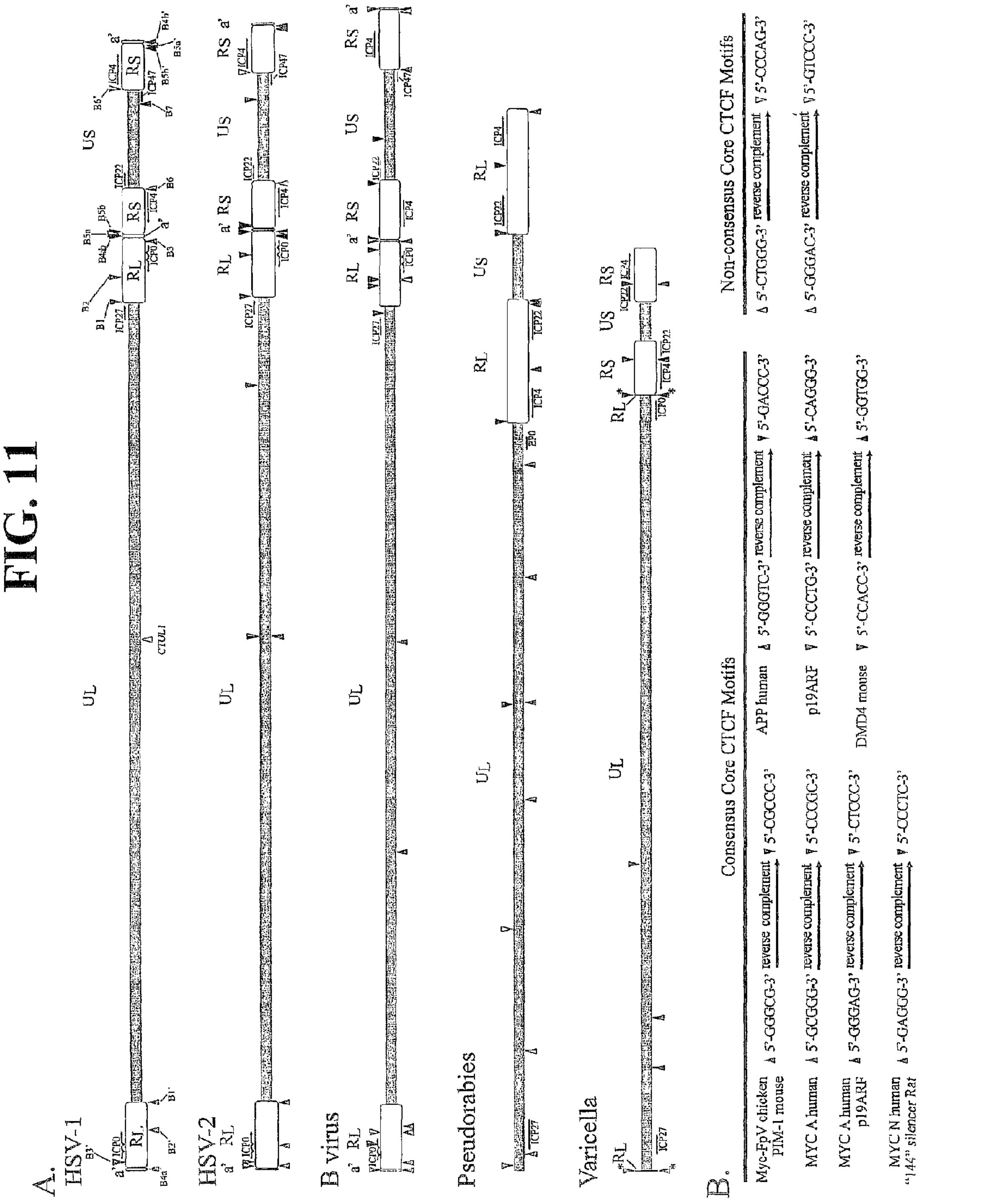
Figure 11A:
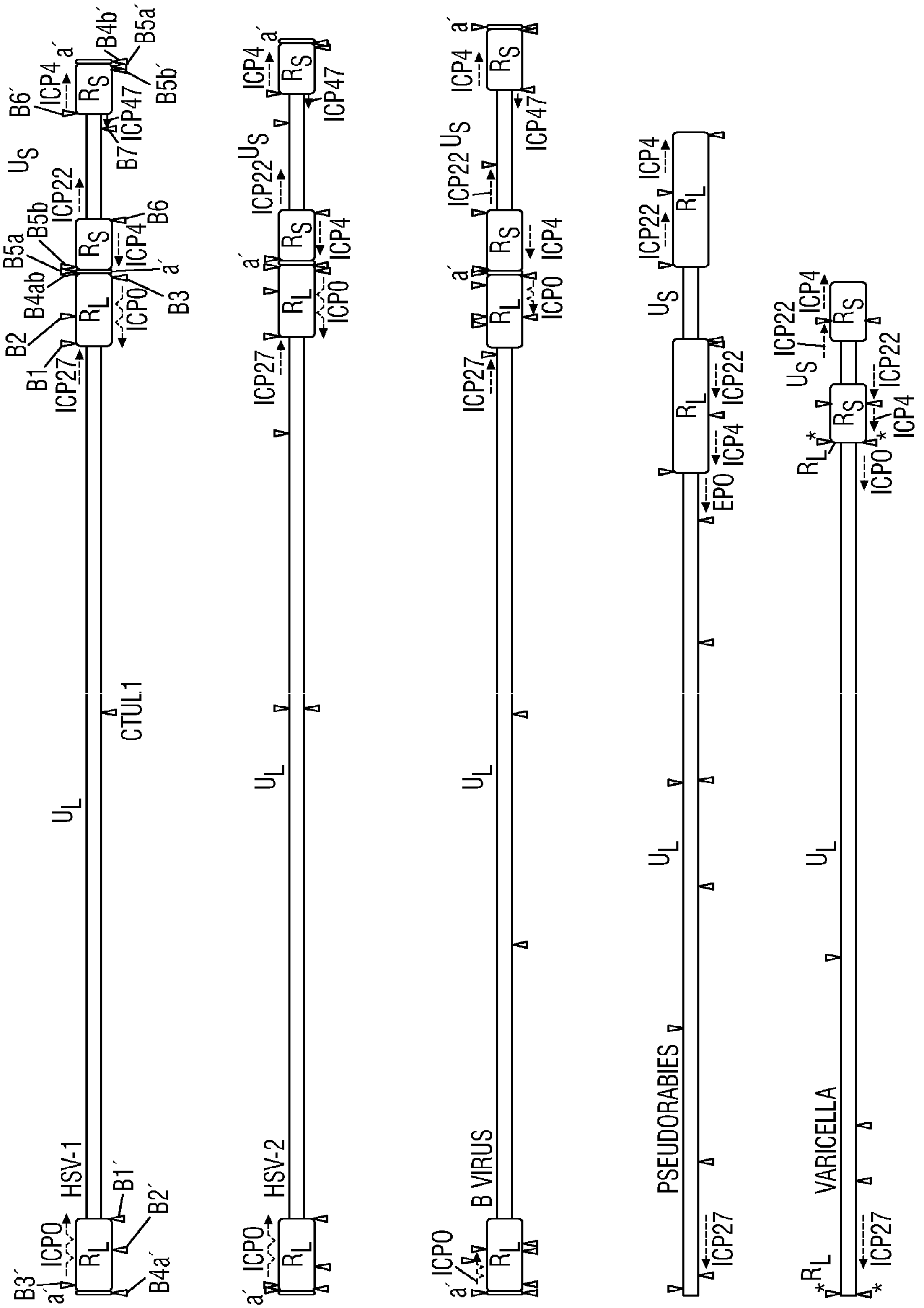
Figure 12A:
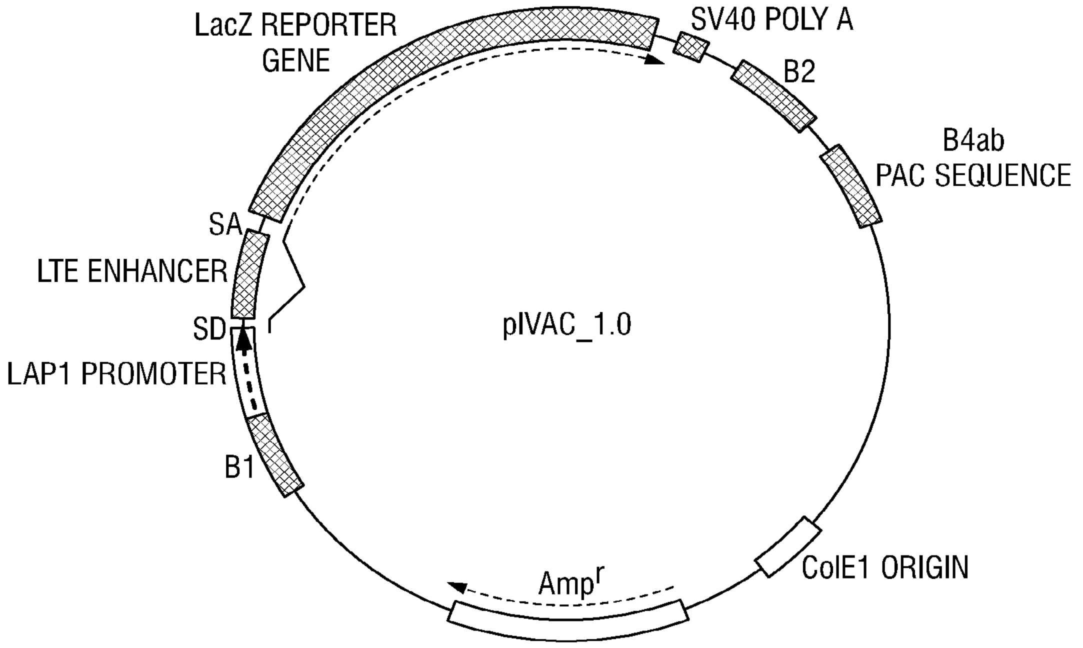
Figure 12B:
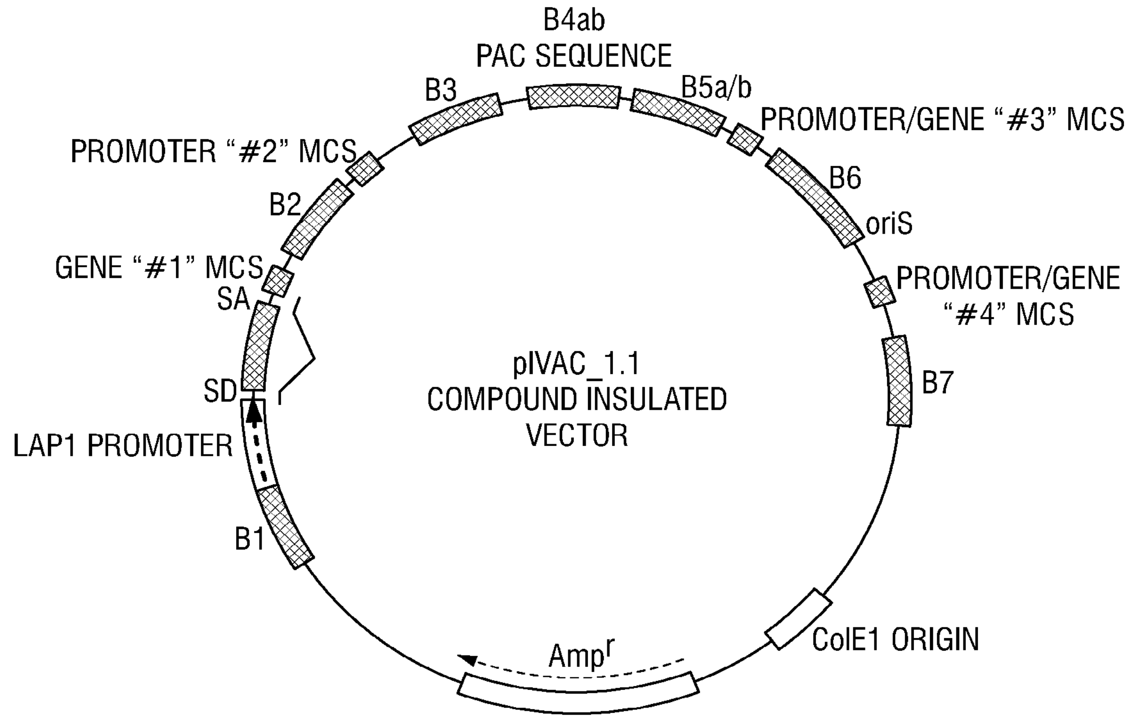

FIG. 11A and FIG. 11B. Clustered CTCF binding sites are conserved across the Alphaherpesvirus family and flank the immediate-early genes. FIG. 11A. An algorithm was used to analyze the HSV-1 strain 17syn+ genome and each respective genome in 1000-bp segments to determine the frequency with which CTCF binding sites (and potential insulators) occur in the positive (direct) or negative (complement) DNA strands. Additionally, tandem repeat analysis was performed to characterize the CTCF motif clustering (1). Analyses were performed using published NCBI GenBank sequence for HSV-2 strain HG52 (NC 001798; McGeoch, D. J.), Suid herpesvirus 1 (pseudorabies virus) (BK001744; Enquist, L. W.), Human herpesvirus 3 strain Dumas (varicella-zoster virus) (X04370; Scott, J. E.), and Cercopithecine herpesvirus 1 (monkey B virus) (NC 004812; Hilliard, J. K.). FIG. 11B. Representative CTCF pentanucleotide motifs found clustered within the Alphaherpesvirus family members. The solid triangles represent consensus CTCF motifs previously described to bind CTCF. The open triangles represent non-consensus CTCF pentanucleotide motifs. Partial solid/open triangles represent clusters composed of interleaved consensus and non-consensus motifs. The pointed end of each triangle reflects the DNA strand direction (direct or complement).

Figure 12A:
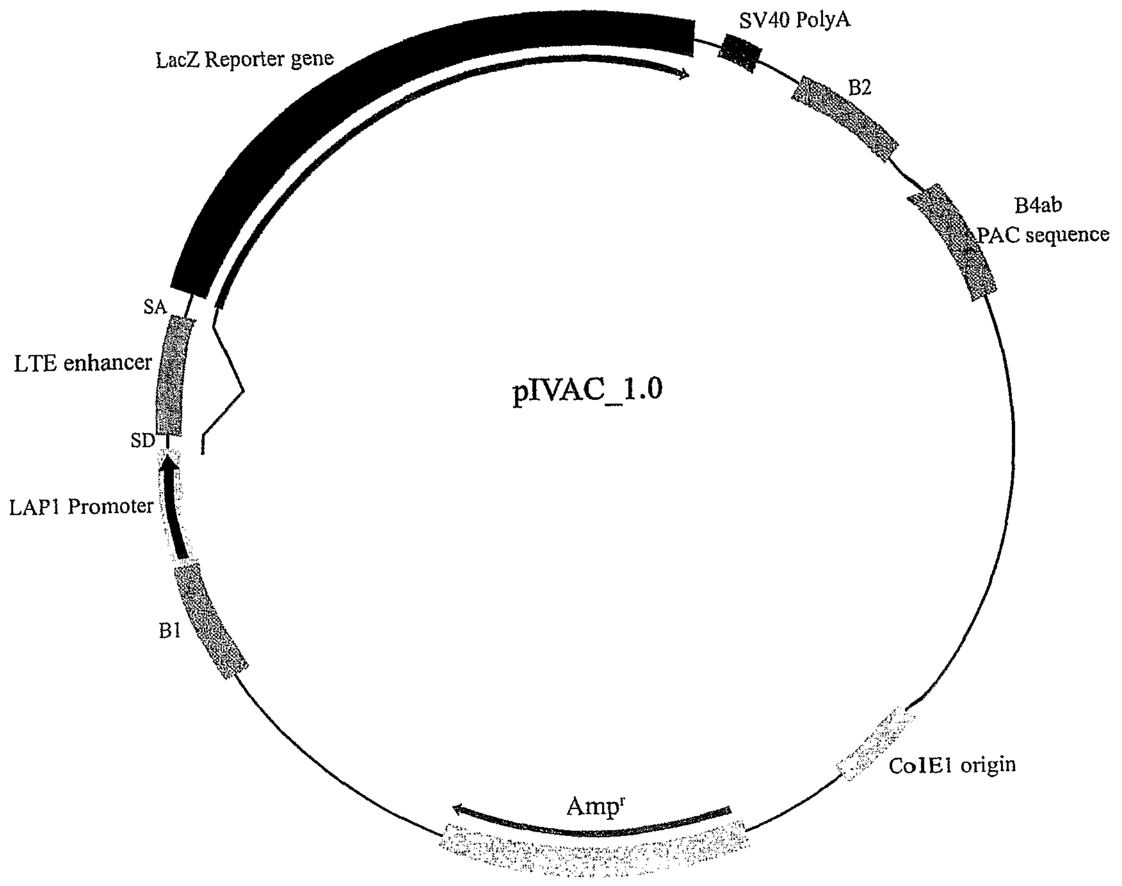
Figure 12B:
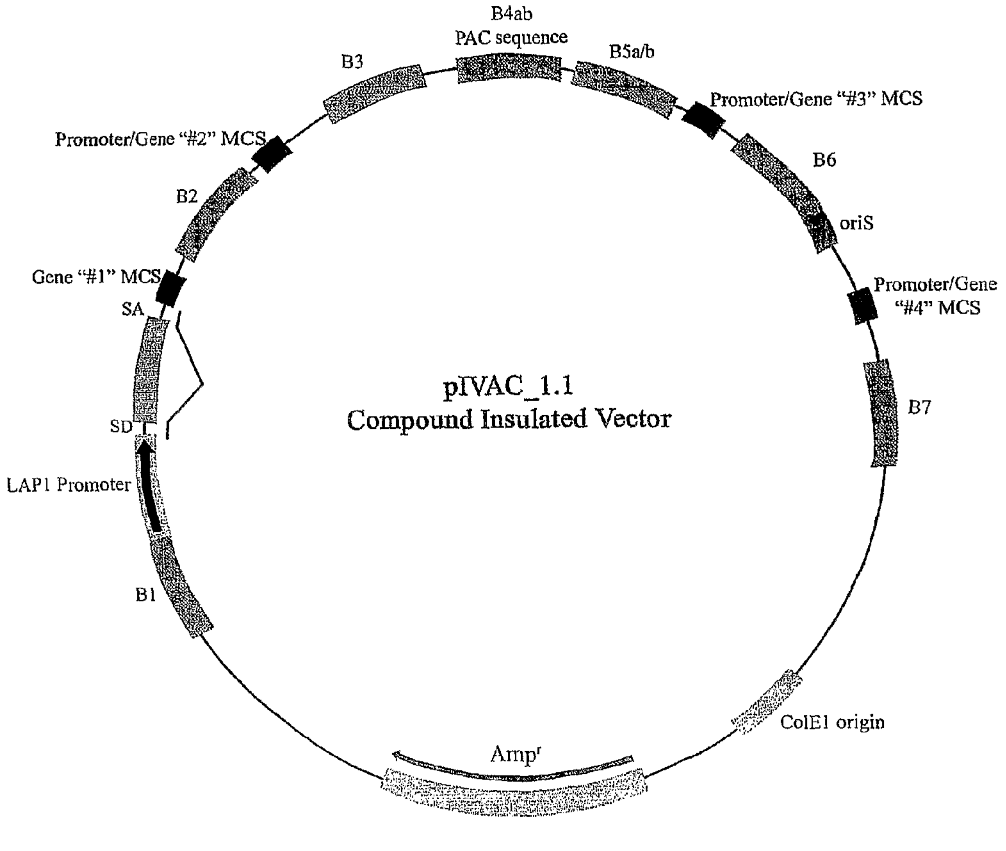
Figure 1:
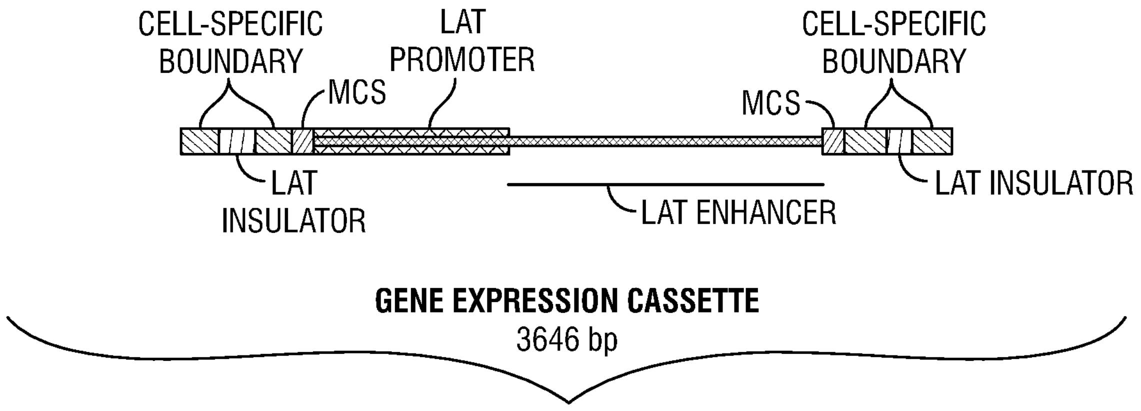
Figure 2:
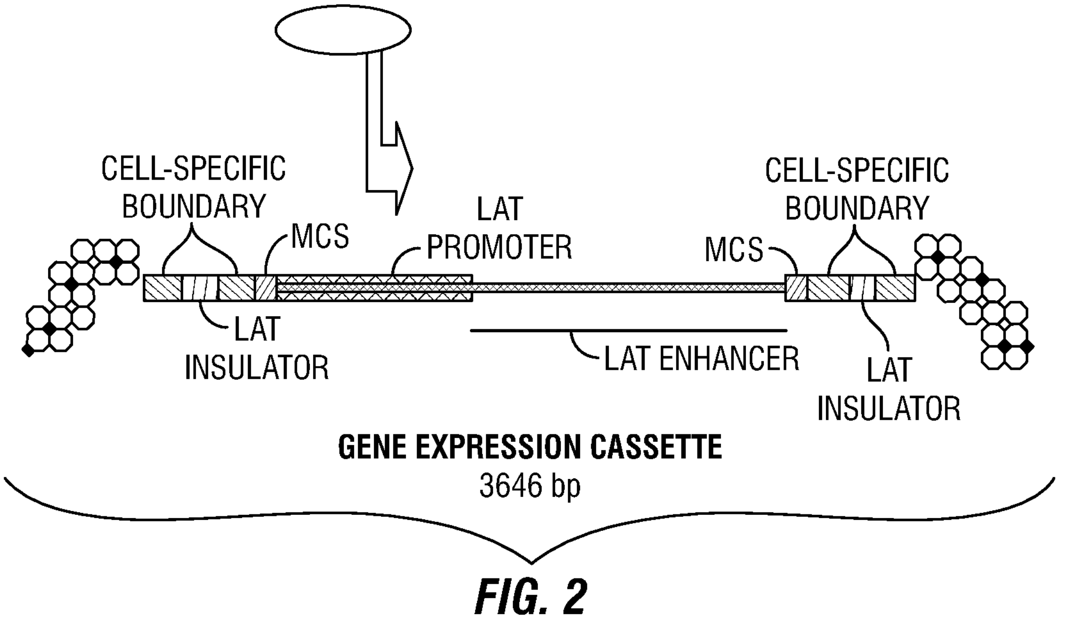
Figure 3A:
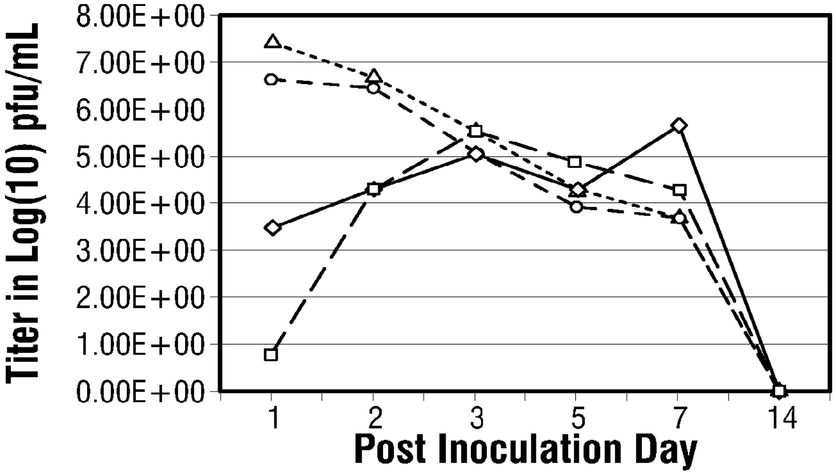
Figure 3B:
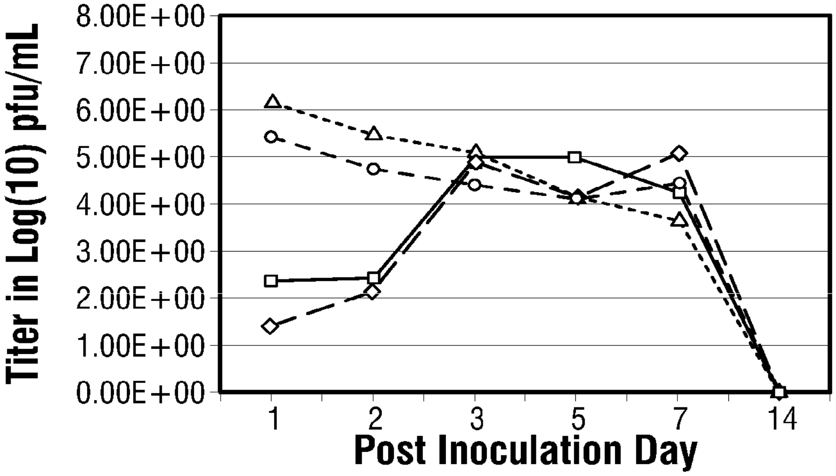
Figure 3C:
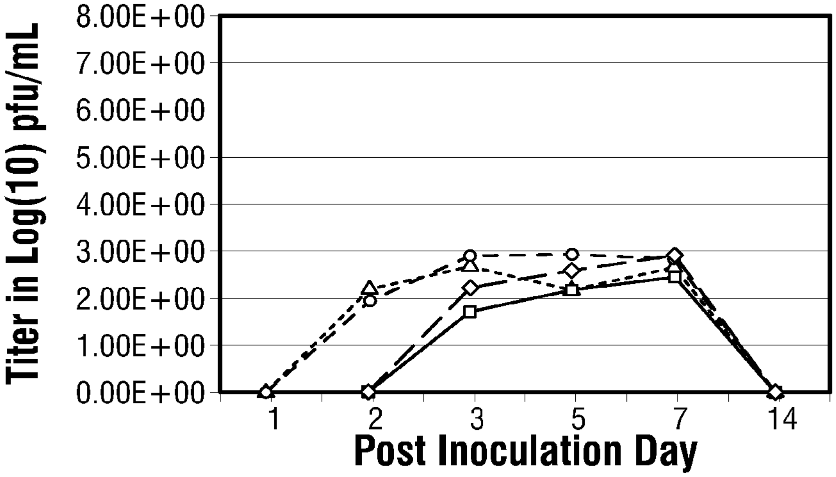
Figure 4:
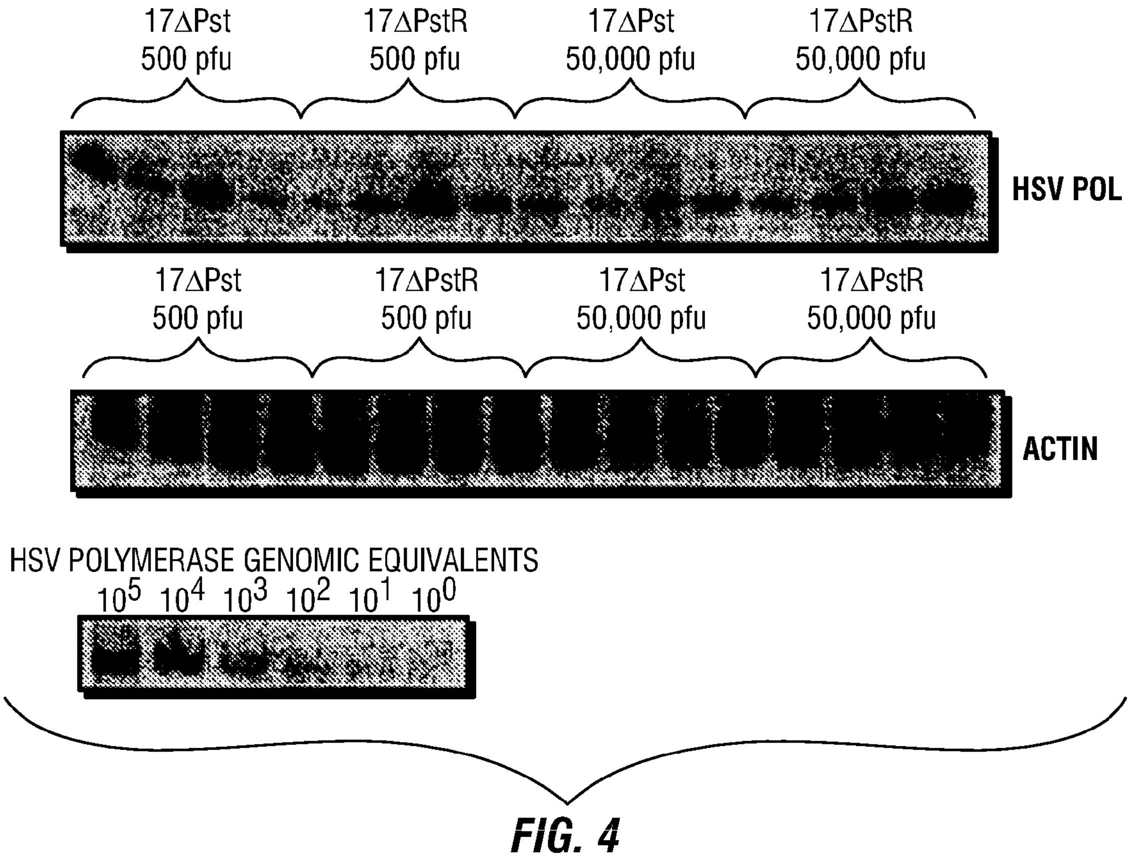
Figure 5:
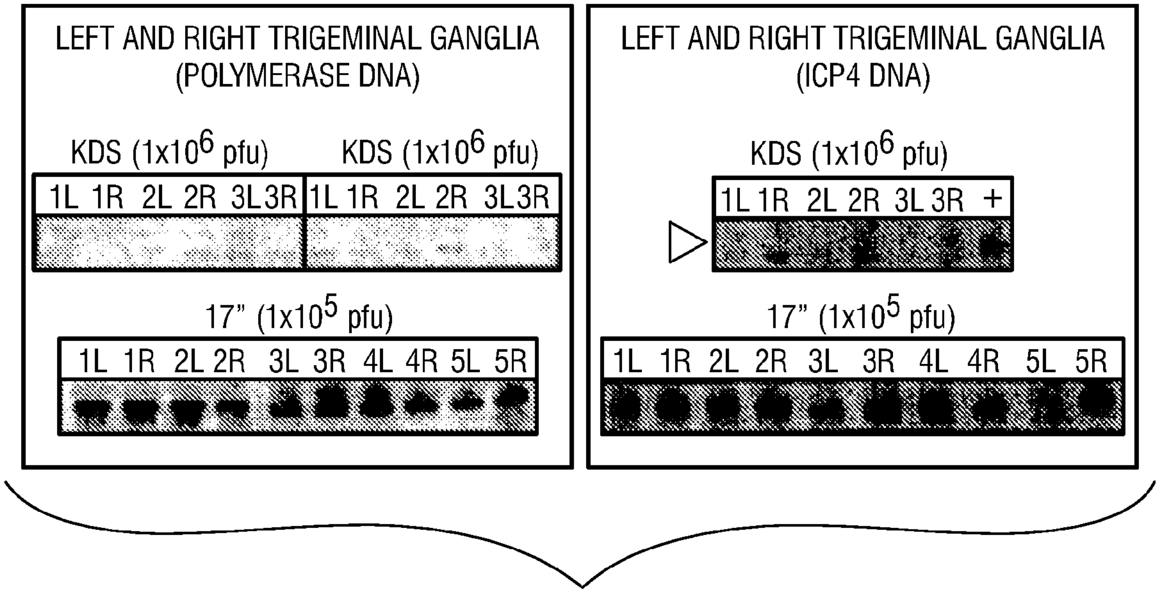
Figure 6A:
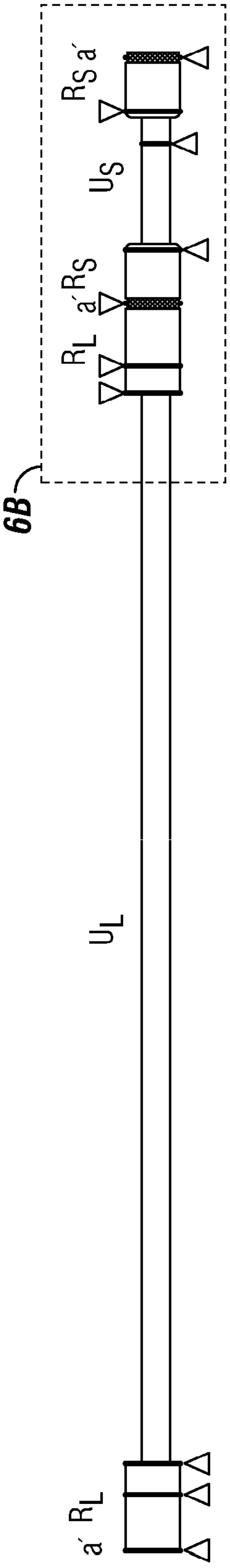
Figure 6B:
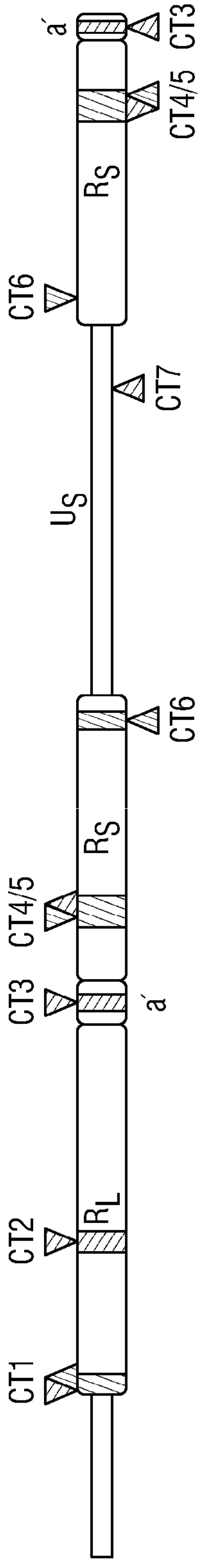
Figure 7A:
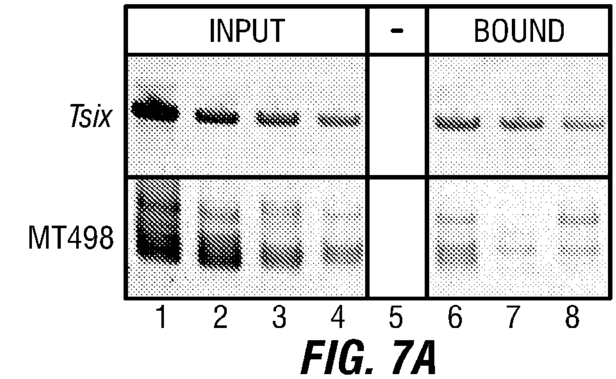
Figure 7B:
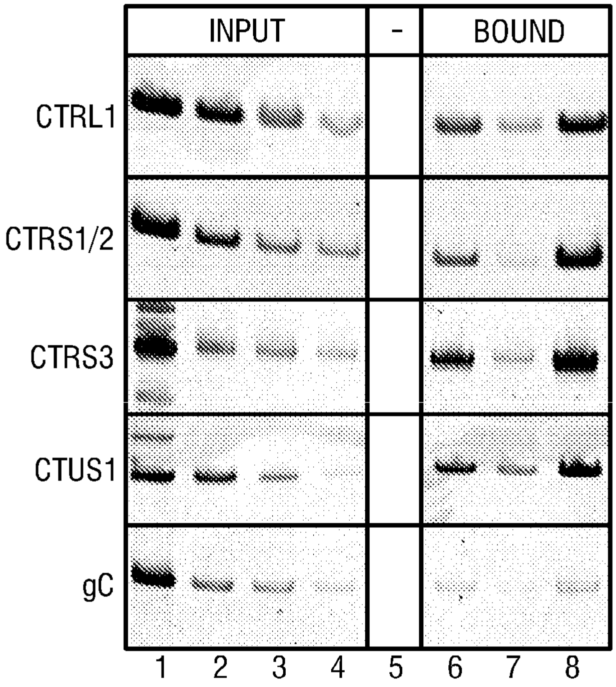
Figure 7C:
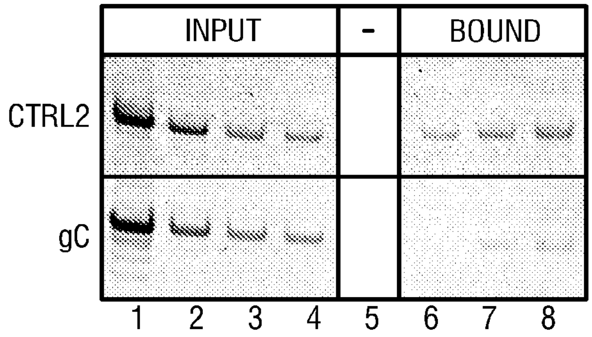
Figure 8A:
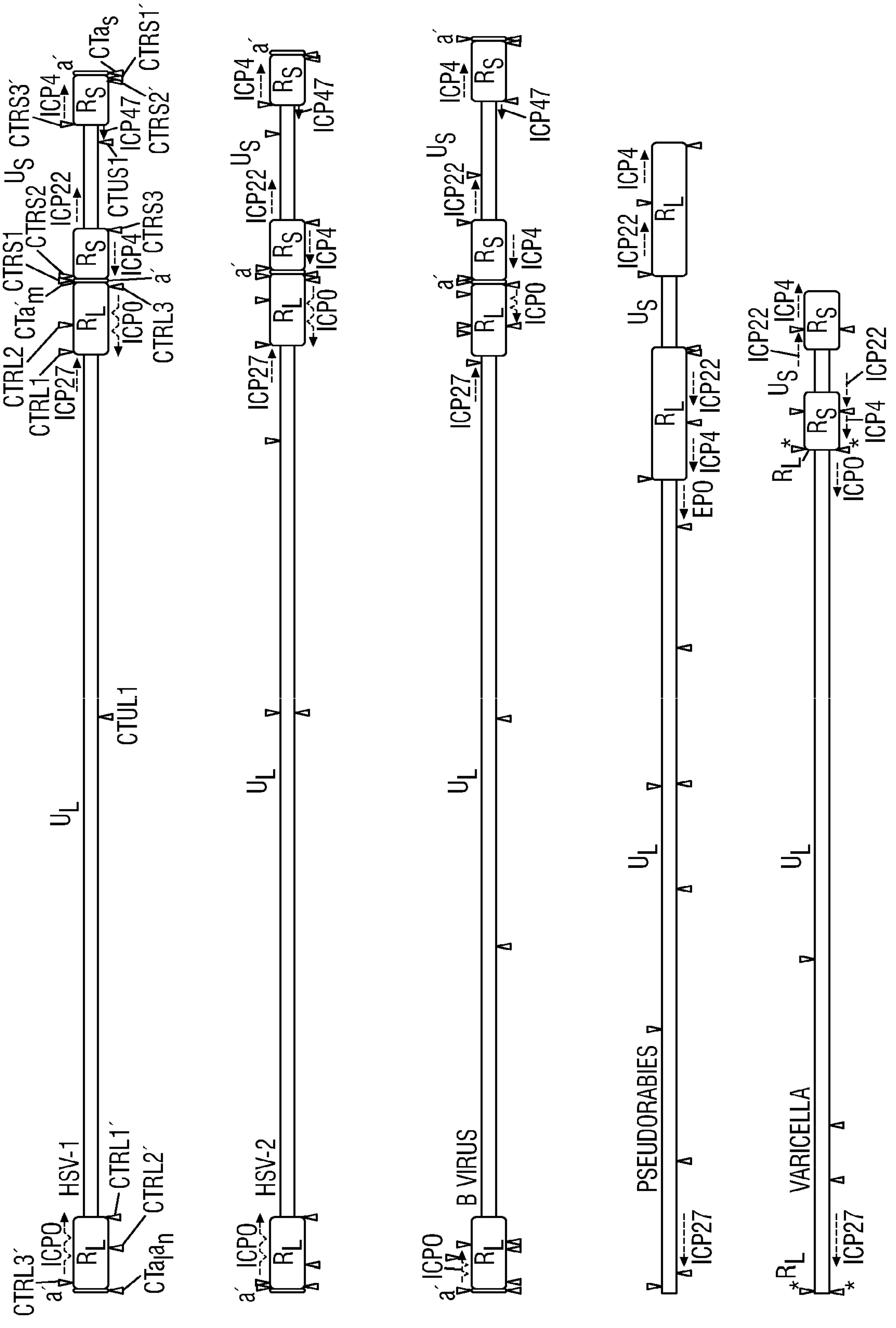
Figure 9A:
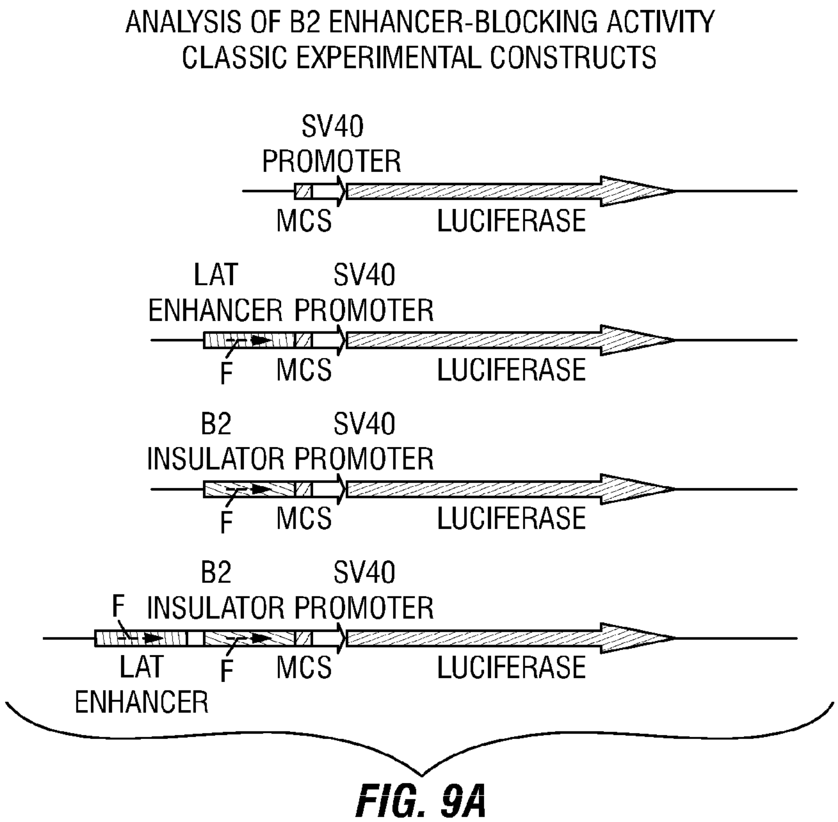
Figure 9B:
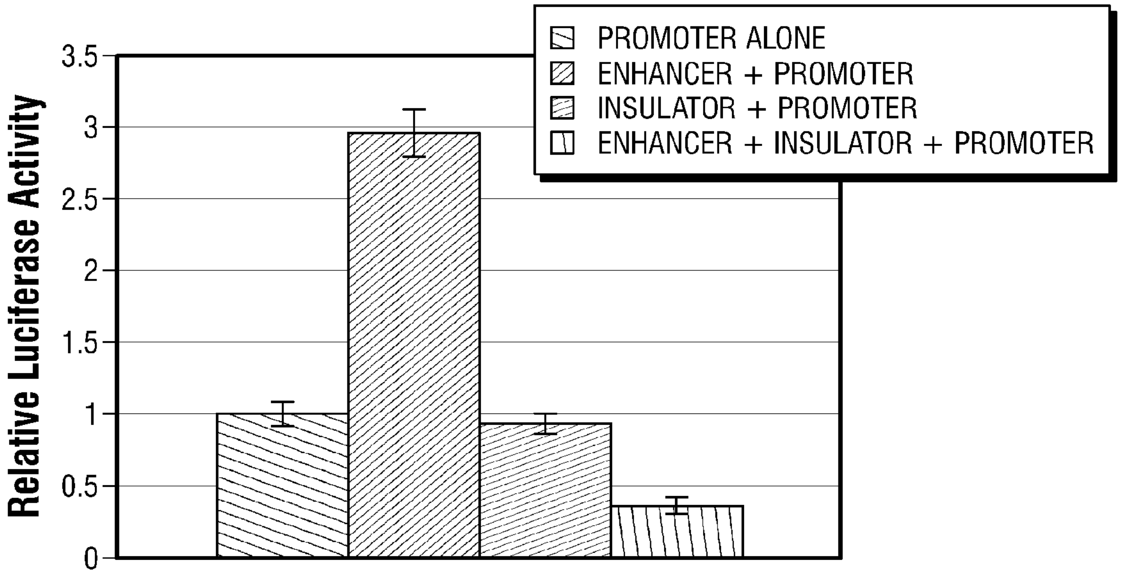
Figure 10:
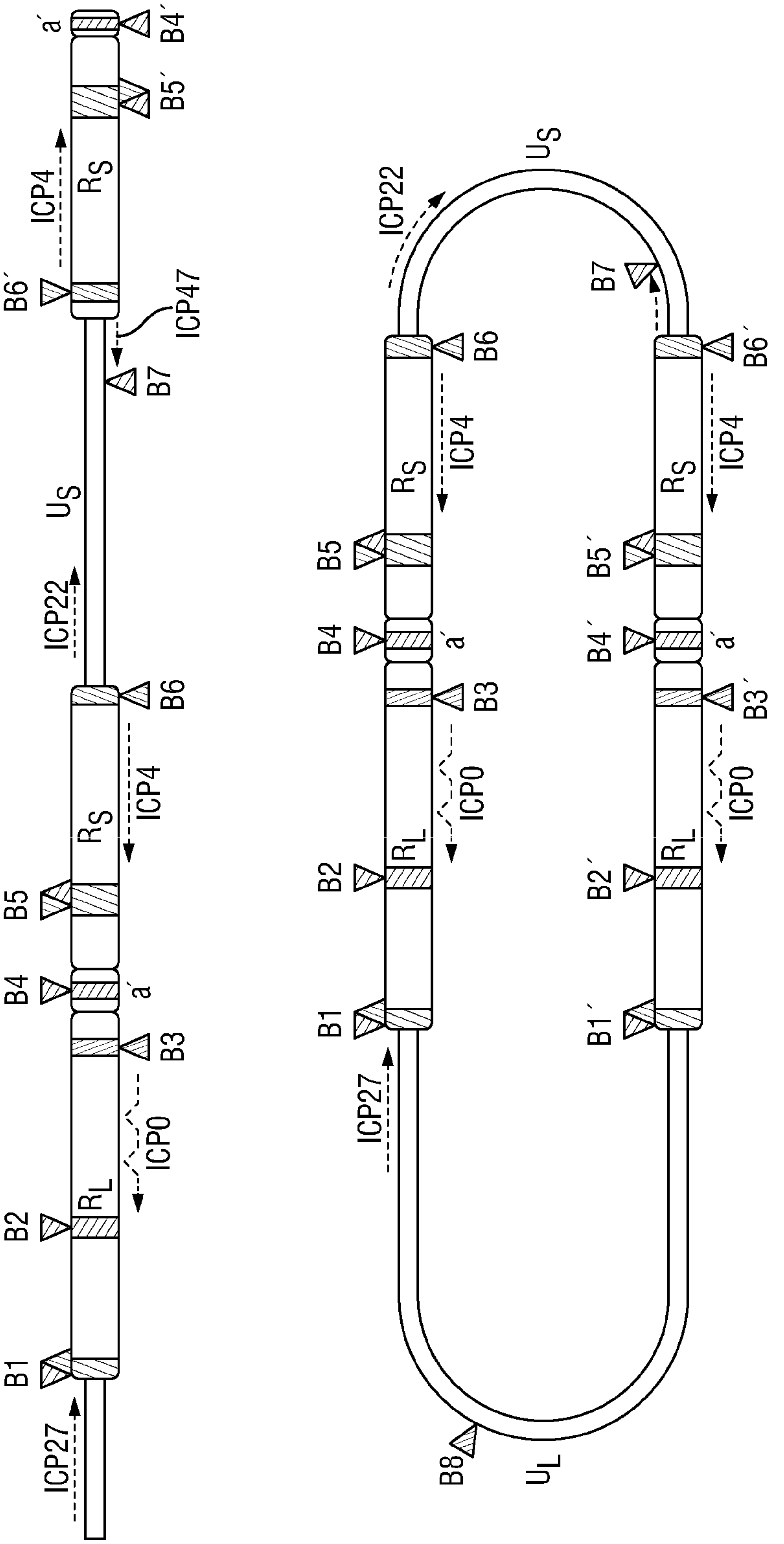

FIG. 12A and FIG. 12B. Plasmid-like viral vectors for gene delivery that embody the novel insulators derived from herpesvirus; titled Insulated Viral Artificial Chromosome (IVAC). FIG. 12A. pIVAC__1.0 vector contains the disclosed novel insulators surrounding neuronal-specific Latency-Associated Promoter 1 (LAP1) promoter and Long Term Expression (LTE) enhancer components, LacZ reporter gene, SV40 PolyA signal for transcription termination, insulator B4 which may contain sequence required for herpesvirus packaging into virion particles, ampicillin resistance gene for selection of the vector within bacterial cells, and the ColE1 origin of replication for high-copy number replication of the vector within *E. coli*. FIG. 12B. pIVAC__1.1 vector represents an extension of pIVAC__1.0 by including all identified insulator sequences from HSV-1 to form a compound insulated vector where several genes may be inserted between insulators and individually regulated within the context of one IVAC vector.

4.0 DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention provides genetic compositions and methods to facilitate sustained administration of one or more therapeutic agents in a regulatable fashion to selected cells and tissues within a mammal, including for example, the human central nervous system. These compositions also prolong general mammalian gene expression, and provide methods for generating animal models of human disease.

The present invention relates to a eukaryotic/mammalian gene expression cassette. Due to novel insulator/boundary elements, the expression cassette can be used for directing permanent regulatable expression of heterologous genes in eukaryotic cells. As such it could be applied to viral vectors for gene delivery, direct gene therapy, transgenic animals, and the development of animal disease models.

Key elements of this invention are derived from Herpes Simplex Virus Type 1 (HSV-1). Herpesviruses possess a unique neurotropic lifestyle characterized by their ability to remain latent in neurons for the lifetime of the infected host cell. The herpes simplex virus type I is an example of the Alphaherpesvirus subfamily that has evolved a unique lifestyle that permits lytic infection in some cell types and the establishment of latency within neurons. Throughout latency, the circularized genome is maintained as a stable nucleosomal episome. Unlike lytic phase transcription, the latent phase transcriptional profile is characterized by the expression of one transcript, the latency-associated transcript (LAT), while the remainder of the genome remains largely transcriptionally silent.

The LAT locus maps to two inverted long repeat units that compose <12% of the total genome. Although this represents an overall small investment in genetic information, it is clear that the LAT locus represents an evolutionarily crucial adaptation required for the viral life-cycle. Aside from LAT, several key immediate-early genes that promote lytic phase transcription also map within this region, although they remain transcriptionally repressed during latency. This extraordinary ability of the LAT locus to escape transcriptional repression suggested that this locus was transcriptionally-privileged and insulated from the repressive effects of the surrounding genome despite its proximity to repressed lytic-phase genes. It has been recently demonstrated that the basis of this region's ability to escape transcriptional repression is at the level of chromatin structure. This unique characteristic further suggested that with suitable development, components of this region may be exploited in the construction of expression cassette(s) that are capable of facilitating persistent/permanent regulatable gene expression. With modification, these novel insulator/boundary elements provide a useful tool for the development of transgenic animals devoid of PEV in addition to the development of constructs for gene therapy, vaccine production, and methods of assaying for gene function.

4.1 Epigenetic Regulation of HSV-1 Latent Gene Expression

HSV-1 latency in sensory neurons is characterized by abundant expression from only one region of the genome: that encoding the HSV-1 latency associated transcript (LAT). The mechanism by which lytic gene expression is repressed is unknown, but the fact that when cellular promoters are placed in the context of the HSV-1 genome are also rapidly silenced as the virus goes latent suggests a global and epigenetic mechanism is involved. It has been previously demonstrated that H3 histones associated with HSV-1 lytic gene promoters are hypoacetylated, whereas ones associated with the LAT promoter/enhancer region are hyperacetylated during latency. This demonstrates the HSV-1 genome is ordered into different chromatin domains and suggests that insulator elements, such as those that organize cellular chromatin exist the HSV-1 genome to act as boundaries separating transcriptionally non-permissive chromatin from active chromatin domains. In support of this hypothesis, several clusters of tandemly repeated binding motifs have been identified for the cellular insulator protein CTCF, and their placement in the HSV-1 genome is consistent with chromatin boundary locations. CTCF-containing insulators have been shown to act as boundary elements, enhancer-blockers as well as silencers. Data have shown that at least one of these elements (which has been termed B2) that separate the LAT enhancer from the ICP0 region possesses enhancer-blocking activity.

4.2 HSV-1 Latency

Herpes simplex virus type 1 (HSV-1) typically initiates infection of the host on epithelial surfaces of the face where the virus replicates locally and spreads to the sensory ganglia of the peripheral nervous system, such as the trigeminal ganglion (TG). While the virus replicates productively in some neurons of the sensory ganglia, in others it establishes a lifelong-latent infection. Periodically, in response to various forms of physiological stress, the virus reactivates and spreads back to the epithelial surface near the site of the original infection, using the nerve axons for transport. While reactivation may occur relatively frequently, it is usually subclinical, and only a small percent of the total latent population reactivates at any one time.

4.3 HSV-1 Latent Transcription

A hallmark of the HSV-1 latent infection of sensory neurons is that only one region of the viral genome is actively and abundantly transcribed, the region encoding the latency associated transcript or LAT. The LAT is an 8.3-8.5 kb poly A RNA that is spliced to yield a 2.0-kb and 1.5-kb intron. Because the intron does not de-branch properly, it is maintained as a stable lariat and has a half-life of over 24 hours. It is this stable intron (also referred to as the major LAT) that was first detected abundantly accumulating in the nuclei of latent neurons, and has been used as a marker for HSV-1 latency. The LAT promoter (LAP1) is transcriptionally complex, and contains elements that resemble cellular promoters more so than other viral lytic promoters. Nonetheless, it has been shown that a downstream enhancer (LTE) is required for full activity of LAP1 as well as for continued expression during latency. While the precise function of the LAT RNA is unknown, deletions of either the LAP1 or the LTE result in a reduced ability to reactivate. In addition, other LAT deletions have been shown to reduce the efficiency of establishment of latency, and be involved in neuronal protection and apoptosis.

While LAT is abundantly transcribed during latency, HSV-1 Ilytic gene expression is repressed. The basis for this repression is unknown. It has been proposed that the lack of activation of the HSV-1 immediate early genes IE genes is due to the fact that certain neurons possess low levels of the cellular transcription factor Oct 1, and this low level of abundance is responsible for the failure to initiate the lytic cascade. However, this doesn't explain how leaky IE gene activity would be repressed, or more importantly why heterologous cellular promoters that are placed in the context of the HSV-1 genome are rapidly silenced. Instead, these observations suggest that a more global and dynamic mechanism is involved in silencing HSV-1 lytic genes during latency. The gradual and global nature of the silencing of HSV-1 lytic genes and transgenes suggested that an epigenetic mechanism such as DNA methylation or histone modifications might play a role in suppressing transcription. Analyses of latent HSV-1 genomes have demonstrated that specific histone modifications (and not DNA methylation) correlate with transcriptional activity of the viral genome during latency. This suggests that histone modifications may play a similar role in regulating HSV-1 latent transcription epigenetically, as they do in regulating transcriptional activity of cellular chromatin.

4.4 Specific Histone Modifications Correlate with Transcriptional Permissiveness Patterns of specific histone modifications have been shown to act as epigenetic markers of eukaryotic gene expression. Specific combinations of acetylation, methylation, phosphorylation and ubiquitination of residues of the N-terminal tails of histones, especially H3 and H4, are associated with differences in transcriptional permissivity has been termed the "histone code". For example, transcriptionally active euchromatin is typically rich in histone H3 acetylated at lysines 9 and 14 (acetyl H3 K9, K14), whereas transcriptionally repressed heterochromatin is typically enriched in histone H3 methylated at the lysine 9 position (H3 K9 trimethyl). These epigenetic markers not only act as markers of the "transcriptional history" of a particular segment of chromatin, but in many cases also recruit cellular enzymes such as Pol II or other chromatin modifying enzymes.

The study of which specific histones are associated with a particular gene or promoter has been greatly facilitated by the availability of specific antisera against individual histone modifications. These antisera are used in chromatin immunoprecipitation assays (ChIP) where the histones are cross-linked to the DNA with formaldehyde, the DNA sonicated into 500-1000 bp fragments, followed by immunoprecipitation with the specific antiserum. The regions of DNA that are associated with the particular histone are identified by PCR, where the precipitated (enriched) chromatin is compared with the input or unbound fraction. By using PCR primers to compare different regions of a chromosome, one can generate a profile of the changes in transcriptional permissiveness as a function of specific histones that are bound.

4.5 Cellular Chromosomes are Organized into Chromatin Domains: Regions of Differing Transcriptional Permissiveness It has long been known that certain regions of cellular chromosomes tended to contain transcriptionally active genes, whereas others (such as the centromeres) were transcriptionally silent. ChIP analyses have expanded this view to provide a higher resolution picture of genes clusters that are transcriptionally permissive. As might be expected, the histone composition of clusters of housekeeping genes is similar amongst different cell and tissue types. On the other hand, developmentally regulated genes and genes that confer cell-specific functions are often clustered, and these cell-type specific transcription domains often possess dramatically different histone profiles. These observations have led to the development of models whereby chromatin is organized into domains based largely on function and transcriptional activity. The identification of regulatory regions flanking many of these domains has shown these regions specifically recruit histone-modifying enzymes that permit the establishment and maintenance of transcriptionally active or transcriptionally repressive histone modifications. Insulators are a class of these cis-acting factors that have been shown to regulate the establishment of chromatin domains.

4.6 Role of Insulators Boundaries, Enhancers and Silencers in Maintaining the Integrity of Transcriptional Domains Chromatin domains are regions of chromatin with similar transcriptional permissivity and that contain similar types of modified histones. Insulators are a general class of cis-acting elements at the boundary of a transcriptional domain that partition the domain from surrounding chromatin regions. Transcriptionally active chromatin domains often contain an en hancer that promotes a transcriptionally active state within that chromatin domain. In contrast, a transcriptionally silent chromatin domain may contain a silencer element, which promotes the formation of transcriptionally repressive heterchromatin within that domain. Insulator elements that flank transcriptionally distinct chromatin domains must effectively insulate one domain from the effects of the enhancer or silencer located in the other.

There are actually several different sub-types of chromatin insulators that are defined based on differences in their functional properties. A boundary or barrier insulator is one that acts to separate one distinct region of chromatin from another. For example a boundary might separate a region of heterochromatin enriched in H3 K9 Me, from a region enriched in H3 (K9 K14) Ac. An insulator can also have enhancer-blocking activity, and prevent enhancing activity from acting upstream of the insulator. In an analogous manner, insulators with barrier activity can block the effect of a silencer, and prevent the spread of heterochromatin from going beyond the barrier element. An important point is that typically, enhancer-blocking and barrier activities of an insulator are polar, and only work in one direction. In addition, an enhancer blocker is specific for blocking the effects of an enhancer, but may not necessarily block the effects of a silencer. Clearly it has been shown that insulator elements act not only to segregate regions of differing chromatin composition, but have also been shown to play a dynamic role in the formation of the chromatin environment on either side of the boundary. This process is mediated by the recruitment of chromatin modifying enzymes, such as histone methyltransferases, histone deacetylases, and histone acetylatransferases. Insulator regions of the genome therefore can be thought of as nucleation sites for the formation of multi-protein complexes that confer different activities and functions based upon their protein composition.

4.7 Role of the Cellular Insulator Protein CTCF in Forming Chromatin Boundaries All known vertebrate insulators that have been characterized to date bind "CCCTC-binding factor" or CTCF. CTCF is an eleven-zinc finger-containing DNA-binding protein that is highly conserved among vertebrates. CTCF is ubiquitously expressed in most cell types and possesses transcriptional activator activity that is regulated by phosphorylation. In addition to "CCCTC", it also binds to several other penta-nucleotide motifs. While a single DNA binding motif has been shown to be sufficient for binding, the binding motifs are often present as clusters of these consensus sequences and the binding to multiple CTCF motif sites affords higher binding affinity. While CTCF binding results in a number of distinct activities, including gene activation and repression, its function in the formation and regulation of chromatin insulators is mediated through interactions with other chromatin-modifying proteins. CTCF has also been proposed to be an essential scaffolding component of chromatin boundaries that may help promote the formations of chromatin loops that attach to specific regions of the nuclear lamina and that segregate chromatin into spatially-separated chromatin domains.

4.8 The LAT Promoter (LAP1) is the Only HSV-1 Promoter Active During Latency The LAT promoter (LAP1) has been shown to be able to drive the expression of a heterologous transgene in mouse sensory ganglia neurons after lytic gene expression had subsided. The LAP1 is arguably one of the most transcriptionally-complex promoters in the HSV-1 genome and contains a number of binding sites for cellular transcription factors including CRE, USF and SP1. Deletion of the core LAP1 promoter elements (202-bp PstI fragment) results in abolishing all detectable LAT expression by in situ hybridization, and >1000-fold reduction in detectable RNA by RT-PCR analysis. In addition, several regions have been that contain elements essential for neuron-specific expression. An additional promoter (LAP2) located downstream of LAP1 has been shown to have some activity during the lytic phase of infection, but not during the latent infection.

While the LAP1 promoter is active during latency, lytic gene promoters fail to drive detectable transgene expression during latency, and lytic gene RNA is below the level of detection in many studies employing Northern blot or RT-PCR analyses. While assessment of RNA levels using very sensitive RT-PCR of latently infected ganglia has detected very low amounts of some viral genes such as tk and ICP4, a recent study argued that these RNAs are likely due to an occasional "spontaneous" reactivating neuron, an event that apparently occurs more frequently than was originally thought. These studies have demonstrated that the LAT is the only abundantly transcribed RNA during HSV-1 latency, and that LAP1 directs its expression in a neuron-specific manner.

4.9 Promoters of HSV-1 Lytic Genes are Rapidly Silenced as the Virus Enters Latency Numerous studies have demonstrated that HSV-1 lytic genes are silenced as the virus enters latency. Following infection of mice by the footpad (f.p.) route, the virus replicates locally in the epithelium to the foot, and then spreads to the dorsal root ganglia (DRG), where acute replication peaks at day 4 (at an inoculum of $5\times10^3$ pfu/mouse). By 14 days p.i., infectious virus and lytic gene expression are below the normal limits of detection (<1000 copies of RNA per mouse), whereas LAT RNA is abundant (>100,000 copies per mouse). Viral recombinants containing lacZ as a reporter have also demonstrated that lytic gene promoters such as dUTPase fail to drive detectable reporter gene expression after day 10. Most importantly, it was shown that cellular promoters such as the mouse phosphoglycerate kinase (PGK) promoter and the metallothionine promoter are rapidly silenced as the virus enters latency. The fact that these cellular promoters contain binding sites for cellular transcription factors, and that they are functional in the context of transgenic mice (as well as from the HSV-1 genome during a lytic infection) suggests that there is a global silencing of viral lytic gene regions that occurs as the virus enters latency.

4.10 The Repression of Lytic Genes During Latency is Associated with Specific Histone Modifications and not with DNA Methylation During HSV-1 latency, gene expression is tightly repressed except for the latency-associated transcript (LAT). The mechanistic basis for this repression is unclear, but its global nature suggests regulation by an epigenetic mechanism such as DNA methylation. Previous work demonstrated that latent HSV-1 genomes are not extensively methylated but these studies lacked the resolution to examine methylation of individual CpGs that could repress transcription from individual promoters during latency. To address this point, established models were employed to predict genomic regions with the highest probability of being methylated and using bisulfite sequencing analyzed the methylation profiles of these regions. No significant methylation of latent DNA isolated from mouse dorsal root ganglia was observed in any of the regions examined, including the ICP4 and LAT promoters. This analysis indicates methylation is unlikely to play a major role in regulating HSV-1 latent gene expression.

Chromatin immunoprecipitation (ChIP) analysis of latently infected mouse DRG involves cross-linking of the histones to the total cellular DNA, followed by sonication to randomly shear the DNA into 500-1000 bp fragments. These fragments are then precipitated with antisera specific for a particular histone modification (such as acetyl H3 K9, K14) and the bound vs. unbound fractions are analyzed by PCR directed at specific regions of the viral genome to assess for relative levels of that histone that are associated with each region. ChIP of the latent HSV-1 DNA repeat regions demonstrated a portion of the LAT region is associated with histone H3 acetylated at lysine 9 and 14, consistent with a euchromatic and non-repressed structure. In contrast, the chromatin associated with the HSV-1 DNA polymerase gene located in the unique long segment was not enriched in H3 acetylated at lysine 9 and 14 suggesting a transcriptionally inactive structure. These data suggest histone composition may be a major regulatory determinant of HSV latent gene expression.

Studies directed at establishing stable, long-term transgene expression in the context of the HSV-1 latent genome revealed that the LAT promoter (LAP1), by itself, was not sufficient to maintain long-term expression in peripheral ganglia. While LAP1 resulted in expression of a longer duration than other heterologous promoters examined, expression persisted only for 3-4 weeks before being silenced. It has been demonstrated that expression could be extended by the inclusion of a region encompassing the 5' exon of LAT that acted as an enhancer for LAT promoter activity as well. This LAT enhancer (LTE) was demonstrated to act in both upstream and downstream positions. These data demonstrated that the LTE acts not only as an enhancer of the LAT promoter, but also acts to maintain long-term expression from this promoter during latency.

4.11 Functional Activity of the HSV-1 B2 Insulator Element

One of the functional characteristics of the insulator elements is the ability to isolate gene expression cassettes from the repressive effects of chromatin surrounding where the insulator cassette is inserted. To this end, several transient assay plasmids have been generated that have permitted the demonstration that the insulator element B2 has enhancer-blocking activity.

4.12 Characterization of HSV Insulator Elements

The HSV-1 insulator elements (depicted in FIG. 1 and FIG. 2) and now referred to as B1 and B2 are novel cis-acting elements capable of insulating the expression cassette and maintaining long-term sustained expression. These elements likely contain multiple binding sites for cellular factors that, in specific combination, confer this unique insulation property as well as their ability to function in a cell-type-specific manner. In order to characterize the component proteins that bind, the inventors have begun dissecting these elements. Reiterated motifs have been identified (referred to as CT-elements) that are contained in B1 and B2, and that contain reiterated binding sites for a cellular insulator protein CTCF. By chromatin immunoprecipitation assay it has been demonstrated that this protein binds to these elements on the latent HSV-1 genome. From these studies, CTCF appears to be an essential scaffolding protein for the B1 and B2 elements, however in itself, binding of this protein is insufficient to exert the key functional properties displayed by the B1 and B2 insulators. The enabling functional properties are likely contained in the regions surrounding the CT elements (FIG. 1 and FIG. 2). Yeast-one and yeast-two hybrid analyses have been employed to identify any other proteins which may be responsible for the activity of the elements. Based on initial analyses, the HSV-1 insulators appear to possess biologically-unique properties from cellular insulator elements that bind CTCF, and these properties are inherent in the unique sequence and combination of other proteins that bind to the HSV-1 insulator elements.

4.13 The HSV-1 Genome Contains Several other Potential Insulato Elements

Figure 10:
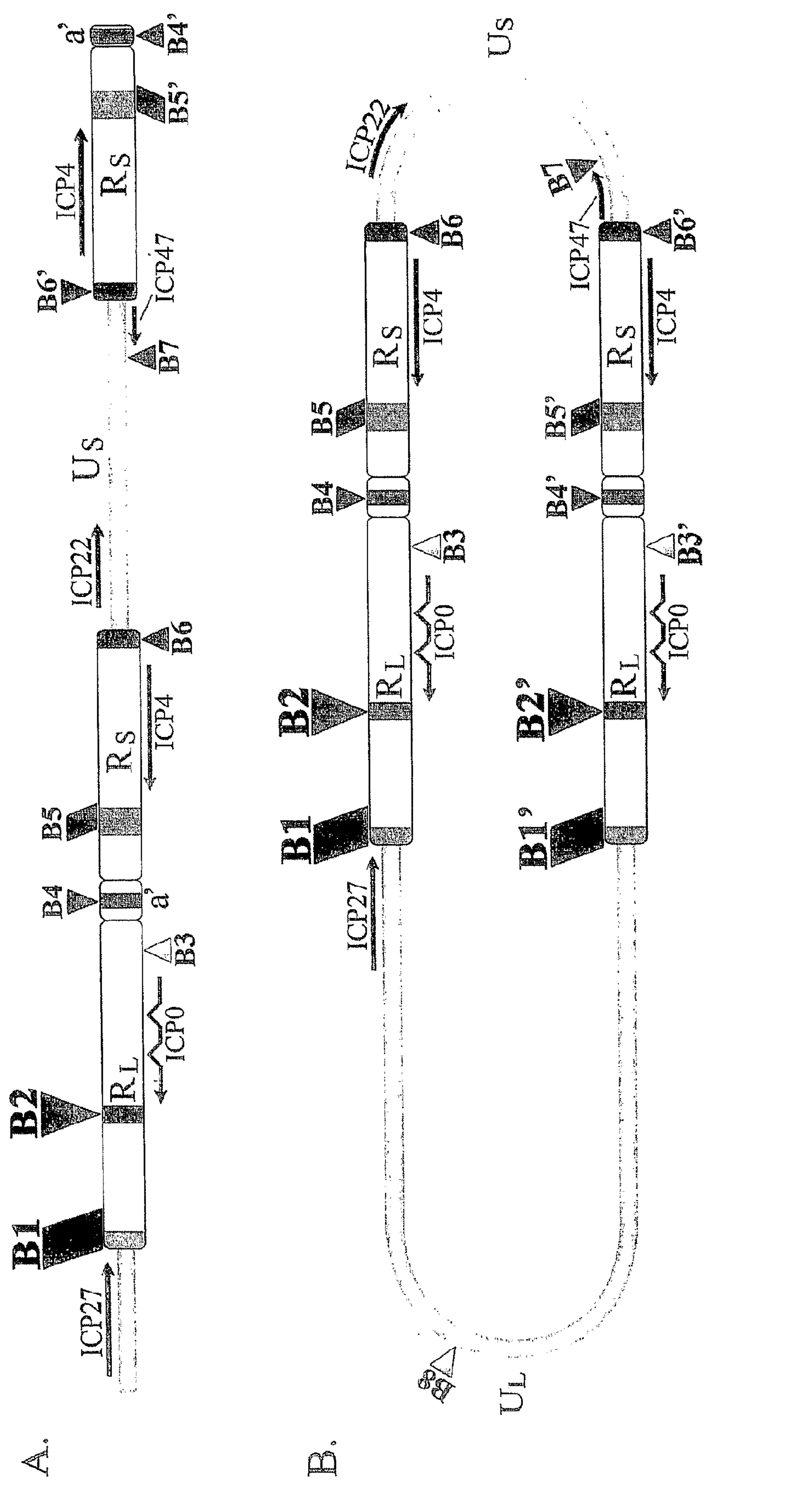

Using the CT elements as a basis, 5 other unique CT element clusters have been identified in the HSV-1 genome (FIG. 10). Based on their ability to bind CTCF, these other clusters of CT elements (B3-B7) appear to have the potential to act as a type of insulator, however they likely display different functional properties from B1 and B2. For example, in their native form they may not be able to insulate gene expression in a manner analogous to B1 and B2, however they may be modified to do so, or to display altered expression profiles for the expression cassette.

4.14 Other Herpesviruses Genomes Also Contain B1 and B2 Homologs

Analyses have been performed on a number of other alphaherpesviruses (for which complete genomic sequence is available, and from these studies, similar clusters of CT elements have been identified which may also act as insulators analogous to those in HSV-1 (FIG. 11). It is likely that these elements (particularly those homologous to B1 and B2) may also be used as components of insulator cassettes. In addition, it is possible that these other herpesvirus elements could be used in conjunction with or in place of the B1 and B2 elements as they may naturally possess modified tropism properties that might be ideally suited to facilitate expression in certain cell or animal host types. Indeed the inventors contemplate that insulator elements may be identified and isolated among many different members of the Herpesvirus family. In addition to the alphaherpesviruses, betaherpesviruses and gammaherpesviruses may also represent important sources for obtaining the insulator elements disclosed in the present invention.

4.15 Uses of HSV-1 Insulator Cassettes in Gutted HSV Vectors

FIG. 12A and FIG. 12B show schematics for a specific example of the use of the HSV-1 insulator cassette in the context of an HSV-1 vector. This is a "gutted" HSV-1 vector, deleted in HSV-1 essential genes (similar to an amplicon). A novel feature of the vector shown in FIG. 12A is that this vector (now termed Insulated Viral Artificial Chromosome or IVAC) contains insulators B1 and B2 bounding the expression cassette thereby enabling sustained long-term expression. This herpes-based example is just one possible implementation of the technology in the context of viral (IVAC) vectors.

4.16 Gene Therapy Vectors

The field of gene therapy offers a promising therapeutic strategy for the treatment of a wide variety of human diseases of the central nervous system including Alzheimer's, Parkinson's, Huntington's Diseases and Fragile-X Mental Retardation Syndrome as examples. Many chronic and progressive diseases require sustained or regulatable administration of the therapeutic gene to achieve successful treatment. Unfortunately, progress via conventional gene therapy has been slow as a result of transgene down-regulation due to host cell silencing mechanisms. These mechanisms include, but are not limited to, histone methylation/deacetylation, DNA methylation, position effects, or transgene copy number. This has limited the usefulness of current gene therapy vector technology for developing treatments for chronic and progressive genetic disorders. This invention addresses this problem by providing a novel set of control elements that permit a gene expression cassette to be insulated from the effects of surrounding DNA, and possesses structural features that maintain a transcriptionally accessible and regulatable environment for the expression of transgenes in a number of viral and cellular systems.

In illustrative embodiments, Herpes Simplex Virus type 1 vectors may be utilized to deliver the gene expression cassettes, because they have many advantages when considering gene delivery vectors. These include the ability to package large DNA insertions. In addition, HSV-I is neurotropic and establishes life-long infection in neurons in which the genome is maintained as a stable episome. Moreover, HSV-1 maintains the ability to infect and replicate within a wide range of human cell lines with high efficiencies.

4.17 Production of Transgenic Animals

Animal models of human disease are often an invaluable asset for use in biomedical research. However, generating transgenic or knock-out animals to accurately model human disease is no trivial task. The insulated nature of the gene expression cassette provides a way to circumvent problems, such as embryonic lethals, associated with generating these animals. For example, current methods may use cre-lox systems to get past embryonic lethal animals, but the gene will be knocked out in all cells. Perhaps there are alternative uses for a particular gene product in various cells. The gene expression cassettes provided by the present invention represent a new and reliable method for gene knock-out within the subset of cells corresponding directly to the cell-type specific boundary and insulation effects of the cassette. Regardless, the ability to maintain the expression cassette in an accessible and transcriptionally-responsive conformation provides the opportunity to regulate gene expression at desired times in development. In addition, the genetic expression elements of the present invention may also be applied to the production of transgenic animals that are to be used for the production of large amounts of a transgene for pharmacologic or agricultural purposes.

It is contemplated that in some instances the genome of a transgenic non-human animal of the present invention will have been altered through the stable introduction of one or more of the genetic expression elements described herein, either native, synthetically modified, or mutated. In particular, such genetic expression elements may be provided to cells of such animals using viral vectors, such as, for example, HSV, lentiviral, retroviral, AV, or rAAV vectors. As used herein, the term "transgenic animal" is intended to refer to an animal that has incorporated exogenous DNA sequences into its genome. In designing a heterologous gene for expression in animals, sequences which interfere with the efficacy of gene expression, such as polyadenylation signals, polymerase II termination sequences, hairpins, consensus splice sites and the like are eliminated. Current advances in transgenic approaches and techniques have permitted the manipulation of a variety of animal genomes via gene addition, gene deletion, or gene modifications (Franz et al., 1997). For example, mosquitoes (Fallon, 1996), trout (Ono et al., 1997), zebrafish (Caldovic and Hackett, 1995), pigs (Van Cott et al., 1997) and cows (Haskell and Bowen, 1995), are just a few of the many animals being studied by transgenics. The creation of transgenic animals that express human proteins such as α-1-antitrypsin, in sheep (Carver et al., 1993); decay accelerating factor, in pigs (Cozzi et al., 1997), and plasminogen activator, in goats (Ebert et al., 1991) has previously been demonstrated. The transgenic synthesis of human hemoglobin (U.S. Pat. No. 5,602,306) and fibrinogen (U.S. Pat. No. 5,639,940) in non-human animals have also been disclosed, each specifically incorporated herein by reference in its entirety. Further, transgenic mice and rat models have recently been described as new directions to study and treat cardiovascular diseases such as hypertension in humans (Franz et al., 1997; Pinto-Siestma and Paul, 1997). The construction of a transgenic mouse model has recently been used to assay potential treatments for Alzheimer's disease (U.S. Pat. No. 5,720,936, specifically incorporated herein by reference in its entirety). It is contemplated in the present invention that transgenic animals contribute valuable information as models for studying the effects of viral vector-delivered therapeutic compositions on correcting genetic defects and treating a variety of disorders in an animal.

4.18 Adeno-Associated Virus

Adeno-associated virus is a single-stranded DNA-containing, non-pathogenic human parvovirus that is being widely investigated as a therapeutic vector for a host of muscle disorders (Muzyczka, 1992; Kessler et al., 1996; Clark et al., 1997; Fisher et al., 1997). Six serotypes of the virus (AAV1-6) were originally described, and two more have recently been identified in rhesus macaques (Gao et al., 2002). Recombinant adeno-associated virus (rAAV) vectors have been developed in which the rep and cap open reading frames of the wild-type virus have been completely replaced by a therapeutic or reporter gene, retaining only the characteristic inverted terminal repeats (ITRs), the sole cis-acting elements required for virus packaging. Using helper plasmids expressing various combinations of the AAV2 rep and AAV1, 2, and 5 cap genes, respectively, efficient cross-packaging of AAV2 genomes into particles containing the AAV1, 2, or 5 capsid protein has been demonstrated (Grimm et al., 2003; Xiao et al., 1999; Zolotukhin et al., 2002; Rabinowitz et al., 2002). The various serotype vectors have demonstrated distinct tropisms for different tissue types in vivo, due in part to their putative cell surface receptors. Although several reports have indicated that rAAV1 vectors efficiently transduce skeletal muscle in general (Fraites et al., 2002; Chao et al., 2001; Hauck and Xiao, 2003), no study to date has reported which of the serotypes, if any, might transduce the diaphragm in particular.

4.19 Promoters and Enhancers

Recombinant vectors form important aspects of the present invention. The term "expression vector or construct" means any type of genetic construct containing a nucleic acid in which part or all of the nucleic acid encoding sequence is capable of being transcribed. In preferred embodiments, expression only includes transcription of the nucleic acid, for example, to generate a therapeutic agent from a transcribed gene that is comprised within one or more of the insulated HSV-derived gene expression cassettes disclosed herein.

Particularly useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively linked," "operably linked," "operatively positioned," "under the control of" or "under the transcriptional control of" means that the promoter is in the correct location and orientation in relation to the nucleic acid segment that comprises the therapeutic gene to properly facilitate, control, or regulate RNA polymerase initiation and expression of the therapeutic gene to produce the therapeutic peptide, polypeptide, ribozyme, or antisense RNA molecule in the cells that comprise and express the genetic construct.

In preferred embodiments, it is contemplated that certain advantages will be gained by positioning the therapeutic agent-encoding polynucleotide segment under the control of one or more recombinant, or heterologous, promoter(s). As used herein, a recombinant or heterologous promoter is intended to refer to a promoter that is not normally associated with the particular therapeutic gene of interest in its natural environment. Such promoters may include promoters normally associated with other genes, and/or promoters isolated from any other bacterial, viral, eukaryotic, or mammalian cell.

Naturally, it will be important to employ a promoter that effectively directs the expression of the therapeutic agent-encoding nucleic acid segment in the cell type, organism, or even animal, chosen for expression. The use of promoter and cell type combinations for protein expression is generally known to those of skill in the art of molecular biology, for example, see Sambrook et al. (1989), incorporated herein by reference. The promoters employed may be constitutive, or inducible, and can be used under the appropriate conditions to direct high-level expression of the introduced DNA segment.

At least one module in a promoter functions to position the start site for RNA synthesis. The best-known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter, such as a β-actin, AAV, AV, CMV or HSV promoter. In certain aspects of the invention, inducible promoters, such as tetracycline-controlled promoters, are also contemplated to be useful in certain cell types.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters that are well known in the art to achieve expression of a transgene is contemplated as well, provided that the levels of expression are sufficient for a given purpose. Tables 1 and 2 below list several elements/promoters that may be employed, in the context of the present invention, to regulate the expression of the therapeutic agents that are comprised within the disclosed insulated HSV-derived gene expression constructs. This list is not intended to be exhaustive of all the possible elements involved in the promotion of transgene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 1

PROMOTER AND ENHANCER ELEMENTS

| PROMOTER/ENHANCER | REFERENCES |
|---|---|
| Immunoglobulin Heavy Chain | Banerji et al., 1983; Gilles et al., 1983; Grosschedl and Baltimore, 1985; Atchinson and Perry, 1986, 1987; Imler et al., 1987; Weinberger et al., 1984; Kiledjian et al., 1988; Porton et al.; 1990 |
| Immunoglobulin Light Chain | Queen and Baltimore, 1983; Picard and Schaffner, 1984 |
| T-Cell Receptor | Luria et al., 1987; Winoto and Baltimore, 1989; Redondo et al.; 1990 |
| HLA DQ a and DQ β | Sullivan and Peterlin, 1987 |
| β-Interferon | Goodbourn et al., 1986; Fujita et al., 1987; Goodbourn and Maniatis, 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al; 1989 |
| Muscle Creatine Kinase | Jaynes et al., 1988; Horlick and Benfield, 1989; Johnson et al., 1989 |
| Prealbumin (Transthyretin) | Costa et al., 1988 |
| Elastase I | Orntz et al., 1987 |
| Metallothionein | Karin et al., 1987; Culotta and Hamer, 1989 |
| Collagenase | Pinkert et al., 1987; Angel et al., 1987a |
| Albumin Gene | Pinkert et al., 1987; Tronche et al., 1989, 1990 |
| α-Fetoprotein | Godbout et al., 1988; Campere and Tilghman, 1989 |
| t-Globin | Bodine and Ley, 1987; Perez-Stable and Constantini, 1990 |
| β-Globin | Trudel and Constantini, 1987 |
| e-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $^{\alpha}$1-Antitrypain | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |

TABLE 1-continued

| PROMOTER AND ENHANCER ELEMENTS | |
|---|---|
| PROMOTER/ENHANCER | REFERENCES |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987; Schaffner et al., 1988 |
| Polyoma | Swartzendruber and Lehman, 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and Villarreal, 1988 |
| Retroviruses | Kriegler and Botchan, 1982, 1983; Levinson et al., 1982; Kriegler et al., 1983, 1984a, b, 1988; Bosze et al., 1986; Miksicek et al., 1986; Celander and Haseltine, 1987; Thiesen et al., 1988; Celander et al., 1988; Choi et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987; Stephens and Hentschel, 1987 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |
| Human Immunodeficiency Virus | Muesing et al., 1987; Hauber and Cullan, 1988; Jakobovits et al., 1988; Feng and Holland, 1988; Takebe et al., 1988; Rosen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

TABLE 2

| INDUCIBLE ELEMENTS | | |
|---|---|---|
| ELEMENT | INDUCER | REFERENCES |
| MT II | Phorbol Ester (TFA)<br>Heavy metals | Palmiter et al., 1982; Haslinger and Karin, 1985; Searle et al., 1985; Stuart et al., 1985; Imagawa et al., 1987, Karin et al, 1987; Angel et al, 1987b; McNeall et al., 1989 |
| MMTV (mouse mammary tumor virus) | Glucocorticoids | Huang et al., 1981; Lee et al., 1981; Majors and Varmus, 1983; Chandler et al., 1983; Lee et al., 1984; Ponta et al., 1985; Sakai et al., 1988 |
| β-Interferon | poly(rI)x<br>poly(rc) | Tavernier et al., 1983 |
| Adenovirus 5 E2 | Ela | Imperiale and Nevins, 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al, 1989 |
| HSP70 | Ela, SV40 Large T Antigen | Taylor et al., 1989; Taylor and Kingston, 1990a, b |
| Proliferin | Phorbol Ester-TPA | Mordacq and Linzer, 1989 |
| Tumor Necrosis Factor | FMA | Hensel et al., 1989 |
| Thyroid Stimulating Hormone a Gene | Thyroid Hormone | Chatterjee et al., 1989 |

As used herein, the terms "engineered" and "recombinant" cells are intended to refer to a cell into which an exogenous nucleic acid segment, such as DNA segment that leads to the transcription of a therapeutic agent, such as a therapeutic peptide, polypeptide, ribozyme, antisense, or catalytic mRNA molecule has been introduced. Therefore, engineered cells are distinguishable from naturally occurring cells, which do not contain a recombinantly introduced exogenous polynucleotide segment. Engineered cells are thus cells having nucleic acid segment introduced through the hand of man.

To express a therapeutic gene in accordance with the present invention one would prepare an insulated HSV-derived gene expression vector that comprises at least a first sequence region that encodes a therapeutic peptide polypeptide ribozyme or antisense mRNA under the control of one or more promoters. To bring a sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded polypeptide. This is the meaning of "recombinant expression" in this context.

4.20 Pharmaceutical Compositions

In certain embodiments, the present invention concerns formulation of one or more of the insulated HSV-derived gene expression cassettes disclosed herein in pharmaceutically acceptable solutions for administration to a cell or an animal, either alone, or in combination with one or more other modalities of therapy. In particular, the present invention contemplates the formulation of one or more viral vectors, virions, or virus particles (or pluralities thereof) that comprise one or more of the disclosed insulated HSV-derived gene expression cassettes.

In such pharmaceutical compositions, it will also be understood that, if desired, the encoded nucleic acid segment, RNA, DNA or PNA compositions that express one or more therapeutic gene product(s) as disclosed herein may be administered in combination with other agents as well, such as, e.g., peptides, proteins or polypeptides or various pharmaceutically-active agents, including one or more systemic or topical administrations of viral vector formulations described herein. In fact, there is virtually no limit to other components that may also be included, given that the additional agents do not cause a significant adverse effect upon contact with the target cells or host tissues. The viral vector compositions may thus be delivered along with various other agents as required in the particular instance. Such compositions may be purified from host cells or other biological sources, or alternatively may be chemically synthesized as described herein. Likewise, such compositions may further comprise substituted or derivatized RNA, DNA, or PNA compositions.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, topical, sublingual, subcutaneous, transdermal, parenteral, intravenous, intranasal, and intramuscular administration and formulation.

In certain circumstances it will be desirable to deliver the pharmaceutical compositions disclosed herein parenterally, intravenously, intramuscularly, or even intraperitoneally as described in U.S. Pat. No. 5,543,158; U.S. Pat. No. 5,641,515 and U.S. Pat. No. 5,399,363 (each specifically incorporated herein by reference in its entirety). Solutions of the active compounds as freebase or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a mammal, and in particular, when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified. In certain embodiments, the compositions of the present invention may be formulated for topical, or transdermal delivery to one or more tissue sites or cell types within the body of the vertebrate being treated. Alternatively, in the embodiments where ex vivo or ex situ modalities are preferred, the compositions of the invention my be used externally from the body of the intended recipient by first contacting a cell suspension or a tissue sample, or other extracorporeal composition with the compositions to facilitate transfer of the viral vectors into the cells or tissues in ex vivo fashion. Following suitable transfection, then, such cells or tissues could be reintroduced into the body of the animal being treated.

4.21 Liposome-, Nanocapsule-, and Microparticle-Mediated Delivery

In certain embodiments, the genetic constructs of the present invention, and/or the virus particles or virions comprising them may further comprise one or more liposomes, nanocapsules, microparticles, microspheres, lipid particles, vesicles, and the like, for enhancing, facilitating, or increasing the effectiveness of introducing the gene therapy constructs of the present invention into suitable host cells, tissues, or organs. In particular, the addition of a lipid particle, a liposome, a vesicle, a nanosphere, or a nanoparticle or the like to the compositions of the invention may serve to enhance or facilitate the delivery of the vectors, virions, or virus particles into the target cells or tissues.

Such formulations may be preferred for the introduction of pharmaceutically acceptable formulations of the nucleic acids or the gene expression cassettes and viral vector constructs disclosed herein. The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-times (Gabizon and Papahadjopoulos, 1988; Allen and Choun, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally resistant to transfection by other procedures including T cell suspensions, primary hepatocyte cultures and PC 12 cells (Renneisen et al., 1990; Muller et al., 1990). In addition, liposomes are free of the DNA length constraints that are typical of viral-based delivery systems. Liposomes have been used effectively to introduce genes, drugs (Heath and Martin, 1986; Heath et al., 1986; Balazsovits et al., 1989; Fresta and Puglisi, 1996), radiotherapeutic agents (Pikul et al., 1987), enzymes (Imaizumi et al., 1990a; Imaizumi et al., 1990b), viruses (Faller and Baltimore, 1984), transcription factors and allosteric effectors (Nicolau and Gersonde, 1979) into a variety of cultured cell lines and animals. In addition, several successful clinical trails examining the effectiveness of liposome-mediated drug delivery have been completed (Lopez-Berestein et al., 1985a; 1985b; Coune, 1988; Sculier et al., 1988). Furthermore, several studies suggest that the use of liposomes is not associated with autoimmune responses, toxicity or gonadal localization after systemic delivery (Mori and Fukatsu, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1980), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins, such as cytochrome c, bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity, and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow, and lymphoid organs.

Alternatively, the invention provides for pharmaceutically acceptable nanocapsule formulations of the compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention. Such particles may be are easily made, as described (Couvreur et al., 1980; Couvreur, 1988; zur Muhlen et al., 1998; Zambaux et al. 1998; Pinto-Alphandry et al., 1995 and U.S. Pat. No. 5,145,684, specifically incorporated herein by reference in its entirety).

4.22 Therapeutic and Diagnostic Kits

The invention also encompasses one or more polynucleotide compositions together with one or more pharmaceutically-acceptable excipients, carriers, diluents, adjuvants, and/or other components, as may be employed in the formulation of particular viral vector formulations, and in the preparation of therapeutic agents for administration to a mammal, and in particularly, to a human, for one or more of the indications described herein for which viral vector-based gene therapy provides an alternative to current treatment modalities. In particular, such kits may comprise one or more viral vector compositions that comprise at least a first gene expression cassette in combination with instructions for using the viral vector in the treatment of such disorders in a mammal, and may typically further include containers prepared for convenient commercial packaging.

As such, preferred animals for administration of the pharmaceutical compositions disclosed herein include mammals, and particularly humans. Other preferred animals include murines, bovines, equines, porcines, canines, and felines. The composition may include partially or significantly purified gene expression cassette-comprising viral vector compositions, either alone, or in combination with one or more additional active ingredients, which may be obtained from natural or recombinant sources, or which may be obtainable naturally or either chemically synthesized, or alternatively produced in vitro from recombinant host cells expressing DNA segments encoding such additional active ingredients.

Therapeutic kits may also be prepared that comprise at least one of the compositions disclosed herein and instructions for using the composition as a therapeutic agent. The container means for such kits may typically comprise at least one vial, test tube, flask, bottle, syringe or other container means, into which the disclosed genetic composition(s) may be placed, and preferably suitably aliquoted. Where a second therapeutic composition is also provided, the kit may also contain a second distinct container means into which this second composition may be placed. Alternatively, the plurality of therapeutic compositions may be prepared in a single pharmaceutical composition, and may be packaged in a single container means, such as a vial, flask, syringe, bottle, or other suitable single container means. The kits of the present invention will also typically include a means for containing the vial(s) in close confinement for commercial sale, such as, e.g., injection or blow-molded plastic containers into which the desired vial(s) are retained.

4.23 Methods of Nucleic Acid Delivery and DNA Transfection

In certain embodiments, it is contemplated that one or more of the viral vector-delivered therapeutic product-encoding RNA, DNA, PNAs and/or substituted polynucleotide compositions disclosed herein will be used to transfect an appropriate host cell. Technology for introduction of viral vectors comprising one or more PNAs, RNAs, and DNAs into target host cells is well known to those of skill in the art.

Several non-viral methods for the transfer of expression constructs into cultured mammalian cells also are contemplated by the present invention for use in certain in vitro embodiments, and under conditions where the use of viral vector-mediated delivery is less desirable. These include calcium phosphate precipitation (Graham and Van Der Eb, 1973; Chen and Okayama, 1987; Rippe et al., 1990) DEAE-dextran (Gopal, 1985), electroporation (Wong and Neumann, 1982; Fromm et al., 1985; Tur-Kaspa et al., 1986; Potter et al., 1984; Suzuki et al., 1998; Vanbever et al., 1998), direct microinjection (Capecchi, 1980; Harland and Weintraub, 1985), DNA-loaded liposomes (Nicolau and Sene, 1982; Fraley et al, 1979; Takakura, 1998) and lipofectamine-DNA complexes, cell sonication (Fechheimer et al., 1987), gene bombardment using high velocity microprojectiles (Yang et al., 1990; Klein et al., 1992), and receptor-mediated transfection (Curiel et al., 1991; Wagner et al., 1992; Wu and Wu, 1987; Wu and Wu, 1988). Some of these techniques may be successfully adapted for in vivo or ex vivo use.

4.24 Expression in Animal Cells

The inventors contemplate that the expression cassettes of the present invention that comprise one or more contiguous nucleic acid sequences that encodes a therapeutic agent of the present invention may be utilized to treat one or more cellular defects in a host cell that comprises the vector. Such cells are preferably animal cells, including mammalian cells such as those obtained from a human or other primates, murine, canine, feline, ovine, caprine, bovine, equine, epine, or porcine species. In particular, the use of such constructs for the treatment and/or amelioration of disorders, dysfunctions, and diseases in a human subject suspected of suffering from such a condition is highly contemplated. The cells may be transformed with one or more viral vectors comprising one or more of the disclosed expression constructs, such that the encoded therapeutic agent is introduced into and expressed in the host cells of the animal is sufficient to alter, reduce, ameliorate or prevent the deleterious or disease conditions either in vitro and/or in vivo.

4.25 Site-Specific Mutagenesis

Site-specific mutagenesis is a technique useful in the preparation of individual peptides, or biologically functional equivalent polypeptides, through specific mutagenesis of the underlying polynucleotides that encode them. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or change the properties of the polynucleotide itself, and/or alter the properties, activity, composition, stability, or primary sequence of the encoded polypeptide.

In certain embodiments of the present invention, the inventors contemplate the mutagenesis of the disclosed genetic constructs to alter the activity or effectiveness of such constructs in increasing or altering their therapeutic activity, or to effect higher or more desirable introduction in a particular host cell or tissue. Likewise in certain embodiments, the inventors contemplate the mutagenesis of the therapeutic genes comprised in such viral vectors themselves, or of the viral vector delivery vehicle to facilitate improved regulation of the particular therapeutic construct's activity, solubility, stability, expression, or efficacy in vitro, in situ, and/or in vivo.

The techniques of site-specific mutagenesis are well known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation that result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing. Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

A number of template dependent processes are available to amplify the target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Another method for amplification is the ligase chain reaction (referred to as LCR), disclosed in Eur. Pat. Appl. Publ. No. 320,308 (specifically incorporated herein by reference in its entirety). In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in PCT Intl. Pat. Appl. Publ. No. PCT/US87/00880, incorporated herein by reference in its entirety, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[α-thio] triphosphates in one strand of a restriction site (Walker et al., 1992), may also be useful in the amplification of nucleic acids in the present invention.

Strand Displacement Amplification (SDA) is another method of carrying out isothermal amplification of nucleic acids that involves multiple rounds of strand displacement and synthesis, i.e. nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Sequences can also be detected using a cyclic probe reaction (CPR). In CPR, a probe having a 3' and 5' sequences of non-target DNA and an internal or "middle" sequence of the target protein specific RNA is hybridized to DNA which is present in a sample. Upon hybridization, the reaction is treated with RNaseH, and the products of the probe are identified as distinctive products by generating a signal that is released after digestion. The original template is annealed to another cycling probe and the reaction is repeated. Thus, CPR involves amplifying a signal generated by hybridization of a probe to a target gene specific expressed nucleic acid.

Still other amplification methods described in Great Britain Pat. Appl. No. 2 202 328, and in PCT Intl. Pat. Appl. Publ. No. PCT/US89/01025, each of which is incorporated herein by reference in its entirety, may be used in accordance with the present invention. In the former application, "modified" primers are used in a PCR-like, template and enzyme dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh et al., 1989; PCT Intl. Pat. Appl. Publ. No. WO 88/10315, incorporated herein by reference in its entirety), including nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer that has sequences specific to the target sequence. Following polymerization, DNA/RNA hybrids are digested with RNase H while double stranded DNA molecules are heat-denatured again. In either case the single stranded DNA is made fully double stranded by addition of second target-specific primer, followed by polymerization. The double stranded DNA molecules are then multiply transcribed by a polymerase such as T7 or SP6. In an isothermal cyclic reaction, the RNAs are reverse transcribed into DNA, and transcribed once again with a polymerase such as T7 or SP6. The resulting products, whether truncated or complete, indicate target-specific sequences.

Eur. Pat. Appl. Publ. No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of *E. coli* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Intl. Pat. Appl. Publ. No. WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "RACE" (Frohman, 1990), and "one-sided PCR" (Ohara et al., 1989) which are well-known to those of skill in the art.

Methods based on ligation of two (or more) oligonucleotides in the presence of nucleic acid having the sequence of the resulting "di-oligonucleotide", thereby amplifying the di-oligonucleotide (Wu and Dean, 1996, incorporated herein by reference in its entirety), may also be used in the amplification of DNA sequences of the present invention.

4.26 Biological Functional Equivalents

Modification and changes may be made in the structure of the gene expression cassettes, or to the viral vectors comprising them, as well as modification to the the therapeutic agents encoded by them and still obtain functional vectors, viral particles, and virion that encode one or more therapeutic agents with desirable characteristics. As mentioned above, it is often desirable to introduce one or more mutations into a specific polynucleotide sequence. In certain circumstances, the resulting encoded polypeptide sequence is altered by this mutation, or in other cases, the sequence of the polypeptide is unchanged by one or more mutations in the encoding polynucleotide.

When it is desirable to alter the amino acid sequence of a polypeptide to create an equivalent, or even an improved, second-generation molecule, the amino acid changes may be achieved by changing one or more of the codons of the encoding DNA sequence, according to Table 3.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

TABLE 3

| AMINO ACIDS | | | CODONS |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | AGC ACC ACG ACU |
| Valine | Val | V | GUA GUC GUG GUU |
| Tryptophan | Trp | W | UGG |
| Tyrosine | Tyr | Y | UAC UAU |

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

4.27 Ribozymes

In certain embodiments, aspects of the invention concerns the use of the genetic expression constructs and gene expression cassettes to deliver catalytic RNA molecules (ribozymes) to selected mammalian cells and tissues to effect a reduction or elimination of expression of one or more native DNA or mRNA molecules, so as to prevent or reduce the amount of the translation product of such mRNAs. Ribozymes are biological catalysts consisting of only RNA. They promote a variety of reactions involving RNA and DNA molecules including site-specific cleavage, ligation, polymerization, and phosphoryl exchange (Cech, 1989; Cech, 1990). Ribozymes fall into three broad classes: (1) RNAse P, (2) self-splicing introns, and (3) self-cleaving viral agents. Self-cleaving agents include hepatitis delta virus and components of plant virus satellite RNAs that sever the RNA genome as part of a rolling-circle mode of replication. Because of their small size and great specificity, ribozymes have the greatest potential for biotechnical applications. The ability of ribozymes to cleave other RNA molecules at specific sites in a catalytic manner has brought them into consideration as inhibitors of viral replication or of cell proliferation and gives them potential advantage over antisense RNA. Indeed, ribozymes have already been used to cleave viral targets and oncogene products in living cells (Koizumi et al., 1992; Kashani-Sabet et al., 1992; Taylor and Rossi, 1991; von-Weizsacker et al., 1992; Ojwang et al., 1992; Stephenson and Gibson, 1991; Yu et al., 1993; Xing and Whitton, 1993; Yu et al., 1995; Little and Lee, 1995).

Two kinds of ribozymes have been employed widely, hairpins and hammerheads. Both catalyze sequence-specific cleavage resulting in products with a 5N hydroxyl and a 2N,3N-cyclic phosphate. Hammerhead ribozymes have been used more commonly, because they impose few restrictions on the target site. Hairpin ribozymes are more stable and, consequently, function better than hammerheads at physiologic temperature and magnesium concentrations.

A number of patents have issued describing various ribozymes and methods for designing ribozymes. See, for example, U.S. Pat. Nos. 5,646,031; 5,646,020; 5,639,655; 5,093,246; 4,987,071; 5,116,742; and 5,037,746, each specifically incorporated herein by reference in its entirety. However, the ability of ribozymes to provide therapeutic benefit in vivo has not yet been demonstrated.

Although proteins traditionally have been used for catalysis of nucleic acids, another class; of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlatch et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 (specifically incorporated herein by reference) reports that certain ribozymes can act as endonucleases with a sequence-specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Six basic varieties of naturally occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. (1992). Examples of hairpin motifs are described by Hampel et al. (Eur. Pat. Appl. Publ. No. EP 0360257), Hampel and Tritz (1989), Hampel et al. (1990) and U.S. Pat. No. 5,631,359 (specifically incorporated herein by reference). An example of the hepatitis δ virus motif is described by Perrotta and Been (1992); an example of the RNaseP motif is described by Guerrier-Takada et al. (1983); Neurospora VS RNA ribozyme motif is described by Collins (Saville and Collins, 1990; Saville and Collins, 1991; Collins and Olive, 1993); and an example of the Group I intron is described in U.S. Pat. No. 4,987,071 (specifically incorporated herein by reference). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

In certain embodiments, it may be important to produce enzymatic cleaving agents that exhibit a high degree of specificity for the RNA of a desired target, such as one of the sequences disclosed herein. The enzymatic nucleic acid molecule is preferably targeted to a highly conserved sequence region of a target mRNA. Such enzymatic nucleic acid molecules can be delivered exogenously to specific cells as required, although in preferred embodiments the ribozymes are expressed from DNA or RNA vectors that are delivered to specific cells.

Small enzymatic nucleic acid motifs (e.g., of the hammerhead or the hairpin structure) may also be used for exogenous delivery. The simple structure of these molecules increases the ability of the enzymatic nucleic acid to invade targeted regions of the mRNA structure. Alternatively, catalytic RNA molecules can be expressed within cells from eukaryotic promoters (e.g., Scanlon et al., 1991; Kashani-Sabet et al., 1992; Dropulic et al., 1992; Weerasinghe et al., 1991; Ojwang et al., 1992; Chen et al., 1992; Sarver et al., 1990). Those skilled in the art realize that any ribozyme can be expressed in eukaryotic cells from the appropriate DNA vector. The activity of such ribozymes can be augmented by their release from the primary transcript by a second ribozyme (Int. Pat. Appl. Publ. No. WO 93/23569, and Int. Pat. Appl. Publ. No. WO 94/02595, both hereby incorporated by reference; Ohkawa et al., 1992; Taira et al., 1991; and Ventura et al., 1993).

Ribozymes may be added directly, or can be complexed with cationic lipids, lipid complexes, packaged within liposomes, or otherwise delivered to target cells. The RNA or RNA complexes can be locally administered to relevant tissues ex vivo, or in vivo through injection, aerosol inhalation, influsion pump or stent, with or without their incorporation in biopolymers.

Ribozymes may be designed as described in Int. Pat. Appl. Publ. No. WO 93/23569 and Int. Pat. Appl. Publ. No. WO 94/02595 (each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Hammerhead or hairpin ribozymes may be individually analyzed by computer folding (Jaeger et al., 1989) to assess whether the ribozyme sequences fold into the appropriate secondary structure, as described herein. Those ribozymes with unfavorable intramolecular interactions between the binding arms and the catalytic core are eliminated from consideration. Varying binding arm lengths can be chosen to optimize activity. Generally, at least 5 or so bases on each arm are able to bind to, or otherwise interact with, the target RNA.

Ribozymes of the hammerhead or hairpin motif may be designed to anneal to various sites in the mRNA message, and can be chemically synthesized. The method of synthesis used follows the procedure for normal RNA synthesis as described in Usman et al. (1987) and in Scaringe et al. (1990) and makes use of common nucleic acid protecting and coupling groups, such as dimethoxytrityl at the 5'-end, and phosphoramidites at the 3'-end. Average stepwise coupling yields are typically >98%. Hairpin ribozymes may be synthesized in two parts and annealed to reconstruct an active ribozyme (Chowrira and Burke, 1992). Ribozymes may be modified extensively to enhance stability by modification with nuclease resistant groups, for example, 2'-amino, 2'-C-allyl, 2'-flouro, 2'-o-methyl, 2'-H (for a review see e.g., Usman and Cedergren, 1992). Ribozymes may be purified by gel electrophoresis using general methods or by high-pressure liquid chromatography and resuspended in water.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Perrault et al, 1990; Pieken et al., 1991; Usman and Cedergren, 1992; Int. Pat. Appl. Publ. No. WO 93/15187; Int. Pat. Appl. Publ. No. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

A preferred means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells (Elroy-Stein and Moss, 1990; Gao and Huang, 1993; Lieber et al., 1993; Zhou et al., 1990). Ribozymes expressed from such promoters can function in mammalian cells (Kashani-Sabet et al., 1992; Ojwang et al., 1992; Chen et al., 1992; Yu et al., 1993; L'Huillier et al., 1992; Lisziewicz et al., 1993). Although incorporation of the present ribozyme constructs into adeno-associated viral vectors is preferred, such transcription units can be incorporated into a variety of vectors for introduction into mammalian cells, including but not restricted to, plasmid DNA vectors, other viral DNA vectors (such as adenovirus vectors), or viral RNA vectors (such as retroviral, semliki forest virus, sindbis virus vectors).

Sullivan et al. (Int. Pat. Appl. Publ. No. WO 94/02595) describes general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraocular, retinal, subretinal, intraperitoneal, intracerebroventricular, intrathecal delivery, and/or direct injection to one or more tissues of the brain. More detailed descriptions of ribozyme and rAAV vector delivery and administration are provided in Int. Pat. Appl. Publ. No. WO 94/02595 and Int. Pat. Appl. Publ. No. WO 93/23569, each specifically incorporated herein by reference.

Ribozymes and the AAV vectored-constructs of the present invention may be used to inhibit gene expression and define the role (essentially) of specified gene products in the progression of one or more neural diseases, dysfunctions, cancers, and/or disorders. In this manner, other genetic targets may be defined as important mediators of the disease. These studies lead to better treatment of the disease progression by affording the possibility of combination therapies (e.g., multiple ribozymes targeted to different genes, ribozymes coupled with known small molecule inhibitors, or intermittent treatment with combinations of ribozymes and/or other chemical or biological molecules).

4.28 Antisense Oligonucleotides

In certain embodiments, the gene expression constructs of the invention, and the viral vectors comprising them will find utility in the delivery of one or more antisense oligonucleotides or polynucleotides for inhibiting the expression of a selected mammalian mRNA in a host cell that has been transformed with the construct.

In the art the letters, A, G, C, T, and U respectively indicate nucleotides in which the nucleoside is Adenosine (Ade), Guanosine (Gua), Cytidine (Cyt), Thymidine (Thy), and Uridine (Ura). As used in the specification and claims, compounds that are "antisense" to a particular PNA, DNA or mRNA "sense" strand are nucleotide compounds that have a nucleoside sequence that is complementary to the sense strand. It will be understood by those skilled in the art that the present invention broadly includes oligonucleotide compounds that are capable of binding to the selected DNA or mRNA sense strand. It will also be understood that mRNA includes not only the ribonucleotide sequences encoding a protein, but also regions including the 5'-untranslated region, the 3'-untranslated region, the 5'-cap region and the intron/exon junction regions.

The invention includes compounds which are not strictly antisense; the compounds of the invention also include those oligonucleotides that may have some bases that are not complementary to bases in the sense strand provided such compounds have sufficient binding affinity for the particular DNA or mRNA for which an inhibition of expression is desired. In addition, base modifications or the use of universal bases such as inosine in the oligonucleotides of the invention are contemplated within the scope of the subject invention.

The antisense compounds may have some or all of the phosphates in the nucleotides replaced by phosphorothioates (X=S) or methylphosphonates ($X=CH_3$) or other $C_{1-4}$ alkylphosphonates. The antisense compounds optionally may be further differentiated from native DNA by replacing one or both of the free hydroxy groups of the antisense molecule with $C_{1-4}$ alkoxy groups ($R=C_{1-4}$ alkoxy). As used herein, $C_{1-4}$ alkyl means a branched or unbranched hydrocarbon having 1 to 4 carbon-atoms.

The disclosed antisense compounds also may be substituted at the 3' and/or 5' ends by a substituted acridine derivative. As used herein, "substituted acridine," means any acridine derivative capable of intercalating nucleotide strands such as DNA. Preferred substituted acridines are 2-methoxy-6-chloro-9-pentylaminoacridine, N-(6-chloro-2-methoxyacridinyl)-O-methoxydiisopropylaminophosphinyl-3-aminopropanol, and N-(6-chloro-2-methoxyacridinyl)-O-methoxydiisopropylaminophosphinyl-5-aminopentanol. Other suitable acridine derivatives are readily apparent to persons skilled in the art. Additionally, as used herein "P(O)(O)-substituted acridine" means a phosphate covalently linked to a substitute acridine.

As used herein, the term "nucleotides" includes nucleotides in which the phosphate moiety is replaced by phosphorothioate or alkylphosphonate and the nucleotides may be substituted by substituted acridines.

In one embodiment, the antisense compounds of the invention differ from native DNA by the modification of the phosphodiester backbone to extend the life of the antisense molecule. For example, the phosphates can be replaced by phosphorothioates. The ends of the molecule may also be optimally substituted by an acridine derivative that intercalates nucleotide strands of DNA. Intl. Pat. Appl. Publ. No. WO 98/13526 and U.S. Pat. No. 5,849,902 (each specifically incorporated herein by reference in its entirety) describe a method of preparing three component chimeric antisense compositions, and discuss many of the currently available methodologies for synthesis of substituted oligonucleotides having improved antisense characteristics and/or half-life.

The reaction scheme involves $^1$H-tetrazole-catalyzed coupling of phosphoramidites to give phosphate intermediates that are subsequently reacted with sulfur in 2,6-lutidine to generate phosphate compounds. Oligonucleotide compounds are prepared by treating the phosphate compounds with thiophenoxide (1:2:2 thiophenol/triethylamine/tetrahydrofuran, room temperature, 1 hr). The reaction sequence is repeated until an oligonucleotide compound of the desired length has been prepared. The compounds are cleaved from the support by treating with ammonium hydroxide at room temperature for 1 hr and then are further deprotected by heating at about 50° C. overnight to yield preferred antisense compounds.

Selection of antisense compositions specific for a given gene sequence is based upon analysis of the chosen target sequence and determination of secondary structure, $T_m$, binding energy, relative stability, and antisense compositions were selected based upon their relative inability to form dimers, hairpins, or other secondary structures that would reduce or prohibit specific binding to the target mRNA in a host cell. Highly preferred target regions of the mRNA, are those that are at or near the AUG translation initiation codon, and those sequences that were substantially complementary to 5' regions of the mRNA. These secondary structure analyses and target site selection considerations were performed using v.4 of the OLIGO primer analysis software (Rychlik, 1997) and the BLASTN 2.0.5 algorithm software (Altschul et al., 1997).

4.29 EXEMPLARY DEFINITIONS

In accordance with the present invention, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from native sources, chemically synthesized, modified, or otherwise prepared in whole or in part by the hand of man.

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, the preferred methods and compositions are described herein. For purposes of the present invention, the following terms are defined below:

A, an: In accordance with long standing patent law convention, the words "a" and "an" when used in this application, including the claims, denotes "one or more".

Expression: The combination of intracellular processes, including transcription and translation undergone by a polynucleotide such as, for example, a structural gene to synthesize the encoded peptide or polypeptide.

Promoter: a term used to generally describe the region or regions of a nucleic acid sequence that regulates transcription.

Regulatory Element: a term used to generally describe the region or regions of a nucleic acid sequence that regulates transcription.

Structural gene: A gene or sequence region that is expressed to produce an encoded peptide or polypeptide.

Transformation: A process of introducing an exogenous polynucleotide sequence (e.g., a vector, a recombinant DNA or RNA molecule) into a host cell or protoplast in which that exogenous nucleic acid segment is incorporated into at least a first chromosome or is capable of autonomous replication within the transformed host cell. Transfection, electroporation, and naked nucleic acid uptake all represent examples of techniques used to transform a host cell with one or more polynucleotides.

Transformed cell: A host cell whose nucleic acid complement has been altered by the introduction of one or more exogenous polynucleotides into that cell.

Transgenic cell: Any cell derived or regenerated from a transformed cell or derived from a transgenic cell, or from the progeny or offspring of any generation of such a transformed host cell.

Vector: A nucleic acid molecule (typically comprised of DNA) capable of replication in a host cell and/or to which another nucleic acid segment can be operatively linked so as to bring about replication of the attached segment. A plasmid, cosmid, or a virus is an exemplary vector.

The terms "substantially corresponds to", "substantially homologous", or "substantial identity" as used herein denotes a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared. The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides. Desirably, which highly homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described by Pearson and Lipman (1988).

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by the hand of man in a laboratory is naturally-occurring. As used herein, laboratory strains of rodents that may have been selectively bred according to classical genetics are considered naturally occurring animals.

As used herein, a "heterologous" is defined in relation to a predetermined referenced gene sequence. For example, with respect to a structural gene sequence, a heterologous promoter is defined as a promoter which does not naturally occur adjacent to the referenced structural gene, but which is positioned by laboratory manipulation. Likewise, a heterologous gene or nucleic acid segment is defined as a gene or segment that does not naturally occur adjacent to the referenced promoter and/or enhancer elements.

"Transcriptional regulatory element" refers to a polynucleotide sequence that activates transcription alone or in combination with one or more other nucleic acid sequences. A transcriptional regulatory element can, for example, comprise one or more promoters, one or more response elements, one or more negative regulatory elements, and/or one or more enhancers.

As used herein, a "transcription factor recognition site" and a "transcription factor binding site" refer to a polynucleotide sequence(s) or sequence motif(s) which are identified as being sites for the sequence-specific interaction of one or more transcription factors, frequently taking the form of direct protein-DNA binding. Typically, transcription factor binding sites can be identified by DNA footprinting, gel mobility shift assays, and the like, and/or can be predicted on the basis of known consensus sequence motifs, or by other methods known to those of skill in the art.

As used herein, the term "operably linked" refers to a linkage of two or more polynucleotides or two or more nucleic acid sequences in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

"Transcriptional unit" refers to a polynucleotide sequence that comprises at least a first structural gene operably linked to at least a first cis-acting promoter sequence and optionally linked operably to one or more other cis-acting nucleic acid sequences necessary for efficient transcription of the structural gene sequences, and at least a first distal regulatory element as may be required for the appropriate tissue-specific and developmental transcription of the structural gene sequence operably positioned under the control of the promoter and/or enhancer elements, as well as any additional cis sequences that are necessary for efficient transcription and translation (e.g., polyadenylation site(s), mRNA stability controlling sequence(s), etc.

The term "substantially complementary," when used to define either amino acid or nucleic acid sequences, means that a particular subject sequence, for example, an oligonucleotide sequence, is substantially complementary to all or a portion of the selected sequence, and thus will specifically bind to a portion of an mRNA encoding the selected sequence. As such, typically the sequences will be highly complementary to the mRNA "target" sequence, and will have no more than 1, 2, 3, 4, 5, 6, 7, 8, 9, or 10 base mismatches throughout the complementary portion of the sequence. In many instances, it may be desirable for the sequences to be exact matches, i.e. be completely complementary to the sequence to which the oligonucleotide specifically binds, and therefore have zero mismatches along the complementary stretch. As such, highly complementary sequences will typically bind quite specifically to the target sequence region of the mRNA and will therefore be highly efficient in reducing, and/or even inhibiting the translation of the target mRNA sequence into polypeptide product.

Substantially complementary oligonucleotide sequences will be greater than about 80 percent complementary (or '% exact-match') to the corresponding mRNA target sequence to which the oligonucleotide specifically binds, and will, more preferably be greater than about 85 percent complementary to the corresponding mRNA target sequence to which the oligonucleotide specifically binds. In certain aspects, as described above, it will be desirable to have even more substantially complementary oligonucleotide sequences for use in the practice of the invention, and in such instances, the oligonucleotide sequences will be greater than about 90 percent complementary to the corresponding mRNA target sequence to which the oligonucleotide specifically binds, and may in certain embodiments be greater than about 95 percent complementary to the corresponding mRNA target sequence to which the oligonucleotide specifically binds, and even up to and including 96%, 97%, 98%, 99%, and even 100% exact match complementary to all or a portion of the target mRNA to which the designed oligonucleotide specifically binds.

Percent similarity or percent complementary of any of the disclosed sequences may be determined, for example, by comparing sequence information using the GAP computer program, version 6.0, available from the University of Wisconsin Genetics Computer Group (UWGCG). The GAP program utilizes the alignment method of Needleman and Wunsch (1970). Briefly, the GAP program defines similarity as the number of aligned symbols (i.e., nucleotides or amino acids) that are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess (1986), (2) a penalty of 3.0 for each gap and an additional 0.10 penalty for each symbol in each gap; and (3) no penalty for end gaps.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Insulated Herpesvirus-Derived Gene Expression Cassette for Sustained and Regulatable Gene Expression This example describes the use of DNA elements derived/isolated from Herpes Simplex Virus type I (HSV-I) in the construction of a gene expression cassette capable of facilitating persistent/long-term and regulatable transgene expression. A novel and enabling feature of this invention is that the cassette is bounded by control elements that protect and insulate the gene expression portion of the cassette from the influence of DNA and chromatin structure that lie outside of the cassette, when the cassette is inserted into a viral vector, cellular, animal or human genome. These control elements effectively maintain the expression cassette in an accessible and transcriptionally-responsive conformation. This novel cassette therefore would allow predictable and sustained [permanent regulatable expression (PRE)] OR [silencing-resistant] expression of a transgene regardless of where the cassette was inserted in a viral vector or a host genome. A key feature of this expression cassette is that it prevents transcription of a gene in a viral vector or transgene from being shut down with time due to chromatin effects of the surrounding DNA. Solving this transcriptional shut-down problem greatly extends the application of existing viral vector and gene delivery technologies.

An integral part of this invention is the expression cassette (FIG. 1), and the novel and key features are the insulating elements that bound the cassette and protect the elements between them from silencing effects of the surrounding chromatin (FIG. 2). As mentioned, this cassette has applications in viral vector, transgenics and other gene delivery applications. The initial embodiment of the invention may be examined in the context of an HSV-1 gene therapy vector construct. Note that, while in this particular embodiment will direct expression from this cassette in a neuron-specific manner, key control elements such as the promoter and enhancer could be replaced with similar elements conferring different tissue/cell-type specificities without altering the PRE properties of the insulating elements.

5.1.1 Expression Cassette-LAT Insulator/Boundary 1 (I/B 1) Element, Promoter(s), LAT Enhancer, Heterologuos Gene(s), LAT Insulator/Boundary 2 (I/B 2) Element (FIG. 1)

The components of the expression cassette invention consist of a LAT insulator/boundary 1 (I/B1) element, a promoter, the LAT enhancer region flanked by splice donor and splice acceptor sites, a heterologous transgene, and a LAT insulator/boundary 2 (I/B 2) element linked together in that order. The order of the constructs components serves to facilitate permanent and regulatable (in the case of inducible promoter(s)) gene expression. The term "permanent regulatable expression" is taken to mean expression of a heterologous gene(s) from the invention construct for the duration of the host-cell(s) life.

5.1.1.1 LAT Insulater/Boundary 1 (I/B 1) Element

The LAT insulator/boundary 1 (I/B 1) element is defined here as the region comprising HSV1 nucleotides 8,365-9,273 (GenBank NC 001806: from SwaI-AatII sites), fragments or derivatives of this region, including homologous regions from other alphaherpesviruses that may confer alternative regulation, but are capable of conferring permanent regulatable expression of heterologous genes in the expression cassette comprising the invention.

5.1.1.2 Promoters

A promoter refers to any transcriptional promoter that corresponds to a region of DNA involved in binding of RNA polymerase to initiate transcription. This region of DNA may range in size and complexity from minimal promoters to promoters including upstream activating sequences and enhancers/silencer elements. Within the context of the initial embodiment of this invention, the promoter consists of the HSV-1 latency active promoter 1 (LAP1) comprising nucleotides 117,938-118,843 (GenBank NC 001806: from SmaI-SacII sites) or pHB22F nucleotides 1,173-2,013 (Berthomme et al., 2000). This promoter allows neuronal-specific expression. Other promoters with different cell-type/tissue specificity could be employed, as well as ones capable of regulation.

5.1.1.3 LAT Enhancer

An enhancer element refers to any cis-acting sequence that increases the utilization eukaryotic transcriptional promoters. Enhancers can function in either orientation and in any location (upstream or downstream) relative to the promoter. Within the context of the invention, the LAT enhancer consists of the HSV-1 sequence corresponding to the LAT 5' exon and comprises from about nucleotide 118,975 to about nucleotide 120,471 (GenBank Accession No. NC_001806) or pHB22F nucleotides 2,050-3,546 (Berthomme et al., 2000). Other enhancers with different cell/tissue-specific or expression properties could also be substituted.

5.1.1.4 Heterolgous Genes

The term heterologous gene comprises any gene other than genes found present within the delivery vector encompassing the expression cassette. The term gene refers collectively to any nucleic acid sequence that is capable of being transcribed and therefore includes sequences encoding mRNA, tRNA, and rRNA. With respect to the growing field of RNAi, the sequence may be in the sense or antisense orientation to the promoter and used to inhibit a target host cell gene. On the other hand, sequences encoding mRNA may include either 5' and/or 3' untranslated regions, transcription stop signals, polyadenylation signals, and/or downstream enhancer/silencer elements. The heterologous gene may encode a polypeptide for therapeutic use or for use in developing animal models of human disease. Additionally, the heterologous gene may encode antigenic polypeptides for use in vaccine development, the gene may encode a marker gene like green fluorescent protein, or the gene may encode polypeptides that function in the regulation of other genes.

5.1.1.5 LAT Insulator/Boundary 2 (I/B 2) Element

The LAT insulator/boundary 2 (I/B 2) element is defined here as the region comprising HSV1 nucleotides 120,208-120,940 (GenBank NC_001806: PCR fragment tagged with SpeI and NotI respectively), fragments or derivatives of this region, including homologous regions from other alphaherpesviruses that may confer alternative regulation, but are capable of conferring permanent regulatable expression of heterologous genes in the expression cassette comprising the invention.

5.2 Example 2

Wide Variations in Herpes Simplex Virus Type 1 Inoculum Dose and Latency-Associated Transcript Expression Phenotype do not Alter the Establishment of Latency in the Rabbit Eye Model The latency-associated transcript (LAT) is required for efficient reactivation of herpes simplex virus type 1 from latent infection in the rabbit eye model, but LAT's mechanism of action is unknown. In addition to reactivation, the LAT region seems to correspond to multiple functions, with some LAT deletion mutants exhibiting increased virulence, increased neuronal death and restricted establishment of latency. While a LAT promoter deletion mutant (17ΔPst) seems to be primarily restricted in reactivation in the rabbit, subtle effects on virulence or the establishment of latency cannot be precluded at the normal high levels of virus inoculum used in the rabbit model. Since such additional LAT phenotypes may be more evident with lower doses of virus, the influence of initial viral inoculum and LAT expression on the progression of acute infection and the establishment of latency was evaluated. Both virus recovery rates and viral genome loads in rabbit corneas and trigeminal ganglia have been assayed. Results show that (i) in the corneas and trigeminal ganglia, the maximum amount of virus present during acute infection is independent of the LAT genotype and inoculum dose, although greater viral yields are obtained earlier with higher inoculum doses, and (ii) the range in numbers of latent genomes detected in the ganglia is independent of the inoculum dose and the LAT genotype and therefore no difference in establishment of latency is observed.

Herpes simplex virus type 1 (HSV-1) establishes latency in neurons of sensory ganglia innervating the site of initial infection. The virus can reactivate spontaneously or under conditions of stress to cause a recurrent infection. During latency, the genome forms an episome in neuronal nuclei from which no viral replication occurs (Mellerick and Fraser, 1987; Rock and Fraser, 1983). Approximately one-third of the latently infected neurons express high levels of a single transcript, termed the latency-associated transcript (LAT) (Gressens and Martin, 1994; Mehta et al., 1995). This transcript is important for reactivation, even though LAT does not seem to encode a protein (Hill et al., 1990; Leib et al., 1989).

While LAT is required for efficient reactivation in animal models, its mechanism is not well understood. One factor that complicates these analyses is that observations vary depending on the animal model (Perug et al., 2001) and the HSV strain (Mitchell et al., 2003; Sawtell et al., 1998) used. The two most common models employed are the rabbit and mouse. In the rabbit eye model, latency is established in trigeminal ganglia (TG) following corneal inoculation. Reactivation, either spontaneous or induced by iontophoresis of epinephrine, is scored by recovery of infectious virus in the tear film (Berman and Hill, 1985; Hill et al., 1986; Nesburn et al., 1967). In the mouse model, latency is established in the trigeminal or dorsal root ganglia following inoculation of corneas or rear footpads, respectively. Viral reactivation from ganglia can be induced by thermal stress, as demonstrated by the presence of infectious virus in the ganglia, or by explant cocultivation of dissected ganglia on cultured cells (Sawtell and Thompson, 1992b; Stevens and Cook, 1971).

Mutants with large LAT deletions have been reported to have reduced numbers of latent viral genomes in neurons of both mice and rabbits (Perng et al., 2000a; Perng et al., 2000b; Sawtell and Thompson, 1992a; Thompson and Sawtell, 2001). This suggests that functions corresponding to the LAT region are involved in the establishment of latency. In contrast, mutants with smaller LAT deletions, such as 17ΔPst (a LAT promoter mutant) and 17Δ348 (a 5' exon deletion mutant), do not demonstrate significant differences in total numbers of latent HSV-1 genomes (Bloom et al., 1994; Bloom et al., 1996; Devi-Rao et al., 1994. This suggests that either the establishment function in the LAT region maps to a region independent of the LAT promoter (LAP1) or that a defect in establishment exhibited by the mutants with smaller deletions was below the limit of detection in the previous studies.

The possibility existed that the dose of virus used in rabbit infections, which involve a relatively large inoculum ($1\times10^5$ to $5\times10^5$ PFU/eye), may mask subtle replication or establishment deficits inherent in these LAT mutants. Therefore, the course of the acute infection in the rabbit eye model was examined using 1,000-fold-lower inoculation doses of 17ΔPst and the corresponding rescue strain. Differences in acute infection kinetics and levels of establishment of latency were not detected by this method. The observation that peak establishment occurs with even low-dose inocula suggests that saturation of latent sites occurs relatively early. To determine the contribution of the initial inoculum to establishment, rabbits were infected with a nonreplicating HSV-1 recombinant, KD6 ($ICP4^-$). While this recombinant is capable of establishing latency in the rabbit TG following ocular infection, the total number of latent genomes is much lower than that seen after infection with wild-type virus, indicating that peripheral replication contributes to maximal establishment of latency.

5.2.1 Materials and Methods 5.2.1.1 Cells and Viruses

Virus was propagated on cultured rabbit skin (RS) cells. Titers of viral stocks were determined on RS cells grown in minimal essential medium supplemented with 5% fetal bovine serum and antibiotics (Tran et al., 2002). Acute infection titers in eye swabs, corneas and TG were determined on primary rabbit kidney cells grown in minimal essential medium supplemented with 7% fetal bovine serum and antibiotics (Hill et al., 1998). The following HSV-1 genotypes previously described were used in these experiments: wild-type strain 17syn+; 17ΔPst, a recombinant with a 202-bp portion of the LAT promoter (nucleotides 118,664 to 118,866) deleted, and the corresponding rescue strain, 17ΔPstR (Devi-Rao et al., 1994); 17Δ348, a LAT recombinant with bases 119,007 to 119,355 deleted, and the corresponding rescue strain, 17Δ348R (Bloom et al., 1996); RHA-6, a recombinant expressing the 5' portion of LAT by virtue of having nucleotides 120,290 to 120,467 removed and replaced with a 442-bp fragment of simian virus 40 encoding the cleavage-polyadenylation signal site (Bloom et al., 1996); and KD6, a recombinant in which both copies of the ICP4 coding sequence have been deleted to yield a nonreplicating virus (Dobson et al., 1990). The KD6 stocks were propagated on complementing E5 cells (DeLuca et al., 1985), and the number of $ICP4^+$ revertants was determined by passage and titration on RS cells (nonpermissive for $ICP4^-$ mutants). All stocks used in this study had less than one revertant per $10^6$ PFU of $ICP4^-$ plaques.

5.2.1.2 Infections

Lightly scarified rabbit eyes were inoculated with the indicated number of PFU in 25-μl aliquots. Rabbits were sacrificed between 1 and 7 days postinfection (dpi) for acute studies, and their corneas and TG were harvested. Latently infected TG were recovered from rabbits 40 dpi. All data presented in individual Tables 5 to 7 and FIG. 3A, FIG. 3B and FIG. 3C are results from separate and independent experiments, each performed on groups of rabbits that were infected and analyzed at the same time.

5.2.1.3 DNA Extraction

Dissected corneas or ganglia were incubated with 0.6 ml of extraction buffer (25 mM EDTA, 100 mM NaCl, 1% sodium dodecyl sulfate, 10 mM Tris [pH 7.5]) and 50 μl of proteinase K solution (15 mg/ml) overnight at 48° C. DNA was extracted three times with phenol-chloroform (1:1) and once with chloroform. DNA was precipitated with ethanol overnight and pelleted by centrifugation. The pellet was washed once with 70% ethanol, air dried, and dissolved in 200 μl of water.

5.2.1.4 Analysis of the Relative Amounts of Viral DNA by PCR™

Semiquantitative PCR™ analysis incorporating [$\alpha$-$^{32}$P] dCTP is able to detect 1 pg of purified HSV-1 DNA by comparison to a control plasmid containing a subcloned fragment of the VP5 gene. When purified viral DNA was mixed with uninfected ganglia, fewer than 1,000 viral genomes could be detected. This PCR™ method was also able to detect the viral DNA from a single infected cell. Actin gene primer sets were used to amplify DNA corresponding to cellular genomes to normalize product intensities. The signals were determined by densitometry, and the ratios were calculated (Bloom et al., 1994).

Amplification by PCR™ was carried out as previously described (Bloom et al., 1994) by using the primer sets illustrated in Table 4 for the actin and HSV-1 VP5 genes. The products were radiolabeled for autoradiography and image quantitation by addition of 0.2 μCi of [$\alpha$-$^{32}$P]dCTP. The reactions were carried out in an M. J. Research thermal cycler as follows: denaturation, 94° C. for 30 sec; annealing, 55° C. for 30 sec; and extension, 72° C. for 60 sec. The final cycle was terminated with a 10-min extension step. For each reaction, 20 μl (10%) of the DNA sample was used and the final volume of the reaction mixture was 100 μl. One-fifth of the amplified product (corresponding to 2% of the original material) was fractionated on 6% polyacrylamide gels in Tris-borate-EDTA buffer. The PCR™ signals were visualized by scanning an appropriately exposed autoradiogram using a Deskcan II scanner (Hewlett-Packard). The signals were quantified by densitometry using IP Lab Gel software (Signal Analysis Corporation) in accordance with operational instructions.

5.2.1.5 PCR Analysis to Determine Relative Levels of Latent Viral DNA and Wild-Type Revertants For these experiments, PCR™ primers specific for the HSV-1 DNA polymerase gene were used to quantitate latent HSV-1 genomes, and the cellular actin gene served as an internal standard for normalizing levels of latent viral DNA among samples. PCR™ primers specific for the HSV-1 ICP4 gene (Table 4) were also used for analysis of the KD6 viral recombinant to confirm that the HSV-1 genomes detected were not due to wild-type revertants. PCRs were performed in a 50-μl final volume consisting of 40.5 μl of sterile $H_2O$, 1 μl each of both forward and reverse primers (600 ng/μl), 1 μl of deoxynucleoside triphosphates (1.25 mM each), 5 μl of 10×AS buffer [Tris-Cl, KCl, $(NH_4)_2SO_4$, 15 mM $MgCl_2$ (pH 8.7); Qiagen], 1 μl of respective DNA sample, and 0.5 μl of HotStar Taq DNA polymerase (5 U/μl; Qiagen). The amplification profile consisted of a step at 95° C. for 15 min to activate the Taq, followed by one cycle of 94, 55 and 72° C. for 3 min, followed by 30 identical cycles of 1 min each (Ericomp Twinblock System, Easy Cycler). PCR™ products were resolved on 5% polyacrylamide gels, stained with SYBR Green (Molecular Probes), and scanned with a Storm PhosphorImager (Molecular Dynamics) using a 450-nm-wavelength laser. Relative numbers of latent genomes were determined by establishing the ratio of HSV-1 polymerase product to cellular actin within sample. Viral polymerase-specific PCR™ products were compared to a plasmid titration mixture containing the subcloned target sequence spiked into processed, uninfected rabbit TG tissue. The signal intensity of each sample was compared to that of this titration mixture to determine the relative number of latent HSV-1 molecules in each sample. Dilutions (twofold) of all samples were performed to determine the appropriate amount of sample yielding a linear response and falling within the linear range of the standard curve.

TABLE 4

PCR ™ PRIMERS

| Gene Target | Primer Pair | Product Size (bp) |
|---|---|---|
| HSV-1 VP5 gene | 5'-TGAACCCCAGCCCCAGAAACC-3' (SEQ ID NO:1)<br>5'-CGAGTAAACCATGTTAAGGACC-3' (SEQ ID NO:2) | 149 |
| HSV-1 ICP4 gene | 5'-CTGATCACGCGGCTGCTGTACACC-3' (SEQ ID NO:3)<br>5'-GGTGATGAAGGAGCTGCTGTTGCG-3' (SEQ ID NO:4) | 144 |
| HSV-1 DNA poly-merase gene | 5'-CATCACCGACCCGGAGAGC-3' (SEQ ID NO:5)<br>5'-GGGCCAGGCGCTTGTTGGTGTA-3' (SEQ ID NO:6) | 92 |
| Rabbit actin gene | 5'-AAGATCTGGCACCACACCTT-3' (SEQ ID NO:7)<br>5'-CGAACATGATCTGGGTCATC-3' (SEQ ID NO:8) | 110 |

5.2.1.6 Statistical Analyses

Results in Tables 2, 3 and 4 were analyzed using factorial analyses of variance with within-subject (nesting of tissue and virus strain combinations within an animal) arrangement of treatments Post hoc evaluation of means following a significant overall model fit and significant interactions was conducted using protected t tests and a simulation method to correct alpha levels for the number of comparisons carried out (Edwards and Berry, 1987).

TABLE 5

RELATIVE AMOUNTS OF VIRAL DNA (EXPRESSED AS THE RATIOS OF VP5 DNA TO ACTIN DNA) AT A HIGH DOSE OF INOCULATION (500,000 PFU)[a]

| | Mean value ± SEM in corneas for: | | Mean value ± SEM in ganglia for: | |
|---|---|---|---|---|
| dpi | 17ΔPst | 17ΔPstR | 17ΔPst | 17ΔPstR |
| 1 | 1.51 ± 0.54 | 1.19 ± 0.99 | 0.12 ± 0.12 | 0.23 ± 0.19 |
| 2 | 2.29 ± 0.76 | 1.40 ± 0.94 | 0.65 ± 0.26 | 0.37 ± 0.28 |
| 3 | 2.11 ± 0.32 | 2.38 ± 0.59 | 1.10 ± 0.26 | 1.86 ± 0.66 |
| 5 | 2.31 ± 0.64 | 1.59 ± 0.18 | 1.80 ± 0.36 | 1.74 ± 0.39 |
| 7 | 2.16 ± 1.30 | 2.01 ± 0.27 | 0.80 ± 0.20 | 0.54 ± 0.40 |
| 14 | 0.44 ± 0.14 | 0.36 ± 0.34 | 0.43 ± 0.30 | 0.21 ± 0.23 |

[a]Rabbits' eyes were inoculated with 500,000 PFU of 17ΔPst or 17ΔPstR (rescuestrain). At the indicated times postinfection, the rabbits (two rabbits per virus per timepoint) were sacrificedand corneas (four per virus per time point) and TG (four per virus per time point) weredissected. Total DNA was isolated from the tissue and amplified with VP5 and actin geneprimer sets in combination. The relative amounts of viral DNA (ratios of VP5 DNA to actin DNA)were determined by densitometry.

TABLE 6

RELATIVE AMOUNTS OF VIRAL DNA IN CORNEAS AND TG DURING ACUTE INFECTIONS FOLLOWING LOW-DOSE INOCULATION WITH VIRUSES OF DIFFERENT LAT GENETYPES[a]

| | | Mean value ± SEM[b] in: | |
|---|---|---|---|
| Virus | dpi | Corneas | Ganglia |
| 17syn+ | 1 | 0.21 ± 0.12 | 0.03 ± 0.01 |
| | 2 | 0.82 ± 0.55 | 0.03 ± 0.02 |
| | 3 | 0.88 ± 0.46 | 0.07 ± 0.04 |
| | 5 | 0.79 ± 0.87 | 0.49 ± 0.48 |
| | 7 | 1.42 ± 0.49 | 0.50 ± 0.31 |
| | 21 | 0.22 ± 0.09 | 0.22 ± 0.13 |
| 17ΔPst | 1 | 0.27 ± 0.16 | 0.03 ± 0.30 |
| | 2 | 0.37 ± 0.24 | 0.08 ± 0.30 |
| | 3 | 0.51 ± 0.36 | 0.05 ± 0.30 |
| | 5 | 1.44 ± 0.56 | 0.39 ± 0.30 |
| | 7 | 0.83 ± 0.79 | 0.16 ± 0.30 |
| | 21 | 0.30 ± 0.23 | 0.25 ± 0.31 |
| 17Δ348 | 1 | 0.40 ± 0.28 | 0.04 ± 0.04 |
| | 2 | 0.23 ± 0.22 | 0.03 ± 0.04 |
| | 3 | 0.36 ± 0.27 | 0.03 ± 0.04 |
| | 5 | 0.80 ± 0.55 | 0.31 ± 0.04 |
| | 7 | 0.83 ± 0.70 | 0.21 ± 0.21 |
| | 21 | 0.23 ± 0.12 | 0.28 ± 0.21 |
| 17Δ348R | 1 | 0.30 ± 0.33 | 0.03 ± 0.01 |
| | 2 | 0.59 ± 0.47 | 0.03 ± 0.01 |
| | 3 | 0.92 ± 0.67 | 0.17 ± 0.35 |
| | 5 | 1.83 ± 0.69 | 0.61 ± 0.42 |
| | 7 | 1.83 ± 1.45 | 0.74 ± 0.70 |
| | 21 | 0.22 ± 0.10 | 0.22 ± 0.01 |
| RHA-6 | 1 | 0.10 ± 0.13 | 0.04 ± 0.03 |
| | 2 | 0.07 ± 0.09 | 0.03 ± 0.02 |
| | 3 | 0.67 ± 0.35 | 0.07 ± 0.04 |
| | 5 | 1.20 ± 0.35 | 0.46 ± 0.34 |
| | 7 | 0.79 ± 0.65 | 0.57 ± 0.34 |
| | 21 | 0.15 ± 0.11 | 0.33 ± 0.15 |

[a]Rabbit eyes were inoculated with 500 PFU of 17syn+, 17ΔPst, 17Δ348, 17Δ348R, andRHA-6. At the indicated dpi, corneas and TG (four each per virus per time point)were dissected and the relative amounts of viral DNA were determined.

[b]Relative amounts of viral DNA are presented as the ratios of the HSVVP5 gene to the cellular actin gene as determined by PCR ™. Means and standarderrors of the mean (SEM) are presented as least-squares mean values and were calculatedas described above.

TABLE 7

RELATIVE AMOUNTS OF VIRAL DNA PRESENT IN TG DURING LATENCY IN RABBITS INFECTED WITH DIFFERENT DOSES OF VIRUS[a]

| Virus, dose | Rabbit tattoo no. (left or right TG)[b] | HSV-1 DNA (mean no. of genome equivalents) | Amt. of viral DNA (mean ± SEM)[c] |
|---|---|---|---|
| 17ΔPst, 500 PFU | A3 (L) | 30,000 | 18,300 ± 7,888 |
| | A3 (R) | 2,000 | |
| | A5 (L) | 40,000 | |
| | A5 (R) | 1,200 | |
| 17ΔPstR (rescue strain), 500 PFU | A9 (L) | 800 | 12,200 ± 7,888 |
| | A9 (R) | 8,000 | |
| | A10 (L) | 30,000 | |
| | A10 (R) | 10,000 | |
| 17ΔPst, 50,000 PFU | A26 (L) | 1,200 | 10,750 ± 7,888 |
| | A26 (R) | 1,800 | |
| | A30 (L) | 3,000 | |
| | A30 (R) | 11,000 | |
| 17ΔPstR (rescue strain), 50,000 PFU | A31 (L) | 8,000 | 16,500 ± 7,888 |
| | A31 (R) | 3,000 | |
| | A32 (L) | 15,000 | |
| | A32 (R) | 40,000 | |

[a]Rabbits were inoculated with the indicated doses of 17ΔPstR or 17ΔPst inboth eyes. Total DNA was isolated from latently infected ganglia (40 dpi) and analyzedby PCR ™ amplification with actin and VP5 gene primer sets. Data are from fourTG per dose per virus per time point.

[b]L, left; R, right.

[c]Relative amounts of viral DNA are expressed as the number of genome equivalentsof HSV determined following semiquantitative PCR ™ for the HSV DNA polymerasegene and are standardized to the amount of cellular actin present in each sample. Standardcurves were generated using known amounts of HSV polymerase target DNA in order tocalculate the number of genomes present in each sample. Means and standard errors of themean (SEM) were calculated as described above.

5.2.2 Results

5.2.2.1 Acute Replication in Rabbit Corneas and TG in High-Versus Low-Dose Infections The contributions of both LAT expression and inoculation dose were analyzed over the course 10 of acute ocular infection of rabbits with either 500 or 500,000 PFU of 17ΔPst or 17ΔPstR (rescue strain)/eye. Infectious virus yields during the acute infection were measured in tear swabs, corneas and TG (FIG. 3A, FIG. 3B and FIG. 3C). At high viral doses ($5\times10^5$ PFU), titers were highest in the tears and corneas on the first dpi. These levels tended to reach a lower plateau by days 3 through 7, and the virus was undetectable by day 14. Virus titers in TG increased during the first 3 days of infection, followed by 3 days (days 3 to 7 postinfection) of sustained virus titers, with the peak occurring during this period. As in the case of the corneas, virus was not detectable by day 14. Infection of rabbits with an inoculum of 500 PFU resulted in the detection of less infectious virus in the eye swabs and corneas at 1 and 2 dpi. However, by day 3, the amounts of infectious virus present in these samples were indistinguishable from those in the samples from rabbits infected with $5\times10^5$ PFU (FIG. 1A and FIG. 1B). A similar lag was evident in the ability to detect infectious virus in TG of rabbits receiving the 500-PFU inoculum (FIG. 1C), and it was not until days 5 to 7 that TG from rabbits infected with 500 PFU of each virus contained amounts of infectious virus similar to those contained in the TG from rabbits infected with $5\times10^5$ PFU. When the replication curves of the two different viruses, 17ΔPst and 17ΔPstR, were compared, they were roughly colinear and not significantly different for either the eye swabs, corneas or TG. So, while the infecting dose clearly affected the initial infection kinetics, it did not significantly alter maximal virus yields. In addition, the ability to express LAT had no identifiable effects on acute replication in the eyes or TG.

5.2.2.2 Analysis of Viral DNA Levels in Corneas and TG During Acute Infection While the use of 1,000-fold-lower inoculum doses of 17ΔPst and its rescue strain did not identify any differences in viral yields during the acute infection, the possibility remained that there might be detectable differences in genome loads. PCR™ analysis to determine the relative amounts of viral DNA present in corneas and TG following both high-dose ($5\times10^5$ PFU per eye) and low-dose (500 PFU per eye) infection was performed. The relative amounts of viral DNA present in corneas and TG following high-dose infection did not show significant differences based on LAT genotypes at any time points (Table 5). The course of infection was then examined following a much lower dose infection (500 PFU per eye). In general, the amounts of HSV-1 DNA detected in the corneas versus those detected in the TG paralleled the findings from infectious virus assays. As with the high-titer infections, relative amounts of HSV-1 DNA in corneas were greater than those in TG during the entire acute infection course (Table 6). Comparison of the data in Tables 5 and 6 revealed a delay in the increases in viral DNA in the lower-dose infections, and the peak values for viral DNA occurred at the same time points as in the infectious virus assays (FIG. 3A, FIG. 3B and FIG. 3C). Since the assay results for viral DNA seemed to parallel the data obtained for infectious virus and also permitted the detection of viral genomes as the virus entered latency, several different LAT mutations were evaluated in a low-dose infection by using this method of analysis. In addition to the LAT promoter deletion recombinant, 17ΔPst, the recombinants 17Δ348, its rescue strain, and RHA-6 were included in this analysis. These other two recombinants differ in LAT expression and/or reactivation phenotypes; 17Δ348 expresses LAT but exhibits significant reactivation impairment following epinephrine induction, whereas RHA-6, which contains a simian virus 40 cleavage-polyadenylation sequence in the middle of the 2.0-kb LAT intron, expresses LAT and reactivates normally (Bloom et al., 1994).

Rabbits inoculated with 500 PFU of reactivation-impaired viral recombinants (17Δ348 and 17ΔPst) demonstrated significantly decreased amounts of viral DNA in TG during the acute phase of infection compared to rabbits inoculated with the wild type, 17syn+, and RHA-6 (Table 6). At day 5 postinfection, the mean value for the reactivation-impaired mutants (0.35±0.19 [ratio of VP5 DNA to actin DNA]) was marginally significantly different (P=0.068) from that for the normal reactivators (0.56±0.38). Mean values for HSV DNA at day 7 (0.29±0.18 for reactivation-impaired viruses and 0.63±0.31 for normally reactivating viruses) were again significantly different (P=0.006), but by the time the active acute infection had cleared (21 days), all TG values were statistically indistinguishable for all of the viruses tested. Therefore, during the initial phase of the low-dose infection, there was a transient period (days 3 to 7) during which somewhat less viral DNA was detected in the TG following infection with the LAT recombinants containing deletions in the LAT region. As the infection progressed and then resolved (day 21), this difference was no longer seen.

5.2.2.3 The Relative Amounts of Latent Vival DNA in TG of Rabbits Infected with the Wild Type or LAT Mutants were Similar Regardless of Infecting Dose The amount of viral DNA in ganglia following clearance of the acute infection suggested that viral genome loads in the ganglia were independent of LAT genotype and infecting dose. This observation was extended to a strict latency time point by using semiquantitative PCR™ to carefully compare relative amounts of latent viral DNA over a range of infecting doses (FIG. 4 and Table 7). Rabbit corneas inoculated with 500 to 50,000 PFU/eye were sacrificed 40 dpi to determine the amount of latent HSV-1. Comparison of 17ΔPst with its rescue strain at an inoculum of 500 PFU resulted in mean numbers of genome equivalents that overlapped when standard error and statistical analyses were applied (P=0.94; least-squares means analysis). A similar comparison of the mean numbers of HSV-1 genome equivalents of these two recombinants following a 50,000-PFU infection indicated that that there was no statistical significance assignable to differences in the latent infections established by 17ΔPst and 17ΔPstR (P=0.95). Next, an analysis of differences in numbers of latent genomes present as a function of infecting inoculum was performed. Comparisons of 17ΔPst at 500 versus 50,000 PFU and 17ΔPstR at 500 versus 50,000 PFU resulted in P values of 0.94 and 0.97, respectively. In summary, no statistical difference in numbers of viral genomes was detected as a function of either LAT genotype or initial virus dose. As with the high-titer infections examined in Table 5, neither dose nor LAT genotype affected DNA levels in latently infected TG.

5.2.2.4 A Nonreplicating HSV-1 Recombinant Established a Latent Infection in the TG but at Lower Levels than Wild-Type Virus The analysis of the course of the acute infection as a function of dose seemed to indicate that, in the rabbit eye model, the ultimate amount of DNA that established latency in the TG was only a small fraction of the amount that reached the ganglia during the entire course of the acute infection. This result was not surprising; however, comparison of the relative levels of DNA accumulation observed in the high-dose and low-dose infections suggested that a "saturating threshold" of HSV DNA in the ganglia, or the ultimate amount of latent DNA, might actually be reached relatively early during the acute infection. This raised the question as to the relative role that the input inoculum might have on the establishment of a latent infection, particularly the normal high-dose inocula used in the rabbit model. To further assess the contribution of input inoculum versus the need for ocular replication for efficient establishment of latency, a nonreplicating ($ICP4^-$) HSV-1 recombinant (KD6) was used. The amount of HSV-1 DNA was determined by PCR™ using TG from rabbits inoculated with $10^5$ or $10^6$ PFU of this virus at 14 dpi (FIG. 5). While TG of rabbits inoculated with KD6 contained detectable HSV genomes, overall numbers were lower than those observed using replication-competent HSV-1 strain 17syn+. PCR™ analysis of these ganglia (using primers specific for the ICP4 gene) indicated that the DNA present was not due to ICP4 revertants. These results demonstrated that while nonreplicating HSV-1 recombinants could seed the TG and establish a latent infection, replication was required to achieve wild-type levels of establishment. These data also suggested that while a high-dose inoculum can result in a significant amount of HSV-1 DNA in the TG at 1 dpi, much of this DNA (and the DNA that ultimately establishes a latent infection in the rabbit TG) is the product of replication.

5.2.3 Discussion

LAT has been suggested to play a role in protecting neurons from death or apoptosis during the initial stages of establishment (Perng et al., 2000a; Thompson and Sawtell, 2001; Thompson and Sawtell, 2000). These observations have been made with mutants that carry deletions extending from the entire LAT promoter into the 2.0-kb intron and that often display altered virulence. While such effects were never observed with the 202-bp LAT promoter mutant (17ΔPst), the statistical power required for discerning threefold (or less) establishment or virulence defects is difficult to achieve in the rabbit model (Bloom et al., 1994). The goal of this study was to determine whether subtle deficits in replication or establishment were detectable using inocula of 500 and 50,000 PFU, doses that are 10- and 1,000-fold lower than normal 17ΔPst inocula in the rabbit eye model. The hope was that additional multiple rounds of replication permitted by the lower inoculum doses might amplify subtle replicative or establishment defects.

No significant differences in the amounts of infectious virus produced during the acute infection in corneas and ganglia or in the numbers of latent genomes in rabbit TG were observed. A slight, but statistically significant, decrease in DNA accumulation was observed at days 3 to 7 of the acute infection in the case of several of the LAT mutations that are correlated with reactivation defects. The fact that DNA levels in the TG were comparable to those for the normally reactivating viruses at day 21 (and during latency) suggests that this DNA accumulation defect was transient and that 17ΔPst's defect in reactivation in the rabbit eye model was not simply the result of less DNA being present in the ganglia during latency. While statistical analyses cannot rule out the possibility that 17ΔPst may have a very subtle reduction in overall establishment of latency, it is unlikely that a decreased amount of DNA alone is the primary basis of the dramatic restriction in reactivation displayed by LAT mutants.

One possible explanation for not seeing the effect on establishment reported for other LAT deletion mutants is that the other studies have employed recombinants with relatively large deletions (Perng et al., 2000b; Thompson and Sawtell, 2001). The fact that these other deletions encompass not only the LAT promoter but also the 5' exon and part of the intron suggests that the primary effect on establishment observed in these systems may be mediated by a distinct genetic element that lies outside of the 202-bp LAT promoter deletion in 17ΔPst. Previous studies have shown that a promoter element (LAP2) exists downstream of the primary latent LAT promoter and that this promoter is active in acutely infected ganglia (Chen et al., 1995; Goins et al., 1994; Nicosia et al., 1993). It should be pointed out that while the LAP1 deletion in 17ΔPst eliminates almost all latent LAT expression, transcription from the LAP2 promoter can still be detected in acute ganglia. Therefore, the contribution of this element to the course of the acute and/or establishment phases of infection is not eliminated and may therefore suggest a role for this downstream region in these processes.

Another observation is that lower (and probably more physiologically relevant) doses of viruses are sufficient to efficiently establish latency in the rabbit TG. It is interesting that increasing inoculum does not decrease the scatter in total levels of establishment observed in the rabbit TG over a range of doses. This scatter is likely due to variability in the numbers of nerve termini that are physically accessible to the initial inoculum and local replication of the virus in the cornea. The fact that 17ΔPst and 17PstR show similar wide and overlapping ranges of establishment in the rabbit TG but that 17ΔPst exhibits a 5- to 10-fold reduction in the number of rabbits or eyes that can be adrenergically induced to reactivate (Bloom et al., 1996; Jarman et al., 2002) highlights longstanding observation that, at least in the rabbit, the absolute genome load seems to be secondary to the genotype of the HSV strain in determining the potential for reactivation.

While this suggests that the level of establishment, as measured by the amount of HSV-1 DNA present in the TG during latency, is not the primary defect in 17ΔPst's ability to reactivate, it does not rule out the idea that LAT plays some role in establishment. In fact, it is very possible that 17ΔPst may be altered in a function that substantially impacts the quality of HSV-1 establishment, such as the efficient regulation of transcription or accessibility of the HSV latent genome, a possibility first suggested by Chen et al. (1997). It is also possible that 17ΔPst alters the establishment program, perhaps resulting in pushing of the HSV latent infection to populations of neurons that are less permissive for induced reactivation. It should be pointed out that the numbers of latently infected neurons, phenotypic distribution, and the numbers of genome copies per neuron have not been analyzed with these mutants in the rabbit. These have been shown to be critical parameters defining the potential to reactivate in the mouse (Sawtell, 1998; Sawtell et al., 1998). Future studies will be required to investigate how these parameters are altered in the case of 17ΔPst.

Another interesting finding was that the amount of HSV-1 DNA detected in the corneas remained high at 21 dpi. While latent-stage (28 dpi or later) corneas from rabbits infected at low doses (such as the day-21 corneas for which results are shown in Table 6) were not examined, a previous study that examined reactivation of $LAT^+$ viruses versus that of $LAT^-$ viruses in the rabbit model revealed that (i) there were relatively high amounts of HSV DNA detected in the corneas of rabbits infected with 17syn+ and the 17ΔPst rescue strain and, interestingly, (ii) there was approximately 10-fold less HSV DNA in the corneas of rabbits infected with the LAT promoter deletion recombinant 17ΔPst. In contrast, no significant differences in amounts of HSV DNA present in the TG from rabbits infected with these three viruses were detected (Devi-Rao et al., 1997). One interpretation of these data is that the presence of HSV-1 DNA in the corneas is actually the result of persistent seeding that is the result of reactivation from the TG and the fact that less 17ΔPst was detected in the corneas at latent-stage times suggests that this virus's decreased ability to reactivate results in substantially less seeding of the corneas. The findings in the present example that there were relatively high (and comparable) amounts of HSV DNA in the corneas of rabbits infected with both $LAT^+$ and $LAT^-$ viruses at days 14 and 21 suggests that by day 21 the DNA resulting from the acute infection-establishment phase of the latent infection had not yet cleared from the corneas. Indeed, this supports the rationale of waiting until at least 28 dpi for analysis of latency.

This study provided the additional opportunity to monitor the course of an HSV-1 ocular infection in the rabbit as a function of dose. Not surprisingly, peak acute titers in the tears, corneas, and TG were delayed by several days when lower inocula were used. Interestingly, peak levels of viral DNA in the TG were reached slightly earlier, suggesting that maximum establishment of the latent DNA pool occurs fairly early and at relatively low inoculation doses. This in turn suggests that corneas provide a limited number of entry sites into the nervous system (or number of available neuronal termini), which become saturated relatively quickly. To address this question more directly, a nonreplicating virus, KD6, was used (Dobson et al., 1990; Sedarati et al., 1993). Since this virus cannot undergo any replication in the cornea, it allows assessment of the amount of viral DNA delivered to the TG as a direct function of input. Results indicate that while significant establishment of latency is achieved, even doses of $10^6$ PFU yield approximately a 10-fold lower amount of DNA than that seen with a lower inoculum of 17syn+. This indicates that while a nonreplicating virus can establish latency in TG, replication is required to establish maximal latent infections. This requirement is likely due to mechanical barriers that must be overcome to efficiently gain access to the nerve termini projecting to the TG. While infecting the corneal surface (even with scarification) provides access to many nerve termini, replication and cell-to-cell spread are much more important factors.

5.3 Example 3

CTCF Binds Several Clusters of CTCF Consensus Motifs within the HSV-1 Genome During Latency The present example identifies the location of putative boundaries that separate the transcriptionally permissive LAT region, from the surrounding regions of hypoacetylation and transcriptional repression. A previous study had suggested that these boundaries were located within a ~5 kb region both 5' to and 3' to the region of the LAT that is hyperacetylated during latency. These data demonstrate that sequence analysis of these 5' and 3' regions identified clusters of a repeated motif for a cellular protein known as CTCF, a protein known to have a role in the formation of cellular boundaries. These two clusters of CTCF motifs are contained in a region of approximately 250 bp each, one 5' to the LAT promoter, near the RL and UL junctions, and the other in the region encoding the LAT intron. ChIP analysis using an antibody specific for CTCF demonstrated that, during a latent infection of murine dorsal root ganglia (DRG), these two sites are enriched in CTCF, suggesting that these 250 bp elements may contain the core nucleation sites for the formation of a functional chromatin boundary. The formation of such a boundary surrounding the LAT enhancer may play an essential role in insulating the LAT enhancer, which confers activity of the LAT promoter during latency, from acting in a transcriptionally permissive manner on ICP0, or other lytic genes in the region.

Further analysis of the HSV-1 genome revealed the existence of four other clusters of CTCF motifs. ChIP analysis revealed that during a latent infection of murine DRG, these sites are also enriched in CTCF binding. Interestingly, if these motifs all were to form functional boundaries, each of the HSV-1 IE genes would exist in a separate chromatin domain. Finally, analysis of the genomes of other alphaherpesviruses for which sequence is available reveals that these CTCF motifs and their placement flanking IE genes are conserved among this group. This suggests that the organization of the IE genes (and LAT) into separate chromatin domains may be an important regulatory component of the control of alphaherpesviral latent gene expression and may contribute in a mechanistic way to the control of latency and reactivation.

5.3.1 Materials and Methods 5.3.1.1 Viruses and Cells

Sequence analyses were performed using published NCB1 GenBank sequence for HSV-1 strain 17 (NC 001806; McGeoch), HSV-2 strain HG52 (NC 001798; McGeoch), Suid herpesvirus 1 (pseudorabies virus) (BK001744; Enquist), Human herpesvirus 3 strain Dumas (varicella-zoster virus) (X04370; Scott), and Cercopithecine herpesvirus 1 (monkey B virus) (NC 004812; Hilliard). All ChIP experiments were performed using a low passage stock of HSV-1 strain 17syn+ prepared from a master stock obtained from J. Stevens. The virus was amplified and titrated on rabbit skin cells (RSC) using Eagle's minimal essential medium (MEM, Life Technologies) supplemented with 5% calf serum (Life Technologies) and antibiotics (250 U of penicillin/mL, 250 μg of streptomycin/mL, and 292 μg of L-glutamine/mL).

5.3.1.2 Mouse Infections

Four- to six-week old female Out-bred ND4 Swiss mice (Harlan) were anesthetized by Halothane inhalation and pretreated with 0.05 ml of a 10% (wt/vol in water) sterile saline solution injected under each rear footpad. At 3-4 hr after pretreatment, the mice were anesthetized by intramuscular injection of 0.010-0.020 ml of a cocktail of acepromazine (2.5-3.75 mg/kg), xylazine (7.5-11.5 mg/kg) and ketamine (30-45 mg/kg) and infected bilaterally on the rear footpads with 1.5×104 PFU/mouse. The keratinized epithelium was lightly abraded with an emery board, and the inoculum was applied to the feet in a volume of 50 μl/mouse. The inoculum was spread over the surface of the footpad with the side of the pipette tip, and the virus was allowed to adsorb for 30-45 min while the mice remained under anesthesia on their backs. Mice were sacrificed at >28 days p.i. for latent studies. Care was taken to ensure that the ganglia were removed and processed as quickly as possible postmortem (between 3 and 5 min per mouse).

5.3.1.3 Identification of Consensus CTCF Binding Motifs

The frequency with which CCCTC or CTCCC motifs are found within the HSV-1 genome was calculated by the formulas R=fCCCTC/1000 and R=fCTCCC/1000, where f is the frequency of the indicated CTCF-binding motif, and R is the resulting ratio. The entire viral genome was analyzed as 1000 bp segments using a Visual Basic program, and the results output to Microsoft Excel and graphed. Regions that exhibited high frequencies of motif occurrence were further analyzed for motif clustering (Benson, 1999). Tandem repeat analysis was also applied to a group of alphaherpersviruses to screen for similar CTCF motif clusters.

5.3.1.4 Chromatin Immunoprecipitation (Chip)

ChIP assays were performed as previously described (20) with minor modification. Briefly, steps were as follows. All solutions used prior to the collection of chrom atin-antibody complexes contained protease inhibitors at the following concentrations: aprotinin (U.S. Biochemicals), 15 μg/ml; leupeptin (U.S. Biochemicals), 1 μg/ml; and phenylmethylsulfonyl fluoride (Sigma), 10 μg/ml. All steps were performed at 4° C. unless noted otherwise. DRG were removed from mice at a minimum of 28 days p.i. and homogenized in ice-cold phosphate-buffered saline. Formaldehyde (final concentration, 1% [vol/vol]) was added to the homogenate to cross-link chromatin, and samples were incubated at room temperature for 10 min with shaking. Cross-linking was arrested by adding glycine (0.125 M final concentration), and the homogenate incubated for an additional 5 min at room temperature with shaking. The homogenate was then pelleted, washed 3 times with phosphate-buffered saline, then resuspended in SDS lysis buffer (Upstate Biotechnology) and incubated a minimum of 10 min on ice.

The cell lysate was sonicated to shear the chromatin into a population of fragments with a median size range of 500-1, 000 bp as determined by agarose gel electrophoresis. The sheared chromatin was diluted by the addition of 10 volumes of ice-cold ChIP dilution buffer (Upstate Biotechnology) and incubated with salmon sperm DNA-protein A agarose (50%) slurry (Upstate Biotechnology) for 2 hr to reduce non-specific binding. Beads were removed by centrifugation and sheared chromatin incubated with 2 μL of anti-CTCF (Upstate Biotechnology) at a concentration of 2 μg/mL of antibody per 1 mL pre-cleared chromatin overnight with shaking.

Chromatin-antibody complexes were collected by incubation with salmon sperm DNA-protein A-agarose (50%) slurry and subsequent collection of beads by centrifugation. Bead pellets were washed one time each in low-salt, high-salt, and LiCl immune complex wash buffers followed by two washes with TE buffer (all Upstate Biotechnology). Antibody-chromatin complexes were eluted from beads by incubation with freshly made, preheated (65° C.) elution buffer (0.1% SDS, 0.1M $NaHCO_3$). NaCl was added to eluates (final concentration of 0.2 M) and they were incubated at 65° C. for 4 hr. The eluates were then treated with RNase A and proteinase K, and the DNA was purified using a Qiaquick PCR™ purification kit (Qiagen).

5.3.1.5 PCR™ Analysis of Chips

Following collection of the chromatin-antibody complexes with salmon sperm-protein A agarose beads, the unbound supernatant (subsequently referred to as "input") was removed and purified in a manner similar to the bound ChIP fraction described above. Serial dilutions of input were used as reference in order to determine the relative enrichments of different DNA targets in the bound ChIP fraction. PCRs on input dilutions and the bound ChIP fraction were performed simultaneously using HotStar Taq (Qiagen) at cycles that produced product within the linear range, which was typically attained between 30-38 cycles. Initial stage PCR™ cycle conditions used were as follows: 15 min at 95° C., 3 min at 94° C., 3 min at 55° C., and 3 min at 72° C. Subsequent, repeated cycles were as follows: 1 min at 94° C., 1 min at 55° C., and 1 min at 72° C. (repeated 30-38 times). PCR™ primers used for ChIP analysis are listed in Table 8.

TABLE 8

| PCR ™ PRIMERS | | | |
|---|---|---|---|
| DNA Target | Sequence | Product Size (bp) | Accession No. (nucleotide no.) |
| Mouse Tsix Site A[a] | 5'-GGAGCCTAAACCTGTCTGTC-3' (forward) (SEQ ID NO:9) 5'-GTGTGTCATAGCTCAAGAGG-3' (reverse) (SEQ ID NO:10) | 139 | AJ421479 (137291-137430) |
| Mouse MT498[a] | 5'-ACTCAGTCCAAACATATACAAGATGC-3' (forward) (SEQ ID NO:11) 5'-CTATCTACAACAAACTTCTCCTGGG-3' (reverse) (SEQ ID NO:12) | 185 or 149[b] | NT_039554 (1203018-1203201) |
| HSV-1 CT1 | 5'-GCATGCGTCGCCCAAC-3' (forward) (SEQ ID NO:13) 5'-CAGTTAGATTGCATGTGATC-3' (reverse) (SEQ ID NO:14) | 89 | NC_001806 (117067-117156) |
| HSV-1 CT2 | 5'-CTCTGTGGTTAACACCAGAG-3' (forward) (SEQ ID NO:15) 5'-GTCTGTCTTGGATGTATCGC-3' (reverse) (SEQ ID NO:16) | 204 | NC_001806 (120461-120665) |
| HSV-1 CT4/5 | 5'-CAACGCTACTGCAAAAC-3' (forward) (SEQ ID NO:17) 5'-GACGGGGTGCTGTAAC-3' (reverse) (SEQ ID NO:18) | 97 | NC_001806 (127149-127426) |
| HSV-1 CT6 | 5'-CACGAACGACGGGAGCG-3' (forward) (SEQ ID NO:19) 5'-CACCCAAGGTGCTTACC-3' (reverse) (SEQ ID NO:20) | 248 | NC_001806 (132140-132388) |
| HSV-1 CT7 | 5'-CGTGATCGCCTGTCTCC-3' (forward) (SEQ ID NO:21) 5'-CATTGCCAATCGAACCC-3' (reverse) (SEQ ID NO:22) | 179 | NC_001806 (143513-143692) |
| HSV-1 gC | 5'-CCTTGCCGTGGTCCTGTGGA-3' (forward) (SEQ ID NO:23) 5'-GTTGGGGTTTGGGGTCGATG-3' (reverse) (SEQ ID NO:24) | 186 | NC_001806 (96331-96517) |

[a]Chao et al., 2002.
[b]The MT498 locus is polymorphic within the amplicon.

All PCR™ products were resolved on 7.5% polyacrylamide gels, stained with SYBR Green (Molecular Probos) and detected using a Storm 860 Fluorimager (Molecular Dynamics). Band intensities for each PCR™ product were determined using ImageQuant Software V1.2. For data shown in Table 9, band intensities for input samples were graphed, a linear regression applied, and an eqution for the line determined, all using Kaleidegraph software. The equation for the line was used to determine the total relative enrichment of the PCR™ products generated using the same primer set on DNA from the precipitated (bound) ChIP fraction. The enrichment of one DNA region over another in a given bound ChIP fraction was determined by comparing the relative enrichment quantity obtained for two DNA regions of interest. These comparisons yield fold difference of enrichment of one DNA target over another by dividing the larger relative enrichment value by the smaller relative enrichment value. In all cases, the immunoprecipitated samples were compared with serial dilutions of the input, and mean values and standard deviations were calculated.

TABLE 9

PCR ™ DETERMINATION OF THE RELATIVE ENRICHMENT OF CTCF AT IDENTIFIED CTCF MOTIF CLUSTERS FOLLOWING CHIP

| Panel[a] | PCR ™ Primers | Experiment No.[b] | Sample, No. of Cycles | Dilution[c] | Fluorescence[d] | IP Value[e] | Mean ± SD IP Value |
|---|---|---|---|---|---|---|---|
| A | Tsix Site A | | Input, 36 | 0.01 | $2.319 \times 10^6$ | | |
| | | | | 0.005 | $1.766 \times 10^6$ | | |
| | | | | 0.0025 | $1.171 \times 10^6$ | | |
| | | 1 | IP, 36 | 0.1 | $1.575 \times 10^6$ | 0.004 | |
| | | 2 | IP, 36 | 0.1 | $1.174 \times 10^6$ | 0.003 | 0.003 ± 0.001 |
| | | 3 | IP, 36 | 0.1 | $6.967 \times 10^5$ | 0.002 | |

TABLE 9-continued

PCR ™ DETERMINATION OF THE RELATIVE ENRICHMENT OF CTCF AT IDENTIFIED CTCF MOTIF CLUSTERS FOLLOWING CHIP

| Panel[a] | PCR ™ Primers | Experiment No.[b] | Sample, No. of Cycles | Dilution[c] | Fluorescence[d] | IP Value[e] | Mean ± SD IP Value |
|---|---|---|---|---|---|---|---|
| | MT498 | | Input, 35 | 0.01 | $2.219 \times 10^6$ | | |
| | | | | 0.005 | $1.159 \times 10^6$ | | |
| | | | | 0.0025 | $7.199 \times 10^5$ | | |
| | | 1 | IP, 35 | 0.1 | $8.159 \times 10^5$ | 0.003 | |
| | | 2 | IP, 35 | 0.1 | $2.298 \times 10^5$ | 0.002 | 0.002 ± 0.001 |
| | | 3 | IP, 35 | 0.1 | $2.418 \times 10^5$ | 0.002 | |
| B | CT1 | | Input, 38 | 0.1 | $2.998 \times 10^6$ | | |
| | | | | 0.05 | $1.565 \times 10^6$ | | |
| | | | | 0.025 | $4.192 \times 10^5$ | | |
| | | 1 | IP, 38 | 0.1 | $1.801 \times 10^6$ | 0.046 | |
| | | 2 | IP, 38 | 0.1 | $5.505 \times 10^5$ | 0.027 | 0.071 ± 0.060 |
| | | 3 | IP, 38 | 0.1 | $2.981 \times 10^6$ | 0.139 | |
| | CT4/5 | | Input, 35 | 0.1 | $1.1162 \times 10^6$ | | |
| | | | | 0.05 | $4.7241 \times 10^5$ | | |
| | | | | 0.025 | $2.4803 \times 10^5$ | | |
| | | 1 | IP, 35 | 0.1 | $6.4805 \times 10^5$ | 0.046 | |
| | | 2 | IP, 35 | 0.1 | $1.9476 \times 10^4$ | 0.022 | 0.056 ±0.040 |
| | | 3 | IP, 35 | 0.1 | $1.7140 \times 10^6$ | >0.1 | |
| | CT6 | | Input, 38 | 0.1 | $6.2552 \times 10^5$ | | |
| | | | | 0.05 | $3.6653 \times 10^5$ | | |
| | | | | 0.025 | $1.5552 \times 10^5$ | | |
| | | 1 | IP, 38 | 0.1 | $1.1460 \times 10^6$ | >0.1 | |
| | | 2 | IP, 38 | 0.1 | $1.5976 \times 10^5$ | 0.026 | 0.075 ± 0.043 |
| | | 3 | IP, 38 | 0.1 | $2.0132 \times 10^6$ | >0.1 | |
| | CT7 | | Input, 33 | 0.1 | $7.8063 \times 10^5$ | | |
| | | | | 0.05 | $2.8792 \times 10^5$ | | |
| | | | | 0.025 | $2.2306 \times 10^4$ | | |
| | | 1 | IP, 33 | 0.1 | $9.0591 \times 10^5$ | >0.1 | |
| | | 2 | IP, 33 | 0.1 | $4.2321 \times 10^5$ | 0.041 | 0.080 ± 0.034 |
| | | 3 | IP, 33 | 0.1 | $1.5675 \times 10^6$ | >0.1 | |
| | gC | | Input, 33 | 0.1 | $4.578 \times 10^5$ | | |
| | | | | 0.05 | $2.961 \times 10^5$ | | |
| | | | | 0.025 | $8.640 \times 10^4$ | | |
| | | 1 | IP, 33 | 0.1 | $1.268 \times 10^5$ | 0.028 | |
| | | 2 | IP, 33 | 0.1 | $4.110 \times 10^4$ | 0.023 | 0.028 ± 0.006 |
| | | 3 | IP, 33 | 0.1 | $2.129 \times 10^5$ | 0.034 | |
| C | CT2 | | Input, 35 | 0.1 | $3.003 \times 10^5$ | | |
| | | | | 0.05 | $1.869 \times 10^5$ | | |
| | | | | 0.025 | $1.300 \times 10^5$ | | |
| | | 1 | IP, 35 | 0.01 | $6.408 \times 10^4$ | 0.02 | |
| | | 2 | IP, 35 | 0.01 | $1.175 \times 10^5$ | 0.025 | 0.025 ± 0.006 |
| | | 3 | IP, 35 | 0.01 | $1.566 \times 10^5$ | 0.031 | |
| | gC | | Input, 34 | 0.1 | $8.234 \times 10^5$ | | |
| | | | | 0.05 | $5.124 \times 10^5$ | | |
| | | | | 0.025 | $3.956 \times 10^5$ | | |
| | | 1 | IP, 34 | 0.01 | $8.610 \times 10^4$ | 0.016 | |
| | | 2 | IP, 34 | 0.01 | $9.404 \times 10^4$ | 0.017 | 0.017 ± 0.001 |
| | | 3 | IP, 34 | 0.01 | $1.727 \times 10^5$ | 0.018 | |

[a]Samples included either input (mock-immunoprecipitated) or IP (immunoprecipitated with anti-CTCF) samples that were analyzed by PCR ™. Values reflect quantitations of FIG. 7A, FIG. 7B and FIG. 7C samples.

[b]ChiP analyses were conducted using samples processed from three independent experiments.

[c]Input and IP samples were serially diluted as indicated.

[d]PCR ™ products were resolved by polyacrylamide gel electrophoresis and stained with SYBR green. The band intensities were imaged on a Storm 860 instrument and measured using ImageQuant software.

[e]The data from input dilutions were fit by linear regression (Kaleidagraph). The IP fluorescence value was calculated from the linear fit of the input dilution data.

5.3.2 Results

5.3.2.1 The HSV-1 Genome Contains Clusters of Binding Motifs for the Cellular Protein CTCF Previous studies indicated that a region of the latent HSV-1 genome encompassing the LAT promoter and extending through the region encoding the LAT 5' exon is significantly enriched in the specifically modified histone H3 acetyla (K9, K14), whereas the ICP0 promoter, and UL54 are under-enriched in this histone. This suggested that chromatin boundaries might be present to separate these regions of differing transcriptional permissivity and histone composition. The resolution of the previous study focused attention on the 5-kb region upstream of the LAT promoter, and a similar 5-kb region downstream of the region encoding the LAT 5' exon. Upon examination of the sequence in these regions, clusters of two different consensus motifs (5'CTCCC3' and 5'CCCTC3') were identified for the cellular protein CTCF in these regions surrounding the hyperacetylated portion of the LAT locus. The HSV-1 genome contains clustered CTCF binding sites. An algorithm that searched for CCCTC or CTCCC motifs was used to analyze the HSV-1 genome in 1000-bp segments to determine the frequency with which these CTCF binding sites occur in the positive (direct) and negative (complement) DNA strands. Sequence analysis of the identified segments containing a high frequency of motifs reveals a clustering of the CTCF motifs. What is interesting to note is that these clusters contain multiple copies of the CTCF motifs, and that these motifs are periodically separated by intervening sequences (FIGS. 6A and 6B). For example, the cluster (CT2) that is located within the region encoding the LAT intron (FIG. 6B) contains 9 copies of the CTCF motif "CTCCC" separated by 8 reiterations of the sequence "ACG-CACCCCCA" (SEQ ID NO:25). The cluster (CT1) located upstream of the LAT promoter, near the UL/RL junction possesses a slightly different arrangement (FIG. 6A) with 23 copies of the CTCF motif "CTCCC" interspersed by alternating reiterations of "CT" and "CCCT." In addition, the CT1 cluster also contains 22 copies of the alternate CTCF motif "CCCTC" that are interleaved within the same sequence containing the CTCCC motif. For this reason in FIGS. 6A-6B, the reiteration of a single repeat motif has been depicted as a triangle (as in CT2), and the cluster containing the interleaved "double motifs" as a double triangle (CT1).

TABLE 10

| Motif | Sequence |
|---|---|
| CT1 | 5'-TAACTGGCTCCCCTCTCCCCCCTCTCCCCTCTCCCCCCTCT CCCCTCTCCCCCCCTCTCCCCTCTCCCCCCCTCTCCCCTCTCCC CCCCTCTCCCCTCTCCCCCCCTCTCCCCTCTCCCCCCCTCTCCC CTCTCCCCCCCTCTCCCCTCTCCCCCCCTCTCCCCTCTCCCCCC CTCTCCCCTCTCCCCCCCTCTCCCCTCTGCTCTTT-3' (SEQ ID NO:26) |
| CT2 | 5'-CTCTGTGGTTAACACCAGAGCCTGCCCAACATAGGCCCCCC ACTCCCACGCACCCCCACTCCCACGCACCCCCACTCCCACGCAC CCCCACTCCCACGCACCCCCACTCCCACGCACCCCCACTCCCAC GCACCCCCACTCCCACGCACCCCCACTCCCACGCACCCCCACTC CCACGCATCCCCGCGATACATCCAACACAGAC-3' (SEQ ID NO:27) |
| CT3 | 5'-CGGCGTCTGGCCGCTCCTCCCCCCGCTCCTCCCCCCGCTCC TCCCCCCGCTCCTCCCCCCGCTCCTCCCCCCGCTCCTCCCCCCG CTCCTCCCCCCGCTCCTCCCCCCGCTCCTCCCCCGCTCCTCCCC CCGCTCCTCCCCCCGCTCCTCCCCCCGCTCCTCCCCCCGCTCCT CCCCCCGCTCCTCCCCCCGCTCCTCCCCCCGCTCCTCCCCCCGC TCCTCCCCCCGCTCCCGCGGCC-3' (SEQ ID NO:28) |
| CT4/5 | 5'-CACCACCGCCCCCTCCCCAGCCCCAGCCCTCCCCAGCCCCA GCCCTCCCCGGCCCCAGCCCTCCCCGGCCCCAGCCCTCCCCGGC CCCAGCCCTCCCCGGCCCCAGCCCTCCCCGGCCCCAGCCCTCCC CGGCCCCAGCCCTCCCCGGCGCGTCCCGCGCTCCCTCGGGGGGG TTCGGGCATCTCTACCTCAGTGCCGCCAATCTCAGGTCAGAGAT CCAAACCCTCCGGGGGCGCCCGCGCACCACCACCGCCCCTCGCC CCCTCCCGCCCCTCGCCCCCTCCCGCCCCTCGCCCCCTCCCGCC CCTCGCCCCCTCCCGCCCCTCGCCCCCTCCCGCCCCTCGCCCCC TCCCGCCCCTCGCCCCCTCCCGCCCCTCGCCCCCTCCCGCCCCT CGCCCCCTCCCGCCCCTCGCCCCCTCCCGCCCCTCGCCCCCTCC CGCCCCTCGCCCCCTCCCGCCCCTCGCCCCCTCCCGCCCCTCGC CCCCTCCCGCCCCTCGCCCCCTCCCGCCCCTCGCCCCCTCCCGC CCCTCGCCCCCTCCCGCCCCTCGCCCCCTCCCGCCCCTCGCCCC CTCCCGCCCCTC-3' (SEQ ID NO:29) |
| CT6 | 3'-CTCCCCCCCTGCGCCCCCGCCTCCTCCCCCCTGCGCCCCCG CCTCCTCCCCCCTGCGCCCCCGCCTCCTCCCCCTGCGCCCCCGC CTCCTCCCCCCTGCGCCCCCGCCTCCTCCC-5' (SEQ ID NO:30) |
| CT7 | 3'-CCCTCACCCACCCACCCCTCACCCACCCACCCCTCACCCAC CCACCCCTCACCCACCCACCCCTCACCCACCCACCCCTCACCCA CCCACCCCTCACCCACCCACCCCTCACCCACCCACCCCTCACCC ACCCACCCCTC-5' (SEQ ID NO:31) |

Additional analysis of both strands of the HSV-1 genome using a motif searching algorithm identified 4 other significant clusters of these two motifs in the HSV-1 genome (FIGS. 6A-6B). These are CT3 (located within the "a" sequence region), CT4/5 (located within the RS regions at that the 3' end of the coding region for ICP4), CT6 (located in the RS regions, 5' to the ICP4 promoter) and CT7 (located within the US near the US/RS junction). As depicted in FIGS. 6A-6B, some of these CT clusters contain reiterations of only a single type of CTCF motif, as in the case of CT2 (CT3, CT6, and CT7), while CT4/5 contains 51 reiterations of the CCCTC motif, and 29 copies of the CTCCC motif interleaved. The clustered motifs are present on both strands of the genome, and possess a striking symmetry when viewed on a linear depiction of the genome and when viewed on a circular depiction, it can be seen that these CT clusters organize the HSV-1 genome into 11 separate domains. In this arrangement, each of the IE genes, as well as the 5' end of LAT, are contained within a separate domain compartment.

5.3.2.2 Chip Analysis Reveals that the CT Clusters are Enriched in CTCF During Latency Since sequence analysis revealed that the HSV-1 genome contains clustered CTCF motifs, it was sought to determine whether the cellular protein CTCF binds these clusters during latency. Chromatin immunoprecipitation (ChIP) analysis was performed on chromatin extracted from the DRG of mice latently infected with HSV-1 strain 17syn+. Dilutions of input DNA were subjected to PCR™ with each respective primer set to serve as controls for relative primer efficiencies. Furthermore, Input dilutions served as a reference for determining the relative enrichment of CTCF within the IP samples at the various target DNA clusters. To validate the ChIP, PCR™ primers for regions of the mouse genome that had been shown to be positive (Tsix) and negative (MT498) for CTCF binding were employed (Lee et al.). ChIP analysis of three independent ChIP experiments revealed significant enrichment of CTCF at the Tsix locus (FIG. 7A) when compared to the MT498 negative control, consistent with a previous report (Lee et al.). This validation provided a basis for the analysis and comparison of CTCF binding at specific viral regions. PCR™ primers specific for the various identified CTCF motif clusters were used to screen the same three IP samples for CTCF binding (FIG. 7B and FIG. 7C). As with the cellular controls, the viral CTCF clusters show significant enrichment of CTCF as opposed to the glycoprotein C (gC) region, which does not contain CTCF motif clusters. Due to the proximity and limited resolution of ChIP analysis with sonicated chromatin (500-1000 bp) PCR™ analysis was performed with primers to the CT4/5 region but may not be able to distinguish between enrichment at the CT3 region since there is less than 700-bp difference between these clusters. Nevertheless, enrichment of CTCF at the motif clusters within the HSV-1 latent genome is comparable to, and often exceeds, the enrichment seen with the cellular controls.

5.3.2.3 Clusters of CTCF Motifs are Conserved Among other Alphaherpesviruses If the clusters of CTCF motifs identified in HSV-1 play an important role in establishing chromatin boundaries in a manner that regulates latent and lytic gene transcription, one might expect these motifs to be conserved among the alphaherpesviruses. In order to investigate this hypothesis, CTCF motif analysis was performed on the genomic sequence of several other alphaherpesviruses for which sequence was available. As depicted in FIGS. 8A-8E, clusters of CTCF motifs were identified in all of the viruses analyzed, including HSV-2 strain HG-52, Cercopithecine herpesvirus 1 (Herpesvirus simiae or B-virus), varicella zoster virus (VZV) strain Dumas and Pseudorabies virus (PrV). Even though several of these viruses contained an alternative CTCF motif (CCCGC, CGCCC, CCCTG, or GTCCC) (Table 11), the striking feature is that these motifs all occurred in tandem cluster, and in a similar configuration as observed in HSV-1. Specifically, the repeats are situated in such a manner that each of the immediate early genes are bounded by a pair of these clusters (when the genome is viewed in a circular configuration). Taken together, these data indicate the clustering of these sequence motifs is highly conserved evolutionarily across even relatively distinct members of the alphaherpesvirus family.

TABLE 11

| Virus | Cluster No. | Cluster Nucleotide Position | Putative Insulator Motif Sequence (Repeat Motif Sequence) | SEQ ID NO: |
|---|---|---|---|---|
| HSV-1 | 1 | 98-320 | GGAGCGGGGGGA | SEQ ID NO:32 |
| | 2 | 988-1040 | CCCCCGCGA | SEQ ID NO:33 |
| | 3 | 5726-5877 | GGGGGTGCGTGGGAGT | SEQ ID NO:34 |
| | 4 | 9032-9212 | GGGGAGAGGGGAGAGGG | SEQ ID NO:35 |
| | 5 | 71605-71814 | TGGGGC | SEQ ID NO:36 |
| | 6 | 117158-117340 | CTCCCCTCTCCCCCCCT | SEQ ID NO:37 |
| | 7 | 120494-120645 | GCACCCCCACTCCCAC | SEQ ID NO:38 |
| | 8 | 125331-125383 | CGCGGGGGT | SEQ ID NO:39 |
| | 9 | 126051-126273 | CCGCTCCTCCCC | SEQ ID NO:40 |
| | 10 | 126571-126709 | CCCTCCCCGGCCCCAG | SEQ ID NO:41 |
| | 11 | 126810-127142 | CCGCCCCTCGCCCCCTC | SEQ ID NO:42 |
| | 12 | 132388-132513 | GGGCGGAGGAGGGGGGACGCGG | SEQ ID NO:43 |
| | 13 | 143712-143864 | TGGGTGGGTGGGGAG | SEQ ID NO:44 |
| | 14 | 145676-145845 | CCCCCTCCTCCGCCCCCGCGTC | SEQ ID NO:45 |
| | 15 | 151091-151423 | CGAGGGGCGGGAGGGGG | SEQ ID NO:46 |
| | 16 | 151524-151662 | GCCGGGGAGGGCTGGG | SEQ ID NO:47 |
| | 17 | 151960-152128 | GGAGCGGGGGGA | SEQ ID NO:48 |
| HSV-2 | 1 | 444-546 | CCCGCCGCCGGGGTC | SEQ ID NO:49 |
| | 2 | 943-1070 | CCCCTCCGACCCCCTGACG | SEQ ID NO:50 |
| | 3 | 4653-4770 | CCGCCTCCTCCTCCT | SEQ ID NO:51 |
| | 4 | 9043-9193 | CGCGCGGCGGCCGGGCGGGGG | SEQ ID NO:52 |
| | 5 | 72098-72266 | GGCAGGGGCGGCTGG | SEQ ID NO:53 |
| | 6 | 106045-106165 | CCTCCCGCC | SEQ ID NO:54 |
| | 7 | 118057-118207 | GCGCGCCCCCGCCCGGCCGCC | SEQ ID NO:55 |
| | 8 | 123643-123779 | GCCCGACCCCC | SEQ ID NO:56 |
| | 9 | 126180-126307 | GGGGGTCGGAGGGGCGTCA | SEQ ID NO:57 |
| | 10 | 126766-126806 | CCGGCGGCGGGGACC | SEQ ID NO:58 |
| | 11 | 127466-127490 | CCCGCGGCCGCCTCC | SEQ ID NO:59 |
| | 12 | 127672-127914 | CCGCCCGCCCGACCC | SEQ ID NO:60 |
| | 13 | 133227-133644 | CCGGGGGGACGGG | SEQ ID NO:61 |
| | 14 | 144419-144448 | CCCCCCCGTCG | SEQ ID NO:62 |
| | 15 | 148097-148366 | CCCCGTCC | SEQ ID NO:63 |
| | 16 | 158828-154070 | CGGGGGTCGGGCGGG | SEQ ID NO:64 |
| | 17 | 154252-154287 | CGCGGGGGAGGCGGC | SEQ ID NO:65 |
| Herpes B virus | 1 | 119-156 | CCGGGAGCCCGC | SEQ ID NO:66 |
| | 2 | 1289-1356 | GCGGGCGGTCC | SEQ ID NO:67 |
| | 3 | 3548-3634 | GCCCAGGCCCGC | SEQ ID NO:68 |
| | 4 | 3658-3738 | GCCCGGCGCCCAAGTCGC | SEQ ID NO:69 |
| | 5 | 5164-5245 | CCAGAAGCAGAGAGGGGCGGGGGCTCC | SEQ ID NO:70 |
| | 6 | 5247-5367 | GGAGAAGCACAAGACCCACACACGCGCG GCAGGGGCACGGAGGCGGGGGGAGGCCC GGGA | SEQ ID NO:71 |
| | 7 | 6057-6167 | AGGGGGGCGAGGGGA | SEQ ID NO:72 |
| | 8 | 43039-43135 | GGGGGTGCGGGGGCGGT | SEQ ID NO:73 |
| | 9 | 71555-71764 | GGGCAGCAG | SEQ ID NO:74 |
| | 10 | 115968-116247 | CCTCCCCTCCCCCGCGCCCC | SEQ ID NO:75 |
| | 11 | 119694-119796 | CCTTCGCCTCGCCCG | SEQ ID NO:76 |
| | 12 | 120491-120611 | CTCCCGGGCCTGCCCCCGCCTCCGTGCCC CTGCCGCGCGTGTGTGGGTCTCGGGCTTC TC | SEQ ID NO:77 |
| | 13 | 120613-120694 | GGGAGCCCCCGCCCCTCTCTGCTTCTG | SEQ ID NO:78 |
| | 14 | 124502-124569 | GCGGACCGCGC | SEQ ID NO:79 |
| | 15 | 125702-125739 | GGGCGGGCTCCC | SEQ ID NO:80 |
| | 16 | 125966-126051 | CTCCCGTCCCC | SEQ ID NO:81 |
| | 17 | 133423-133805 | CCCCGCGCACCCCTCGCCCTCCCCTC | SEQ ID NO:82 |
| | 18 | 139332-139450 | CCACCCCCGCCCCCACCA | SEQ ID NO:83 |
| | 19 | 148619-149001 | GGGCGAGGGGTGCGCGGGGGAGGGGA | SEQ ID NO:84 |
| | 20 | 156373-156458 | GGGAGGGGGAC | SEQ ID NO:85 |
| | 21 | 156685-156722 | CCGGGAGCCCGC | SEQ ID NO:86 |
| Pseudo-rabies | 1 | 746-963 | CCTTTCCCCCAACCCCCTCGTTCCCC | SEQ ID NO:87 |
| | 2 | 2320-2682 | GGGGAGATGGGGAGAGGAGAT | SEQ ID NO:88 |
| | 3 | 16212-16802 | GGGACGGAGGGGAGA | SEQ ID NO:89 |
| | 4 | 32674-32879 | CCCCAAGTCC | SEQ ID NO:90 |
| | 5 | 50181-50276 | GGGACGGCGGG | SEQ ID NO:91 |

TABLE 11-continued

| Virus | Cluster No. | Cluster Nucleotide Position | Putative Insulator Motif Sequence (Repeat Motif Sequence) | SEQ ID NO: |
|---|---|---|---|---|
| | 6 | 63110-63319 | CGCCCTCTCTCCCAC | SEQ ID NO:92 |
| | 7 | 63388-63459 | AAGGGGTCTCT | SEQ ID NO:93 |
| | 8 | 80325-80545 | TGGGGGAGAGGA | SEQ ID NO:94 |
| | 9 | 95518-95623 | GGGGGGAGTCT | SEQ ID NO:95 |
| | 10 | 101376-101501 | GCATAACCCCTCCCCCTAATCT | SEQ ID NO:96 |
| | 11 | 108490-108688 | TGTGGTGGTCTCTGTGTTG | SEQ ID NO:97 |
| | 12 | 117279-117687 | GGGGTGGAGACGGTGGAGGGAGAGGGG AGTGGGAT | SEQ ID NO:98 |
| | 13 | 117752-117841 | GGGGGAGTCC | SEQ ID NO:99 |
| | 14 | 126761-126850 | GGACTCCCCC | SEQ ID NO:100 |
| | 15 | 126915-127323 | CTCTCCCTCCACCGTCTCCACCCCATCCC ACTCCC | SEQ ID NO:101 |
| | 16 | 135914-136112 | ACCACCACACAAGACAGAG | SEQ ID NO:102 |
| | 17 | 143101-143226 | GGGGGAGGGGTTATGCAGATTA | SEQ ID NO:103 |
| Varicella | 1 | 13953-14208 | GAGGGAGAGGCGGAG | SEQ ID NO:104 |
| | 2 | 20692-21017 | GCGGGATCGGGCTTTCGGGAAGCGGCCG AGGTGGGCGCGACG | SEQ ID NO:105 |
| | 3 | 41453-41519 | GCCCGCGCA | SEQ ID NO:106 |
| | 4 | 109762-109907 | CCCCGCCGATGGGGAGGGGGCGCGGTA | SEQ ID NO:107 |
| | 5 | 119990-120135 | CATCGGCGGGGTACCGCGCCCCCTCCC | SEQ ID NO:108 |

Example 4

Development of HSV-1 Insulater Cassette

To demonstrate that the HSV-1 Insulator Cassette (containing B1 and B2) is capable of maintaining sustained expression of a reporter gene in the context of a gutted HSV-1 vector (Insulated Viral Artificial Chromosome or IVAC), the test vectors (and a control vector lacking the insulators) may be delivered to mouse dorsal root ganglia. Quantitative analysis of the transgene expression as a function of time (e.g., 4, 14, 21, 40, 80, 160, 320 days, etc.) may then be used as an indication of the effectiveness of the disclosed constructs.

To demonstrate that the insulation cassette works in the context of a transgenic animal (e.g., a transgenic mouse) following insertion into cellular chromosomes, populations of transgenic mice may be created (as well as a control group that lacks the insulation cassette). Assessment of tissue-specific expression may be determined as well as analysis of changes in the surrounding chromatin profile (e.g., by ChIP using antibodies specific for different histone modifications) to assess ability of insulator to protect surrounding chromatin from effects of the enhancer contained within the cassette. Quantitative analysis of the transgene expression as a function of time (e.g., 4, 14, 21, 40, 80, 160, 320 days) in a number of individual founders (taking into account different sites of integration) may also be used as an indication of the effectiveness of the disclosed constructs.

To further characterize functional properties of B1 and B2 and to identify proteins involved in function, analysis of enhancer-blocking properties of B1 as well as cell-type specific characteristics of B1 and B2 may be performed using transient assays. Likewise, yeast-one hybrid analysis of regions to the left and right of the CT elements may be examined to identify cellular proteins that confer: 1) insulation properties, 2) enhancer-blocking properties, as well as 3) cell-type specific properties. In a similar fashion, yeast-two hybrid analyses may be performed of regions to the left and right of the CT elements to identify cellular proteins that confer: 1) insulation properties, 2) enhancer-blocking properties; and as well 3) cell-type specific properties, in combination with CTCF binding.

5.5 Example 5

Sequence of Exemplary Human Herpesvirus Genomes

Examples of illustrative human Herpesvirus genomes from which insulator cassette sequences may be obtained for use in practice of the present invention are illustrated in SEQ ID NO: 109, SEQ ID NO:110, and SEQ ID NO:11 in the accompanying sequence listing. While no means an exhaustive list, the sequences of human herpesvirus 1, 2, and 3 are representative of the viral genomes from which the insulator sequences of the present invention may be obtained.

SEQ ID NO:109 Human Herpesvirus 1 (GenBank Accession No. NC_001806)

SEQ ID NO:110 Human Herpesvirus 2 (GenBank Accession No. NC_001798)

SEQ ID NO:111 Human Herpesvirus 3 (GenBank Accession No. NC_001348)

6.0 REFERENCES

The following references, to the extent that they provide exemplary procedural or other details supplementary to those set forth herein, are specifically incorporated herein by reference.

U.S. Pat. No. 4,237,224, issued Dec. 2, 1980.
U.S. Pat. No. 4,554,101, issued Nov. 19, 1985.
U.S. Pat. No. 4,683,195, issued Jul. 28, 1987.
U.S. Pat. No. 4,683,202, issued Jul. 28, 1987.
U.S. Pat. No. 4,800,159, issued Jan. 24, 1989.
U.S. Pat. No. 4,883,750, issued Nov. 28, 1989.
U.S. Pat. No. 5,145,684, issued Sep. 8, 1992.
U.S. Pat. No. 5,399,363, issued Mar. 21, 1995.
U.S. Pat. No. 5,466,468, issued Nov. 14, 1995.
U.S. Pat. No. 5,543,158, issued Apr. 6, 1996.
U.S. Pat. No. 5,552,157, issued Sep. 3, 1996.
U.S. Pat. No. 5,565,213, issued Oct. 15, 1996.
U.S. Pat. No. 5,567,434, issued Oct. 22, 1996.
U.S. Pat. No. 5,602,306, issued Feb. 11, 1997.
U.S. Pat. No. 5,639,940, issued Jun. 17, 1997.
U.S. Pat. No. 5,641,515, issued Jun. 24, 1997.

U.S. Pat. No. 5,720,936, issued Feb. 24, 1998.
U.S. Pat. No. 5,738,868, issued Apr. 14, 1998.
U.S. Pat. No. 5,741,516, issued Apr. 21, 1998.
U.S. Pat. No. 5,795,587, issued Aug. 18, 1998.
Int. Pat. Appl. No. PCT/US87/00880.
Int. Pat. Appl. No. PCT/US89/01025.
Int. Pat. Appl. Publ. No. WO 88/10315.
Int. Pat. Appl. Publ. No. WO 89/06700.
Eur. Pat. Appl. Publ. No. EP 0329822.
Eur. Pat. Appl. Publ. No. 320,308.
Great Britain Appl. No. 2202328.
Ahmed, M., M. Lock, C. G. Miller, and N. W. Fraser. 2002. Regions of the herpes simplex virus type 1 latency-associated transcript that protect cells from apoptosis in vitro and protect neural cells in vivo. J. Virol 76:717-729.
Allen and Choun, "Large unilamellar liposomes with low uptake into the reticuloendothelial system," *FEBS Lett.,* 223:42-46, 1987.
Angel, Bauman, Stein, Dellus, Rahmsdorf and Herrlich, "12-0-tetradecanoyl-phorbol-13-acetate induction of the human collagenase gene is mediated by an inducible enhancer element located in the 5' flanking region," *Mol. Cell. Biol.,* 7:2256, 1987a.
Angel, Imagawa, Chiu, Stein, Imbra, Rahmsdorf, Jonat, Herrlich and Karin, "Phorbol ester-inducible genes contain a common cis element recognized by a TPA-modulated trans-acting factor," *Cell,* 49:729, 1987b.
Atchison and Perry, "The role of the kappa enhancer and its binding factor NF-kappa B in the developmental regulation of kappa gene transcription," *Cell,* 48:121, 1987.
Awad, T. A., J. Bigler, J. E. Ulmer, Y. J. Hu, J. M. Moore, M. Lutz, P. E. Neiman, S. J. Collins, R. Renkawitz, V. V. Lobanenkov, and G. N. Filippova. 1999. Negative transcriptional regulation mediated by thyroid hormone response element 144 requires binding of the multivalent factor CTCF to a novel target DNA sequence. J Biol Chem 274:27092-8.
Balazsovits et al., "Analysis of the effect of liposome encapsulation on the vesicant properties, acute and cardiac toxicities, and antitumor efficacy of doxorubicin," *Cancer Chemother. Pharmacol.,* 23:81-86, 1989.
Banerji, Olson and Schaffner, "A lymphocyte-specific cellular enhancer is located downstream of the joining region in immunoglobulin heavy-chain genes," *Cell,* 35:729, 1983.
Banerji, Rusconi and Schaffner, "Expression of a β-globin gene is enhanced by remote SV40 DNA sequences," *Cell,* 27:299, 1981.
Baranov et al., "Local and distant transfection of mdx muscle fibers with dystrophin and LacZ genes delivered in vivo by synthetic microspheres," *Gene Ther.,* 6:1406-14, 1999.
Bell, A. C., A. G. West, and G. Felsenfeld. 1999. The protein CTCF is required for the enhancer blocking activity of vertebrate insulators. Cell 98:387-96.
Bell, A. C., and G. Felsenfeld. 2000. Methylation of a CTCF-dependent boundary controls imprinted expression of the Igf2 gene. Nature 405:482-5.
Benson, "Tandem repeats finder: a program to analyze DNA sequences," *Nucleic Acids Res.,* 27:573-80, 1999.
Berkhout, Silverman and Jeang, "tat trans-activates the human immunodeficiency virus through a nascent RNA target," *Cell,* 59:273, 1989.
Berman and Hill, "Spontaneous ocular shedding of HSV-1 in latently infected rabbits," *Investig. Opthalmol. Vis. Sci.,* 26:587-590, 1985.
Berthomme, H., J. Lokensgard, L. Yang, T. Margolis, and L. T. Feldman. 2000. Evidence for a bidirectional element located downstream from the herpes simplex virus type 1 latency-associated promoter that increases its activity during latency. J. Virol. 74:3613-3622.
Berthomme, H., J. Thomas, P. Texier, A. Epstein, and L. T. Feldman. 2001. Enhancer and long-term expression functions of herpes simplex virus type 1 latency-associated promoter are both located in the same region. J Virol 75:4386-93.
Berthomme, Lokensgard, Yang, Margolis and Feldman, "Evidence for a bidirectional element located downstream from the herpes simplex virus type 1 latency-associated promoter that increases its activity during latency," *J. Virol.,* 74:3613-3622, 2000.
Bestor, "Gene silencing as a threat to the success of gene therapy." *J. Clin. Invest.,* 105:409-11, 2000.
Blanar, Baldwin, Flavell and Sharp, "A gamma-interferon-induced factor that binds the interferon response sequence of the MHC Class I gene, H-2Kb," *EMBO J.,* 8:1139, 1989.
Bloom, D. C., G. B. Devi-Rao, J. M. Hill, J. G. Stevens, and E. K. Wagner. 1994. Molecular analysis of herpes simplex virus type 1 during epinephrine induced reactivation of latently infected rabbits in vivo. J. Virol. 68:1283-1292.
Bloom, D. C., J. T. Hill, E. K. Wagner, L. F. Feldman, and J. G. Stevens. 1996. A 348-bp region in the latency associated transcript facilitates herpes simplex virus type 1 reactivation. J. Virol. 70:2449-2459.
Bloom, Devi-Rao, Hill, Stevens and Wagner, "Molecular analysis of herpes simplex virus type 1 during epinephrine induced reactivation of latently infected rabbits in vivo," *J. Virol.,* 68:1283-92, 1994.
Bloom, Hill, Wagner, Feldman and Stevens, "A 348-bp region in the latency-associated transcript facilitates herpes simplex virus type 1 reactivation," *J. Virol.,* 70:2449-59, 1996.
Bodine and Ley, "An enhancer element lies 3' to the Human A gamma globin gene," *EMBO J.,* 6:2997, 1987.
Boshart, Weber, Jahn, Dorsch-Hasler, Fleckenstein and Schaffner, "A very strong enhancer is located upstream of an immediate early gene of human cytomegalovirus," *Cell,* 41:521, 1985.
Bosze, Thiesen and Charnay, "A transcriptional enhancer with specificity for erythroid cells is located in the long terminal repeat of the friend murine leukemia virus," *EMBO J.,* 5:1615, 1986.
Braddock, Chambers, Wilson, Esnouf, Adams, Kingsman and Kingsman, "HIV-I tat activates presynthesized RNA in the nucleus," *Cell,* 58:269, 1989.
Bulla and Siddiqui, "The Hepatitis B virus enhancer modulates transcription of the Hepatitis B virus surface-antigen gene from an internal location," *J. Virol.,* 62:1437, 1986.
Buning et al., "Receptor targeting of adeno-associated virus vectors," *Gene Ther.,* 10:1142-51, 2003.
Caldovic and Hackett Jr., "Development of position-independent expression vectors and their transfer into transgenic fish," *Mol. Mar. Biol. Biotechnol.,* 4(1):51-61, 1995.
Campbell and Villarreal, "Functional analysis of the individual enhancer core sequences of polyoma virus: cell-specific uncoupling of DNA replication from transcription," *Mol. Cell. Biol.,* 8:1993, 1988.
Campere and Tilghman, "Postnatal repression of the α-fetoprotein gene is enhancer independent," *Genes and Dev.,* 3:537, 1989.
Campo, Spandidos, Lang and Wilkie, "Transcriptional control signals in the genome of bovine papilloma virus Type 1," *Nature,* 303:77, 1983.
Capecchi, "High efficiency transformation by direct microinjection of DNA into cultured mammalian cells," *Cell,* 22(2):479-488, 1980.

Carver, Dalrymple, Wright, Cottom, Reeves, Gibson, Keenan, Barrass, Scott, Colman, et al., "Transgenic livestock as bioreactors: stable expression of human α-1-antitrypsin by a flock of sheep," *Biotechnology NY,* 11(11): 1263-1270, 1993.

Celander and Haseltine, "Glucocorticoid regulation of murine leukemia virus transcription elements is specified by determinants within the viral enhancer region," *J. Virology,* 61:269, 1987.

Celander, Hsu and Haseltine, "Regulatory elements within the murine leukemia virus enhancer regions mediate glucocorticoid responsiveness," *J. Virology,* 62:1314, 1988.

Chandler, Maler and Yamamoto, "DNA sequences bound specifically by glucocorticoid receptor in vitro render a heterlogous promoter hormone responsive in vivo," *Cell,* 33:489, 1983.

Chandran, Roy, Mishra, "Recent trends in drug delivery systems: liposomal drug delivery system—preparation and characterization," *Indian J. Exp. Biol.,* 35(8):801-809, 1997.

Chang, Erwin and Lee, "Glucose-regulated protein (GRP94 and GRP78) genes share common regulatory domains and are coordinately regulated by common trans-acting factors," *Mol. Cell. Biol.,* 9:2153, 1989.

Chao et al., "Several log increase in therapeutic transgene delivery by distinct adeno-associated viral serotype vectors," *Mol. Ther.,* 2:619-23, 2000.

Chao, Monahan, Liu, Samulski and Walsh, "Sustained and complete phenotype correction of hemophilia B mice following intramuscular injection of AAV1 serotype vectors," *Mol. Ther.,* 4:217-22, 2001.

Chao, W., K. D. Huynh, R. J. Spencer, L. S. Davidow, and J. T. Lee. 2002. CTCF, a candidate trans-acting factor for X-inactivation choice. Science 295:345-7.

Chatterjee, Lee, Rentoumis and Jameson, "Negative regulation of the thyroid-stimulating hormone α gene by thyroid hormone: Receptor interaction adjacent to the TATA box," *Proc. Natl. Acad. Sci. U.S.A.,* 86:9114, 1989.

Chen and Okayama, "High-efficiency transformation of mammalian cells by plasmid DNA," *Mol. Cell. Biol.,* 7:2745-2752, 1987.

Chen, Kramer, Schaffer and Coen, "A viral function represses accumulation of transcripts from productive-cycle genes in mouse ganglia latently infected with herpes simplex virus," *J. Virol.,* 71:5878-84, 1997.

Chen, Schmidt, Goins and Glorioso, "Two herpes simplex virus type 1 latency-active promoters differ in their contributions to latency-associated transcript expression during lytic and latent infections," *J. Virol.,* 69:7899-908, 1995.

Choi, Chen, Kriegler and Roninson, "An altered pattern of cross-resistance in multi-drug-resistant human cells results from spontaneous mutations in the MDR-1 (P-glycoprotein) gene," *Cell,* 53:519, 1988.

Clark, Sferra and Johnson, "Recombinant adeno-associated viral vectors mediate long-term transgene expression in muscle," *Hum. Gene Ther.,* 8:659-69, 1997.

Cohen, Walter and Levinson, "A repetitive sequence element 3' of the human c-Ha-ras1 gene has enhancer activity," *J. Cell. Physiol.,* 5:75, 1987.

Costa, Lai, Grayson and Darnell, "The cell-specific enhancer of the mouse transthyretin (prealbumin) gene binds a common factor at one site and a liver-specific factor(s) at two other sites," *Mol. Cell. Biol.,* 8:81, 1988.

Coune, "Liposomes as drug delivery system in the treatment of infectious diseases: potential applications and clinical experience," *Infection,* 16(3):141-147, 1988.

Couvreur et al., "Nanocapsules, a new lysosomotropic carrier," *FEBS Lett.,* 84:323-326, 1977.

Couvreur et al., "Tissue distribution of antitumor drugs associated with polyalkylcyanoacrylate nanoparticles," *J. Pharm. Sci.,* 69(2):199-202, 1980.

Couvreur, "Polyalkyleyanoacrylates as colloidal drug carriers," *Crit. Rev. Ther. Drug Carrier Syst.,* 5:1-20, 1988.

Cozzi, Tucker, Langford, Pino-Chavez, Wright, O'Connell, Young, Lancaster, McLanghlin, Hunt, Bordin, White, "Characterization of pigs transgenic for human decay-accelerating factor," *Transplantation,* 64(10):1383-1392, 1997.

Cripe, Haugen, Turk, Tabatabai, Schmid, Durst, Gissmann, Roman and Turek, "Transcriptional regulation of the human papilloma virus-16 E6-E7 promoter by a keratinocyte-dependent enhancer, and by viral E2 trans-activator and repressor gene products: Implications for cervical carcinogenesis," *EMBO J.,* 6:3745, 1987.

Croyle, Cheng and Wilson, "Development of formulations that enhance physical stability of viral vectors for gene therapy," *Gene Ther.,* 8:1281-90, 2001.

Culotta and Hamer, "Fine mapping of a mouse metallothionein gene metal-response element," *Mol. Cell. Biol.,* 9:1376, 1989.

Curiel, Agarwal, Wagner, Cotten, "Adenovirus enhancement of transferrin-polylysine-mediated gene delivery," *Proc. Natl. Acad. Sci. USA,* 88(19):8850-8854, 1991.

Dandolo, Blangy and Kamen, "Regulation of polyma virus transcription in murine embryonal carcinoma cells," *J. Virology,* 47:55, 1983.

Das, P. M., K. Ramachandran, J. vanWert, and R. Singal. 2004. Chromatin immunoprecipitation assay. Biotechniques 37:961-9.

De Villiers, Schaffner, Tyndall, Lupton and Kamen, "Polyoma virus DNA replication requires an enhancer," *Nature,* 312:242, 1984.

DeLuca, McCarthy and Schaffer, "Isolation and characterization of deletion mutants of herpes simplex virus type 1 in the gene encoding immediate-early regulatory protein ICP4," *J. Virol.,* 56:558-70, 1985.

Deschamps, Meijlink and Verma, "Identification of a transcriptional enhancer element upstream from the proto-oncogene Fos," *Science,* 230:1174, 1985.

Devi-Rao, Aguilar, Rice, Garza, Bloom, Hill and Wagner, "Herpes simplex virus genome replication and transcription during induced reactivation in the rabbit eye," *J. Virol.,* 71:7039-47, 1997.

Devi-Rao, Bloom, Stevens and Wagner, "Herpes simplex virus type 1 DNA replication and gene expression during explant induced reactivation of latently infected murine sensory ganglia," *J. Virol.,* 68:1271-82, 1994.

Devi-Rao, G. B., D. C. Bloom, J. G. Stevens, and E. K. Wagner. 1994. Herpes simplex virus type 1

DNA replication and gene expression during explant induced reactivation of latently infected murine sensory ganglia. J. Virol. 68:1271-1282.

Dobie, Mehtali, McClenaghan and Lathe, "Variegated gene expression in mice," *Trends Genet.,* 13:127-30, 1997.

Dobson, A. T., F. Sederati, R. G. Devi, W. M. Flanagan, M. J. Farrell, J. G. Stevens, E. K. Wagner, and L. T. Feldman. 1989. Identification of the latency-associated transcript promoter by expression of rabbit beta-globin mRNA in mouse sensory nerve ganglia latently infected with a recombinant herpes simplex virus. J Virol 63:3844-51.

Dobson, A. T., T. P. Margolis, W. A. Gomes, and L. T. Feldman. 1995. In vivo deletion analysis of the Herpes simplex virus type 1 latency associated transcript promoter. J. Virol. 69:2264-2270.

Dobson, Margolis, Sedarati, Stevens and Feldman, "A latent, nonpathogenic HSV-1-derived vector stably expresses beta-galactosidase in mouse neurons," *Neuron* 5:353-60, 1990.

Douglas, Davis, Illum, "Nanoparticles in drug delivery," *Crit. Rev. Ther. Drug Carrier Syst.,* 3(3):233-261, 1987.

Dressler, G. R., D. L. Rock, and N. W. Fraser. 1987. Latent herpes simplex virus type 1 DNA is not extensively methylated in vivo. J Gen Virol 68:1761-1765.

Du, M., L. G. Beatty, W. Zhou, J. Lew, C. Schoenherr, R. Weksberg, and P. D. Sadowski. 2003. Insulator and silencer sequences in the imprinted region of human chromosome 11p15.5. Hum Mol Genet 12:1927-39.

Ebert, Selgrath, DiTullio, Denman, Smith, Memon, Schindler, Monastersky, Vitale, Gordon, "Transgenic production of a variant of human tissue-type plasminogen activator in goat milk: generation of transgenic goats and analysis of expression," *Biotechnology NY,* 9(9):835-838, 1991.

Edbrooke, Burt, Cheshire and Woo, "Identification of cis-acting sequences responsible for phorbol ester induction of human serum amyloid a gene expression via a nuclear-factor-κB-like transcription factor," *Mol. Cell. Biol.,* 9:1908, 1989.

Edlund, Walker, Barr and Rutter, "Cell-specific expression of the rat insulin gene: Evidence for role of two distinct 5' flanking elements," *Science,* 230:912, 1985.

Edwards and Berry, "The efficiency of simulation-based multiple comparisons," *Biometrics,* 43:913-28, 1987.

Engel, N., A. G. West, G. Felsenfeld, and M. S. Bartolomei. 2004. Antagonism between DNA hypermethylation and enhancer-blocking activity at the H19 DMD is uncovered by CpG mutations. Nat Genet 36:883-8.

Faller and Baltimore, "Liposome encapsulation of retrovirus allows efficient super infection of resistant cell lines," *J. Virol.,* 49(1):269-272, 1984.

Fallon, "Transgenic insect cells: mosquito cell mutants and the dihydrofolate reductase gene," *Cytotechnology,* 20(1-3):23-31, 1996.

Farrell, M. J., A. T. Dobson, and L. T. Feldman. 1991. Herpes simplex virus latency-associated transcript is a stable intron. Proc. Natl. Acad. Sci. U.S.A. 88:790-794.

Fechheimer et al., "Transfection of mammalian cells with plasmid DNA by scrape loading and sonication loading," *Proc. Natl. Acad. Sci. USA,* 84:8463-8467, 1987.

Feldman, L., A. R. Ellison, C. C. Voytek, L. Yang, P. Krause, and T. P. Margolis. 2002. Spontaneous molecular reactivation of herpes simplex virus type 1 latency in mice. Proc Natl Acad Sci USA 99:978-83.

Feng and Holland, "HIV-I tat trans-activation requires the loop sequence within tar," *Nature,* 334:6178, 1988.

Firak and Subramanian, "Minimal transcription enhancer of simian virus 40 is a 74-base-pair sequence that has interacting domains," *Mol. Cell. Biol.,* 6:3667, 1986.

Fisher et al., "Recombinant adeno-associated virus for muscle directed gene therapy," *Nat. Med.,* 3:306-12, 1997.

Foecking and Hofstetter, "Powerful and versatile enhancer-promoter unit for mammalian expression vectors," *Gene,* 45(1):101-105, 1986.

Fraites, Jr., et al., "Correction of the enzymatic and functional deficits in a model of Pompe disease using adeno-associated virus vectors," *Mol. Ther.,* 5:571-78, 2002.

Fraley et al., "Entrapment of a bacterial plasmid in phospholipid vesicles: Potential for gene transfer," *Proc. Natl. Acad. Sci. USA,* 76:3348-3352, 1979.

Franz, Mueller, Haartong, Frey, Katus, "Transgenic animal models: new avenues in cardiovascular physiology," *J. Mol. Med.,* 75(2):115-119, 1997.

Fresta and Puglisi, "Application of liposomes as potential cutaneous drug delivery systems. In vitro and in vivo investigation with radioactively labelled vesicles," *J. Drug Target,* 4(2):95-101, 1996.

Frohman, Downs, Kashio, Brinster, "Tissue distribution and molecular heterogeneity of human growth hormone-releasing factor in the transgenic mouse," *Endocrinology,* 127(5):2149-2156, 1990.

Fromm, Taylor, Walbot, "Expression of genes transferred into monocot and dicot plant cells by electroporation," *Proc. Natl. Acad. Sci. USA,* 82(17):5824-5828, 1985.

Fujita, Shibuya, Hotta, Yamanishi and Taniguchi, "Interferon-β gene regulation: tandemly repeated sequences of a synthetic 6-bp oligomer function as a virus-inducible enhancer," *Cell,* 49:357, 1987.

Gabizon and Papahadjopoulos, "Liposomes formulations with prolonged circulation time in blood and enhanced uptake by tumors," *Proc. Natl. Acad. Sci. USA,* 85:6949-6953, 1988.

Gao et al., "Novel adeno-associated viruses from rhesus monkeys as vectors for human gene therapy," *Proc. Natl. Acad. Sci. USA,* 99:11854-59, 2002.

Gilles, Morris, Oi and Tonegawa, "A tissue-specific transcription enhancer element is located in the major intron of a rearranged immunoglobulin heavy-chain gene," *Cell,* 33:717, 1983.

Gloss, Bernard, Seedorf and Klock, "The upstream regulatory region of the human papilloma virus-16 contains an E2 protein-independent enhancer which is specific for cervical carcinoma cells and regulated by glucocorticoid hormones," *EMBO J.,* 6:3735, 1987.

Godbout, Ingram and Tilghman, "Fine-structure mapping of the three mouse α-fetoprotein gene enhancers," *Mol. Cell. Biol.,* 8:1169, 1988.

Goins, Sternberg, Croen, Krause, Hendricks, Fink, Straus, Levine and Glorioso, "A novel latency-active promoter is contained within the herpes simplex virus type 1 UL flanking repeats," *J. Virol.,* 68:2239-52, 1994.

Goins, W. F., L. R. Sternberg, K. D. Croen, P. R. Krause, R. L. Hendricks, D. J. Fink, S. E. Straus, M. Levine, and J. C. Glorioso. 1994. A novel latency-active promoter is contained within the herpes simplex virus type 1 UL flanking repeats. J. Virol. 68:2239-2252.

Goodbourn and Maniatis, "Overlapping positive and negative regulatory domains of the human β-interferon gene," *Proc. Natl. Acad. Sci. USA,* 85:1447, 1988.

Goodbourn, Burstein and Maniatis, "The human β-interferon gene enhancer is under negative control," *Cell,* 45:601, 1986.

Gopal, "Gene transfer method for transient gene expression, stable transfection, and cotransfection of suspension cell cultures," *Mol. Cell Biol.,* 5:1188-1190, 1985.

Graham and van der Eb, "Transformation of rat cells by DNA of human adenovirus 5," *Virol.,* 54(2):536-539, 1973.

Greene, Böhnlein and Ballard, "HIV-1, and normal T-cell growth: Transcriptional strategies and surprises," *Immunol. Today,* 10:272, 1989.

Gressens and Martin, "In situ polymerase chain reaction: localization of HSV-2 DNA sequences in infections of the nervous system," *J. Virol. Methods,* 46:61-83, 1994.

Grimm, Kay and Kleinschmidt, "Helper virus-free, optically controllable, and two-plasmid-based production of adeno-associated virus vectors of serotypes 1 to 6," *Mol. Ther.,* 7:839-50, 2003.

Grosschedl and Baltimore, "Cell-type specificity of immunoglobulin gene expression is regulated by at least three DNA sequence elements," *Cell,* 41:885, 1995.

Harland and Weintraub, "Translation of mRNA injected into Xenopus oocytes is specifically inhibited by antisense RNA," *J. Cell Biol.,* 101(3):1094-1099, 1985.

Haskell and Bowen, "Efficient production of transgenic cattle by retroviral infection of early embryos," *Mol. Reprod. Dev.,* 40(3):386-390, 1995.

Haslinger and Karin, "Upstream promoter element of the human metallothionein-II gene can act like an enhancer element," *Proc. Natl. Acad. Sci. USA,* 82:8572, 1985.

Hauber and Cullen, "Mutational analysis of the trans-activation-responsive region of the human immunodeficiency virus Type I long terminal repeat," *J. Virol.,* 62:673, 1988.

Hauck and Xiao, "Characterization of tissue tropism determinants of adeno-associated virus type 1," *J. Virol.,* 77:2768-74, 2003.

Heath and Martin, "The development and application of protein-liposome conjugation techniques," *Chem. Phys. Lipids,* 40:347-358, 1986.

Heath et al., "Liposome-mediated delivery of pteridine antifolates to cells: in vitro potency of methotrexate and its α and gamma substituents," *Biochim. Biophys. Acta,* 862:72-80, 1986.

Hen, Borrelli, Fromental, Sassone-Corsi and Chambon, "A mutated polyoma virus enhancer which is active in undifferentiated embryonal carcinoma cells is not repressed by adenovirus-2 E1A products," *Nature,* 321:249, 1986.

Henry-Michelland et al., "Attachment of antibiotics to nanoparticles; Preparation, drug-release and antimicrobial activity in vitro," *Int. J. Pharm.,* 35:121-127, 1987.

Hensel, Meichle, Pfizenmaier and Kronke, "PMA-responsive 5' flanking sequences of the human TNF gene," *Lymphokine Res.,* 8:347, 1989.

Herr and Clarke, "The SV40 enhancer is composed of multiple functional elements that can compensate for one another," *Cell,* 45:461, 1986.

Herrera, F. J., and S. J. Triezenberg. 2004. VP16-dependent association of chromatin-modifying coactivators and underrepresentation of histones at immediate-early gene promoters during herpes simplex virus infection. J Virol 78:9689-96.

Hill, Dudley, Shimomura and Kaufman, "Quantitation and kinetics of induced HSV-1 ocular shedding," *Curr. Eye Res.,* 5:241-46, 1986.

Hill, J. M., F. Sedarati, R. T. Javier, E. K. Wagner, and J. G. Stevens. 1990. Herpes simplex virus latent phase transcription facilitates in vivo reactivation. Virology 174:117-25.

Hill, Sedarati, Javier, Wagner and Stevens, "Herpes simplex virus latent phase transcription facilitates in vivo reactivation," *Virology,* 174:117-25, 1990.

Hill, Wen and Halford, "Pathogenesis and molecular biology of HSV latency and ocular reactivation in the rabbit," In Herpes Simplex Virus Protocols, Vol. 10., Brown and MacLean (ed.), Humana Press, Totowa, N.J., pp. 291-316, 1998.

Hirochika, Browker and Chow, "Enhancers and trans-acting E2 transcriptional factors of papilloma viruses," *J. Virol.,* 61:2599, 1987.

Hirsch, Gaugler, Deagostini-Bauzin, Bally-Cuif and Gordis, "Identification of positive and negative regulatory elements governing cell-type-specific expression of the neural-cell-adhesion-molecule gene," *Mol. Cell. Biol.,* 10:1959, 1990.

Holbrook, Gulino and Ruscetti, "cis-acting transcriptional regulatory sequences in the Gibbon ape leukemia virus (GALV) long terminal repeat," *Virology,* 157:211, 1987.

Horlick and Benfield, "The upstream muscle-specific enhancer of the rat muscle creatine kinase gene is composed of multiple elements," *Mol. Cell. Biol.,* 9:2396, 1989.

Huang, Ostrowski, Berard and Hagar, "Glucocorticoid regulation of the Ha-MuSV p21 gene conferred by sequences from mouse mammary tumor virus," *Cell,* 27:245, 1981.

Hwang, Lim and Chae, "Characterization of the s-phase-specific transcription regulatory elements in a DNA-replication-independent testis-specific H2B (TH2B) histone gene," *Mol. Cell. Biol.,* 10:585, 1990.

Imagawa, Chin and Karin, "Transcription factor AP-2 mediates induction by two different signal-transduction pathways: Protein kinase C and cAMP," *Cell,* 51:251, 1987.

Imaizumi et al., "Liposome-entrapped superoxide dismutase ameliorates infarct volume in focal cerebral ischemia," *Acta. Neurochirurgica Suppl.,* 51:236-238, 1990b.

Imaizumi et al., "Liposome-entrapped superoxide dismutase reduces cerebral infarction in cerebral ischemia in rats," *Stroke,* 21(9):1312-1317, 1990a.

Imbra and Karin, "Phorbol ester induces the transcriptional stimulatory activity of the SV40 enhancer," *Nature,* 323:555, 1986.

Imler, Lemaire, Wasvlyk and Waslyk, "Negative regulation contributes to tissue specificity of the immunoglobulin heavy-chain enhancer," *Mol. Cell. Biol.,* 7:2558, 1987.

Imperiale and Nevins, "Adenovirus 5 E2 transcription unit: An E1A-inducible promoter with an essential element that functions independently of position or orientation," *Mol. Cell. Biol.,* 4:875, 1984.

Jakobovits, Smith, Jakobovits and Capon, "A discrete element 3' of human immunodeficiency virus 1 HIV-1) and HIV-2 mRNA initiation sites mediates transcriptional activation by an HIV trans-activator," *Mol. Cell. Biol.,* 8:2555, 1988.

Jameel and Siddiqui, "The human Hepatitis B virus enhancer requires transacting cellular factor(s) for activity," *Mol. Cell. Biol.,* 6:710, 1986.

Jarman, Loutsch, Devi-Rao, Marquart, Banaszak, Zheng, Hill, Wagner and Bloom, "The region of the HSV-1 latency-associated transcript required for epinephrine-induced reactivation in the rabbit does not include the 2.0 kb intron," *Virology,* 292:59-69, 2002.

Jarman, R. G., E. K. Wagner, and D. C. Bloom. 1999. LAT expression during an acute HSV infection in the mouse. Virology 262:384-397.

Jaynes, Johnson, Buskin, Gartside and Hauschka, "The muscle creatine kinase gene is regulated by multiple upstream elements, including a muscle-specific enhancer," *Mol. Cell. Biol.,* 8:62, 1988.

Jenuwein, T., and C. D. Allis. 2001. Translating the histone code. Science 293:1074-1080.

Johnson, K. D., and E. H. Bresnick. 2002. Dissecting long-range transcriptional mechanisms by chromatin immunoprecipitation. Methods 26:27-36.

Johnson, Wold and Hauschka, "Muscle creatine kinase sequence elements regulating skeletal and cardiac muscle expression in transgenic mice," *Mol. Cell. Biol.,* 9:3393, 1989a.

Kadesch and Berg, "Effects of the position of the simian virus 40 enhancer on expression of multiple transcription units in a single plasmid," *Mol. Cell. Biol.,* 6:2593, 1986.

Karin, Haslinger, Heguy, Dietlin and Cooke, "Metal-responsive elements act as positive modulators of human metallothionein-IIa enhancer activity," *Mol. Cell. Biol.,* 7:606, 1987.

Katinka, Vasseur, Montreau, Yaniv and Blangy, "Polyoma DNA sequences involved in the control of viral gene expression in murine embryonal carcinoma cells," *Nature,* 290:720, 1981.

Katinka, Yaniv, Vasseur and Blangy, "Expression of polyoma early functions in mouse embryonal carcinoma cells depends on sequence rearrangements in the beginning of the late region," *Cell,* 20:393, 1980.

Kawamoto et al., "AAV6 vectors promote efficient transduction and gene dissemination through myocardium in vivo," *Mol. Ther.,* 7:S228, 2003.

Kawamoto, Makino, Niw, Sugiyama, Kimura, Anemura, Nakata and Kakunaga, "Identification of the human β-actin enhancer and its binding factor," *Mol. Cell. Biol.,* 8:267, 1988.

Kent, J. R., P. Y. Zeng, D. Atanasiu, J. Gardner, N. W. Fraser, and S. L. Berger. 2004. During lytic infection herpes simplex virus type 1 is associated with histones bearing modifications that correlate with active transcription. J Virol 78:10178-86.

Kessler et al., "Gene delivery to skeletal muscle results in sustained expression and systemic delivery of a therapeutic protein," *Proc. Natl. Acad. Sci. USA,* 93:14082-87, 1996.

Kiledjian, Su and Kadesch, "Identification and characterization of two functional domains within the murine heavy-chain enhancer," *Mol. Cell. Biol.,* 8:145, 1988.

Klamut, Gangopadyhay, Worton and Ray, "Molecular and functional analysis of the muscle-specific promoter region of the Duchenne muscular dystrophy gene," *Mol. Cell. Biol.,* 10:193, 1990.

Klein, Wolf, Wu, Sanford, "High-velocity microprojectiles for delivering nucleic acids into living cells. 1987," *Biotechnology,* 24:384-386, 1992.

Koch, Benoist and Mathis, "Anatomy of a new B-cell-specific enhancer," *Mol. Cell. Biol.,* 9:303, 1989.

Kramer, M. F., and D. M. Coen. 1995. Quantification of transcripts from the ICP4 and thymidine kinase genes in mouse ganglia latently infected with herpes simplex virus. J. Virol. 69:1389-1399.

Kriegler and Botchan, "A retrovirus LTR contains a new type of eukaryotic regulatory element," In: *Eukaryotic Viral Vectors*, Gluzman, Ed., Cold Spring Harbor, Cold Spring Harbor Laboratory, N.Y., 1982.

Kriegler and Botchan, "Enhanced transformation by a simian virus 40 recombinant virus containing a Harvey murine sarcoma virus long terminal repeat," *Mol. Cell. Biol.* 3:325, 1983.

Kriegler, Perez and Botchan, "Promoter substitution and enhancer augmentation increases the penetrance of the SV40 a gene to levels comparable to that of the Harvey murine sarcoma virus Ras gene in morphologic transformation," In: *Gene Expression*, Hamer and Rosenberg, Eds., New York, Alan R. Liss, 1983.

Kriegler, Perez, Defay, Albert and Liu, "A novel form of TNF/cachectin is a cell-surface cytotoxix transmembrane protein: Ramifications for the complex physiology of TNF," *Cell,* 53:45, 1988.

Kriegler, Perez, Hardy and Botchan, "Transformation mediated by the SV40 T antigens: separation of the overlapping SV40 early genes with a retroviral vector," *Cell,* 38:483, 1984a.

Kriegler, Perez, Hardy and Botchan, "Viral integration and early gene expression both affect the efficiency of SV40 transformation of murine cells: Biochemical and biological characterization of an SV40 retrovirus," In: *Cancer Cells 2/Oncogenes and Viral Genes*, Van de Woude, Levine, Topp and Watson, Eds., Cold Spring Harbor, Cold Spring Harbor Laboratory, 1984b.

Kubat, N. J., A. L. Amelio, N. V. Giordani, and D. C. Bloom. 2004. The Herpes Simplex Virus Type 1 Latency-Associated Transcript (LAT) Enhancer/rcr Is Hyperacetylated during Latency Independently of LAT Transcription. J Virol 78:12508-18.

Kubat, N. J., R. K. Tran, P. McAnany, and D. C. Bloom. 2004. Specific histone tail modification and not DNA methylation is a determinant of herpes simplex virus type 1 latent gene expression. J Virol 78:1139-49.

Kuby, *In: Immunology,* 2nd Edition. W.H. Freeman & Company, New York, 1994.

Kuhl, De La Fuenta, Chaturvedi, Parinool, Ryals, Meyer and Weissman, "Reversible silencing of enhancers by sequences derived from the human IFN-α promoter," *Cell,* 50:1057, 1987.

Kunz, Zimmerman, Heisig and Heinrich, "Identification of the promoter sequences involved in the Interleukin-6-dependent expression of the rat α-2-macroglobulin gene," *Nucl. Acids Res.,* 17:1121, 1989.

Kwoh, Davis, Whitfield, Chappelle, DiMichele, Gingeras, "Transcription-based amplification system and detection of amplified human immunodeficiency virus type 1 with a bead-based sandwich hybridization format," *Proc. Natl. Acad. Sci. USA,* 86(4):1173-1177, 1989.

Kyte and Doolittle, "A simple method for displaying the hydropathic character of a protein," *J. Mol. Biol.,* 157(1): 105-132, 1982.

Larsen, Harney and Moore, "Repression mediates cell-type-specific expression of the rat growth hormone gene," *Proc. Natl. Acad. Sci. U.S.A.,* 83:8283, 1986.

Lasic, "Novel applications of liposomes," *Trends Biotechnol.,* 16(7):307-321, 1998.

Laspia, Rice and Mathews, "HIV-1 tat protein increases transcriptional initiation and stabilizes elongation," *Cell,* 59:283, 1989.

Latchman, D. S. 1999. Regulation of DNA virus transcription by cellular POU family transcription factors. Rev. Med. Virol. 9:31-38.

Latimer, Berger and Baumann, "Highly conserved upstream regions of the $\alpha_1$-antitrypsin gene in two mouse species govern liver-specific expression by different mechanisms," *Mol. Cell. Biol.,* 10:760, 1990.

Lee et al., "Functional analysis of the steroid hormone control region of mouse mammary tumor virus," *Nucleic Acids Res.,* 12(10):4191-4206, 1984.

Lee, Mulligan, Berg and Ringold, "Glucocorticoids regulate expression of dihydrofolate reductase cDNA in mouse mammary tumor virus chimaeric plasmids," *Nature,* 294: 228, 1981.

Leib, Bogard, Kosz, Hicks, Coen, Knipe and Schaffer, "A deletion mutant of the latency-associated transcript of herpes simplex virus type 1 reactivates from the latent state with reduced frequency," *J. Virol.,* 63:2893-900, 1989.

Leib, D. A., C. L. Bogard, V. M. Kosz, K. A. Hicks, D. M. Coen, D. M. Knipe, and P. A. Schaffer. 1989. A deletion mutant of the latency-associated transcript of herpes simplex virus type 1 reactivates from the latent state with reduced frequency. J Virol 63:2893-900.

Levinson, Khoury, VanDeWoude and Gruss, "Activation of SV40 genome by 72-base-pair tandem repeats of Moloney sarcoma virus," *Nature,* 295:79, 1982.

Lin, Cross, Halden, Dragos, Toledano and Leonard, "Delineation of an enhancer like positive regulatory element in the interleukin-2 receptor α-chain gene," *Mol. Cell. Biol.,* 10:850, 1990.

Litt, M., M. Simpson, C. Gaszner, C. D. Allis, and G. Felsenfeld. 2001. Correlation between histone lysine methylation and developmental changes at the chicken β-globin locus. Science 293.

Litt, M., M. Simpson, F. Recillas-Targa, M. Prioleau, and G. Felsenfeld. 2001. Transitions in histone acetylation reveal boundaries of three separately regulated neighboring loci. EMBO 20:2224-2455.

Liu, Nishikawa, Clemens and Huang, "Transfer of full-length Dmd to the diaphragm muscle of Dmd(mdx/mdx) mice through systemic administration of plasmid DNA," *Mol. Ther.,* 4:45-51, 2001.

Lokensgard, J. R., D. C. Bloom, A. T. Dobson, and L. T. Feldman. 1994. Long-term promoter activity during herpes simplex virus latency. J. Virol. 68:7148-7158.

Lokensgard, J. R., H. Berthomme, and L. T. Feldman. 1997. The latency-associated promoter of herpes simplex virus type 1 requires a region downstream of the transcription start site for long-term expression during latency. J. Virol. 71:6714-6719.

Lopez-Berestein et al., "Liposomal amphotericin B for the treatment of systemic fungal infections in patients with cancer: a preliminary study" *J. Infect. Dis.,* 2151:704, 1985a.

Lopez-Berestein et al., "Protective effect of liposomal-amphotericin B against *C. albicans* infection in mice," *Cancer Drug Delivery,* 2:183, 1985b.

Luria, Gross, Horowitz and Givol, "Promoter enhancer elements in the rearranged α-chain gene of the human T-cell receptor," *EMBO J.,* 6:3307, 1987.

Lusky and Botchan, "Transient replication of bovine papilloma virus Type 1 plasmids: cis and trans requirements," *Proc. Natl. Acad. Sci. U.S.A.,* 83:3609, 1986.

Lusky, Berg, Weiher and Botchan, "Bovine papilloma virus contains an activator of gene expression at the distal end of the early transcription unit," *Mol. Cell. Biol.* 3:1108, 1983.

Lutz, M., L. J. Burke, G. Barreto, F. Goeman, H. Greb, R. Arnold, H. Schultheiss, A. Brehm, T. Kouzarides, V. Lobanenkov, and R. Renkawitz. 2000. Transcriptional repression by the insulator protein CTCF involves histone deacetylases. Nucleic Acids Res 28:1707-13.

MacLean, A. R., and S. M. Brown. 1987. Deletionand duplication variants around the long repeats of HSV-1 strain 17. J. Gen. Virol. 68:3019-3031.

Mah et al., "Improved method of recombinant AAV2 delivery for systemic targeted gene therapy," *Mol. Ther.,* 6:106-12, 2002.

Majors and Varmus, "A small region of the mouse mammary tumor virus long terminal repeat confers glucocorticoid hormone regulation on a linked heterologous gene," *Proc. Natl. Acad. Sci. U.S.A.,* 80:5866, 1983.

Maloy et al., In: Microbial Genetics, 2nd Edition, Jones and Barlett Publishers, Boston, Mass., 1994.

Maniatis et al., "Molecular Cloning: a Laboratory Manual," Cold Spring Harbor Laboratory, Cold Spring Harbor, N.Y., 1982.

March, Madison and Trapnell, "Pharmacokinetics of adenoviral vector-mediated gene delivery to vascular smooth muscle cells: modulation by poloxamer 407 and implications for cardiovascular gene therapy," *Hum. Gene Ther.* 6:41-53, 1995.

Margalit, "Liposome-mediated drug targeting in topical and regional therapies," *Crit. Rev. Ther. Drug Carrier Syst.,* 12(2-3):233-261, 1995.

Margolis, T. P., D. C. Bloom, A. T. Dobson, L. T. Feldman, and J. G. Stevens. 1993. Decreased reporter gene expression during latent infection with HSV LAT promoter constructs. Virology 197:585-92.

McNeall, Sanchez, Gray, Chesterman and Sleigh, "Hyperinducible gene expression from a metallotionein promoter containing additional metal-responsive elements," *Gene,* 76:81, 1989.

Mehta, Maggioncalda, Bagasra, Thikkavarapu, Saikumari, Valyi-Nagy, Fraser and Block, "In situ DNA PCR and RNA hybridization of herpes simplex virus sequences in trigeminal ganglia of latently infected mice," *Virology,* 206:633-40, 1995.

Mellerick and Fraser, "Physical state of the latent herpes simplex virus genome in a mouse model system: evidence suggesting an episomal state," *Virology,* 158:265-75, 1987.

Miksicek, Heber, Schmid, Danesch, Posseckert, Beato and Schutz, "Glucocorticoid responsiveness of the transcriptional enhancer of Moloney murine sarcoma virus," *Cell,* 46:203, 1986.

Mitchell, B. M., D. C. Bloom, R. J. Cohrs, D. H. Gilden, and P. G. Kennedy. 2003. Herpes simplex virus-1 and varicella-zoster virus latency in ganglia. J Neurovirol 9:194-204.

Mitchell, Bloom, Cohrs, Gilden and Kennedy, "Herpes simplex virus-1 and varicella-zoster virus latency in ganglia," *J. Neurovirol.,* 9:194-204, 2003.

Mordacq and Linzer, "Co-localization of elements required for phorbol ester stimulation and glucocorticoid repression of proliferin gene expression," *Genes and Dev.,* 3:760, 1989.

Moreau, Hen, Wasylyk, Everett, Gaub and Chambon, "The SV40 base-repair repeat has a striking effect on gene expression both in SV40 and other chimeric recombinants," *Nucl. Acids Res.,* 9:6047, 1981.

Mori and Fukatsu, "Anticonvulsant effect of DN-1417 a derivative of thyrotropin-releasing hormone and liposome-entrapped DN-1417 on amygdaloid-kindled rats," *Epilepsia,* 33(6):994-1000, 1992.

Moufarrej and Bertorini, "Respiratory insufficiency in adult-type acid maltase deficiency," *South. Med. J.,* 86:560-67, 1993.

Muesing, Smith and Capon, "Regulation of mRNA accumulation by a human immunodeficiency virus trans-activator protein," *Cell,* 48:691, 1987.

Muller et al., "Efficient transfection and expression of heterologous genes in PC12 cells," *Cell, Biol.,* 9(3):221-229, 1990.

Muller et al., "Random peptide libraries displayed on adeno-associated virus to select for targeted gene therapy vectors," *Nat. Biotechnol.,* 21:1040-46, 2003.

Muzyczka, "Use of adeno-associated virus as a general transduction vector for mammalian cells," *Curr Top Microbiol Immunol.,* 158:97-129, 1992.

Nakayama, J., J. C. Rice, B. D. Strahl, C. D. Allis, and S. I. Grewal. 2001. Role of histone H3 lysine 9 methylation in epigenetic control of heterochromatin assembly. Science 292:110-3.

Nesburn, Elliot and Leibowitz, "Spontaneous reactivation of experimental herpes simplex keratitis in rabbits," *Arch. Ophthalmol.,* 78:523-29, 1967.

Ng, Gunning, Liu, Leavitt and Kedes, "Regulation of the human β-actin promoter by upstream and intron domains," *Nuc. Acids Res.*, 17:601, 1989.

Nicolau and Gersonde, "Incorporation of inositol hexaphosphate into intact red blood cells, I. fusion of effector-containing lipid vesicles with erythrocytes," *Naturwiss enschaften* (Germany), 66(11):563-566, 1979.

Nicolau and Sene, "Liposome-mediated DNA transfer in eukaryotic cells," *Biochein. Biophys. Acta*, 721:185-190, 1982.

Nicosia, Deshmane, Zabolotny, Valyi-Nagy and Fraser, "Herpes simplex virus type 1 latency-associated transcript (LAT) promoter deletion mutants can express a 2-kilobase transcript mapping to the LAT region," *J. Virol.*, 67:7276-83, 1993.

Nicosia, M., S. L. Deshmane, J. M. Zabolotny, T. Valyi-Nagy, and N. W. Fraser. 1993. Herpes simplex virus type 1 latency-associated transcript (LAT) promoter deletion mutants can express a 2-kilobase transcript mapping to the LAT region. J Virol 67:7276-83.

Ohara, Dort, Gilbert, "One-sided polymerase chain reaction: the amplification of cDNA," *Proc. Natl. Acad. Sci. USA*, 86(15):5673-5677, 1989.

Ohlsson, R., R. Renkawitz, and V. Lobanenkov. 2001. CTCF is a uniquely versatile transcription regulator linked to epigenetics and disease. Trends Genet 17:520-7.

Ondek, Sheppard and Herr, "Discrete elements within the SV40 enhancer region display different cell-specific enhancer activities," *EMBO J.*, 6:1017, 1987.

O'Neill, L. P., and B. M. Turner. 2003. Immunoprecipitation of native chromatin: NChIP. Methods 31:76-82.

Ono, Hirose, Miyazaki, Yamamoto, Matsumoto, "Transgenic medaka fish bearing the mouse tyrosinase gene: expression and transmission of the transgene following electroporation of the orange-colored variant," *Pigment Cell Res.*, 10(3):168-175, 1997.

Ornitz, Hammer, Davison, Brinster and Palmiter, "Promoter and enhancer elements from the rat elastase I gene function independently of each other and of heterologous enhancers," *Mol. Cell. Biol.*, 7:3466, 1987.

Palmer, Branston, Lilley, Robinson, Groutsi, Smith, Latchman and Coffin, "Development and optimization of herpes simplex virus vectors for multiple long-term gene delivery to the peripheral nervous system," *J. Virol.*, 74:5664-5618, 2000.

Palmiter, Chen and Brinster, "Differential regulation of metallothionein-thymidine kinase fusion genes in transgenic mice and their offspring," *Cell*, 29:701, 1982.

Pech, Rao, Robbins and Aaronson, "Functional identification of regulatory elements within the promoter region of platelet-derived growth factor 2," *Mol. Cell. Biol.*, 9:396, 1989.

Perabo et al., "In vitro selection of viral vectors with modified tropism: the adeno-associated virus display," *Mol. Ther.*, 8:151-57, 2003.

Perez-Stable and Constantini, "Roles of fetal γ-globin promoter elements and the adult β-globin 3' enhancer in the stage-specific expression of globin genes," *Mol. Cell. Biol.*, 10:1116, 1990.

Perng, G. C., S. M. Slanina, A. Yukht, H. Ghiasi, A. B. Nesbum, and S. L. Wechsler. 2000. The latency-associated transcript gene enhances establishment of herpes simplex virus type 1 latency in rabbits. J. Virol. 74:1885-1891.

Perng, G.-C., E. C. Dunkel, P. A. Geary, S. M. Slanina, H. Ghiasi, R. Kaiwar, A. B. Nesburn, and S. L. Wechsler. 1994. The latency-associated transcript gene of herpes simplex virus type 1 (HSV-1) is required for efficient in vivo spontaneous reactivation of HSV-1 from latency. J. Virol. 68:8045-8055.

Perng, Jones, Ciacci-Zanella, Stone, Henderson, Yukht, Slanina, Hofman, Ghiasi, Nesburn and Wechsler, "Virus-induced neuronal apoptosis blocked by the herpes simplex virus latency-associated transcript," *Science*, 287:1500-03, 2000a.

Perng, Slanina, Ghiasi, Nesburn and Wechsler, "The effect of latency-associated transcript on the herpes simplex virus type 1 latency-reactivation phenotype is mouse strain-dependent," *J. Gen. Virol.*, 82:1117-22, 2001.

Petrof et al., "Efficiency and functional consequences of adenovirus-mediated in vivo gene transfer to normal and dystrophic (mdx) mouse diaphragm," *Am. J. Respir. Cell Mol. Biol.*, 13:508-17, 1995.

Petrof, "Respiratory muscles as a target for adenovirus-mediated gene therapy," *Eur. Respir. J.*, 11:492-97, 1998.

Picard and Schaffner, "A Lymphocyte-specific enhancer in the mouse immunoglobulin kappa gene," *Nature*, 307:83, 1984.

Pikul et al., "In vitro killing of melanoma by liposome-delivered intracellular irradiation, *Arch. Surg.*, 122(12):1417-1420, 1987.

Pinkert, Ornitz, Brinster and Palmiter, "An albumin enhancer located 10 kb upstream functions along with its promoter to direct efficient, liver-specific expression in transgenic mice," *Genes and Dev.*, 1:268, 1987.

Pinto-Alphandary, Balland, Couvreur, "A new method to isolate polyalkylcyanoacrylate nanoparticle preparations," *J. Drug Target*, 3(2):167-169, 1995.

Pinto-Sietsma and Paul, "Transgenic rats as models for hypertension," *J. Hum. Hypertens.*, 11(9):577-581, 1997.

Ponnazhagan, Mahendra, Kumar, Thompson and Castillas, "Conjugate-based targeting of recombinant adeno-associated virus type 2 vectors by using avidin-linked ligands," *J. Virol.*, 76:12900-07, 2002.

Ponta, Kennedy, Skroch, Hynes and Groner, "Hormonal response region in the mouse mammary tumor virus long terminal repeat can be dissociated from the proviral promoter and has enhancer properties," *Proc. Natl. Acad. Sci. U.S.A.*, 82:1020, 1985.

Porton, Zaller, Lieberson and Eckhardt, "Immunoglobulin heavy-chain enhancer is required to maintain transfected γ2A gene expression in a pre-B-cell line," *Mol. Cell. Biol.*, 10: 1076, 1990.

Potter et al., "Enhancer-dependent expression of human κ immunoglobulin genes introduced into mouse pre-B lymphocytes by electroporation," *Proc. Natl. Acad. Sci. USA*, 81:7161-7165, 1984.

Prokop and Bajpai, "Recombinant DNA Technology I," Conference on Progress in Recombinant DNA Technology Applications, Potosi, Mch., Jun. 3-8, 1990, *Ann. N.Y. Acad. Sci.*, 646:1-383, 1991.

Queen and Baltimore, "Immunoglobulin gene transcription is activated by downstream sequence elements," *Cell*, 35:741, 1983.

Quinn, Farina, Gardner, Krutzsch and Levens, "Multiple components are required for sequence recognition of the AP1 site in the Gibbon ape leukemia virus enhancer," *Mol. Cell. Biol.*, 9:4713, 1989.

Quintanar-Guerrero, Allemann, Doelker, Fessi, "Preparation and characterization of nanocapsules from preformed polymers by a new process based on emulsification-diffusion technique," *Phamr. Res.*, 15(7):1056-1062, 1998.

Raben et al., "Targeted disruption of the acid alpha-glucosidase gene in mice causes an illness with critical features of both infantile and adult human glycogen storage disease type II," *J. Biol. Chem.*, 273:19086-92, 1998.

Rabinowitz et al., "Cross-packaging of a single adeno-associated virus (AAV) type 2 vector genome into multiple AAV serotypes enables transduction with broad specificity," *J. Virol.*, 76:791-801, 2002.

Rea, S., F. Eisenhaber, D. O'Carroll, B. D. Strahl, Z. W. Sun, M. Schmid, S. Opravil, K. Mechtler, C. P. Ponting, C. D. Allis, and T. Jenuwein. 2000. Regulation of chromatin structure by sire-specific histone H3 methyltransferases. Nature 406:593-599.

Redondo, Hata, Brocklehurst and Krangel, "A T-cell-specific transcriptional enhancer within the human T-cell receptor δ locus," *Science*, 247:1225, 1990.

Reisman and Rotter, "Induced expression from the Moloney murine leukemia virus long terminal repeat during differentiation of human myeloid cells is mediated through its transcriptional enhancer," *Mol. Cell. Biol.*, 9:3571, 1989.

Renneisen, "Inhibition of expression of human immunodeficiency virus-1 in vitro by antibody-targeted liposomes containing antisense RNA to the env region," *J. Biol. Chem.*, 265(27):16337-16342, 1990.

Resendez Jr., Wooden and Lee, "Identification of highly conserved regulatory domains and protein-binding sites in the promoters of the rat and human genes encoding the stress-inducible 78-kilodalton glucose-regulated protein," *Mol. Cell. Biol.*, 8:4579, 1988.

Rice, M. K., G. B. Devi-Rao, and E. K. Wagner. 1993. Latent phase transcription by alphaherpesviruses, p. 305-324. In K. Adolph (ed.), Genome Research in Molecular Medicine and Virology. Academic Press, Orlando.

Ripe, Lorenzen, Brenner and Breindl, "Regulatory elements in the 5' flanking region and the first intron contribute to transcriptional control of the mouse α-1-type collagen gene," *Mol. Cell. Biol.*, 9:2224, 1989.

Rippe et al., "DNA-mediated gene transfer into adult rat hepatocytes in primary culture," *Mol. Cell Biol.*, 10:689-695, 1990.

Rittling, Coutinho, Amarm and Kolbe, "AP-1/jun-binding sites mediate serum inducibility of the human vimentin promoter," *Nuc. Acids Res.*, 17:1619, 1989.

Rock and Fraser, "Detection of HSV-1 genome in central nervous system of latently infected mice," *Nature*, 302: 523-25, 1983.

Rosen, Sodroski and Haseltine, "The location of cis-acting regulatory sequences in the human T-cell lymphotropic virus type III (HTLV-111/LAV) long terminal repeat," *Cell*, 41:813, 1988.

Sakai, Helms, Carlstedt-Duke, Gustafsson, Rottman and Yamamoto, "Hormone-mediated repression: A negative glucocorticoid-response element from the bovine prolactin gene," *Genes and Dev.*, 2:1144, 1988.

Sakamoto et al., "Micro-dystrophin cDNA ameliorates dystrophic phenotypes when introduced into mdx mice as a transgene," *Biochem. Biophys. Res. Commun.*, 293:1265-72, 2002.

Sambrook et al., "Molecular Cloning: A Laboratory Manual," Cold Spring Harbor Laboratory, Cold Spring Harbor, N.Y., 1989.

Satake, Furukawa and Ito, "Biological activities of oligonucleotides spanning the F9 point mutation within the enhancer region of polyoma virus DNA," *J. Virology*, 62:970, 1988.

Sawtell and Thompson, "Herpes simplex virus type 1 latency associated transcription unit promotes anatomical site-dependent establishment and reactivation from latency," *J. Virol.*, 66:2157-69, 1992a.

Sawtell and Thompson, "Rapid in vivo reactivation of herpes simplex virus in latently infected murine ganglionic neurons after transient hyperthermia," *J. Virol.*, 66:2150-56, 1992b.

Sawtell, "The probability of in vivo reactivation of herpes simplex virus type 1 increases with the number of latently infected neurons in the ganglia," *J. Virol.*, 72:6888-92, 1998.

Sawtell, Poon, Tansky and Thompson, "The latent herpes simplex virus type 1 genome copy number in individual neurons is virus strain specific and correlates with reactivation," *J. Virol.*, 72:5343-50, 1998.

Schaffner, Schirm, Muller-Baden, Wever and Schaffner, "Redundancy of information in enhancers as a principle of mammalian transcription control," *J. Mol. Biol.*, 201:81, 1988.

Sculier et al., "Pilot study of amphotericin B entrapped in sonicated liposomes in cancer patients with fungal infections," *J. Cancer Clin. Oncol.*, 24(3):527-538, 1988.

Searle, Stuart and Palmiter, "Building a metal-responsive promoter with synthetic regulatory elements," *Mol. Cell. Biol.*, 5:1480, 1985.

Sedarati, Margolis and Stevens, "Latent infection can be established with drastically restricted transcription and replication of the HSV-1 genome," *Virology*, 192:687-91, 1993.

Segal, "Biochemical Calculations" 2nd Edition. John Wiley & Sons, New York, 1976.

Seiler et al., "Thixotropic solutions enhance viral-mediated gene transfer to airway epithelia," *Am. J. Respir. Cell Mol. Biol.*, 27:133-40, 2002.

Sharp and Marciniak, "HIV Tar: An RNA enhancer?" *Cell*, 59:229, 1989.

Shaul and Ben-Levy, "Multiple nuclear proteins in liver cells are bound to Hepatitis B virus enhancer element and its upstream sequences," *EMBO J.*, 6:1913, 1987.

Sherman, Basta, Moore, Brown and Ting, "Class II box consensus sequences in the HLA-DRα gene: Transcriptional function and interaction with nuclear proteins," *Mol. Cell. Biol.*, 9:50, 1989.

Shi and Bartlett, "RGD inclusion in VP3 provides adeno-associated virus type 2 (AAV2)-based vectors with a heparan sulfate-independent cell entry mechanism," *Mol. Ther.*, 7:515-25, 2003.

Shi, Arnold and Bartlett, "Insertional mutagenesis of the adeno-associated virus type 2 (AAV2) capsid gene and generation of AAV2 vectors targeted to alternative cell-surface receptors," *Hum. Gene Ther.*, 12:1697-711, 2001.

Sleigh and Lockett, "SV40 enhancer activation during retinoic-acid-induced differentiation of F9 embryonal carcinoma cells," *J. EMBO*, 4:3831, 1985.

Spalholz, Yang and Howley, "Transactivation of a bovine papilloma virus transcriptional regulatory element by the E2 gene product," *Cell*, 42:183, 1985.

Spandau and Lee, "Trans-activation of viral enhancers by the Hepatitis B virus X protein," *J. Virology*, 62:427, 1988.

Spandidos and Wilkie, "Host-specificities of papilloma virus, Moloney murine sarcoma virus and simian virus 40 enhancer sequences," *EMBO J.*, 2:1193, 1983.

Spivack, J. G., and N. W. Fraser. 1987. Detection of herpes simplex virus type 1 transcripts during latent infection in mice. J. Virol 61:3841-3847.

Stedman et al., "The mdx mouse diaphragm reproduces the degenerative changes of Duchenne muscular dystrophy," *Nature*, 352:536-39, 1991, Stephens and Hentschel, "The bovine papilloma virus genome and its uses as a eukaryotic vector," *Biochem. J.,* 248:1, 1987.

Stevens and Cook, "Latent herpes simplex virus in spinal ganglia of mice," *Science,* 173:843-45, 1971.

Stevens, J. G., E. K. Wagner, R. G. B. Devi, M. L. Cook, and L. T. Feldman. 1987. RNA complementary to a herpesvirus alpha gene mRNA is prominent in latently infected neurons. Science 235:1056-9.

Strahl, B. D., and C. D. Allis. 2000. The language of covalent histone modifications. Nature 403:41-5.

Stuart, Searle and Palmiter, "Identification of multiple metal regulatory elements in mouse metallothionein-I promoter by assaying synthetic sequences," *Nature,* 317:828, 1985.

Sullivan and Peterlin, "Transcriptional enhancers in the HLA-DQ subregion," *Mol. Cell. Biol.,* 7:3315, 1987.

Suzuki, Shin, Fjuikura, Matsuzaki, Takata, "Direct gene transfer into rat liver cells by in vivo electroporation," *FEBS Lett.,* 425(3):436-440, 1998.

Swartzendruber and Lehman, "Neoplastic differentiation: Interaction of simian virus 40 and polyoma virus with murine teratocarcinoma cells," *J. Cell. Physiology,* 85:179, 1975.

Takakura, "Drug delivery systems in gene therapy," *Nippon Rinsho,* 56(3):691-695, 1998.

Takebe, Seiki, Fujisawa, Hoy, Yokota, Arai, Yoshida and Arai, "SRα promoter: An efficient and versatile mammalian cDNA expression system composed of the simian virus 40 early promoter and the R-U5 segment of human T-cell leukemia virus Type 1 long terminal repeat," *Mol. Cell. Biol.,* 8:466, 1988.

Tavernier, Gheysen, Duerinck, Can der heyden and fiers, "Deletion mapping of the inducible promoter of human IFN-β gene," *Nature,* 301:634, 1983.

Taylor and Kingston, "Ela trans-activation of human HSP70 gene promoter substitution mutants is independent of the composition of upstream and TATA elements," *Mol. Cell. Biol.,* 10:176, 1990b.

Taylor and Kingston, "Factor substitution in a human HSP70 gene promoter: TATA-dependent and TATA-independent interactions," *Mol. Cell. Biol.,* 10: 165, 1990a.

Taylor, Solomon, Weiner, Paucha, Bradley and Kingston, "Stimulation of the human heat-shock protein 70 promoter in vitro by simian virus 40 large T antigen," *J. Biol. Chem.,* 264:15160, 1989.

Thiesen, Bosze, Henry and Charnay, "A DNA element responsible for the different tissue specificities of friend and Moloney retroviral enhancers," *J. Virology,* 62:614, 1988.

Thomas, D. L., M. Lock, J. M. Zabolotny, B. R. Mohan, and N. W. Fraser. 2002. The 2-kilobase intron of the herpes simplex virus type 1 latency-associated transcript has a half-life of approximately 24 hours in SY5Y and COS-1 cells. J Virol 76:532-40.

Thompson and Sawtell, "Herpes simplex virus type 1 latency-associated transcript gene promotes neuronal survival," *J. Virol.,* 75:6660-75, 2001.

Thompson and Sawtell, *Science,* 289:1651, 2000.

Tran, Lieu, Aguilar, Wagner and Bloom, "Altering the expression kinetics of VP5 results in altered virulence and pathogenesis of herpes simplex virus type 1 in mice," *J. Virol.,* 76:2199-205, 2002.

Treisman, "identification of a protein-binding site that mediates transcriptional response to the c-fos gene to serum factors," *Cell,* 46(4):567-574, 1986.

Tronche, Rollier, Bach, Weiss and Yaniv, "The rat albumin promoter: Cooperation with upstream elements is required when binding of APF/HNF 1 to the proximal element is partially impaired by mutation or bacterial methylation," *Mol. Cell. Biol.,* 9:4759, 1989.

Tronche, Rollier, Herbomel, Bach, Cereghini, Weiss and Yaniv, "Anatomy of the rat albumin promoter," *Mol. Biol. Med.,* 7:173, 1990.

Trudel and Constantini, "A 3' enhancer contributes to the stage-specific expression of the human β-globin gene," *Genes and Dev.,* 6:954, 1987.

Tur-Kaspa et al., "Use of electroporation to introduce biologically active foreign genes into primary rat hepatocytes," *Mol. Cell Biol.,* 6:716-718, 1986.

Tyndall, La Mantia, Thacker, Favaloro and Kamen, "A region of the polyoma virus genome between the replication origin and late protein-coding sequences is required in cis for both early gene expression and viral DNA replication," *Nuc. Acids. Res.,* 9:6231, 1981.

Van Belle et al., "Effects of poloxamer 407 on transfection time and percutaneous adenovirus-mediated gene transfer in native and stented vessels," *Hum. Gene Ther.,* 9:1013-24, 1998.

Van Cott, Lubon, Russell, Butler, Gwazdauskas, Knight, Drohan, Velander, "Phenotypic and genotypic stability of multiple lines of transgenic pigs expressing recombinant human protein C," *Transgenic Res.,* 6(3):203-212, 1997.

Vanbever, Fouchard, Jadoul, De Morre, Preat, Marty, "In vivo noninvasive evaluation of hairless rat skin after high-voltage pulse exposure," *Skin Parmacol. Appl. Skin Physiol.,* 11(1):23-34, 1998.

Vannice and Levinson, "Properties of the human Hepatitis B virus enhancer: Position effects and cell-type nonspecificity," *J. Virology,* 62:1305, 1988.

Vasseur, Kress, Montreau and Blangy, "Isolation and characterization of polyoma virus mutants able to develop in multipotential murine embryonal carcinoma cells," *Proc. Natl. Acad. Sci. U.S.A.,* 77:1068, 1980.

Wagner, E. K., and D. C. Bloom. 1997. Experimental investigation of herpes simplex virus latency. Clin. Micro. Reviews 10:419-443.

Wagner, Zatloukal, Cotten, Kirlappos, Mechtler, Curiel, Birnstiel, "Coupling of adenovirus to transferrin-polylysine/DNA complexes greatly enhances receptor-mediated gene delivery and expression of transfected genes," *Proc. Natl. Acad. Sci. USA,* 89(13):6099-6103, 1992.

Walker et al., "Strand displacement amplification—an isothermal, in vitro DNA amplification technique," *Nucleic Acids Res.,* 20(7):1691-6, 1992.

Wang and Calame, "SV40 enhancer-binding factors are required at the establishment but not the maintenance step of enhancer-dependent transcriptional activation," *Cell,* 47:241, 1986.

Weber, De Villiers and Schaffner, "An SV40 'enhancer trap' incorporates exogenous enhancers or generates enhancers from its own sequences," *Cell,* 36:983, 1984.

Weinberger, Jat and Sharp, "Localization of a repressive sequence contributing to B-cell specificity in the immunoglobulin heavy-chain enhancer," *Mol. Cell. Biol.,* 8:988, 1984.

West, A. G., M. Gaszner, and G. Felsenfeld. 2002. Insulators: many functions, many mechanisms. Genes Dev. 16:271-288.

West, A. G., S. Huang, M. Gaszner, M. D. Litt, and G. Felsenfeld. 2004. Recruitment of histone modifications by USF proteins at a vertebrate barrier element. Mol Cell 16:453-63.

Winoto and Baltimore, "αβ-lineage-specific expression of the α T-cell receptor gene by nearby silencers," *Cell,* 59:649, 1989.
Wong and Neumann, "Electric field mediated gene transfer," *Biochim. Biophys. Res. Commun.,* 107(2):584-587, 1982.
Wu and Dean, "Functional significance of loops in the receptor binding domain of *Bacillus thuringiensis* CryIIIA delta-endotoxin," *J. Mol. Biol.,* 255(4):628-640, 1996.
Wu and Wu, "Evidence for targeted gene delivery to HepG2 hepatoma cells in vitro," *Biochemistry,* 27:887-892, 1988.
Wu and Wu, "Receptor-mediated in vitro gene transfections by a soluble DNA carrier system," *J. Biol. Chem.,* 262: 4429-4432, 1987.
Wu et al., "Mutational analysis of the adeno-associated virus type 2 (AAV2) capsid gene and construction of AAV2 vectors with altered tropism," *J. Virol.,* 74:8635-47, 2000.
Wu, T.-T., Y.-H. Su, T. M. Block, and J. M. Taylor. 1996. Evidence that two latency associated transcripts of herpes simplex type 1 are non-linear. J. Virol. 70:5962-5967.
Xiao et al., "Gene therapy vectors based on adeno-associated virus type 1," *J. Virol.,* 73:3994-4003, 1999.
Yang et al., "Adenovirus-mediated dystrophin minigene transfer improves muscle strength in adult dystrophic (MDX) mice," *Gene Ther.,* 5:369-79, 1998.
Yang et al., "In vivo and in vitro gene transfer to mammalian somatic cells by particle bombardment," *Proc. Natl. Acad. Sci. USA,* 87:9568-9572, 1990.
Yusufzai, T. M., H. Tagami, Y. Nakatani, and G. Felsenfeld. 2004. CTCF tethers an insulator to subnuclear sites, suggesting shared insulator mechanisms across species. Mol Cell 13:291-8.
Yutzey, Kline and Konieczny, "An internal regulatory element controls troponin I gene expression," *Mol. Cell. Biol.,* 9:1397, 1989.
Zambaux, Bonneaux, Gref, Maincent, Dellacherie, Alonso, Labrude, Vigneron, "Influence of experimental paparmeters on the characteristics of poly(lactic acid) nanoparticles prepared by a double emulsion method," *J. Controlled Release,* 50(1-3):31-40, 1998.
Zolotukhin et al., "Production and purification of serotype 1, 2, and 5 recombinant adeno-associated viral vectors," *Methods,* 28:158-67, 2002.
zur Muhlen, Schwarz, Mehnert, "Solid lipid nanoparticles (SLN) for controlled drug delivery—drug release and release mechanism," *Eur. J. Pharm. Biopharm.,* 45(2):149-155, 1998.
Zwaagstra, J. C., H. Ghiasi, A. B. Nesburn, and S. L. Wechsler. 1991. Identification of a major regulatory sequence in the latency associated transcript (LAT) promoter of herpes simplex virus type 1 (HSV-1). Virology 182:287-297.
Zwaagstra, J. C., J. C. Ghiasi, S. M. Slanina, A. B. Nesburn, S. C. Wheatley, K. Lillycrop, J. Wood, D. S. Latchman, K. Patel, and S. L. Wechsler. 1990. Activity of herpes simplex virus type 1 latency-associated transcript (LAT) promoter in neuron-derived cells: Evidence for neuron specificity and for a large LAT transcript. J. Virol. 64:5019-5028.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. An expression vector comprising a gene expression cassette comprising, in 5' to 3' order:

(a) a first nucleic acid segment comprising a first isolated HSV LAT insulator/boundary region that consists of a contiguous nucleotide sequence from about nucleotide 8365 to about nucleotide 9273 of SEQ ID NO:109, SEQ ID NO: 110, or SEQ ID NO: 111, operably positioned 5' of a second nucleic acid segment that comprises a selected polynucleotide of interest operably linked to a first promoter that expresses the polynucleotide in a selected host cell; and (b) a third nucleic acid segment comprising a second isolated HSV LAT insulatory/boundary region that consists of a contiguous nucleotide sequence from about nucleotide 120,208 to about nucleotide 120,940 of SEQ ID NO:109, SEQ ID NO: 110, or SEQ ID NO: 111, operably positioned 3' of the first and the second nucleic acid segments, wherein the gene expression cassette is up to about 10,000 nucleotides in length.

2. The expression vector of claim 1, wherein the second nucleic acid segment further comprises: (c) a first enhancer operably linked to the polynucleotide of interest.

3. The expression vector of claim 2, wherein the first enhancer comprises an isolated HSV LAT enhancer.

4. The expression vector of claim 1, wherein the first promoter comprises an isolated HSV LAP1 promoter.

5. The expression vector of claim 4, wherein the first promoter is an isolated HSV LAP1 promoter that consists of a sequence region of from about nucleotide 117,938 to about 118,843 of any one of SEQ ID NO:109, SEQ ID NO:110, and SEQ ID NO: 111.

6. The expression vector of claim 1, wherein the second nucleic acid segment further comprises at least a first multiple cloning region operably positioned 3' of the first promoter.

7. The expression vector of claim 6, wherein the second nucleic acid segment further comprises at least a second multiple cloning region operably positioned 5' of the first promoter.

8. The expression vector of claim 7, wherein the selected polynucleotide of interest is comprised within the second multiple cloning region.

9. The expression vector of claim 8, wherein the selected polynucleotide of interest comprises or encodes a first therapeutic agent that is selected from the group consisting of a peptide, a polypeptide, a ribozyme, a catalytic RNA molecule, an antisense oligonucleotide, and an antisense polynucleotide.

10. A recombinant viral vector, comprising the expression vector of claim 1.

11. An expression vector that comprises, in 5' to 3' order:

(a) a first isolated nucleic acid segment comprising a first isolated HSV LAT insulator/boundary region that consists of a contiguous nucleotide sequence from about nucleotide 8365 to about nucleotide 9273 of SEQ ID NO:109, SEQ ID NO:110, or SEQ ID NO:111;

(b) a second isolated nucleic acid segment comprising a first multiple cloning region; and (c) a third isolated nucleic acid segment comprising a second isolated HSV LAT insulatory/boundary region that consists of a contiguous nucleotide sequence from about nucleotide 120,208 to about nucleotide 120,940 of SEQ ID NO:109, SEQ ID NO:110, or SEQ ID NO:111.

12. A virus, virion, or plurality of viral particles that comprises the expression vector of claim 1 or claim 11.

13. The virus, virion, or plurality of viral particles of claim 12, wherein the vector, virus, virion, or plurality of viral particles is of retroviral, adenoviral, adeno-associated viral, or herpes viral origin.

14. The virus, virion, or plurality of viral particles of claim 13, comprising a gutless HSV vector, a gutless AV vector, a gutless AAV vector, a recombinant HSV vector, a recombinant AV vector, or a recombinant AAV vector.

15. An isolated mammalian host cell that comprises:

(a) the expression vector of claim 1 or claim 11; or (b) a viral vector, virion, or plurality of viral particles that comprises the expression vector.

16. A pharmaceutical composition comprising:

(a) the expression vector of claim 1 or claim 11; or (b) a viral vector, virion, or plurality of viral particles that comprises the expression vector.

17. The expression vector of claim 11, wherein the first multiple cloning region further comprises a selected polynucleotide of interest operably linked to a first promoter than expresses the polynucleotide in a selected mammalian host cell.

18. The expression vector of claim 17, wherein the selected polynucleotide of interest is operably linked to an enhancer element that, comprises an isolated HSV LAT enhancer element.

19. The expression vector of claim 17, wherein the selected polynucleotide of interest encodes a first therapeutic agent.

20. The expression vector of claim 19, wherein the first therapeutic agent is selected from the group consisting of a peptide, a polypeptide, a ribozyme, a catalytic RNA molecule, an antisense oligonucleotide, and an antisense polynucleotide.

21. The expression vector of claim 17, wherein the first promoter is an isolated HSV LAP1 promoter that consists of a sequence region of from about nucleotide 117,938 to about 118,843 of any one of SEQ ID NO:109, SEQ ID NO:110, and SEQ ID NO:111.

22. The expression vector of claim 11, further comprising a fourth isolated nucleic acid segment that comprises a second multiple cloning region.

23. The expression vector of claim 22, wherein the selected polynucleotide of interest is comprised within the second multiple cloning region.

24. The expression vector of claim 22, wherein the second multiple cloning region is operably positioned 3' of, or 5' of, the first promoter.

* * * * *

UNITED STATES PATENT AND TRADEMARK OFFICE

CERTIFICATE OF CORRECTION

PATENT NO. : 9,023,617 B2
APPLICATION NO. : 10/590136
DATED : May 5, 2015
INVENTOR(S) : David C. Bloom et al.

It is certified that error appears in the above-identified patent and that said Letters Patent is hereby corrected as shown below:

On the Title Page below the Abstract change 11 Drawing Sheets to read 12 Drawing Sheets.

IN THE DRAWINGS

Applicants hereby request that the informal drawings, FIG. 1 - FIG. 12B, be replaced with the Replacement Formal Drawing sheets (FIG. 1 - FIG. 12B).

Signed and Sealed this
Twenty-seventh Day of October, 2015

Michelle K. Lee
*Director of the United States Patent and Trademark Office*

CONSENSUS CORE CTCF MOTIFS

Myc-FpV chicken / PIM-1 mouse — ▲ 5'-GGGCG-3' reverse complement ▽ 5'-CGCCC-3'

MYC A human — ▲ 5'-GCGGG-3' reverse complement ▽ 5'-CCCGC-3'

MYC A human p19ARF — ▲ 5'-GGGAG-3' reverse complement ▽ 5'-CTCCC-3'

MYC N human "144" silencer Rat — ▲ 5'-GAGGG-3' reverse complement ▽ 5'-CCCTC-3'

APP human — ▲ 5'-GGGTC-3' reverse complement ▽ 5'-GACCC-3' p19ARF — ▽ 5'-CCCTG-3' reverse complement ▲ 5'-CAGGG-3'

DMD4 mouse — ▽ 5'-CCACC-3' reverse complement ▲ 5'-GGTGG-3'

NON-CONSENSUS CORE CTCF MOTIFS

▲ 5'-CTGGG-3' reverse complement ▽ 5'-CCCAG-3'

▲ 5'-GGGAC-3' reverse complement ▽ 5'-GTCCC-3'

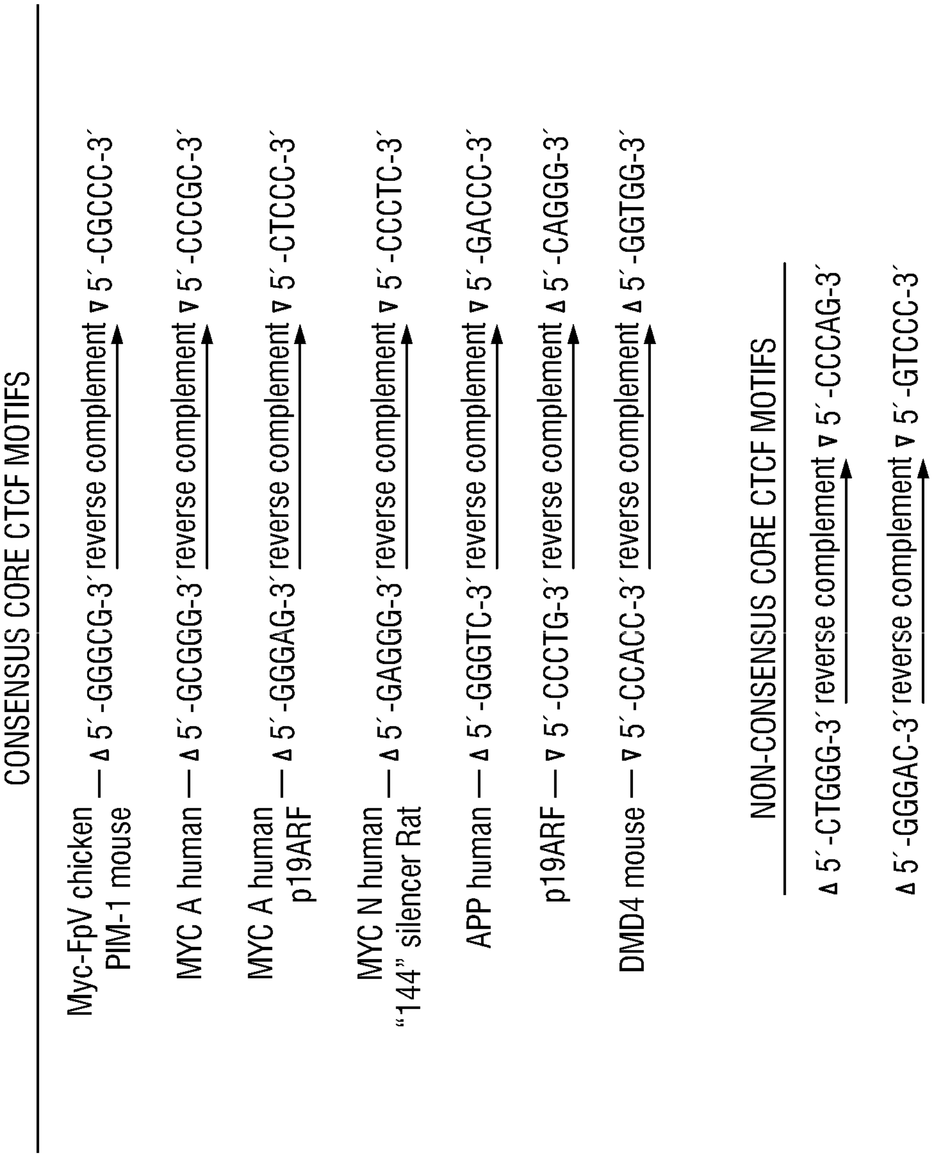

FIG. 8B

CONSENSUS CORE CTCF MOTIFS

Myc-FpV chicken PIM-1 mouse — ∆ 5′-GGGCG-3′ reverse complement → ∇ 5′-CGCCC-3′

MYC A human — ∆ 5′-GCGGG-3′ reverse complement → ∇ 5′-CCCGC-3′

MYC A human p19ARF — ∆ 5′-GGGAG-3′ reverse complement → ∇ 5′-CTCCC-3′

MYC N human "144" silencer Rat — ∆ 5′-GAGGG-3′ reverse complement → ∇ 5′-CCCTC-3′

APP human — ∆ 5′-GGGTC-3′ reverse complement → ∇ 5′-GACCC-3′ p19ARF — ∇ 5′-CCCTG-3′ reverse complement → ∆ 5′-CAGGG-3′

DMD4 mouse — ∇ 5′-CCACC-3′ reverse complement → ∆ 5′-GGTGG-3′

NON-CONSENSUS CORE CTCF MOTIFS

∆ 5′-CTGGG-3′ reverse complement → ∇ 5′-CCCAG-3′

∆ 5′-GGGAC-3′ reverse complement → ∇ 5′-GTCCC-3′

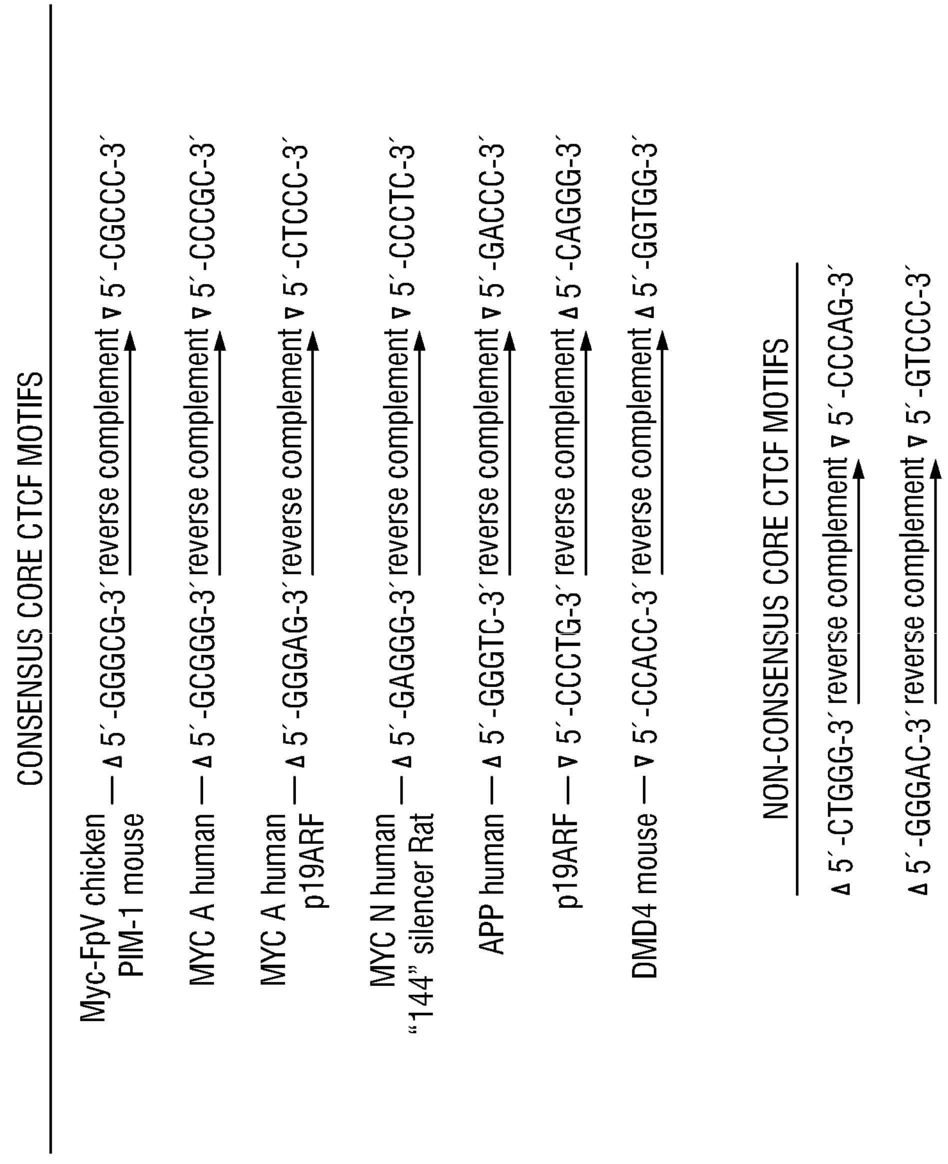

*FIG. 11B*